US007727713B2

(12) United States Patent
Pedersen et al.

(10) Patent No.: US 7,727,713 B2
(45) Date of Patent: Jun. 1, 2010

(54) TEMPLATED MOLECULES AND METHODS FOR USING SUCH MOLECULES

(75) Inventors: Henrik Pedersen, Bagsvaerd (DK); Alex Haahr Gouilaev, Veksø Sjaelland (DK); Thomas Franch, Odense C (DK); Christian Klarner Sams, Frederiksberg C (DK); Eva Kampmann Olsen, Herlev (DK); Frank Abilgaard Sløk, København N (DK); Gitte Nystrup Husemoen, København N (DK); Jakob Felding, Charlottenlund (DK); Lene Hyldtoft, Virum (DK); Mads Nørregaard-Madsen, Birkerød (DK); Michael Anders Godskesen, Vedbaek (DK); Sanne Schrøder Glad, Ballerup (DK); Thomas Thisted, Frederikssund (DK); Per-Ola Freskgård, Vellinge (SE); Anette Holtmann, Ballerup (DK)

(73) Assignee: Nuevolution A/S, Copenhagen (DK)

( * ) Notice: Subject to any disclaimer, the term of this patent is extended or adjusted under 35 U.S.C. 154(b) by 176 days.

(21) Appl. No.: 10/175,539

(22) Filed: Jun. 20, 2002

(65) Prior Publication Data
US 2004/0049008 A1  Mar. 11, 2004

Related U.S. Application Data

(60) Provisional application No. 60/364,056, filed on Mar. 15, 2002, provisional application No. 60/299,443, filed on Jun. 21, 2001.

(30) Foreign Application Priority Data

Jun. 20, 2001  (DK)  ................ 2001 00962

(51) Int. Cl.
C12Q 1/68  (2006.01)
C12Q 1/70  (2006.01)
G01B 33/53  (2006.01)
C07H 21/00  (2006.01)
C07H 21/02  (2006.01)
A61K 38/00  (2006.01)

(52) U.S. Cl. .................. 435/6; 435/5; 435/7.1; 435/7.2; 435/91.1; 536/22.1; 536/23.1; 536/25.3; 530/300; 530/350

(58) Field of Classification Search .................. 435/5, 435/6, 7.1, 7.2, 91.1, 91.11; 536/22.1, 23.1, 536/25.3; 530/300, 350
See application file for complete search history.

(56) References Cited

U.S. PATENT DOCUMENTS 4,822,731 A  4/1989  Watson et al.

(Continued)

FOREIGN PATENT DOCUMENTS

DE  196 46 372  6/1997

(Continued)

OTHER PUBLICATIONS

Nemoto, N et al. "In vitro virus: bonding of mRNA bearing puromycin at the 3'-terminal end to the C-terminal end of its encoded protein on the ribosome in vitro". FEBS Lett. Sep. 8, 1997;414(2):405-8.

(Continued)

Primary Examiner—Jezia Riley
(74) Attorney, Agent, or Firm—Iver P. Cooper

(57) ABSTRACT

The present invention relates to a method for synthesizing templated molecules. In one aspect of the invention, the templated molecules are linked to the template which templated the synthesis thereof. The intion allows the generation of libraries which can be screened for e.g. therapeutic activity.

241 Claims, 100 Drawing Sheets

U.S. PATENT DOCUMENTS

| | | | |
|---|---|---|---|
| 5,047,519 | A | 9/1991 | Hobbs, Jr. et al. |
| 5,476,930 | A | 12/1995 | Getsinger et al. |
| 5,503,805 | A | 4/1996 | Sugarman et al. |
| 5,571,903 | A | 11/1996 | Gryaznov |
| 5,573,905 | A | 11/1996 | Lerner et al. |
| 5,639,603 | A | 6/1997 | Dower et al. |
| 5,665,975 | A | 9/1997 | Kedar et al. |
| 5,681,943 | A | 10/1997 | Letsinger et al. |
| 5,708,153 | A | 1/1998 | Dower et al. |
| 5,723,598 | A | 3/1998 | Lerner et al. |
| 5,741,643 | A | 4/1998 | Gryaznov et al. |
| 5,770,358 | A | 6/1998 | Dower et al. |
| 5,780,613 | A | 7/1998 | Letsinger et al. |
| 5,789,162 | A | 8/1998 | Dower et al. |
| 5,830,658 | A | 11/1998 | Gryaznov et al. |
| 5,843,650 | A | 12/1998 | Segev |
| 5,948,648 | A | 9/1999 | Khan et al. |
| 6,056,926 | A | 5/2000 | Sugarman et al. |
| 6,060,596 | A | 5/2000 | Lerner et al. |
| 6,096,875 | A | 8/2000 | Khan et al. |
| 6,140,493 | A | 10/2000 | Dower et al. |
| 6,143,497 | A | 11/2000 | Dower et al. |
| 6,143,503 | A | 11/2000 | Baskerville et al. |
| 6,165,717 | A | 12/2000 | Dower et al. |
| 6,165,778 | A | 12/2000 | Kedar et al. |
| 6,197,555 | B1 | 3/2001 | Khan et al. |
| 6,207,446 | B1 | 3/2001 | Szostak et al. |
| 6,248,568 | B1 | 6/2001 | Khan et al. |
| 6,297,053 | B1 | 10/2001 | Stemmer |
| 6,416,949 | B1 | 7/2002 | Dower et al. |
| 6,429,300 | B1 | 8/2002 | Kurz et al. |
| 6,593,088 | B1 | 7/2003 | Saito et al. |
| 6,620,587 | B1 | 9/2003 | Taussig et al. |
| 2003/0004122 | A1 | 1/2003 | Beigelman et al. |
| 2003/0113738 | A1* | 6/2003 | Liu et al. ............. 435/6 |
| 2005/0025766 | A1 | 2/2005 | Liu |
| 2005/0042669 | A1 | 2/2005 | Liu |

FOREIGN PATENT DOCUMENTS

| | | |
|---|---|---|
| EP | 0324616 B1 | 7/1989 |
| EP | 0 643 778 | 10/1993 |
| EP | 0604552 | 7/1994 |
| EP | 0695305 | 10/1994 |
| EP | 0830363 A1 | 11/1996 |
| EP | 0773227 | 5/1997 |
| EP | 0776330 | 6/1997 |
| EP | 1533385 | 5/2005 |
| WO | 9005785 | 5/1990 |
| WO | 9105058 | 4/1991 |
| WO | WO 93/03172 | 2/1993 |
| WO | WO 93/06121 A1 | 4/1993 |
| WO | 9512608 | 5/1995 |
| WO | 9609316 | 3/1996 |
| WO | 9612014 | 4/1996 |
| WO | 9831700 | 7/1998 |
| WO | WO 98/56904 | 12/1998 |
| WO | 0021909 | 4/2000 |
| WO | 0023458 | 4/2000 |
| WO | WO 00/23458 A1 | 4/2000 |
| WO | 0032823 | 6/2000 |
| WO | 0047775 | 8/2000 |
| WO | WO 00/61775 * | 10/2000 |
| WO | WO 00/61775 A1 | 10/2000 |
| WO | WO 01/00876 | 1/2001 |
| WO | WO 02/074929 A2 | 9/2002 |
| WO | 02102820 | 12/2002 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03082901 | 10/2003 |
| WO | 2004001042 | 12/2003 |
| WO | 2004009814 | 1/2004 |
| WO | 2004013070 | 2/2004 |
| WO | 2004016767 | 2/2004 |
| WO | 2004024929 | 3/2004 |
| WO | 2004039825 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004110964 | 12/2004 |
| WO | 2005003778 | 1/2005 |
| WO | 2005026387 | 3/2005 |

OTHER PUBLICATIONS

Roberts, RW et al. "RNA-peptide fusions for the in vitro selection of peptides and proteins". Proc Natl Acad Sci U S A. Nov. 11, 1997;94(23):12297-302.

Kurz, M et al. "An efficient synthetic strategy for the preparation of nucleic acid-encoded peptide and protein libraries for in vitro evolution protocols" Fourth International Electronic Conference on Synthetic Organic Chemisty (ECSOC-4), www.mdpi.org/ecsoc-4.htm. Sep. 1-30, 2000.

Kurz, M et al. Psoralen phot-crosslinked mRNA-puromycin conjugates: a novel template for the rapid and facile preparation of mRNA-protein fusions. Nucleic Acids Res. Sep. 15, 2000;28(18):E83.

Benner, SA. "Expanding the genetic lexicon: incorporating non-standard amino acids into proteins by ribosome-based synthesis". Trends Biotechnol. May 1994;12(5):158-63.

Mendel, D."Site-directed mutagenesis with an expanded genetic code". Annu. Rev. Biophys. Biomol. Struc. 1995. 24:435-62.

Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.

Liu DR et al. "Progress toward the evolution of an organism with an expanded genetic code". Proc Natl Acad Sci USA. Apr. 27, 1999;96(9):4780-5.

Liu, R et al. "Optimized synthesis of RNA-protein fusions for in vitro protein selection". Methods Enzymol. 2000;318;268-93.

Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.

Eilman J.A., et al. "Biosynthetic method for introducing Unnatural Amino acids site specifically into proteins". Methods Enzymol. 2002. 301-336 (1992).

Dower, WJ et al. "In vitro selection as a powerful tool for the applied evolution of proteins and peptides".Current Opinion in Chemical Biology, 2002, 6:390-398.

Gartner, ZJ et al. "Multistep small-molecule synthesis programmed by DNA templates". J. Am. Chem. Soc. vol. 124, No. 35, 2002, 10304-10306.

Calderone, CT et al. "Directing otherwise incompatible reactions in a single solution by using DNA-templated organic synthesis". Angew Chem Int Ed, 2002, 41, No. 21. 4104-4108.

Gartner, ZJ et al. "Two enabling architectures for DNA-templated organic synthesis". Angew. Chem Int. Ed. 2003, 42, No. 12, 1370-1375.

Rosenbaum, DM et al. "Efficient and sequence-specific DNA-templated polymerization of peptide nucleic acid aldehydes". J. Am. Chem. Soc. vol. 125, No. 46, 2003, 13924-13925.

Li, X et al. "Stereoselectivity in DNA-templated organic synthesis and its origins". J. Am. Chem. Soc. vol. 125, No. 34, 2003, 10188-10189.

Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.

Otto, S et al. S"Recent developments in dynamic combinatorial chemistry". Current opinion in Chemical Biology 2002, 6: 321-327.
Pavia, MR. "The Chemical generation of molecular diversity". http://www.netsci.org/Science/Combichem/feature01.html.
Braun, E, et al. "DNA-templated assembly and electrode attachment of a conducting silver wire". Nature, vol. 391, Feb. 19, 1998, 775-778.
Tanaka, K et al. "Synthesis of a novel nucleoside for alternative DNA base pairing through metal complexation" J. Org. Chem. 1999, 64, 5002-5003.
Weizman, H et al. "2,2'-Bipyridine ligandoside: a novel building block for modifying DNA with intra-duplex metal complexes". J. Am. Chem. Soc. 2001, 123, 3375-3376.
Frutos, AG et al. "Demonstration of a word design strategy for DNA computing on surfaces". Nucleic Acids Research, 1997, vol. 25, No. 23, 4748-4757.
Loweth, CJ et al. "DNA-based assembly of gold nanocrystals". Angew. Chem. Int. Ed. 1999, 38, No. 12. 1808-1812.
DeWitt, SH et al. "Diversomers": an approach to nonpeptide, nonoligomeric chemical diversity. Proc. Natl. Acad. Sci, USA, vol. 90, pp. 6909-6913, Aug. 1993.
Nielsen, J et al. "Synthetic methods for the implementation of encoded combinatorial chemistry". J. Am. Chem. Soc. 1993, 115, 9812-9813.
Ohlmeyer, MHJ et al. "Complex synthetic chemical libraries indexed with molecular tags". Proc. Natl. Acad, Sci, USA, vol. 90, pp. 10922-10926, Dec. 1993, Chemistry.
Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.
Luo, P et al. "Analysis of the structure and stability of a backbone-modified oligonucleotide: implications for avoiding product inhibition in catalytic template-directed synthesis". J. Am. Chem. Soc. 1998, 120, 3019-3031.
Luther, A et al. "Surface-promoted replication and exponential amplification of DNA analogues". Nature, vol. 396, Nov. 19, 1998, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramström, O et al. "In situ generation and screening of a dynamic combinatorial carbohydrate library against concanavalin A". ChemBioChem, 2000, 1, 41-48.
Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.
Roberts, SI et al. "Simultaneous selection, amplification and isolation of pseudo-peptide receptor by an immobilised N-methyl ammonium ion template". Chem. Commun., 2002, 938-939.
Elghanian, R et al. "Selective colorimetric detection of polynucleotides based on the distance-dependent optical properties of gold nanoparticles". Science, vol. 277, Aug. 22, 1997.
Doyon, J.B et al. "Highly sensitive in vitro selections for DNA-linked synthetic small molecules with protein binding affinity and specificity" *J. Am. Chem. Soc*, Sep. 16, 2003, pp. 1-2 and S1-S8.
Kanan, M.W et al. "Reaction discovery enabled by DNA-templated synthesis and in vitro selection" *Nature*, vol. 431, Sep. 30, 2004, pp. 545-549.
"Finding reactions in a haystack: Try'em all, see what works" *Meeting American Chemical Society*, Sep. 10, 2004, vol. 305, Science.
"The Nucleus", Jan. 2004, vol. LXXXII, No. 5, R. Grubina; "Summer Research Report: R. Grubina on DNA Templated Synthesis for Small Molecule Library", p. 10-14.
Nazarenko et al., "A closed tube format for amplification and detection of DNA based on energy transfer", Nucleic Acids Research, 1997, vol. 25, No. 12, p. 2516-2521.
Chan et al., "Intra-tRNA distance measurements for nucleocapsid protein-dependent tRNA unwinding during priming of HIV reverse transcription", PNAS vol. 96, p. 459-464, Jan. 1999.

DNA-templated synthesis as a basis for the evolution of synthetic molecules. Liu DR, Gartner ZJ, Kanan MW, Calderone CT Abstracts of Papers of the American Chemical Society 225: 612-ORGN, Part 2, Mar. 2003.
Rodriguez et al., "Template-directed extension of a guanosine 5'-phosphate covalently attached to an oligodeoxycytidylate template", J Mol Evol (1991) 33:477-482.
Inoue et al, Oligomerization of (Guanosine 5'-phosphor)-2-methylimidazolide on Poly(C), J. Mol. Biol. (1982), 162, 201-217.
C. B. Chen et al., "Template-directed synthesis on Oligodeoxycytidylate and Polydeoxycytidylate templates" J. Mol. Biol. 1985, 181, 271.
H. Rembold et al., "Single-strand regions of Poly(G) act as templates for oligo(C) synthesis" J. Mol. Evol. 1994, 38, 205.
T. Inoue et al., "A nonenzymatic RNA polymerase model", Science 1983, 219, p. 859-862.
O. L. Acevedo et al., "Non-enzymatic transcription of an oligonucleotide 14 residues long", J. Mol. Biol. 1987, 197, p. 187-193.
C. Böhler et al.,"Template switching between PNA and RNA oligonucleotides", Nature 1995, 376, 578-581.
Acevedo et al., "Template-directed oligonucleotide ligation on hydroxylapatite", Nature vol. 321, Jun. 19, 1986, p. 790-792.
Piccirilli, "RNA seeks its maker", Nature vol. 376, Aug. 17, 1995, p. 548-.
A. W. Schwartz et al., "Template-directed synthesis of novel, nucleic acid-like structures", Science 1985, 228, 585-7.
Halpin et al.: DNA display III. Solid-phase organic synthesis on uprotected DNA. PLoS Biol. Jul. 2004;2(7):E175. Epub Jun. 22, 2004.
Halpin et al.: DNA display II. Genetic manipulation of combinatorial chemistry libraries for small-molecule evolution. PLoS Biol. Jul. 2004;2(7):E174. Epub Jun. 22, 2004.
Halpin et al.: DNA display I. Sequence-encoded routing of DNA populations. PLoS Biol. Jul. 2004;2(7):E173. Epub Jun. 22, 2004.
"Highly Sensitive In Vitro Selections for DNA-Linked Synthetic Small Molecules with Protein Binding Affinity and Specificity" Doyon, J. B.; Snyder, T. M.; Liu, D. R. J. Am. Chem. Soc. 125, 12372-12373 (2003).
"Translation of DNA into Synthetic N-Acyloxazolidines" Li, X.; Gartner, Z. J.; Tse, B. N.; Liu, D. R. J. Am. Chem. Soc. 126, 5090-5092 (2004).
"DNA-Templated Organic Synthesis: Nature's Strategy for Controlling Chemical Reactivity Applied to Synthetic Molecules" Li, X.; Liu, D. R. Angew. Chem. Int. Ed. 43, 4848-4870 (2004).
"DNA-Templated Organic Synthesis and Selection of Library of Macrocyles" Gartner, Z. J.; Tse, B. N.; Grubina, R.; Doyon, J. B.; Snyder, T. M.; Liu, D. R. Science 305, 1601-1605 (2004).
"Nucleic Acid-Templated Synthesis as a Model System for Ancient Translation" Calderone, C. T. and Liu, D. R. Curr. Opin. Chem. Biol. 8, 645-653 (2004).
"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).
"Translating DNA into synthetic Molecules", David R. Liu, PLoS Biology, Jul. 2004, vol. 2, Iss. 7, p. 905-6.
"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.
Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.
Brenner, Sydney and Richard A. Lerner. "Encoded Combinatorial Chemistry," *Proc. Natl. Acad. Sci. USA*, vol. 89, pp. 5381-5383, Jun. 1992.

Bruick, Richard K. et al. "Template-Directed Ligation of Peptides to Oligonucleotides," *Chemistry and Biology 1996*, vol. 3 No. 1.

Visscher, J. and Alan W. Scwartz. "Template-Directed Synthesis of Acyclic Oligonucleotide Analogues," *J Mol Evol* (1988) 28:3-6.

Walder, Joseph A. et al. "Complementary carrier Peptide Synthesis: General Strategy and Implications for Prebiotic Origin of Peptide Synthesis," Department of Chemistry, and Department of Biochemistry and Molecular Biology, Northwestern University, Evanston, Illinois 60201.

Walder, et al., "Complementary carrier peptide synthesis: general strategy and implications for prebiotic origin of peptide synthesis", *Proc Natl Acad Sci USA*, vol. 76(1), pp. 51-55, 1979.

Tamura K, et al., "Oligonucleotide-directed peptide synthesis in a ribosome- and ribozyme-free system", *Proc Natl Acad Sci USA*, vol. 98 (4), pp. 1393-1397, 2001.

Lewis, RJ, et al., "Ligation of oligonucleotides by pyrimidine dimers—a missing 'link' in the origin of life?", *Nature*, vol. 298 (5872), pp. 393-396, Jul. 22, 1982.

Liu, J, et al., "Template-directed photoligation of oligodeoxyribonucleotides via 4-thiothymidine", *Nucleic Acids Res.*, vol. 26(13), pp. 3300-3304, Jul. 1, 1998.

Fujimoto, et al., "Template-directed photoreversible ligation of deoxyoligonucleotides via 5-Vinyldeoxyuridine", *J. Am. Chem. Soc.*, vol. 122, pp. 5646-5647, 2000.

Fujimoto, et al., Template-directed reversible photocircularization of DNA via 5-vinyldeoxycytidine, vol. 41, pp. 6451-6454, 2000.

Fujimoto, et al., "Template directed photochemical synthesis of branched oligodeoxynucleotides via 5-carboxyvinyldeoxyuridine", *Tetrahedron Letters*, vol. 41:49, pp. 9437-9440, 2000.

Gryaznov, et al., "Chemical Ligation of oligonucleotides in the presence and absence of a template", *J. Amer. Chem. Soc.*, vol. 115, pp. 3808-3809, 1993.

Gryaznov SM, et al., "Template controlled coupling and recombination of oligonucleotide blocks containing thiophosphoryl groups", *Nucleic Acids Res.*, vol. 21(6), pp. 1403-1408, 1993.

Gryaznov, SM, et al., "Enhancement of selectivity in recognition of nucleic acids via chemical autoligation", *Nucleic Acids Res.*, vol. 22(12), pp. 2366-2369, 1994.

Herrlein, MK, et al., "Selective chemical autoligation on a double-stranded DNA template", *Nucleic Acids Res.*, vol. 22(23), pp. 5076-5078, Nov. 25, 1994.

Letsinger, RL, et al., "Chemical and photochemical ligation of oligonucleotide blocks", *Nucleosides and Nucleotides*, vol. 16(5&6), pp. 643-652 (1997).

Visscher, J., et al., "Template-directed oligomerization catalyzed by a polynucleotide analog", *Science*, vol. 244(4902), pp. 329-331, Apr. 21, 1989.

Visscher, J., et al., "Oligomerization of deoxynucleoside-bisphosphate dimers: template and linkage specificity", *Orig Life Evol Biosph*, vol. 19(1), pp. 3-6, 1989.

Zhan, ZJ, et al., "Chemical Amplification through template-directed synthesis", *J. Am. Chem. Soc.*, vol. 119, pp. 12420-12421, 1997.

Bruick, RK, et al., "A simple procedure for constructing 5'-amino terminated oligodeoxynucleotides in aqueous solution", *Nucleic Acids Res.*, vol. 25(6), pp. 1309-1310, Mar. 15, 1997.

Albagli, D, et al., "Chemical amplification (CHAMP) by a continuous, self-replicating oligonucleotide-based system", *J. Am. Chem. Soc.*, vol. 121, pp. 6954-6955, 1999, Pub. on the web Jul. 14, 1999.

Xu, Y, et al., "Rapid and Selective selenium-mediated autoligation of DNA strands", *J. Am. Chem. Soc.*, vol. 122, pp. 9040-9041, 2000, Pub. on web Aug. 31, 2000.

Xu, Y, et al., "Nonenzymatic autoligation in direct three-color detection of RNA and DNA point mutations", *Nat Biotechnol.*, vol. 19(2), pp. 148-152, Feb. 2001.

Li, X, et al., "DNA-catalyzed polymerization", *J. Am. Chem. Soc.*, vol. 124(5), pp. 746-747, Feb. 6, 2002.

Czlapinski, JL, et al., "Nucleic acid template-directed assembly of metallosalen-DNA conjugates", *J. Am. Chem. Soc.*, vol. 123(35), pp. 8618-8619, Sep. 5, 2001, published on the web Aug. 10, 2001.

Leitzel, JC, et al., "Template-directed ligation: from DNA towards different versatile templates", *Chem Rec.*, vol. 1(1), pp. 53-62, 2001, published online Jan. 30, 2001.

Schmidt, JG, et al., "Information transfer from peptide nucleic acids to RNA by template-directed syntheses", *Nucleic Acids Res.*, vol. 25(23), pp. 4797-4802, Dec. 1, 1997.

Gartner, Z., et al., "The generality of DNA-templated synthesis as a basis for evolving non-natural small molecules", *J Am Chem Soc.*, vol. 123(28), pp. 6961-6963, Jul. 18, 2001.

Gartner, et al., "Expanding the reaction scope of DNA-templated synthesis", *Angew. Chem. Int. Ed.*, vol. 41, No. 10, pp. 1796-1800, 2002, published May 15, 2002.

Bittker, JA, et al., "Recent advances in the in vitro evolution of nucleic acids", *Curr Opin Chem Biol*, vol. 6(3), pp. 367-374, Jun. 2002, Review Pub. on the web Mar. 20, 2002.

Summerer, D, et al., "DNA-templated synthesis: more versatile than expected", *Angew Chem Int Ed Engl*, vol. 41(1), pp. 89-90, Jan. 4, 2002.

Storhoff, JJ., et al., "Programmed Materials Synthesis with DNA", *Chem. Rev.*, vol. 99(7), pp. 1849-1862, Jul. 14, 1999.

Mirkin, CA, "Programming the assembly of two- and three-dimensional architectures with DNA and nanoscale inorganic building blocks", *Inorg Chem*, vol. 39(11), pp. 2258-2272, May 29, 2000.

Waybright, SM, et al., "Oligonucleotide-directed assembly of materials: defined oligomers", *J Am Chem Soc.*, vol. 123(9), pp. 1828-1833, Mar. 7, 2001, Pub. on web Feb. 7, 2001.

Smith, Bruce, et al., "DNA-guided assembly of proteins as a pathway to an assembler", (http://www.wadsworth.org/albcon97/abstract/krummena.htm) The 1997 Albany Conference: Biomolecular Motors and Nanomachines.

Berger, M, et al., "Universal bases for hybridization, replication and chain termination", *Nucleic Acids Research*, Oxford University Press, vol. 28, No. 15, pp. 2911-2914, Aug. 1, 2000.

Keiler, KC, et al., "Role of peptide tagging system in degradation of proteins synthesized from damaged messenger RNA", *Science*, vol. 271, pp. 990-993, Feb. 16, 1996.

Salas, J, et al., "Biosynthetic polydeoxynucleotides as direct templates for polypeptide synthesis", *Journal of Biological Chemistry*, vol. 243, No. 6, pp. 1012-1015, 1968.

\* cited by examiner

Figure 1. Chemical Display – Principle.
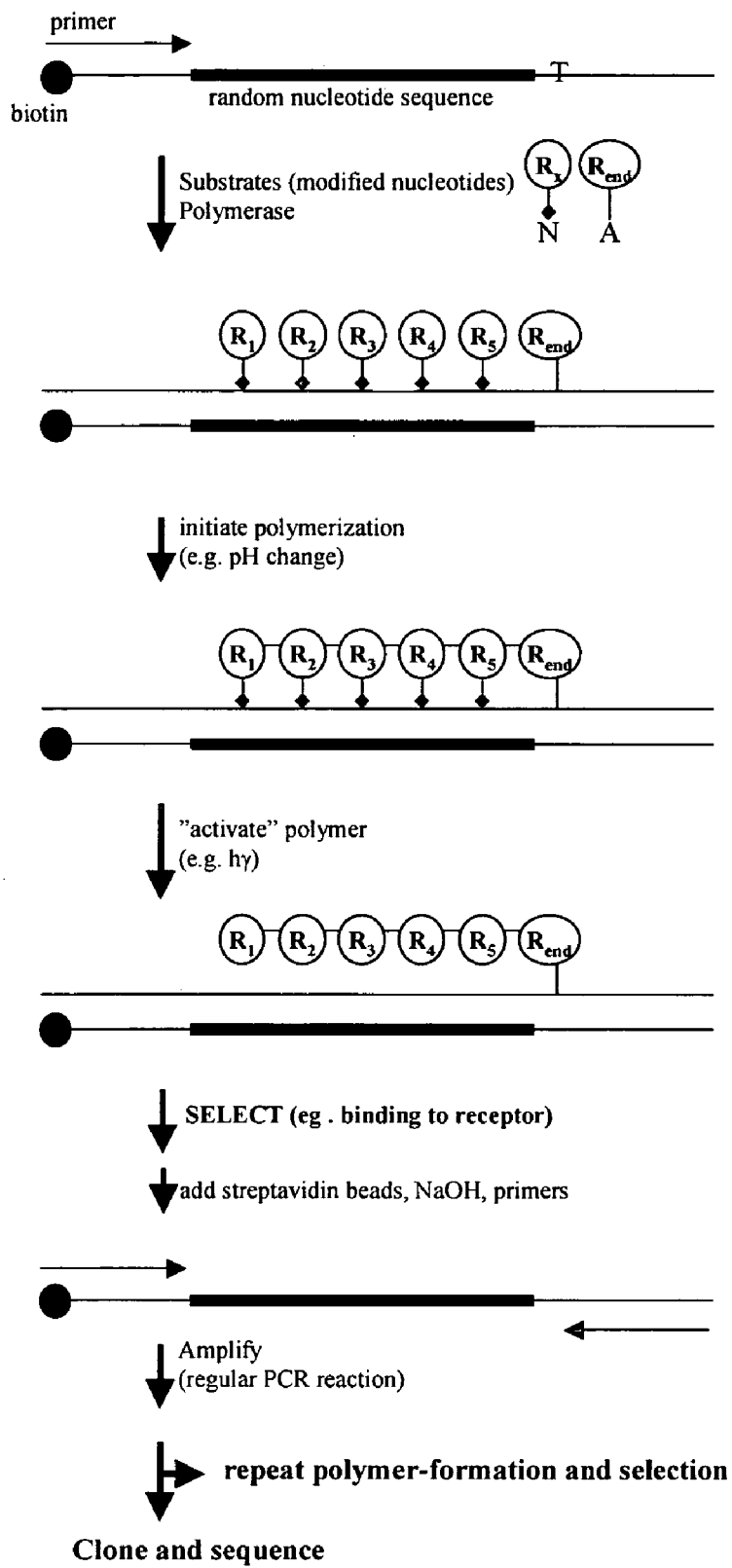

Figure 2a. An expanded set of base pairs.
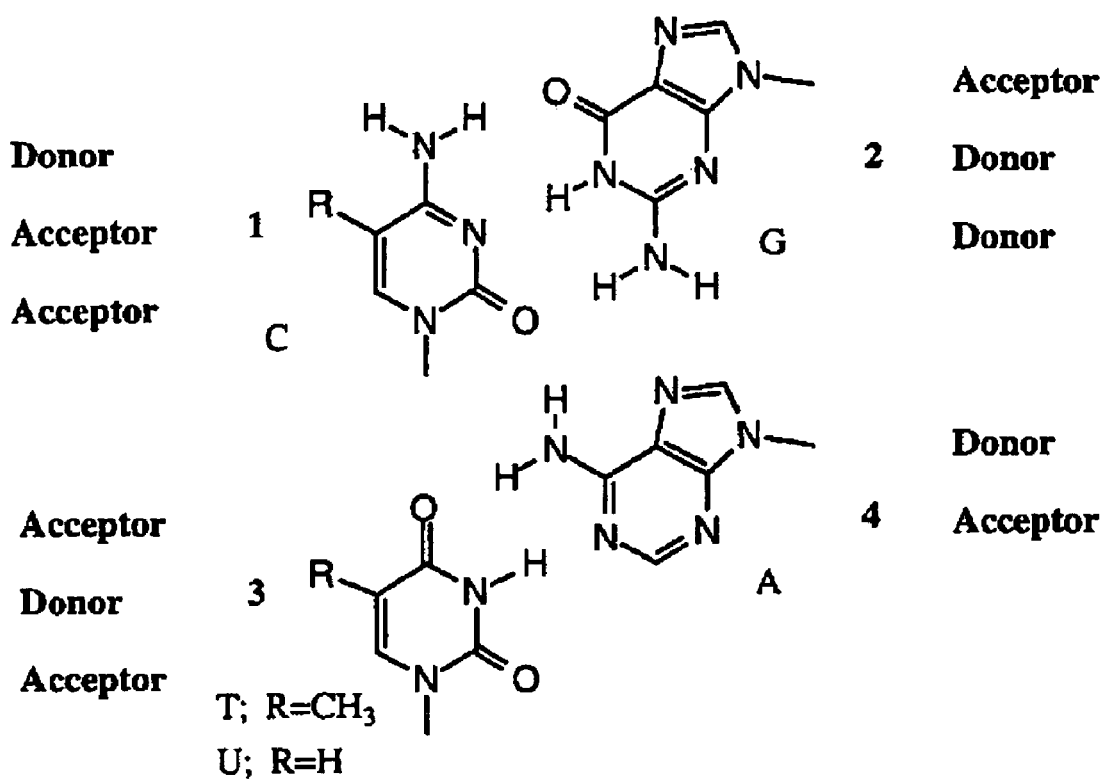

Figure 2b. An expanded set of base pairs.
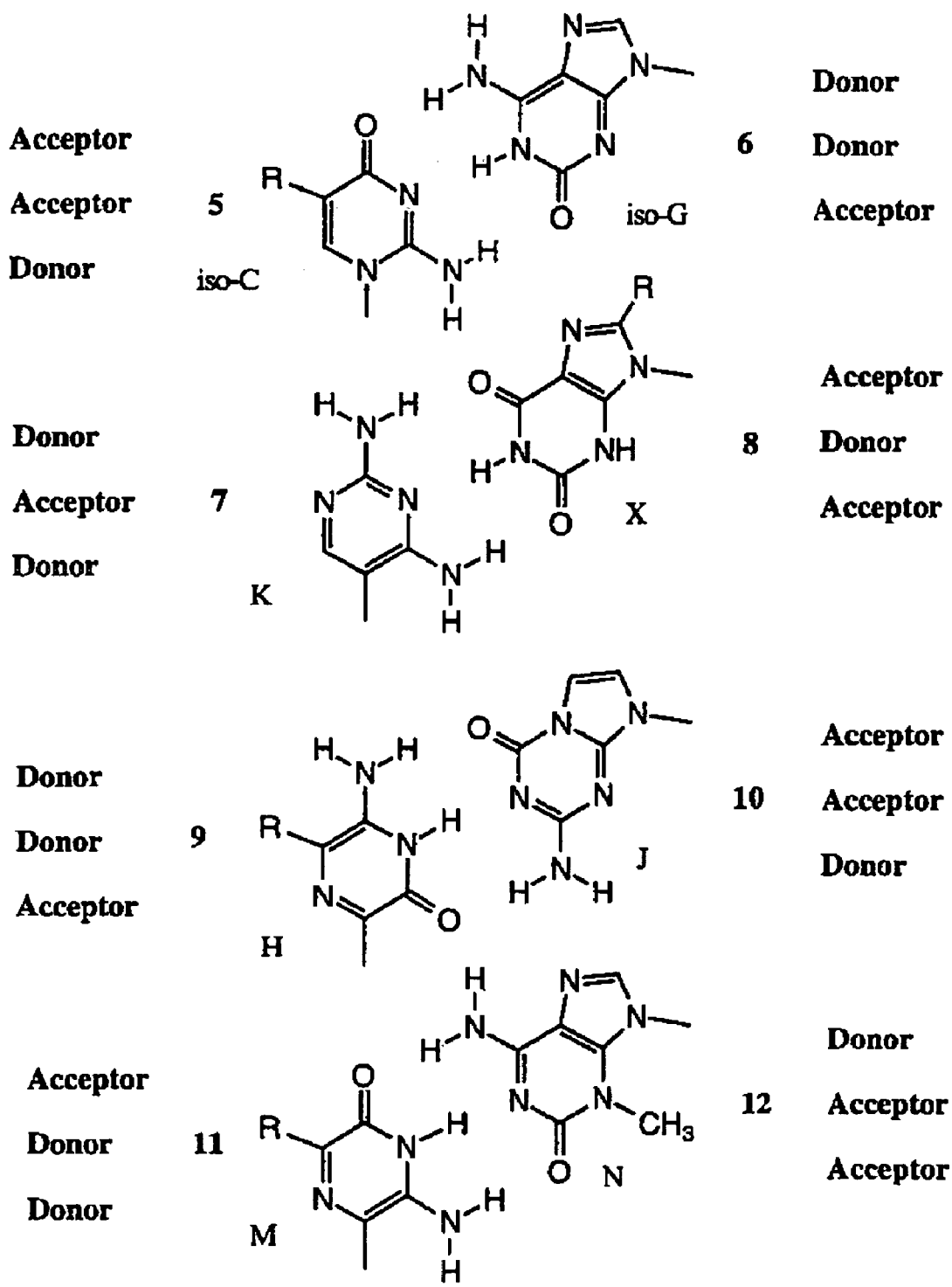

building blocks (template)

Figure 6.
A derivatized nucleotide as building block.
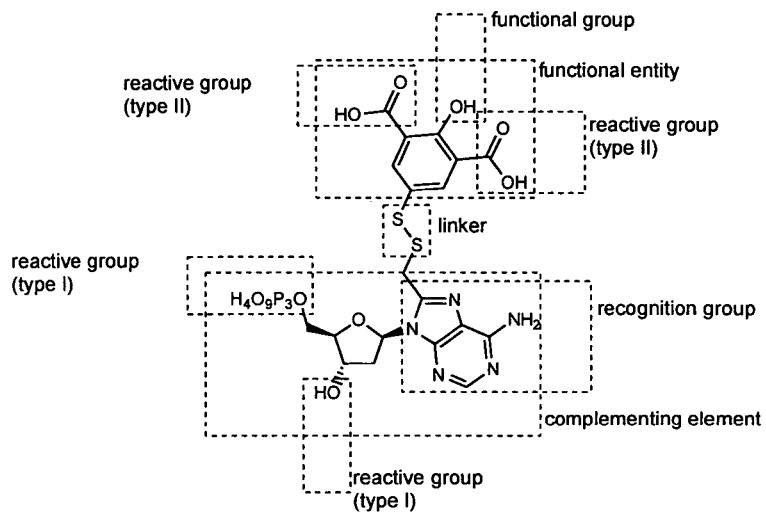
A derivatized di-nucleotide as building block.
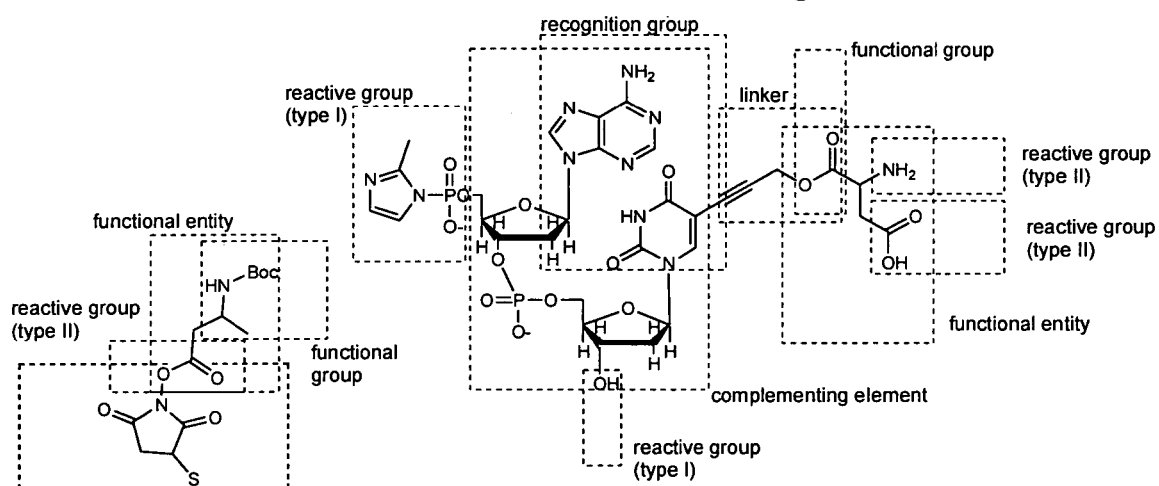
A derivatized oligo-nucleotide as building block.
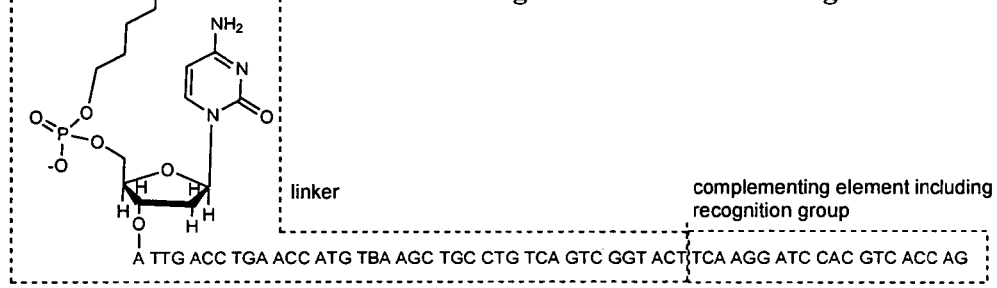

Figure 7. C-terminal tagging of a β-peptide - incorporation, polymerization and activation. an example
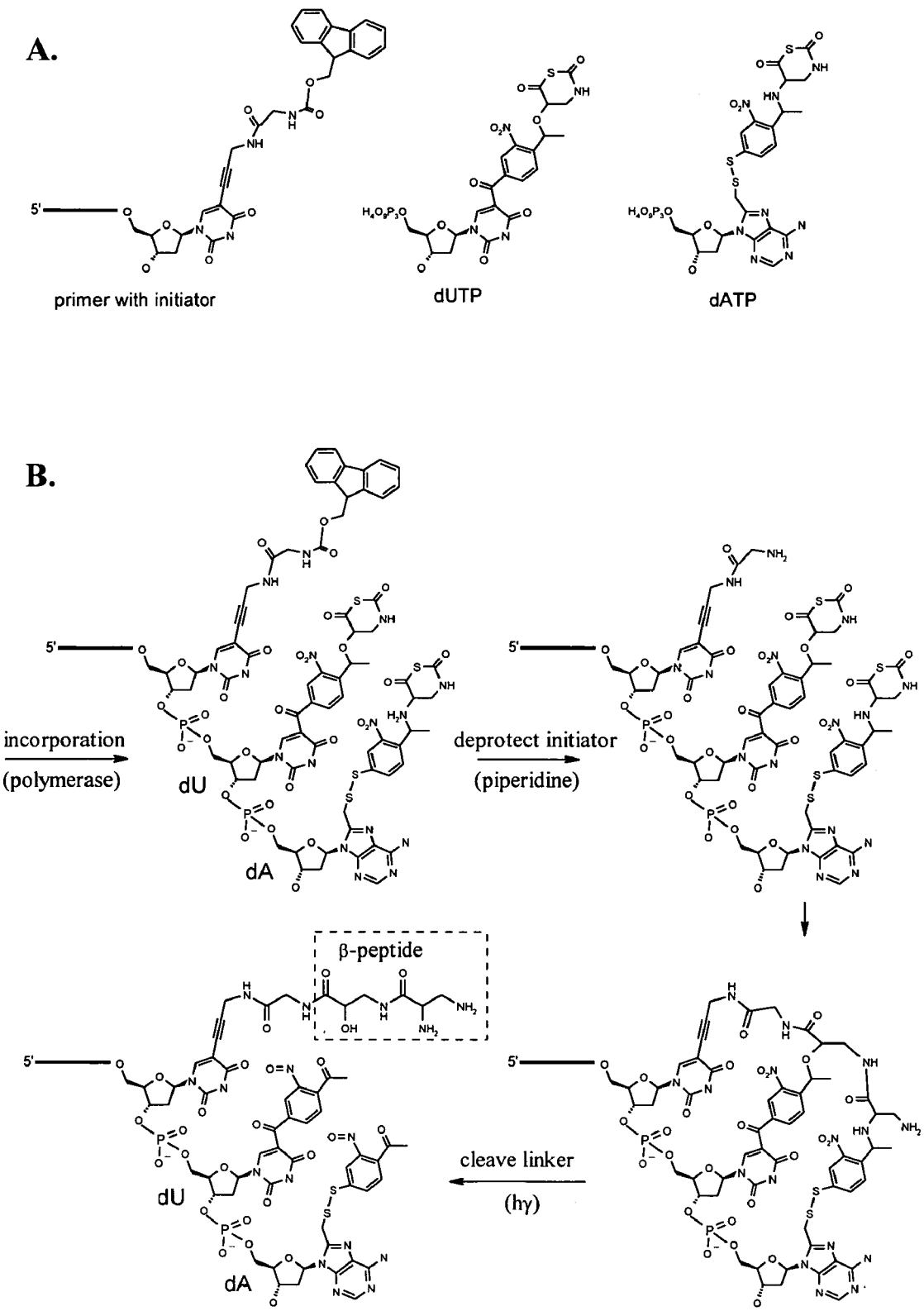

Figure 7. C-terminal tagging of a β-dipeptide - incorporation, polymerization and activation.
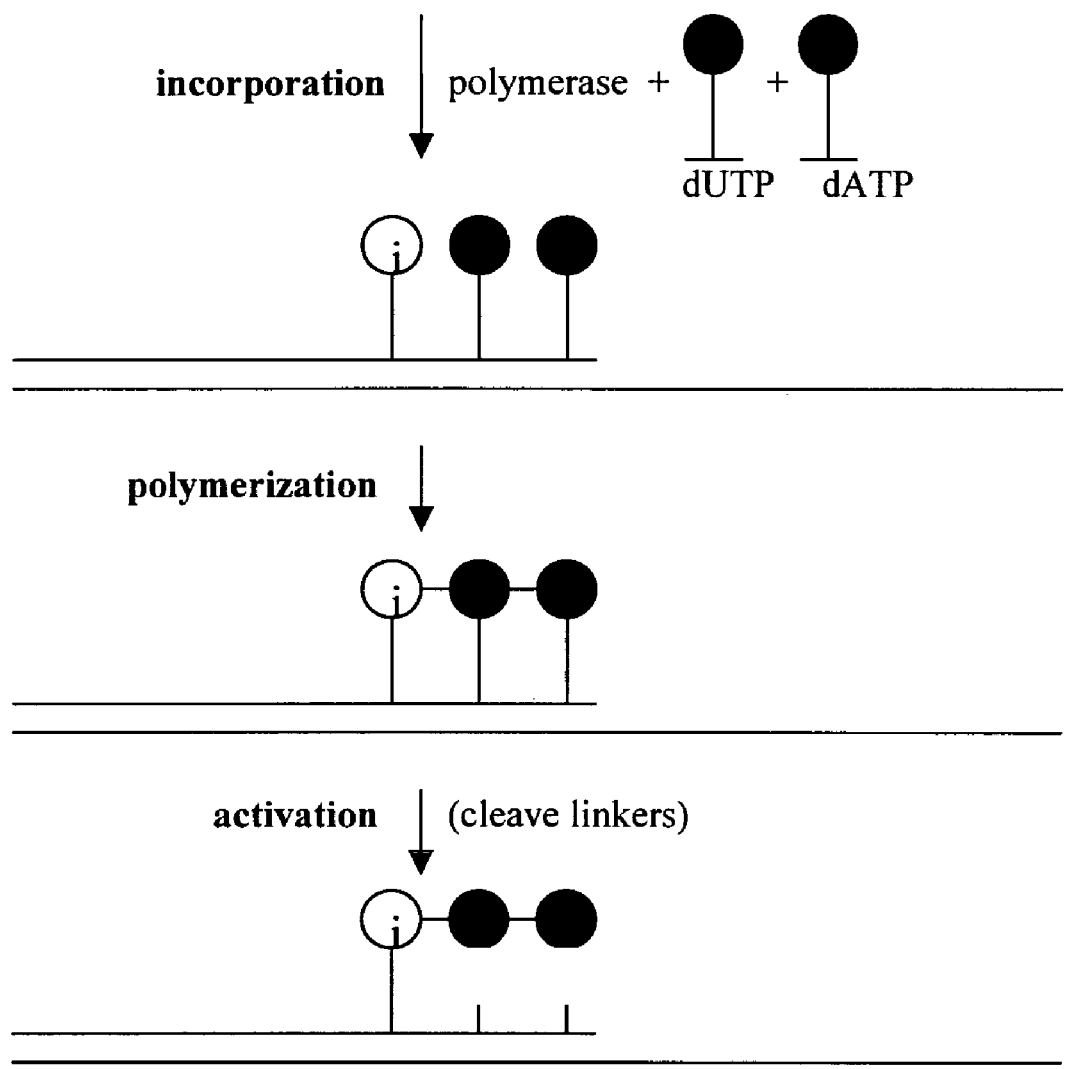

Figure 8. N-teminal tagging of a β-dipeptide - incorporation, polymerization and activation.
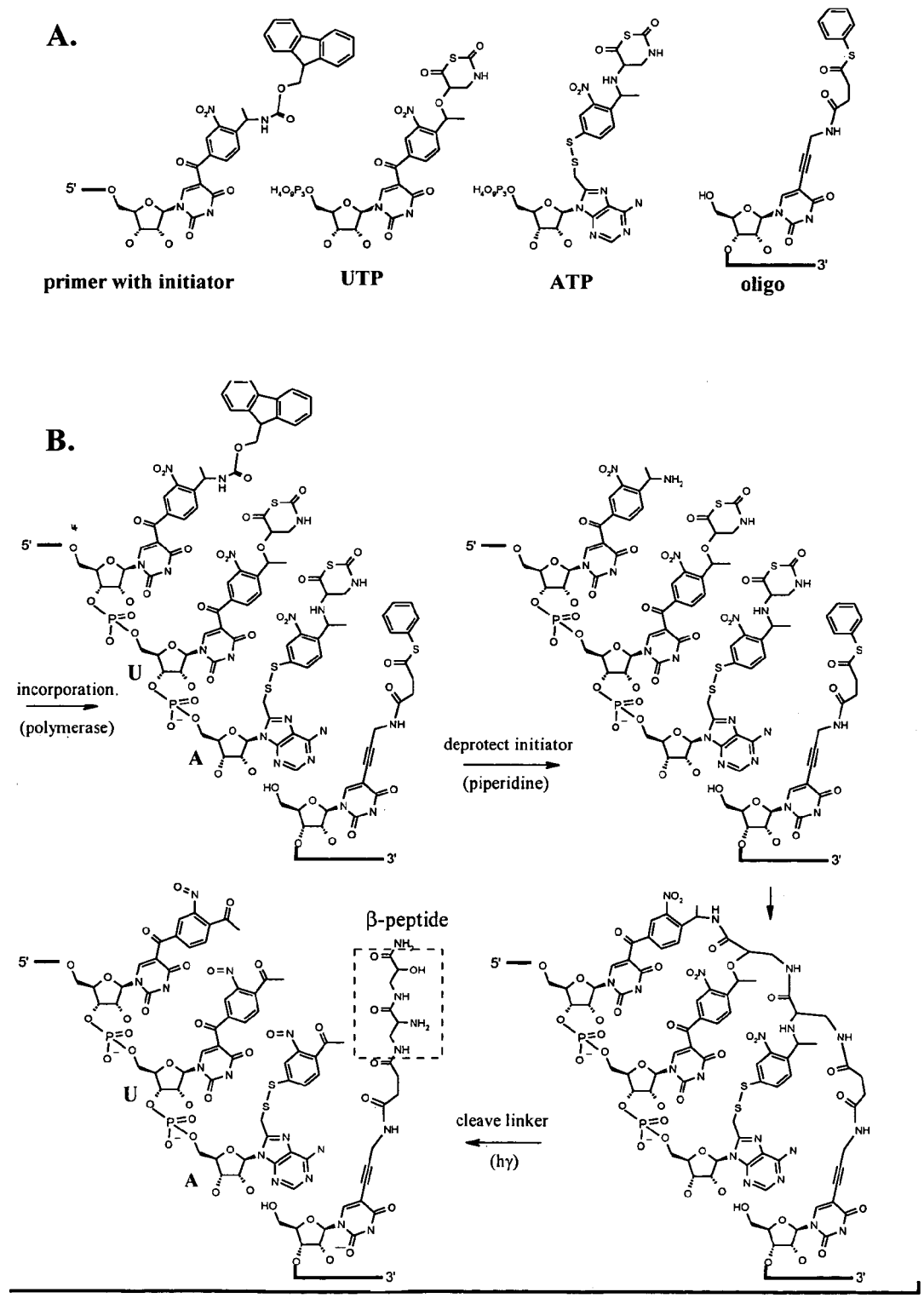

Figure 8. N-teminal tagging of a β-dipeptide - incorporation, polymerization and activation.
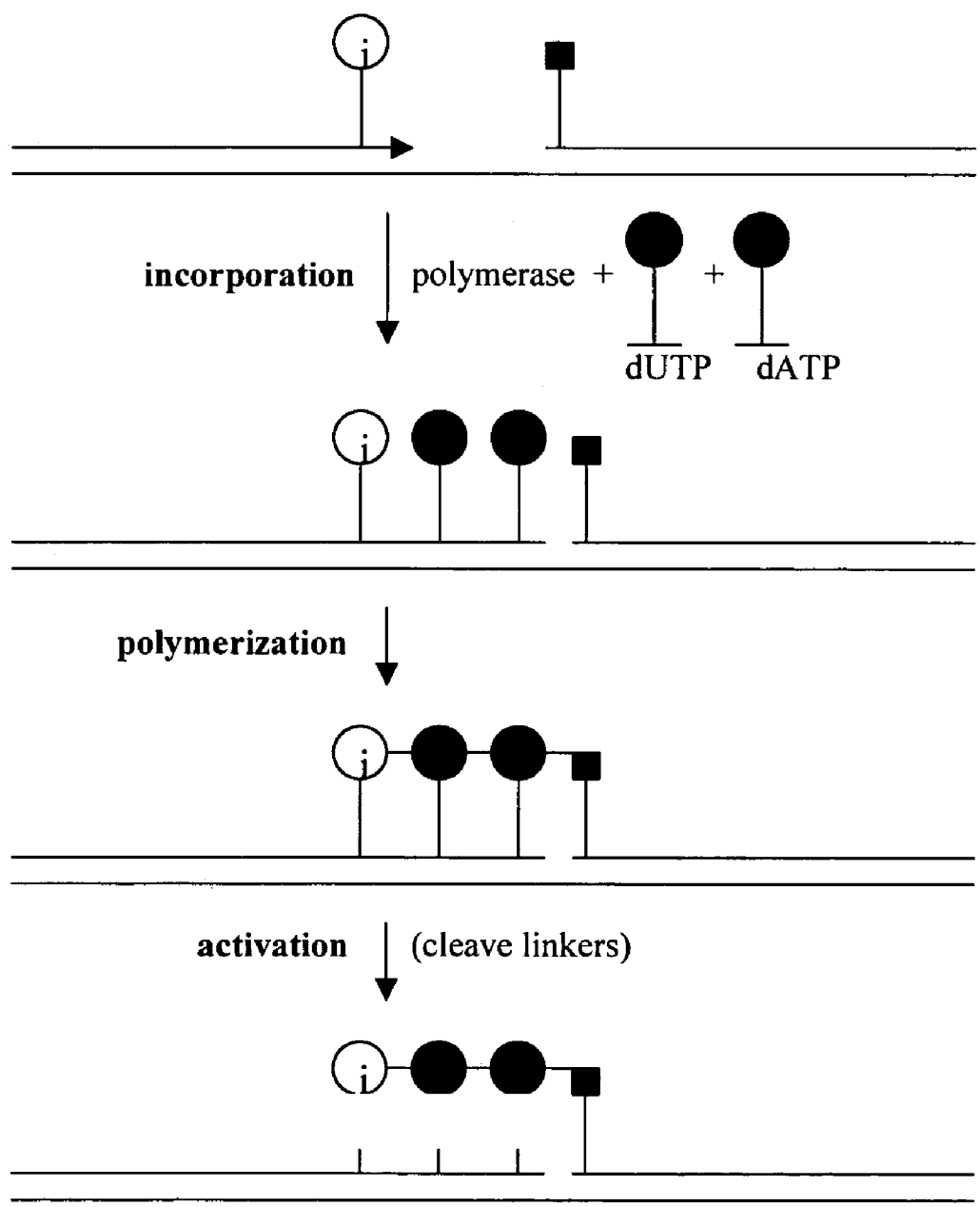

Figure 9. Nucleotide-derivatives that are known to be incorporated by polymerases
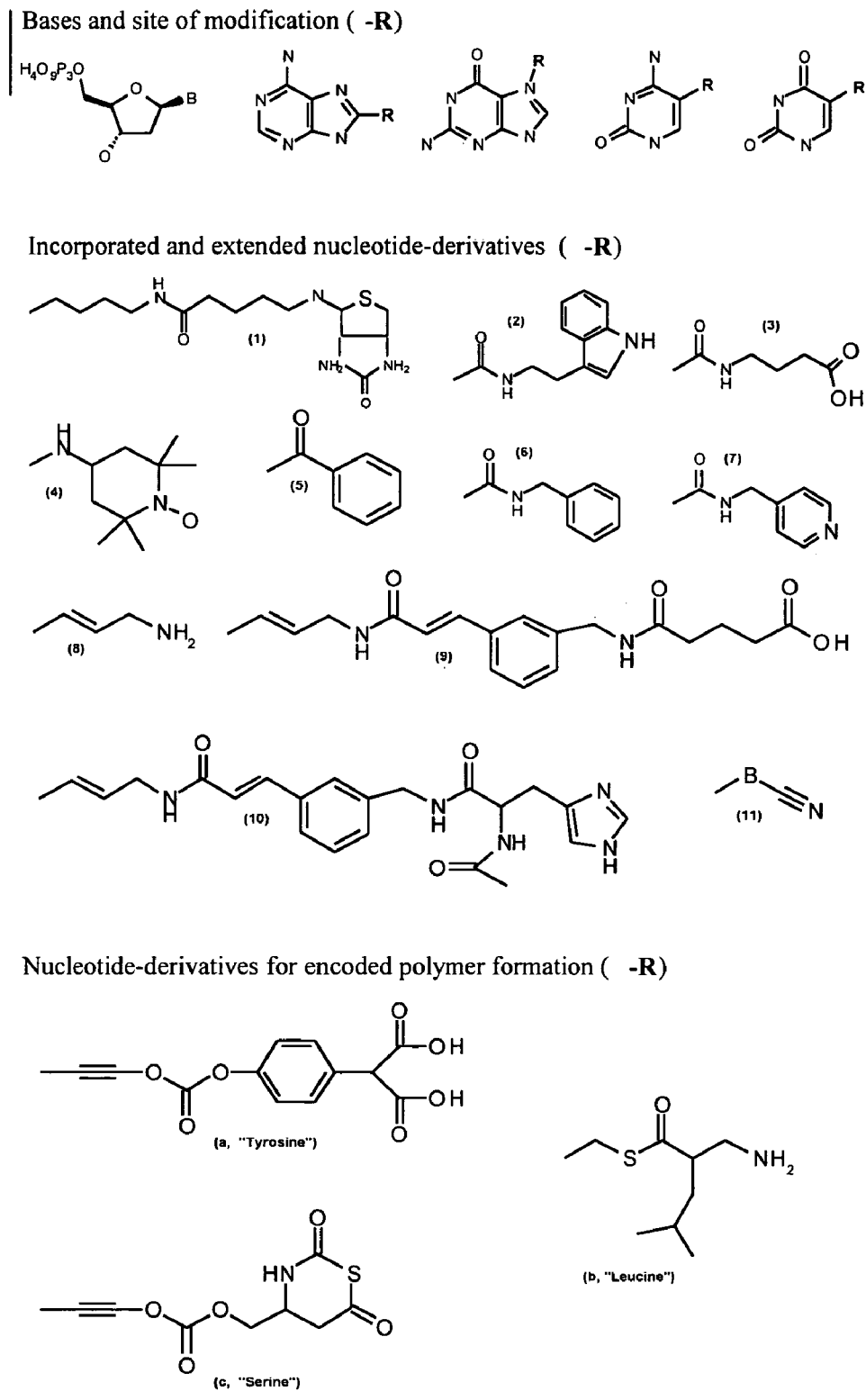

Figure 10. Cleavable linkers and protection groups, cleaving agents and cleavage products.
A. Base (nucleophilic) cleavage.
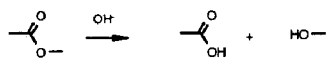
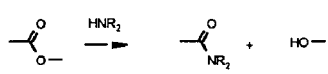
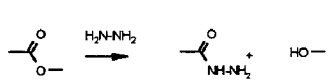
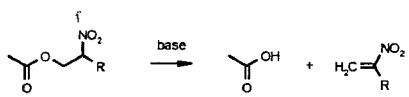
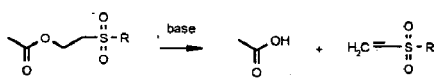
B. Photocleavage
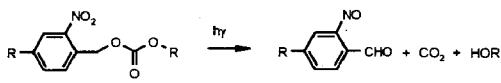
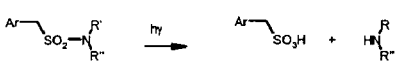
C. Acid cleavage
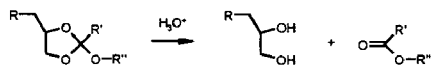
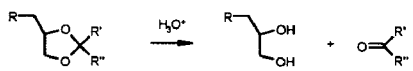
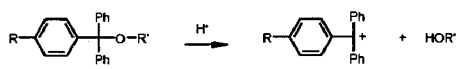
D. Catalytic cleavage.
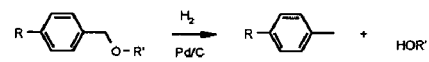
E. Enzymatic cleavage.
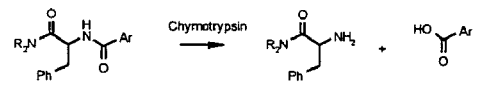
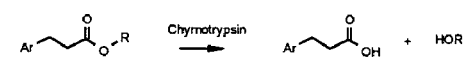
F. Cleavage by temperature increase.
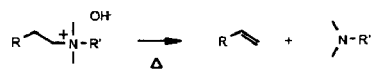
G. Miscellaneous
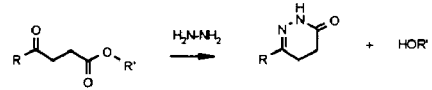

Figure 11. Polymerization by reaction between neighboring reactive groups type II.
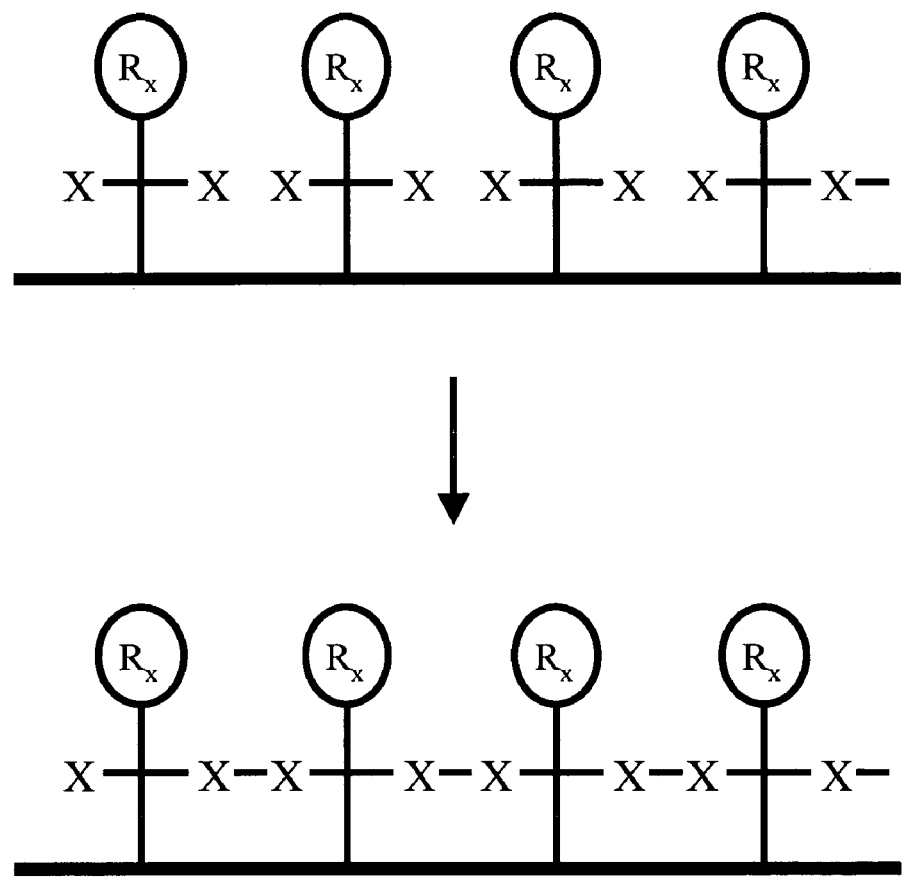

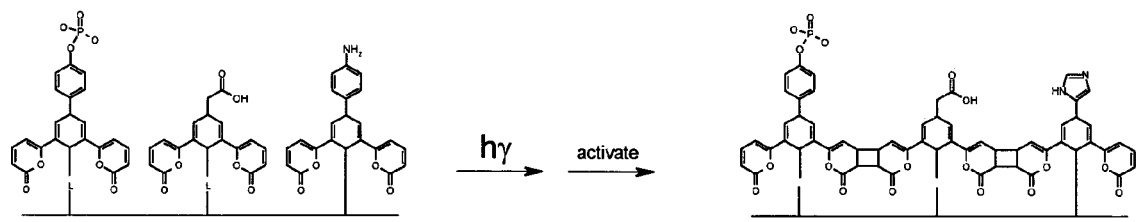
Figure 11, ex.1. Coumarin-based polymerization.

Figure 12. Polymerization between neighboring non-identical reactive groups type II.
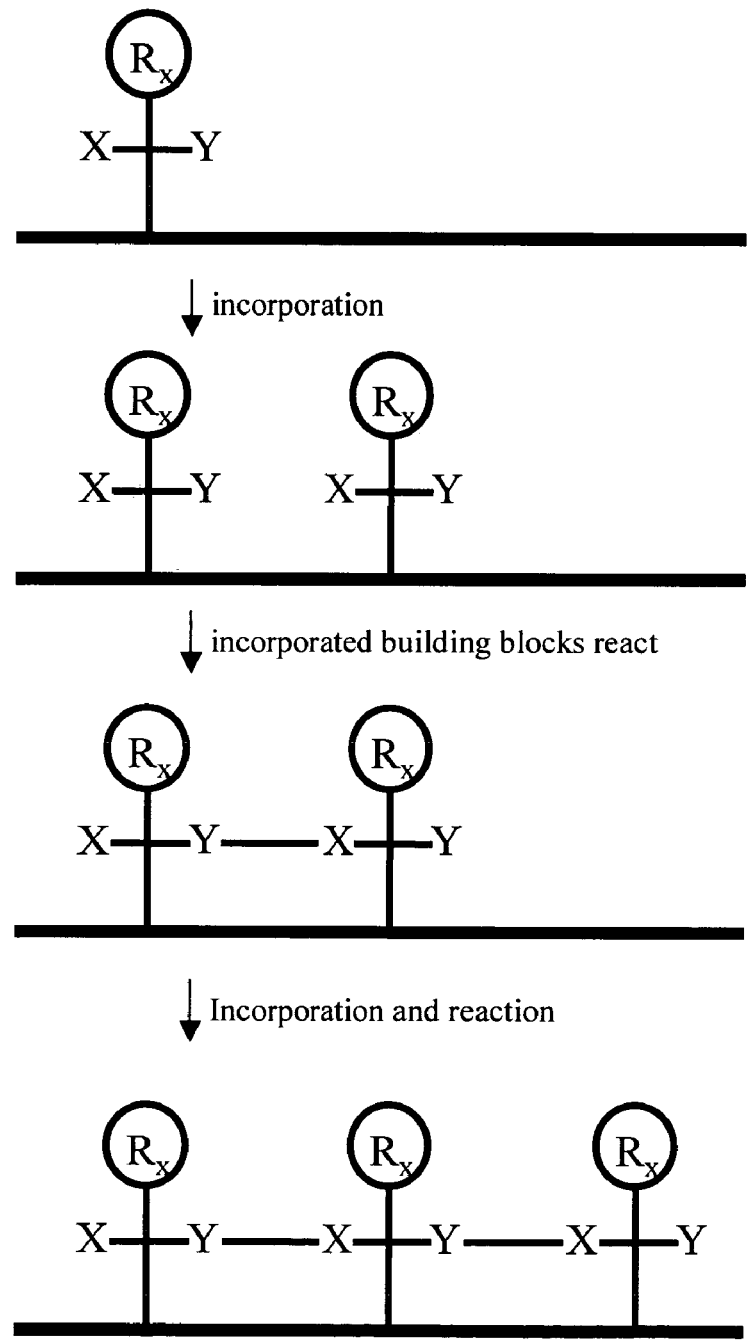

Figure 13. Cluster formation in the absence of directional polymerization.
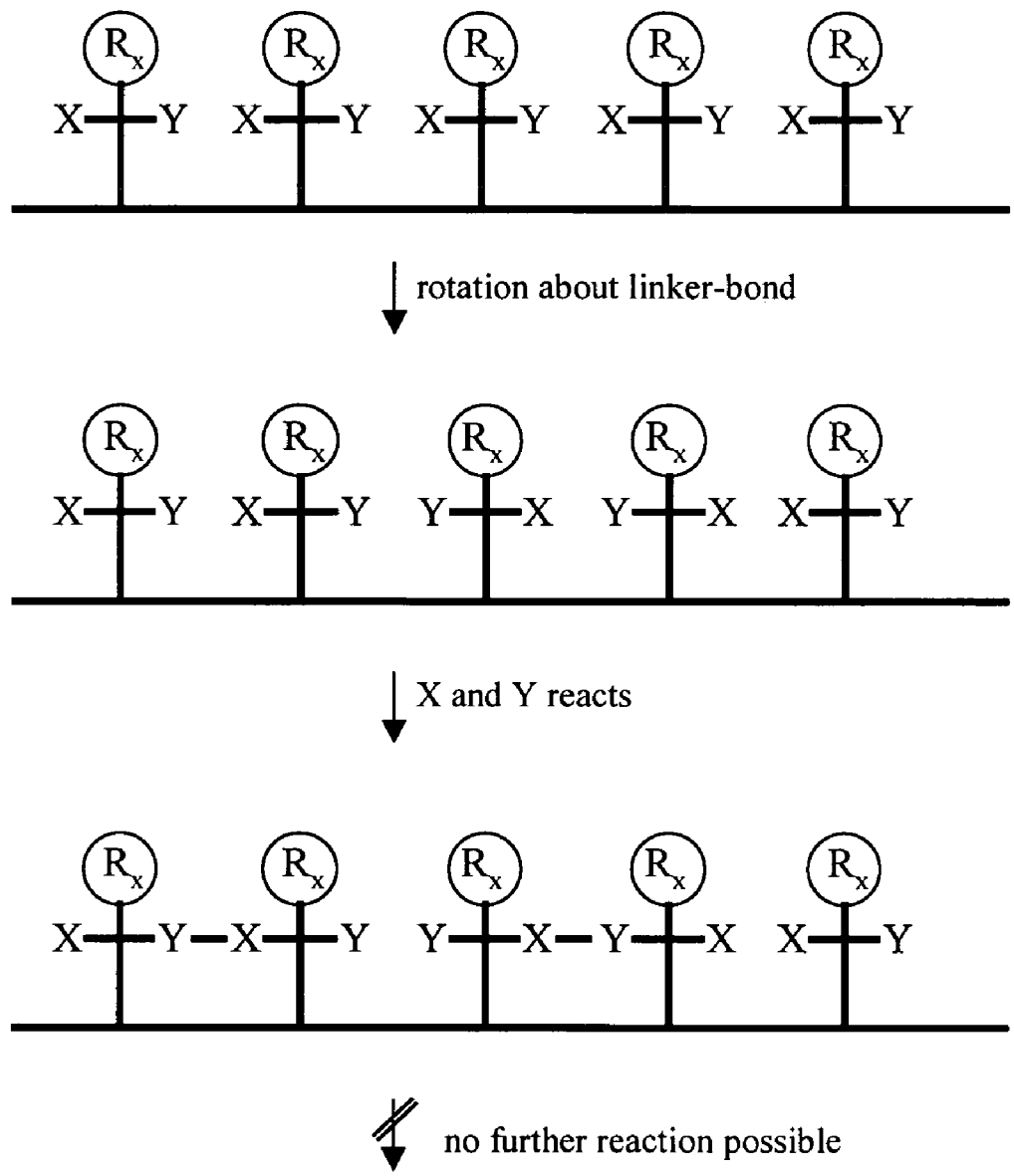

Figure 14. Zipping-polymerization and simultaneous activation.
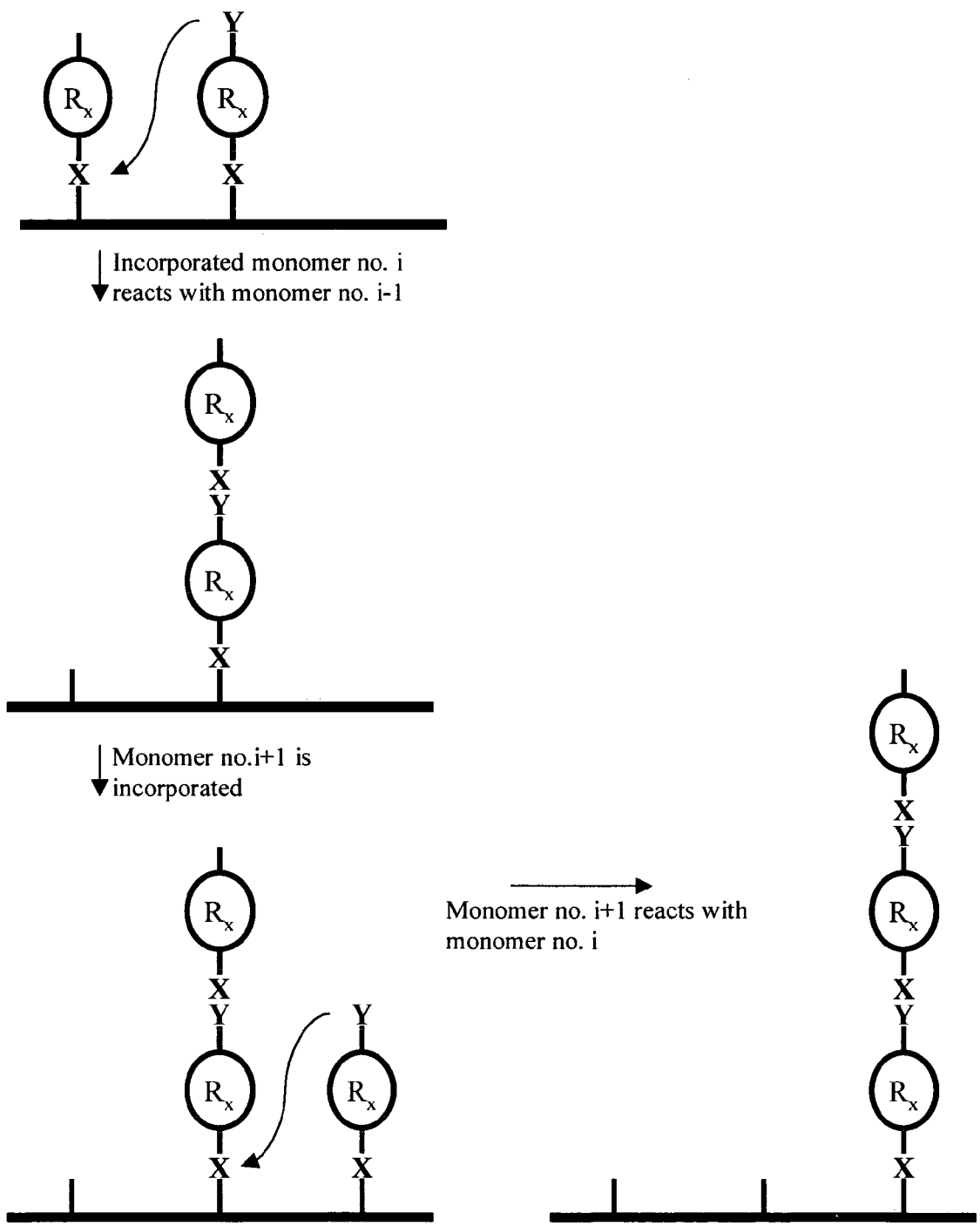

Figure 14, example 1. Polymerization and activation (thioesters)
A.
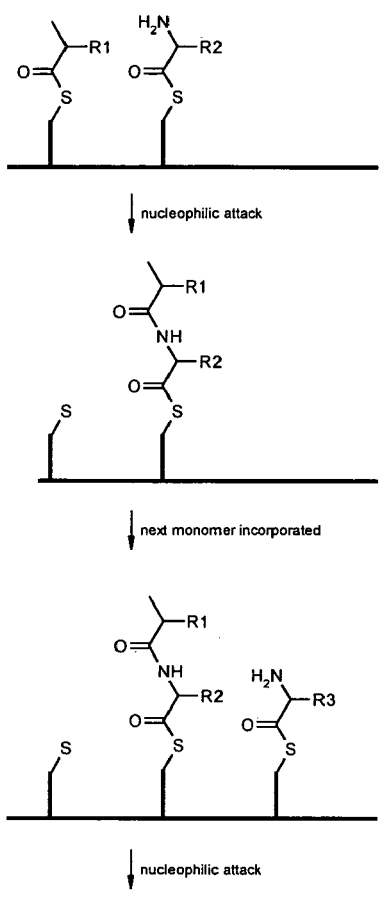
B.
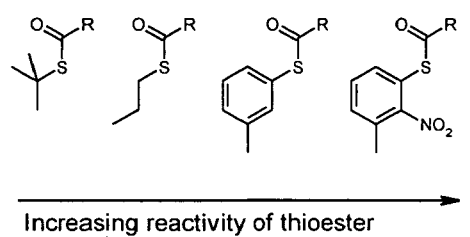
Increasing reactivity of thioester Figur 14, example 2. Polyamine formation and activation
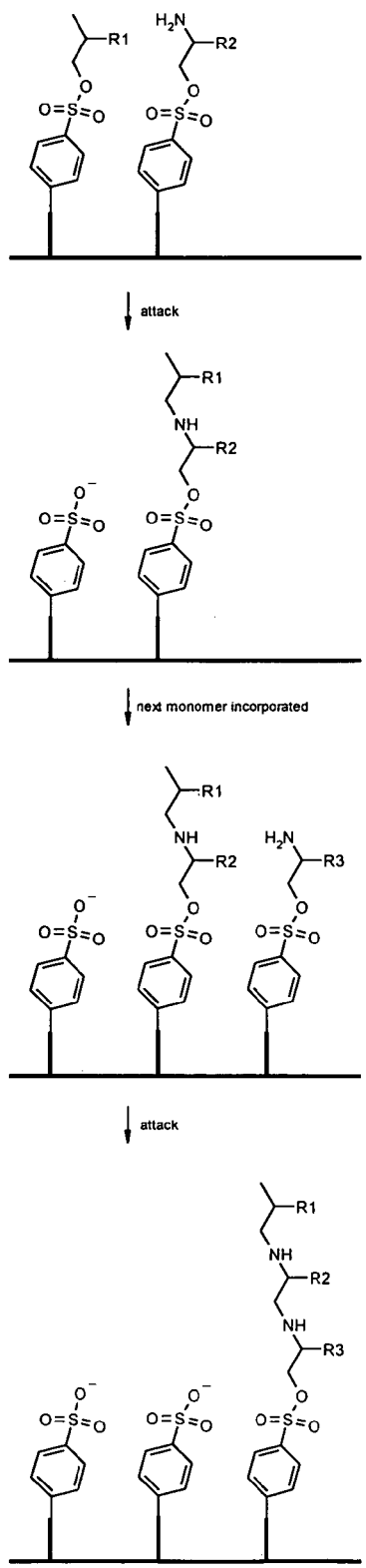

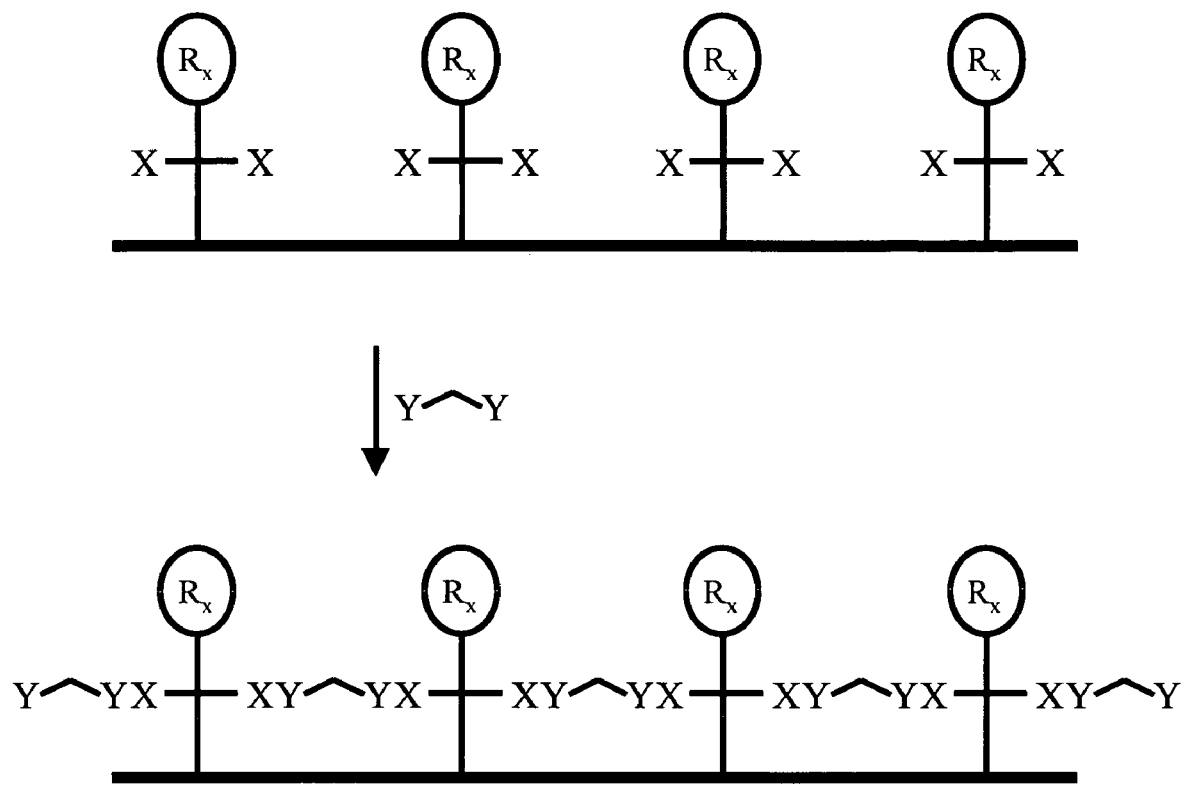
Figure 15. "Fill-in" polymerization (symmetric XX monomers).

Figure 15, example 1. Poly-imine formation by fill-in polymerization.
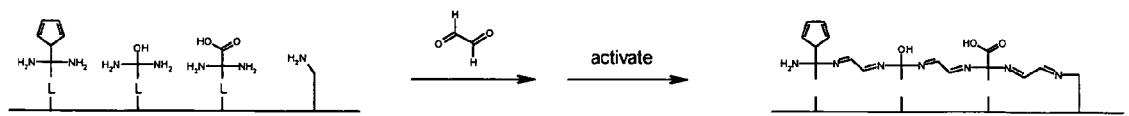

Figure 15, example 2. Polyamide formation.
A.
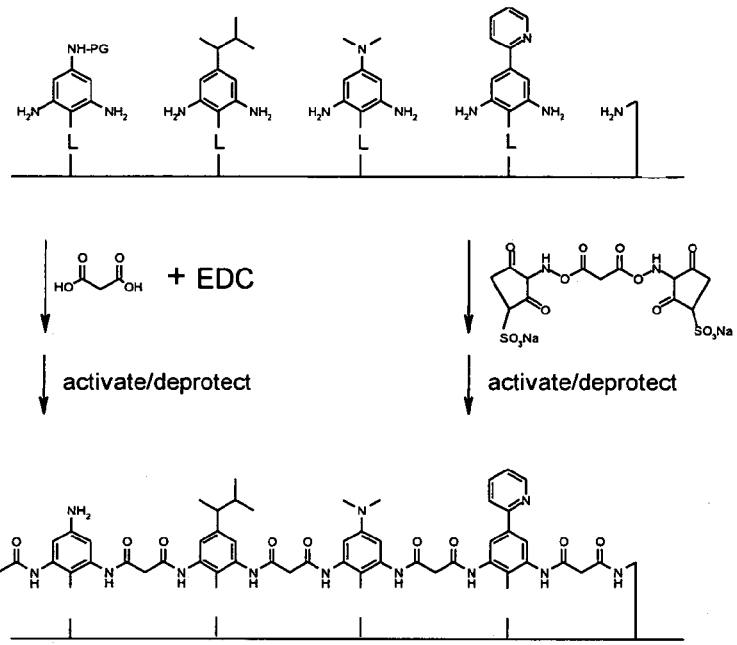
B.
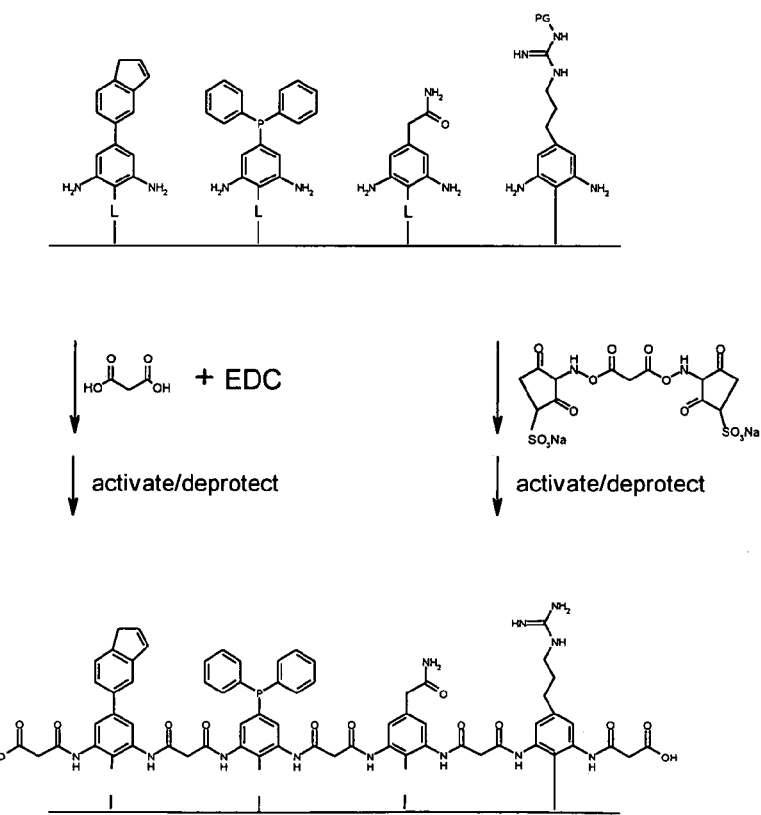

Figure 15, xample 3. Polyurea formation
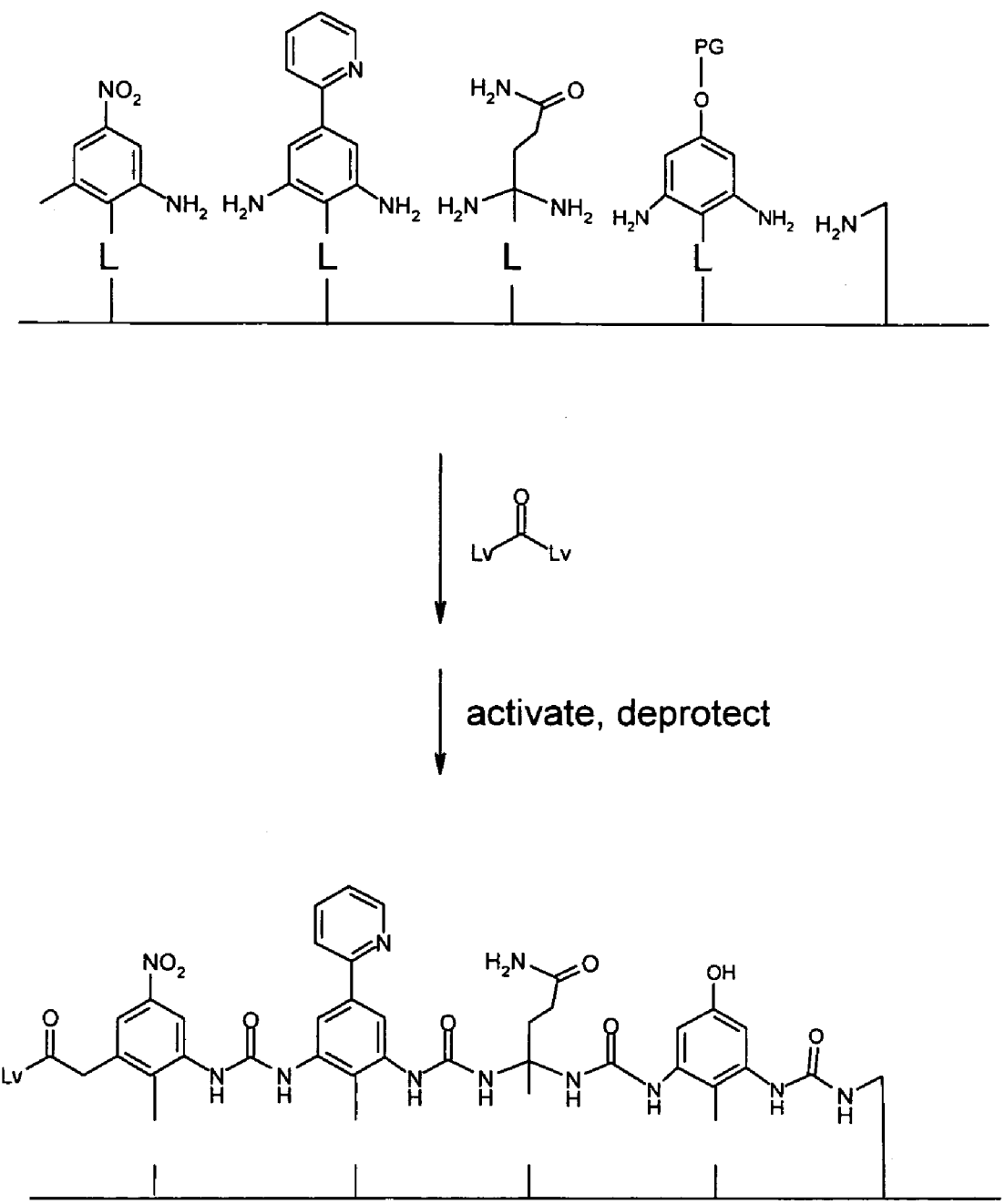

Figure 15, example 4. Chiral and achiral polyamide backbone formation
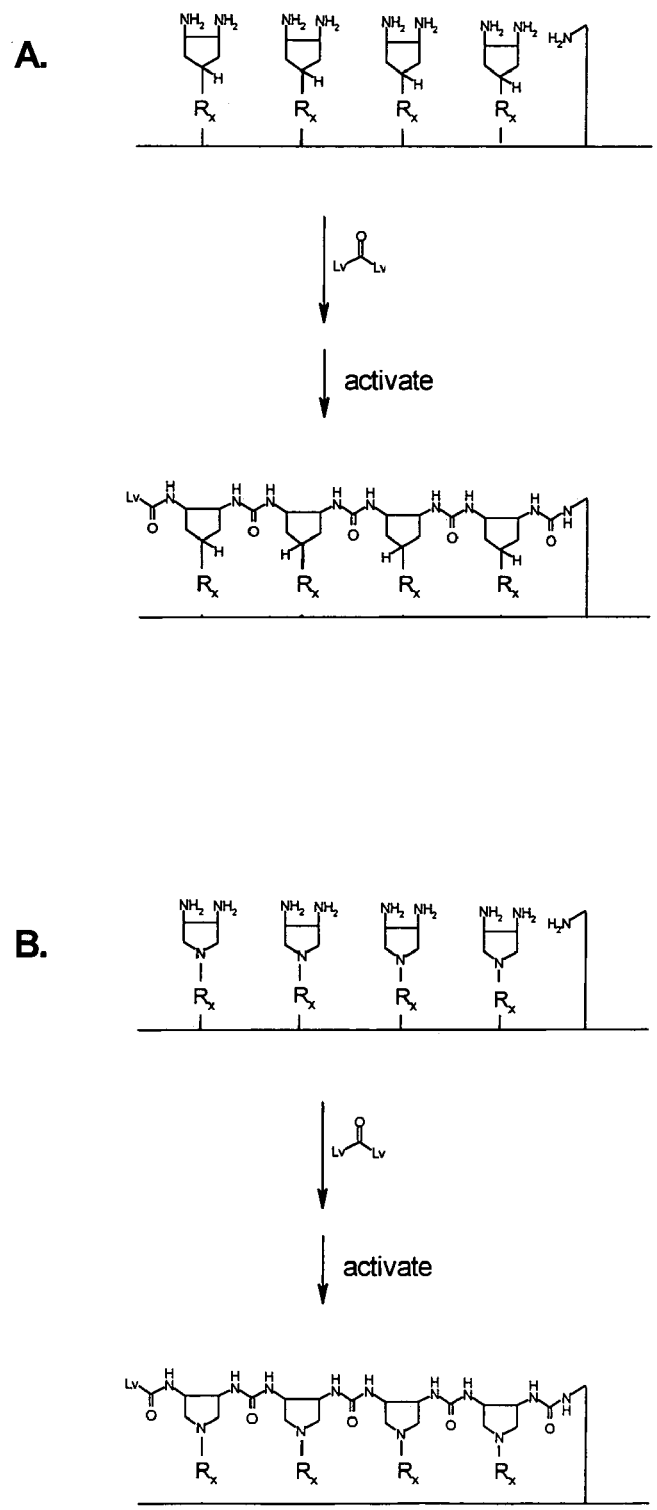

Figure 15, example 5. Polyphosphodiester formation.
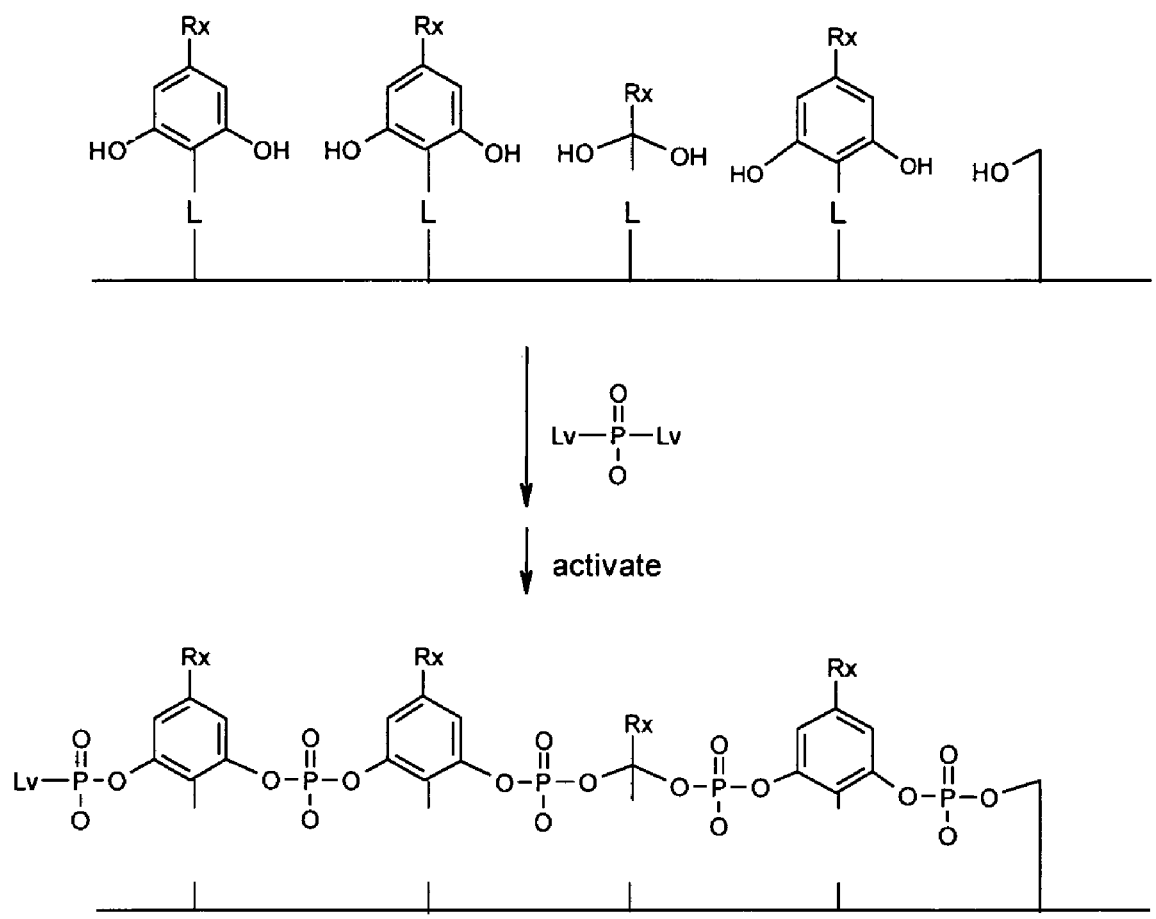

Figure 15, example 6. Polyphosphodiester formation with one reactive group in each monomer building
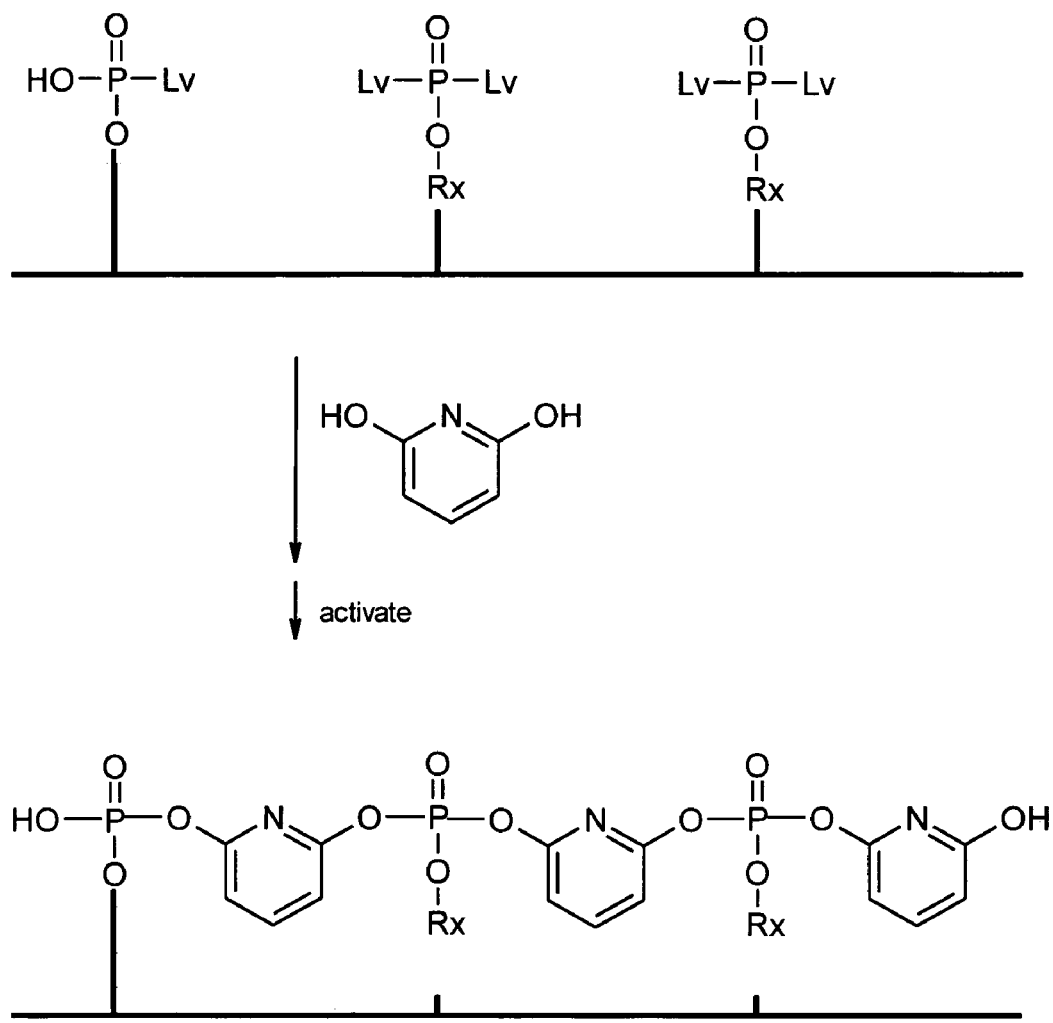

Figure 15, example 7. Pericyclic, "fill-in" polymerization.
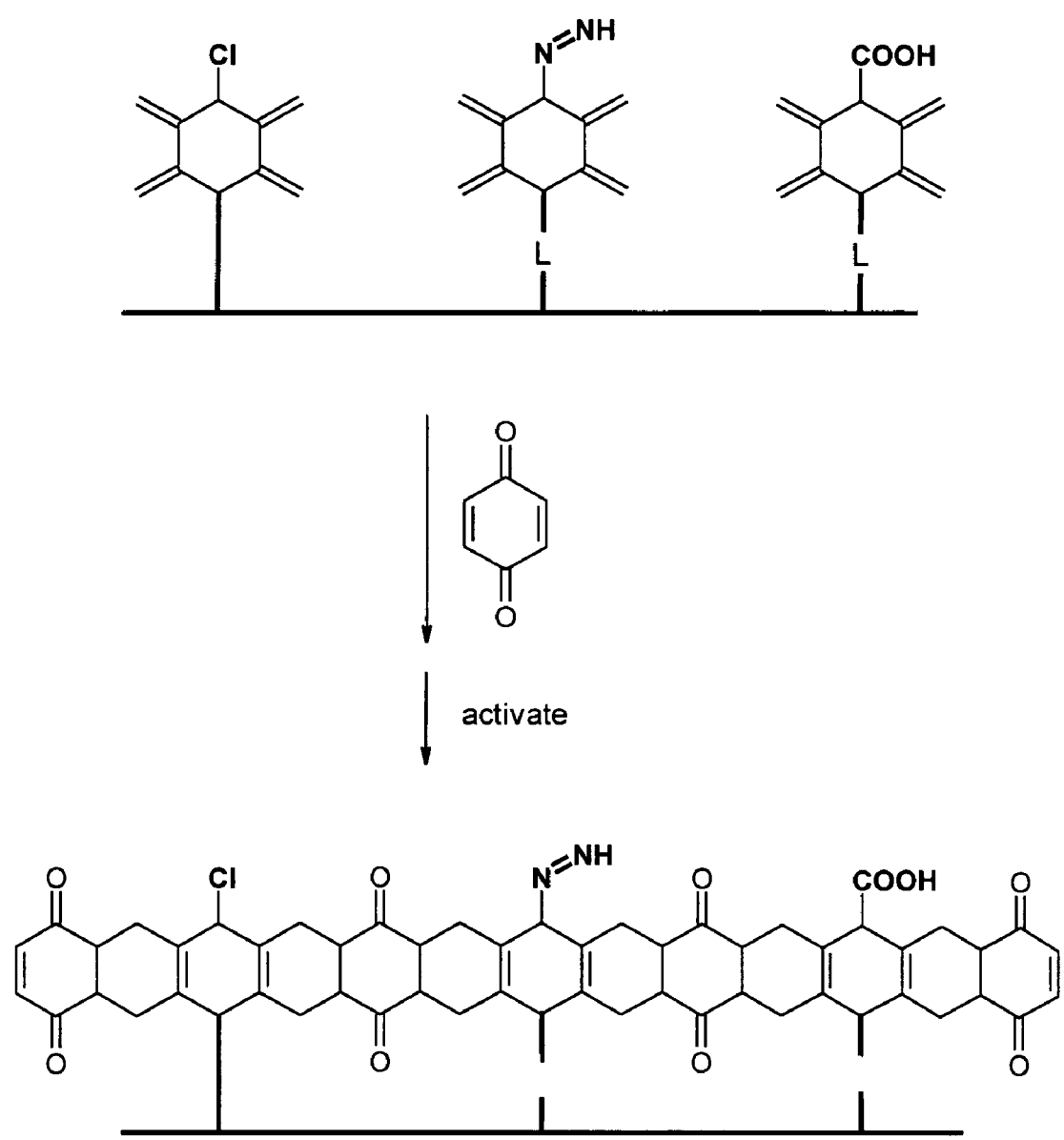

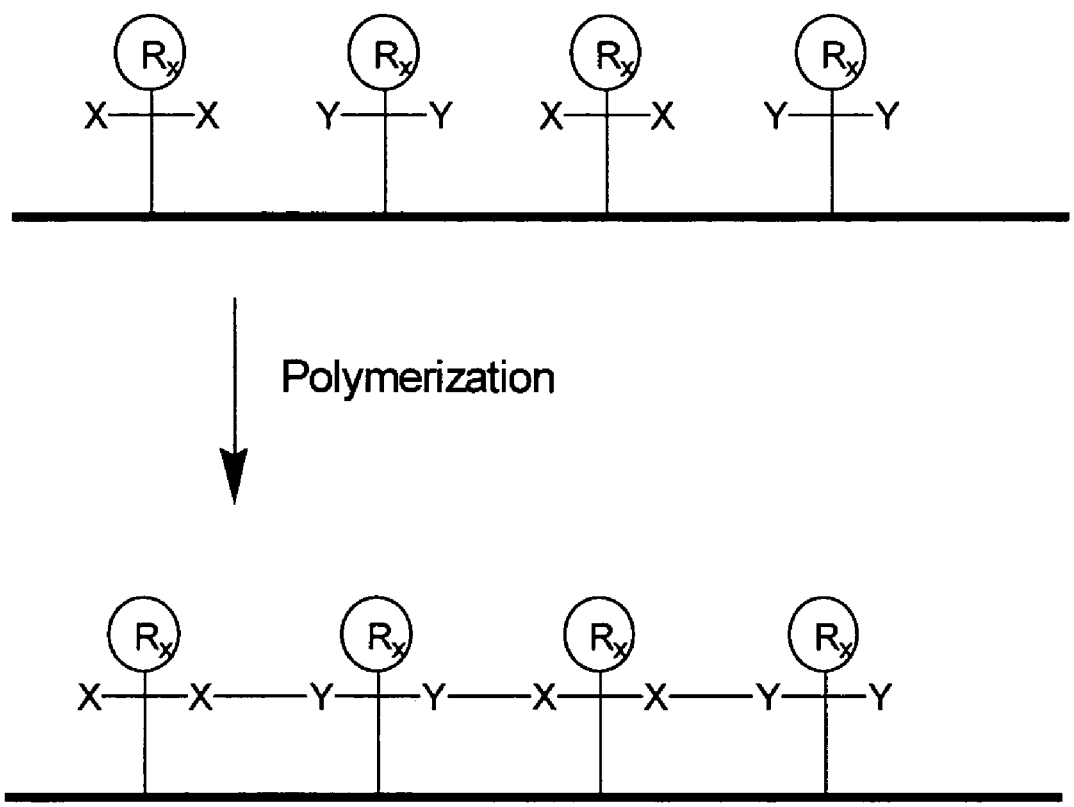
Figure 16. Encoded fill-in

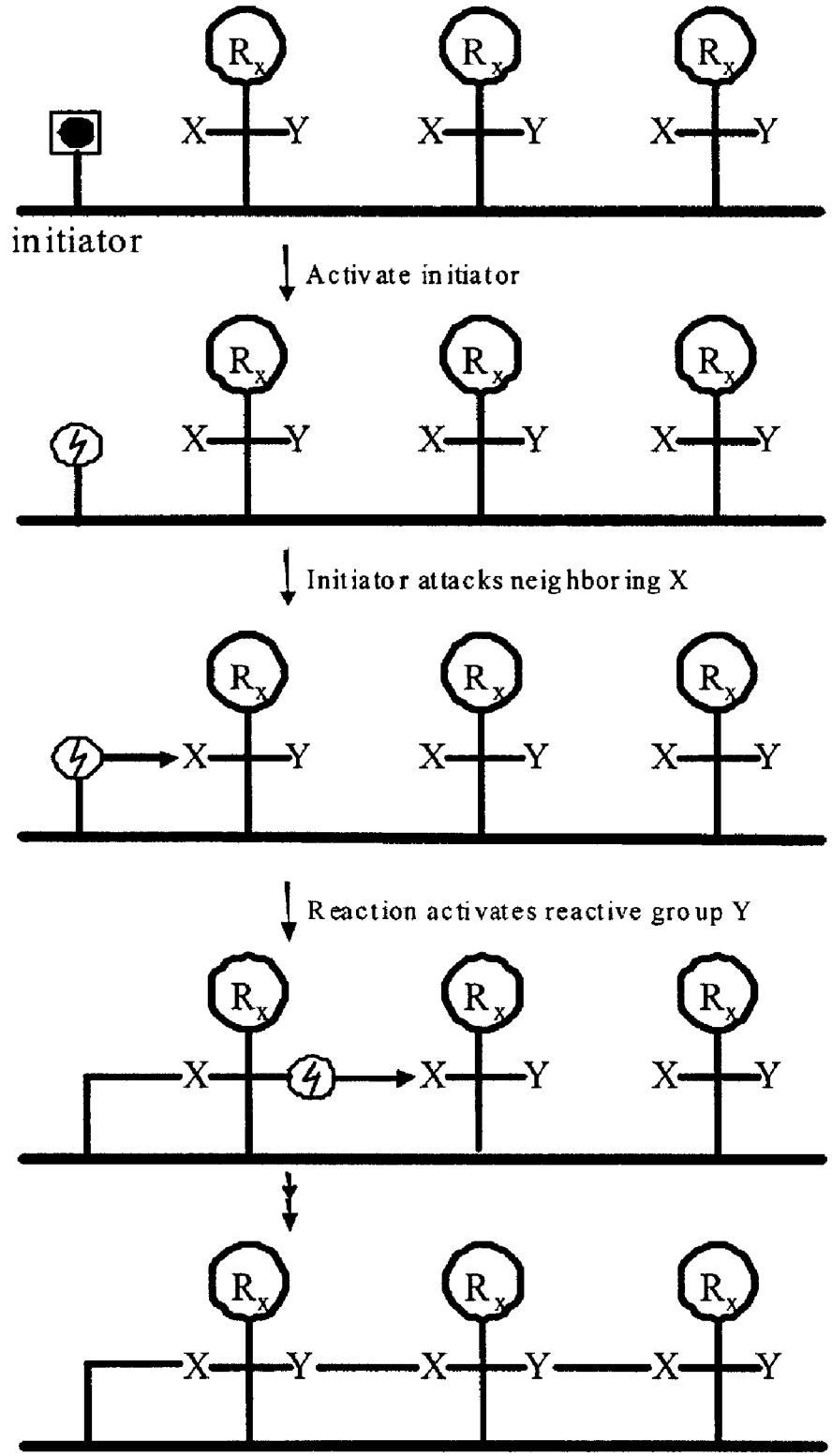
Figure 18A: "Zipping" polymerization.

Figure 18B: example 1. Radical polymerization
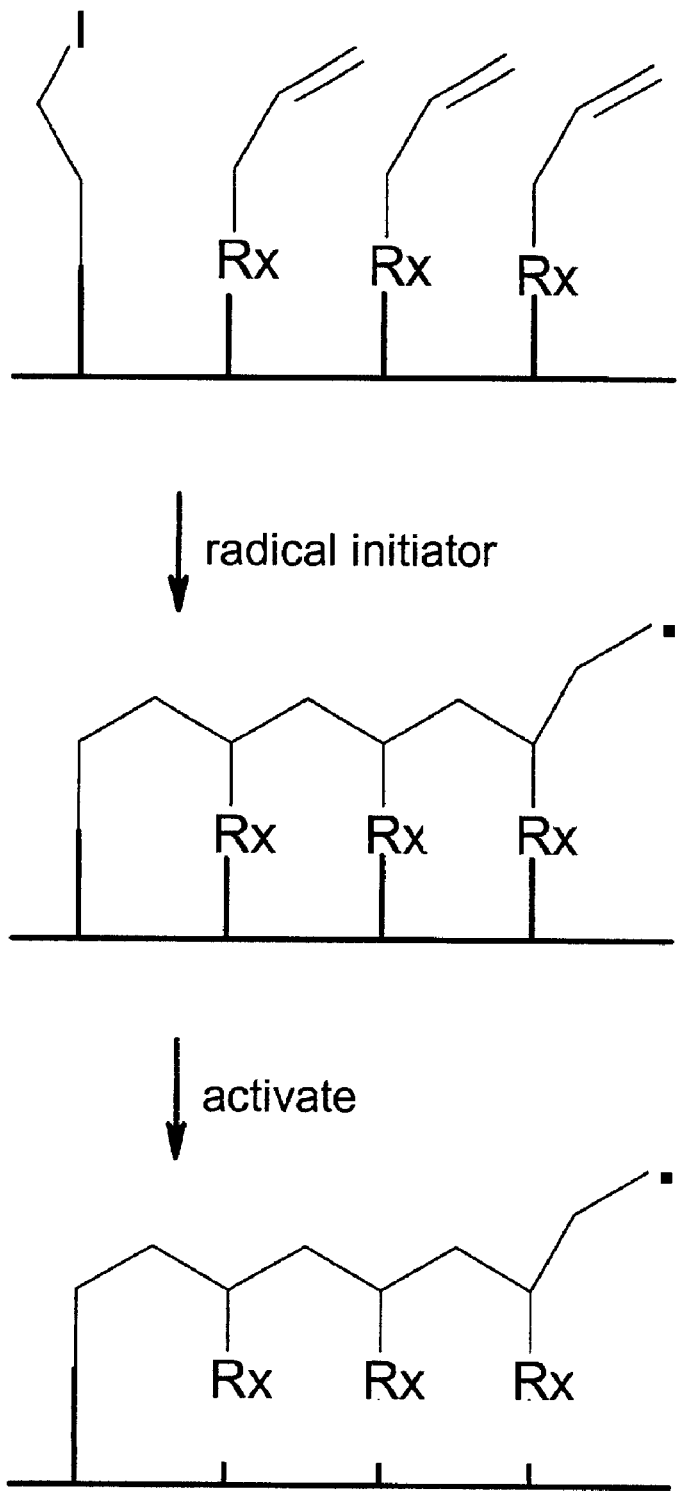

Figure 18C: example 2. Cationic polymerization
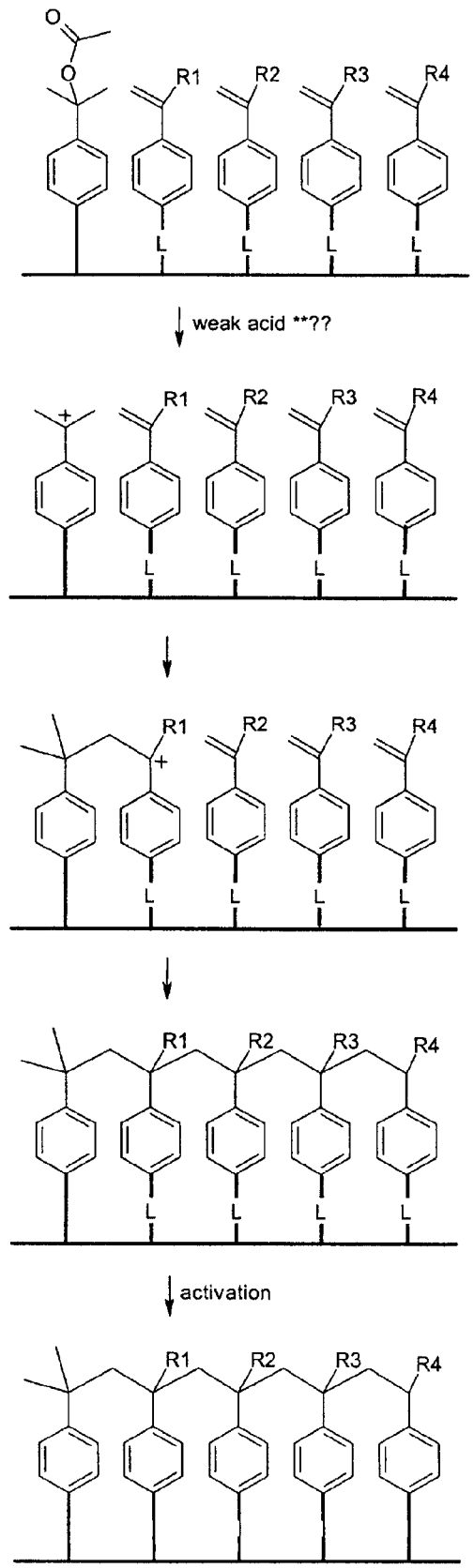

FIG. 19C
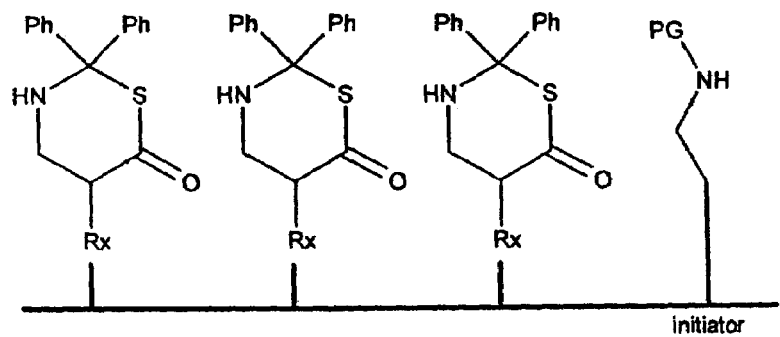
deprotect nucleophile
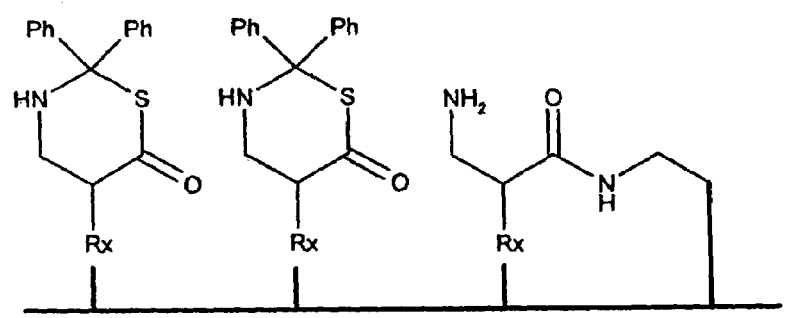
activate
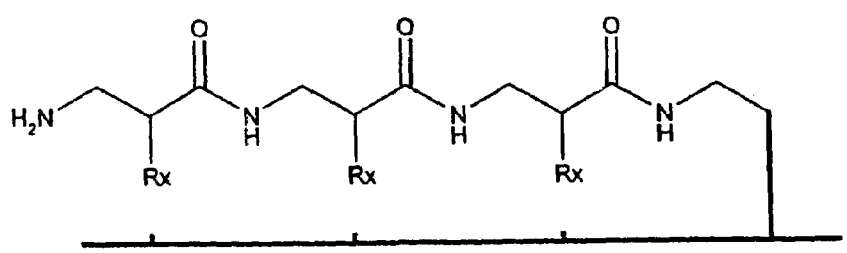

Figure 20. Zipping-polymerization and activation by rearrangement.
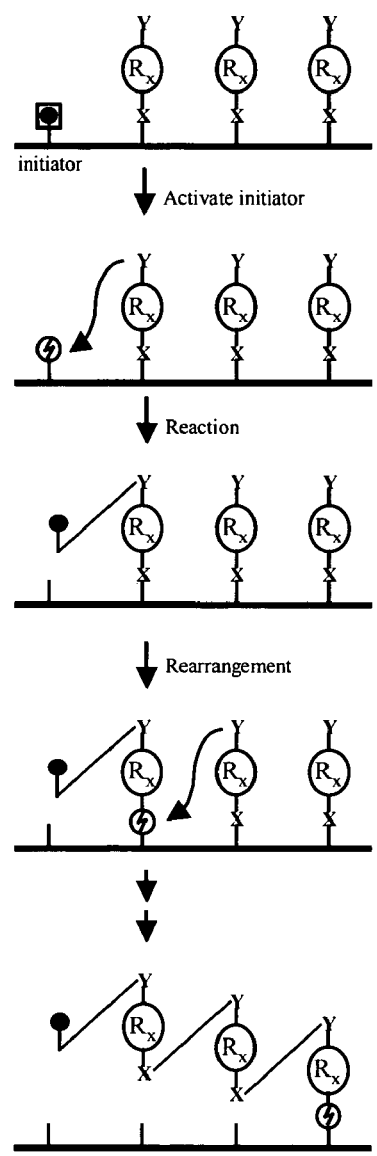

Figure 21. Zipping-polymerization and activation by ring opening.
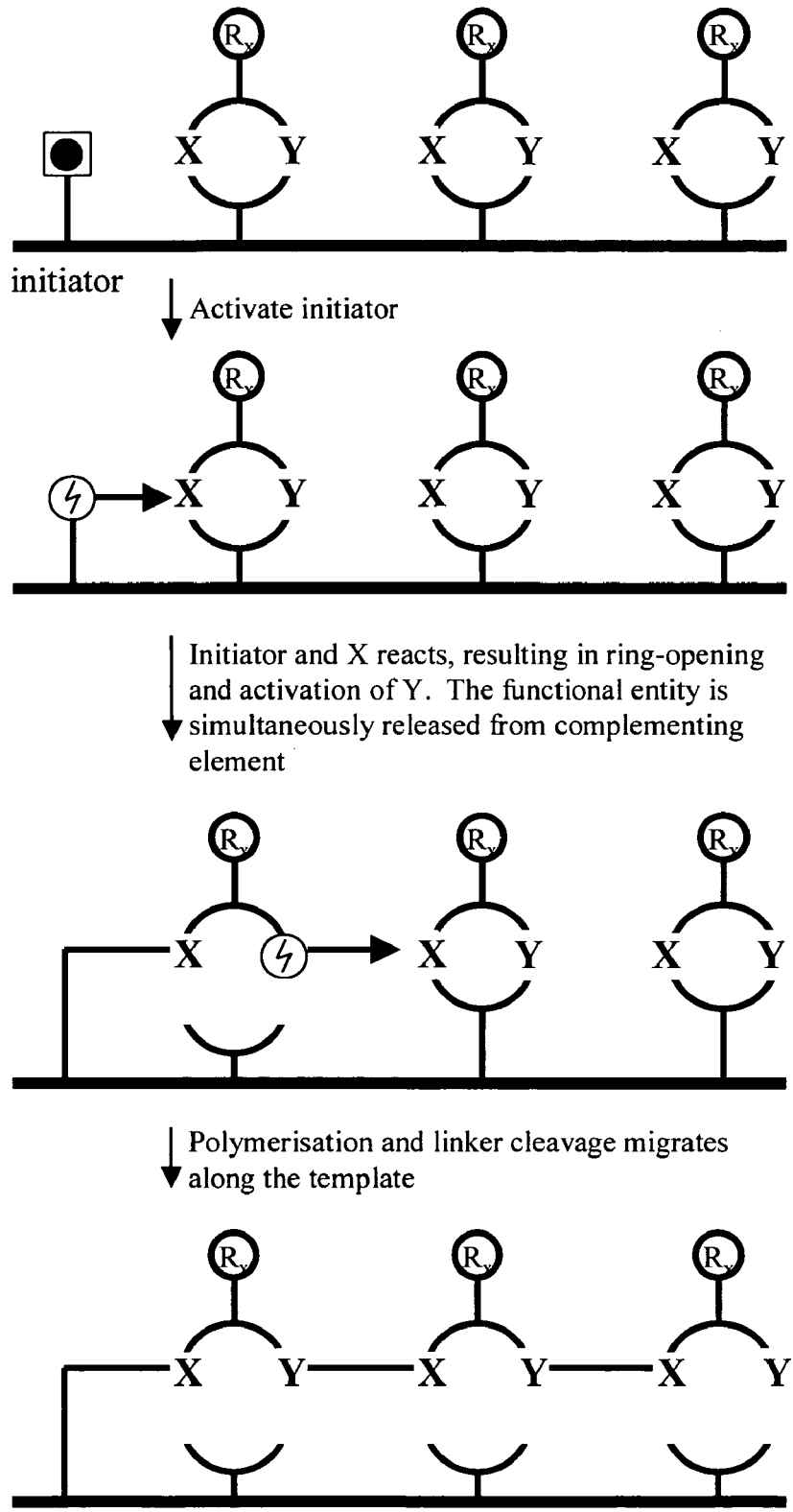

Figure 22. Directional polymer formation using fixed functional units.
A.
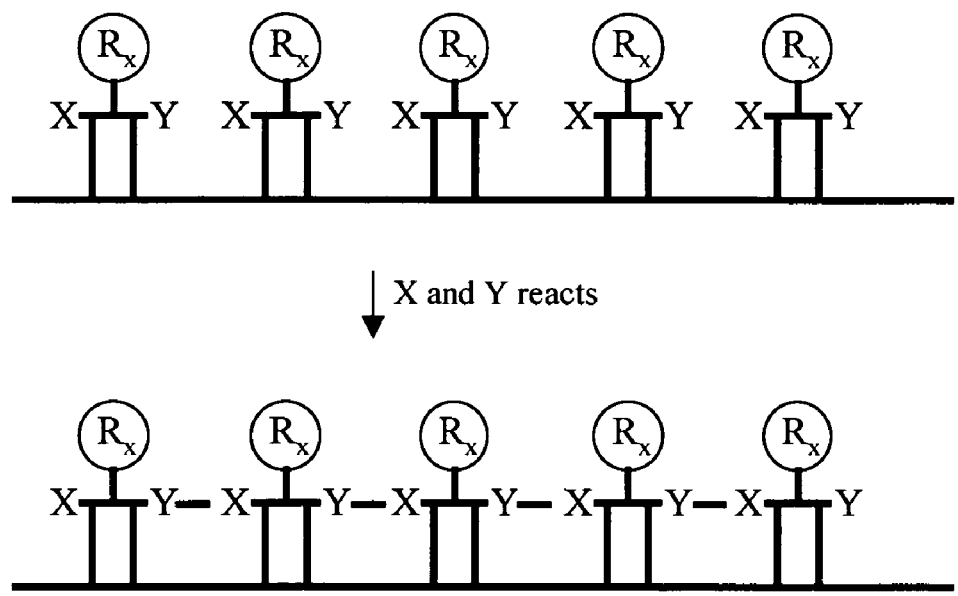
B.
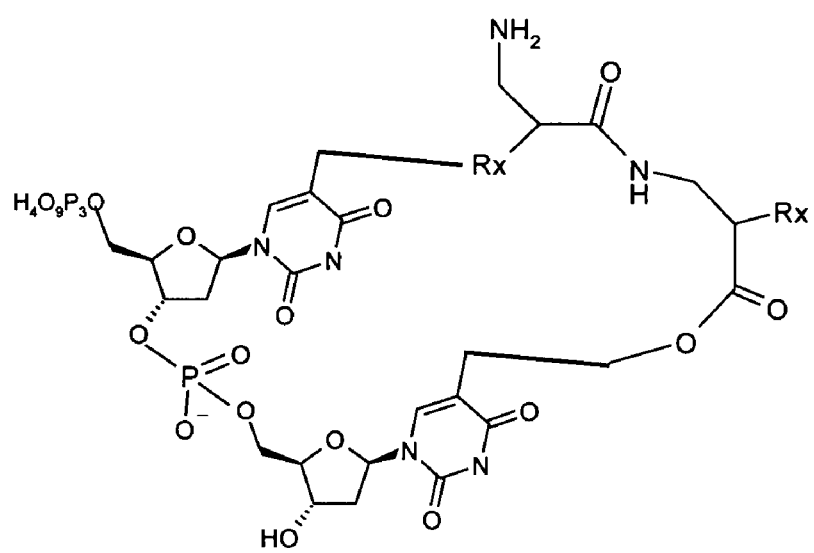

Figure 24.
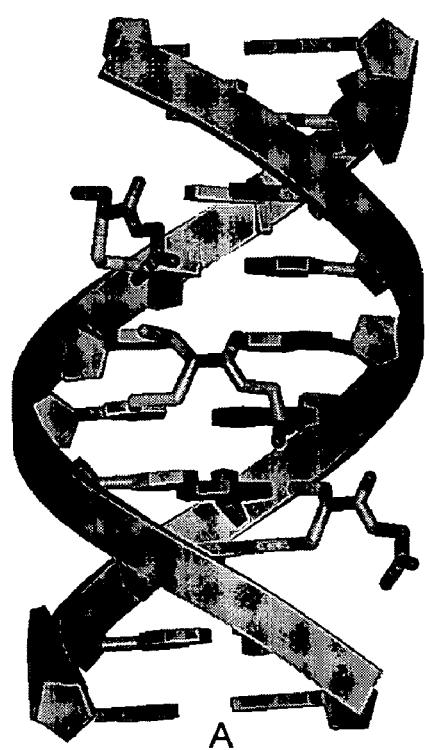
A
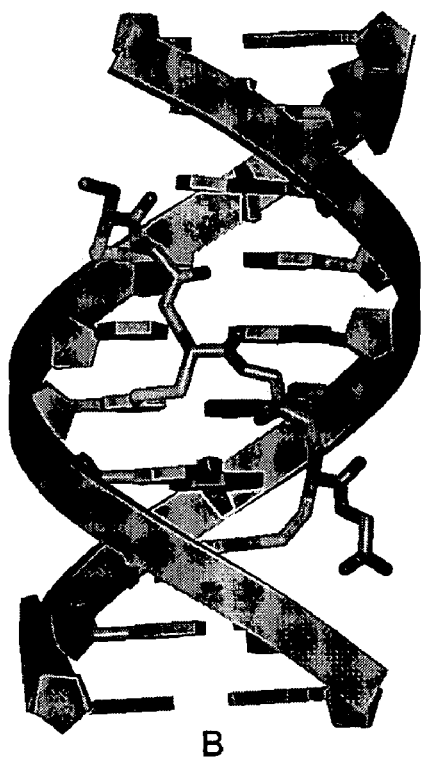
B
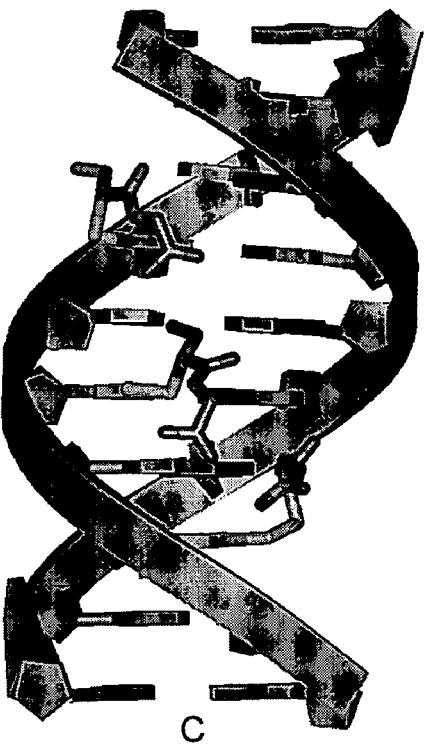
C
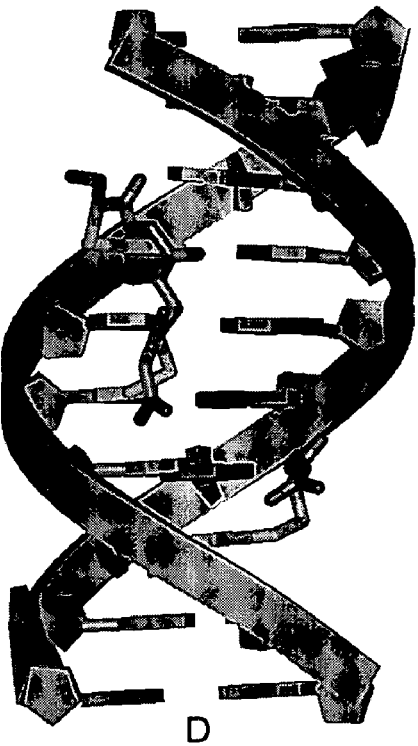
D

Figure 24. Cont.
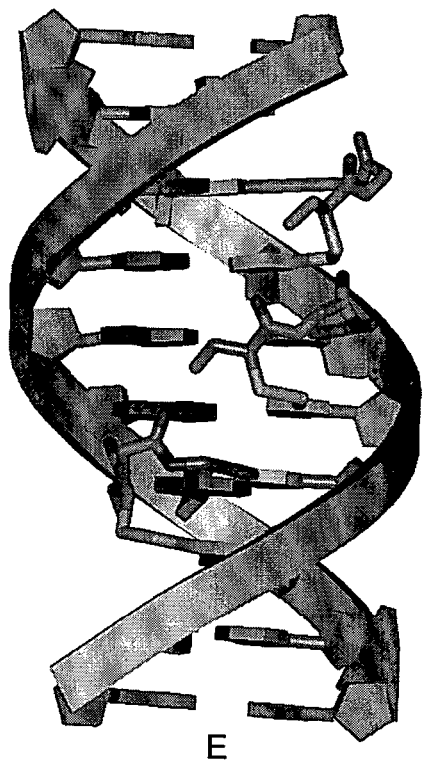
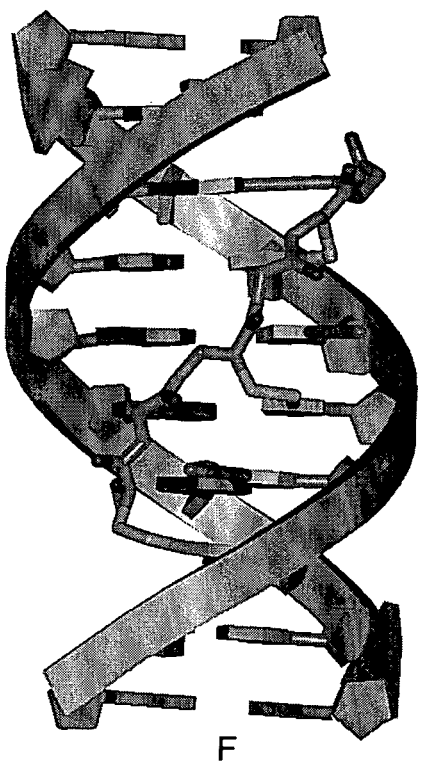
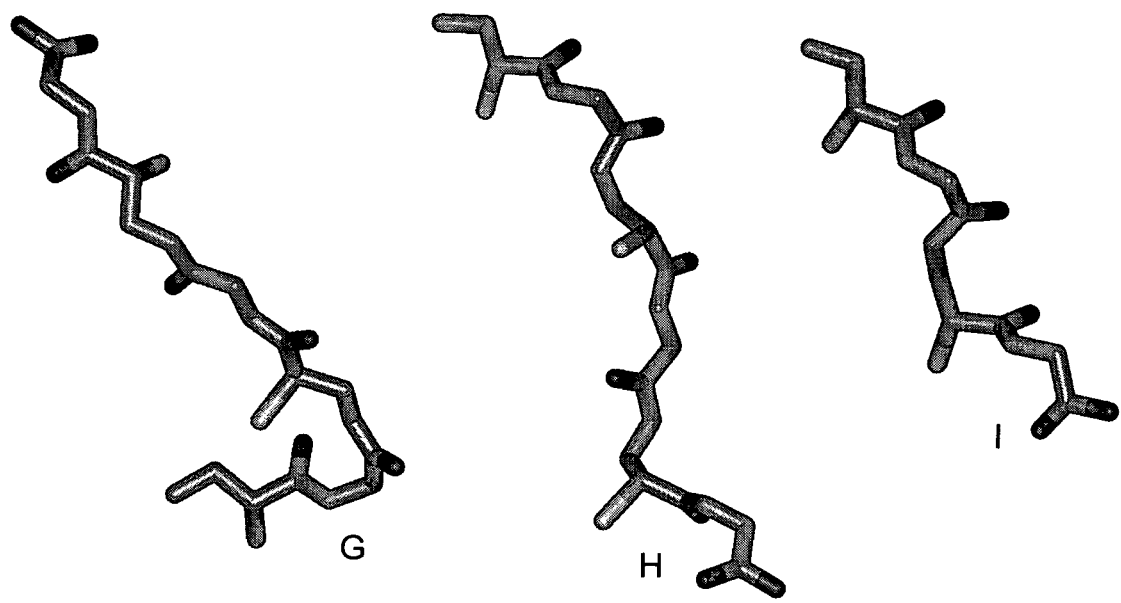

Figure 25.
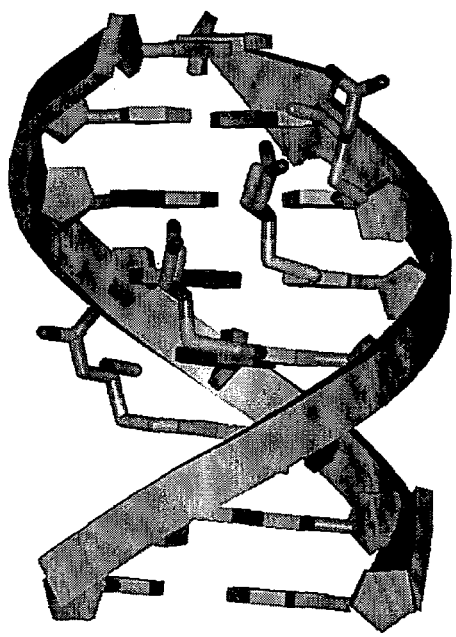
A
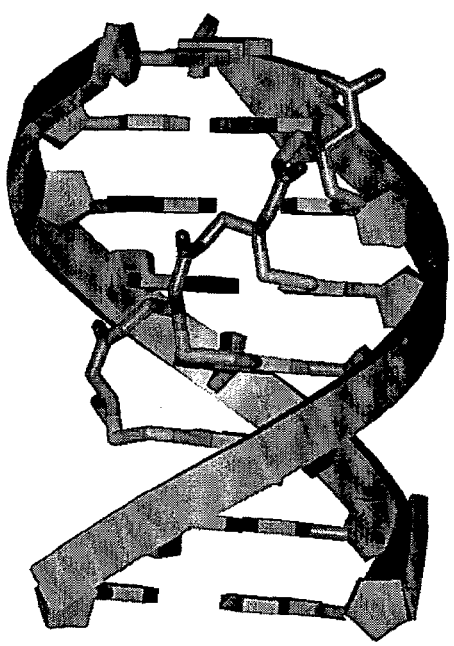
B
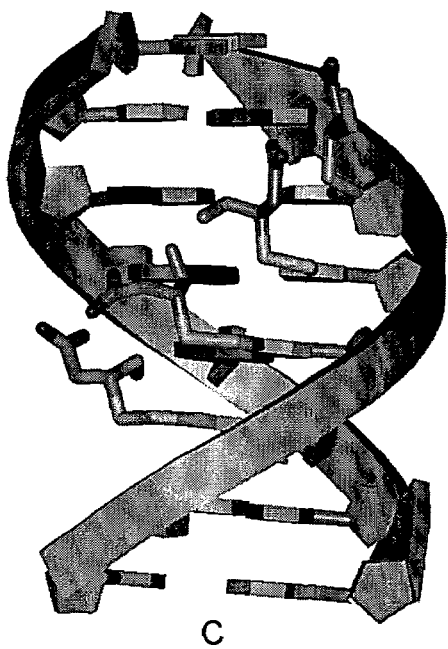
C
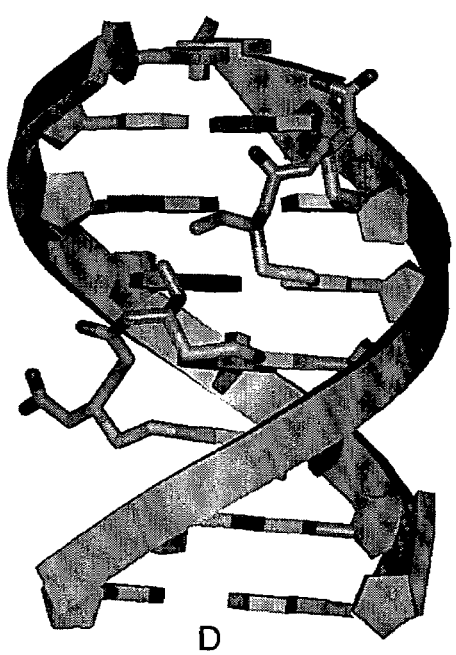
D

Figure 25. Cont.
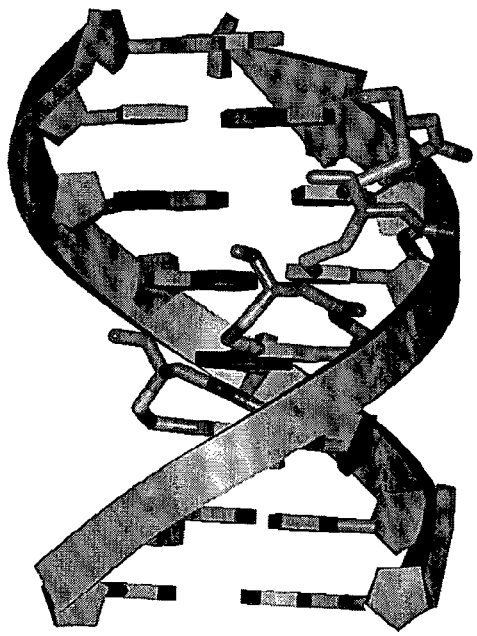
E
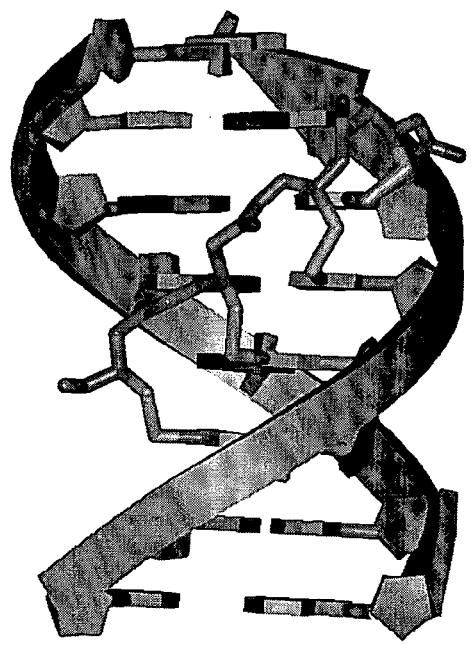
F
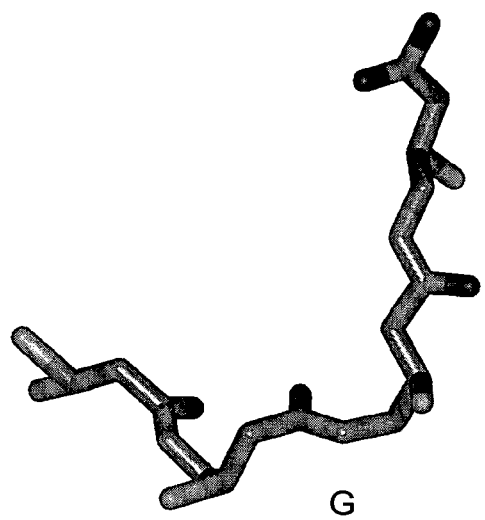
G
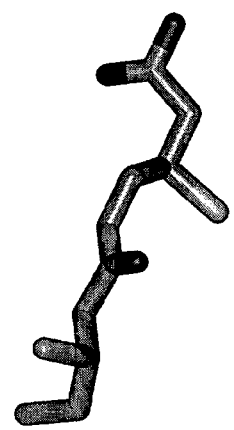
H

Figure 26. Chemical Display – principle.
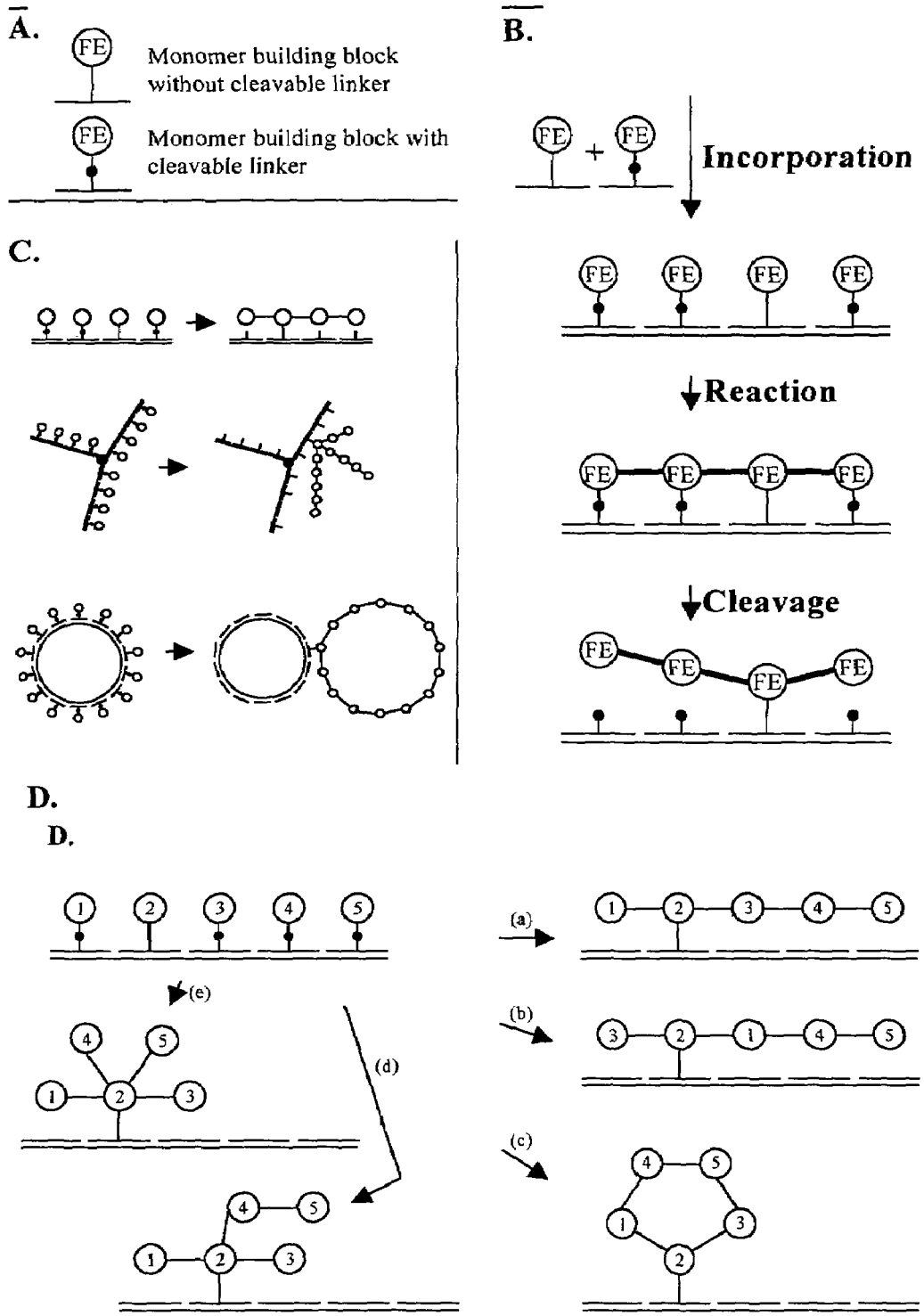

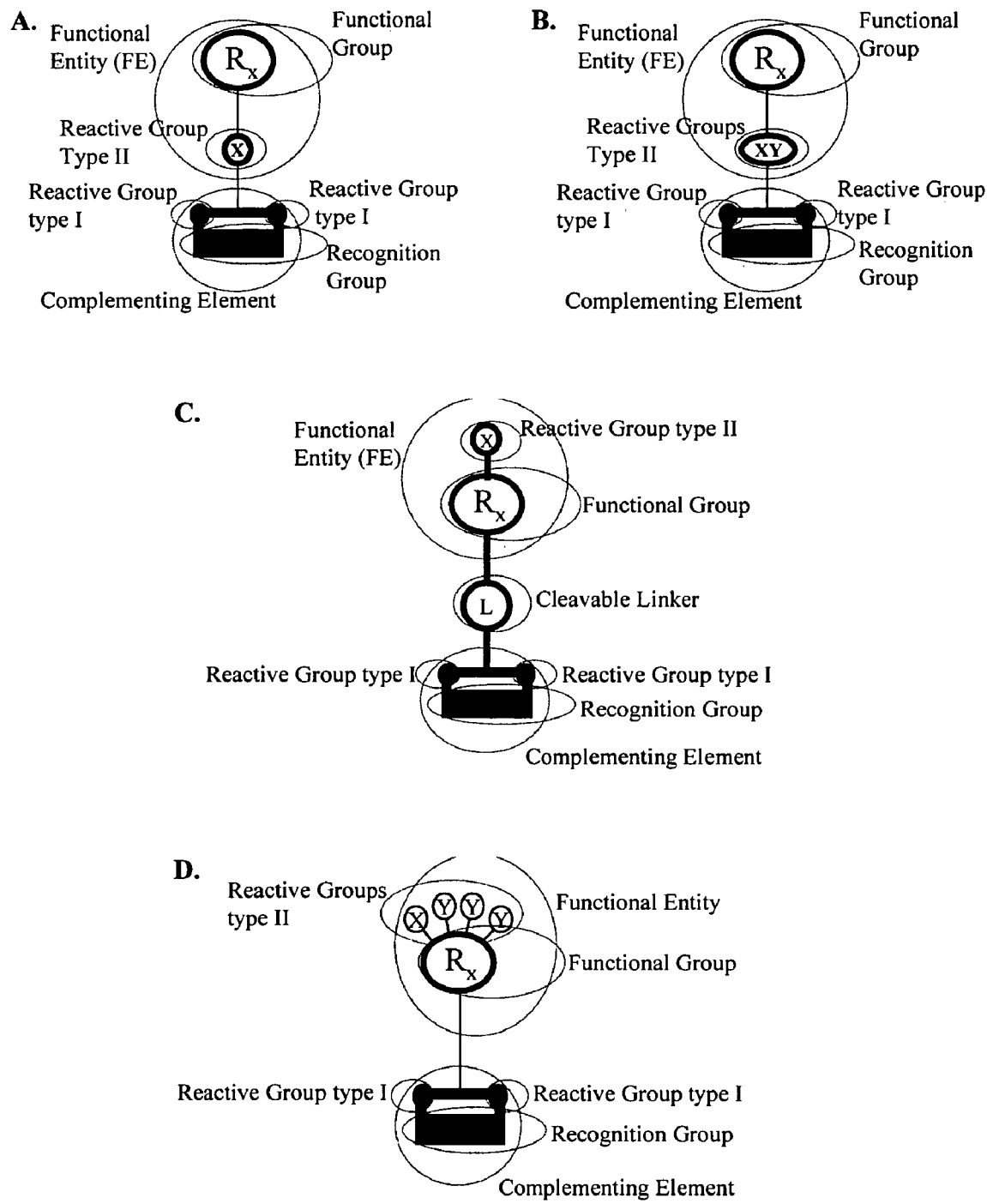
Figure 28. Monomer building blocks.

Figure 29. Templating involving simultaneous reaction and activation.
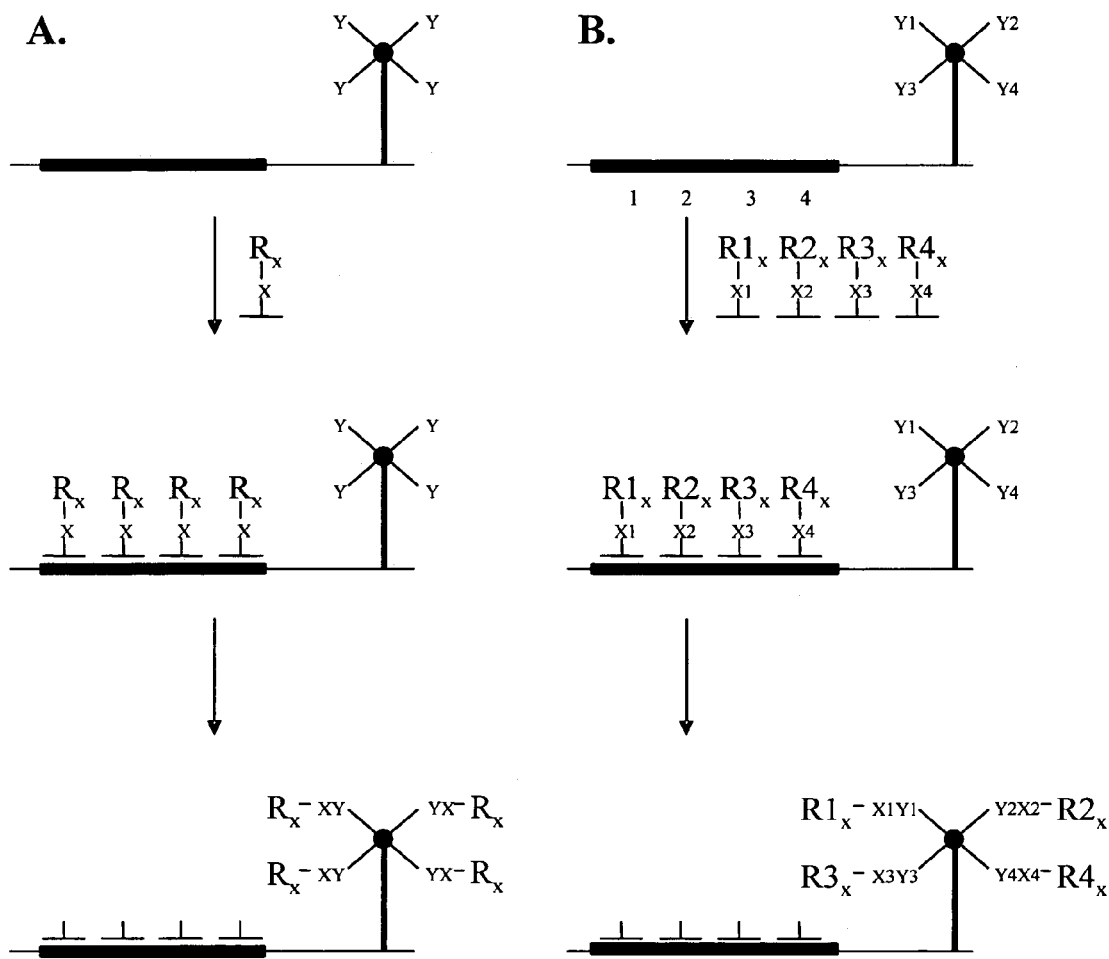

Fig 30. Reaction types allowing simultaneous reaction and activation.

Nucleophilic substitution using activation of electrophiles

Fig. 30A. Acylating monomer building blocks - principle

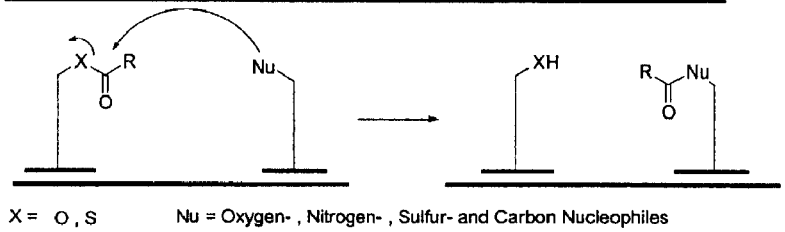

X = O, S        Nu = Oxygen- , Nitrogen- , Sulfur- and Carbon Nucleophiles

Fig. 30B. Acylation
Amide formation by reaction of amines with activated esters

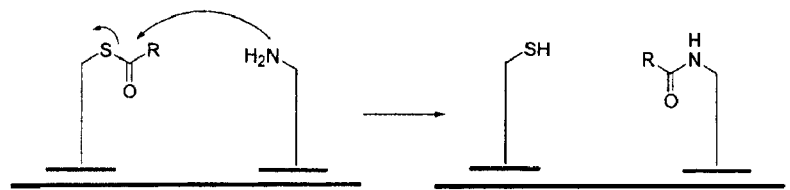

Fig. 30C. Acylation
Pyrazolone formation by reaction of hydrazines with β–Ketoesters

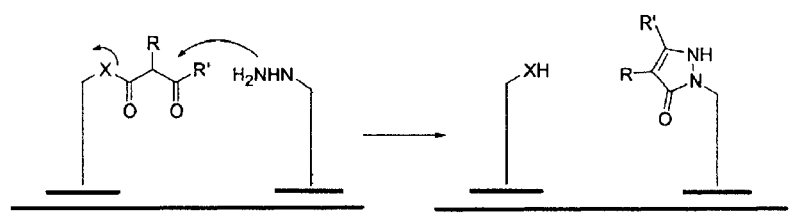

Fig. 30D. Acylation
Isoxazolone formation by reaction of hydroxylamines with β–Ketoesters

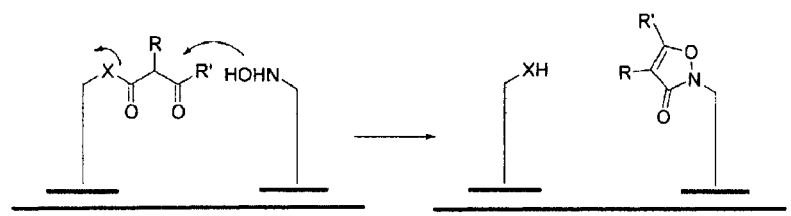

Figure 30, continued

Fig. 30E. Acylation
Pyrimidine formation by reaction of thioureas with β-Ketoesters

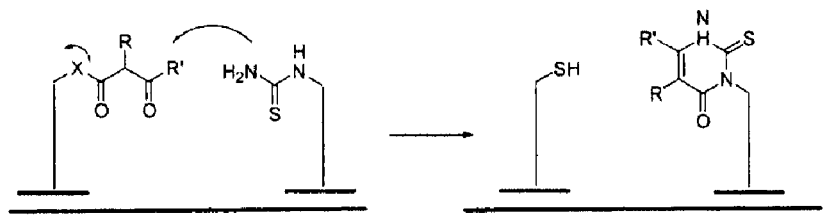

Fig. 30F. Acylation
Pyrimidine formation by reaction of ureas with Malonates

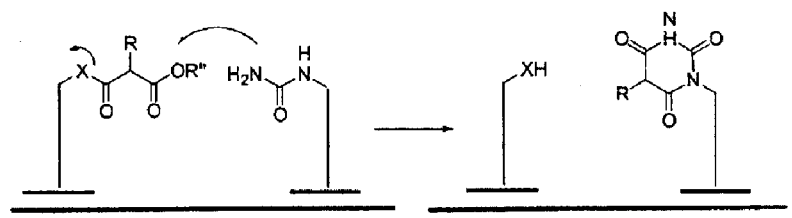

Fig. 30G. Acylation
Coumarine or quinolinone formation by a Heck reaction followed by a nucleophilic substitution

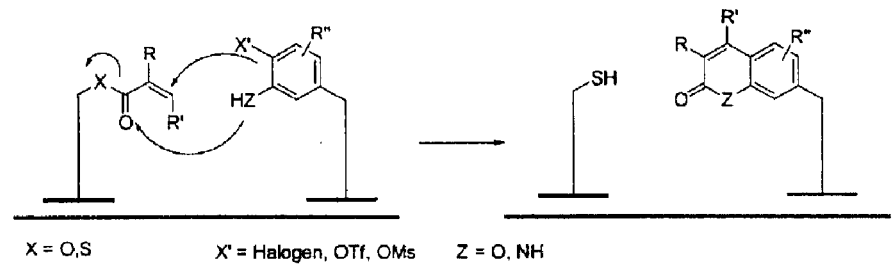

X = O,S     X' = Halogen, OTf, OMs     Z = O, NH

Fig. 30H. Acylation
Phthalhydrazide formation by reaction of Hydrazines and Phthalimides

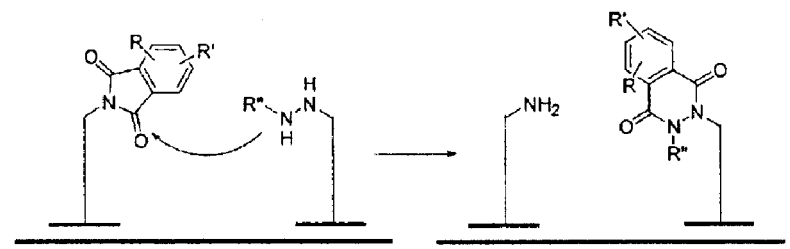

Figure 30, continued

Fig. 30I. Acylation
Diketopiperazine formation by reaction of Amino Acid Esters

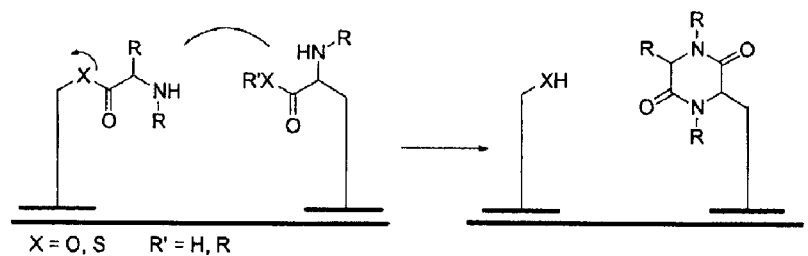

X = O, S    R' = H, R

Fig. 30J. Acylation
Hydantoin formation by reaction of Urea and α-substituted Esters

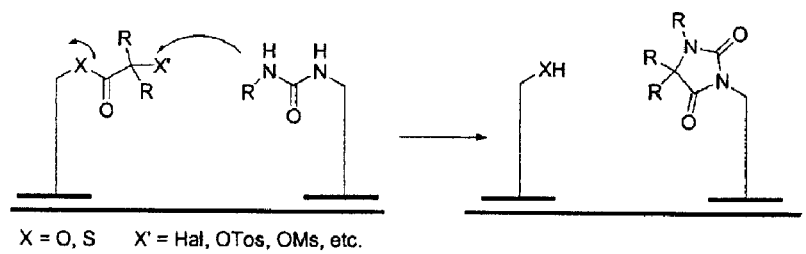

X = O, S    X' = Hal, OTos, OMs, etc.

Fig. 30K. Alkylating monomer building blocks - principle
Alkylated compounds by reaction of Sulfonates with Nucleofiles

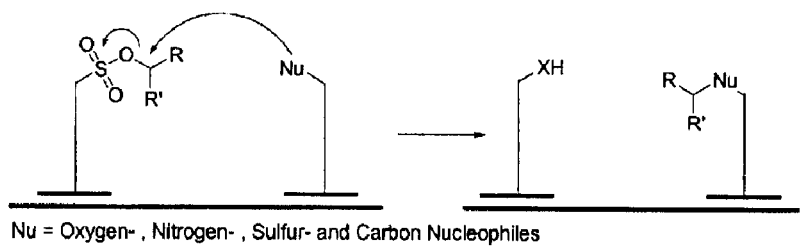

Nu = Oxygen-, Nitrogen-, Sulfur- and Carbon Nucleophiles

Fig. 30L. Vinylating monomer building blocks - principle

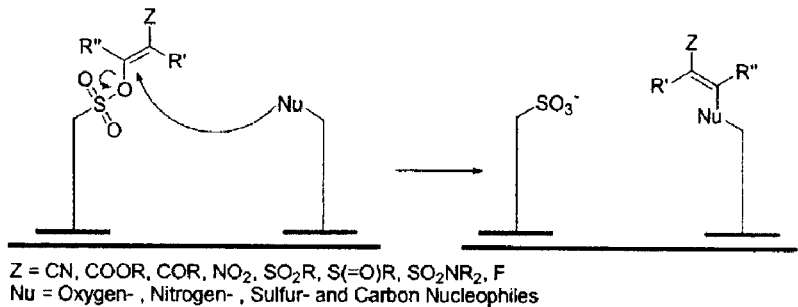

Z = CN, COOR, COR, $NO_2$, $SO_2R$, $S(=O)R$, $SO_2NR_2$, F
Nu = Oxygen-, Nitrogen-, Sulfur- and Carbon Nucleophiles

Figure 30, continued

Fig. 30M. Heteroatom electrophiles
Disulfide formation by reaction of Pyridyl disulfide with Mercaptanes

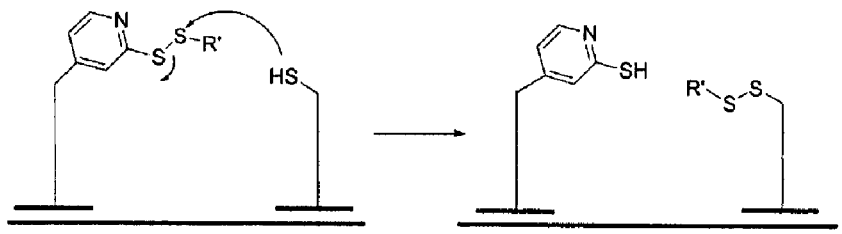

Fig. 30N. Acylation
Benzodiazepinone formation by reaction of Amino Acid Esters and Amino Ketones

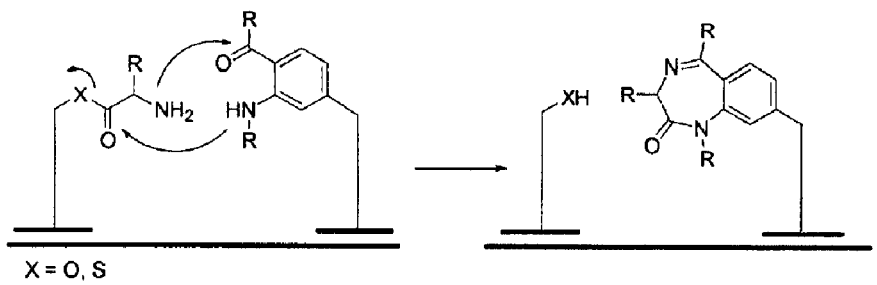

Addition to carbon-hetero multiple bonds

Fig. 30O. Wittig/Horner-Wittig-Emmons reagents
Substituted alkene formation by reaction of Phosphonates with Aldehydes or Ketones

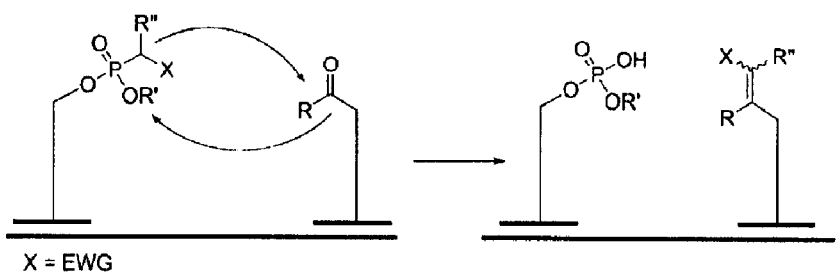

Figure 30, continued
Transition metal catalysed reactions

Fig. 30P. Arylation
Biaryl formation by the reaction of Boronates with Aryls or Heteroaryls

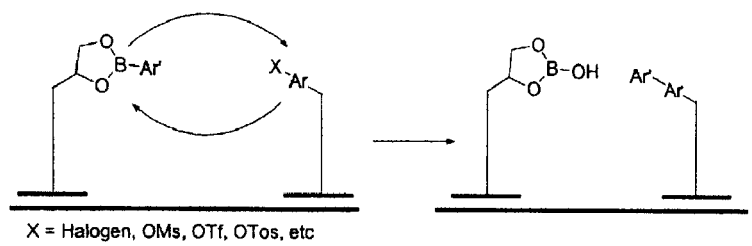

X = Halogen, OMs, OTf, OTos, etc

Fig. 30Q. Arylation
Biaryl formation by the reaction of Boronates with Aryls or Heteroaryls

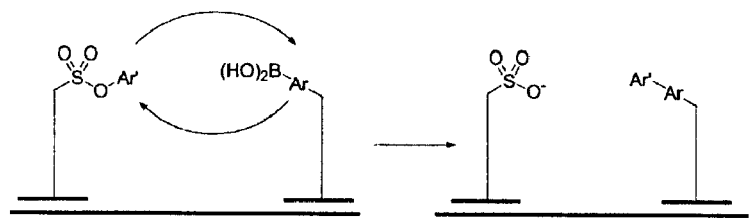

Fig. 30R. Arylation
Vinylarene formation by the reaction of alkenes with Aryls or Heteroaryls

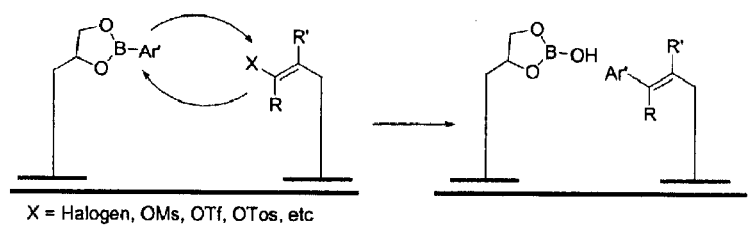

X = Halogen, OMs, OTf, OTos, etc

Figure 30, continued
Fig. 30S. Alkylation
Alkylation of arenes/hetarens by the reaction with Alkyl boronates

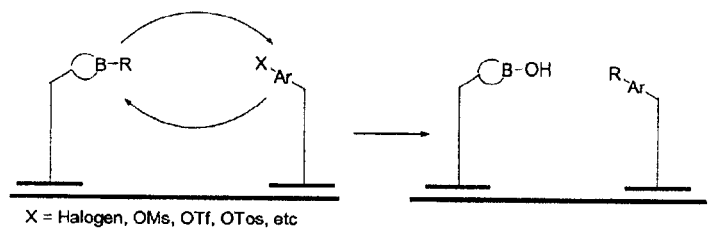

X = Halogen, OMs, OTf, OTos, etc

Fig. 30T. Alkylation
Alkylation of arenas/hetarenes by reaction with enolethers

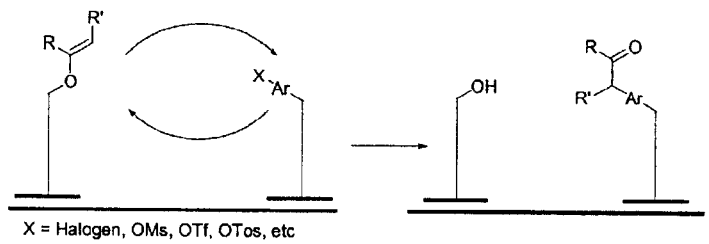

X = Halogen, OMs, OTf, OTos, etc

Nucleophilic substitution using activation of nucleophiles

Fig. 30U. Condensations
Alkylation of aldehydes with enolethers or enamines

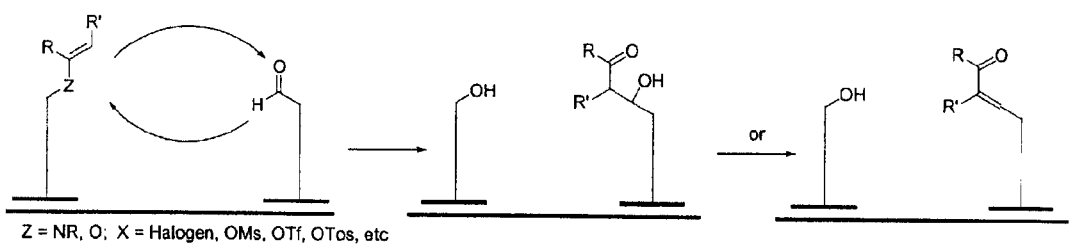

Z = NR, O; X = Halogen, OMs, OTf, OTos, etc

Figure 30, continued
Fig. 30V. Alkylation
Alkylation of aliphatic halides or tosylates with enolethers or enamines
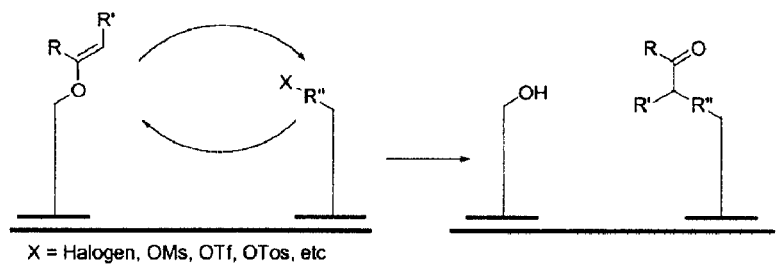
X = Halogen, OMs, OTf, OTos, etc
Cycloadditions
Fig. 30W. [2+4] Cycloadditions
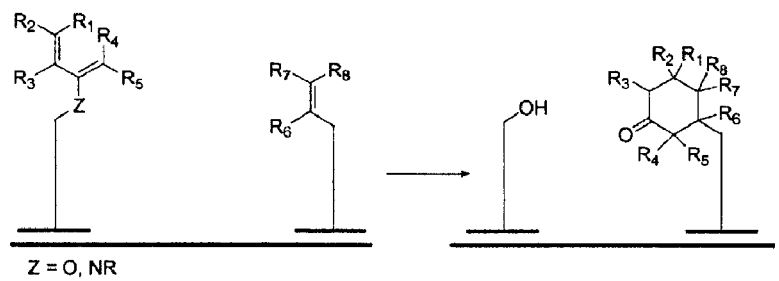
Z = O, NR
Fig. 30X. [2+4] Cycloadditions
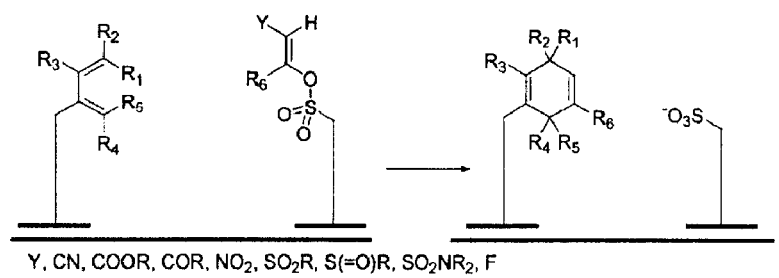
Y, CN, COOR, COR, $NO_2$, $SO_2R$, S(=O)R, $SO_2NR_2$, F
Fig. 30Y. [3+2] Cycloadditions
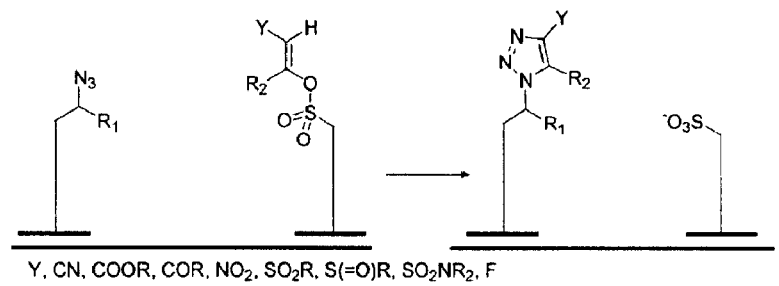
Y, CN, COOR, COR, $NO_2$, $SO_2R$, S(=O)R, $SO_2NR_2$, F Figure 30, continued
Fig. 30Z. [3+2] Cycloadditions
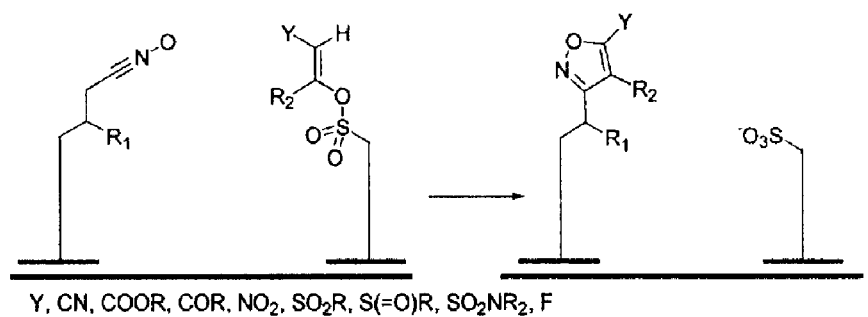
Y, CN, COOR, COR, NO$_2$, SO$_2$R, S(=O)R, SO$_2$NR$_2$, F Figure 31. Templating involving non-simultaneous reaction and activation.

Figure 32. Pairs of reactive groups X,Y and the resulting bond XY.
Fig. 32A: Nucleophilic substitution reaction
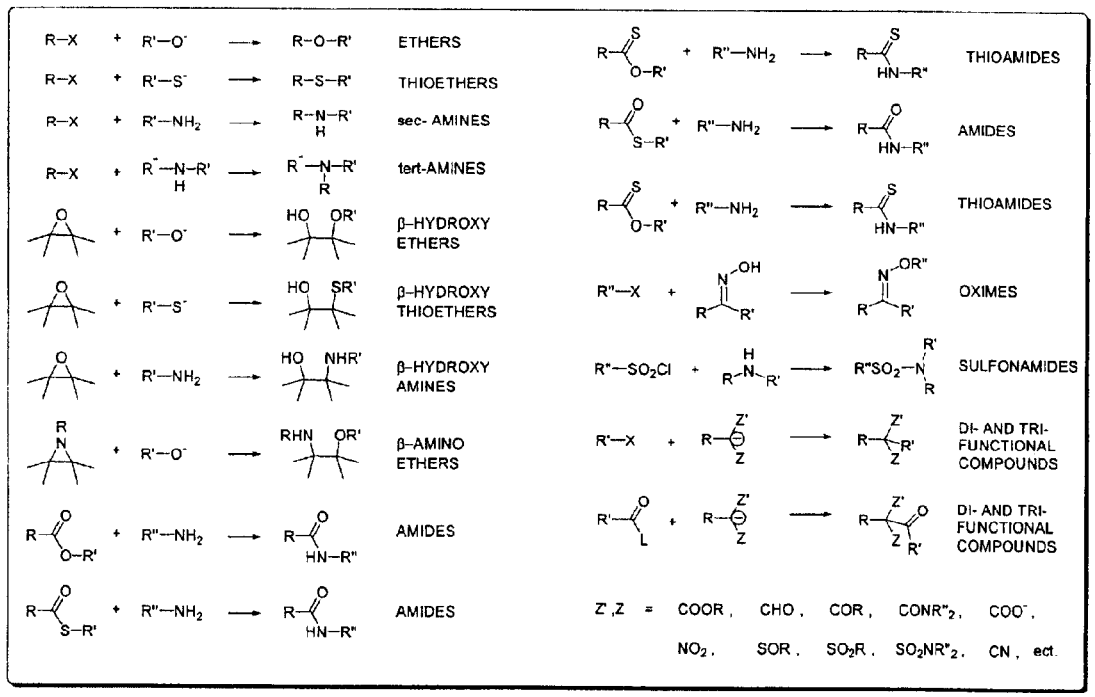
Fig. 32B:
Aromatic nucleophilic substitution
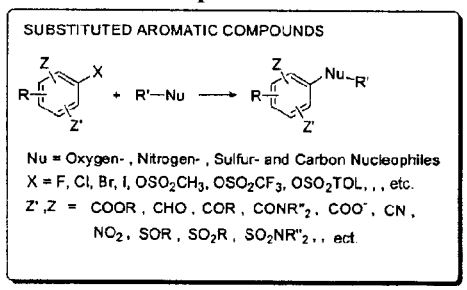
Fig. 32C:
Transition metal catalysed reactions
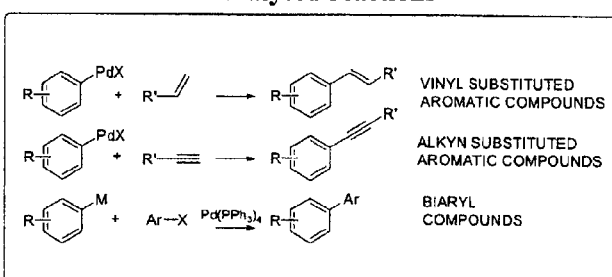

Figure 32, continued
Fig. 32D: Addition to carbon-carbon multiple bonds
Fig. 32E: Addition to carbon-multiple bonds
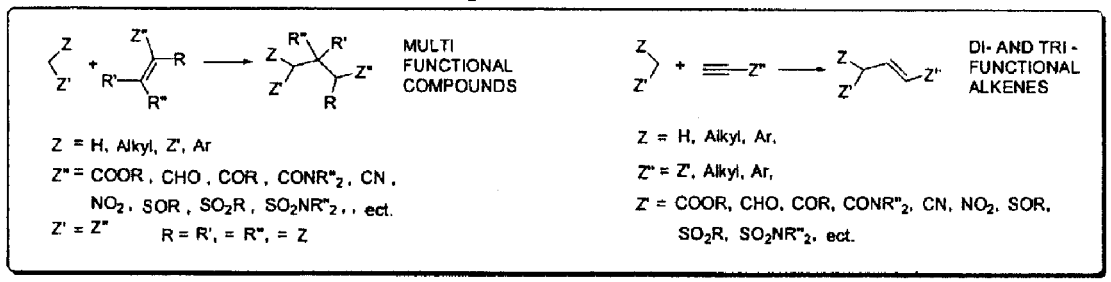
Fig. 32F: Cycloaddition to multiple bonds
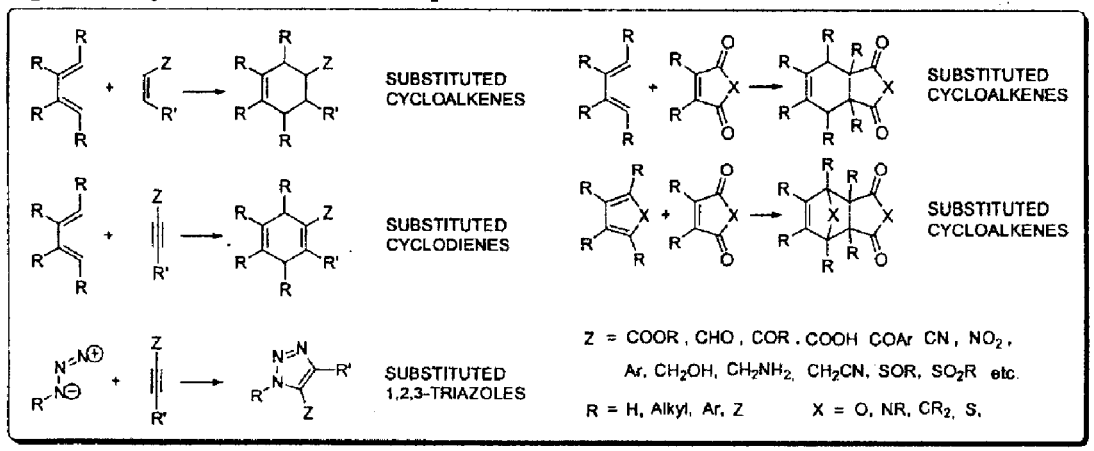

Figure 32, continued
Fig. 32G: Addition to carbon-hetero multiple bonds
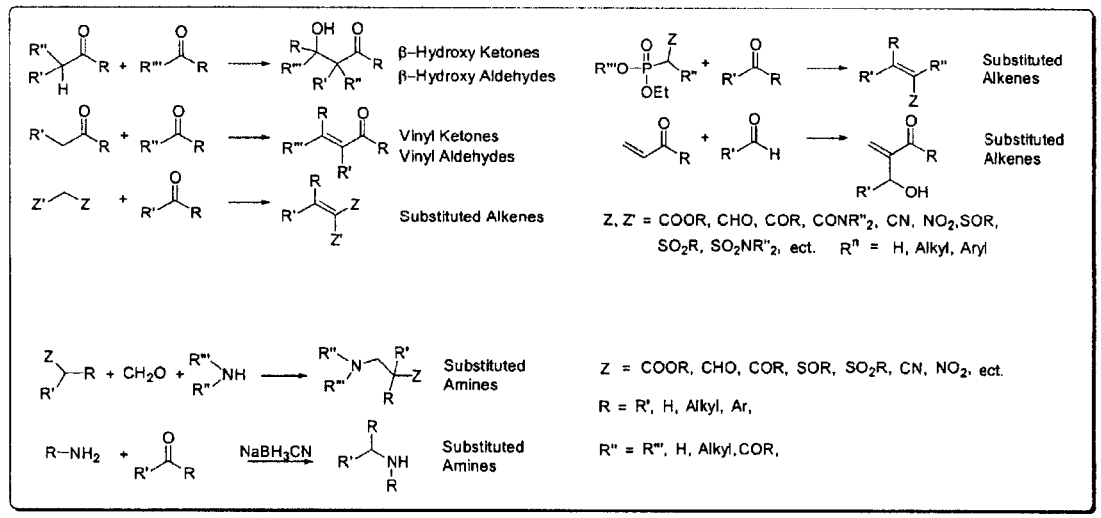

Fig. 33. Anchorage - Examples
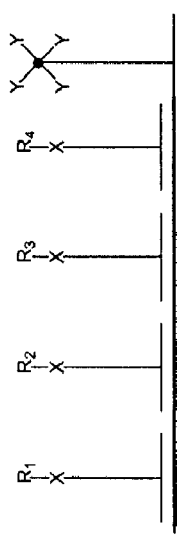
Fig. 33A.
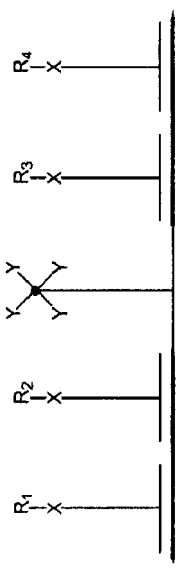
Fig. 33B.
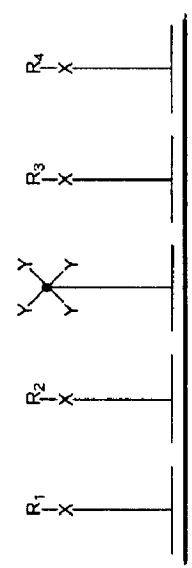
Fig. 33C.

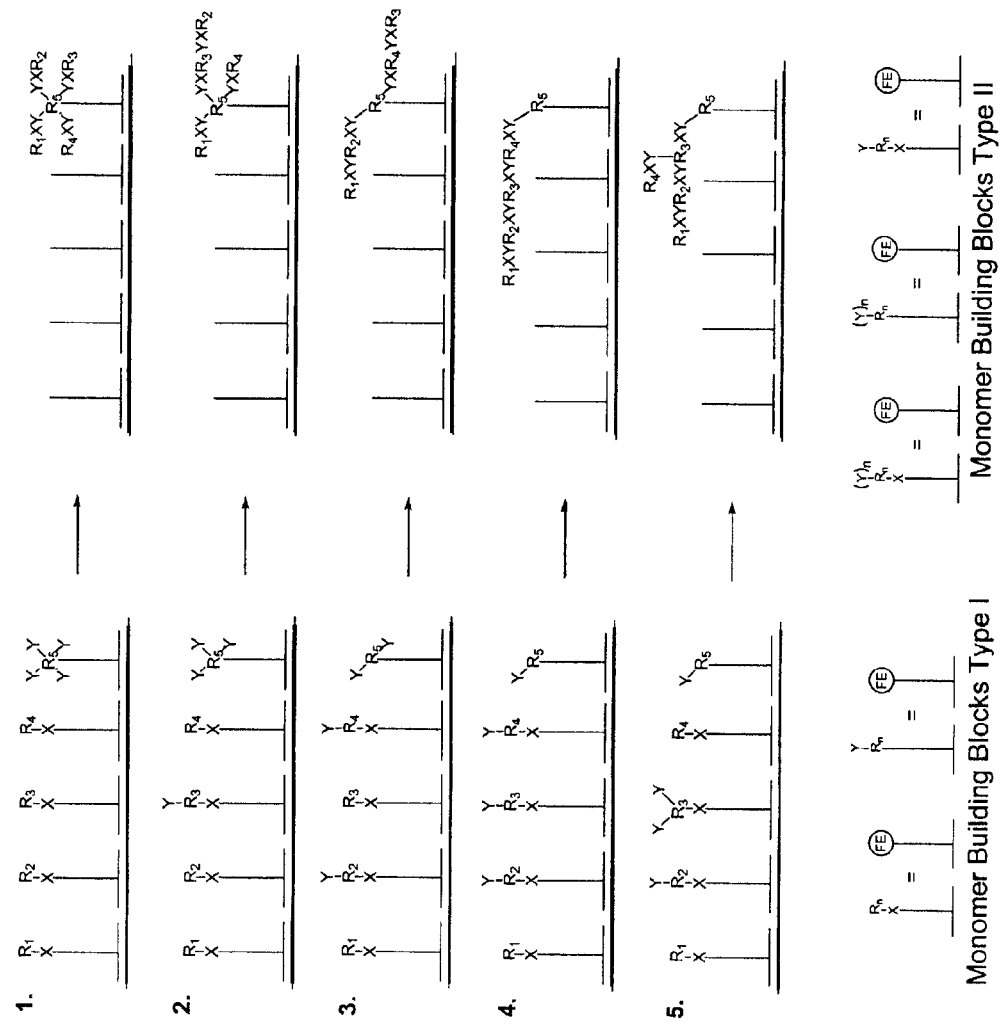
Fig. 34. Branching and Scrambling

Fig. 35. Monomer Building Blocks – Examples of Linker Design

Fig. 36. Formation of Monomer Building Blocks – Examples
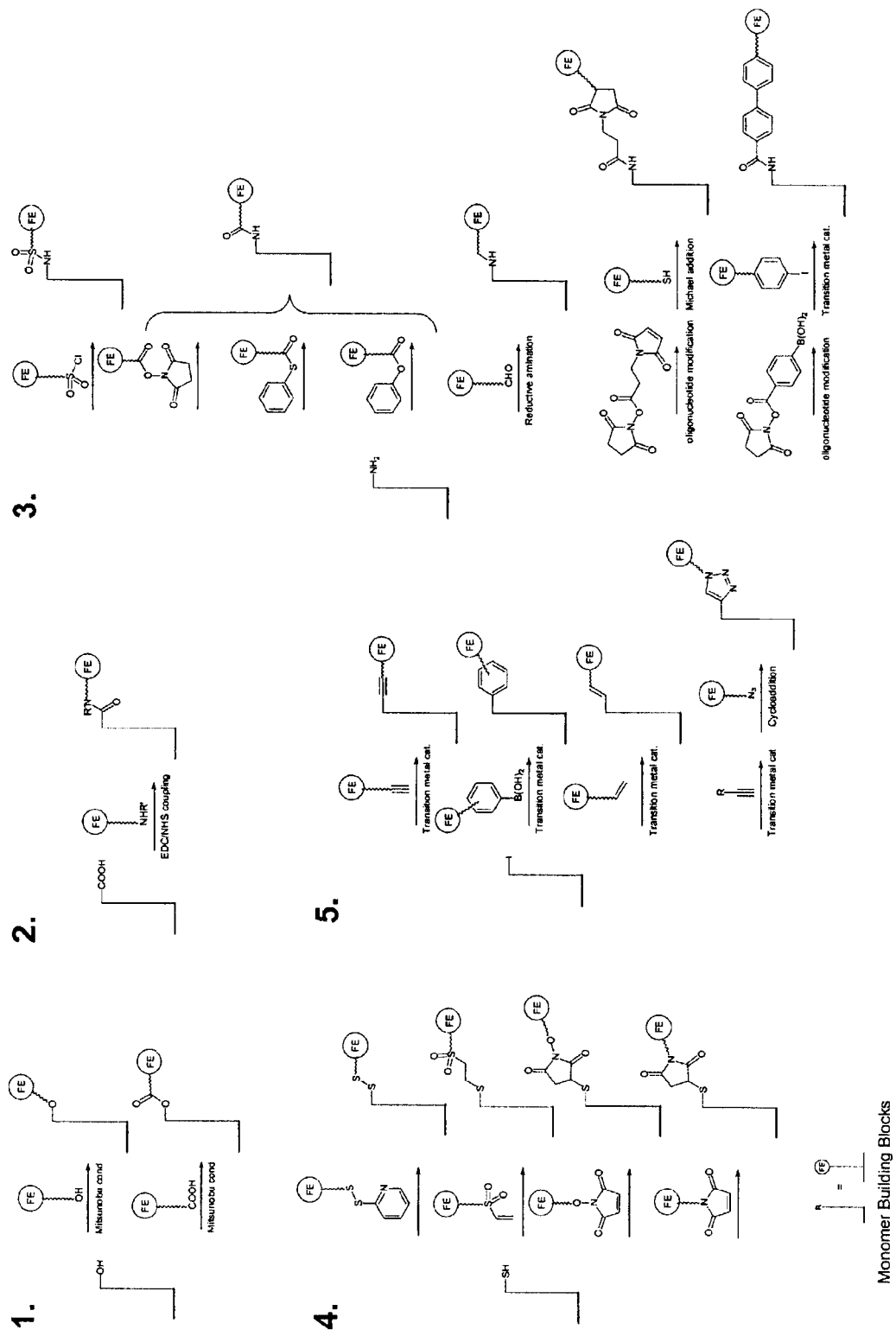

Figure 37. A derivatized oligonucleotide as building block.
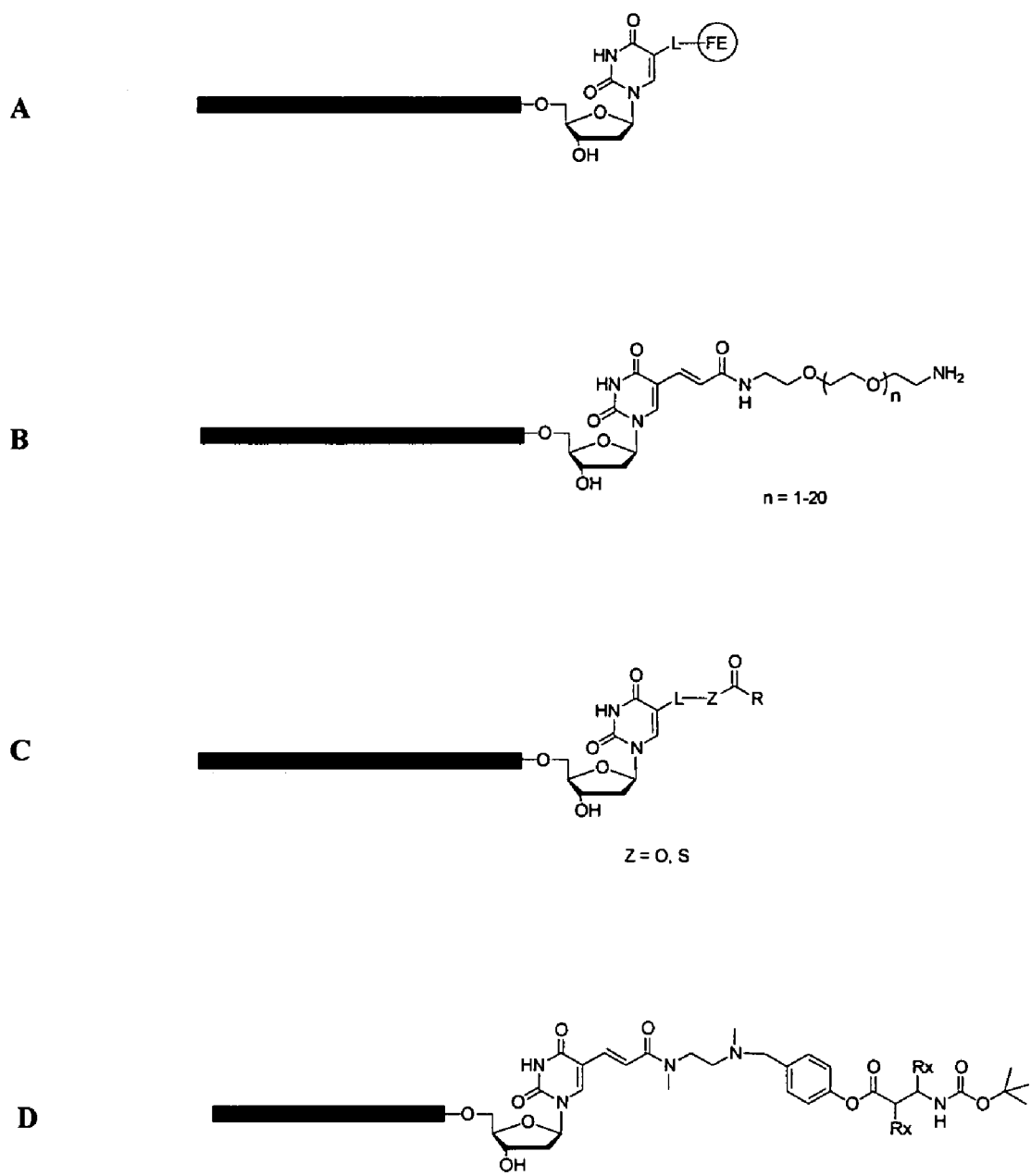

Figure 38. An oligonucleotide-based monomer building block. Example of complementing element design, allowing for high monomer diversity.

A. 

| BOX | sequence | monomer diversity |
|---|---|---|
| 1 | XXXXXATATTTXXXXX | 1024 |
| 2 | XXXATTTTAXXXXXXX | 1024 |
| 3 | XXXATTTTAXXXXXXX | 1024 |
| 4 | XXATXXATXXATXXXX | 1024 |
| 5 | GCCCGATTAAAXXCCG | 4 |
| 6 | XAXAXTTXTTXXXGGG | 128 |

X = G or C

B.  Coding Element (BOX 1)  GCGCGATATTTGGGCC
    Complementing Element  CGCGCTATAAACCCGG Coding Element (BOX 6)  GAGAGTTCTTCGCGGG
    Complementing Element  CTCTCAAGAAGCGCCC

Figure 38, continued.
C.
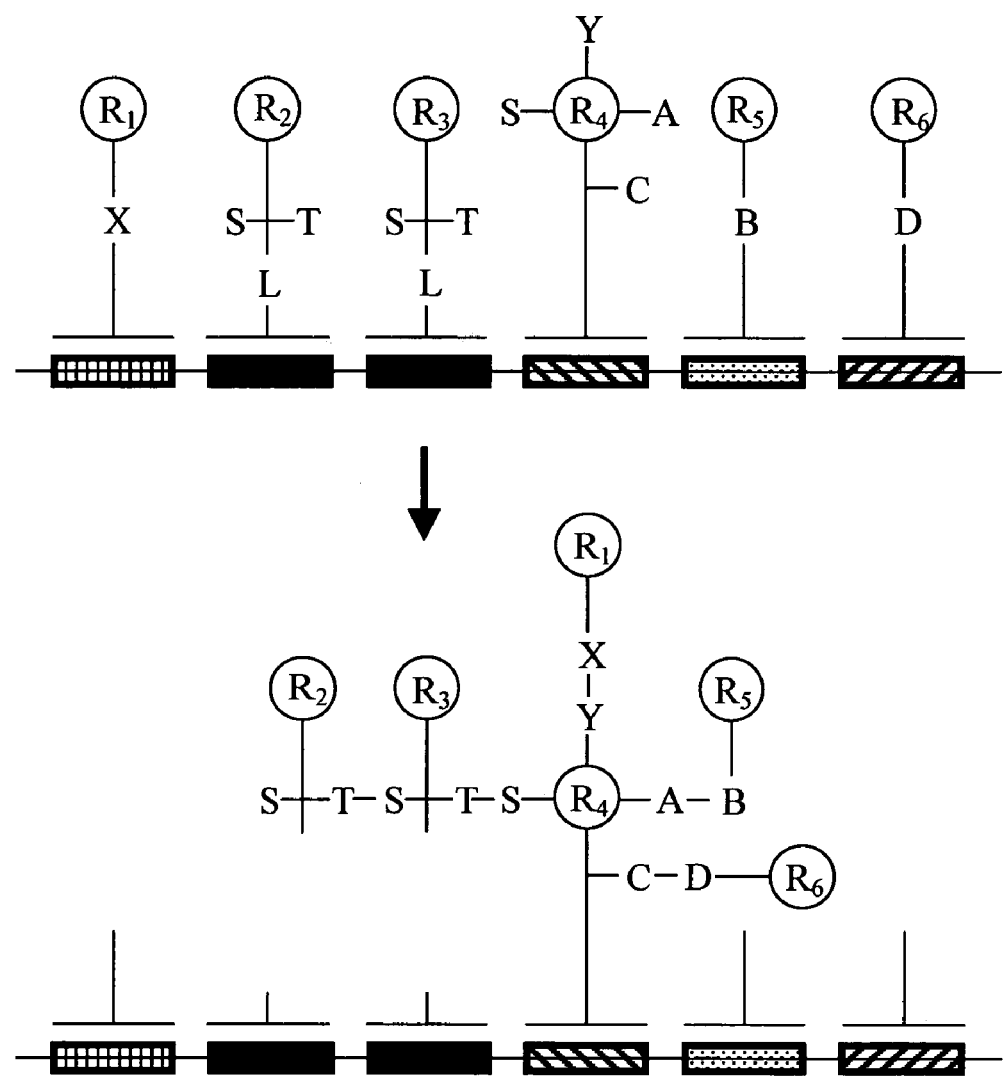

A typical panning protocol for selection of templated molecules

Array of templated molecules

Fig. 41. Use of Rigid or Partially Rigid Linkers

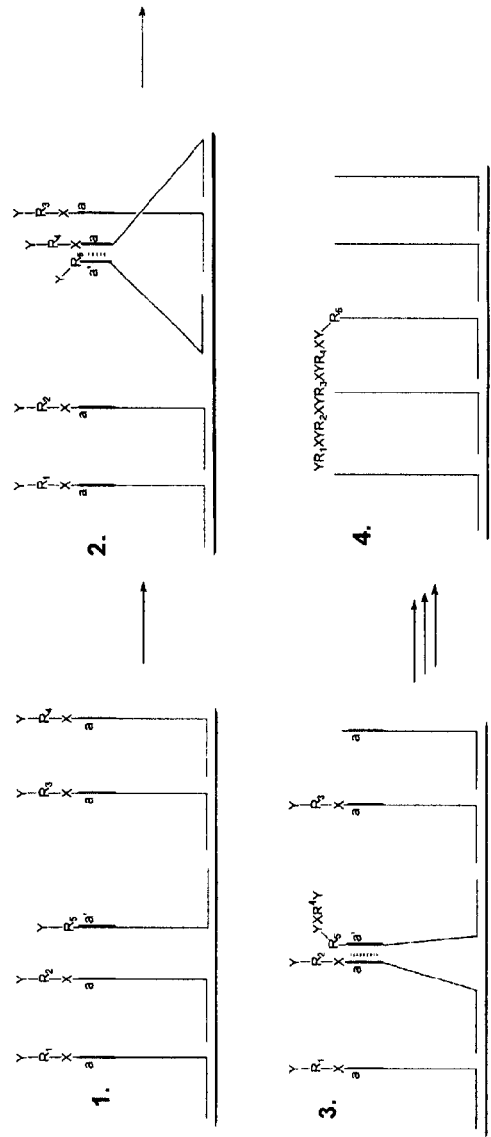

Fig. 42. Use of Zipper Box

Fig. 42A.

Fig. 42B. Example of a building block in which the zipper box consists of an oligonucleotide sequence:

X= Carboxy-dT Glen cat.no. 10-1035-
Z= Amino-Modifier Glen C6 dT 10-1039-

Oligo1
5'-CGACCTCTGGATTGCATGGTCATGGCTGACTGTCCGTCGAATGTGTCCAGTTACX
    Annealing region              Linker region                Zipper region Oligo2
5'-ZGTAACACCTGTGTAAGCTGCCTGTCAGTCGGTACTGACCTGTCGAGCATCCAGCT
   Zipper region       Linker region                  Annealing region Figure 43. Templated synthesis of organic compounds – examples.

Figure 43, continued

Fig. 44. Polymer encoding – Examples: peptide (α, β), peptoid or hydrazino peptide Fig. 45. Polymer encoding – Examples: α, β, γ, ω-peptide through use of NTA units

Fig. 46. Double templating

Figure 46, continued
   Fig. 46C. Example 1: Double templating
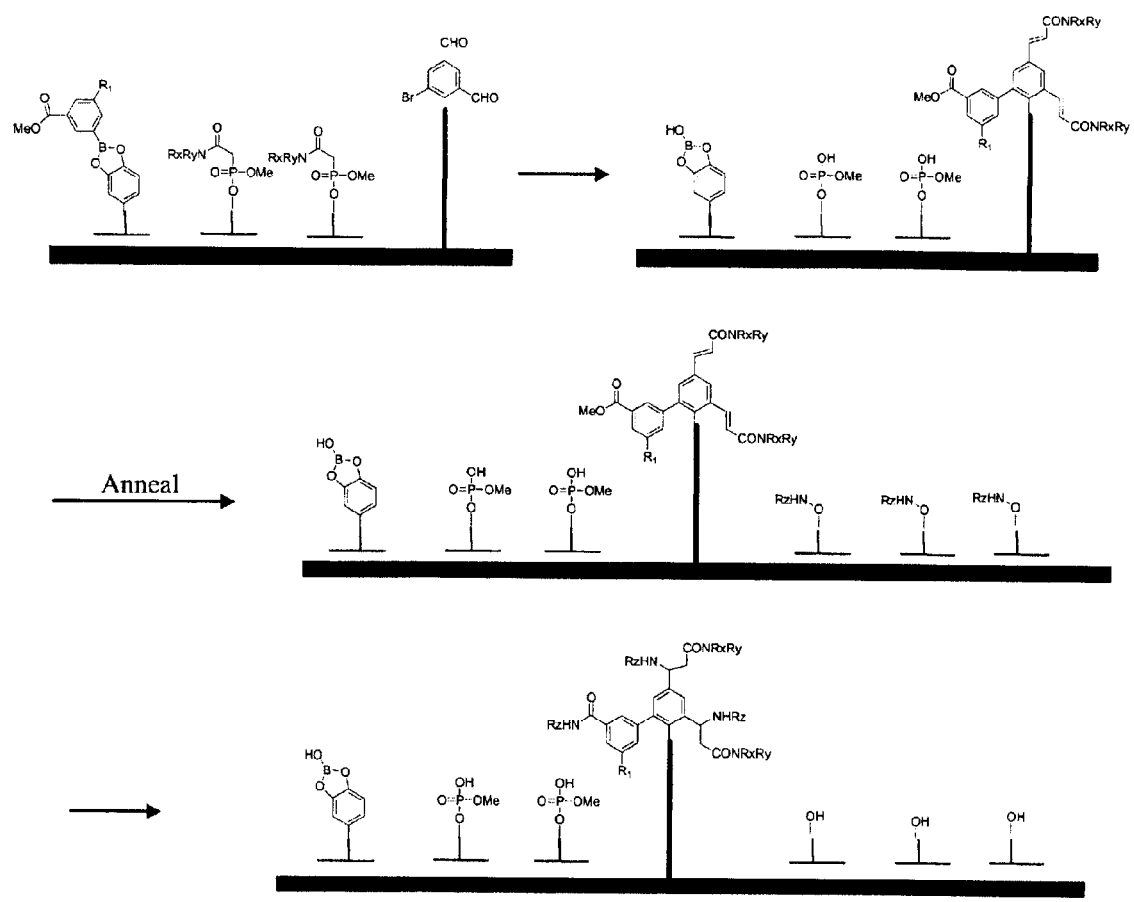

Figure 47. Cleavable Linkers

A. Linker for the formation of Ketones, Aldehydes, Amides and Acids

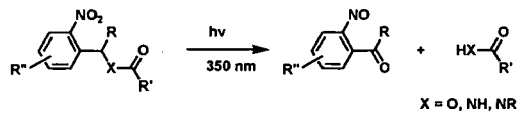

B. Linker for the formation of Ketones, Amides and Acids

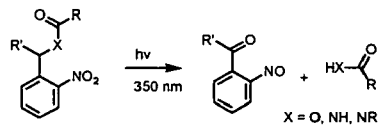

C. Linker for the formation of Aldehydes and Ketones

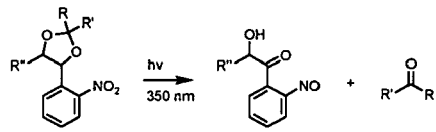

D. Linker for the formation of Alcohols and Acids

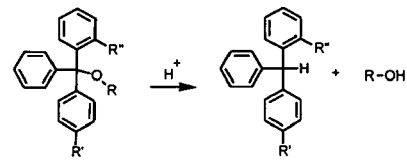

E. Linker for the formation of Amines and Alcohols

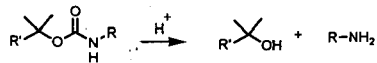

F. Linker for the formation of Esters, Thioesters, Amides and Alcohols

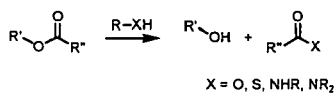

G. Linker for the formation of Sulfonamides and Alcohols

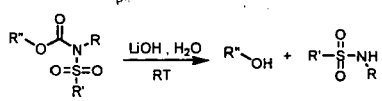

H. Linker for the formation of Ketones, Amines and Alcohols

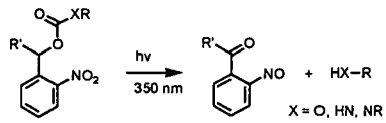

I. Linker for the formation of Ketones, Amines, Alcohols and Mercaptanes

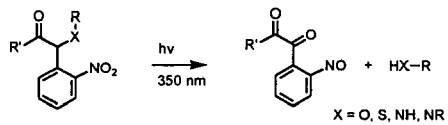

J. Linker for the formation of Biaryl and Bihetaryl

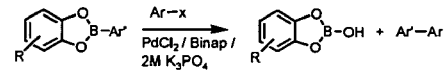

K. Linker for the formation of Benzyles, Amines, Anilins Alcohols and Phenoles

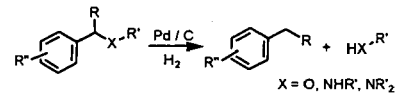

L. Linker for the formation of Mercaptanes

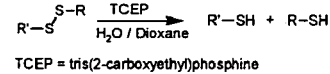

TCEP = tris(2-carboxyethyl)phosphine

M. Linker for the formation of Glycosides

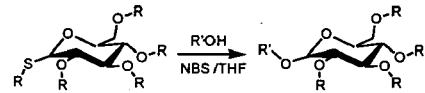

N. Linker for the formation of Aldehydes and Glyoxylamides

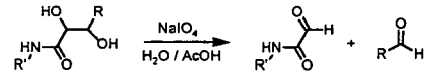

O. Linker for the formation of Aldehydes, Ketones and Aminoalcohols

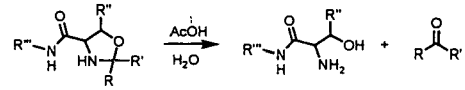

Figure 48. Post-templating modification of templated molecule
Fig. 48A
Rearrangement and cleavage in one step, eg:
A1
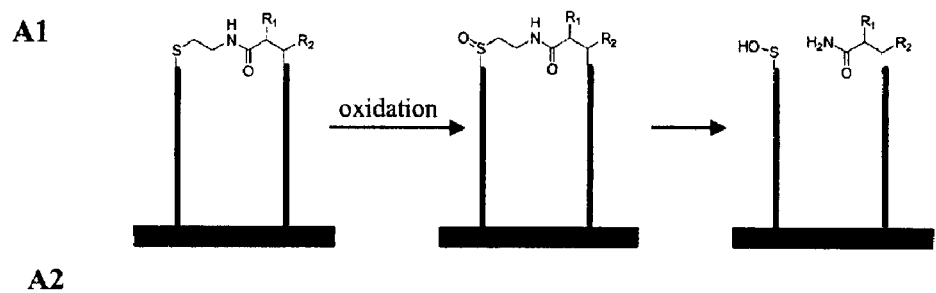
A2
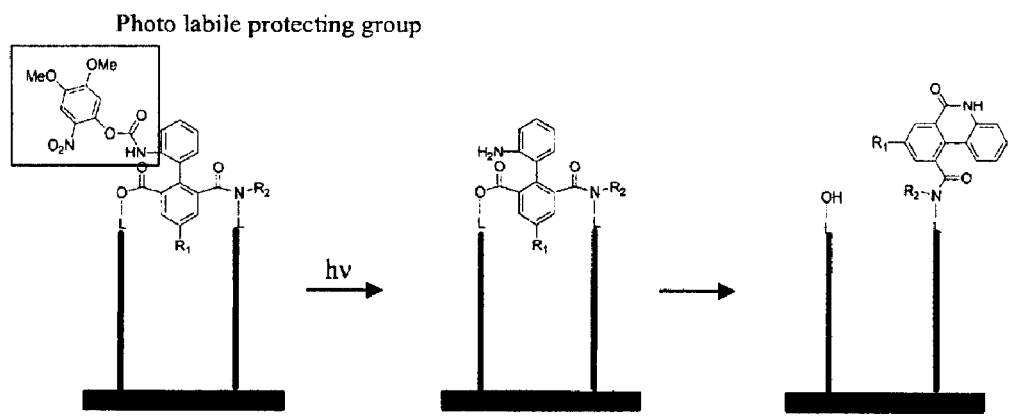
Fig. 48B
Reaction of functional groups present in a templated molecule
B1 Intramolecular Michael addition:
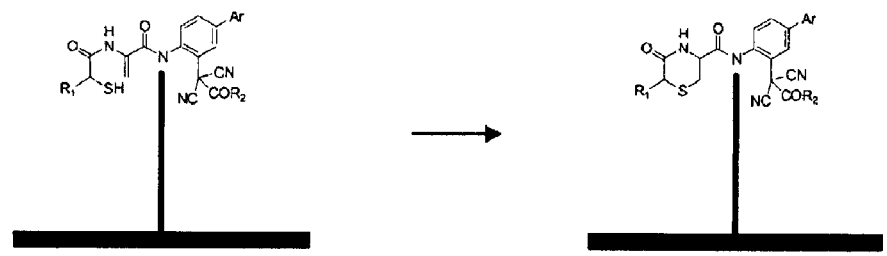

Figure 48, continued
B2 Intermolecular Michael addition:
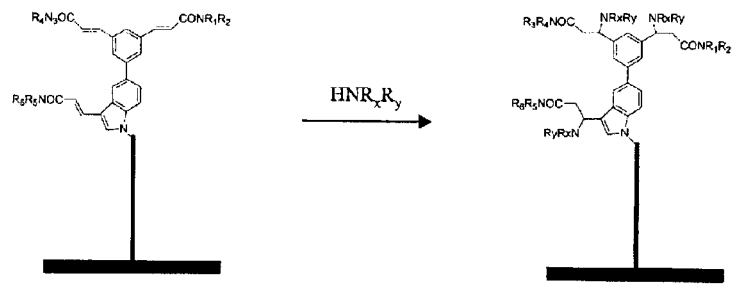
B3 Reaction of phenylenediamines and aldehydes to form benzimidazoles:
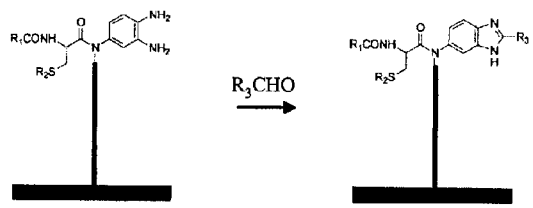
B4 Reduction of multiple bonds:
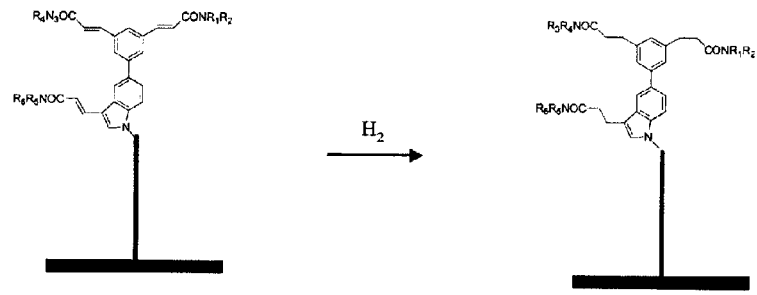
Fig. 48 C Post templating modification of linker to extend the spacing between the template and the templated molecule.
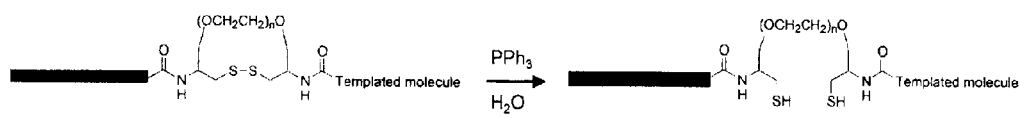

TEMPLATED MOLECULES AND METHODS FOR USING SUCH MOLECULES

The present application claims the benefit of U.S. Provisional Application No. 60/299,443, filed Jun. 21, 2001 and 60/364,056, file Mar. 15, 2002.

TECHNICAL FIELD OF THE INVENTION

Biological systems allow template-directed synthesis of α-peptides. The present invention enables a system that allows template-directed synthesis of other types of polymers as well as α-peptides. The present invention relates to templated molecules and templated molecules linked to a predetermined template. The templated molecules comprise a sequence of functional groups that are linked together. Each functional group is initially linked to an element capable of complementing a predetermined coding element of the template. Following complementation of a coding element, or complementation of a plurality of coding elements, the appended functional groups are linked and the templated moleculed is formed.

BACKGROUND

The central dogma in biology describes the flow of information as a one-way process from DNA to RNA to polypeptide. Accordingly, DNA is transcribed by a RNA polymerase into mRNA; and the mRNA is subsequently then translated into protein by the ribosomes and tRNAs.

The direct relation between the DNA and the protein, i.e., the fact that the sequence of triplet codons defines the sequence of α-amino acid residues in a polypeptide, has allowed the development of numerous molecular biological methods, in which the experimenter manipulates the DNA (mutagenizes, recombines, deletes, inserts, etc), and then uses in vivo systems (e.g., microbes) or in vitro systems (e.g., Zubay in vitro expression systems) to transfer the resulting changes from the DNA level to the level of the templated polypeptide, i.e., to mutate, recombine, delete, insert, etc. the polypeptide.

Several systems have been invented that allows a flow of information from polypeptide to DNA. These systems are phage display, ribosome/polysome display, peptides-on-plasmid display, and other systems. These systems introduce a physical link between the template (e.g., DNA) and the templated molecule (polypeptide). As a result, it is possible, from a population of templated molecules linked to the template that templated the synthesis of the molecule, to first enrich for a desired characteristic of the templated molecule (e.g., binding of the templated molecule to an affinity column), and then amplify the enriched population of templated molecules through amplification of its template (DNA or RNA), followed by translation of the amplified templates. These methods have been used to identify polypeptides with novel and/or improved features from libraries consisting of from a million to about $10^{15}$ polypeptides.

The critical feature of the prior art systems is the amplifiability of the templated molecule, through amplification of its template. Thus, after the selection step in which molecules with the desired property are enriched, the enriched population may be amplified and then taken through yet a selection step, etc.—the process of selection-and-amplification may be repeated many times. In this way the "noise" of the selection assay is averaged out over several selection-and-amplification rounds, and even if the individual selection step only enriches e.g. 10-fold, a theoretical enrichment of $10^{12}$ can be reached after 12 selection-and-amplification rounds. Had the molecules not been amplifiable, the same enrichment would have had to be achieved in a single screening step, which means that the enrichment in this one step would have had to be $10^{12}$, and the assay should still have the same overall stringency (accuracy). This is practically impossible with current technologies.

In the field of chemistry, a different combinatorial approach has been developed. This approach involved the parallel synthesis of millions of related compounds, in an array (where each position defined a specific compound), or on beads (where one bead carried many copies of the same compound). The population of compounds were then screened for desired characteristics. Importantly, this type of combinatorial library has no means for amplification, and therefore requires the use of very stringent screening methods, as explained above. Recently, the trend in for example medicinal chemistry has therefore been to use less diverse, but better characterized libraries.

Principles for tagging chemical libraries have also been developed. For example, systems that employed DNA oligos to tag molecule libraries have been developed as exemplified herein below. The tag is used as a means of identification, but cannot be used to template the synthesis of the tagged molecule. Therefore, despite the tag, these systems still require a very efficient screening method.

The below listed references illustrate some of the above-mentioned short-comings of the prior art methods in the field of the invention.

EP 0 604 552 B1 relates to a method for synthesizing diverse collections of oligomers. The invention involves the use of an identifier tag to identify the sequence of monomers in an oligomer. The identifier tags facilitate subsequent identification of reactions through which members of a library of different synthetic compounds have been synthesised in a component by component fashion.

EP 0 643 778 B1 relates to encoded combinatorial chemical libraries. Each of a collection of polypeptides is labelled by an appended "genetic" tag, itself constructed by chemical synthesis, to provide a "retro-genetic" way of specifying each polypeptide.

EP 0 773 227 A1 relates to a method for preparing a new pharmaceutical drug or diagnostic reagent, which includes the step of screening, against a ligand or receptor, a library of different synthetic compounds obtainable by synthesis in a component by component fashion.

U.S. Pat. No. 4,863,857 relates to a method for determining the amino acid sequence of a polypeptide complementary to at least a portion of an original peptide or protein. In one aspect the method involves: (a) determining a first nucleotide sequence of a first nucleic acid coding for the biosynthesis of at least a portion of the original peptide or protein; (b) ascertaining a second nucleotide sequence of a second nucleic acid which base-pairs with the first nucleotide sequence of the first nucleic acid, the first and second nucleic acids pairing in antiparallel directions; and (c) determining the amino acid sequence of the complementary polypeptide by the second nucleotide sequence when read in the same reading frame as the first nucleotide sequence.

U.S. Pat. No. 5,162,218 relates to polypeptide compositions having a binding site specific for a particular target ligand and further having an active functionality proximate the binding site. The active functionality may be a reporter molecule, in which case the polypeptide compositions are useful in performing assays for the target ligand. Also disclosed are methods for preparing polypeptides having active functionalities proximate their binding site, said method comprising the step of combining the polypeptide specific for the target ligand with an affinity label having a reactive group attached thereto. The reactive group is then covalently attached to an amino acid side chain proximate the binding site and cleaved from the substrate. The substrate is subsequently eluted, leaving a moiety of the reactive group covalently attached to the polypeptide. The active funtionality may then be attached to the moiety.

U.S. Pat. No. 5,270,170 relates to a random peptide library constructed by transforming host cells with a collection of recombinant vectors that encode a fusion protein comprised of a DNA binding protein and a random peptide and also encode a binding site for the DNA binding protein. The fusion protein can be used for screening ligands. The screening method results in the formation of a complex comprising the fusion protein bound to a receptor through the random peptide ligand and to the recombinant DNA vector through the DNA binding protein.

U.S. Pat. No. 5,539,082 relates to a novel class of compounds, known as peptide nucleic acids capable of binding complementary ssDNA and RNA strands more strongly than a corresponding DNA. The peptide nucleic acids generally comprise ligands such as naturally occurring DNA bases attached to a peptide backbone through a suitable linker.

U.S. Pat. No. 5,574,141 relates to functionalized carrier materials for the simultaneous synthesis and direct labeling of oligonucleotides as primers for template-dependent enzymatic nucleic acid syntheses. The polymeric carriers are loaded with nucleic acid building blocks which in turn contain labelling groups or precursors thereof. The polymeric carrier loaded in this way serves as a solid or liquid phase for the assembly of oligonucleotides which can be used as primers for a template-dependent enzymatic nucleic acid synthesis such as in sequencing analysis or in the polymerase chain reaction (PCR).

U.S. Pat. No. 5,573,905 relates to an encoded combinatorial chemical library comprised of a plurality of bifunctional molecules having both a chemical polymer and an identifier oligonucleotide sequence that defines the structure of the chemical polymer. Also described are the bifunctional molecules of the library, and methods of using the library to identify chemical structures within the library that bind to biologically active molecules in preselected binding interactions.

U.S. Pat. No. 5,597,697 relates to a screening assay for inhibitors and activators of RNA and DNA-dependent nucleic acid polymerases. The invention provides methods for the identification and discovery of agents which are inhibitors and activators of RNA and DNA-dependent nucleic acid polymerases. The essential feature of the invention is the incorporation of a functional polymerase binding site sequence (PBS) into a nucleic acid molecule which is chosen for its ability to confer a discernible characteristic via its sequence specific activity such that the incorporation of the PBS renders the nucleic acid molecule a functional template for a predetermined RNA or DNA-template directed nucleic acid polymerase. In the presence of the polymerase, suitable primer molecules, and any necessary accessory molecules, catalytic extension of the strand of nucleic acids complementary to the template occurs, resulting in a partial or total elimination of (or increase in) the characteristic conferring activity of the reporter-template molecule described due to the antisense effects of the complementary strand or other polymerase-mediated effects.

U.S. Pat. No. 5,639,603 relates to a method for synthesizing and screening molecular diversity by means of a general stochastic method for synthesizing compounds. The method can be used to generate large collections of tagged compounds that can be screened to identify and isolate compounds with useful properties.

U.S. Pat. No. 5,698,685 relates to a morpholino-subunit combinatorial library and a method for generating a compound capable of interacting specifically with a selected macromolecular ligand. The method involves contacting the ligand with a combinatorial library of oligomers composed of morpholino subunits with a variety of nucleobase and non-nucleobase side chains. Oligomer molecules that bind specifically to the receptor are isolated and their sequence of base moieties is determined. Also disclosed is a combinatorial library of oligomers useful in the method and novel morpholino-subunit polymer compositions.

U.S. Pat. No. 5,708,153 relates to a method for synthesizing diverse collections of tagged compounds by means of a general stochastic method for synthesizing random oligomers on particles. A further aspect of the invention relates to the use of identification tags on the particles to facilitate identification of the sequence of the monomers in the oligomer.

U.S. Pat. No. 5,719,262 relates to a novel class of compounds, known as peptide nucleic acids, which bind complementary DNA and RNA strands more strongly than the corresponding DNA or RNA strands, and exhibit increased sequence specificity and solubility. The peptide nucleic acids comprise ligands selected from a group consisting of naturally-occurring nucleobases and non-naturally-occurring nucleobases attached to a polyamide backbone, and contain alkylamine side chains.

U.S. Pat. No. 5,721,099 relates to encoded combinatorial chemical libraries encoded with tags. Encoded combinatorial chemistry is provided, whereby sequential synthetic schemes are recorded using organic molecules, which define choice of reactant, and stage, as the same or different bit of information. Various products can be produced in the multi-stage synthesis, such as oligomers and synthetic non-repetitive organic molecules. Particularly, pluralities of identifiers may be used to provide a binary or higher code, so as to define a plurality of choices with only a few detachable tags. The particles may be screened for a characteristic of interest, particularly binding affinity, where the products may be detached from the particle or retained on the particle. The reaction history of the particles which are positive for the characteristic can be determined by the release of the tags and analysis to define the reaction history of the particle.

U.S. Pat. No. 5,723,598 relates to an encoded combinatorial chemical library comprised of a plurality of bifunctional molecules having both a chemical polymer and an identifier oligonucleotide sequence that defines the structure of the chemical polymer. Also described are the bifunctional molecules of the library, and methods of using the library to identify chemical structures within the library that bind to biologically active molecules in preselected binding interactions.

U.S. Pat. No. 5,770,358 relates to tagged synthetic oligomer libraries and a general stochastic method for synthesizing random oligomers. The method can be used to synthesize compounds to screen for desired properties. The use of identification tags on the oligomers facilitates identification of oligomers with desired properties.

U.S. Pat. No. 5,786,461 relates to peptide nucleic acids having amino acid side chains. A novel class of compounds, known as peptide nucleic acids, bind complementary DNA and RNA strands more strongly than the corresponding DNA or RNA strands, and exhibit increased sequence specificity and solubility. The peptide nucleic acids comprise ligands selected from a group consisting of naturally-occurring nucleobases and non-naturally-occurring nucleobases attached to a polyamide backbone, and contain alkylamine side chains.

U.S. Pat. No. 5,789,162 relates to a method for synthesizing diverse collections of oligomers. A general stochastic method for synthesizing random oligomers on particles is disclosed. A further aspect of the invention relates to the use of identification tags on the particles to facilitate identification of the sequence of the monomers in the oligomer.

U.S. Pat. No. 5,840,485 relates to topologically segregated, encoded solid phase libraries. Libraries of synthetic test compounds are attached to separate phase synthesis supports that also contain coding molecules that encode the structure of the synthetic test compound. The molecules may be polymers or multiple nonpolymeric molecules. The synthetic test compound can have backbone structures with linkages such as amide, urea, carbamate (i.e., urethane), ester, amino, sulfide, disulfide, or carbon-carbon, such as alkane and alkene, or any combination thereof. The synthetic test compound can also be molecular scaffolds, or other structures capable of acting as a scaffolding. The invention also relates to methods of synthesizing such libraries and the use of such libraries to identify and characterize molecules of interest from among the library of synthetic test compounds.

U.S. Pat. No. 5,843,701 relates to systematic polypeptide evolution by reverse translation and a method for preparing polypeptide ligands of target molecules wherein candidate mixtures comprised of ribosome complexes or mRNA:polypeptide copolymers are partitioned relative to their affinity to the target and amplified to create a new candidate mixture enriched in ribosome complexes or mRNA:polypeptide copolymers with an affinity to the target.

U.S. Pat. No. 5,846,839 relates to a method for hard-tagging an encoded synthetic library. Disclosed are chemical encryption methods for determining the structure of compounds formed in situ on solid supports by the use of specific amine tags which, after compound synthesis, can be deencrypted to provide the structure of the compound found on the support.

U.S. Pat. No. 5,922,545 relates to methods and compositions for identifying peptides and single-chain antibodies that bind to predetermined receptors or epitopes. Such peptides and antibodies are identified by methods for affinity screening of polysomes displaying nascent peptides.

U.S. Pat. No. 5,958,703 relates to methods for screening libraries of complexes for compounds having a desired property such as the capacity to bind to a cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound U.S. Pat. No. 5,986,053 relates peptide nucleic acid complexes of two peptide nucleic acid strands and one nucleic acid strand. Peptide nucleic acids and analogues of peptide nucleic acids are used to form duplex, triplex, and other structures with nucleic acids and to modify nucleic acids. The peptide nucleic acids and analogues thereof also are used to modulate protein activity through, for example, transcription arrest, transcription initiation, and site specific cleavage of nucleic acids.

U.S. Pat. No. 5,998,140 relates to methods and compositions for forming complexes intracellularly between dsDNA and oligomers of heterocycles, aliphatic amino acids, particularly omega-amino acids, and a polar end group. By appropriate choice of target sequences and composition of the oligomers, complexes are obtained with low dissociation constants.

U.S. Pat. No. 6,060,596 relates to an an encoded combinatorial chemical library comprised of a plurality of bifunctional molecules having both a chemical polymer and an identifier oligonucleotide sequence that defines the structure of the chemical polymer. Also described are the bifunctional molecules of the library, and methods of using the library to identify chemical structures within the library that bind to biologically active molecules in preselected binding interactions.

U.S. Pat. No. 6,080,826 relates to Template-directed ring-closing metathesis and ring-opening metathesis polymerization of functionalized dienes. Functionalized cyclic olefins and methods for making the same are disclosed. Methods include template-directed ring-closing metathesis ("RCM") of functionalized acyclic dienes and template-directed depolymerization of functionalized polymers possessing regularly spaced sites of unsaturation. Although the template species may be any anion, cation, or dipolar compound, cationic species, especially alkali metals, are preferred. Functionalized polymers with regularly spaced sites of unsaturation and methods for making the same are also disclosed. One method for synthesizing these polymers is by ring-opening metathesis polymerization ("ROMP") of functionalized cyclic olefins.

U.S. Pat. No. 6,127,154 relates to compounds which possess a complementary structure to a desired molecule, such as a biomolecule, in particular polymeric or oligomeric compounds, which are useful as in vivo or in vitro diagnostic and therapeutic agents are provided. Also, various methods for producing such compounds are provided.

U.S. Pat. No. 6,140,493 relates to a method for synthesizing diverse collections of oligomers. A general stochastic method for synthesizing random oligomers is disclosed and can be used to synthesize compounds to screen for desired properties. Identification tags on the oligomers facilitates identification of oligomers with desired properties.

U.S. Pat. No. 6,140,496 relates to building blocks for preparing oligonucleotides carrying non-standard nucleobases that can pair with complementary non-standard nucleobases so as to fit the Watson-Crick geometry. The resulting base pair joins a monocyclic six membered ring pairing with a fused bicyclic heterocyclic ring system composed of a five member ring fused with a six member ring, with the orientation of the heterocycles with respect to each other and with respect to the backbone chain analogous to that found in DNA and RNA, but with a pattern of hydrogen bonds holding the base pair together different from that found in the AT and GC base pairs (a "non-standard base pair").

U.S. Pat. No. 6,143,497 relates to a method for synthesizing diverse collections of random oligomers on particles by means of a general stochastic method. Also disclosed are identification tags located on the particles and used to facilitate identification of the sequence of the monomers in the oligomer.

U.S. Pat. No. 6,165,717 relates to a general stochastic method for synthesizing random oligomers on particles. Also disclosed are identification tags located on the particles to facilitate identification of the sequence of the monomers in the oligomer.

U.S. Pat. No. 6,175,001 relates to functionalized pyrimidine nucleosides and nucleotides and DNA's incorporating same. The modified pyrimidine nucleotides are derivatized at C5 to contain a functional group that mimics the property of a naturally occurring amino acid residues. DNA molecules containing the modified nucleotides are also provided.

U.S. Pat. No. 6,194,550 B1 relates to systematic polypeptide evolution by reverse translation, in particular a method for preparing polypeptide ligands of target molecules wherein candidate mixtures comprised of ribosome complexes or mRNA:polypeptide copolymers are partitioned relative to their affinity to the target and amplified to create a new candidate mixture enriched in ribosome complexes or mRNA:polypeptide copolymers with an affinity to the target.

U.S. Pat. No. 6,207,446 B1 relates to methods and reagents for the selection of protein molecules that make use of RNA-protein fusions.

U.S. Pat. No. 6,214,553 B1 relates to methods and reagents for the selection of protein molecules that make use of RNA-protein fusions.

WO 91/05058 relates to a method for the cell-free synthesis and isolation of novel genes and polypeptides. An expression unit is constructed onto which semi-random nucleotide sequences are attached. The semi-random nucleotide sequences are first transcribed to produce RNA, and then translated under conditions such that polysomes are produced. Polysomes which bind to a substance of interest are then isolated and disrupted; and the released mRNA is recovered. The mRNA is used to construct cDNA which is expressed to produce novel polypeptides.

WO 92/02536 relates to a method for preparing polypeptide ligands of target molecules wherein candidate mixtures comprised of ribosome complexes or mRNA:polypeptide copolymers are partitioned relative to their affinity to the target and amplified to create a new candidate mixture enriched in ribosome complexes or mRNA:polypeptide copolymers with an affinity to the target.

WO 93/03172 relates to a method for preparing polypeptide ligands of target molecules wherein candidate mixtures comprised of ribosome complexes or mRNA:polypeptide copolymers are partitioned relative to their affinity to the target and amplified to create a new candidate mixture enriched in ribosome complexes or mRNA:polypeptide copolymers with an affinity to the target.

WO 93/06121 relates to a general stochastic method for synthesizing random oligomers on particles. Also disclosed are identification tags located on the particles to facilitate identification of the sequence of the monomers in the oligomer.

WO 00/47775 relates to a method for generating RNA-protein fusions involving a high-salt post-translational step.

Additional references of relevance for present invention includes Bain et al. Nature, vol. 356, 1992, 537-539; Barbas et al. Chem. Int. Ed. vol. 37, 1998. 2872-2875; Benner Reviews; Blanco et al. Analytical Biochemistry vol. 163, 1987, 537-545; Brenner et al. Proc. Natl. Acad. Sci. Vol. 89, 1992, 5381-5383; Bresler et al. Biochimica et Biophysica Acta vol. 155, 1968, 465-475; Dewey et al. J. Am. Chem. Soc. Vol. 117, 1995, 8474-8475; Dietz et al. Photochemistry and photobiology vol. 49, 1989, 121-129; Gryaznov et al. J. Am. Chem. Soc. vol. 115, 1993, 3808-3809; Gryaznov et al. Nucleic Acids Research vol. 21, 1993, 1403-1408; Elmar Gocke Mutation Research vol. 248, 1991, 135-143; Haeuptle et al. Nucleic Acids Research, 14, 1986, 1427-1448; Hamburger et al. Biochimica et Biophysica Acta, 213, 1970, 115-123; Hamza A. El-Dorry Biochimica et Biophysica Acta vol. 867, 1986, 252-255; Herrera-Estrella et al. The EMBO Journal, 7, 1988, 4055-4062; Heywood et al. Biochemistry vol. 57, 1967, 1002-1009; Heywood et al. J. Biol. Chem. Vol. 7, 1968, 3289-3296; Hooper et al. Eur. J. Clin. Microbiol. Infect. Dis. Vol. 10, 1991, 223-231; Houdebine et al. Eur. J. Biochem., 63, 1976, 9-14; Johnson et al. Biochemistry vol. 25, 1986, 5518-5525; Kinoshita et al. Nucleic Acids Symposium Series vol. 34, 1995, 201-202; Leon et al. Biochemistry vol. 26, 1987, 7113-7121; Maclean et al. Proc. Natl. Acad. Sci. USA vol. 94, 1997, 2805-2810; Mattheakis et al. Proc. Natl. Acad. Sci. USA vol. 91, 1994, 9022-9026; Menninger et al. Antimicrobial Agents and Chemotherapy, 21, 1982, 811-818; Menninger. Biochimica et Biophysica Acta, 240, 1971, 237-243; Mirzabekov Methods in Enzymology vol. 170, 1989, 386-408; Nikolaev et al. Nucleic Acids Research vol. 16, 1988, 519-535; Noren et al. Science vol. 24, 1989, 182-188; Pashev et al. TIBS vol. 16, 1991, 323-326; Pargellis et al. The Journal of Biological Chemistry, 263, 1988, 7678-7685; Pansegrau et al. The journal of biological chemistry vol. 265, 1990, 10637-10644; Peeters et al. FEBS Lett. vol. 36, 1973, 217-221; Roberts et al. Proc. Natl. Acad. Sci. USA vol. 94, 1997, 12297-12302; Schmidt et al. Nucleic Acids Research vol. 25, 1997, 4797-4802; Schutz et al. Nucleic Acids Research, 4, 1977, 71-84; Solomon et al. Proc. Natl. Acad. Sci USA vol. 82, 1985, 6470-6474; Sugino et al. Nucleic Acids Research, 8, 1980, 3865-3874; Tarasow et al. Nucleic Acids Sciences vol. 48, 1998, 29-37; Wiegand et al. Chemistry and Biology vol. 4, 1997, 675-683; and Wower et al. Proc. Natl. Acad. Sci. USA., 86, 1989, 5232-5236.

SUMMARY OF THE INVENTION

The present invention solves in a general way the above-mentioned problems and short-comings of the prior art. The invention relates to a system for templating molecules in general, such as polymers, and the template enables templated synthesis of the polymers, allowing in preferred embodiments amplification of the polymer. The system therefore has the same overall characteristics as the natural system (information flow from template to templated molecule), as well as the characteristics of the recently invented ribosome-mediated systems (e.g., phage display), namely the physical link between template and templated molecule. However, the present invention does not involve ribosomes or tRNAs, and therefore allows templating of a wide array of different polymers, including polymers that cannot be synthesised in a natural system based on ribosome-mediated translation of nucleic acids.

The templating process of the invention has significant advantages over the prior art. As the amplification of the recovered molecules (i.e., their templates) can be done by a parallel process in which all the recovered templates are present in the same compartment (e.g., reagent tube or microtiter-plate well), and where the molecules are proportionately amplified, no human intervention such as sequencing of the individual molecules is necessary. This is a huge advantage since a typical recovery after a first selection round involves e.g. $10^{10}$ different molecules, when the starting material is a library of e.g. $10^{15}$ molecules. When working with such high numbers of molecules, it is practically impossible to "amplify" $10^{10}$ molecules by copying the molecules one-at-a-time, i.e., to "amplify" the molecules in a serial process.

The present invention generally relates to templated molecules and complexes comprising such molecules linked to a template that has directed the template-directed synthesis of the templated molecule. In one aspect, the templated molecules and the complexes are obtainable according to the methods of the present invention.

The present invention also discloses methods for synthesizing such templated molecules and/or complexes, methods for targeting such molecules and/or complexes to a target species. The templated molecules are preferably synthesised from building blocks comprising a functional entity comprising a functional group and reactive group capable of covalently linking functional groups and forming a templated molecule. The functional entity of a building block is separated from a complementing element by a cleavable linker, or a selectively cleavable linker. The complementing element is capable of complementing a predetermined coding element of the template, thus ensuring a one-to-one relationship between a coding element—or a complementing element—and a functional entity, or a functional group.

Also disclosed are methods for identifying the sequence of functional groups of a templated molecule, as well as methods for therapy and diagnostic methods exploiting the templated molecules according to the invention.

The methods of the invention do not involve ribosome mediated translation of ribonucleic acids. Also, when the templated molecules are peptides comprising either i) exclusively α-amino acids, or ii) substantially exclusively naturally occurring amino acids, such as at least 80 percent, for example 90 percent, such as 95 percent, naturally occurring amino acids, the template does not comprise or essentially consist of a ribonucleic acid.

A template denotes a sequence of coding elements, wherein each coding element is linked to a neighbouring coding element. A complementing template denotes a sequence of complementing elements, wherein each complementing element is linked to neighbouring complementing element.

Following complementation of a coding element by a complementing element, or complementation of a plurality of coding elements by a plurality of complementing elements, each complementing element will define an appended functional group capable of being linked—without forming part of the complementing template itself—to a neighbouring functional group defined by a neighbouring complementing element. Accordingly, in one preferred embodiment, the functional group does not participate in the complementation of a coding element in so far as no direct reaction or hybridization takes place between the coding element and the functional group. The term "reaction" means any reactive contact that results in the formation of an interaction—covalent or non-covalent—between the functional group and the coding element. In another embodiment, the functional group of a templated molecule forms part of the complementing template.

As each complementing element is capable of recognising a predetermined coding element of a template, and as each coding element in turn defines a predetermined functional group, the sequence of coding elements of the template will template the synthesis of the templated molecule comprising a predetermined sequence of covalently linked functional groups.

According to preferred embodiments of the present invention, it is possible
i) to link a templated molecule comprising a plurality of functional groups to the template that templated the synthesis of the templated molecule,
ii) to link neighbouring functional groups simultaneously with the complementation of neighbouring coding elements by complementing elements defining said functional groups,
iii) to link neighbouring functional groups after the complementation of neighbouring coding elements by complementing elements defining said functional groups,
iv) to link neighbouring functional groups simultaneously with the formation of a complementing template,
v) to link neighbouring functional groups after the formation of a complementing template,
vi) to cleave one or more links between complementing elements of a complementing template without cleaving links between functional groups of a templated molecule, and vice versa, and
vii) to cleave the at least one linker separating the at least one functional entity from the at least one complementing element of a building block without cleaving the complementing template,
viii) to cleave the at least one linker separating the at least one functional entity from the at least one complementing element of a building block without cleaving the link between the functional groups of the templated molecule, and
ix) to cleave the at least one linker separating the at least one functional entity from the at least one complementing element of a building block without cleaving the complementing template and without cleaving the link between the functional groups of the templated molecule.

Provided that complementation of neighbouring coding elements is achieved, the neighbouring, functional groups of the templated molecule are capable of being linked irrespective of whether a complementing template is formed. Also, it is possible to link neighbouring functional groups and subsequently cleave the cleavable linker separating the functional entity from the complementing element defining said functional entity without cleaving the link between neighbouring functional groups of a templated molecule. Cleavable linkers are cleavable under conditions wherein a selectively cleavable linker is not cleavable. Accordingly, it is possible to cleave the cleavable linkers linking complementing elements and functional groups in a templated molecule without at the same time cleaving selectively cleavable linkers linking—in the same templated molecule—a subset of complementing elements and functional groups. It is thus possible to obtain a complex comprising a templated molecule and the template that has directed the template-mediated synthesis of the templated molecule, wherein the template and the templated molecule are linked by one or more, preferably one, selectively cleavable linker(s).

The generation of additional templated molecules can be directed by the template without any need for sequencing or any other form of characterisation. This is not possible using prior art "tags" generated by step-by-step synthesis. Accordingly, the complexes of the invention comprising a templated molecule linked to a template makes it possible to rapidly select and amplify desirable, templated molecules.

In a first aspect, the present invention provides a method for synthesising a templated molecule comprising a plurality of functional groups, said method comprising the steps of
i) providing at least one template comprising a sequence of n coding elements,
  wherein each coding element comprises at least one recognition group capable of recognising a predetermined complementing element, and
  wherein n is an integer of more than 1,
ii) providing a plurality of building blocks, wherein each building block comprises
  a) at least one complementing element comprising at least one recognition group capable of recognising a predetermined coding element,
  b) at least one functional entity comprising at least one functional group and at least one reactive group, and
  c) at least one linker separating the at least one functional entity from the at least one complementing element, iii) contacting each of said coding elements with a complementing element capable of recognising said coding element,
iv) optionally, obtaining a complementing element, and
v) obtaining a templated molecule comprising covalently linked, functional groups by linking, by means of a reaction involving reactive groups, a functional group of at least one functional entity to a functional group of another, functional entity,
   wherein the templated molecule is capable of being linked by means of a linker to the complementing template or template that templated the synthesis of the templated molecule, and
   wherein the synthesis of the templated molecule does not involve ribosome mediated translation of a nucleic acid.

In another aspect, the present invention relates to a templated molecule, a plurality of the same or different templated molecules, wherein preferably each of the templated molecules are obtainable by a method for synthesizing templated molecules according to the present invention.

As the templated molecule and the template are separate entities capable of being linked by a single linker, the invention also relates to complexes comprising a templated molecule liked to the template that templated the synthesis of the templated molecule. The template capable of templating the synthesis of the templated molecule comprises either a sequence of coding elements, or a sequence of complementing elements, in which case the template is a complementing template. Accordingly, it is possible to cleave links between functional groups of a templated molecule without cleaving a complementing template or template that templated the synthesis of the templated molecule.

In another aspect there is provided a method for synthesising a complex comprising a templated molecule linked to the template that templated the synthesis of the templated molecule, wherein the templated molecule and the complex comprising the templated molecule linked to the template that templated the synthesis of the templated molecule are obtainable by the method for synthesis thereof according to the invention.

In further aspects of the invention there is provided a composition comprising a plurality of templated molecules, wherein each or at least some of the templated molecules are linked to the template that templated the synthesis of the templated molecule, in which case there is provided a plurality of complexes each comprising a templated molecule linked to the template that templated the synthesis of the templated molecule. The compositions may also comprise a templated molecule and—unlinked thereto—the template that templated the synthesis of the templated molecule.

The amplifiability of the templated molecules of a library provides a library with a unique feature. This unique feature involves e.g. that a huge number of templated molecules can be screened by taking the library through repetitive processes of selection-and-amplification, in a parallel process where the library of molecules is treated as a whole, and where it is not necessary to characterise individual molecules (or even the population of molecules) between selection-and-amplification rounds.

It is possible according to various preferred embodiments of the invention to screen e.g. more than or about $10^3$ different templated molecules, such as more than or about $10^4$ different templated molecules, for example more than or about $10^5$ different templated molecules, such as more than or about $10^6$ different templated molecules, for example more than or about $10^7$ different templated molecules, such as more than or about $10^8$ different templated molecules, for example more than or about $10^9$ different templated molecules, such as more than or about $10^{10}$ different templated molecules, for example more than or about $10^{11}$ different templated molecules, such as more than or about $10^{12}$ different templated molecules, for example more than or about $10^{13}$ different templated molecules, such as more than or about $10^{14}$ different templated molecules, for example more than or about $10^{15}$ different templated molecules, such as more than or about $10^{16}$ different templated molecules, for example more than or about $10^{17}$ different templated molecules, such as more than or about $10^{18}$ different templated molecules.

As one may perform many repetitive rounds of parallel selection and parallel amplification processes, it is possible to enrich only e.g. 100 fold in each round, and still get a very efficient enrichment, of e.g. $10^{14}$ fold over a number of selection-and-amplification rounds (theoretically a $10^{14}$ fold enrichment is obtained after seven rounds each enriching 100 fold). To obtain a similar enrichment of $10^{14}$ fold using a non-amplifiable library, would require screening conditions allowing $10^{14}$ fold enrichment in one "round"—and this is not practically possible using state-of-the-art screening technologies. The templated molecules and/or the templates can furthermore be bound to a solid or semi-solid support.

In even further aspects the methods of the invention—individually or as a combination—relates to
a method for screening a composition of complexes or templated molecules potentially having a predetermined activity,
a method for assaying the predetermined activity potentially associated with the complexes or the templated molecules,
a method for selecting complexes or templated molecules having a predetermined activity,
a method for amplifying the template that templated the synthesis of the templated molecule having, or potentially having a predetermined activity, and
a method for amplifying the template that templated the synthesis of the templated molecule having, or potentially having, a predetermined activity, said method comprising the further step of obtaining the templated molecule in an at least two-fold increased amount.

In yet another aspect there is provided a method for altering the sequence of a templated molecule, including generating a templated molecule comprising a novel or altered sequence of functional groups, wherein the method comprises the step of mutating the template that templated the synthesis of the original templated molecule. The method preferably comprises the steps of
i) providing a first template capable of templating the first templated molecule, or a plurality of such templates capable of templating a plurality of first templated molecules,
ii) modifying the sequence of the first template, or the plurality or first templates, and generating a second template, or a plurality of second templates,
   wherein said second template(s) is capable of templating the synthesis of a second templated molecule, or a plurality of second templated molecules,
   wherein said second templated molecule(s) comprises a sequence of covalently linked, functional groups that is not identical to the sequence of functional groups of the first templated molecule(s), and optionally
iii) templating by means of said second template(s) a second templated molecule, or a plurality of such second templated molecules.

The above-mentioned method exploits that a templated synthesis (FIG. 1) in one embodiment involves a single-stranded, modifiable intermediate in the form of a template. In the case where this template comprises a nucleotide strand comprising deoxyribonucleotides or ribonucleotides, most molecular biological methods can be applied to modify the template, and therefore to modify the templated polymer.

The below-mentioned list of molecular biological methods that can be applied to the templated polymers of this invention is therefore far from comprehensive, but merely serves to illustrate that almost any relevant molecular biological method can be applied to the templated polymers as a result of the present invention.

In cases where nucleotides with non-natural bases are part of the template, some of the molecular biology methodologies may not be applicable. This will primarily depend on the substrate specificty of the enzymes involved (e.g., the Taq DNA polymerase in a PCR reaction; restriction enzyme in USE protocol; etc). Also, methods that involve an in vivo step (e.g., transformation of E. coli for amplification of plasmid DNA) may only have a limited feasibility for those nucleotides. Several nucleotides with non-natural bases are, however, known to be incorporated into oligonucleotides by several wildtype and mutant polymerases, and therefore, the use of nucleotides with non-natural bases does not seriously limit the number of in vitro molecular biology methods that can be applied to templated molecules.

TABLE 1

Molecular Biology applicable to the templated polymers of this invention

In vivo and in vitro amplification, recombination and mutagenesis
Kunkel site-directed mutagenesis, using one or multiple (e.g., 50) different mutagenic oligos at below-saturating concentrations, i.e., generating a combinatorial library
USE (Unique Site-directed Elimination), using one or multiple (e.g., 50 different mutagenic oligos) at below-saturating concentrations, i.e., generating a combinatorial library
PCR (Polymerase Chain Reaction)
LCR (Ligase Chain Reaction)
PCR shuffling, including family shuffling (shuffling sequences containing blocks with particular homology), and directed shuffling where oligos are spiked into the reaction to direct the shuffling process in a certain direction
Other types of shuffling, e.g. homologous recombination in yeast; shuffling protocols as developed at the companies Phylos, Energy Biosystems, Diversa and by Frances Arnold.
Cassette mutagenesis
Other polymerase- or PCR-based methods, e.g., overlap extension, gene synthesis, and error-prone PCR
Chemical or UV-induced mutagenesis
Wildtype or variant template synthesis and translation into templated polymer (wildtype in this respect means the template sequence that will template the synthesis of the known ("wildtype") polymer; variant in this respect means a partly randomised or spiked template sequence that will template the synthesis of a variant of the known polymer)
Specific cleavage by restriction enzymes
Ligation by DNA or RNA ligases; "gene splicing"
Affinity selections (using the template-templated polymer complex)
Sequencing
Arraying the polymers on "DNA chips", by using the template as a tag that binds a DNA array Instead of isolating the (underivatized) template strand, it may be desirable to apply the molecular biological methods to either the template-complementing template double-helix or to the derivatized complementing template. The derivatized template may at this point contain unpolymerized functional entities; polymerized functional entities; or a trace left behind from the cleaving of the linker that connected the functional entity and the complementing element. Many polymerases and other enzymes are known to accept DNA- or RNA-templates with a high degree of derivatization. Therefore, many in vitro methods involving polymerases and other enzymes are likely to be feasible using the (derivatized) complementing template as starting point. It will primarily depend on the substrate- or template specificity of the enzymes involved whether it will be feasible to use the derivatized complementing template as a starting point for the molecular biological method in question. The skilled person will be capable of evaluating the feasibility of various practical approaches in this respect.

The present invention also pertains to building blocks used for synthesising the templated molecule and to complexes comprising such building blocks. In another aspect there is provided the use of a building block for the synthesis of a templated molecule according to the invention. In a preferred embodiment of this aspect, the templated molecule comprises or essentially consists of a molecular entity capable of binding to another molecular entity in the form of a target moleculer entity or a binding partner.

The templated molecule is preferably a medicament capable of being administered in a pharmaceutically effective amount in a pharmaceutical composition to an individual and treating a clinical condition in said individual in need of such treatment.

In other aspects of the invention there are provided a pesticidal composition, an insecticidal composition, a bacteriocidal composition, and a fungicidal composition, as well as methods for preparing such compositions and uses thereof, wherein each of said compositions comprise a templated molecule according to the invention in an amount effective to achieve a desired effect.

In still further aspects there is provided a method for identifying a pharmaceutical agent, or a diagnostic agent, wherein said method comprises the step of screening a plurality of drug targets with at least one predetermined, templated molecule, and identifying a pharmaceutical agent, or a diagnostic agent, in the form of candidate templated molecules capable of interacting with said drug targets.

In yet another aspect there is provided a method for identifying a target, including a drug target, wherein said method comprises the step of screening a plurality of ligands or receptor moieties with at least one predetermined, templated molecule, and identifying drug targets in the form of ligands or receptor moieties capable of interacting with said templated molecules.

The present invention also relates to any isolated or purified templated molecule having an affinity for a predetermined target, including a drug target, as well as to targets, including drug targets, in the form of ligands, receptor moieties, enzymes, cell surfaces, solid or semi-solid surfaces, as well as any other physical or molecular entity or surface having an affinity for a predetermined templated molecule.

In even further aspects of the invention there is provided a method for treatment of an individual in need thereof, said method comprises the step of administering to the individual a pharmaceutically effective amount of a molecule identified by a method of the present invention and having an affinity for a predetermined target, including a drug target.

In a still further aspect there is provided a method for treatment of an individual in need thereof, said method comprises the step of administering to the individual a pharmaceutically effective amount of an isolated or purified ligand or receptor moiety having an affinity for a predetermined templated molecule according to the invention. The isolated or purified ligand or receptor moiety is preferably identified by the above-mentioned method of identification of the invention.

The present invention may be performed in accordance with several embodiments. In a first embodiment the step of contacting the complementing element with the coding element involves one or more polymerases or transcriptases. Thus, in accordance with this embodiment the building blocks is a nucleotide derivative. In one aspect of this first embodiment, the building blocks are mononucleotides, however the building blocks may be a di- or oligonucleotides. While mononucleotides are the natural substrate for polymerases and transscriptses, oligonucleotides are incorporable in accordance with the method of WO 01/16366. The mono- or oligonucleotide derivative serves as the complementing element. One or more linker(s) is/are attached at one end to the mono- or oligonucleotide derivative and at the other end to a functional entity. Especially, in the case in which the complementing element is a mononucleotide derivative, it is preferred that the linker is attached so that the functional entity is projecting into the major groove of a double stranded helix to allow adjacent functional entities to form a linkage to each other.

In a second embodiment of the invention, building blocks comprising an mono- or oligonucleotide as complementing element are chemically ligated together. Several methods for chemical ligation are know in the art, such as the 5'-phospho-imidazolid method (Visscher, J.; Schwartz, A. W. Journal of Molecular Evolution 1988, 28, 3-6. And Zhao, Y.; Thorson, J. S. J. Org. Chem. 1998, 63, 7568-7572) or the 3'-phosphothioate method (Alvarez et al. J. Org. Chem. (1999), 64, 6319-28 Pirrung et al. J. Org. Chem. (1998), 63, 241-46).

In a third embodiment of the invention, building blocks comprising an oligonucleotide as complementing element is ligated together using a ligase enzyme.

In a fourth embodiment of the invention, the building blocks comprise an oligonucleotide as complementing element, said oligonucleotide having a sufficient length to adhere to the template without the need for ligation to a primer or an other complementing element.

The building blocks are in general adapted to the method used for contacting the complementing element with the template and production of the templated molecule. As an example, the linker may be relatively short when a mononucleotide derivative is used, while the linker needs to be considerable longer when an oligonucleotide is used as building block.

BRIEF DESCRIPTION OF THE FIGURES

The following symbols are used in the following figures to indicate general characteristics of the system: In FIGS. 1, 7C, 8C, 11, 11 ex.1, 12, 13, 14, 14 ex. 1-2, 15, 15 ex. 1-7, 17, 17 ex. 1, 17, 17 ex. 1-2, 19, 19 ex. 1-3, 20, 21, and 22A, a long horizontal line symbolizes a template, complementing template or the complex of the template with the complementing template. For clarity, in some of the figures only the polymerization step, not the activation step, has been included. Rx denotes functional groups.

FIG. 1. Chemical Display of Templated Molecules—The principle.

The protocol for the chemical display of templated molecules can be divided into 6 steps, i) incorporation, ii) polymerization, iii) activation, iv) selection/screening, v) amplification, and vi) characterization. Incorporation involves the incorporation of building blocks into the complementing template, which sequence is determined by the template.

Incorporation may be mediated by enzymes such as polymerase or ligase. The template comprises primer binding sites at one or both ends (allowing the amplification of the template). The remaining portion of the template may be of random, partly random or predetermined sequence. The complementing elements preferably comprises of a functional entity, a complementing element and a linker connecting the functional entity and the complementing element. Detailed examples of selected complementing elements, their incorporation, polymerization and activation are shown in (FIGS. 7 and 8).

Polymerization involves reactions between the incorporated building blocks, thereby forming covalent bonds between the functional entities, in addition to the functional bonds that already exist between the complementing elements.

Activation involves cleaving some, all but one, or all of the linkers that connect the sequence of functional entities to the template or complementing template having templated the templated molecule comprising the functional entities. Activation may also involve separating the template and the complementing template without cleaving the linkers connecting the functional entities and the complementing template.

Selection or screening involves enriching the population of template-templated molecule pairs for a desired property.

Amplification involves producing more of the template-templated molecule pairs, by amplification of the template or complementing template, and producing more of the template-templated molecule pairs, for further rounds of selection/screening, or for sequencing or other characterization.

Cloning and sequencing involves the cloning of the isolated templates or complementing templates, followed by characterization. In some cases, it may be desirable to sequence the population of isolated templates or complementing templates, wherefore cloning of individual sequences are not required.

FIGS. 2A and 2B. An expanded set of base pairs.

The figure discloses a set of natural and non-natural base pairs that obeys Watson-Crick hydrogen-bonding rules. The base pairs are disclosed in U.S. Pat. No. 6,037,120, incorporated herein by reference.

Figure 3:
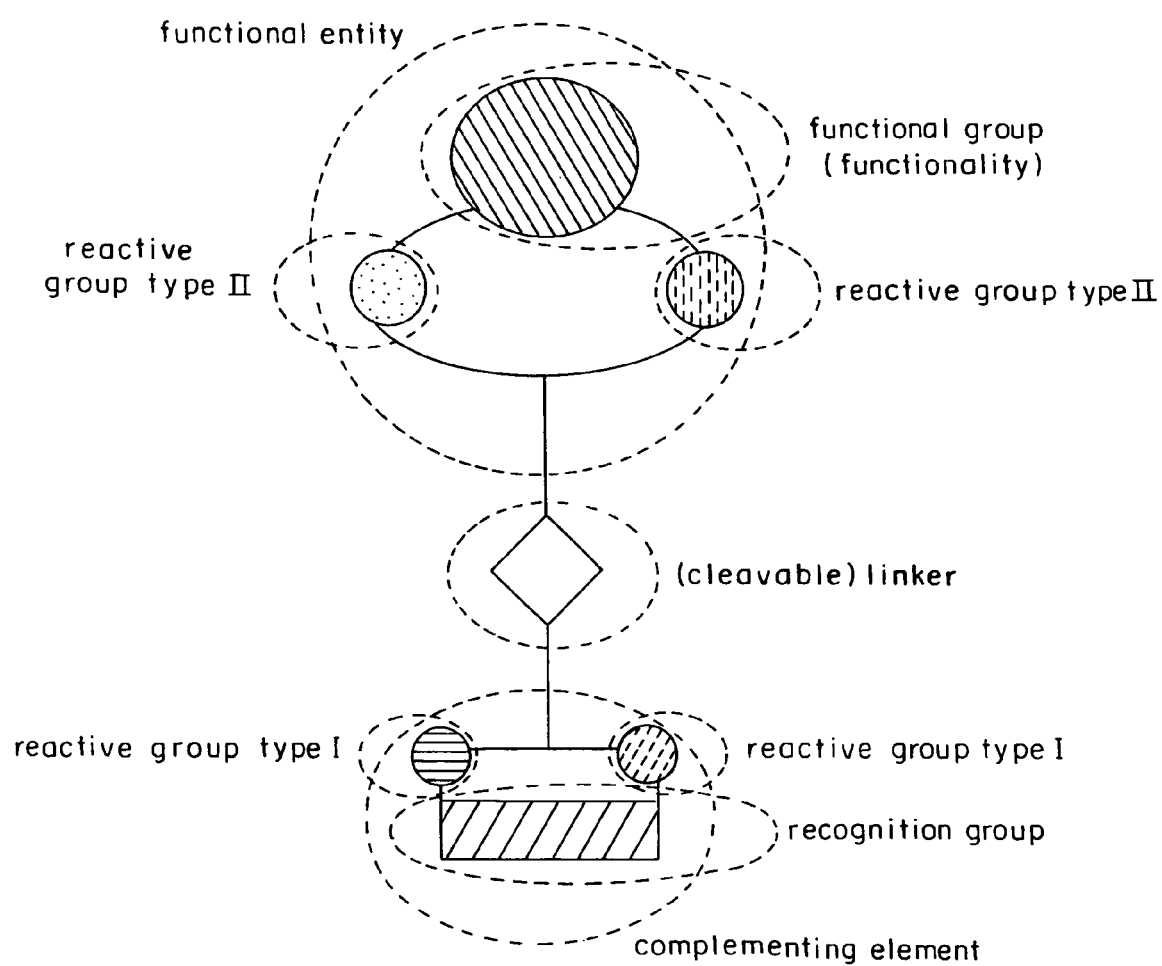

FIG. 3. A monomer building block.

A building block comprises or essentially consists of a functional entity, connected through a selectively cleavable linker to a complementing element. Each complementing element has two reactive groups (type I), which may react with two other complementing elements. The complementing element contains a recognition group that interacts with a complementary coding element (coding element not shown). The functional entity in this example comprises or essentially consists of two reactive groups (type II), which may react with reactive groups of other functional entitie(s), and a functional group, also called a functionality. The reactive groups of type II, and the molecular moiety that connects them, will become (part of) the backbone in the resulting encoded polymer.

Figure 4:
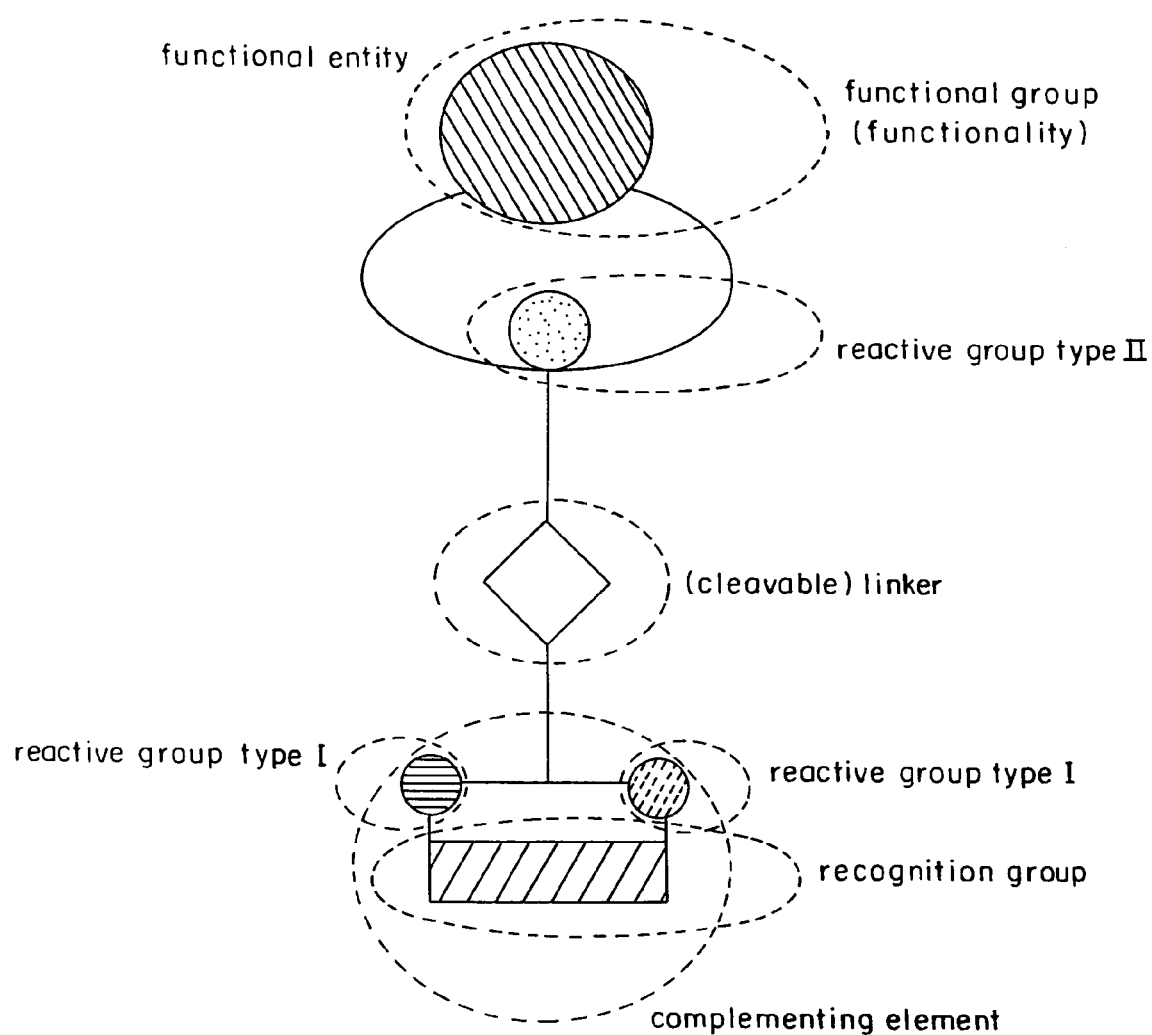
Figure 5A:
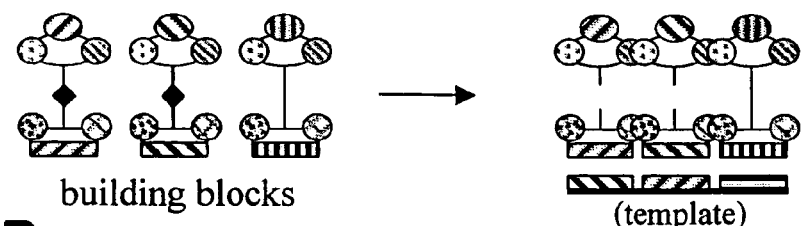
Figure 5B:
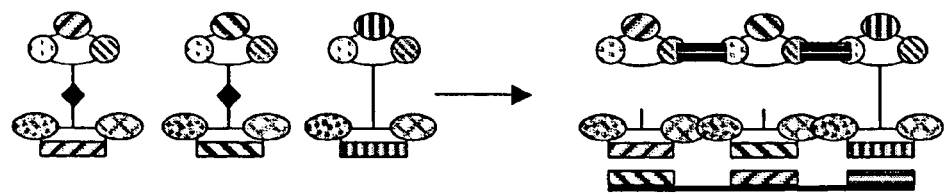
Figure 5C:
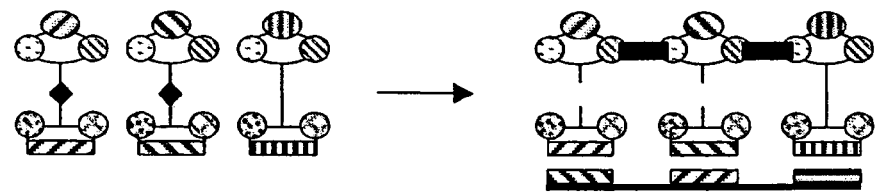
Figure 5D:
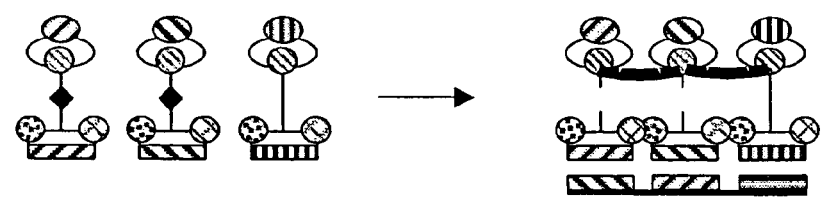

FIG. 4. A monomer building block with only one reactive group type II.

A building block comprises or essentially consists of a functional entity, connected through a selectively cleavable linker to a complementing element. Each complementing element has two reactive groups (type I), which may react with other complementing elements. The complementing element contains a recognition group that interacts with a complementary coding element (coding element not shown). The functional entity in this example comprises or essentially consists of a reactive group type II, which may react with reactive groups of other functional entities, and a functional group, also called a functionality. The reactive group type II will become (part of) the backbone in the resulting encoded polymer.

FIG. 5. Building blocks and the polymers resulting from template directed incorporation of the building blocks and their polymerization and activation FIG. 3 discloses a detailed description of features of individual building blocks. Three different complementing elements are shown, each linked to a specific functional entity. The right half of the figure includes the template which directs the incorporation of the building blocks by complementary base pairing.

A). The reactive groups type I of the complementing element react, whereby a part of the reactive group is lost (e.g., $PP_i$ in the incorporation of nucleoside triphosphates). In the shown example, the polymerization of reactive groups type II also results in loss of part of the reactive groups. The backbone of the resulting polymer comprises or essentially consists of part of the original reactive groups type II and the molecular entity that connects the reactive groups. Part of the linker remains attached to the functional entity.

B). The reactive groups type I react as in (A). The reactive groups type II do not react directly, but rather a "bridging molecule" is added. Upon reaction with this bridging molecule, part of the reactive group is lost. The cleavable linker used in this example is a so-called "traceless linker" and therefore the functional entity is released with no trace of the linker molecule.

C). Incorporation in this case does not involve coupling of the individual complementing elements, i.e., does not lead to the reaction of the reactive groups type I. The reactive groups type II react with bridging molecules as in (B).

D). The functional entity contains only one reactive group type II. The reactive group type II reacts with a bridging molecule.

FIG. 6. A derivatized nucleotide as building block

The nucleotide building block comprises or essentially consists of the complementing element (the nucleotide) and a functional entity (in this case a dicarboxylic acid) connected by means of a selectively cleavable linker (here a disulfide). The reactive groups type I of the nucleotide are the triphosphate and the hydroxyl group, as indicated. The recognition group of the nucleotide is the base. The functional entity comprises or essentially consists of a functional group (a hydroxyl), two reactive groups type II (carboxylic acids), and a backbone structure (aromatic ring) connecting the two reactive groups. Finally, the linker (disulfide) is cleavable by for example DTT.

A Derivatized Di-nucleotide as Building Block

The complementing element is a modified dA-dU di-nucleotide that comprises the recognition group, in this case the adenine and uracil bases. It is connected to the functional entity (here an amino acid) via a cleavable propargylester linkage. Upon basic cleavage, the linker releases the functional group, a carboxylic acid. The reactive groups of type I of the di-nucleotide are the hydroxyl group and the phophoro(2-methyl)imidazolide. Reactive groups of type II are the amino group and the carboxylic acid of the amino acid as indicated.

A Derivatized Oligo-nucleotide as Building Block

The complementing element is the last 20 bases of the oligonucleotide shown. It is linked to the functional entity, a N-Boc beta amino acid, via an oligo-nucleotide comprising 40 bases (B is an internal biotin incorporated using the commercially available phosphoramidite (10-1953-95 from Glen research) including a cytosine deoxyribonucleotide that has been modified at the 5'-phosphato group with a mercaptohexane spacer connected to an N-hydroxysuccinimid moiety. Reactive group of type II is the carboxylic acid bound to the oxygen atom of the N-hydroxysuccinimid moiety. It is susceptible to nucleophillic attack by e.g. an amine.

FIG. 7. C-terminal tagging of a β-dipeptide—incorporation, polymerization and activation.

A) Structures of the primer and two monomer building blocks. The initiator molecule is attached to the 5-position of the 3'-terminal dU of the primer. The initiator is a Fmoc-protected amine. The dUTP-derivative carries a photoprotected hydroxyl group. The hydroxyl group is coupled to the N-thiocarboxyanhydride (NTA) ring structure. The dATP-derivative is modified at the 7 position. A photoprotected amine is coupled the NTA.

B) The primer (which is annealed to the template, not shown in figure) is extended from its 3'-end through incorporation of the dUTP and dATP by a polymerase. Then the initiator is activated by piperidine, which releases the primary amine. The primary amine attacks the neighboring NTA, which opens the NTA rings structure, releases CSO, and as a result, produces a primary amine. This primary amine now attacks the next NTA unit in the array. As a result, a polymer, attached through its functional groups (OH and $NH_2$) to the DNA strand, is formed. Finally, the linkers connecting the DNA strand with the NTA units, are cleaved. The resulting polymer in this case is a β-peptide, carrying the functional groups OH and $NH_2$, encoded by the DNA sequence dUdA. In the shown example, the sequence 5'-dUdA-3' encodes a β-peptide in the C-terminal to N-terminal direction, as opposed to Natures encoding system where 5' to 3' RNA encodes an α-peptide in the N- to C-terminal direction. The β-peptide is attached to the encoding DNA through its C-terminal end.

C) Schematic representation of the incorporation, polymerisation and activation. The encoded polymer becomes attached to the encoding molecule (DNA) through the initiator molecule.

FIG. 8. N-teminal tagging of a β-dipeptide—incorporation, polymerization and activation.

A) Structures of the primer, two monomer building blocks, and an oligo. The initiator molecule is attached to the 5-position of the 3'-terminal U of the primer. The primer is complementary to the upstream part of the template. The initiator is a Fmoc-protected amine. The UTP-derivative carries a photoprotected hydroxyl group. The hydroxyl group is attached to the N-thiocarboxyanhydride (NTA) ring structure. The ATP-derivative is modified at the 7 position. A photo-protected amine is attached to the NTA. The oligo is complementary to the downstream sequence of the template. The oligo carries a reactive thioester attached to the U at the oligo's 5'end. The stability of the thioester in water can be modified as desired by changing the structure of the thioester-component (in the example, the thiol-component is a thiophenol).

B) The primer (which is annealed to the template, not shown in figure) is extended from its 3'-end through incorporation of the UTP and ATP by a polymerase. Then the initiator is activated by piperidine, which releases the primary amine. The primary amine attacks the neighboring NTA, which opens the NTA rings structure, releases CSO, and as a result, produces a primary amine. This primary amine now attacks the next NTA unit in the array. As a result, a polymer, attached through its functional groups (OH and $NH_2$) to the RNA strand, is formed. Finally, the linkers connecting the RNA strand with the NTA units are cleaved. The resulting polymer is a β-peptide, carrying the functional groups —OH and —NH$_2$, encoded by the ribonucleic acid sequence UA. The sequence 5'-UA-3' encodes a β-dipeptide in the N-terminal to C-terminal direction, similar to the way that Nature encodes α-peptides. The β-peptide is attached to the encoding RNA through its N-terminal end.

C) Schematic representation of the incorporation, polymerisation and activation. Upon cleavage of a subset of linkers, the encoded polymer becomes attached to the downstream oligonucleotide.

FIG. 9. Nucleotide-derivatives that are known to be incorporated into RNA or DNA strands by DNA or RNA polymerases.

Top: Nucleotide, the four bases and the site of attachment of the molecular moiety (R).

Center: Nucleotides with appendices (R) that are accepted as substrates by polymerases.

Bottom: Nucleotides with appendices (R) that may be used with the present invention. Compound (a) would be used in for example fill-in experiments (see FIG. 15). Compound (b) would be used for example in zipping polymerization reactions (see FIGS. 14 and 14, example 1). Compound (c) would be used for example in ring-opening polymerization reactions (see FIGS. 18 and 18, example 1).

FIG. 10. Cleavable linkers and protection groups.

Cleavable linkers and protection groups, agents that may be used for their cleavage and the products of cleavage.

FIG. 11. Polymerization by reaction between neighboring reactive groups type II.

For clarity, only the polymerization reaction (and not the activation) is shown in the figure. X represents the reactive groups type II of the functional entity. In this case the two reactive groups type II are identical.

Polymerization (reaction of X with X to form XX) either happens spontaneously when the monomer building block has been incorporated, or is induced by a change of conditions (e.g. pH), or by the addition of an inducing factor (chemical or UV exposure, for example)

FIG. 11 ex.1. Coumarin-based polymerization.

Light-induced reaction of the coumarin units, followed by activation (cleavage of the linker), results in a polymer backbone of aromatic and aliphatic ring structures. Examples of functional groups (phosphate, carboxylic acid and aniline) are shown.

FIG. 12. Polymerization between neighboring non-identical reactive groups type II.

In this example, X may react with Y but not another X. Likewise, Y does not react with Y. Polymerization can either happen during the incorporation of building blocks (as shown in the figure), or after incorporation of several building blocks.

FIG. 13. Cluster formation in the absence of directional polymerisation.

When the incorporated monomers are not fixed with regard to rotation about the bond that links the functional entities to the complementing elements, cluster formation may result, as shown in the figure.

This represents a significant problem for longer polymers. The problem may be solved by (i) fixing the incorporated monomers in a preferred orientation which does not allow X and Y (reactive groups type II) to exchange positions in the array (e.g., by coupling the functional entity and the complementing element via a double bond or two bonds, e.g. coupling the functional entity both to the base and the ribose of a nucleotide, or to the two bases of a dinucleotide), (ii) employing directional polymerisation ("zipping", see for example FIG. 17), or (iii) setting up conditions that ensure that the monomers react during or right after incorporation into the complementing template, i.e., each monomer reacts with the previously incorporated monomer before the next monomer is incorporated (see for example FIG. 14, with example).

FIG. 14. Zipping-polymerization and simultaneous activation.

Polymerization results in activation of the polymer. The geometry of the reaction between X and Y is in this example the same for all monomers participating in the polymerization FIG. 14, example 1. Simultaneous incorporation, polymerisation and activation—formation of peptides.

(A). Nucleotide derivatives, to which amino acids thioesters have been appended, are incorporated. During or after incorporation of a nucleotide-derivative, the amine attacks the carbonyl of the (previously incorporated) neighboring nucleotide. This results in formation of an amide bond, which extends the peptide one unit. When the next monomer is incorporated, this may attack the thioester carbonyl, resulting in cleavage of the dipeptide from the nucleotide, to form a tripeptide. The process continues further downstream the complementing template, until incorporation of nucleotide derivatives stops. Importantly, the geometry of the nucleophilic attack remains unchanged. As the local concentration of nucleophilic amines is much higher on the template than in solution, reactions in solution is not expected to significantly affect the formation of the correct encoded polymer. Furthermore, the reactivity of the amine with the ester may be tuned in several ways. Parameters that will affect the reactivity include: (i) pH and temperature, (ii) length, point of attachment to the nucleotide, and characteristics (charge, rigidity, hydrophobicity, structure) of the linker that connects the ester and the nucleotide, (iii) nature of ester (thio-, phospho-, or hydroxy-ester); (iv) the nature of the substituent on the sulfur (see (B) below). In addition, the efficiency of correct polymer formation is also affected by the rate of incorporation and rate of reaction once incorporated. The rate of incorporation is determined by kcat and Km. The kcat and Km values may be tuned by changing the conditions (pH, concentration of nucleotides, salts, templates and enzymes), by choice of enzyme, or by changing the characteristics of the enzyme by protein engineering. Also, the nature and size of the nucleotide-derivatives may influence its rate of incorporation.

This general scheme involving incorporation, polymerisation and activation during or right after building block incorporation, can be applied to most nucleophilic polymerisation reactions, including formation of various types of peptides, amides, and amide-like polymers (e.g., mono-, di-, tri-, and tetra-substituted α-, β-, γ-, and Ω-peptides, polyesters, polycarbonate, polycarbamate, polyurea), using similar structures.

(B). Four different thioesters with different substituents and therefore different reactivity towards nucleophiles.

FIG. 14, example 2. Simultaneous incorporation, polymerization and activation—formation of a polyamine.

This figure shows a "rolling-circle polymerization reaction" where the chain containing the nucleophilic center attacks the electrophile attached to the DNA-part, using this DNA-part as the leaving group.

FIG. 15. "Fill-in" polymerization (symmetric xx monomers).

Fill-in polymerization by reaction between reactive groups type II ("X" in the figure) and bridging molecules (Y-Y) in figure).

For clarity, only the polymerization reaction (not the activation) is shown in the figure. The thick line represents double or single stranded nucleic acid or nucleic acid analog. X represents the reactive groups type II of the functional entity. In this case the two reactive groups type II are identical. (Y-Y) is added to the mixture before, during or after incorporation of the monomer building blocks. Likewise, significant reaction between X and Y may take place during or after incorporation of the monomers.

FIG. 15, ex.1. Poly-imine formation by fill-in polymerization.

Dialdehyde is added in excess to incorporated diamines. As a result, a poly-imine is formed. In the example, the polymer carries the following sequence of functional groups: cyclopentadienyl, hydroxyl, and carboxylic acid.

FIG. 15, example 2. Polyamide formation.

After incorporation of nucleotides to which have been appended di-amines, EDC (1-Ethyl-3-(3-dimethylaminopropyl)carbodiimide) and dicarboxylic acid is added in excess to the primary amines on the oligonucleotide using standard coupling conditions. Alternatively, a di-(N-hydroxy-succinimide ester) may be added in excess, at a pH of 7-10. As a result, two amide-bonds are formed between two neighboring nucleotide-appendices. After this polymerisation, the appendices are separated from the oligonucleotide backbone (activation), leaving one linker intact, and the protected functional groups are deprotected to expose the functional groups. The final result is a DNA-tagged polyamide.

An alternative route to polyamides would be to incorporate nucleotides to which had been appended di-carboxylic acids, and then add di-amines and EDC, to form amide bonds between individual nucleotides of the oligonucleotide. Alternatively, the nucleotide derivatives might contain N-hydroxy-succinimidyl (NHS) esters, which would react with the added amines without the need to add EDC. Initially, this latter method was considered to be problematic in the case where incorporation is mediated by a polymerase, as the NHS-esters probably would react with amines on the polymerase, potentially inhibiting the activity of the polymerase. However, practical experiments have shown that it is possible to incorporate NHS-derivatised nucleotides.

(A). The backbone of the resulting polymer comprises or essentially consists of amide-bonded aromatic rings. The substituents of this example are a protected primary amine, a branched pentyl group, a tertiary amine and a pyrimidyl. The primary amine is protected in order to avoid its reaction with the dicarboxylic acid. Appropriate protecting groups would be for example Boc-, Fmoc, benzyloxycarbonyl (Z, cbz), trifluoroacetyl, phthaloyl, or other amino protecting groups described e.g. in (T. W. Green and Peter G. M. Wuts (1991), Protective Groups in Organic Synthesis).

(B). The backbone comprises or essentially consists of aromatic rings, connected by amide bonds. The substituents are indanyl, diphenylphosphinyl, carboxamidoethyl and guanidylpropyl, the latter two representing the asparagine side chain, and the arginine side chain, respectively. The guanidyl function is protected, as it is more reactive than standard amines. An appropriate protecting group would be Mtr (4-methoxy-2,3,6-trimethylbenzenesulfonyl), Mts (mesitylene-2-sulfonyl) or Pbf (2,2,4,6,7-pentamethyldihydro-benzifuran-5-sulfonyl).

FIG. 15, example 3. Polyurea formation.

The incorporated nucleotide derivatives react with phosgen or a phosgen-equivalent such as CDI to form a polyurea. The linkers are cleaved and the protected hydroxyl is deprotected.

Appropriate leaving groups (Lv) are chloride, imidazole, nitrotriazole, or other good leaving groups commonly employed in organic synthesis FIG. 15, Example 4. Chiral and achiral polyurea backbone formation.

In this example, the functional group Rx is used as a cleavable linker, that generates the desired functional group upon activation. In both (A) and (B), a polyurea is formed.

In (A), the functional group is attached to the backbone via a chiral carbon. The hydrogen on this carbon is drawn to emphasize this. Before polymerisation, there is free rotation about the bond connecting the chiral carbon and the functional group. When the reactive groups type II (the amines) react with the phosgen equivalent (e.g., a carbonyldiimidazole) to form the polymer, the building blocks may be inserted in either of two orientations (as indicated by the position of the hydrogen, left or right). As a result, each residue of the polymer has two possible chiral forms. Therefore, a given encoding molecule will encode a polymer with a specific sequence of residues, but an encoded polymer of 5 or 15 residues will have $2^5=32$ or $2^{15}=32768$ stereoisomers, respectively. In certain cases it may be advantageous to incorporate such additional structural diversity in the library (for example when the polymer is relatively short). In other cases such additional diversity is not desirable, as the screening efficiency may become compromised, or it may become too difficult to deconvolute the structure of a polymer that has been isolated in a screening process, together with the other stereoisomers encoded by the same encoding molecule (for example when the polymer is long).

In (B), the chiral carbon of (A) has been replaced by a nitrogen. As a result, the resulting polymer backbone is achiral, and the encoding molecule encodes one specific structure.

FIG. 15, example 5. Polyphosphodiester formation.

The incorporated nucleotide derivatives react with the activated phosphodiester to form a polyphosphodiester. Then the linkers are cleaved, resulting in a polyphosphodiester, attached through a linker to the encoding molecule.

An example of an appropriate leaving groups (Lv) is imidazole.

FIG. 15, example 6. Polyphosphodiester formation with one reactive group type ii in each monomer building block.

Each incorporated nucleotide contains an activated phosphodiester. Upon addition of a dihydroxylated compound such as 1,3-dihydroxypyridine, a functionalised polyphosphodiester is formed. Finally, the functional groups Rx are liberated from the complementing template by cleavage of the protection groups/cleavable linker that connected them to the oligonucleotide.

FIG. 15, example 7. Pericyclic, "fill-in" polymerization.

After incorporation of the nucleotide-derivatives, 1,4-benzoquinone is added in excess, resulting in the formation of a polycyclic compound. Finally, the polymeric structure is activated by cleaving the linkers that connect the polymer to the nucleotides, except for one (non-cleavable) linker which is left intact.

FIG. 16. Encoded "Fill-in".

Fill-in by encoding is performed by the method depicted. The encoded fill-in moiety is the Y—$R_x$—Y of the second building block. Using this method it is possible to link two functional entities X—$R_x$—X by a predetermined functional entity Y—$R_x$—Y. In some embodiments this may be of advantage because the encoded fill-in functional entity Y—$R_x$—Y does not have to be the same through out the molecule, as is the case for the method shown in FIG. 15.

Figure 17A:
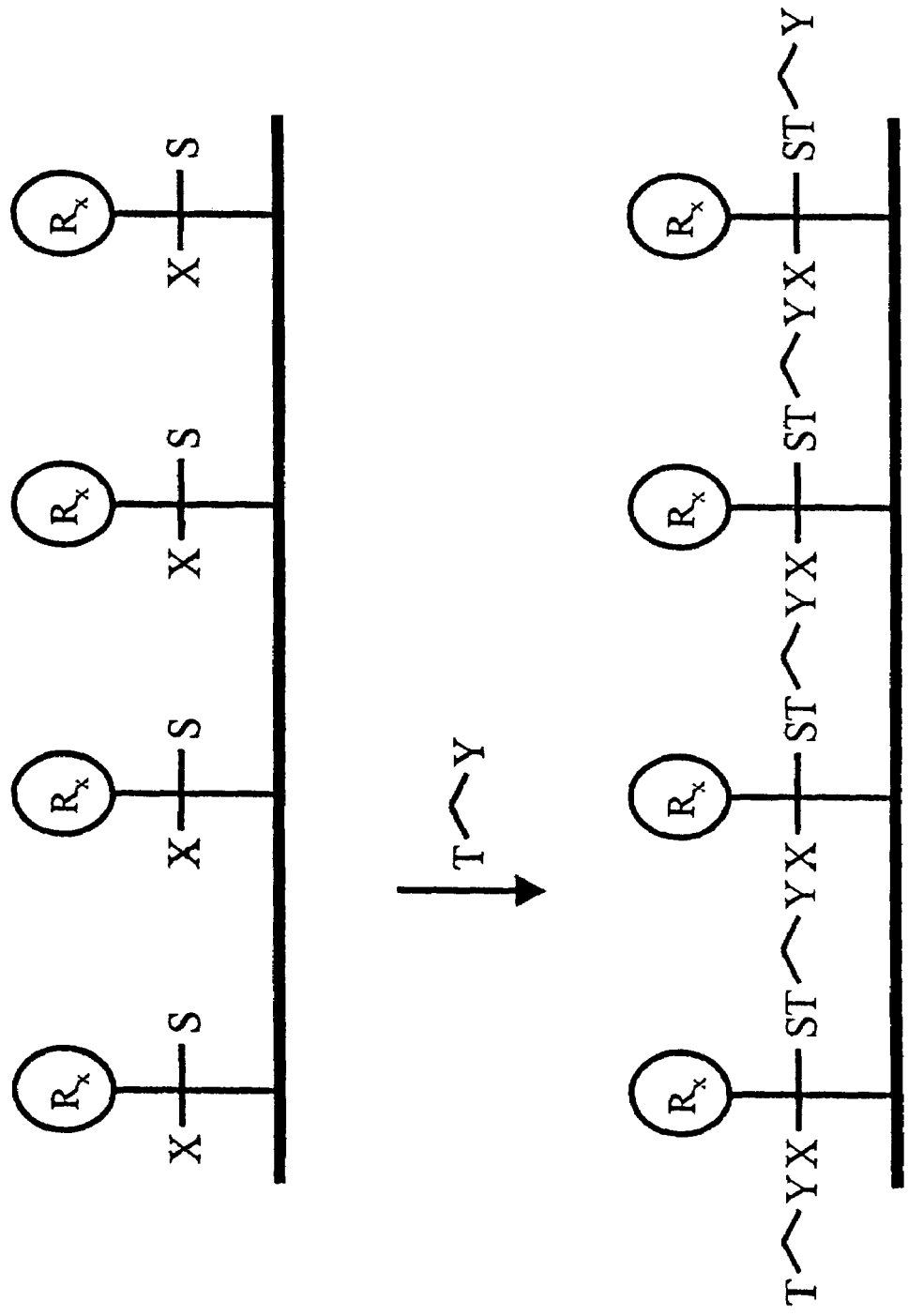

FIG. 17A. "Fill-in" polymerization (asymmetric XS monomers).

Fill-in polymerization by reaction between reactive groups type II ("X" and "S" in the figure) and bridging molecules (T-Y) in figure).

For clarity, only the polymerization reaction (not the activation) is shown. The thick line represents double or single stranded nucleic acid or nucleic acid analog. X and S represent the reactive groups type II of the functional entity. In this case the two reactive groups type II are non-identical. (T-Y) is added to the mixture before, during or after incorporation of the monomer building blocks. Likewise, significant reaction between X and Y, and between S and T may take place during or after incorporation of the monomers.

Figure 17B:
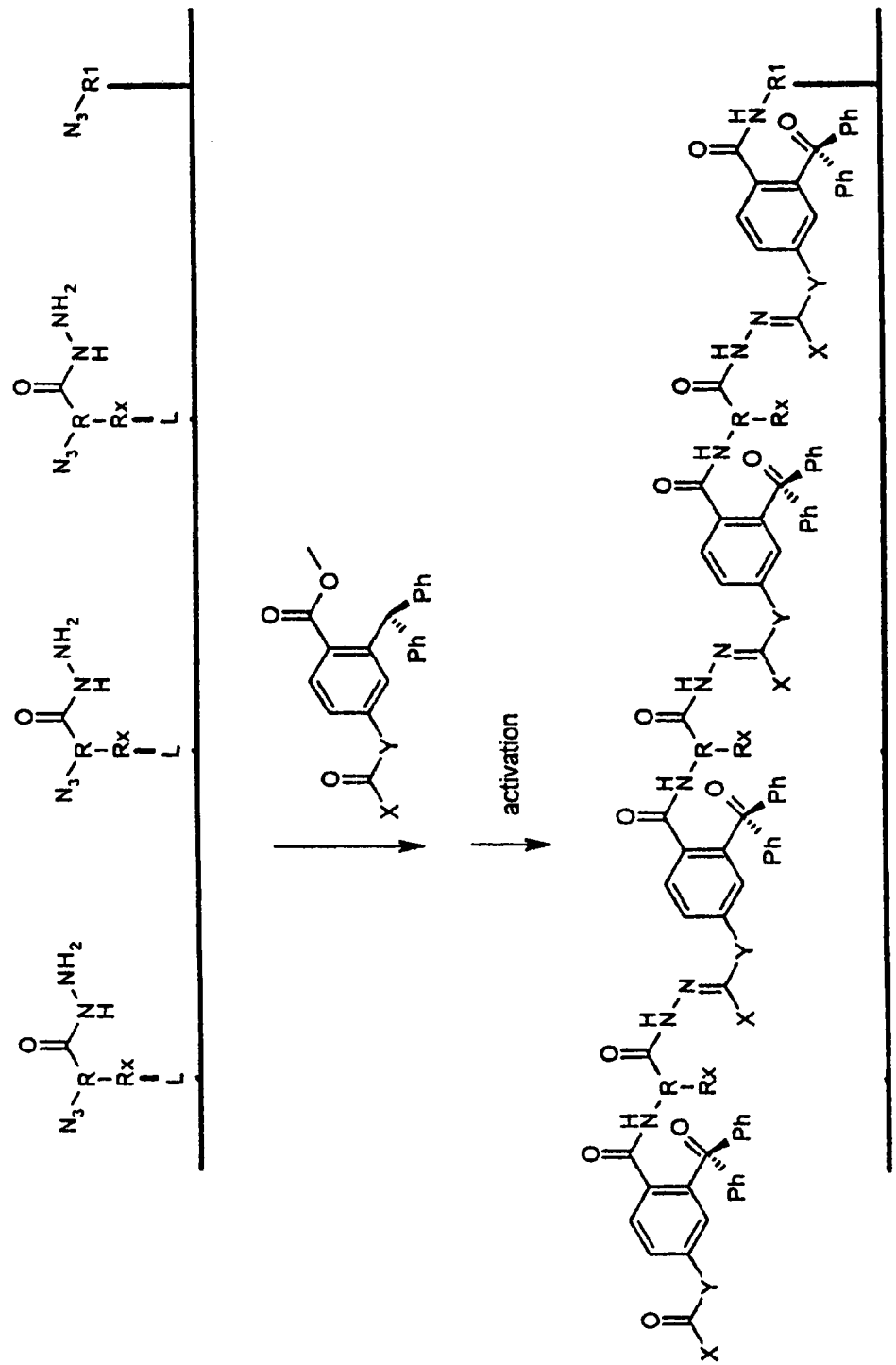

FIG. 17B. Fill-in polymerization by modified Staudinger ligation and ketone-hydrazide reaction.

The reactive groups (type II) X and S of the building blocks are azide and hydrazide. The added molecule that fills the gaps between the building blocks carry a ketone and a phosphine moiety. The reactions between a ketone and a hydrazide, and between a azide and a phosphine, are very chemoselective. Therefore, most functional groups Rx can be employed without the need for protection during the polymerization reactions. Examples for the molecular moieties R, R1, X and Y may be found in (Mahal et al. (1997), Science 276, pp. 1125-1128; Saxon et al. (2000), Organic Letters 2, pp.2141-2143).

FIG. 18A. "Zipping" polymerization.

The initiator molecule (typically located at one of the ends of the nascent polymer) is activated, for example by deprotection or by a change in pH. The initiator then reacts with the reactive group X of the neighbouring monomer. This activates the reactive group Y for attack on the neighbouring X. Polymerisation then travels to the other end of the molecule in a "zipping" fashion, until all the desired monomers have been connected. The activation of the initiator (and reactive groups Y) may be both for attack by it on the neighbouring reactive group, or activation of it for attack by the neighbouring reactive group.

FIG. 18B, example 1. Radical polymerization.

The initiator molecule, an iodide, is activated by the addition of a radical initiator, for example ammonium persulfate, AIBN (azobis-isobutyronitrile) or other radical chain reaction initiators. The radical attacks the neighboring monomer, to form a new radical and a bond between the first two monomers. Eventually the whole polymer is formed, and the polymer may be activated, which simultaneously creates the functional groups Rx.

FIG. 18C, example 2. Cationic polymerisation.

A cation is created by the exposure of the array to strong Lewis acid. The double bond of the neighbouring monomer reacts with this cation, whereby the positive charge migrates to the neighbouring monomer. Eventually the whole polymer is formed, and finally it is activated.

Figure 19A:
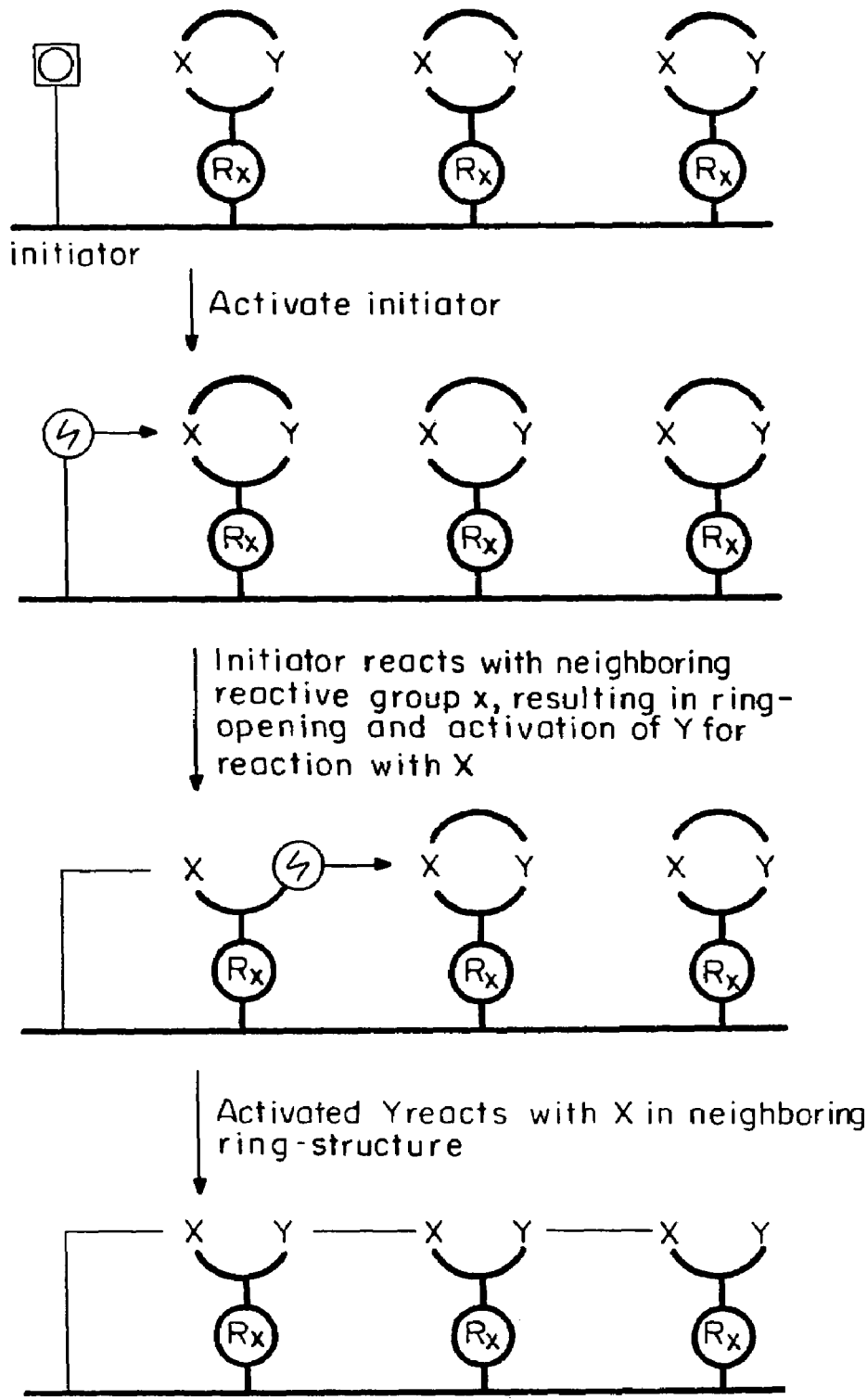

FIG. 19A. Zipping polymerization by ring opening.

The initiator reacts with the reactive group X in the ring structure, which opens the ring, whereby the reactive group Y in the same functional entity is activated for reaction with a reactive group X in a neighboring functional entity.

Figure 19B:
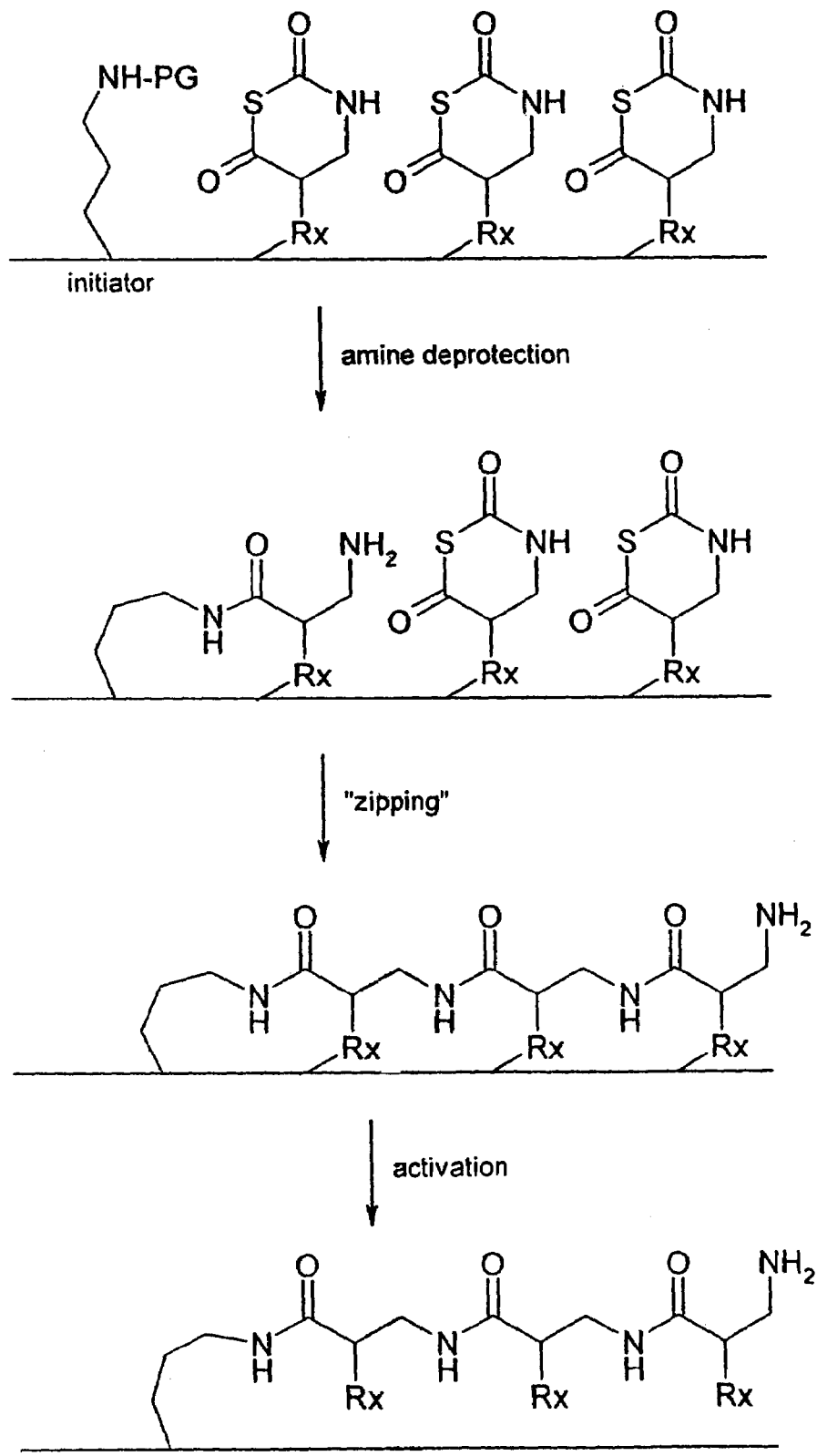

FIG. 19B. "Zipping" polymerization of N-thiocarboxyanhydrides, to form β-peptides.

After incorporation of the building blocks, the initiator is deprotected. The primary amine then attacks the carbonyl of the neighbouring N-thiocarboxyanhydride (NTA) unit. As a result, CSO is released, and a primary amine is generated. This amine will now react with the next NTA unit in the array, and eventually all the NTA units will have reacted, to form a b-peptide. Finally, the oligomer is activated.

A number of changes to this set-up can be envisaged. For example, instead of thiocarboxyanhydrides, one might use carboboxyanhydrides. The initiator might be protected with a base- or photolabile group. If a base-labile protection group is chosen, the stability of the carboxyanhydride must be considered. At higher pH it may be advantageous to use carboxyanhydrides rather than thiocarboxyanhydrides. Finally, the initiator might be unprotected and for example coupled to the primer. In this case the concentration of the initiator in solution will be very low (typically nanomolar to micromolar), wherefore only an insignificant amount of initiator will react with the carboxyanhydrides. After or during incorporation of the building blocks the local concentration of initiator and carboxyanhydride will be much higher, leading to efficient polymerization.

Other types of peptides and peptide-like polymers (e.g., mono-, di-, tri-, and tetrasubstituted α-, β-, γ-, and Ω-peptides, polyesters, polycarbonate, polycarbamate, polyurea) can be made, using similar cyclic structures. For example, α-peptides can be made by polymerization of 5-membered carboxyanhydride rings.

FIG. 19C, "Zipping" polymerization of 2,2-diphenylthiazinanone units to form β-peptides.

The deprotected nucleophile, a primary amine, attacks the carbonyl of the neighboring thioester, thereby forming an amide bond. The released thiol reorganizes, to form a thioketone. As a result a free primary amine is generated, which attacks the carbonyl of a neighboring thioester, etc. Eventually an α-substituted β-peptide is formed, linked through its C-terminal end. The reactivity of the primary amine with the ester may be modified for example by the choice of ester (thioester or regular ester), pH during the polymerization reaction and the choice of substituents on the aromatic ring(s). The relative reactivity of the secondary amine contained in the cyclic moiety and the primary amine released upon ring-opening, may be adjusted by the bulk at the carbon between the secondary amine and the thioester. For example, replacing the two aromatic rings with one aromatic ring will decrease the bulk around the secondary amine, making it more nucleophilic, whereas the nucleophilicity of the primary amine that is formed upon ring-opening is not affected by the bulk at this position. Other peptides and amide-like polymers may be formed by this principle. For example, γ-peptides may be formed by polymerization of 7-membered thiazinanone rings.

Figure 19D:
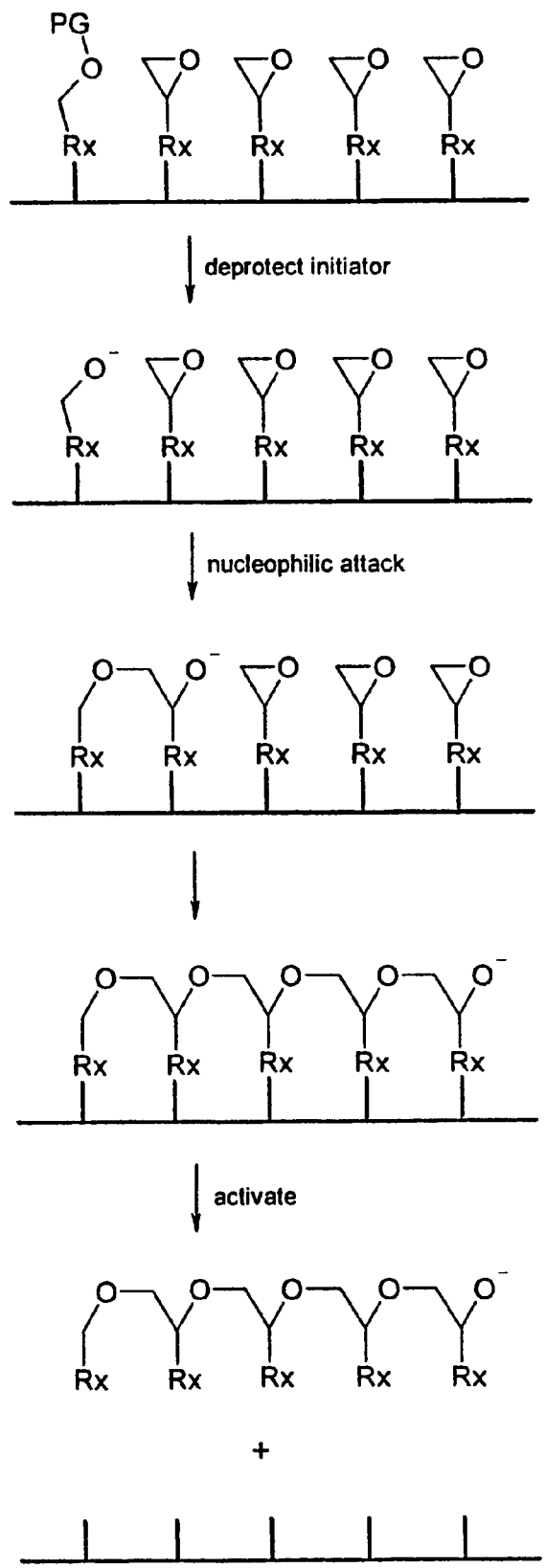

FIG. 19D, Polyether formation by ring-opening polymerisation.

The initiator is deprotected by for example base or acid. The formed anion the nattacks the epoxide of the neighboring monomer, to form a ether-bond. As a result, an anion is formed in the neighboring unit. This attacks the next monomer in the array, and eventually the full-length polyether has been formed. Depending on the conditions the attack will be at the most or least hindered carbon of the epoxide (under acidic or basic conditions, respectively).

In the final step, the encoded polyether is activated. In this case, the polymer is fully released from the encoding molecule. The screening for relevant characteristics (e.g., effect in a cell-based assay or enzymatic activity) may be performed in microtiter wells or micelles, each compartment containing a specific template molecule and the templated polyether, in many copies. In this way, the template and templated molecule is physically associated (by the boundaries of the compartment), and therefore the templates encoding polyethers with interesting characteristics may be collected from those compartments, pooled, amplified and "translated" into more copies of polyethers which may then be exposed to a new round of screening.

FIG. 20. Zipping-polymerization and activation by rearrangement.

The initiator is activated for attack by Y. Reaction of initiator and Y results in release of the initiator from the complementing element. Upon reaction with the initiator, a rearrangement of the building block molecule takes place, resulting in activation of X for reaction with Y. After a number of reactions and rearrangements, a polymer has been formed.

FIG. 21. Zipping-polymerization and activation by ring opening.

Reaction of the initiator with X in the ring structure opens the ring, resulting in activation of Y. Y can now react with X in a neighboring functional entity. As a result of ring-opening, the functional entities are released from the complementing elements.

FIG. 22. Directional polymer formation using fixed functional units.
  (A) The functional entity of a building block may be attached to the complementing element through two linkers. This may fix the functional entity in a given orientation relative to the complementing template. As a result, rotation around the linker that connects functional entity and complementing element (as depicted in FIG. 13) is not possible, and cluster formation therefore unlikely.
  (B) Two linkers connect the two bases of a dinucleotide-derivative with the functional unit, which in this case is a dipeptide. Incorporation of such dinucleotide derivatives into a double helical structure will position the amine (X in (A) above) in proximity to the ester (Y in (A) above). This ester may be activated, for example as a N-hydroxysuccinimide ester. After reaction of the amine and the ester, a polypeptide is formed. This polypeptide will be a directional polymer, with N-to-C-terminal directionality. In the present case, the polymerisation reaction will cleave the ester from the base to which it is linked. Therefore, activation of the formed polymer only requires cleavage of the linker that connects the base at the 3'-end of the dinucleotide with the amino-terminal end of the functional entity.
    Rotational fixation of the functional entity relative to the complementing element may be achieved in other ways. For example, the functional entity may be coupled to the complementing element through a double bond, or it may be attached through two bonds to the base and ribose moity of a nucleotide, respectively, or it may be coupled to different positions on the ribose or base. Finally, it is also possible to link to the phosphate moity, especially of a dinucleotide.

Figure 23:
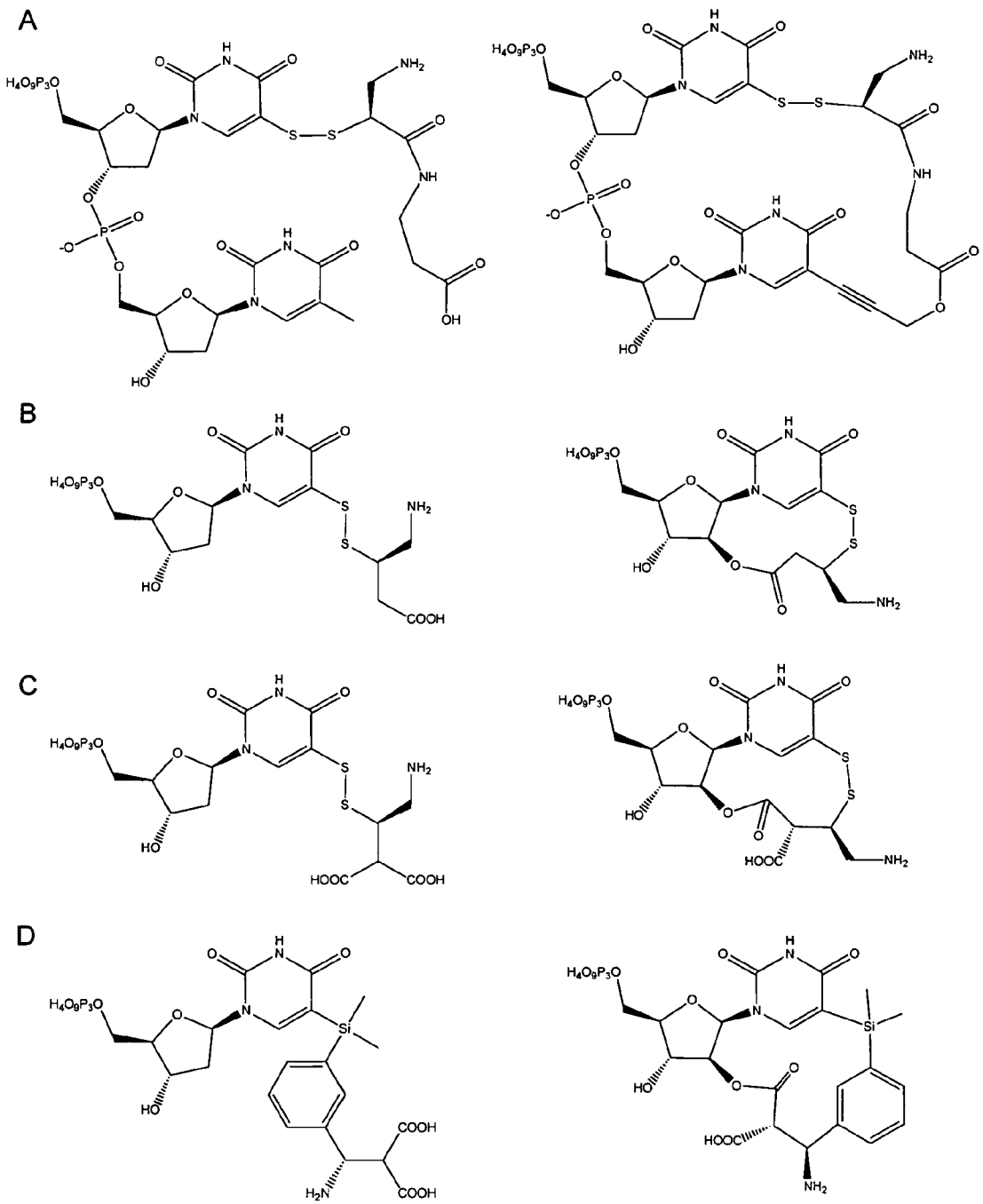

FIG. 23 shows four examples of bifunctional FEs attached via a single linker to the parent nucleotide (left) or with an additional linker using a second attachment point (right). The second attachment can be anywhere on a neighbour nucleotide (A), on the sugar moiety of the parent nucleotide (B, linked through ester functionality or C, with ester functionality free, and D, also with ester functionality free), it can be another base position of the parent nucleotide (not shown), or the FE could be linked to the phosphate backbone (not shown).

FIG. 24 show a DNA double helix (upper strand 5'-GCTTTTTTAG-3') bearing linker-FE 1A attached in different ways. DNA backbones are shown as arrows, sugars and bases as rings. Linker-FE atoms are depicted in stick representation and coloured by atom. A. Example of a conformation bearing singly-attached FEs. B. Most probable product of A. C. Example of a singly-attached FE configuration leading to clustering and thereby to an incomplete product, D. E. Minimum energy conformation bearing doubly-attached FEs and the only possible product, F. G. Stick representation of the released product from F. H. Stick representation of the released product from B. I. Stick representation of the released product from D.

FIG. 25 show a DNA double helix (upper strand 5'-GCTTTTAG-3') bearing linker-FE 1B attached in different ways. DNA backbones are shown as arrows, sugars and bases as rings. Linker-FE atoms are depicted in stick representation and coloured by atom. A. Minimum energy conformation bearing singly-attached FEs. B. Most probable product of A. C. Example of a singly-attached FE configuration leading to clustering and thereby to an incomplete product, D. E. Minimum energy conformation bearing doubly-attached FEs and the only possible product, F. G. Stick representation of the released product from B and F. H. Stick representation of the released product from D.

FIG. 26. Templating of molecules—principle and variations.

In the FIGS. 26-27, 29-31, 33-35, 37-49, and 53, the template, the complementing template, both the template and the complementing template, or a complementing element is indicated by a horizontal (bold) line. In FIGS. 26-28, 35-37, and 39, a circle is used to indicate a functional entity.
  A. Monomer building blocks used in this figure. A black dot indicates a cleavable linker.
  B. General principle.
    Step 1—Incorporation. The monomer building blocks are specifically incorporated into a complimentary template, by specific interaction between coding elements (of the template) and complementing elements (of the monomer building blocks).
    Step 2—Reaction. A reaction is induced by which functional entities (FE) of the individual monomer building blocks become coupled, by reaction of reactive groups type II.
    Step 3—Activation. Some or all of the linkers connecting the FE units with complementing elements are cleaved, thereby partly or fully releasing the templated molecule.
    Step 4 (not shown in figure)—Screening, Amplification and Modification. The template-templated molecule complexes may be taken through a screening process that enriches the pool for complexes with desired features. Then the templates of the enriched pool may be amplified and modified, by e.g. mutagenic PCR, and the templated molecules regenerated by performing step 1-3.
  C. Templating of linear, branched and circular templates.
    Linear, branched and circular templates may generate linear, branched and circular templated molecules. In the example shown, the branched template may be generated by incorporation of a modified nucleotide (e.g., carrying a thiol) into an oligonucleotide, followed by reaction with an oligonucleotide containing a thiol-reactive component (e.g., a maleimide-unit at one end). The circular template may likewise be a oligonucleotide, carrying reactive groups at the end that may react to covalently close the circle (e.g., thiols at both ends of the oligonucleotide could form an disulfide bond). Upon cleavage of all but one of the linkers connecting the FEs and complementing elements, a circular templated molecule is formed, attached to the template at one point.

D. Templating of linear, branched, circular and scrambled linear molecules by linear template.
 (a) A linear templated molecule with the same sequence of FEs as obtained after incorporation, but before reaction, of the monomer building blocks. (b) A linear templated molecule with a scrambled sequence, i.e., the sequence of the FEs in the templated molecule does not correspond to the sequence obtained right after incorporation, but before reaction of the FEs. (c) A circular templated molecule obtained by pairwise reaction of the following FEs with each other: FE1/FE2, FE2/FE3, FE3/FE5, FE5/FE4, FE4/FE1. (d) A branched molecule obtained by pairwise reaction of the following functional entities with each other: FE1/FE2, FE2/FE3, FE2/FE4, and FE4/FE5. (e) A branched molecule obtained by pairwise reaction of the following functional entities with each other: FE1/FE2, FE2/FE4, FE2/FE5, FE2/FE3.

Figure 27A:
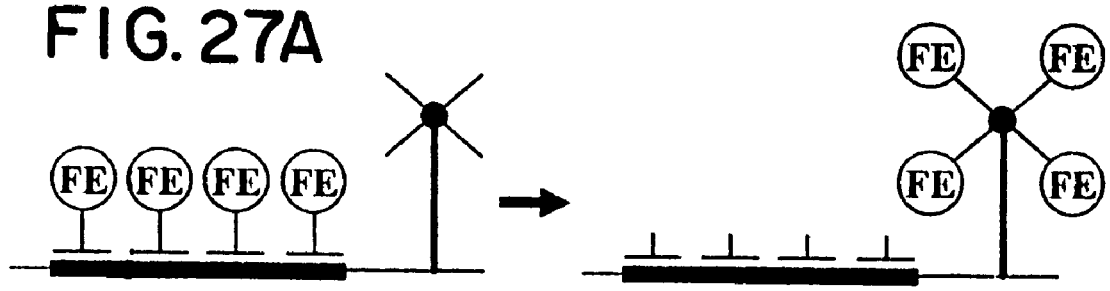
Figure 27B:
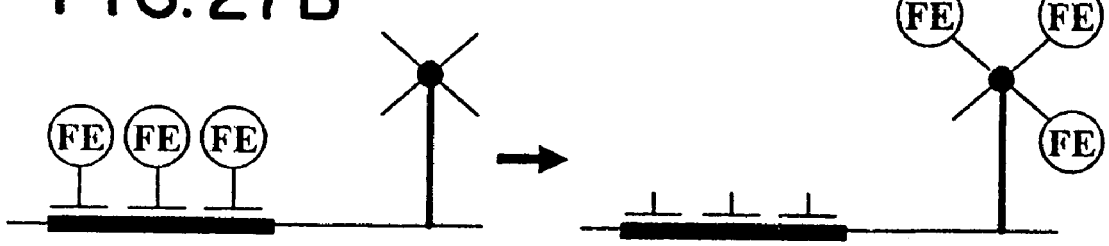
Figure 27C:
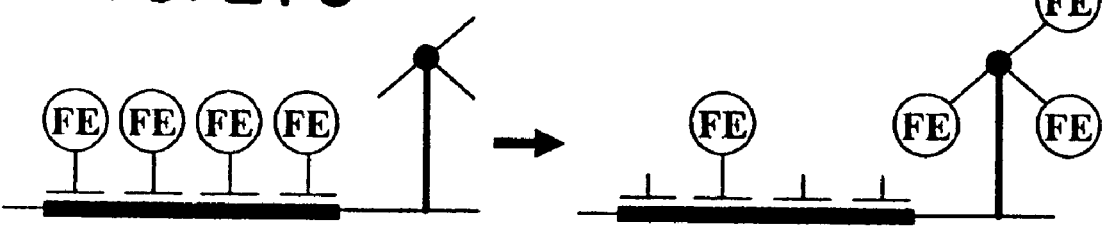
Figure 31A:
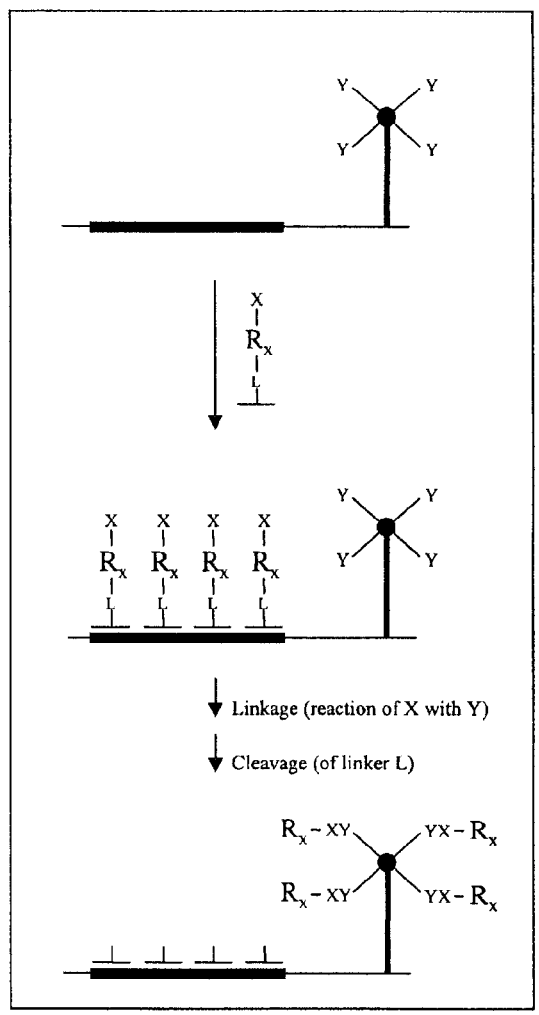
Figure 31B:
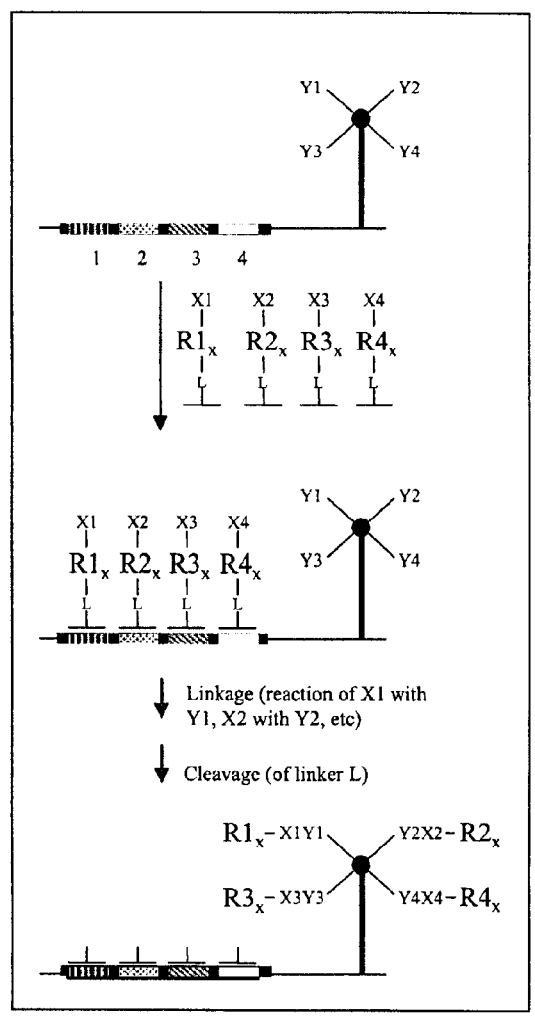

FIG. 27. Non-equal number of reactive groups (X) and (Y). The number of reactive groups (X) can be higher than, equal to, or lower than the number of reactive groups (Y). When the number of (X) and (Y) are different, scrambling results. In the figure the scaffold (the molecular moiety to which the functional groups of the monomer building blocks become attached) is directly attached to the template. The scaffold may also be part of a monomer building block (i.e., the functional entity of the monomer building block comprises a scaffold moiety, including reactive groups type II (Y).

(A). Number of encoded reactive groups X per template equals the number of reactive groups (Y) on the anchorage point (also called the scaffold).

(B). Number of encoded reactive groups X per template is less than the number of encodable substituent positions Y on the scaffold. This leads to scrambling regarding which of the reactive groups (Y) on the scaffold (anchorage point) will react with an (X) on the monomer building blocks.

C. Number of encoded reactive groups X per template is larger than the number of reactive groups on the scaffold. This leads to scrambling regarding which of the reactive groups (Y) on the scaffold (anchorage point) will react with a reactive group (X) on the monomer building blocks.

FIG. 28. Monomer building blocks.
(A) A monomer building block with one reactive group type II (X), connecting the functional group (Rx) with the complementing element. This type of monomer building block may be used for the simultaneous reaction and activation protocol (FIG. 14).
(B) A monomer building block with two reactive groups type II (X and Y), connecting the complementing element and the functional group (Rx).
(C) A monomer building block with one reactive group type II (X). The reactive group (X) does not link the functional group (Rx) and the complementing element, wherefore a linker (L) is needed for the activation step (in order to release the functional entity from the complementing element)
(D) A monomer building block with four reactive groups type II (Y). The four reactive groups and the functional group Rx may serve as a scaffold, onto which substituents (encoded by monomers complementing the same template) are coupled through reaction of reactive groups (X) on these monomer building blocks with the reactive groups (Y) on this monomer building block. In this example, no cleavable linker is indicated. Therefore, after the templating reactions the templated molecule may be attached to the template through the linker of this monomer building block.

FIG. 29. Templating involving simultaneous reaction and activation.

Templating using 4 monomer building blocks each with one reactive group type II (X), and an anchorage point carrying 4 reactive groups (Y). The reaction of X and Y involves simultaneous activation (cleavage) which releases X from the complementing element.

(A) The reactive groups type II (X) are of similar kind.
(B) The reactive groups type II (X1, X2, X3, X4) are of different kinds, i.e. the pairwise reactions between reactions X1/Y1, X2/Y2, X3/Y3, and X4/Y4 are orthogonal or partly orthogonal. For example, X1 preferably reacts with Y1, not Y2, Y3 or Y4. The anchorage point may be attached directly to the template, or to the complementing template. In case the anchorage point is attached to a complementing element, as a whole it is considered a monomer building block.

FIG. 30. Reaction types allowing simultaneous reaction and activation.

Different classes of reactions are shown which mediate translocation of a functional group from one monomer building block to another, or to an anchorage point. The reactions have been grouped into three different classes: Nucleophilic substitutions, addition-elimination reactions, and transition metal catalyzed reactions These reactions are compatible with simultaneous reaction and activation (as described in general terms in FIG. 14).

(FIG. 30A) Reaction of nucleophiles with carbonyls. As a result of the nucleophilic substitution, the functional group R is translocated to the monomer building block initially carrying the nucleophile.

(FIG. 30B) Nucleophilic attack by the amine on the thioester leads to formation of an amide bond, in effect translocating the functional group R of the thioester to the other monomer building block.

(FIG. 30C) Reaction between hydrazine and β-ketoester leads to formation of pyrazolone, in effect translocating the R and R' functional groups to the other monomer building block.

(FIG. 30D) Reaction of hydroxylamine with β-ketoester leads to formation of the isoxazolone, thereby translocating the R and R' groups to the other monomer building block.

(FIG. 30E) Reaction of thiourea with β-ketoester leads to formation of the pyrimidine, thereby translocating the R and R' groups to the other monomer building block.

(FIG. 30F) Reaction of urea with malonate leads to formation of pyrimidine, thereby translocating the R group to the other monomer building block.

(FIG. 30G) Depending on whether Z=O or Z=NH, a Heck reaction followed by a nucleophilic substitution leads to formation of coumarin or quinolinon, thereby translocating the R and R' groups to the other monomer building block.

(FIG. 30H) Reaction of hydrazine and phthalimides leads to formation of phthalhydrazide, thereby translocating the R and R' groups to the other monomer building block.

(FIG. 30I) Reaction of amino acid esters leads to formation of diketopiperazine, thereby translocating the R group to the other monomer building block.

(FIG. 30J) Reaction of urea with α-substituted esters leads to formation of hydantoin, and translocation of the R and R' groups to the other monomer building block.

(FIG. 30K) Alkylation may be achieved by reaction of various nucleophiles with sulfonates. This translocates the functional groups R and R' to the other monomer building block.

(FIG. 30L) Reaction of a di-activated alkene containing an electron withdrawing and a leaving group, whereby the alkene is translocated to the nucleophile.

(FIG. 30M) Reaction of disulfide with mercaptane leads to formation of a disulfide, thereby translocating the R' group to the other monomer building block.

(FIG. 30N) Reaction of amino acid esters and amino ketones leads to formation of benzodiazepinone, thereby translocating the R group to the other monomer building block.

(FIG. 30O) Reaction of phosphonates with aldehydes or ketones leads to formation of substituted alkenes, thereby translocating the R'' group to the other monomer building block.

(FIG. 30P) Reaction of boronates with aryls or heteroaryls results in transfer of an aryl group to the other monomer building block (to form a biaryl).

(FIG. 30Q) Reaction arylsulfonates with boronates leads to transfer of the aryl group.

(FIG. 30R) Reaction of boronates with vinyls (or alkynes) results in transfer of an aryl group to the other monomer building block to form a vinylarene (or alkynylarene).

(FIG. 30S) Reaction between aliphatic boronates and arylhalides, whereby the alkyl group is translocated to yield an alkylarene.

(FIG. 30T) Transition metal catalysed alpha-alkylation through reaction between an enolether and an arylhallide, thereby translocating the aliphatic part.

(FIG. 30U) Condensations between e.g. enamines or enolethers with aldehydes leading to formation of alpha-hydroxy carbonyls or alpha,beta-unsaturated carbonyls. The reaction translocates the nucleophilic part.

(FIG. 30V) Alkylation of alkylhalides by e.g. enamines or enolethers. The reaction translocates the nucleophilic part.

(FIG. 30W) [2+4] cycloadditions, translocating the diene-part.

(FIG. 30X) [2+4] cycloadditions, translocating the ene-part.

(FIG. 30Y) [3+2] cycloadditions between azides and alkenes, leading to triazoles by translocation of the ene-part.

(FIG. 30Z) [3+2] cycloadditions between nitriloxides and alkenes, leading to isoxazoles by translocation of the ene-part.

FIG. 31. Templating involving non-simultaneous reaction and activation: Reaction of reactive groups (type II), followed by cleavage of the linkers that connect functional entities with complementing elements.

Templating using 4 monomer building blocks each with one reactive group type II (X), and an anchorage point carrying 4 reactive groups (Y). The reaction of X and Y does not involve simultaneous activation (cleavage), wherefore the reaction of X and Y is followed by cleavage of the linker L, which releases the functional group Rx from the complementing element.

(FIG. 31A) The reactive groups type II (X) are of similar kind, i.e., they may react with the same type of reactive group (Y). (FIG. 31B) The reactive groups type II (X1, X2, X3, X4) are of different kinds, i.e. the reactions between X1/Y1, X2/Y2, X3/Y3, and X4/Y4 are orthogonal or partly orthogonal. For example, X1 preferably reacts with Y1, not Y2, Y3 or Y4. The anchorage point may be attached directly to the template, or to the complementing template. In case the anchorage point is attached to a complementing element, as a whole it is considered a monomer building block.

FIG. 32. Pairs of reactive groups (X) and (Y), and the resulting bond (XY).

A collection of reactive groups that may be used for templated synthesis are shown, along with the bonds formed upon their reaction. FIG. 32A, depicts nucleophilic substitution reactions; FIG. 32B. aromatic nucleophilic substitutions; FIG. 32C, transition metal catalyzed reactions; FIG. 32D, addition to carbon-carbon multiple bonds; FIG. 32E, addition to carbon-multiple bonds; FIG. 32F, cycloaddition to multiple bonds; FIG. 32G, addition to carbon hetero multiple bonds. After reaction, activation (cleavage) may be required (see FIG. 31).

FIG. 33. Anchorage sites for the templated molecule.

The templated molecule may be attached to the template that encodes it (FIG. 33A) through a linker that is connected directly to the template near the end of the template, or (FIG. 33B) through a linker that is connected directly to the template, at a more central position on the template, or (FIG. 33C) by way of a monomer building block carrying the anchorage point (a reactive group that becomes the linkage to the templated molecule).

FIG. 34. Scrambling.

When the functional entities react after incorporation of the monomer building blocks, the position or sequence of functional groups in the templated molecule may not always be uniquely determined by the template sequence.

(1) The functional groups R1, R2, R3, and R4 may take any of the four positions on the scaffold molecule (i.e., the reactive group X of a monomer building block may react with any of the reactive groups Y on the anchorage point.

(2) The sequence of one arm of this branched molecule may be e.g. R5-R3-R2 (as shown), or R5-R2-R3 (not shown), or R5-R4-R3 (not shown), or any other of a number of possible sequences. Also, the identity of the functional group coupled to e.g. the left part of the molecule, may be either of any of R1, R2, R3, or R4.

(3) As in (2), a number of possible sequences of functional groups are possible, in addition to the shown sequence R1-R2-R5-R4-R3.

(4) Here a non-scrambled templated molecule is shown, in which the sequence of the functional entitities when incorporated corresponds to the sequence of the templated molecule (R1-R2-R3-R4-R5). When desired, scrambling may be partly or fully avoided by directional encoding or the use of for example zipper boxes in the linkers (see FIGS. 40, 44-47).

(5) As in (2) and (3), a number of possible sequences and positions of the functional entities are possible.

FIG. 35. Monomer building blocks—examples of linker design.

Different designs of monomer building blocks are shown, used in various schemes of templating.

The complementing element may be represented by an oligonucleotide, to which a linker carrying the functional entity is attached. The linker may occupy an internal position with respect to the complementing element or alternatively occupy a terminal position. Both the complementing element and the linker may be made up of an oligonucleotide (DNA, RNA, LNA, PNA, other oligomers capable of hybridizing to the linker of a monomer building block and mixtures thereof). The horizontal part represents the complementing element, and the vertical part represents the linker.

The portion of the linker marked "a" may be present or absent. Region "a" represents an interaction region of which one preferred embodiment is a sequence of nucleotides. Region "a" may be annealed to a complementary single stranded nucleotide sequence "a" in order to make the linker more rigid. Alternatively region "a" may be used for interaction with other monomer building blocks (i.e. zipper box see FIG. 42), whereby the functional entities of such two monomer building blocks will be brought in close proximity, which will increase probability of reaction between these two functional entities. Other uses of such regions includes interaction between different monomer building blocks whereby directional encoding may be achieved. "Nu" is a nucleophile that may react with an electrophile "E".

Different designs of monomer building blocks are shown, used in various schemes of templating.

(FIG. 35A) The complementing element may be an oligonucleotide, to which a linker carrying the functional entity is attached to the central part of the oligonucleotide. The portion of the linker marked "a" may represent a nucleotide sequence to which a single stranded nucleotide may be annealed in order to make the linker more rigid.

(FIG. 35B) Both the complementing element and the linker may be made up of an oligonucleotide. The horizontal part here represents the complementing element, and the vertical part represents the linker. The linker may contain a sequence "a" that functions as a zipper box (see FIG. 42).

(FIG. 35C) The monomer building blocks of (C) is an initiator or anchorage point which may be used to initiate the encoding process.

FIG. 36 Preparation of functional entities to oligonucleotide-based monomer building blocks.

Reactions and reagents are shown that may be used for the coupling of functional entities to modified oligonucleotides (modified with thiol, carboxylic acid, halide, or amine), without significant reaction with the unmodified part of the oligonucleotide or alternatively, connective reactions for linkage of linkers to complementing elements. Commercially, mononucleotides are available for the production of starting oligonucleotides with the modifications mentioned.

FIG. 37 Oligonucleotide-based monomer building blocks. Examples of linker and functional entity (FE) design and synthesis.

Examples are shown where the complementing elements of the monomer building blocks comprises oligonucleotides of length e.g. 8-20 nucleotides (oligonucleotide is drawn as a thick black line). Part of or all of the oligonucleotide may comprise the complementing element. In the case where only part of the oligonucleotide represents the complementing element, the remaining portion of the oligonucleotide may constitute a linker. In the examples, a linker is attached to the base on the 3'- or 5'-end of the oligonucleotide. This linker may be attached on any nucleotide in the oligonucleotide sequence, and also, it may be attached to any molecular moiety on the oligonucleotide, as long as it does not abolish specific interaction of the complementing element with the template.

(A) A monomer building block in which the linker (L) connects the base of the terminal nucleotide with the functional entity.

(B) A monomer building block in which a polyethylene glycol (PEG) linker of between one and twenty ethylene glycol units connects the complementing element with the functional entity which contains a nucleophile (a primary amine).

(C) A monomer building block in which a linker (L) connects the functional entity which contains an electrophile (an ester or thioester).

(D) A monomer building block comprising a Boc-protected amine (which may be deprotected with mild acid), and an ester. The deprotected amine may react with an ester of another monomer building block, to give an amide bond.

FIG. 38. Oligonucleotide-based monomer building blocks. Example of coding and complementing element design, allowing for high monomer diversity.

(A) Template carrying 6 coding elements (BOX 1-6), each containing a partly random sequence (X specifies either C or G), and a constant sequence that is identical for all sequences in the group (e.g., all BOX 1 sequences carry a central ATATTT sequence). By using C and G only (or, alternatively, A and T only), the individual sequences (e.g., the sequences belonging to the group of BOX 1 sequences), have almost identical annealing temperatures wherefore mis-annealing is insignificant. In the example, BOX 2 and BOX 3 are identical wherefore BOX 2 and BOX 3 may encode the same type of functional entities (comprising the same type of reactive groups of type II). The attachment point of the linker that connects the complementing element and the functional entity is not specified in the figure. Ideally, the linker is attached to a nucleotide in the constant region, in order to avoid bias in the annealing process.

(B) Example of coding element sequences. Example BOX 1 and BOX 6 sequences are shown. The example BOX1 sequence represents one specific sequence out of 1024 different sequences that anneal specifically to the corresponding BOX 1 complementing elements; the example BOX 6 sequence represents one specific sequence out of 128 different sequences that anneal to the corresponding BOX 6 complementing elements.

(C) Templating using six monomers. Five classes of coding elements are used (BOX 2 and 3 are of the same class, i.e., the corresponding complementing elements of this class may anneal to both BOX 2 and 3). Reactive groups type II X and Y react; S and T react; A and B react; and C and D react. In the example the X/Y pair is orthogonal to S/T orthogonal to A/B orthogonal to C/D. Reaction of X with Y results in cleavage of R1 from the complementing element and translocation to R4. Reaction of S and T, followed by cleavage of the linker L leads to translocation of R2 and R3 onto R4. Reaction of A with B, and C with D translocates R5 and R6 to R4. In this example, the functional entity of the monomer binding to BOX 4 serves as a "scaffold" onto which is added various substituents.

Figure 39:
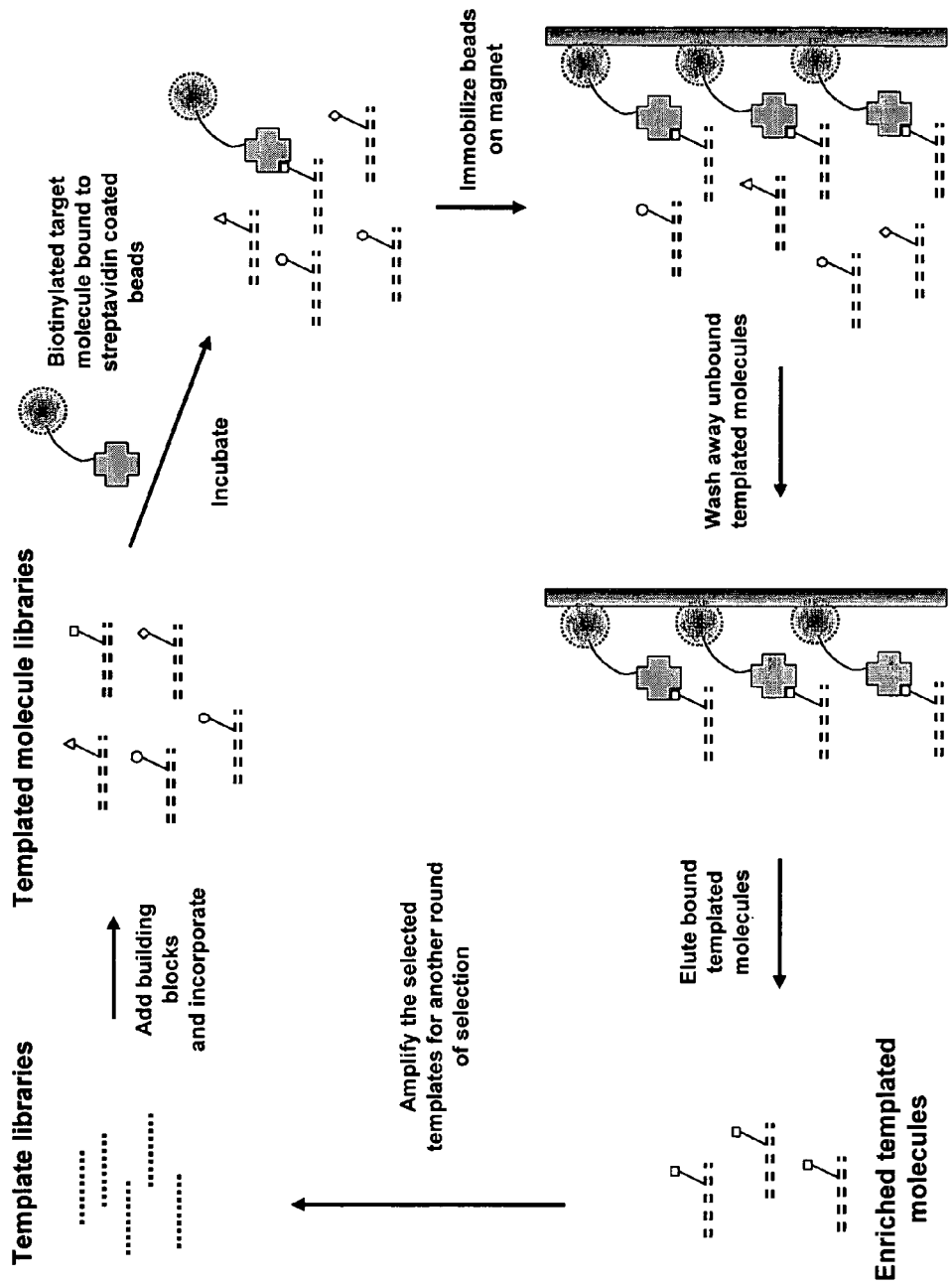

FIG. 39: A typically panning protocol for selection of templated molecules

Templates presenting the various small molecule variants are produced by DNA encoding technology. These templated molecules are incubated with the immobilized target molecule. Templated molecules with low affinity for the target are washed away. The remaining templated molecules are eluted and the template is amplified using PCR. The enriched templates are then ready to be used as a coding strand for the next cycle.

Figure 40:
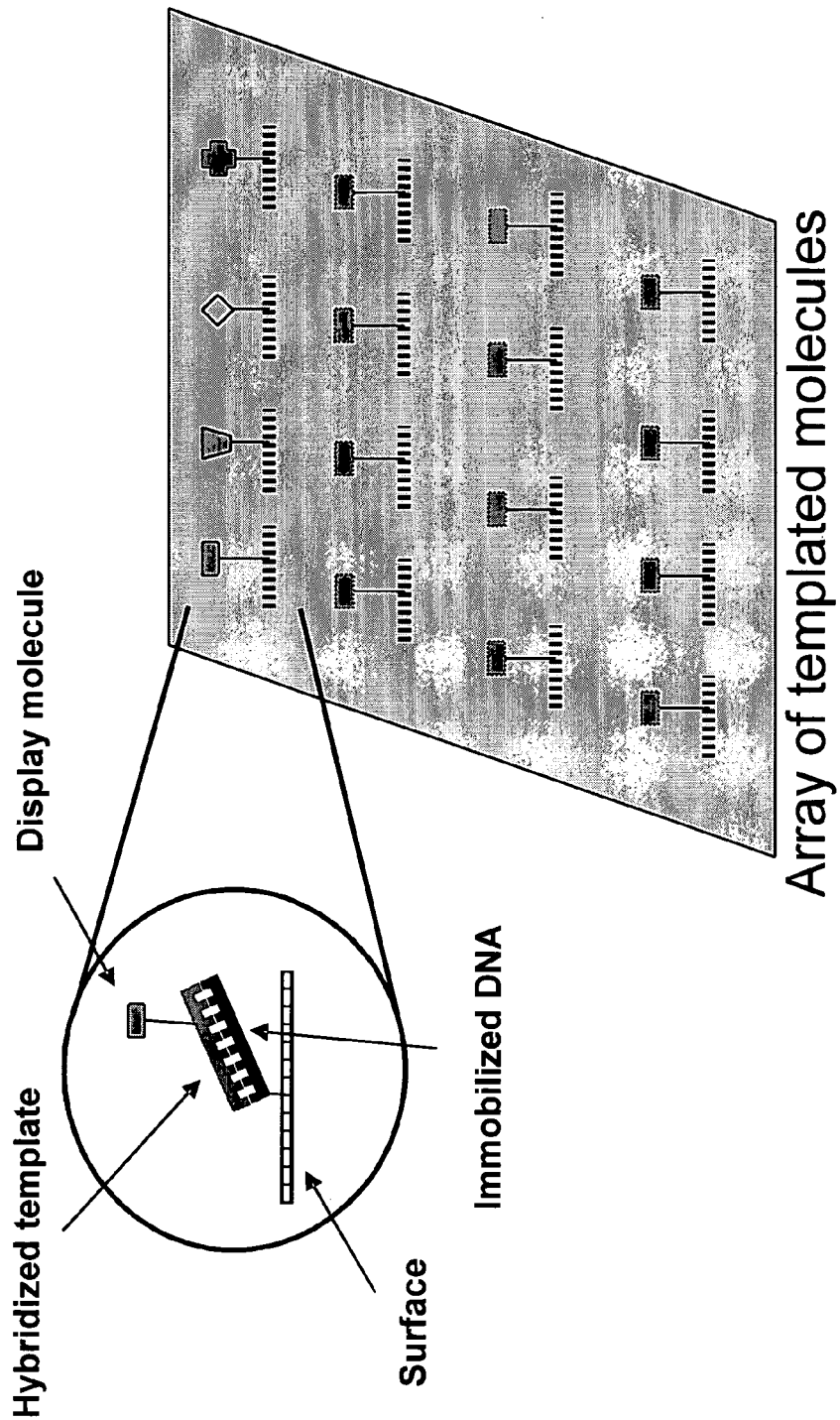
Figure 41A:
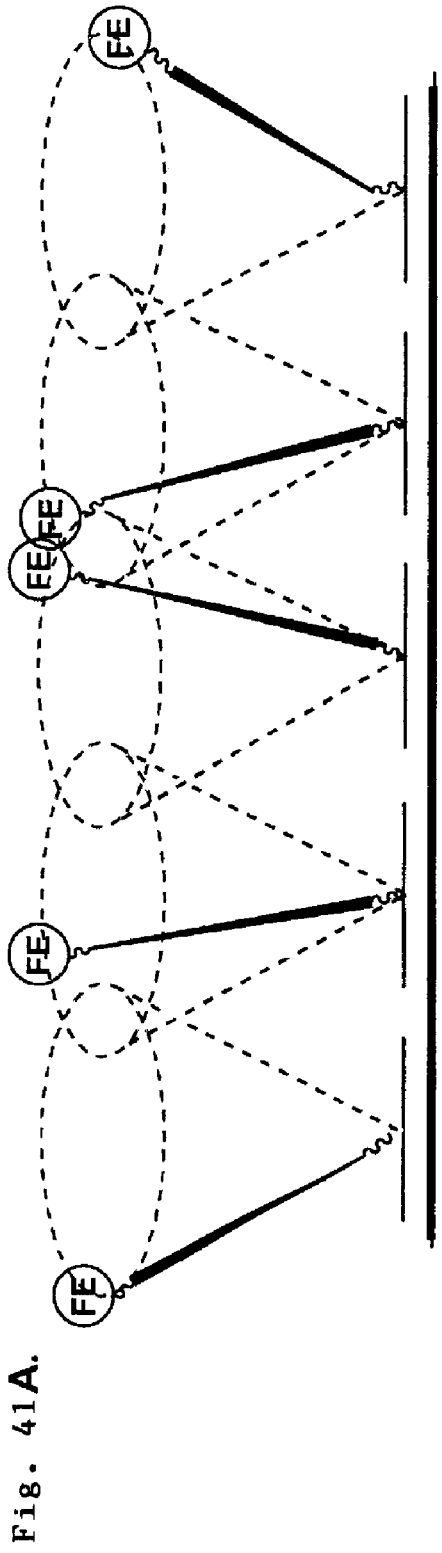
Figure 41B:
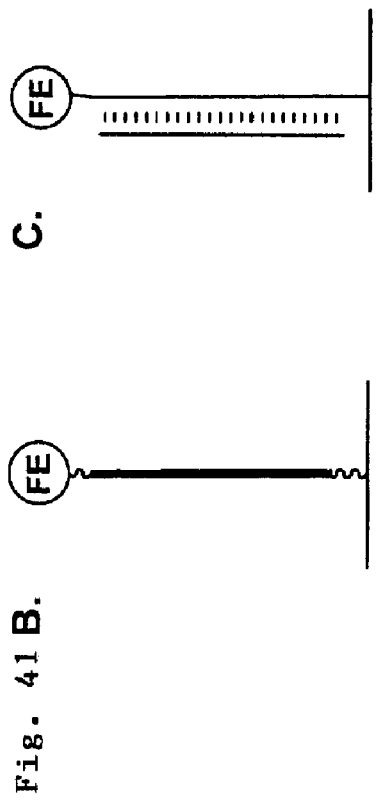

FIG. 40: Array of templated molecules

The figure shows a templated molecule chip. A DNA library is spotted in array format on a suitable surface. The templated molecule library (single-stranded template DNA) is added and allows hybridizing to the complement DNA strand. This will allow site-specific immobilization of the templated molecules. A biological sample containing target molecules is added and non-bound material is washed off. The final step is the detection of bound material in each single spot.

FIG. 41. Use of rigid or partially rigid linkers to increase probability of reaction between the functional entities of the incorporated monomer building blocks.

(FIG. 41A) By using linkers comprising one or more flexible regions ("hinges") and one or more rigid regions, the probability of two functional entities getting into reactive contact may be increased.

(FIG. 41B) Symbol used for monomer building block with a rigid part and two flexible hinges.

(FIG. 41C) A monomer building block with the characteristics described in (FIG. 41B): The monomer building block contains an oligonucleotide as complementing element (horizontal line), and a oligonucleotide as linker connecting the functional entity (FE) with the complementing element. Annealing of a complementary sequence to the central part of the linker leads to formation of a rigid double helix; at either end of the linker a single-stranded region remains, which constitutes the two flexible hinges.

FIG. 42. Use of zipper box to increase probability of reaction between the functional entities of the incorporated monomer building blocks.

(FIG. 42A) The linkers in this example carry zipper boxes (a) or (a'), that are complementary. By operating at a temperature that allows transient interaction of (a) and (a'), the reactive groups X and Y are brought into close proximity during multiple annealing events, which has the effect of keeping X and Y in close proximity in a larger fraction of the time than otherwise achievable. Alternatively, one may cycle the temperature between a low temperature (where the zipper boxes pairwise interacts stably), and a higher temperature (where the zipper boxes are apart, but where the complementing element remains stably attached to the coding element of the template). By cycling between the high and low temperature several times, a given reactive group X is exposed to several reactive groups Y, and eventually will react to form an XY bond.

(FIG. 42B) Sequences of two oligonucleotide-based monomer building blocks. The region constituting the complementing element, linker and zipper box is indicated.

FIG. 43. Templated synthesis of organic compounds—examples.

(FIG. 43A) Three monomer building blocks are used. Each monomer building block comprises an activated ester (reactive group of type II, (X)) where the ester moiety carries a functional group Rx. Upon reaction between the esters and the amines on the scaffold (scaffold may be attached to the template), amide bonds are formed, and the Rx groups are now coupled to the scaffold via amide bonds. This is thus an example of simultaneous reaction (amide formation) and activation (release of the Rx moiety from the complementing elements), see FIG. 29.

(FIG. 43B) Analogously to (A), three amines react with three esters to form three amide bonds, thereby coupling the functional groups Rx to the scaffold moiety. However, as opposed to (A), the scaffold is here encoded by the template.

(FIG. 43C) Three monomer building blocks are used. The nucleophilic amine at the far right (part of the anchorage point) attacks the ester carbonyl of the third monomer; the amine of the third monomer attacks the thioester of the second monomer, and the Horner-Wittig Emmans reagent of the first monomer reacts with the aldehyde of the third monomer under alkaline conditions.

This forms the templated molecule. The double bond may be post-templating modified by hydrogenation to form a saturated bond, or alternatively, subjected to a Michael addition.

(FIG. 43D) The thiol of the scaffold reacts with the pyridine-disulfide of monomer 1. The amine of the scaffold reacts with the ester of the second monomer. The double nitril activated alpha-position is acylated by the monomer 3's thioester in the presence of base. The aryliodide undergoes Suzuki coupling with the arylboronate of monomer 4 to yield the biaryl moiety.

(FIG. 43E) Monomer 1 acylates the primary amine. The aryliodide undergoes a Suzuki coupling by monomer 2 and the benzylic amine is acylated by monomer 3.

Acylation of the hydrazine followed by cyclization leads to formation of an hydroxypyrazole. The arylbromide undergoes Suzuki coupling with the aryl boronate of monomer 1 and finally (FIG. 43F) the aldehyde reactions with the Horner-Wittig-Emmons reagent of monomer 4 to yield an alpha, beta-unsaturated amide, which may be further functionalized by either reduction with $H_2$/Pd—C or undergo Michael addition with nucleophiles.

Figure 44:
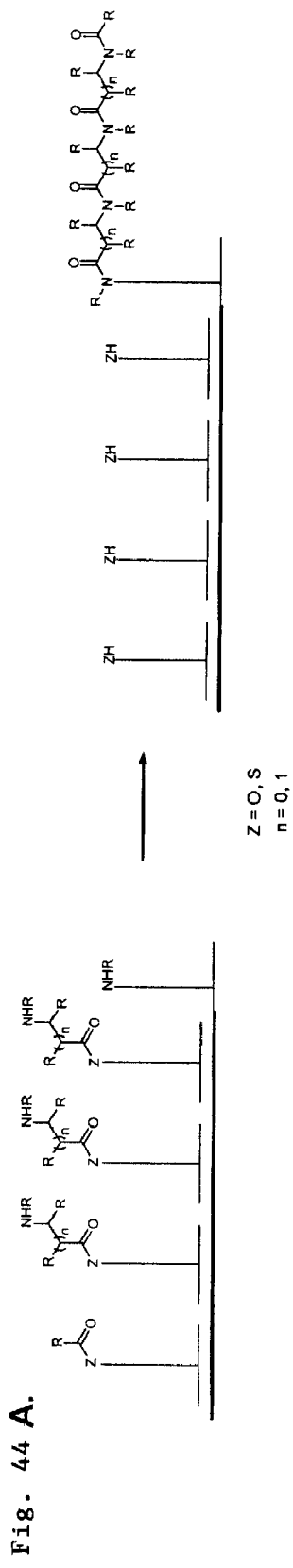
Figure 44:
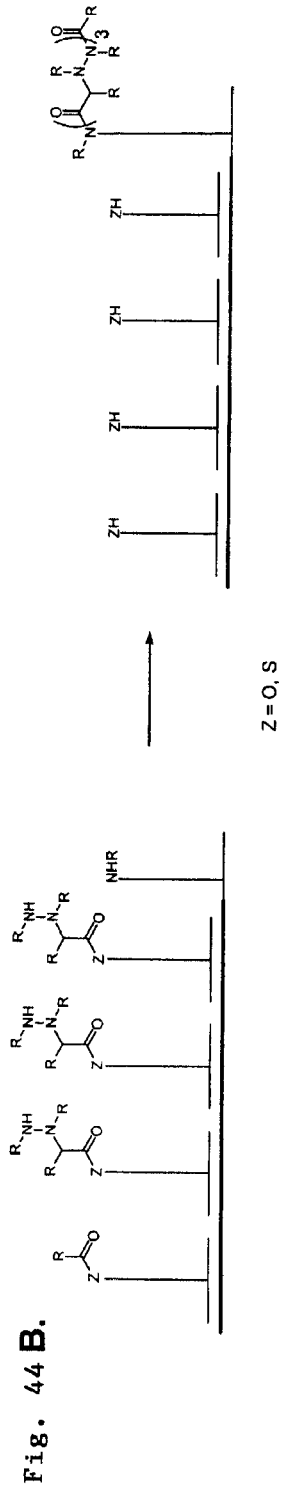

FIG. 44. α- and β-peptides, hydrazino peptides and peptoids. Encoding by use of oligonucleotide-based monomer building blocks.

Figure 43A:
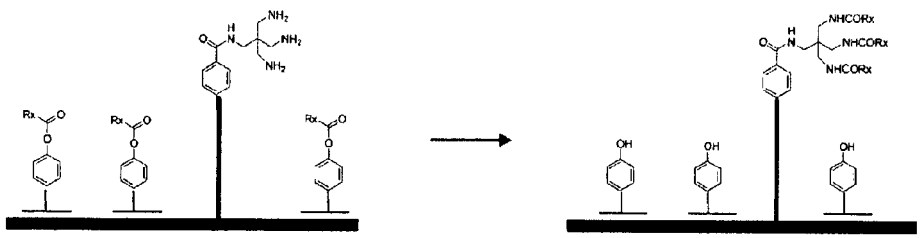
Figure 43B:
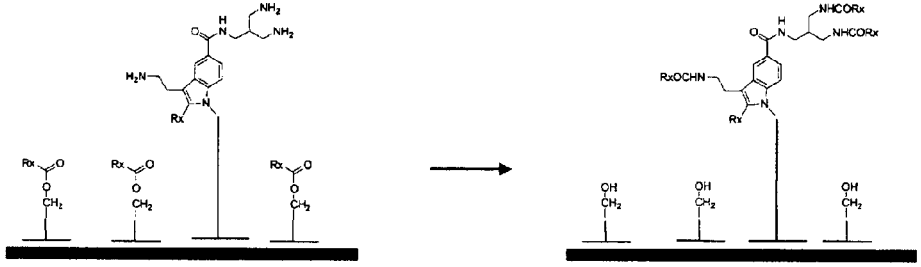
Figure 43C:
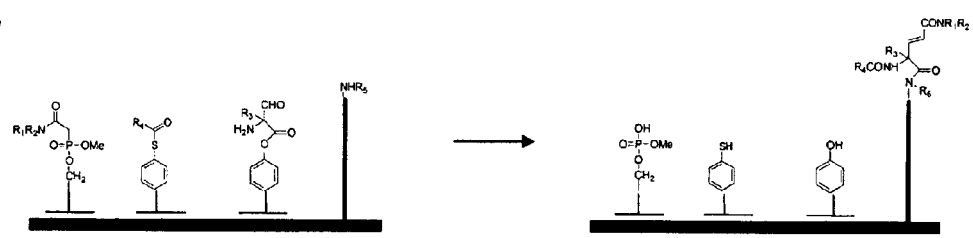
Figure 43D:
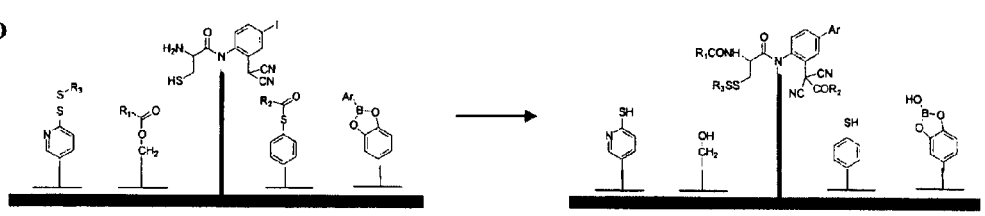
Figure 43E:
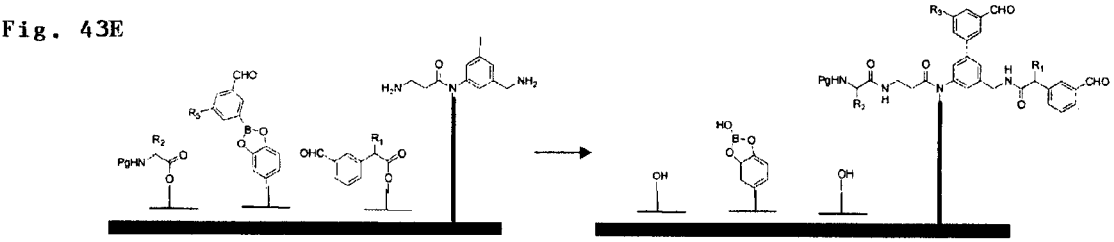
Figure 43F:
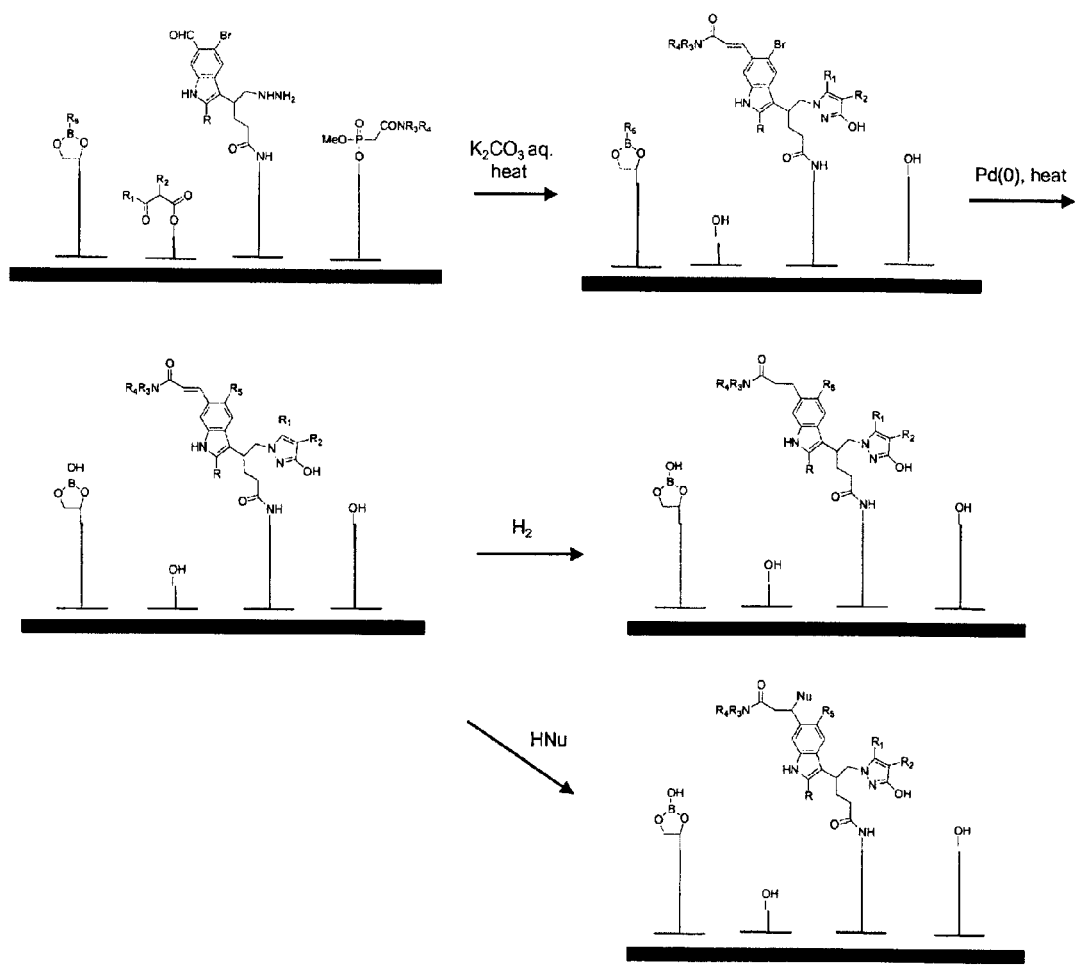

It is shown how templated synthesis may be used to generate α- and β-peptides (FIG. 43A), hydrazino peptides (FIG. 43B) and peptoids (FIG. 43A).

Figure 45:
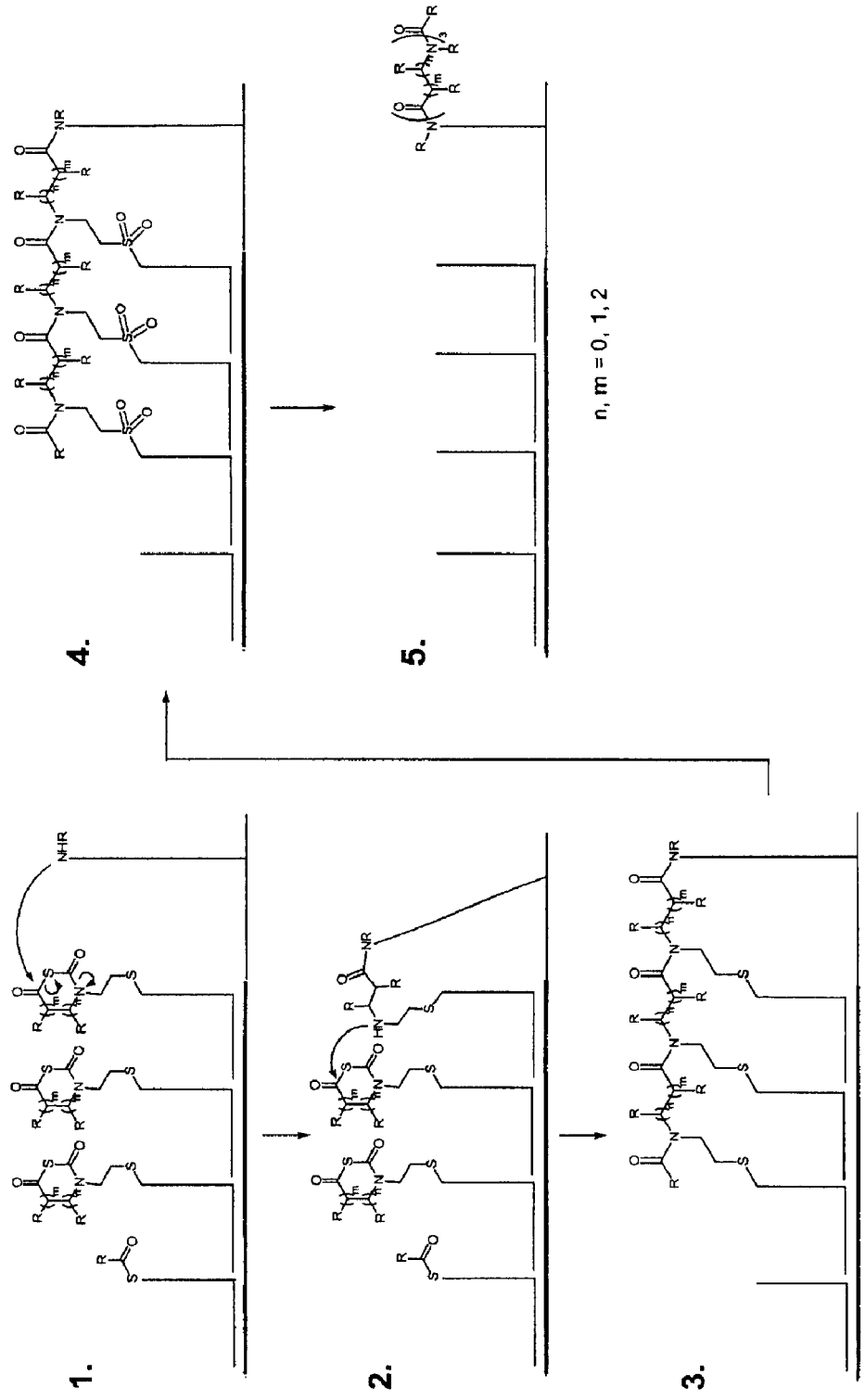

FIG. 45. Templating of α-, β-, γ-, and ω-peptide through use of cyclic anhydrides It is shown how templated synthesis may be used to generate α-, β-, γ- and ω-peptides, through the use of cyclic anhydrides.

Figure 46:
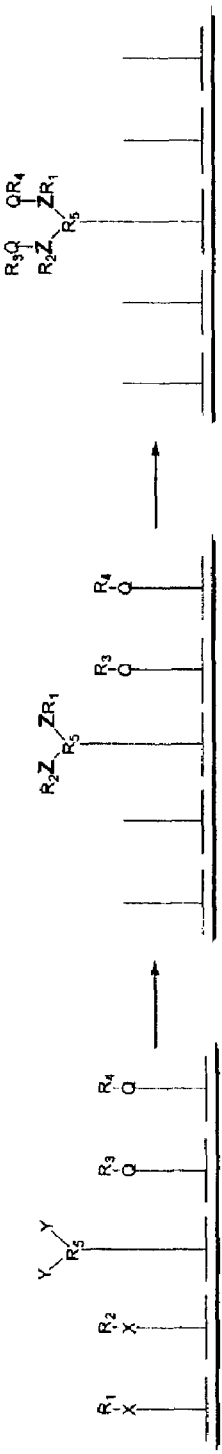
Figure 46:
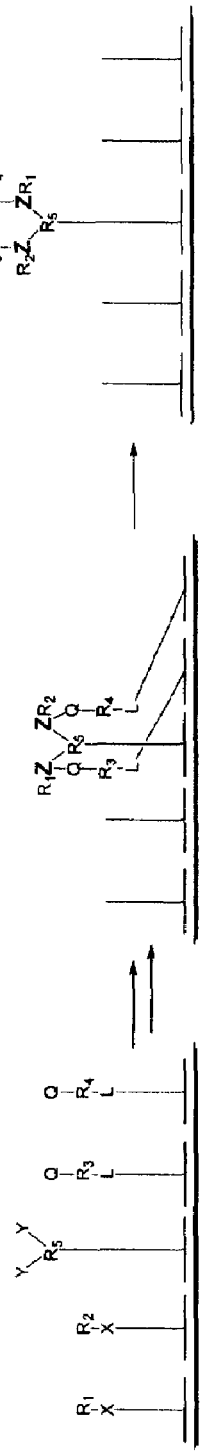

FIG. 46. Generation of new reactive groups upon reaction of the reactive groups X and Y.

In cases where the reaction of X and Y leads to formation of a new reactive group Z, this may be exploited to increase the diversity of the templated molecule, by incorporating monomer building blocks carrying reactive groups Q that react with Z.

(FIG. 46A) X and Y react to form Z, which in itself does lead to release from the complementing element. Upon reaction of Z with Q, and cleavage of the linker that connects Z to the complementing element, the templated molecule is formed.

(FIG. 46B) In this case, reaction of X and Y to form Z simultaneously cleaves the linker connecting X to the complementing element. Upon reaction of Z with Q, the templated molecule is formed.

FIG. 46C, example 1. Templated synthesis by generating a new reactive group.

The reaction of the functional entities of the first three monomer building blocks leads to formation of two double bonds, which may react with two hydroxylamines carried in by the monomer building blocks added in the second step, and leads to formation of an ester, which may react with the an hydroxylamine, carried in by the monomer added in the second step. Finally, the linkers are cleaved, generating the templated molecule.

FIG. 47. Cleavable linkers.

Cleavable linkers, the conditions for their cleavage, and the resulting products are shown.

FIG. 48. Post-templating modification of templated molecule.

After the templating process has been performed, the templated molecules may be modified to introduce new characteristics. This list describes some of these post-templating modifications. FIG. 48A, rearrangement and cleavage in one step; FIG. 48B, reaction of functional groups present in a templated molecule; FIG. 48C, post-templating modification of linker to extend the spacing between the template and the templated molecule.

Figure 49:
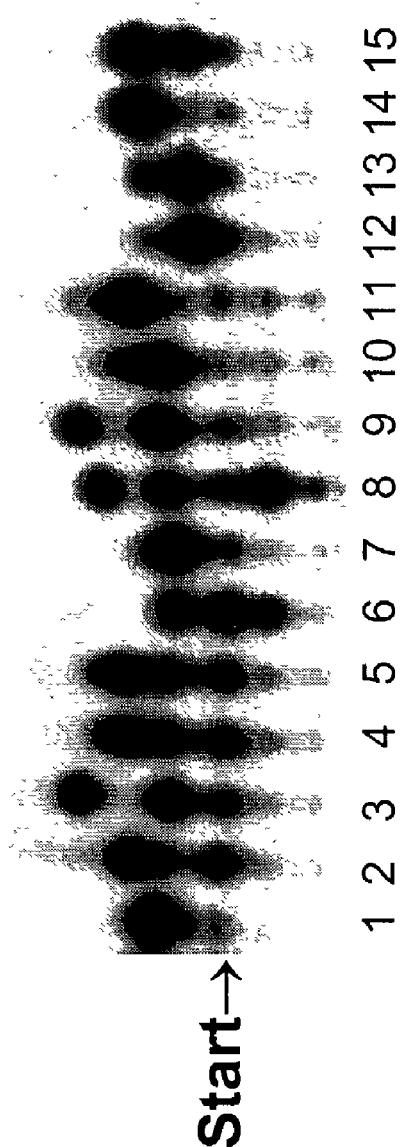
Figure 50:
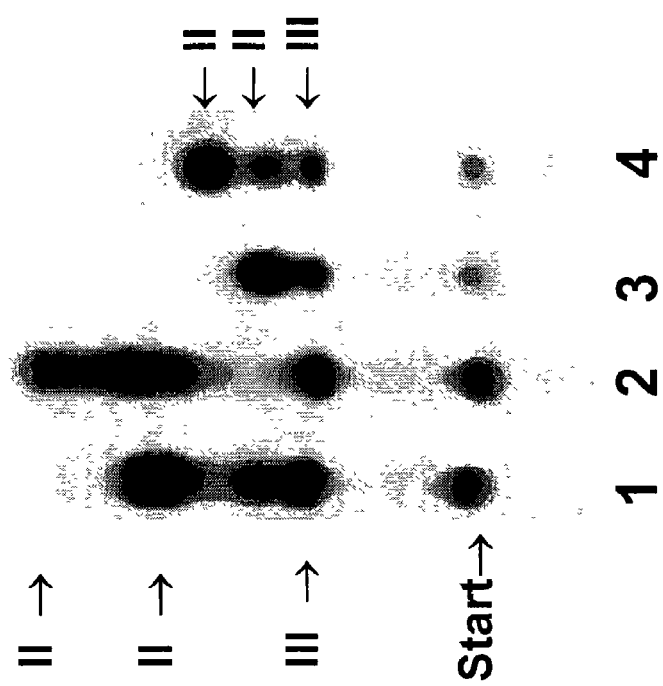
Figure 51:
Figure 52:
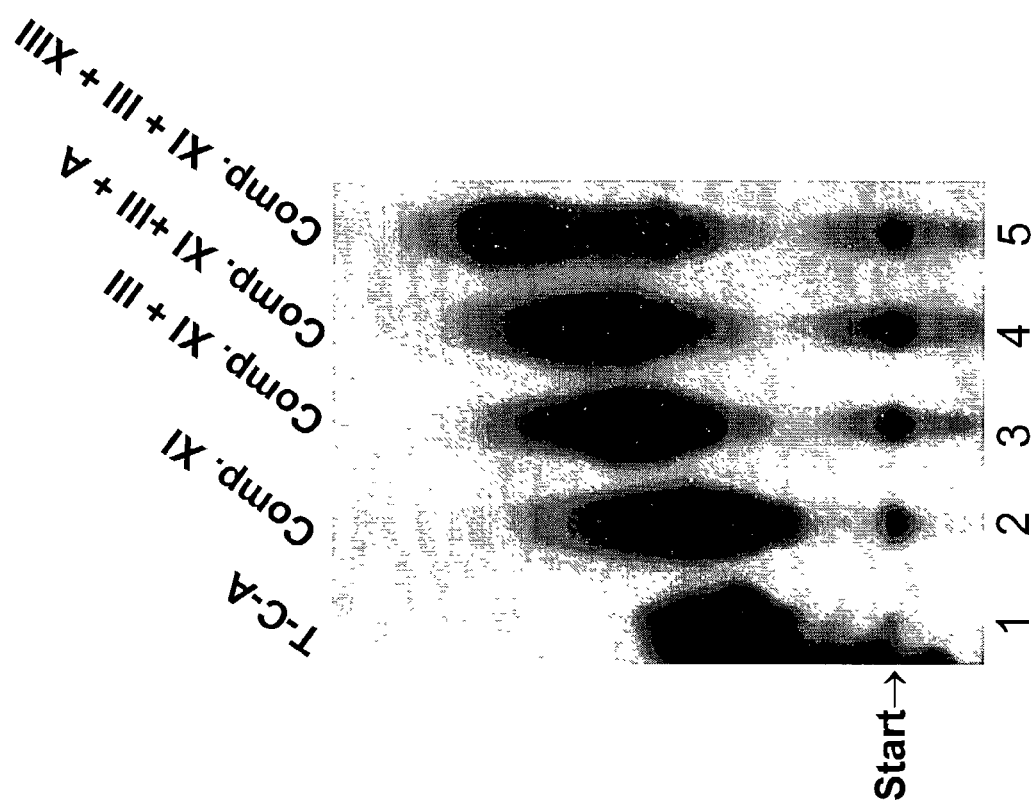
Figure 53:
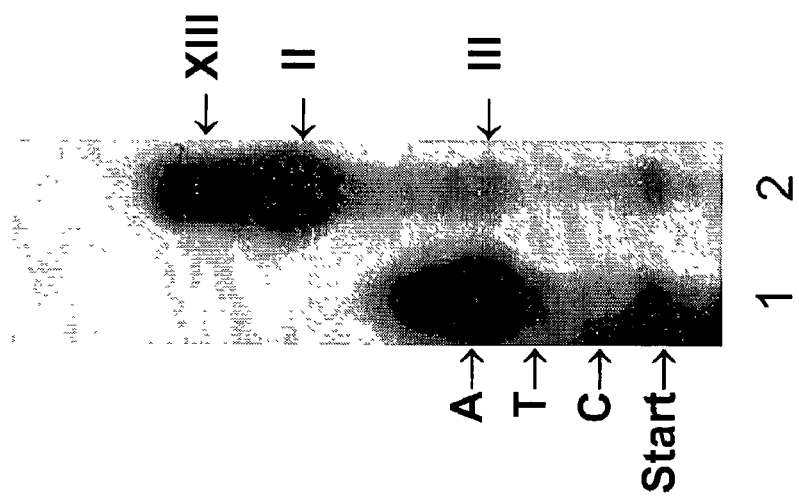
Figure 54:
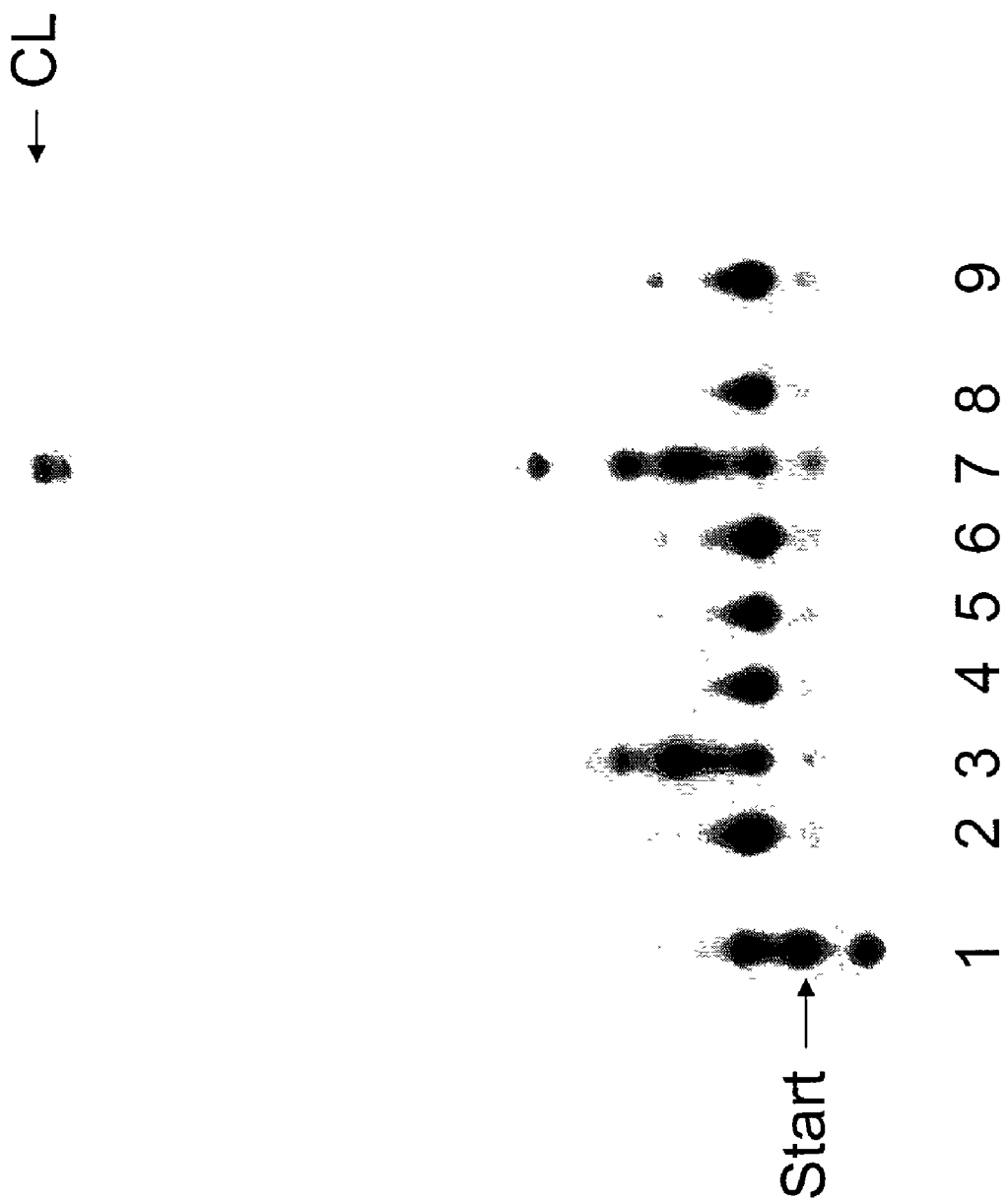

FIG. 49 shows the result of example 64.
FIG. 50 shows the result of example 65.
FIG. 51 shows the result of example 66.
FIG. 52 shows the result of example 67.
FIG. 53 shows the result of example 68.
FIG. 54 shows the result of example 72.

Figure 55A:
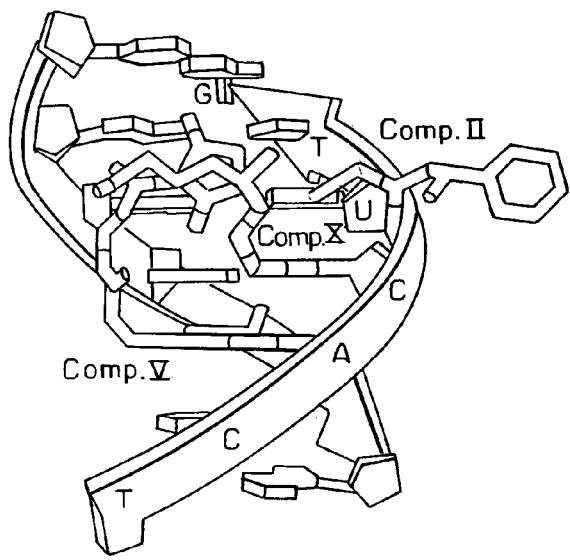

FIG. 55A DNA template with three modified nucleotides (Compound V activated by NHS) incorporated (all shown in stick models coloured by residue).

Figure 55B:
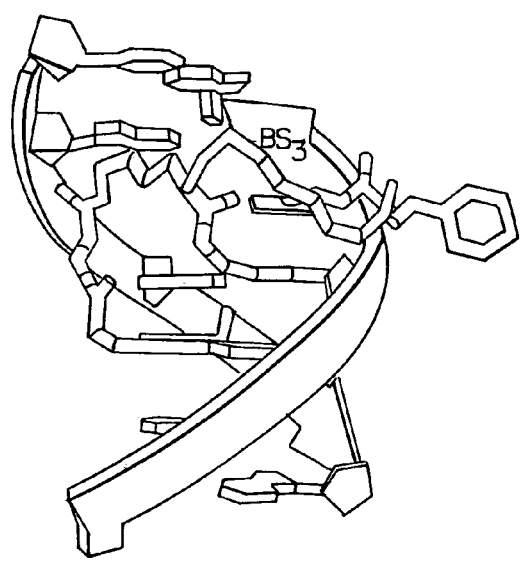

FIG. 55B DNA template bearing modifications after 1) reaction between compound X and compound V and 2) bridging of compound X and compound II using added reagent $BS_3$.

Figure 55C:
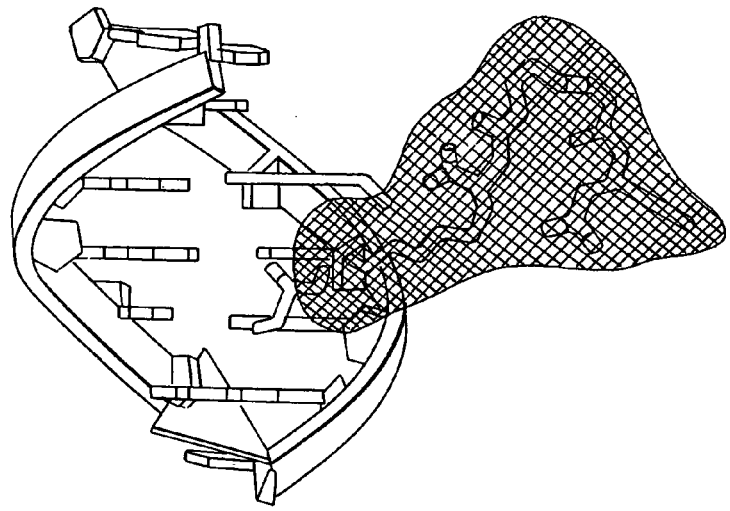

FIG. 55C DNA displaying the templated molecule after hydrolysis of the two hydrolyzable ester elements. All modifications are shown in stick representation and in addition the end product is highlighted by its surface.

Figure 56:
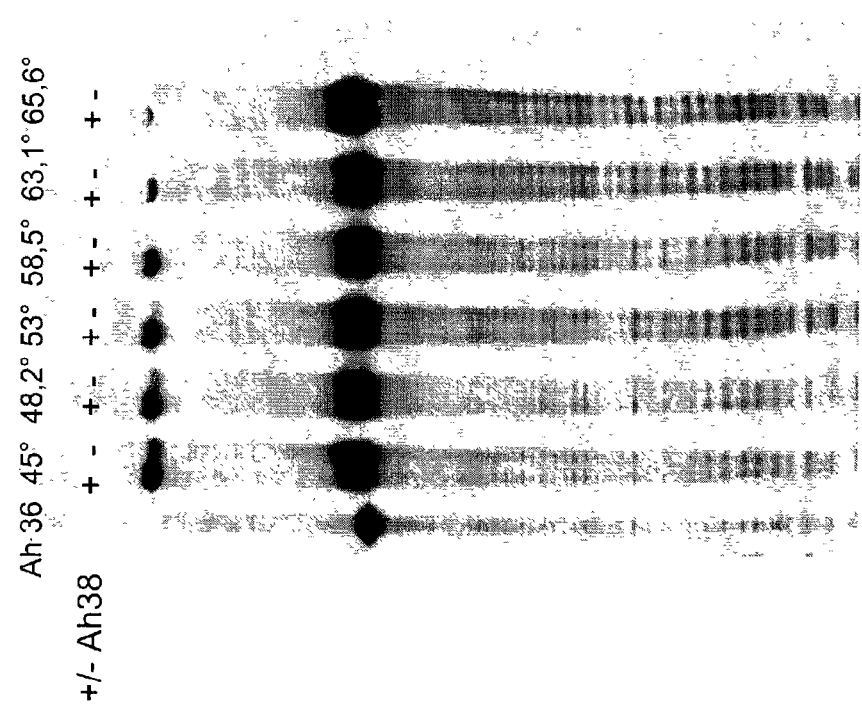

FIG. 56 show the result of example 99.

Figure 57A:
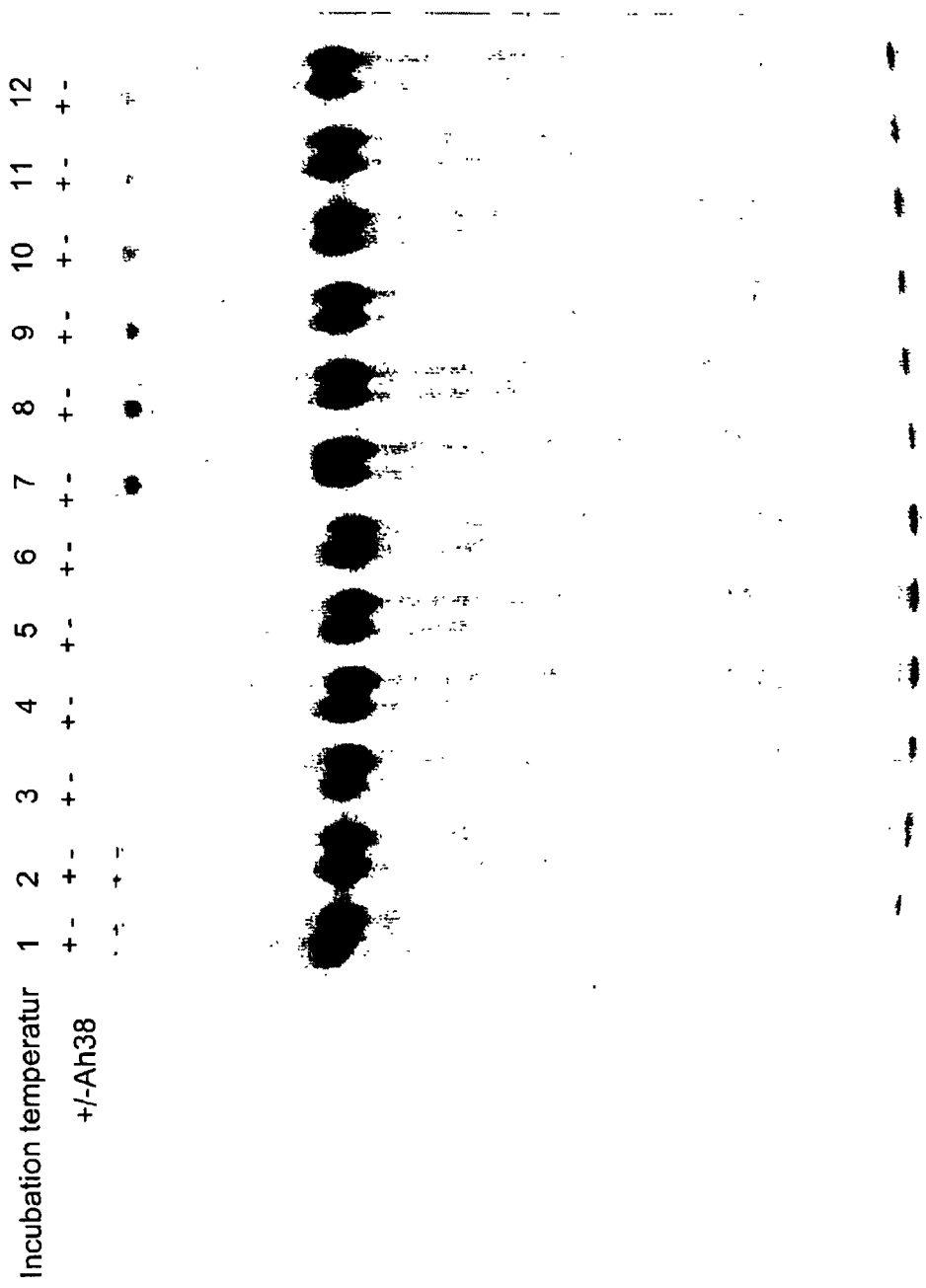

FIGS. 57A and B show the result of example 99.

Figure 58A:
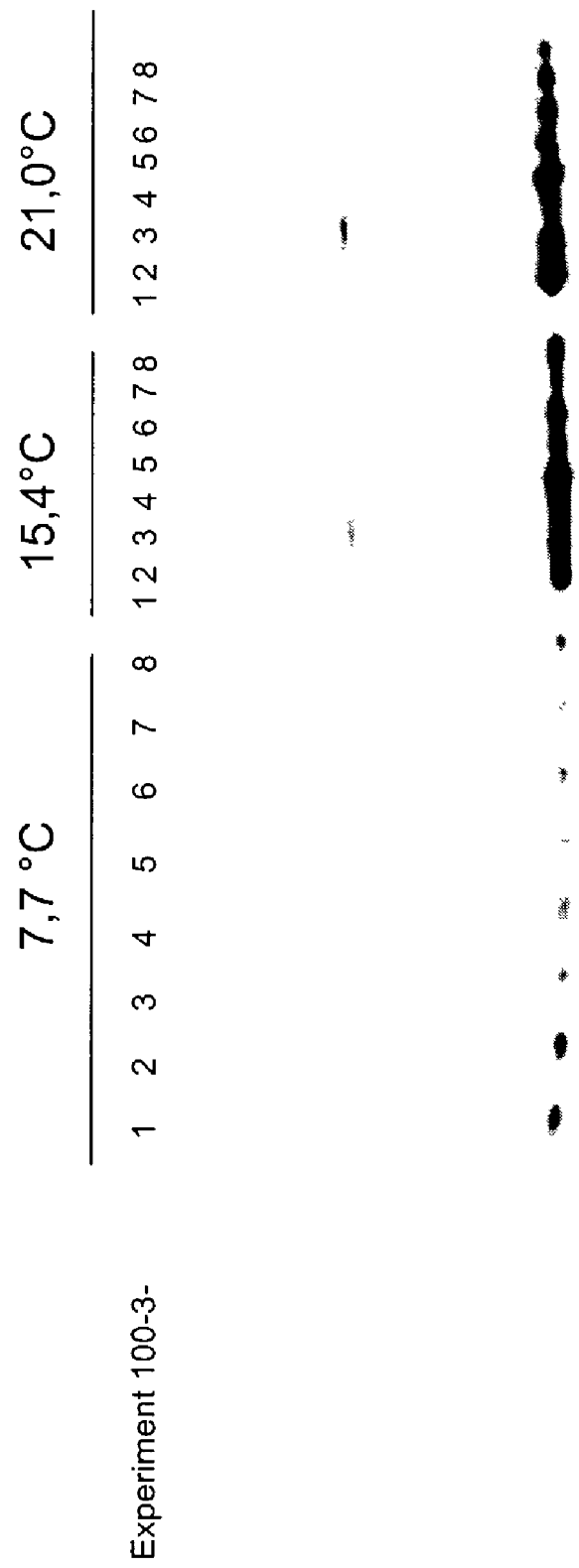

FIGS. 58A and B show the result of example 99.

Figure 59:
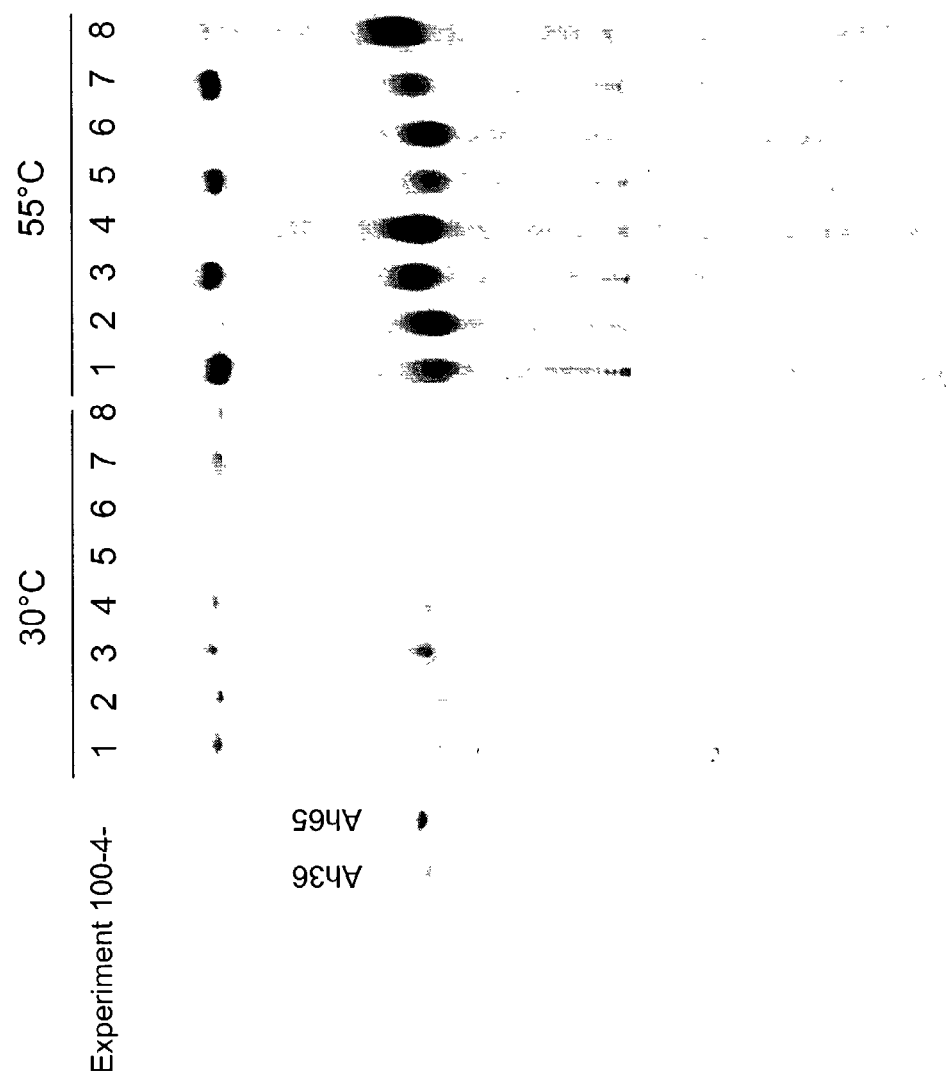

FIG. 59 shows the result of example 99.

Figure 60:

FIG. 60 shows the result of example 102.

Figure 61:
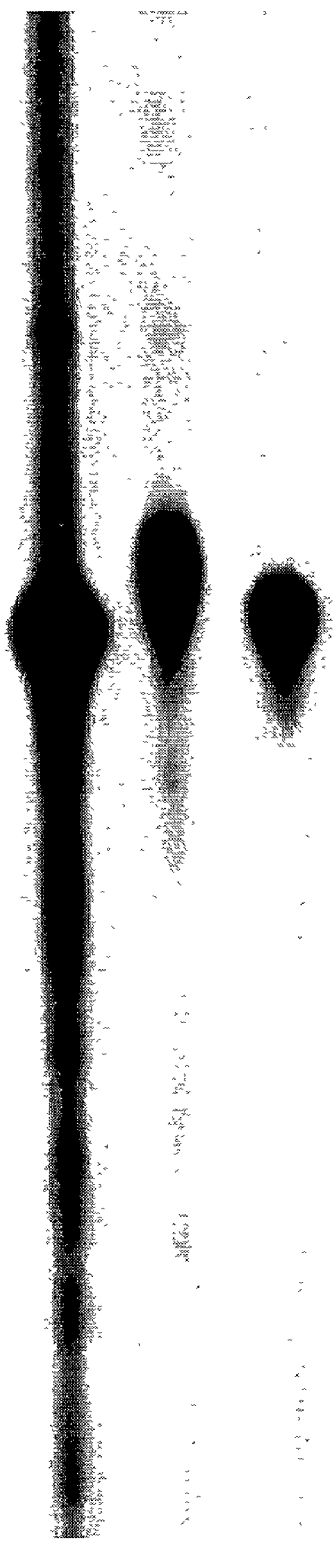

FIG. 61 show the result of example 104.

Figure 62:
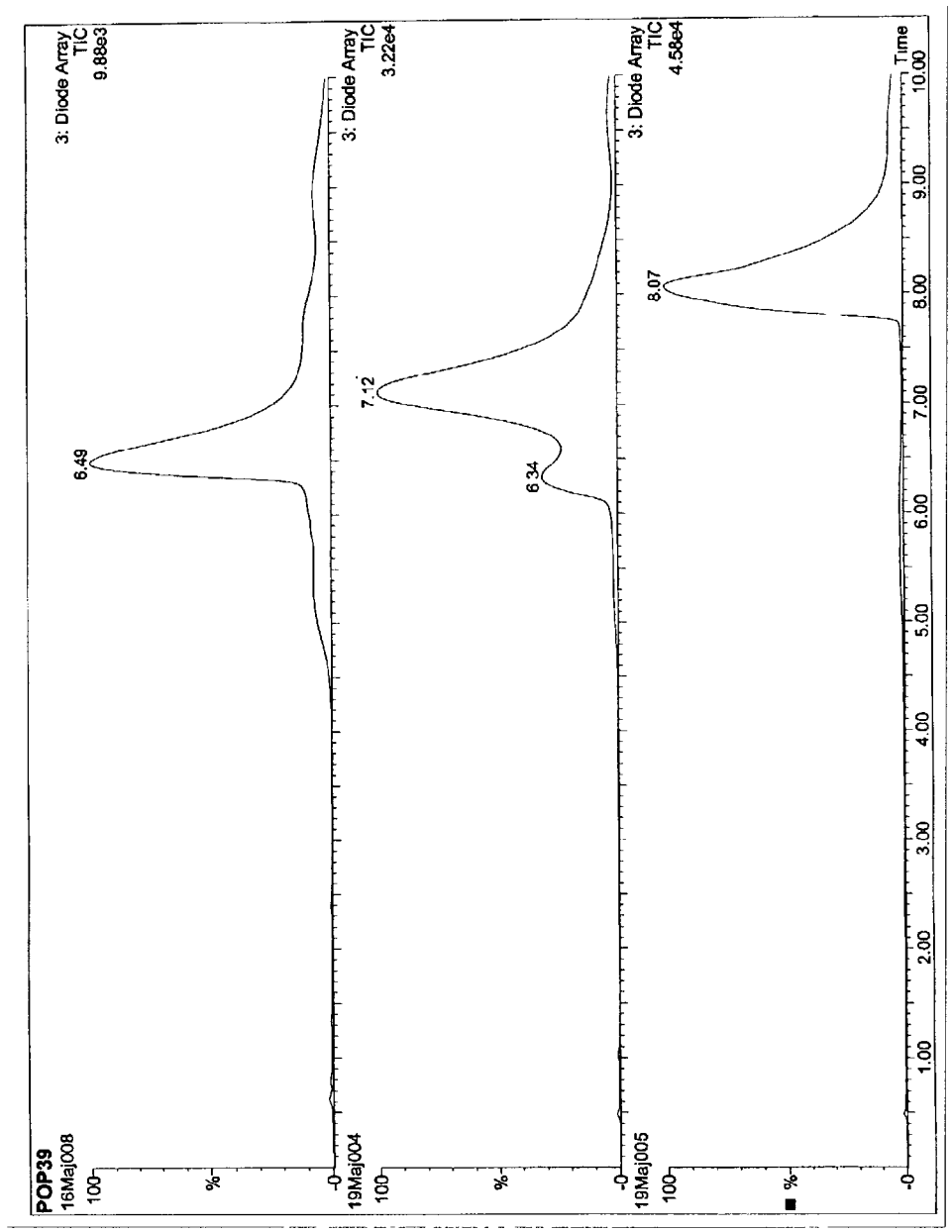

FIG. 62 show the result of example 105.

Figure 63:
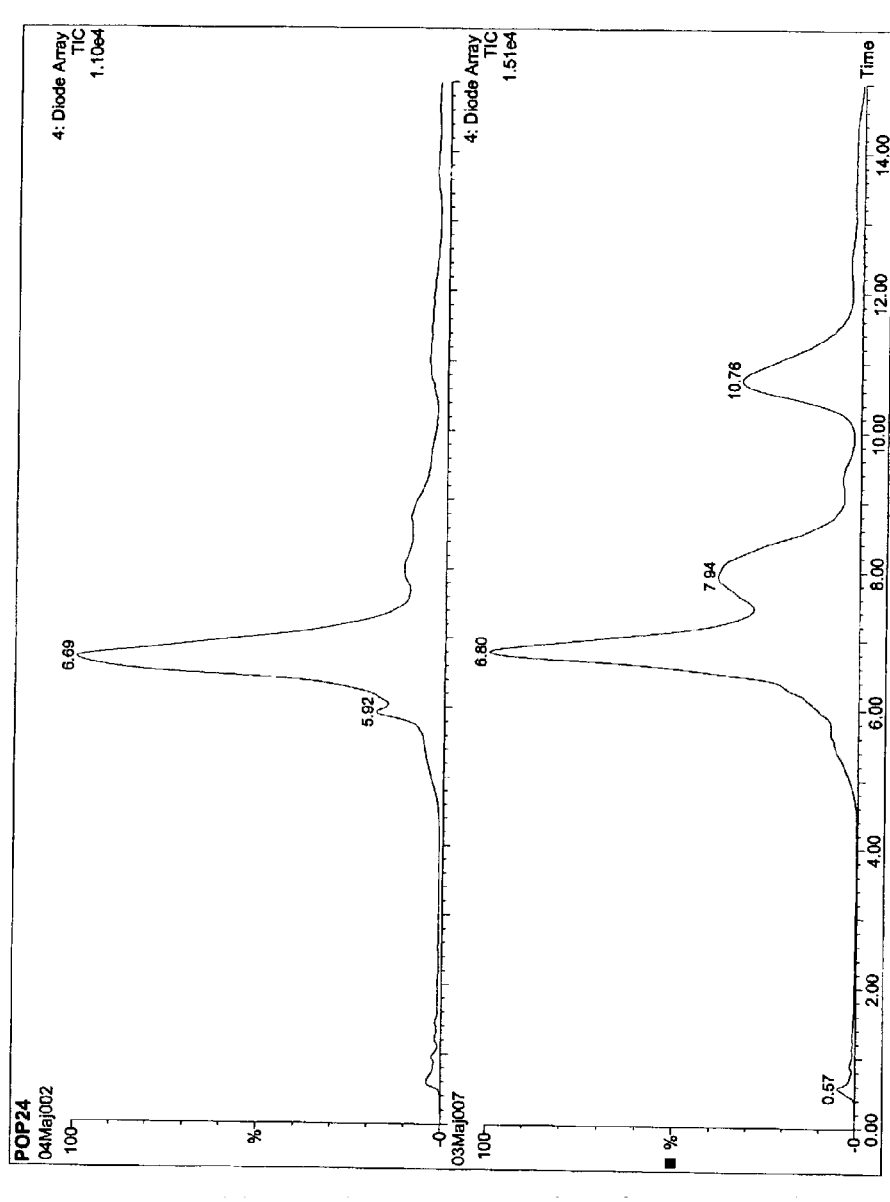

FIG. 63 show the result of example 106.

Figure 64:
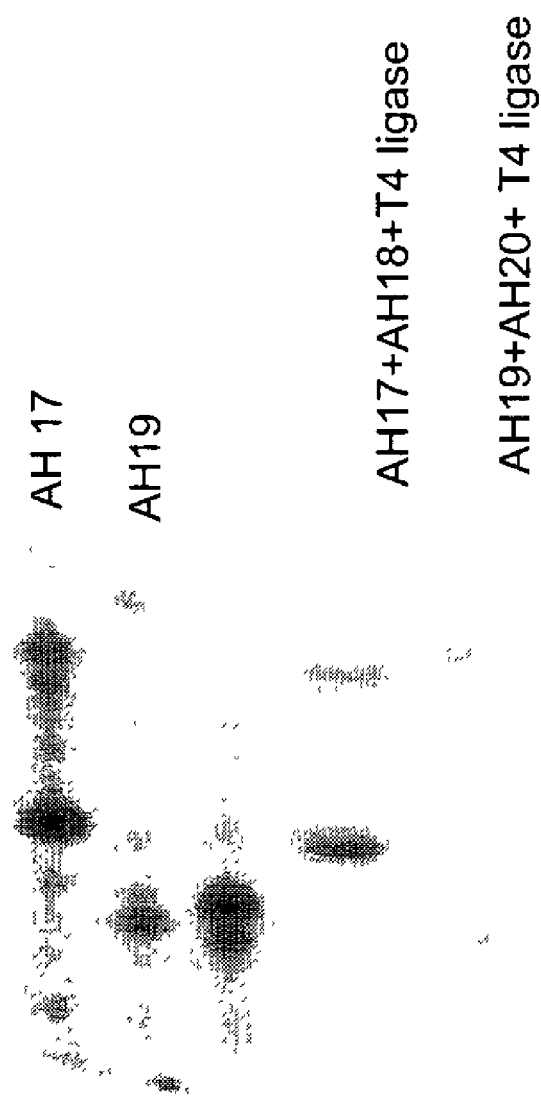

FIG. 64 show the result of example 112.

DEFINITIONS

α-peptide: Peptide comprising or essentially consisting of at least two α-amino acids linked to one another by a linker including a peptide bond.

Amino acid: Entity comprising an amino terminal part ($NH_2$) and a carboxy terminal part (COOH) separated by a central part comprising a carbon atom, or a chain of carbon atoms, comprising at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 2 herein below. Non-natural amino acids are those not listed in Table 2. Examples of non-natural amino acids are those listed e.g. in 37 C.F.R. section 1.822(b)(4), all of which are incorporated herein by reference. Further examples of non-natural amino acids are listed herein below. Amino acid residues described herein can be in the "D" or or "L" isomeric form.

TABLE 2

Natural amino acids and their respective codes.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |

TABLE 2-continued

Natural amino acids and their respective codes.

| Symbols | | |
|---|---|---|
| 1-Letter | 3-Letter | Amino acid |
| R | Arg | arginine |
| D | Asp | aspartic acid |
| N | Asn | asparagine |
| C | Cys | cysteine |

Amino acid precursor: Moiety capable of generating an amino acid residue following incorporation of the precursor into a peptide.

Amplifying: Any process or combination of process steps that increases the number of copies of a templated molecule. Amplification of templated molecules may be carried out by any state of the art method including, but not limited to, a polymerase chain reaction to increase the copy number of each template, and using the templates for synthesising additional copies of the templated molecules comprising a sequence of functional groups resulting from the synthesis of the templated molecule being templated by the template. Any amplification reaction or combination of such reactions known in the art can be used as appropriate as readily recognized by those skilled in the art. Accordingly, templated molecules can be amplified by using the polymerase chain reaction (PCR), ligase chain reaction (LCR), in vivo amplification of cloned DNA, and the like. The amplification method should preferably result in the proportions of the amplified mixture being essentially representative of the proportions of templates of different sequences in a mixture prior to amplification.

Base: Nitrogeneous base moiety of a natural or non-natural nucleotide, or a derivative of such a nucleotide comprising alternative sugar or phosphate moieties. Base moieties include any moiety that is different from a naturally occurring moiety and capable of complementing one or more bases of the opposite nucleotide strad of a double helix.

Building block: Species comprising a) at least one complementing element comprising at least one recognition group capable of recognising a predetermined coding element, b) at least one functional entity comprising a functional group and a reactive group, and c) at least one linker separating the at least one functional entity from the at least one complementing element, wherein the building block does not comprise a ribosome. Preferred building blocks are capable of being incorporated into a nucleotide strand and/or capable of being linked by reactions involving reactive groups of type I and/or type II as described herein.

Cleavable linker: Residue or bond capable of being cleaved under predetermined conditions.

Cleaving: Breaking a chemical bond. The bond may be a covalent bond or a non-covalent bond.

Coding element: Element of a template comprising a recognition group and capable of recognising a predetermined complementing element of a building block. The recognition may result from the formation of a covalent bond or from the formation of a non-covalent bond between corresponding pairs of coding elements and complementing elements capable of interacting with one another.

Coding element complementation: Contacting a coding element with a predetermined complementing element capable of recognising said coding element.

Complementing: Process of bringing a coding element into reactive contact with a predetermined complementing element capable of recognising said coding element. When the coding element and the complement element comprises a natural nucleotide comprising a base moiety, predetermined sets of nucleotides are capable of complementing each other by means of hydrogen bonds formed between the base moieties.

Complementing element: Element of a building block. Linked to at least one functional entity by means of a linker. See coding element.

Complementing template: A sequence of complementing elements, wherein each complementing element is covalently linked to a neighbouring complementing element. A complementing element is capable of recognising a predetermined coding element. The complementing template may be linear or branched.

Complex: Templated molecule linked to the template that templated the synthesis of the templated molecule. The template can be a complementing template as defined herein that is optionally hybridised or otherwise attached to a corresponding template of linked coding elements.

Contacting: Bringing e.g. corresponding reactive groups or corresponding binding partners or hybridization partners into reactive contact with each other. The reactive contact is evident from a reaction or the formation of a bond or a hybridization between the partners.

Corresponding binding partners: Binding partners capable of reacting with each other.

Corresponding reactive groups: Reactive groups capable of reacting with each other.

Functional entity: Entity forming part of a building block. The functional entity comprises a functional group and a reactive group capable of linking neighbouring, functional groups.

Functional group: Group forming part of a templated molecule. The sequence of functional groups in a templated molecule is a result of the capability of the template to template the synthesis of the templated molecule.

Interacting: Used interchangably with contacting. Bringing species such as e.g. corresponding binding partners in the form of e.g. coding elements and complementing elements into reactive contact with each other. The reaction may be mediated by recognition groups forming corresponding binding partners by means of covalent or non-covalent bonds. The interaction may occur as a result of mixing a template comprising a plurality of coding elements with a plurality of building blocks.

Ligand: Used herein to describe a templated molecule capable of targeting a target molecule. In a population of candidate template molecules, a ligand is one which binds with greater affinity than that of the bulk population. In a candidate mixture there can exist more than one ligand for a given target. The ligands can differ from one another in their binding affinities for the target molecule.

Linker: A residue or chemical bond separating at least two species. The species may be retained at an essentially fixed distance, or the linker may be flexible and allow the species some freedom of movement in relation to each other. The link can be a covalent bond or a non-covalent bond. Linked species include e.g. a complementing element and a functional entity of a building block, neighbouring coding elements of a template, neighbouring complementing elements of a complementing template, and neighbouring functional groups of a templated molecule.

Natural nucleotide: Any of the four deoxyribonucleotides, dA, dG, dT, and dC (constituents of DNA), and the four ribonucleotides, A, G, U, and C (constituents of RNA) are the natural nucleotides. Each natural nucleotide comprises or essentially consists of a sugar moiety (ribose or deoxyribose), a phosphate moiety, and a natural/standard base moiety. Natural nucleotides bind to complementary nucleotides according to well-known rules of base pairing (Watson and Crick), where adenine (A) pairs with thymine (T) or uracil (U); and where guanine (G) pairs with cytosine (C), wherein corresponding base-pairs are part of complementary, anti-parallel nucleotide strands. The base pairing results in a specific hybridization between predetermined and complementary nucleotides. The base pairing is the basis by which enzymes are able to catalyze the synthesis of an oligonucleotide complementary to the template oligonucleotide. In this synthesis, building blocks (normally the triphosphates of ribo or deoxyribo derivatives of A, T, U, C, or G) are directed by a template oligonucleotide to form a complementary oligonucleotide with the correct, complementary sequence. The recognition of an oligonucleotide sequence by its complementary sequence is mediated by corresponding and interacting bases forming base pairs. In nature, the specific interactions leading to base pairing are governed by the size of the bases and the pattern of hydrogen bond donors and acceptors of the bases. A large purine base (A or G) pairs with a small pyrimidine base (T, U or C). Additionally, base pair recognition between bases is influenced by hydrogen bonds formed between the bases. In the geometry of the Watson-Crick base pair, a six membered ring (a pyrimidine in natural oligonucleotides) is juxtaposed to a ring system composed of a fused, six membered ring and a five membered ring (a purine in natural oligonucleotides), with a middle hydrogen bond linking two ring atoms, and hydrogen bonds on either side joining functional groups appended to each of the rings, with donor groups paired with acceptor groups.

Neighbouring: Elements, groups, entities or residues located next to one another in a sequence are said to be neighbouring. In cases where two complementing elements, each linked to a functional entity, are linked to one another through one (or more) complementing element(s) that is not linked to a functional entity, the aforementioned complementing elements are said to be neighbouring and said two complementing elements define neighbouring functional entities and neighbouring coding elements that can be linked to one another, either directly or through one (or more) coding element(s).

Non-natural amino acid: Any amino acid not included in Table 2 herein above. Non-natural amino acids includes, but is not limited to modified amino acids, L-amino acids, and stereoisomers of D-amino acids.

Non-natural base pairing: Base pairing among non-natural nucleotides, or among a natural nucleotide and a non-natural nucleotide. Examples are described in U.S. Pat. No. 6,037,120, wherein eight non-standard nucleotides are described, and wherein the natural base has been replaced by a non-natural base. As is the case for natural nucleotides, the non-natural base pairs involve a monocyclic, six membered ring pairing with a fused, bicyclic heterocyclic ring system composed of a five member ring fused with a six membered ring. However, the patterns of hydrogen bonds through which the base pairing is established are different from those found in the natural AT, AU and GC base pairs. In this expanded set of base pairs obeying the Watson-Crick hydrogen-bonding rules, A pairs with T (or U), G pairs with C, iso-C pairs with iso-G, and K pairs with X, H pairs with J, and M pairs with N (FIG. 2). Nucleobases capable of base pairing without obeying Watson-Crick hydrogen-bonding rules have also been described (Berger et al., 2000, Nucleic Acids Research, 28, pp. 2911-2914).

Non-natural nucleotide: Any nucleotide not falling within the definition of a natural nucleotide.

Nucleotide: Nucleotides as used herein refers to both natural nucleotides and non-natural nucleotides capable of being incorporated—in a template-directed manner—into an oligonucleotide, preferably by means of an enzyme comprising DNA or RNA dependent DNA or RNA polymerase activity, including variants and functional equivalents of natural or recombinant DNA or RNA polymerases. Corresponding binding partners in the form of coding elements and complementing elements comprising a nucleotide part are capable of interacting with each other by means of hydrogen bonds. The interaction is generally termed "base-pairing". Nucleotides may differ from natural nucleotides by having a different phosphate moiety, sugar moiety and/or base moiety. Nucleotides may accordingly be bound to their respective neighbour(s) in a template or a complementing template by a natural bond in the form of a phosphodiester bond, or in the form of a non-natural bond, such as e.g. a peptide bond as in the case of PNA (peptide nucleic acids).

Nucleotide analog: Nucleotide capable of base-pairing with another nucleotide, but incapable of being incorporated enzymatically into a template or a complementary template. Nucleotide analogs often includes monomers or oligomers containing non-natural bases or non-natural backbone structures that do not facilitate incorporation into an oligonucleotide in a template-directed manner. However, interaction with other monomers and/or oligomers through specific base pairing is possible. Alternative oligomers capable of specifically base pairing, but unable to serve as a substrate of enzymes, such as DNA polymerases and RNA polymerases, or mutants or functional equivalents thereof, are defined as nucleotide analogs herein. Oligonucleotide analogs includes e.g. nucleotides in which the phosphodiester-sugar backbone of natural oligonucleotides has been replaced with an alternative backbone include peptide nucleic acid (PNA), locked nucleic acid (LNA), and morpholinos.

Nucleotide derivative: Nucleotide or nucleotide analog further comprising an appended molecular entity. Often, derivatized building blocks (nucleotides to which a molecular entity have been appended) can be enzymatically incorporated into oligonucleotides by RNA or DNA polymerases, using as substrate the triphosphate of the derivatized nucleoside. In many cases such derivatized nucleotides are incorporated into the growing oligonucleotide chain with high specificity, meaning that the derivative is inserted opposite a predetermined nucleotide in the template. Such an incorporation will be understood to be a specific incorporation. The nucleotides can be derivatized on the bases, the ribose/deoxyribose unit, or on the phosphate. Preferred sites of derivatization on the bases include the 8-position of adenine, the 5-position of uracil, the 5- or 6-position of cytosine, and the 7-position of guanine. The nucleotide-analogs described below may be derivatized at the corresponding positions (Benner, U.S. Pat. No. 6,037,120). Other sites of derivatization may be used, as long as the derivatization does not disrupt base pairing specificity. Preferred sites of derivatization on the ribose or deoxyribose moieties are the 5', 4' or 2' positions. In certain cases it may be desirable to stabilize the nucleic acids towards degradation, and it may be advantageous to use 2'-modified nucleotides (U.S. Pat. No. 5,958,691). Again, other sites may be employed, as long as the base pairing specificity is not disrupted. Finally, the phosphates may be derivatized. Preferred derivatizations are phosphorothiote. Nucleotide analogs (as described below) may be derivatized similarly to nucleotides. It is clear that the various types of modifications mentioned herein above, including i) derivatization and ii) substitution of the natural bases or natural backbone structures with non-natural bases and alternative, non-natural backbone structures, respectively, can be applied once or more than once within the same molecule.

Oligonucleotide: Used herein interchangebly with polynucleotide. The term oligonucleotide comprises oligonucleotides of both natural and/or non-natural nucleotides, including any combination thereof. The natural and/or non-natural nucleotides may be linked by natural phosphodiester bonds or by non-natural bonds. Oligonucleotide is used interchangeably with polynucleotide.

Oligomer: Molecule comprising a plurality of monomers that may be identical, of the same type, or different. Oligomer is used synonymously with polymer in order to describe any molecule comprising more than two monomers. Oligomers may be homooligomers comprising a plurality of identical monomers, oligomers comprising different monomers of the same type, or heterooligomers comprising different types of monomers, wherein each type of monomer may be identical or different.

Partitioning: Process whereby templated molecules, or complexes comprising such molecules linked to a template, are preferentially bound to a target molecule and separated from templated molecules, or complexes comprising such molecules linked to a template, that do not have an affinity for—and is consequently not bound to—such target molecules. Partitioning can be accomplished by various methods known in the art. The only requirement is a means for separating targeted, templated molecules bound to a target molecule from templated molecules not bound to target molecules. The choice of partitioning method will depend on properties of the target molecule and of the templated molecule and can be made according to principles and properties known to those of ordinary skill in the art.

Peptide: Plurality of covalently linked amino acid residues defining a sequence and linked by amide bonds. The term is used analogously with oligopeptide and polypeptide. The amino acids may be both natural amino acids and non-natural amino acids, including any combination thereof. The natural and/or non-natural amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Plurality: At least two.

Polymer: Templated molecule characterised by a sequence of covalently linked residues each comprising a functional group, including H. Polymers according to the invention comprise at least two residues.

Polynucleotide: See oligonucleotide,

Precursor: Moiety comprising a residue and being capable of undergoing a reaction during template directed synthesis of a templated molecule, wherein the residue part of the precursor is built into the templated molecule.

Reactive group: Corresponding reactive groups being brought into reactive contact with each other are capable of forming a chemical bond linking e.g. a coding element and its complementing element, or coupling functional groups of a templated molecule.

Recognition group: Part of a coding element and involved in the recognition of the complementing element capable of recognising the coding element. Preferred recognition groups are natural and non-natural nitrogeneous bases of a natural or non-natural nucleotide.

Recombine: A recombination process recombines two or more sequences by a process, the product of which is a sequence comprising sequences from each of the two or more sequences. When involving nucleotides, the recombination involves an exchange of nucleotide sequences between two or more nucleotide molecules at sites of identical nucleotide sequences, or at sites of nucleotide sequences that are not identical, in which case the recombination can occur randomly. One type of recombination among nucleotide sequences is referred to in the art as gene shuffling.

Repetitive sequence: Sequence of at least two elements, groups, or residues, occurring more than once in a molecule.

Residue: A polymer comprises a sequence of covalently linked residues, wherein each residue comprises a functional group.

Ribose derivative: Ribose moiety forming part of a nucleoside capable of being enzymatically incorporated into a template or complementing template. Examples include e.g. derivatives distinguishing the ribose derivative from the riboses of natural ribonucleosides, including adenosine (A), guanosine (G), uridine (U) and cytidine (C). Further examples of ribose derivatives are described in e.g. U.S. Pat. No. 5,786,461. The term covers derivatives of deoxyriboses, and analogously with the above-mentioned disclosure, derivatives in this case distinguishes the deoxyribose derivative from the deoxyriboses of natural deoxyribonucleosides, including deoxyadenosine (dA), deoxyguanosine (dG), deoxythymidine (dT) and deoxycytidine (dC).

Selectively cleavable linker: Selectively cleavable linkers are not cleavable under conditions wherein a cleavable linker is cleaved. Accordingly, it is possible to cleave the cleavable linkers linking complementing elements and functional groups in a templated molecule without at the same time cleaving selectively cleavable linkers linking—in the same templated molecule—a subset of complementing elements and functional groups. It is thus possible to obtain a complex comprising a templated molecule and the template that has directed the template-mediated synthesis of the templated molecule, wherein the template and the templated molecule are linked by one or more, preferably one, selectively cleavable linker(s).

Specific recognition: The interaction of e.g. a coding element with preferably one predetermined complementing element. A specific recognition occurs when the affinity of a coding element recognition group for a complementing group results in the formation of predominantly only one type of corresponding binding partners. Simple mis-match incorporation does not exclude a specific recognition of corresponding binding partners. Specific recognition is a term which is defined on a case-by-case basis. In the context of a given interaction between predetermined binding partners, e.g. a templated molecule and a target molecule, a binding interaction of templated molecule and target molecule of a higher affinity than that measured between the target molecule and a candidate template molecule mixture is observed. In order to compare binding affinities, the conditions of both binding reactions must be essentially similar and preferably the same, and the conditions should be comparable to the conditions of the intended use. For the most accurate comparisons, measurements will be made that reflect the interaction between templated molecule as a whole and target as a whole. The templated molecules of the invention can be selected to be as specific as required, either by establishing selection conditions that demand a requisite specificity, or by tailoring and modifying the templated molecules.

Subunit: Monomer of coding element comprising at least one such subunit.

Support: Solid or semi-solid member to which e.g. coding elements can be attached during interaction with at least one complementing element of a building block. Functional molecules or target molecules may also be attached to a solid support during targeting. Examples of supports includes planar surfaces including silicon wafers as well as beads.

Tag: Entity capable of identifying a compound to which it is associated.

Target molecule: Any compound of interest for which a templated molecule in the form of a ligand is desired. A target molecule can be a protein, fusion protein, peptide, enzyme, nucleic acid, nucleic acid binding protein, carbohydrate, polysaccharide, glycoprotein, hormone, receptor, receptor ligand, cell membrane component, antigen, antibody, virus, virus component, substrate, metabolite, transition state analog, cofactor, inhibitor, drug, controlled substance, dye, nutrient, growth factor, toxin, lipid, glycolipid, etc., without limitation.

Template: Template refers to both a template of coding elements and a (complementing) template of complementing elements unless otherwise specified. When referring to a template of coding elements, each coding element is covalently linked to a neighbouring coding element. Each coding element is capable of recognising a predetermined complementing element. The template may be linear or branched. A template of coding elements actively takes part in the synthesis of the templated molecule, and the templating activity involves the formation of specific pairing partners in the form of coding element:complementing element hybrids, wherein the complementing element forms part of a building block also comprising the functional group forming part of the templated molecule. The template is preferably a string of nucleotides or nucleotide analogs. When the template comprises a string of nucleotides, the nucleotides may be natural or non-natural, and may be linked by e.g. phosphorothioate bonds or natural phosphodiester bonds. Nucleotide analogs may be linked e.g. by amide bonds, peptide bonds, or any equivalent means capable of linking nucleotide analogs so as to allow the nucleotide analog string to hybridize specifically with another string of nucleotides or nucleotide analogs. The sugar moiety of a nucleotide or nucleotide analog may be a ribose or a deoxyribose, a ribose derivative, or any other molecular moiety that allows the template or complementing template to hybridise specifically to another string of nucleotides or nucleotide analogs.

Template directed synthesis: Used synonymously with template directed incorporation and templated synthesis. Template directed synthesis is the process, wherein the formation of a templated molecule comprising a sequence of covalently linked, functional groups involves contacting a string of coding elements with particular complementing elements. The process thus defines a one-to-one relationship between coding elements and functional groups, and the contacted coding element of the template directs the incorporation of the functional group into the templated molecule comprising a sequence of covalently linked, functional groups. Accordingly, there is a predetermined one to one relationship between the sequence of functional groups of the templated molecule and the sequence of coding elements of the template that templated the synthesis of the templated molecule. Thus, during the templated synthesis of the templated molecule, a functional group is initially contacting—by means of a linker moiety and/or a complementing element, or otherwise—the coding element capable of templating that particular functional group into the templated molecule. When the template comprises or essentially consists of nucleotides, a template directed synthesis of an oligonucleotide is based on an interaction of each nucleotide with its pairing partner in the template in a one-base-to-one-base pairing manner. The interaction specifies the incorporation of complementing nucleotides opposite their base pairing partners in the template. Consequently, one base, including a heterocyclic base, from each oligonucleotide strand interact when forming specific base-pairs. This base pairing specificity may be achieved through Watson-Crick hydrogen-bonding interactions between the bases, where the bases may be natural (i.e. A, T, G, C, U), and/or non-natural bases such as those e.g. disclosed e.g. in U.S. Pat. No. 6,037,120, incorporated herein by reference. Further examples of non-natural bases are e.g. PNA (peptide nucleic acid), LNA (lock nucleic acid) and morpholinos. Base pairing of oligonucleotides containing non-standard base pairs can be achieved by other means than hydrogen bonding (e.g. interaction between hydrophobic nucleobases with "complementary" structures; Berger et al., 2000, Nucleic Acids Research, 28, pp. 2911-2914). The interacting oligonucleotide strands as well as the individual nucleotides are said to be complementary. The specificity of the interaction between oligomers results from the specific base pairing of a nucleotide with another nucleotide or a predetermined subset of nucleotides, for example A base pairing with U, and C base pairing with G.

Templated: Feature of the templated molecule of the complex comprising a template linked to the templated molecule, wherein the templated molecule is obtainable by template directed synthesis using the template. Thus, one component of the complex (the template) is capable of templating the synthesis of the other component (the templated molecule). The term is also used to describe the synthesis of the templated molecule that involves the incorporation into the templated molecule of functional groups, wherein the incorporation of each functional group involves contacting a coding element with a particular functional group, or with a building block comprising said functional group, wherein the contacted coding element of the template directs the incorporation of functional groups into the templated molecule linked to the template that templated in this way the synthesis of the templated molecule. Thus, during the templated synthesis of the templated molecule, a functional group is initially contacting—either directly or by means of a linker moiety and/or a complementing element—the coding element capable of templating that particular functional group into the templated molecule.

Templated molecule: Molecule comprising a sequence of covalently linked. functional groups, wherein the templated molecule is obtainable by template directed synthesis using the template. Thus, one component of the complex (the template) is capable of templating the synthesis of the other component (the templated molecule). When the template comprises or essentially consists of nucleotides, the template is capable of being amplified, wherein said template amplification results in a plurality of templated molecules, wherein each templated molecule is generated by template directed synthesis using the template. Following amplification of a template, or a complementing template, templated molecules can be generated by a template directed synthesis using either a template of coding elements or a complementing template of complementing elements as a template for the template directed synthesis of the templated molecule.

Templating: Process of generating a templated molecule.

Variant: Template or templated molecule exhibiting a certain degree of identity or homology to a predetermined template or templated molecule, respectively.

DETAILED DESCRIPTION OF THE INVENTION

In one preferred embodiment of the present invention, there is provided a "chemical display of templated molecules" which enables the generation of a huge number of "templated polymers" (e.g. from about $10^3$ to about or more than e.g. $10^{18}$ as described elsewhere herein), wherein each templated molecule is individually linked to a "template" that serves as identification of that individual polymer (its sequence of residues), as well as a means for amplification (many copies of the molecule can be prepared by a process that replicates the template). Preferred embodiments of the invention are disclosed in FIG. 1 illustrating various steps of the method of the invention.

Step 1. Synthesis

Different monomer building blocks are synthesized. Building blocks comprise a functional entity and a complementing element that are linked by means of a cleavable linker (FIGS. 3 and 4). Preferred building blocks comprise a nucleotide to which have been appended a functional entity through a cleavable linker, and where the functional entity comprises or essentially consists of an "activatable" polymer unit (FIG. 6).

Step 2. Incorporation

The building blocks are used as substrates in a template-dependent polymer synthesis. In one embodiment, the building blocks are nucleotide-derivatives and a polymerase is preferably used to incorporate the nucleotide-derivatives into an oligonucleotide strand according to the directions of a oligonucleotide template. As a result, a complementing template (a string of incorporated building blocks) is formed, from which the functional entities protrude. The sequence of functional entities is determined by the sequence of coding elements, such as nucleotides, of the template.

FIG. 1 describes the use of a building block that carries the selectively cleavable linker which, after polymerization and activation, is capable of linking the templated polymer to its template. Alternatively, the selectively cleavable linker can be comprised by an oligo capable of annealing upstream or downstream of the polymer-encoding portion of the template (see for example FIG. 7 or 8), or the link could be to the template directly.

The building block can preferably be incorporated by an enzyme, such as for example DNA polymerase, RNA polymerase, Reverse Transcriptase, DNA ligase, RNA ligase, Taq DNA polymerase, HIV-1 Reverse Transcriptase, Klenow fragment, or any other enzyme that will catalyze the incorporation of complementing elements such as mono-, di- or polynucleotides. In some of these cases, a primer is required (for example DNA polymerase). In other cases, no primer is required (e.g., RNA polymerase).

Step 3. Polymerization

Each functional entity has preferably reacted with neighbouring functional entities to form a polymer during or after formation of the complementing template. A change in conditions, e.g., photolysis, change in temperature, or change in pH, may initiate the polymerisation either during or after complementing template formation.

Step 4. Activation

The formed polymer is preferably released from the complementing elements by cleavage of at least one linker, or a plurality of cleavable linkers, except at one or more predetermined position(s), including a single position, where the linker is not cleavable under conditions resulting in cleavage of the remaining linkers. The result is a templated polymer attached at one or more positions, preferably only at one position, to the template that encodes it.

Step 5. Selection and Amplification

A selection process can subsequently be performed, wherein a huge number of different templated molecules, each attached to the template that directed its synthesis, is challenged with a molecular or physical target (e.g. a biological receptor or a surface), or is exposed to a certain screen. Templated molecules having desired characteristics (e.g., binding to a receptor) are recovered and amplified, by first amplifying the templates, and then using the templates for a new round of templated polymer synthesis. The process of selection and amplification can be repeated several times, until a polymer with appropriate characteristics (e.g., high affinity for the receptor) is isolated.

A typical selection protocol involves the addition of a population (a library) of template-templated molecule complexes to an affinity column, to which a certain molecular target (e.g., a receptor) had been immobilized. After washing the column, the binders are eluted. This eluate consists of an enriched population of template-templated molecule complexes with affinity for the immobilized target molecule. The enriched population may be taken through an amplification round, and then be subjected to yet a selection round, where the conditions optionally may be more stringent. After a number of such selection-and-amplification rounds, an enriched population of high affine binders are obtained.

When selecting for the ability of a templated molecule to become internalized into a cell, the selection step may involve a simple mixing of the population of template-templated molecule complexes with cells. After incubation (to allow the internalization of the template-templated molecule complexes), the cells are washed, and the internalized template-templated molecule complexes may be recovered by lysis of the cells. As above, the template-templated molecule complexes may be amplified and taken through further rounds of selection-and-amplification. After a number of selection-and-amplification rounds, an enriched population of templated molecules with the ability to internalize are obtained.

Building Blocks—Molecular Design

The building blocks (also termed "monomers") is preferably of the general design shown in FIGS. 3 and 4. The monomer in one embodiment comprises the following elements: Complementing element-Linker-Backbone comprising reactive group(s) type II-Functional group, where the complementing element comprises or essentially consists of a recognition group and reactive group(s) type I. In this case the linker is preferably a "traceless linker", i.e., a linker that does not leave any (undesirable) molecular entity on the functional entity. Building blocks with this composition are used in for example (FIG. 15, example 7).

Alternatively, the monomer may have the composition Complementing element-Linker-Functional Group-Backbone containing reactive group(s) type II, in which case the desired functional group is created as a result of cleavage of the linker. Building blocks with this composition are used in for example (FIG. 17, example 1).

The functional groups must be compatible with the desired method for incorporation of complementing elements, their polymerization and activation. Obviously, it is important to preserve the integrity of the template and the templated molecule in these processes.

Functional groups that are not compatible with the conditions of incorporation, polymerization or activation must be protected during these processes, or alternatively, the functional groups must be introduced after these processes have taken place. The latter is done by templating a functional group (e.g., an activated disulfide) that is compatible with the incorporation, polymerization and activation, and that will specifically react with a bifunctional molecule (e.g., a thiol connected to the desirable functional group, $R_x$), added after activation. Alternatively, functionalities may be introduced by e.g. oxidation, or any other form of treatment, of the incorporated functional entities after activation. In this way, functionalities such as components of natural effector molecules or synthetic drugs that are otherwise difficult to handle, may be incorporated.

In some embodiments of the process of the invention as described herein, there is no need for a cleavable linker, as the polymerisation reaction involves cleavage of the linker (FIG. 14 and FIG. 14, example 1).

When being nucleotides, the complementing elements may contain one, two or several nucleotides or nucleotide-analogs. The use of di-, tri- or longer oligonucleotides presents a number of advantages. First, a higher monomer diversity may be encoded by the template. Second, the requirements for the site of attachment of the functional entity to the complementing element becomes more relaxed. Third, there would be less bulk per mononucleotide in the formed polynucleotide, potentially leading to higher display-efficiencies. Fourth, it would allow the display of polymers with longer residue-unit-length. Also, it would allow the display of bigger functional groups.

In cases where a polymerase is employed for the incorporation of nucleotide comprising building blocks, it is preferred that the nucleotides are derivatized in a way that allows their specific and efficient incorporation into the growing strand.

More than 100 different nucleoside- and nucleotide-derivatives are commercially available or can be made using simple techniques (Eaton, Current Opinion in Chemical Biology, 1997, 1: 10-16). Moreover, many nucleotide-derivatives, modified on the bases or the riboses, are incorporated efficiently and specifically by various polymerases, in particular T7 RNA polymerase and Reverse Transcriptase (FIG. 9). Nucleotides with additions of up to 300 Da have been incorporated specifically and efficiently (Wiegand et al., Chemistry and Biology, 1997, 4: 675-683; Fenn and Herman, Analytical Chemistry, 1990, 190: 78-83; Tarasow and Eaton, Biopolymers, 1998, 48: 29-37). In addition to the four natural base pairs (AT or AU, TA or UA, CG, GC), at least 8 base pairs are known to hybridise specifically, some of which are incorporated into oligonucleotides by polymerases in a template-dependent manner.

The incorporation of complementing elements may be catalyzed by chemical or biological catalysts. When the building blocks are nucleotides, particularly relevant catalysts are template-dependent DNA- and RNA-polymerases, including reverse transcriptases, and DNA- and RNA-ligases, ribozymes and deoxyribozymes. Specific examples include HIV-1 Reverse Transcriptase, AMV Reverse Transcriptase, T7 RNA polymerase and T7 RNA polymerase mutant Y639F, Sequenase, Taq DNA polymerase, Klenow Fragment (Large fragment of DNA polymerase 1), DNA-ligase, T7 DNA polymerase, T4 DNA polymerase, T4 DNA Ligase, *E. coli* RNA polymerase, rTh DNA polymerase, Vent DNA polymerase, Pfu DNA polymerase, Tte DNA polymerase, ribozymes with ligase or replicase activities such as described in (Johnston et al., Science, May 18, 2001, pp. 1319-1325), and other enzymes that accept nucleotides and/or oligonucleotides as substrates. Mutant or engineered polymerases with improved characteristics, for example broadened nucleotide substrate specificity, and mutants in which the proofreading function has been eliminated (for example by deleting the nuclease activity), are particularly relevant. The polymerases may use single or double stranded nucleotides as templates, and produce single or double stranded nucleotide products.

Sites of modification that have been shown to be accepted by polymerases include the following non-exhaustive list of examples (See also FIG. 9):

| Nucleotide | Site of modification |
|---|---|
| dATP | 3-position |
| dATP | 7-position |
| dATP | 8-position |
| dATP | 2' (deoxyribose moiety) |
| dTTP | 4' (deoxyribose moiety) |
| dGTP | 7-position |
| dCTP | 2' (deoxyribose moiety) |
| dUTP | 2' (deoxyribose) |
| UTP | 5-position |
| ATP | 8-position |

Terminal transferase, RNA ligases, Polynucleotide kinases and other template independent enzymes that accept nucleotides and/or oligonucleotides as substrates, including engineered or mutant variants, may be used for some of the applications and method variations described in the present invention.

It may be possible to attach the functional entities at other sites in the nucleotide, without eliminating hybridization or incorporation specificity. Particularly when employing complementing elements that are di-, tri- or polynucleotides, it may be possible to attach functional entities at these alternative sites without inhibiting specific incorporation.

Cleavable and Non-cleavable Linkers

A selection of cleavable linkers and protection groups, as well as the agents that cleave them, are illustrated in (FIG. 10). In one aspect of the invention, the linker may be selected from the following list: Carbohydrides and substituted carbohydrides; Vinyl, polyvinyl and substituted polyvinyl; Acetylene, polyacetylene; Aryl/hetaryl, polyaryl/hetaryl and substituted polyaryl/polyhetaryl; Ethers, polyethers such as e.g. polyethylenglycol and substituted polyethers; Amines, polyamines and substituted polyamines; Double stranded, single stranded or partially double stranded natural and unnatural polynucleotides and substituted double stranded, single stranded or partially double stranded natural and unnatural polynucleotides; Polyamides and natural and unnatural polypeptides and substituted polyamides and natural and unnatural polypeptides.

It one aspect of the invention it is preferred that linkers do not react with other linkers, complementing elements or functional entities, in the same monomer or in another monomer. Also, in some of the schemes proposed herein, it is desirable that the linker is not cleaved by the conditions of polymerization. Finally, it is preferred that the conditions of linker cleavage does not affect the integrity of the template, complementing template or functional entities.

Linkers can be cleaved in any number of ways when subjected to predetermined conditions. Linkers may e.g. be cleaved with acid, base, photolysis, increased temperature, added agents, enzymes, ribozymes or other catalysts. Examples of cleavable linkers and their respective protection groups are shown in (FIG. 10), along with the conditions for linker cleavage, and the cleavage products.

To maintain a physical link between the template and the templated molecule, at least one non-cleavable linker is needed. This non-cleavable linker is preferably flexible, enabling it to expose the templated molecule in an optimal way.

Functional Groups

The one or more functional groups that appear on the functional entity may be selected from a variety of chemical groups which gives the templated molecules the desired properties or serves another beneficial purpose, like higher lipophilicity for recovery purposes. A non-limiting selection of functional groups is indicated below: Hydroxy; alkoxy, Hydrogen; Primary, secondary, tertiary amines; Carboxylic acids; Carboxylic acids esters; Phosphates, phosphonates; Sulfonates, sulfonamides; Amides; Carbamates; Carbonates; Ureas; Alkanes, Alkenes, Alkynes; Anhydrides; Ketones; Aldehydes; Nitatrates, nitrites; Imines; Phenyl and other aromatic groups; Pyridines, pyrimidines, purines, indole, imidazole, and heterocyclic bases; Heterocycles; polycycles; Flavins; Halides; Metals; Chelates; Mechanism based inhibitors; Small molecule catalysts; Dextrins, saccharides; Fluorescein, Rhodamine and other fluorophores; Polyketides, peptides, various polymers; Enzymes and ribozymes and other biological catalysts; Functional groups for post-polymerization/post activation coupling of functional groups; Drugs, e.g., taxol moiety, acyclovir moiety, "natural products"; Supramolecular structures, e.g. nanoclusters; Lipids; and Oligonucleotides, oligonucleotide analogs (e.g., PNA, LNA, morpholinos).

Reactive Groups of Type II

A variety of reactive groups II may be used in the templated synthesis. Examples of reactive groups include, but are not limited to N-carboxyanhydrides (NCA), N-thiocarboxyanhydrides (NTA), Amines, Carboxylic acids, Ketones, Aldehydes, Hydroxyls, Thiols, Esters, Thioesters, conjugated system of double bonds, Alkyl halides, Hydrazines, N-hydroxysuccinimide esters, Epoxides, Haloacetyls, UDP-activated saccharides, Sulfides, Cyanates, Carbonylimidazole, Thiazinanones, Phosphines, Hydroxylamines, Sulfonates, Activated nucleotides, Vinylchloride, Alkenes, and quinines.

Polymerization

Reactions that lead to polymer formation are termed polymerization reactions. The major reaction-classes are anionic polymerizations, cationic polymerizations, radical polymerizations, and pericyclic polymerizations.

Although polymerisation reactions in solution is achievable by state of the art methods, polymerisation of functional entities linked to an array as described herein does not constitute standard type reactions. Only a few polymerisation reactions have so far been performed in an array format, and not in connection with the methods of the present invention. Consequently, it will be a matter of molecular design of the functional entities and their linkers and attachment points on the complementing elements (e.g. attachment to the base, ribose or phosphate of a nucleotide), as well as a matter of optimising the polymerisation conditions, in order to preferably reduce minimize or even eliminate any undesirable reactions taking place in solution while increasing or maximizing a correct template-directed polymerisation on the array.

The present invention in one embodiment employs polymerization reactions which are in principle known from the state of the art in the sense that they are routinely used in solution synthesis schemes. However, in the present invention, the reactants (reactive groups) are held in close proximity by their attachment to elements of a complementing template. This increases the local concentration significantly. Typical synthesis schemes in solution use 1 µM-1 mM concentrations of the reactants. When arrayed as disclosed herein, the local concentration will typically be from a thousand-fold to a million-fold higher. As a result, the reactions can in principle be much more efficient. However, the reactions are preferably designed in such a way that the occurrence of undesirable side-reactions are avoided. The molecular design and the polymerization conditions according to the invention reflect this fact and can be further optimised by the skilled person searching for the polymerization conditions and molecular design that maximizes the relative template directed polymerization polymerization in solution.

Depending on the type of initiator and reactive groups, the polymerization may be initiated and/or catalyzed by changes in pH and/or temperature, addition of reactants or catalysts, enzymes or ribozymes, or light, UV or other electromagnetic radiation, etc. Particularly relevant enzymes include proteases, protein ligase (e.g., subtiligase), UDP-glycogen synthetases, CGTases and polyketide synthases. In cases where the conditions and molecular designs have been finely adjusted, so as to allow efficient polymerization of the reactants when arrayed on the complementing template, but insignificant reaction in solution, the polymerization need not be initiated. The increased local concentration in the array simply drives the polymerization.

In the case where incorporation of monomer building blocks are incorporated by an enzyme, one might fuse this enzyme with one of the enzymes mentioned above (e.g., the UDP-glykogen synthetase). This would allow the fusion-protein to first incorporate a monomer through reaction of its reactive groups type I, and right thereafter (as the now-incorporated monomer emerges from the active site of the enzyme), the other half of the fusion-protein (e.g., the UDP-glykogen synthetase) would link the functional entity of that monomer to the functional entity of the previous monomer in the complementing template.

The functional groups (or backbone structures) may have to be protected, in order to not react with the reactive groups or other components of the system during incorporation, polymerization and activation. This may be achieved using standard protection groups, some of which are mentioned in (FIG. 10).

The polymerization reactions described herein below are divided into two major groups, dependent on whether the functional entity is held in a fixed orientation relative to the complementing template.

Group 1: The Functional Entities can Rotate Relative to the Complementing Elements (and can Therefore Rotate Relative to the Complementing Template).

Direct Linkage of Reactive Groups: The Reactive Group Type II of One Monomer React Directly With the Reactive Group Type II of Another Monomer.

a). In one example, the functional entity carries two reactive groups X1 and X2 of the same kind. "Same kind" in this respect means that a given X1 can react with both an identical X1 and a non-identical X2. In (FIG. 11) X1 and X2 are identical, wherefore they are both symbolized with an X. X may react with another X to form XX (FIG. 11). As an example, X might be a thiol (—SH) and the resulting product a disulfide (—SS—). As another example, X could be a coumarin moiety which upon photo-induction reacts with a coumarin moiety of a neighbouring monomer (FIG. 11, example 1).

In most cases, the reaction of X with X results in the loss of an atom or a molecular moiety; in the case of the thiol, for example, two protons are lost upon disulfide formation. The fact that XX (the result of the reaction between two reactive groups type II) does not contain all the components of X plus X, is indicated in (FIG. 5, A) where in fact both types of reactive groups (both type I and II) upon reaction forms a molecular entity that is slightly different from the reactive groups (symbolized by overlapping circles in the figure).

b). The two reactive groups type II may be of a different kind. "Different kind" here means that they react with different types of molecules. For example, X and Y might be nucleophiles and electrophiles, respectively. X and Y react to form XY (FIG. 12). For longer templated molecules, free rotation of the functional entities relative to the complementing template represents a potential problem, if the functional entities do not react until many monomers have been incorporated. In this case, cluster formation (FIG. 13) may result, which decreases the amount of full-length, templated polymers. The problem is, however, only significant for longer polymers; from experience with biological display of α-peptides, such as phage-display and polysome-display, it is known that display efficiencies as low as 1% is enough to isolate peptides with high binding affinity for a given target.

In certain cases the incorporated monomers react right after their incorporation into the complementing template (at which time the next monomer in the complementing template has not been incorporated yet). Therefore, the last incorporated monomer will react with the second-last incorporated monomer, which is already part of the complementing template. As a result, cluster formation will not be a significant problem in this case.

X and Y might be an amine and a carboxylic acid. In the presence of carbodiimide, X and Y will react to form an amide XY.

Another version of this type of polymerization involves the simultaneous polymerization and activation of the polymer (FIG. 14). The monomers do not contain a separate linker moiety; rather, the polymerization reaction leads to activation (release of the functional entity from the complementing template). In this scheme, each monomer is incorporated and reacts with the previously incorporated monomer, leading to the previously incorporated monomers release from the complementing template, before the next monomer is incorporated. (FIG. 14, example 1) shows the use of this principle for the formation of polyamides, in this case β-peptides. The method may obviously be used for other peptides also, as well as any kind of polyamides.

By appropriate design of the monomers, one may generate other types of polymer bonds by nucleophilic substitution reactions, including amide, ester, carbamate, carbonate, phosphonate, phosphodiester, sulfonamide, urea, carbopeptide, glycopeptide, saccharide, hydrazide, disulfide and peptoid bonds.

In (FIG. 14, example 2) the same principle is applied to a different type of reaction, a "rolling circle polymerization reaction". An alkyl sulfonate is here used as an efficient leaving group, to drive the formation of a secondary amine. The result is a functionalized polyamine, attached at one end to the template that directed its synthesis. In an analogous way, one may generate polyether and poly-thioether using similar molecular designs. Polymers that can be generated by the use of the principles described in (FIGS. 14 and 14, example 1 and 2) include oligodeoxynucleotides, oligoribonucleotides, chimeric oligonucleotides, oligonucleotide analogs (e.g., PNA, LNA), peptoids, polypeptides and p-peptides.

"Fill-in" Polymerization: An Additional Molecule Mediates Linkage Between Reactive Groups Type II from Neighbouring Monomers.

a). The functional entitiy carry one or two reactive groups X1 and X2 of the same kind, where X1 cannot react with another X1 or X2. For example, X1 and X2 could be a primary and secondary amine, respectively. In order to polymerize, a compound of the kind Y1-linker-Y2 is added, where Y1 and Y2 are of the same kind. Y can react with X, but is sterically or chemically excluded from reaction with another Y. As a result, a X—Y—Y—X is formed (FIG. 15). As an example, X could be an amine, and Y a activated ester. Upon reaction, this would form an ester-ester bond (X—Y—Y—X) between two functional entities.

It is preferred that the two X of one monomer does not to any significant extent react with the same Y-linker-Y molecule. This can be prevented e.g. by imposing steric constraints on the molecules, e.g., Ys in the Y-linker-Y molecule are further apart than the Xs in the monomer.

(FIG. 15, example 2) provides two examples of "fill-in" polymerization of polyamides. In (FIG. 15, example 2, A and B), the reactive groups type II are amines, and the Y-linker-Y molecule is a dicarboxylic acid or an activated di-ester. In either case, the resulting product is a di-amide polymer. Obviously, the kind of X and Y could be switched, so that in the examples X was a carboxylic acid and Y an amine. Other combinations of X and Y, and their resulting bonds, are given in FIG. 25, which summarizes some of the kinds of polymers that may be generated by the various polymerization principles described in the present patent.

For certain reactions, the linking molecule need only contain one reactive group X. An example is shown in (FIG. 15, example 3A), where the functional entities contain two reactive groups type II (amines), and the added molecule is a phosgen equivalent such as 1,1'-carbonyldiimidazole. The resulting bond is an urea bond. In (FIG. 15, example 5) the monomers contain two hydroxyl groups, to which is added an activated phosphodiester or an activated phosphine derivative such as a bisaminophosphine following activation with tetrazole and oxidation with tert-butylhydroperoxide. The result is a phosphodiester bond.

The functional entity may in certain cases contain only one reactive group type II. An example is shown in (FIG. 15, example 6), where an activated phosphodiester makes up the only reactive group type II of the monomer. Upon reaction with a dihydroxy, a phosphodiesterbackbone is formed.

As yet another example of fill-in polymerization, (FIG. 15, example 7) shows the pericyclic reaction of dienes (functional entity) reacting with alkenes (linking molecule), to form a polycyclic compound.

A general consideration when using the fill-in polymerization principle, is the number of stereoisomers templated by the same template. For example, in (FIG. 15, example 4, A), the functional entity contains two primary amines. The functional entity is connected to the complementing template through a chiral carbon. The functional entity may rotate freely around the bond that connects this chiral atom with the complementing template. Therefore, the reaction of the amines (X) with the linking molecules (activated carbonyls, (Y)) will result in the formation of $2^n$ different isomers, where n is the number of residues of the polymer.

The isomers represent a significant increase in diversity. For example, for a 10-meric polymer, the chirality represents a 1024-fold increase in diversity. This may in certain cases be an advantage, for example if the monomer diversity is low, or if the desire is to make short polymers. However, such "scrambling" of the genetic code (i.e., one template encodes different polymer structures) also decreases the stringency of the selection process. Therefore, in certain cases scrambling is not desirable. One may then choose to connect the functional entities to the complementing elements via non-chiral atoms. In (FIG. 15, example 4, B) is shown an example of an achiral atom (nitrogen) connecting the functional entity with the complementing template. Scrambling may involve cases where one complementing element specifies different isomers (as described above), and scrambling may also involve cases where a complementing element specifies slightly different or entirely different functional entities.

b). The functional entity carries two different reactive groups of type II, X and S (FIG. 16). X does not react with X or S, and vice cersa. Before, during or after incorporation of monomers, molecules of the form T-linker-Y are added. X may react with Y, and S may react with T, leading to formation of X—S-T-Y linkages between the functional entities. It is important to ensure that X and S of one functional entity cannot react with T and Y of one linking molecule. This may be ensured by appropriate design of the structure of the functional entities and linking molecule. (FIG. 16, example 1) provides an example of a functional entity with different reactive groups type II, in this case an azide and a hydrazide (X and S), and a linking molecule with different reactive groups, in this case a phosphine and a ketone (T-linker-Y).

For longer templated molecules, free rotation of the functional entities relative to the complementing template represents a potential problem, if the functional entities do not react until many monomers have been incorporated. In this case, cluster formation (FIG. 13) may result, which decreases the amount of full-length, templated polymers. The problem is, however, only significant for longer polymers, as explained above. If the linking molecules are present during incorporation of the complementing elements, the incorporated monomers may react with the linking molecules right after their incorporation, or in the case of enzyme-mediated incorporation, as soon as they emerge from the active site of the enzyme. Cluster formation will not be a significant problem in these cases.

"Zipping" Polymerization: The Polymerization Reaction Travels from One End of the Template to the Other.

In this approach, the polymerization reaction is directional, i.e., the reaction cascade starts at one end of the complementing template, and the reactions migrate to the other end of the complementing template, thereby forming a templated polymer.

a). General principle (FIG. 18). After incorporation of some or all of the monomer building blocks, polymerization is initiated from one end of the template, and travels down the template. For example, the initiator may be coupled to the first or last complementing element to be incorporated, or it may be coupled to the primer used in DNA polymerase-mediated incorporation of nucleotide-derivatives. Either way, the initiator will react with the neighbouring monomer's reactive group type II, which induces a change in the functional entity of that monomer, allowing this monomer to react with the next monomer in the chain, and so on. Eventually, all the monomers have reacted, and a polymer has been formed.

It may be desirable to protect the initiator, keeping it from reacting with the neighbouring monomer until incorporation is complete, whereafter the initiator is deprotected. This allows the experimenter to remove all non-incorporated initiators and complementing elements before activating the initiator, which eliminates reaction in solution between the initiator and the complementing elements.

Deprotection of the initiator may be by change in pH or temperature, exposure to electromagnetic radiation, or addition of an agent (that removes a protection group, or introduces an initiator at a specific position, or ligates or coordinates to the naïve initiator, to make it a more potent initiator). The agent could be a chemical catalyst or an enzyme, for example an esterase or peptidase.

b). Zipping by radical polymerization (FIG. 18, example 1). The initiator is a alkyliodide, and the functional entities contain a double bond. Upon addition of a radical initiator, for example ammoniumpersulfate, AIBN (azobis-isobutyronitrile) or other radical chain reaction initiators, a radical chain reaction is initiated, whereby the alkenes react to form an extended, functionalized alkane. Eventually, the polymer has been made, and it is activated (cleaved from the complementing template, except at one point). The radical remaining at the end of the polymer may be quenched by a radical termination reaction.

c). Zipping by cationic polymerization (FIG. 18, example 2). The initiator is a Lewis acid. Upon deprotection with acid or other initiation reagent, a cation is generated. The carbocation attacks the double bond of the neighbouring monomer, and as a result a carbocation is generated in this monomer. Eventually, the full-length polymer has been formed, and the polymer is activated.

d). Zipping by nucleophilic (anionic) polymerization (FIG. 18, example 3). In this example, the initiator is a protected hydroxyl anion. The functional entity carries a peroxide. Upon deprotection of the initiator the hydroxyl-anion is formed (e.g., by alkaline deprotection). Under basic conditions, the initiator attacks the neighbouring epoxide at the least hindered carbon in the ring. This in turn generates a hydroxyl-anion, which attacks the neighbouring epoxide. Eventually, the full polymer is formed, and the polyether may be activated. In this example, all of the linkers that connect the polyether to the complementing template are cleaved. This type of polymerization is also an example of ring-opening polymerization.

e). Zipping polymerization by ring opening (FIG. 19). The general principle of ring-opening polymerization is shown. The initiator attacks the reactive group X of the neighbouring monomer. X is part of a ring structure, and as a result of the reaction between the initiator and X, the ring opens, whereby the other reactive group of the monomer is activated for attack on the next monomer in the array. Polymerization travels down the strand, and eventually the full-length polymer has been formed.

f). β-peptide formation by ring-opening polymerization of carboxyanhydrides (FIG. 19, example 1). The deprotected initiator, a nucleophilic amine, attacks the most electrophilic carbonyl of the N-thiocarboxyanhydride, to form an amide. CSO is released, generating a primary amine, which then attacks the next monomer in the array. Eventually polymerization is complete, and the polymer may be activated, creating a β-peptide attached to the complementing template or template through its C-terminal end. The principle may be used to form other types of peptides, for example D- and L-form mono- and disubstituted α-peptides, β-peptides, γ-peptides, carbopeptides and peptoids (poly N-substituted glycin), and other types of polyamides. Also, the principle can be employed for the generation of other polymers, such as polyesters, polyureas, and polycarbamates.

g). β-peptide formation by ring-opening polymerization of thiazinanone units (FIG. 19, example 2). The deprotected initiator attacks the cyclic thioester, to form an amide. As a result, the ring breaks down to release a free thioketone. This generates an amine, which may now attack the thioester of the next monomer in the array. When polymerization has travelled to the other end of the template, it is activated, generating a β-peptide attached to its template through the C-terminal end.

The principle may be used to form other types of peptides, for example D- and L-form mono- and disubstituted α-peptides, β-peptides, γ-peptides, carbopeptides and peptoids (poly N-substituted glycin), and other types of polyamides. Also, the principle can be employed for the generation of other polymers, such as polyesters, polyureas, and polycarbamates.

h) Zipping polymerization by rearrangement (FIG. 20). Upon activation of the initiator, which in this case could be an electrophile, the reactive group type II of the neighbouring monomer attacks the initiator, and as a result, releases the initiator from the complementing element. In the attacking monomer, the reaction of Y with the initiator leads to a rearrangement of the monomer, which results in activation of X, the other reactive group type II of the monomer (for example, the reorganization creates a nucleophile). Then, the next monomer in the array attacks this nucleophile. Eventually, full-length polymer has been formed, attached at one end to the template that directed its synthesis.

i). Zipping and activation in one step (FIG. 21). By appropriate design of the functional entities used for ring-opening polymerization, activation may be achieved as a direct result of the polymerization reaction. By simply turning the functional entity upside-down, i.e., attach the portion of the ring that does not get incorporated into the final polymer to the complementing template, saves the experimenter an activation step (compare FIG. 21 and FIG. 19). As a specific example, attachment of the 2,2-diphenylthiazinanone ring structure of (FIG. 19, example 2) to the complementing elements through one of the phenyl groups would lead to activation as a result of the polymerization reaction.

Group 2: The Functional Entity Cannot Rotate Freely Relative to the Complementing Element In this embodiment, the X and Y reactive groups type II are held in the desired orientation relative to the complementing template (FIG. 22, A). X and Y can therefore react, or react with a linker molecule, without the risk of cluster formation (compare with FIG. 13).

The functional entity may be held in the fixed orientation by a double bond, or by bonds to different atoms in the complementing element. (FIG. 22, B) provides an example, where the functional entity is covalently coupled to the two bases of a dinucleotide (the complementing element is a dinucleotide, the functional entity contains a dipeptide, and the reactive groups are the amine and the ester moieties, respectively).

Polymers that can be made by this method include all of the polymers mentioned in the non-zipping polymerizations above, for example peptides, amides, esters, carbamates, oximes, phosphodiesters, secondary amines, ethers, etc.

The FIGS. 23 to 25 relates to how a cluster formation can be avoided by covalent constrains.

A special situation arises employing bifunctional functional entities (FE) due to a potential free rotation around the linker-nucleotide bond. A bifunctional FE bears two different reactive groups 'X' and 'Y', e.g. both a nucleophile and an electrophile, where 'X' on one FE is meant to react with 'Y' on the neighbour FE either directly or through a cross-linking agent. If all linker-FE units orient identically with respect to the parent nucleotide, directional polymerization will take place and a complete product of say 5 units will be formed ('FIG. 13 top'). However, rotation around the linker-bond of some, but not all, linker-FE entities so that the relative orientation of the two functionalities reverses leads to a clustering situation, where the reacting groups are arranged so that reaction can take place in two different directions ('FIG. 13 bottom'). This unfavourable situation can be avoided by using fixed functional entities thereby preventing rotation around the nucleotide-linker bond. Fixing the FEs may be obtained by attaching the FE not by one but by two covalent bonds (i.e. two linkers) to the nucleotide. The additional bond may be formed directly by one of the functionalities, or the two reactive groups may be attached separate 'arms' on a fixed backbone. In the first situation the additional bond may be broken during the reaction, whereas the additional bond in the latter should be constructed so that also this bond is cleavable after reaction, to release the final product.

The primary attachment points of the linker-FE units are typically within the bases of the nucleotides, preferably position C5 in T/U and C or position C7 in deaza A and deaza G. In order to construct an efficient inhibition of linker-bond rotation, the second bond should preferably be somewhat distant from this attachment point. That is, the second attachment could be anywhere in a neighbour nucleotide, preferably in the base or in the sugar part, it could be a second atom in the same base, preferably position C6 in T/U and C or position C8 or N6 in (deaza)A or (deaza)G, or it could be an atom of the sugar moiety, preferably position C2 or C3. Explicit examples are given in FIG. 23.

It should be noted that nucleotides bearing some of these doubly-attached linkers may be necessary to incorporate by other means than using a polymerase. An alternative to polymerase incorporation is the imidazole approach described elsewhere herein.

In order to show the effect of covalently constraining the FE to ensure directional polymerization a series of computer calculations have been performed on two examples shown in FIGS. 23A and 23B. The purpose is to analyse various modes of attack for each linker-FE construction, estimating the most probable reaction and thereby the most probable product. Therefore, the conformational space covered by the linker-FE unit and the zones occupied by the reactive groups needs to be estimated.

The conformational space of a specific linker-FE system, i.e. the range of the FE, can be estimated by doing a conformational search. Conformational searches can be performed employing various different software and within these programs using different searching methods and is standard knowledge within the field. For systems of the size mentioned in this text it is not possible to perform a converged conformational search, that is, to ensure that enough steps have been taking so that the complete potential energy surface has been covered and thereby that the located minimum energy conformation is truly the global minimum for the molecule. However, the purpose of these calculations is to get a picture of the space allowed to be covered by a linker-FE unit and thereby to estimate the most likely approach of attack between two FEs and the possibility for the reacting groups to get within reaction distance. Efficient conformational searching methods employing a rather limited number of steps fulfill this purpose.

By conformations are here meant individual structural orientations differing by simple rotation about single bonds. Different conformations may in addition give rise to different overall configurations, by which is meant an overall arrangement of the two reactive groups on all modified nucleotides that give rise to one specific direction of reaction. That is, four linker-FE units arranged with all 'X's' in the same direction corresponds to one specific configuration, and four linker-FE units arranged e.g. with two 'X's' pointing in one direction and the two other in the opposite direction corresponds to another specific configuration. Within one configuration many different conformations are possible, but all of these result in the same 'most probable' product since the overall orientation (direction) of reactive groups is preserved.

The calculations performed in this investigation have been performed employing the MacroModel7.2 software from Schrödinger Inc (MMOD72). Within this program package a series of different searching protocols are available, including the 'Mixed Monte Carlo Multiple Minimum/Low Mode' method (MCMM/LM), shown to be very effective in locating energy minima for large complicated systems.

Computational Details

Double-stranded DNA with the base sequence 5'-GCTTTTTTAG-3' (upper strand) (example displayed in FIG. 24) or 5'-GCTTTTAG-3' (upper strand) (example displayed in FIG. 25) was built using HyperChem7 from HyperCube Inc in the most frequent B-conformation. The linker-FE units were built using ChemDraw Ultra 6.0 and Chem3D Ultra 6.0 from ChemOffice. Linker-FE units and DNA were imported into MMOD72. The linkers were then fused to the corresponding nucleotides using the build feature in MMOD72, fusing the methyl carbon atom of the T nucleotides with the appropriate linker atom, in effect creating a modified U nucleotide. In all calculations all DNA atoms were kept frozen, that is, were not allowed to move, in order to decrease the size of the systems and to avoid distortions within the DNA strand. The total system was energy minimised (keeping the DNA atoms frozen) employing the OPLS_AA force field supplied in MMOD72. It was necessary to constrain the dihedral angle bridging the nucleotide and the linker, i.e. the dihedral of N1, C6, C5 and the first linker atom was set to 180.0 degrees and a force constant of between 100 and 1000 applied. Without the constraint none of the MMOD72 force fields preserved the plane, presumably due to a too weak out-of-plane force constant for this particular dihedral.

Conformational analyses were performed using the MCMM/LM method, running 2000 steps with an energy cutoff of 50 kJ/mol, and with a minimum and maximum distance travelled by the fastest moving atom of 3 and 8 Å, respectively. Depending on the specific size of the system, 11-19 torsions were allowed to vary, and finally each conformer was minimized by 500-1000 PR Conjugate Gradient steps (this resulted in most conformers being minimized to within a convergence threshold of 0.05 kJ/mol). The chirality of chiral atoms was preserved during the calculations. In addition, for the systems with covalently constrained linkers one ring closure bond (either the formed amide bond or the base-S bond) was chosen within each ring.

Results

One way of creating a second attachment point is to link one of the functional entities via a breakable bond to a neighbour nucleotide. In effect, this means that dinucleotides in stead of mononucleotides are employed and also that the length of the FE is increased. Using this approach, a series of valid attachment points exist; FIG. 23A is an example of attachment to the same position of the neighbour base. Linker 1A is constructed from a β-dipeptide, with the amino end connected to the 5' base via a disulfide bond prone for reductive cleavage and the carboxy-end directly linked to the 3' base. When reaction takes place the amino group from one dinucleotide-linker-FE unit will break the ester bond of the preceding dinucleotide-linker-FE. Employing the same linker-FE unit without the second attachment point corresponds to employing dipeptides on one-nucleotide-spaced mononucleotides. Such a linker-FE bears two reactive groups on separate arms and has free rotation about the nucleotide-linker bond and is therefore an example of a bifunctional linker-FE which bears the risk of cluster formation in case of lack of directional polymerization. Running 2000 conformational search steps of the singly-attached linker results in 490 unique conformations (849 conformations after 500 minimization steps, 490 after additional 500 steps) with the 'global' minimum located once. The lowest-energy conformation which results in a complete product has rank 8 and is shown in FIG. 24A and the resulting most probable product (still attached the DNA backbone) in FIG. 24B. As can be seen, the reactive groups arrange with all amino groups upwards and all carboxy groups downwards, and the two reactions that are required to give a complete product are straight-forward. The released complete product is shown as FIG. 24H. However, by far the most conformations, including the 'global' minimum, do not have this overall configuration. FIG. 24C shows the conformation of second highest rank and the most probable product is depicted in FIG. 24D. As can be seen, this arrangement of the reactive groups results in the formation of an incomplete product. The two linker-FE units in the 3' end have formed an amide bond, but the 5' linker-FE unit has the opposite overall orientation resulting in two carboxy groups (one from the 5' linker-FE unit and one from the merged 3' linker-FE units) being the two close reactive groups and thus no reaction is possible. Release of this product therefore results in a dimer (and a monomer); the dimer is depicted in FIG. 22. Of the 364 unique conformations within 10 kJ/mol of the located minimum approximately 330 results in the formation of various incomplete products.

Running 2000 conformational search steps of the doubly-attached linker results in 125 unique conformations with the 'global' minimum located nine times. This minimum energy conformation is shown in FIG. 24E, where all FEs are seen to arrange with the amino groups pointing downwards and carboxy groups upwards. Clearly, this overall configuration is the only one possible for the doubly-attached linker, giving rise to only one probable product shown in FIG. 24F (still attached the DNA backbone). Release of this product gives the complete three-unit product, FIG. 24G.

Thus, this example shows first of all that rotation around nucleotide-linker bonds do result in (many) configurations unable to form complete products. However, another important issue is the difference in complete products formed. The FEs employed in this example are constructed from unsubstituted β-amino acids and therefore there is no difference between the complete products shown in FIG. 24G and H. However, using singly-attached FEs the polarity of the formed products can change (i.e. free amino group from the 3' attached FE or free amino group from the 5' attached FE) and thereby potentially very different products can be formed. By employing fixed functional entities only one overall configuration is possible and only one product with one specific polarity can be formed.

Another possibility of attachment point is the sugar of the parent nucleotide, as exemplified in FIG. 23B, C, and D. This choice allows the employment of mononucleotides in stead of linked dinucleotides as mentioned above. Both hydrogens of C2 can be replaced by linker atoms, however, for shorter ring structures it is preferred to use the one facing the same plane as the base does. Carbon 3 of the sugar moiety forms a linkage to the phosphate group, but there is still one attachment possibility left which can be utilised for linker fixation purposes. The same holds for C1, however the space around this substitution possibility is limited. Carbon atoms 4 and 5 of the sugar moiety are quite distant from the base attachment point and therefore require large ring systems to be utilised for this purpose.

Linker-FE 1 B is constructed from a γ-amino acid attached via a disulfide bond prone for reductive cleavage to the C5 position of T/U. The linker-FE unit 1 B is therefore another typical example of a bifunctional linker-FE system capable of rotation of the nucleotide-linker bond which bears the risk of cluster formation due to lack of directional polymerization. A fixation of this FE is shown in example 1B (right) and utilises the C2 position at the same side of the plane as the base. The FE now contains a γ-amino acid linked through the carboxyl group to the sugar via a hydrolysable ester bond and in the amino end to the C5 position of T/U via a disulfide bond prone for oxidation. Doubly-attached linker-FE unit 1B is therefore a bifunctional linker-FE with one reactive group free and the other providing the second attachment. Using almost the same linker-FE unit but letting the carboxyl end free by introducing a second ester group as a hydrolysable linker is shown in example 1 C. Computational analyses of linker-FEs 1B and 1C result in similar conclusions, and results below refer to linker 1B.

Conformational searches of the two different schemes clearly reveal the effect of preventing rotation of the linker bond by additional covalent attachment. Running 2000 conformational search steps of the singly-attached linker-FE results in 445 unique conformations with the 'global' minimum located once. This conformation is shown in FIG. 25A and the resulting most probable product (still attached the DNA backbone) in FIG. 25B. As can be seen this product is the complete product, that is, all four units are linked together via amide bonds. The released complete product is shown as FIG. 25G. However, many other overall configurations are possible for this system, with one example shown in FIG. 25C. The most probable product resulting from the 3C configuration is depicted in FIG. 25D and as can be seen, this arrangement of reactive groups results in the formation of an incomplete product, that is, the linker-FE units are linked two and two together with no possibilities of a merging reaction. Release of this product results in two dimers, depicted in FIG. 25H. Of the 334 unique conformations within 10 kJ/mol of the located minimum approximately 215 results in formation of various incomplete products.

Running 2000 conformational search steps of the doubly-attached FE results in 386 unique conformations with the 'global' minimum located twice. This conformation is shown in FIG. 25E and the resulting most probable product (still attached the DNA backbone) in FIG. 25F. However, since there are no possibilities of interchange of reactive groups, the conformations differ only by minor variations in dihedrals (e.g. rotation of the $CH_2NH_2$ group). Clearly, only one overall configuration is possible for the doubly-attached FE, giving rise to only one probable product, the complete four-unit product (FIG. 25G).

Thus, the computational investigations clearly show that there is extensive rotation around nucleotide-linker bonds and that this flexibility will result in a significant proportion of the formed products not being complete. The calculations also show that using covalently fixed functional entities is one way to prevent linker rotation and thereby effectively secure unidirectional polymerisation. In addition, the complete products that do result from using unconstrained FEs form a diverse group, since there is more than one possibility of arranging the reactive groups in a way that allows reactions between all units to happen. Naturally, these tendencies will be even more pronounced using more than three to four linker-FE units as was applied in these examples.

Building Blocks Capable of Transferring Functional Entities.

The following section describes the formation and use of monomer building blocks capable of transferring a functional entity from one monomer building block to another monomer building block, i.e. two functional entities of two monomer building blocks react, whereby one functional entity is cleaved from its monomer building block under the conditions applied.

General Section

Protection and deprotection of maleimide derivatives:

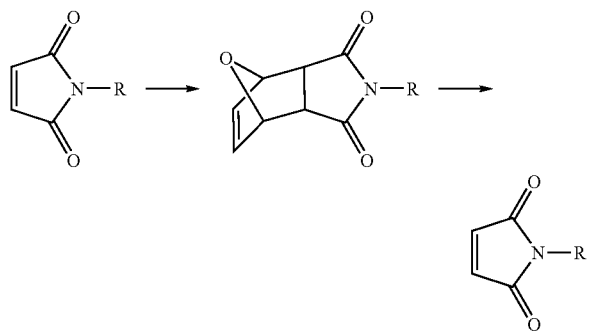

Maleimide derivatives (e.g. R=H, alkyl, aryl, alkoxy etc.) may at any step below, be present in a protected form. Protection is achieved by reaction with furan. Deprotection may be achieved by thermolysis, as described by Masayasu et al., *J. Chem. Soc., Perkin Trans.* 1 (1980) 2122.

A. Acylation Reactions

General route to the formation of acylating monomer building blocks and the use of these:

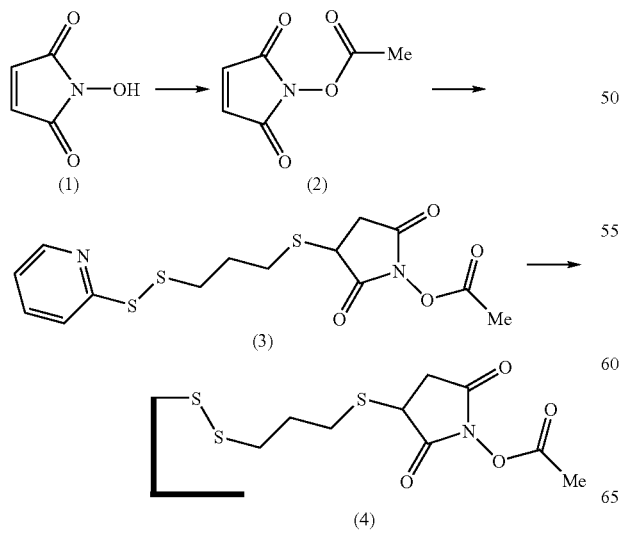

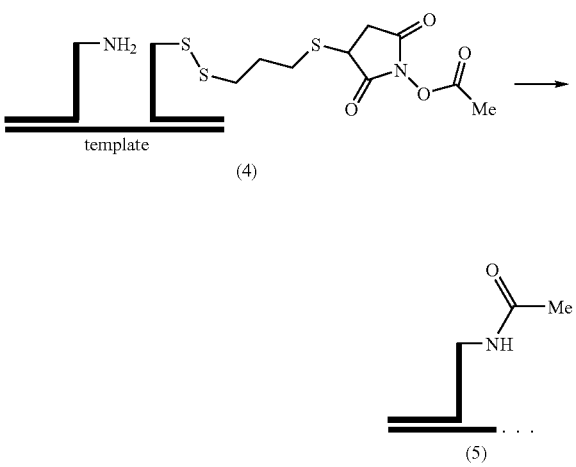

N-hydroxymaleimide (1) may be acylated by the use of an acylchloride e.g. acetylchloride or alternatively acylated in e.g. THF by the use of dicyclohexylcarbodiimide or diisopropylcarbodiimide and acid e.g. acetic acid. The intermediate may be subjected to Michael addition by the use of excess 1,3-propanedithiol, followed by reaction with either 4,4'-dipyridyl disulfide or 2,2'-dipyridyl disulfide. This intermediate (3) may then be loaded onto an oligonucleotide carrying a thiol handle to generate the monomer building block (4). The reaction of this monomer building block with an amine carrying monomer building block is conducted as follows:

The template oligonucleotide (1 nmol) is mixed with a thio oligonucleotide loaded with a building block e.g. (4) (1 nmol) and an amino-oligonucleotide (1 nmol) in hepes-buffer (20 μL of a 100 mM hepes and 1 M NaCl solution, pH=7.5) and water (39 uL). The oligonucleotides are annealed to the template by heating to 50° C. and cooled (2° C./second) to 30° C. The mixture is then left o/n at a fluctuating temperature (10° C. for 1 second then 35° C. for 1 second), to yield template bound (5).

B. Alkylation and C. Vinylation Reactions

General route to the formation of alkylating/vinylating monomer building blocks and use of these:

Alkylating monomer building blocks may have the following general structure:

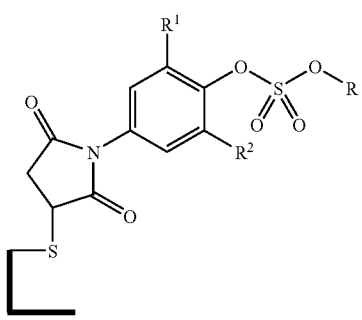

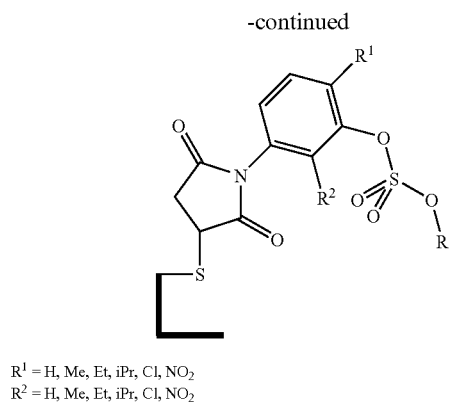

R¹ = H, Me, Et, iPr, Cl, NO₂
R² = H, Me, Et, iPr, Cl, NO₂

R¹ and R² may be used to tune the reactivity of the sulphate to allow appropriate reactivity. Chloro and nitro substitution will increase reactivity. Alkyl groups will decrease reactivity. Ortho substituents to the sulphate will due to steric reasons direct incoming nucleophiles to attack the R-group selectively and avoid attack on sulphur. E.g.

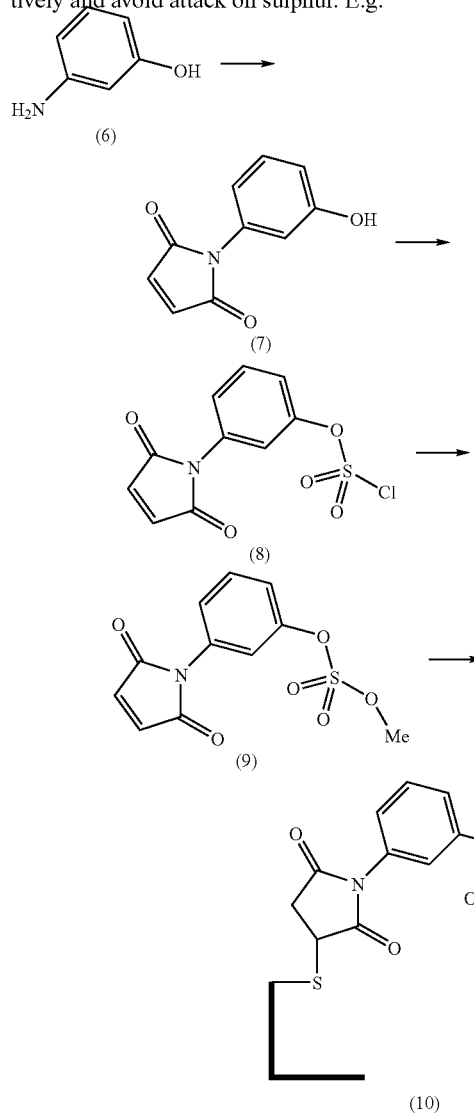

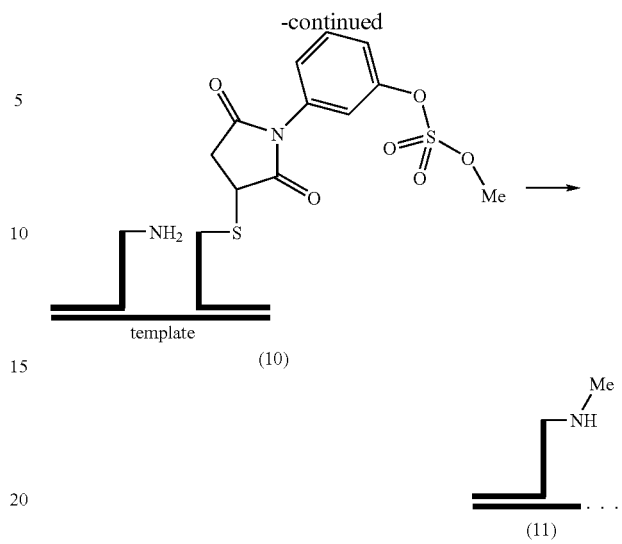

3-Aminophenol (6) is treated with maleic anhydride, followed by treatment with an acid e.g. $H_2SO_4$ or $P_2O_5$, and heat to yield the maleimide (7). The ring closure to the maleimide may also be achieved when an acid stable O-protection group is used by treatment with or $Ac_2O$ with or without heating, followed by O-deprotection. Alternatively reflux in $Ac_2O$, followed by O-deacetylation in hot water/dioxane to yield (7). Further treatment of (7) with $SO_2Cl_2$ with or without triethylamine or potassium carbonate in dichloromethane or a higher boiling solvent will yield the intermediate (8), which may be isolated or directly further transformed into the aryl alkyl sulphate by the quench with the appropriate alcohol, in this case MeOH, whereby (9) will be formed. The organic building block (9) may be connected to an oligo nucleotide, as follows.

A thiol carrying oligonucleotide in buffer 50 mM MOPS or hepes or phosphate pH 7.5 is treated with a 1-100 mM solution and preferably 7.5 mM solution of the organic building block (9) in DMSO or alternatively DMF, such that the DMSO/DMF concentration is 5-50%, and preferably 10%. The mixture is left for 1-16 h and preferably 2-4 h at 25° C. To give the alkylating in this case methylating monomer building block (10).

The reaction of the alkylating monomer building block (10) with an amine carrying monomer building block may be conducted as follows:

The template oligonucleotide (1 nmol) is mixed with a thio oligonucleotide loaded with a building block (1 nmol) (10) and an amino-oligonucleotide (1 nmol) in hepes-buffer (20 μL of a 100 mM hepes and 1 M NaCl solution, pH=7.5) and water (39 uL). The oligonucleotides are annealed to the template by heating to 50° C. and cooled (2° C./second) to 30° C. The mixture is then left o/n at a fluctuating temperature (10° C. for 1 second then 35° C. for 1 second), to yield the template bound methylamine (11).

A vinylating monomer building block may be prepared and used similarily as described above for an alkylating monomer building block. Although instead of reacting the chlorosulphonate (8 above) with an alcohol, the intermediate chlorosulphate is isolated and treated with an enolate or O-trialkylsilylenolate with or without the presence of fluoride. E.g.

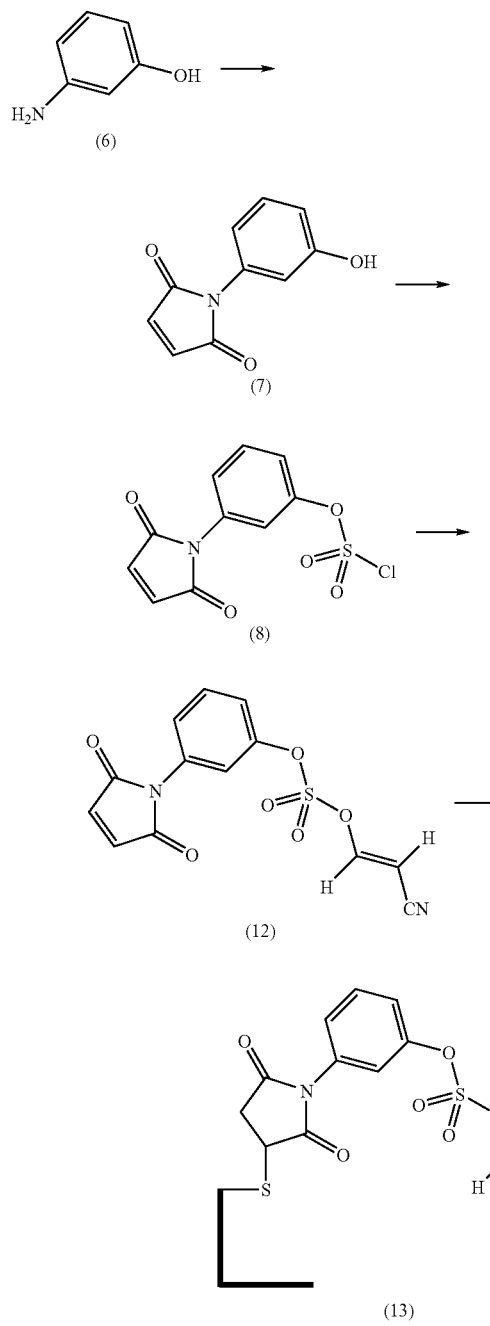

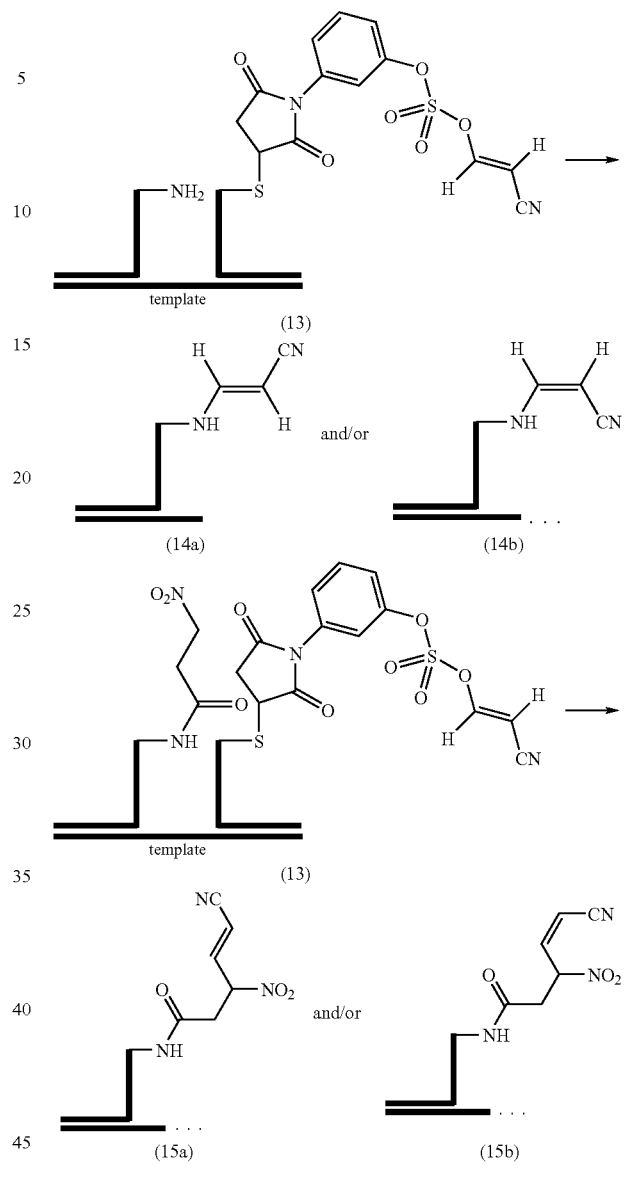

Formation of the vinylating monomer building block (13):

The thiol carrying oligonucleotide in buffer 50 mM MOPS or hepes or phosphate pH 7.5 is treated with a 1-100 mM solution and preferably 7.5 mM solution of the organic building block (12) in DMSO or alternatively DMF, such that the DMSO/DMF concentration is 5-50%, and preferably 10%. The mixture is left for 1-16 h and preferably 2-4 h at 25° C. To give the vinylating monomer building block (13).

The sulfonylenolate (13) may be used to react with amine carrying monomer building block to give an enamine (14a and/or 14b) or e.g. react with an carbanion to yield (15a and/or 15b). E.g.

The reaction of the vinylating monomer building block (13) and an amine or nitroalkyl carrying monomer building block may be conducted as follows:

The template oligonucleotide (1 mmol) is mixed with a thio oligonucleotide loaded with a building block (1 mmol) (13) and an amino-oligonucleotide (1 mmol) or nitroalkyl-oligonucleotide (1 mmol) in 0.1 M TAPS, phosphate or hepes-buffer and 300 mM NaCl solution, pH=7.5-8.5 and preferably pH=8.5. The oligonucleotides are annealed to the template by heating to 50° C. and cooled (2° C./second) to 30° C. The mixture is then left o/n at a fluctuating temperature (10° C. for 1 second then 35° C. for 1 second), to yield template bound (14a/b or 15a/b). Alternative to the alkyl and vinyl sulphates described above may equally effective sulphonates as e.g. (31) (however with R" instead as alkyl or vinyl), described below, be prepared from (28, with the phenyl group substituted by an alkyl group) and (29), and be used as alkylating and vinylating agents.

D. Alkenylidation Reactions

General route to the formation of wittig and HWE monomer building blocks and use of these:

Commercially available building block (16) may be transformed into the NHS ester (17) by standard means, i.e. DCC or DIC couplings.

An amine carrying oligonucleotide in buffer 50 mM MOPS or hepes or phosphate pH 7.5 is treated with a 1-100 mM solution and preferably 7.5 mM solution of the organic building block in DMSO or alternatively DMF, such that the DMSO/DMF concentration is 5-50%, and preferably 10%. The mixture is left for 1-16 h and preferably 2-4 h at 25° C. To give the phosphine bound monomer building block (18). This monomer building block is further transformed by addition of the appropriate alkylhalide, e.g. N,N-dimethyl-2-iodoacetamide as a 1-100 mM and preferably 7.5 mM solution in DMSO or DMF such that the DMSO/DMF concentration is 5-50%, and preferably 10%. The mixture is left for 1-16 h and preferably 2-4 h at 25° C. To give the monomer building block (19). Alternative to this, may the organic building block (17) be P-alkylated with an alkylhalide and then be coupled onto an amine carrying oligonucleotide to yield (19).

An aldehyde bound monomer building block (20), e.g. formed by the reaction between the NHS ester of 4-formylbenzoic acid and an amine carrying oligonucleotide, using conditions similar to those described above, will react with (19) under slightly alkaline conditions to yield the alkene (21).

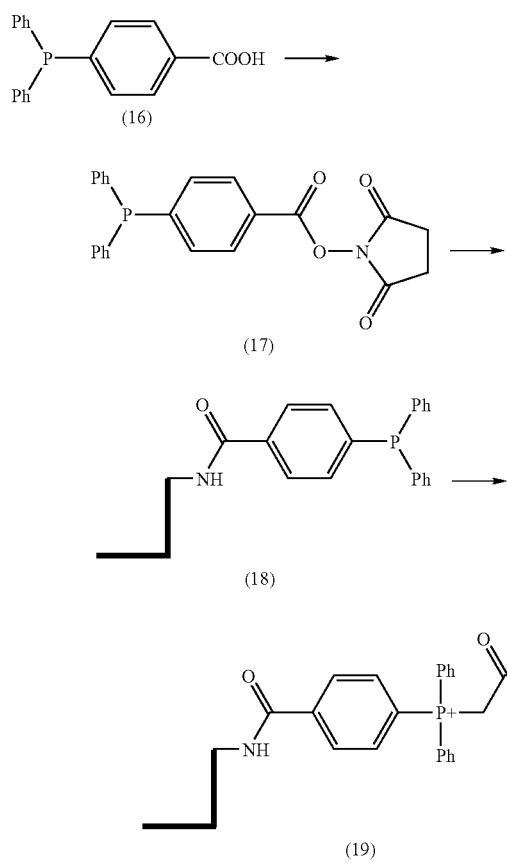

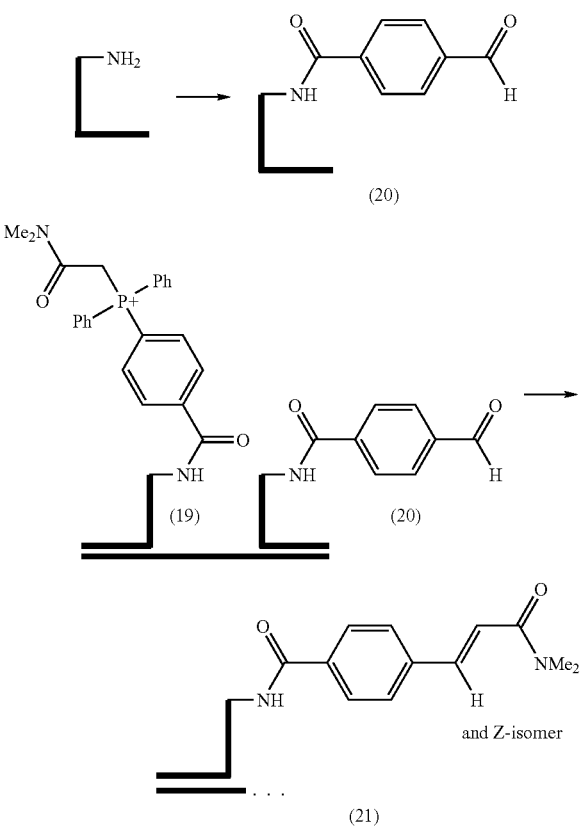

The reaction of monomer building blocks (19) and (20) may be conducted as follows:

The template oligonucleotide (1 mmol) is mixed with monomer building block (19) (1 mmol) and (20) (1 mmol) in 0.1 M TAPS, phosphate or hepes-buffer and 1 M NaCl solution, pH=7.5-8.5 and preferably pH=8.0. The reaction mixture is left at 35-65° C. preferably 58° C. over night to yield template bound (21).

As an alternative to (17) may phosphonates (24) be used instead. They may be prepared by the reaction between diethylchlorophosphite (22) and the appropriate carboxy carrying alcohol. The carboxylic acid is then transformed into the NHS ester (24) and the process and alternatives described above may be applied. Although instead of a simple P-alkylation, the phosphite will undergo Arbuzov's reaction and generate the phosphonate. Monomer building block (25) benefits from the fact that it is more reactive than its phosphonium counterpart (19).

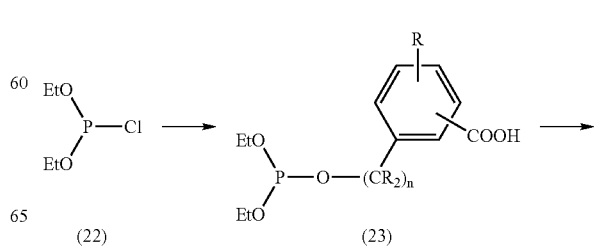

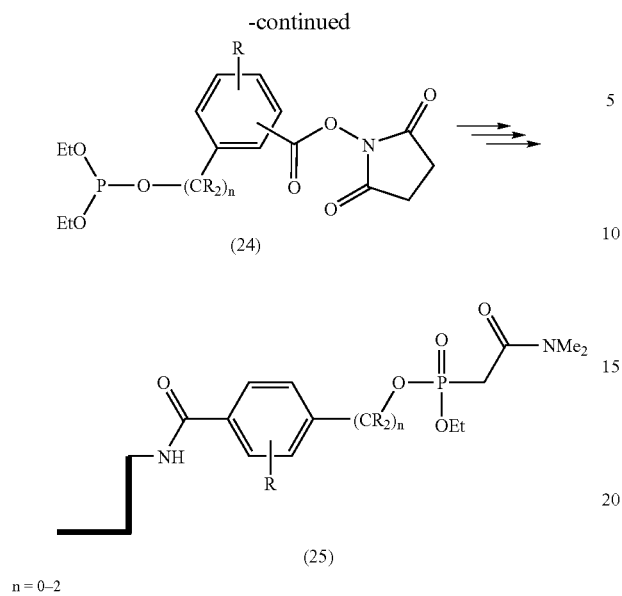

(24)

(25)

n = 0–2

E. Transition Metal Catalyzed Arylation, Hetaylation and Vinylation Reactions Electrophilic monomer building blocks (31) capable of transferring an aryl, hetaryl or vinyl functionality may be prepared from organic building blocks (28) and (29) by the use of coupling procedures for maleimide derivatives to SH-carrying oligonucleotide's described above. Alternative to the maleimide, may NHS-ester derivatives prepared from e.g. carboxybenzensulfonic acid derivatives, be used by coupling of such to an amine carrying oligonucleotide. The R-group of (28) and (29) is used to tune the reactivity of the sulphonate to yield the appropriate reactivity. The transtion metal catalyzed cross coupling is conducted as follows:

A premix of 1.4 mM $Na_2PdCl_4$ and 2.8 mM $P(p-SO_3C_6H_4)_3$ in water left for 15 min was added to a mixture of the template oligonucleotide (1 mmol) and monomer building block (30) and (31) (both 1 mmol) in 0.5 M NaOAc buffer at pH=5 and 75 mM NaCl (final [Pd]=0.3 mM). The mixture is then left o/n at 35-65° C. preferably 58° C., to yield template bound (32).

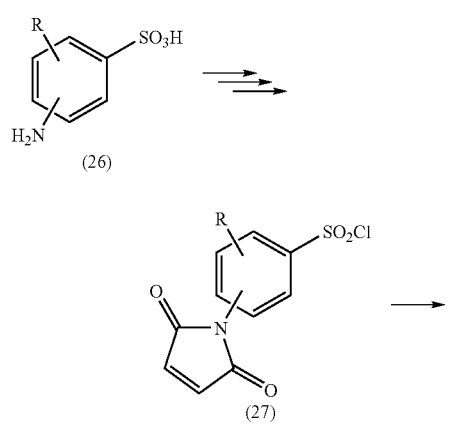

(26)

(27)

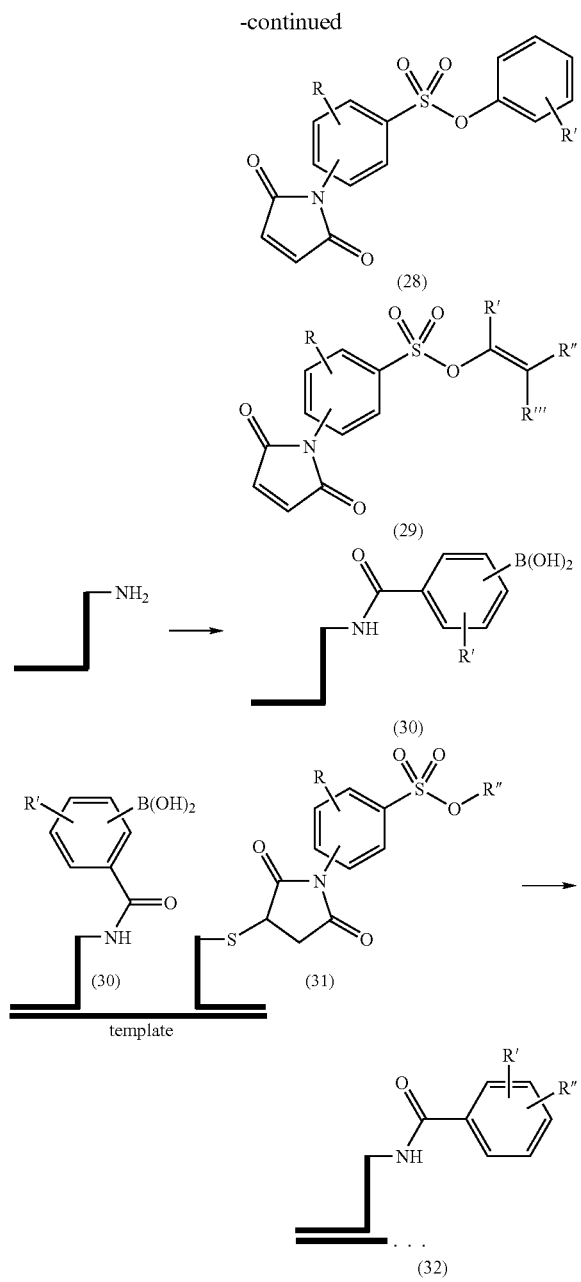

(28)

(29)

(30)

(31)

template (32)

$R'' = $ aryl, hetaryl or vinyl

Corresponding nucleophilic monomer building blocks capable of transferring an aryl, hetaryl or vinyl functionality may be prepared from organic building blocks type (35). This is available by estrification of a boronic acid by a diol e.g. (33), followed by transformation into the NHS-ester derivative. The NHS-ester derivative may then be coupled to an oligonucleotide, by use of coupling procedures for NHS-ester derivatives to amine carrying oligonucleotide's described above, to generate monomer building block type (37). Alternatively, may maleimide derivatives be prepared as described above and loaded onto SH-carrying oligonucleotide's.

The transtion metal catalyzed cross coupling is conducted as follows:

A premix of 1.4 mM $Na_2PdCl_4$ and 2.8 mM $P(p-SO_3C_6H_4)_3$ in water left for 15 min was added to a mixture of the template oligonucleotide (1 mmol) and monomer building block (36) and (37) (both 1 mmol) in 0.5 M NaOAc buffer at pH=5 and 75 mM NaCl (final [Pd]=0.3 mM). The mixture is then left o/n at 35-65° C. preferably 58° C., to yield template bound (38).

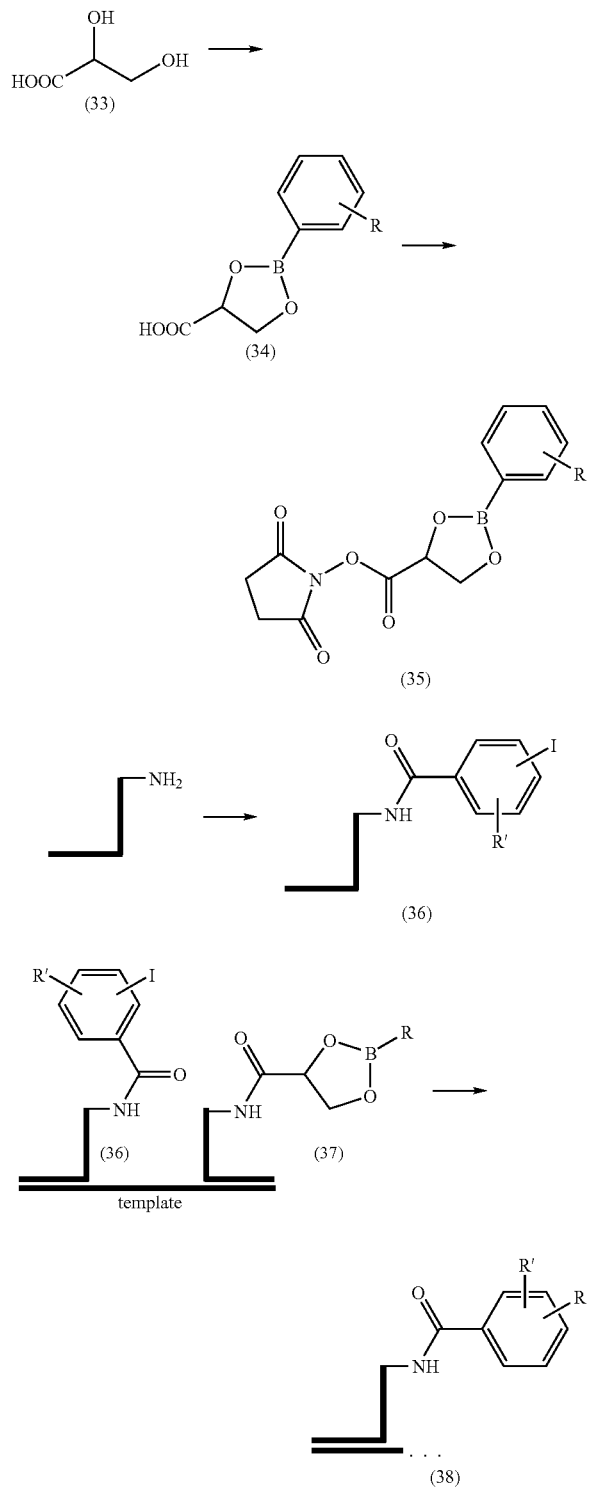

F. Reactions of Enamine and Enolether Monomer Building Blocks

Monomer building blocks loaded with enamines and enolethers may be prepared as follows:

For Z=NHR(R=H, alkyl, aryl, hetaryl), a 2-mercaptoethylamine may be reacted with a dipyridyl disulfide to generate the activated disulfide (40), which may then be condensed to a ketone or an aldehyde under dehydrating conditions to yield the enamine (41).

For Z=OH, 2-mercaptoethanol is reacted with a dipyridyl disulfide, followed by O-tosylation (Z=OTs). The tosylate (40) may then be reacted directly with an enolate or in the presence of fluoride with a O-trialkylsilylenolate to generate the enolate (41). The enamine or enolate (41) may then be coupled onto an SH-carrying oligonucleotide as described above to give the monomer building block (42).

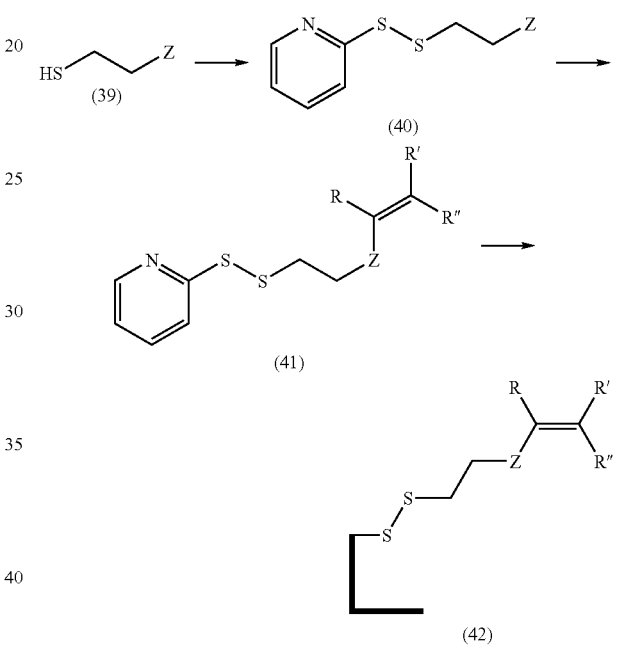

The monomer building blocks (42) may be reacted with a carbonyl carrying oligonucleotide like (44) or alternatively an alkylhalide carrying oligonucleotide like (43) as follows:

The template oligonucleotide (1 mmol) is mixed with monomer building block (42) (1 mmol) and (43) (1 mmol) in 50 mM MOPS, phosphate or hepes-buffer buffer and 250 mM NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield template bound (46), where Z=O or NR. For compounds where Z=NR slightly acidic conditions may be applied to yield product (46) with Z=O.

The template oligonucleotide (1 mmol) is mixed with monomer building block (42) (1 mmol) and (44) (1 mmol) in 0.1 M TAPS, phosphate or hepes-buffer buffer and 300 mM NaCl solution, pH=7.5-8.5 and preferably pH=8.0. The reaction mixture is left at 35-65° C. preferably 58° C. over night or alternatively at a fluctuating temperature (10° C. for 1 second then 35° C. for 1 second) to yield template bound (45), where Z=O or NR. For compounds where Z=NR slightly acidic conditions may be applied to yield product (45) with Z=O.

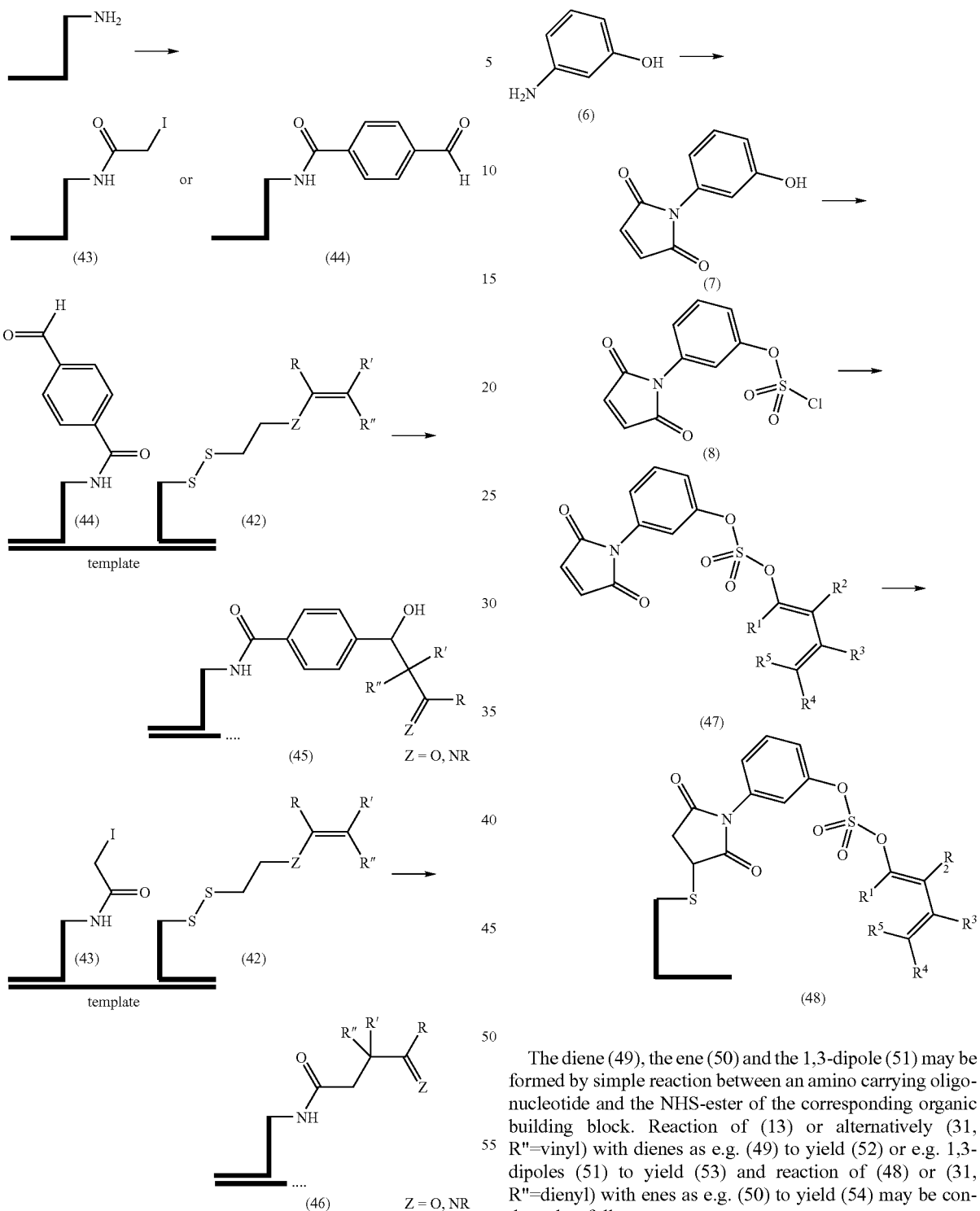

Enolethers type (13) may undergo cycloaddition with or without catalysis. Similarly, may dienolethers be prepared and used. E.g. by reaction of (8) with the enolate or trialkyl-silylenolate (in the presence of fluoride) of an α,β-unsaturated ketone or aldehyde to generate (47), which may be loaded onto an SH-carrying oligonucleotide, to yield monomer building block (48).

The diene (49), the ene (50) and the 1,3-dipole (51) may be formed by simple reaction between an amino carrying oligonucleotide and the NHS-ester of the corresponding organic building block. Reaction of (13) or alternatively (31, R"=vinyl) with dienes as e.g. (49) to yield (52) or e.g. 1,3-dipoles (51) to yield (53) and reaction of (48) or (31, R"=dienyl) with enes as e.g. (50) to yield (54) may be conducted as follows:

The template oligonucleotide (1 mmol) is mixed with monomer building block (13) or (48) (1 mmol) and (49) or (50) or (51) (1 mmol) in 50 mM MOPS, phosphate or hepes-buffer buffer and 2.8 M NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield template bound (52), (53) or (54).

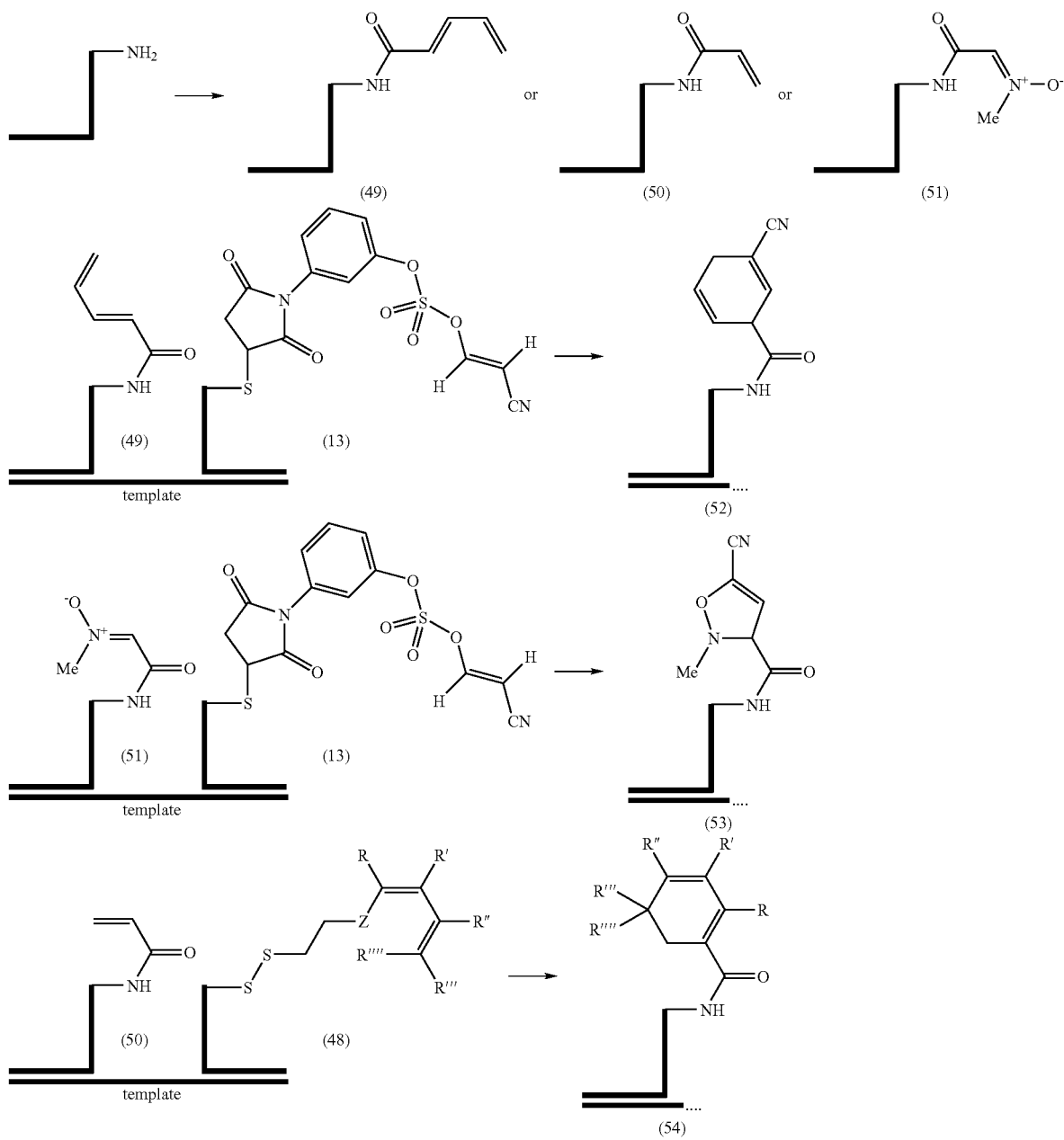

Linker Cleavage

Activation (cleavage of some or all of the linkers connecting the complementing elements and the functional entity) may be done by changes in pH and/or temperature, addition of reactants or catalysts, enzymes or ribozymes, or light, UV or other electromagnetic radiation, etc. Particularly relevant enzymes include proteases, esterases and nucleases. A list of cleavable linkers and the conditions for cleavage is shown in (FIG. 10).

Other cleavable linkers include the 4-hydroxymethyl phenoxyacetic acid moiety, which is cleaved by acid, the 2-[(tert-butyldiphenylsiloxy)methyl]benzoic acid moiety which is celavable with fluoride, and the phosphate of a 2-hydroxymethyl benzoic acid moiety which provides a linker cleavable by the combination of alkaline phosphatase treatment followed by treatment with mild alkaline treatment.

In most cases, it is desirable to have at least two different types of linkers connecting the complementing elements with the funtional entities. This way, it is possible to selectively cleave all but one of the linkers between the complementing template and the functional entities, thereby obtaining a polymer physically linked through just one linker to the template that templated its synthesis. This intact linker should affect the activities of the attached polymer as little as possible, but other than that, the nature of the linker is not considered an essential feature of this invention. The size of the linker in terms of the length between the template and the templated polymer can vary widely, but for the purposes of the invention, preferably the length is in the range from the length of just one bond, to a chain length of about 20 atoms.

Selection and Screening of Templated Molecules

Selection or screening of the templated molecules with desired activities (for example binding to particular target, catalytic activity, or a particular effect in an activity assay) may be performed according to any standard protocol. For example, affinity selections may be performed according to the principles used for phage displayed, polysome-displayed or mRNA-protein fusion displayed peptides. Selection for catalytic activity may be performed by affinity selections on transition-state analog affinity columns (Baca et al., Proc. Natl. Acad. Sci USA. 1997; 94(19):10063-8), or by function-based selection schemes (Pedersen et al., Proc. Natl. Acad. Sci. USA. 1998, 95(18):10523-8). Screening for a desired characteristic may be performed according to standard microtiter plate-based assays, or by FACS-sorting assays.

Use of Libraries of Templated Molecules

Selection of template-displaying molecules that will bind to known targets

The present invention is also directed to approaches that allow selection of small molecules capable of binding to different targets. The template-displaying molecule technology contains a built-in function for direct selection and amplification. The binding of the selected molecule should be selective in that they only coordinate to a specific target and thereby prevent or induce a specific biological effect. Ultimately, these binding molecules should be possible to use e.g. as therapeutic agents, or as diagnostic agents.

Template-displaying molecule libraries can easily be combined with screenings, selections, or assays to assess the effect of binding of a molecule ligand on the function of the target. In a more specific embodiment, the template-displaying method provides a rapid means for isolating and identifying molecule ligands which bind to supra-molecular, macro-supra-molecular, macro-molecular and low-molecular structures (e.g. nucleic acids and proteins, including enzymes, receptors, antibodies, and glycoproteins); signal molecules (e.g. cAMP, inositol triphosphate, peptides, prostaglandins); and surfaces (e.g. metal, plastic, composite, glass, ceramics, rubber, skin, tissue).

Specifically, selection or partitioning in this context means any process whereby the template-displaying molecule complex bound to a target molecule, the complex-target pair, can be separated from template-displaying molecules not bound to the target molecule. Selection can be accomplished by various methods known in the art.

The selection strategy can be carried out so it allows selection against almost any target. Importantly, no steps in this selection strategy need any detailed structural information of the target or the molecules in the libraries. The entire process is driven by the binding affinity involved in the specific recognition/coordination of the molecules in the library to a given target. However, in some applications, if needed, functionality can also be included analogous to selection for catalytic activity using phage display (Soumillion et al. (1994) J. Mol. Biol. 237: 415-22; Pedersen et al. (1998) PNAS. 18: 10523-10528). Example of various selection procedures are described below.

This built-in template-displaying molecule selection process is well suited for optimizations, where the selection steps are made in series starting with the selection of binding molecules and ends with the optimized binding molecule. The single procedures in each step are possible to automate using various robotic systems. This is because there is a sequential flow of events and where each event can be performed separately. In a most preferable setting, a suitable template-displaying molecule library and the target molecule are supplied to a fully automatic system which finally generates the optimized binding molecule. Even more preferably, this process should run without any need of external work outside the robotic system during the entire procedure.

The libraries of template-displayed molecules will contain molecules that could potentially coordinate to any known or unknown target. The region of binding on a target could be into a catalytic site of an enzyme, a binding pocket on a receptor (e.g. GPCR), a protein surface area involved in protein-protein interaction (especially a hot-spot region), and a specific site on DNA (e.g. the major groove). The template-displaying molecule technology will primarily identify molecules that coordinate to the target molecule. The natural function of the target could either be stimulated (agonized) or reduced (antagonized) or be unaffected by the binding of the template-displaying molecules. This will be dependent on the precise binding mode and the particular binding-site the template-displaying molecules occupy on the target. However, it is known that functional sites (e.g. protein-protein interaction or catalytic sites) on different proteins are more prone to bind molecules that other more neutral surface areas on a protein. In addition, these functional sites normally contain a smaller region that seems to be primarily responsible for the binding energy, the so called hot-spot regions (Wells, et al. (1993) Recent Prog. Hormone Res. 48; 253-262). This phenomenon will increase the possibility to directly select for small molecules that will affect the biological function of a certain target.

The template-displaying molecule technology of the invention will permit selection procedures analogous to other display methods such as phage display (Smith (1985) Science 228: 1315-1317). Phage display selection has been used successfully on peptides (Wells & Lowman. (1992) Curr. Op. Struct. Biol. 2, 597-604) proteins (Marks et al. (1992) J. Biol. Chem. 267: 16007-16010) and antibodies (Winter et al. (1994) Annu. Rev. Immunol. 12: 433-455). Similar selection procedures are also exploited for other types of display systems such as ribosome display (Mattheakis et al. (1994) Proc. Natl. Acad. Sci. 91: 9022-9026) and mRNA display (Roberts, et al. (1997) Proc. Natl. Acad. Sci. 94: 12297-302). However, the enclosed invention, the template-displaying molecule technology, will for the first time allow direct selection of target-specific small non-peptide molecules independently of the translation process on the ribosome complex. The necessary steps included in this invention are the amplification of the templates and incorporation and reaction of the monomer building blocks. The amplification and incorporation and the incorporation and reaction are either done in the same step or in a sequential process.

The linkage between the templated molecule (displayed molecule) and DNA replication unit (coding template) allows a rapid identification of binding molecules using various selection strategies. This invention allows a broad strategy in identifying binding molecules against any known target. In addition, this technology will also allow discovery of novel unknown targets by isolating binding molecules against unknown antigens (epitopes) and use these binding molecules for identification and validation (see section "Target identification and validation").

As will be understood, selection of binding molecules from the template-displaying molecule libraries can be performed in any format to identify optimal binding molecules. A typical selection procedure against a purified target will include the following major steps: Generation of a template-displaying molecule library: Immobilization of the target molecule using a suitable immobilization approach; Adding the library to allow binding of the template-displayed molecules; Removing of the non-binding template-displayed molecules; Elution of the template-displayed molecules bound to the immobilized target; Amplification of enriched template-displaying molecules for identification by sequencing or to input for the next round of selection. The general steps are schematically shown in FIG. 39.

In a preferred embodiment, a standard selection protocol using a template-displaying molecule library is to use the bio-panning method. In this technique, the target (e.g. protein or peptide conjugate) is immobilized onto a solid support and the template-displayed molecules that potentially coordinate to the target are the ones that are selected and enriched. However, the selection procedure requires that the bound template-displayed molecules can be separated from the unbound ones, i.e. those in solution. There are many ways in which this might be accomplished as known to ordinary skilled in the art.

The first step in the affinity enrichment cycle (one round as described in FIG. 1) is when the template-displayed molecules showing low affinity for an immobilized target are washed away, leaving the strongly binding template-displayed molecules attached to the target. The enriched population, remaining bound to the target after the stringent washing, is then eluted with, e.g. acid, chaotropic salts, heat, competitive elution with the known ligand or proteolytic release of the target/template molecules. The eluted template-displayed molecules are suitable for PCR, leading to many orders of amplification, i.e. every single template-displayed molecule enriched in the first selection round participates in the further rounds of selection at a greatly increased copy number. After typically three to ten rounds of enrichment a population of molecules is obtained which is greatly enriched for the template-displayed molecules which bind most strongly to the target. This is followed quantitatively by assaying the proportion of template-displaying molecules which remain bound to the immobilized target. The variant template sequences are then individually sequenced.

Immobilisation of the target (peptide, protein, DNA or other antigen) on beads might be useful where there is doubt that the target will adsorb to the tube (e.g. unfolded targets eluted from SDS-PAGE gels). The derivatised beads can then be used to select from the template-displaying molecules, simply by sedimenting the beads in a bench centrifuge. Alternatively, the beads can be used to make an affinity column and the template-displaying libraries suspension recirculated through the column. There are many reactive matrices available for immobilizing the target molecule, including for instance attachment to —$NH_2$ groups and —SH groups. Magnetic beads are essentially a variant on the above; the target is attached to magnetic beads which are then used in the selection. Activated beads are available with attachment sites for —$NH_2$ or —COOH groups (which can be used for coupling). The target can be also be blotted onto nitrocellulose or PVDF. When using a blotting strategy, it is important to make sure the strip of blot used is blocked after immobilization of the target (e.g. with BSA or similar protein).

In another preferred embodiment, the selection or partitioning can also be performed using for example: Immunoprecipitation or indirect immunoprecipitation were the target molecule is captured together with template-displaying binding molecules; affinity column chromatography were the target is immobilized on a column and the template-displaying libraries are flowed through to capture target-binding molecules; gel-shift (agarose or polyacrylamide) were the selected template-displaying molecules migrate together with the target in the gel; FACS sorting to localize cells that coordinates template-displaying molecules; CsCl gradient centrifugation to isolate the target molecule together template-displaying binding molecules; Mass spectroscopy to identify target molecules which are labelled with template-displaying molecules; etc., without limitation. In general, any method where the template-displaying molecule/target complex can be separated from template-displaying molecules not bound to the target is useful.

TABLE 2

Examples of selection method possible to use to identify binding molecules using the template-displaying technology.

| Type of Target | Method of choice |
| --- | --- |
| Soluble receptors | Direct immobilization, Immunoprecipitation, affinity column, FACS sorting, MS. |
| Cell surface receptor | Cell-surface subtraction selection, FACS sorting, Affinity column. |
| Enzyme inhibitors | Direct immobilization, Immunoprecipitation, affinity column, FACS sorting, MS. |
| Surface epitopes | Cell-surface subtraction selection, in-vivo selection, FACS sorting, Affinity column. |

Elution of template-displayed molecules can be performed in different ways. The binding molecules can be released from the target molecule by denaturation, acid, or chaotropic salts and then transferred to another vial for amplification. Alternatively, the elution can be more specific to reduce the background. Elution can be accomplished using proteolysis to cleave a linker between the target and the immobilizing surface or between the displaying molecule and the template. Also, elution can be accomplished by competition with a known ligand. Alternatively, the PCR reaction can be performed directly in the washed wells at the end of the selection reaction.

A possible feature of the invention is the fact that the binding molecules need not be elutable from the target to be selectable since only the encoding template DNA is needed for further amplification or cloning, not the binding molecule itself. It is known that some selection procedure can bind the most avid ligands so tightly as to be very difficult to elute. However the method of the invention can successfully be practiced to yield avid ligands, even covalent binding ligands.

Alternative selection protocol includes a known ligand as fragment of each displayed molecule in the library. That known ligand will guide the selection by coordinate to a defined part on the target molecule and focus the selection to molecules that binds to the same region. This could be especially useful for increasing the affinity for a ligand with a desired biological function but with a too low potency.

A further aspect of the present invention relates to methods of increasing the diversity or complexity of a single or a mixture of selected binding molecules. After the initial selection, the enriched molecules can be altered to further increase the chemical diversity or complexity of the displayed molecules. This can be performed using various methods known to the art. For example, using synthesized randomized oligonucleotides, spiked oligonucleotides or random mutagenesis. The randomization can be focused to allow preferable codons or localized to a predetermined portion or sub-sequence of the template nucleotide sequence. Other preferable method is to recombine templates coding for the binding molecules in a similar manner as DNA shuffling is used on homologous genes for proteins (Stemmer (1994) Nature 370:389-91). This approach can be used to recombine initial libraries or more preferably to recombine enriched encoding templates.

In another embodiment of the invention when binding molecules against specific antigens that is only possible to express on a cell surface, e.g. ion channels or transmembrane receptors, is required, the cells particle themselves can be used as the selection agent. In this sort of approach, cells lacking the specific target should be used to do one or more rounds of negative selection or be present in large excess in the selection process. Here, irrelevant template-displayed molecules are removed. For example, for a positive selection against a receptor expressed on whole cells, the negative selection would be against the untransformed cells. This approach is also called subtraction selection and has successfully been used for phage display on antibody libraries (Hoogenboom et al. (1998) Immunotech. 4: 1-20).

A specific example of a selection procedure can involve selection against cell surface receptors that become internalized from the membrane so that the receptor together with the selected binding molecule can make its way into the cell cytoplasm or cell nucleus. Depending on the dissociation rate constant for specific selected binding molecules, these molecules largely reside after uptake in either the cytoplasm or the nucleus.

The skilled person in the art will acknowledge that the selection process can be performed in any setup where the target is used as the bait onto which the template-displaying molecules can coordinate.

The selection methods of the present invention can be combined with secondary selection or screening to identify molecule ligands capable of modifying target molecule function upon binding. Thus, the methods described herein can be employed to isolate or produce binding molecules which bind to and modify the function of any protein or nucleic acid. It is contemplated that the method of the present invention can be employed to identify, isolate or produce binding molecules which will affect catalytic activity of target enzymes, i.e., inhibit catalysis or modifying substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

A still further aspect of the present invention relates to methods allowing functionality in the selection process can also be included. For example, when enrichment against a certain target have been performed generation a number of different hits, these hits can then directly be tested for functionality (e.g. cell signalling). This can for example be performed using fluorescence-activated cell sorting (FACS).

The altered phenotype may be detected in a wide variety of ways. Generally, the changed phenotype is detected using, for example: microscopic analysis of cell morphology; standard cell viability assays, including both increased cell death and increased cell viability; standard labelling assays such as fluorometric indicator assays for the presence of level of particular cell or molecule, including FACS or other dye staining techniques; biochemical detection of the expression of target compounds after killing the cells; etc. In some cases, specific signalling pathways can be probed using various reporter gene constructs.

Secondary selection methods that can be combined with template-displaying molecule technology include among others selections or screens for enzyme inhibition, alteration or substrate binding, loss of functionality, disruption of structure, etc. Those of ordinary skill in the art are able to select among various alternatives of selection or screening methods that are compatible with the methods described herein.

The binding molecules of the invention can be selected for other properties in addition to binding, For example, during selection; stability to certain conditions of the desired working environment of the end product can be included as a selection criterion. If binding molecules which are stable in the presence of a certain protease is desired, that protease can be part of the buffer medium used during selection. Similarly, the selection can also be performed in serum or cell extracts or any type of media. As will be understood, when utilizing this template-displaying approach, conditions which disrupt or degrade the template should be avoided to allow amplification. Other desired properties can be incorporated, directly into the displaying molecules as will be understood by those skilled in the art. For example, membrane affinity can be included as a property by employing building blocks with high hydrophobicity.

Molecules selected by the template-displaying molecule technology can be produced by various synthetic methods. Chemical synthesis can be accomplished since the structure of selected binding molecules is readily obtained form the nucleic acid sequence of the coding template. Chemical synthesis of the selected molecules is also possible because the building blocks that compose the binding molecules are also known in addition to the chemical reactions that assemble them together.

In a preferred embodiment, the selected binding molecules is synthesized and tested in various appropriate in vitro and in vivo testing to verify the selected candidates for biological effects and potency. This may be done in a variety of ways, as will be appreciated by those in the art, and may depend on the composition of the bioactive molecule.

Target Identification and Validation

In another aspect, the present invention provides methods to identify or isolate targets that are involved in pathological processes or other biological events. In this aspect, the target molecules are again preferably proteins or nucleic acids, but can also include, among others, carbohydrates and various molecules to which specific molecule ligand binding can be achieved. In principal, the template-displaying molecule technology could be used to select for specific epitopes on antigens found on cells, tissues or in vivo. These epitopes might belong to a target that is involved in important biological events. In addition, these epitopes might also be involved in the biological function of the target.

Phage display with antibodies and peptide libraries has been used numerous times successfully in identifying new cellular antigens. (e.g. Pasqualini et al. (1996) Nature 380: 364-366; Pasqualini et al. (2000) Cancer Res. 60: 722-727; Scheffer et al. (2002) Br J Cancer 86: 954-962; Kupsch et al. (1999) Clin Cancer Res. 5: 925-931; Tseng-Law et al. (1999) Exp. Hematol. 27: 936-945; Gevorkian et al. (1998) Clin. Immunol. Immunopathol. 86: 305-309). Especially effective have been selection directly on cells suspected to express cell-specific antigens. Importantly, when selecting for cell-surface antigen, the template molecule can be maintained outside the cell. This will increase the probability that the template molecule will be intact after release for the cell surface.

In vivo selection of template-displayed molecules has tremendous potential. By selecting from libraries of template-displayed molecules in vivo it is possible to isolate molecules capable of homing specifically to normal tissues and other pathological tissues (e.g. tumours). This principle has been illustrated using phage display of peptide libraries (Pasqualini & Ruoslathi (1996) Nature 280: 364-366). This system has also been used in humans to identify peptide motifs that localized to different organs (Arap et al. (2002) Nat. Med. 2:121-127). A similar selection procedure could be used for the template-displaying libraries. The coding DNA in phage display is protected effectively by the phage particle allows selection in vivo. Accordingly, the stability of the template in vivo will be important for amplification and identification. The template can be stabilised using various nucleotide derivatives in a similar way as have been used to stabilise aptamers for in vivo applications (Nolte (1996) Nature Biotechnol. 14: 1116-1121; Pagratis et al. (1997) Nature Biotechnol. 15: 68-72). However, it is reasonable to believe that the template structure will be stabilized against degradation due to the modified bases used for encoding the displayed molecule. Other types of protection are also possible where the template molecule is shielded for the solution using various methods. This could include for example liposomes, pegylation, binding proteins or other sorts of protection. The template molecule could also be integrated into another designed structure that protects the template form external manipulation. Fort example, the linker can be design to be incorporated in vesicles to position the templates inside the vesicle and the displaying molecules on the outside. The arrangement will protect the template molecules from external manipulate and at the same time allow exposure of the displaying molecules to permit selection.

Most antibodies have a large concave binding area which requires to some degree protruding epitopes on the antigens. Also, the antibody molecule is a large macromolecule (150 KDa) which will sterically reduce the access for a number of different antigens (e.g. on a cell surface). The template-displaying technology should be able to access and recognize epitopes inaccessible to antibodies. The small binding molecules will be able to bind into active sites, grooves and other areas on an antigen. The coding template element is also smaller that an antibody which will increase the physical access of the template-binding molecule par. In addition, the diversity and complexity of the template-displaying molecule libraries will be much greater compare to peptide libraries. This will increase the possibility to find molecules that can coordinate to epitopes inaccessible to peptides due to inadequate chemistry. All together, the template-displaying molecule technology has the potential to identify novel antigens which is not possible to identify with antibodies or peptides. One of ordinary skill in the art will acknowledge that various types of cells can be used in the selection procedure. It will also be understood that the selection for new antigens can be performed using subtraction methods as described previously.

Another aspect of the present invention relates to methods to validate the identified target. The identified binding molecules can directly be used if they change the biological response of the target. This can be done either in vitro using any direct or cell-based assay or directly in vivo studying any phenotypic response. The strength of this approach is that the same molecules are used both for identification and validation of various targets. Most favourable, the binding molecules could also directly be used as therapeutic agents.

In another preferred embodiment, the template-displaying molecules are used to pull out the target molecules. This can for instance be achieved by selection against a cDNA library expressed on bacteriophage (libraries vs. libraries). By mixing a template-displaying molecule library with a cDNA library it will be possible to find binding pairs between the small molecules in the template-displaying molecule library and proteins from the cDNA library. One possibility is to mix a phage display library with a template display library and do a selection for either the phage or template library. The selected library is then plated to localized phage clones and the DNA coding for the phage and template displayed molecules can then be identified using PCR. Other types of libraries than cDNA could also be used such as nucleic acids, carbohydrates, synthetic polymer.

In another embodiment of the invention the template-displaying molecule technology can be used to account for in vivo and in vitro drug metabolism. That could include both phase I (activation) and phase II (detoxification) reactions. The major classes of reactions are oxidation, reduction, and hydrolysis. Other enzymes catalyze conjugations. These enzymes could be used as targets in a selection process to eliminate displayed molecule that are prone to coordinate to these enzymes. The templates corresponding to these displayed molecules could subsequently be used to compete or eliminate these molecules when making template-displaying molecule libraries. These obtained libraries will then be free of molecules that will have a tendency of binding to enzymes involved in phase I-II and possible be faster eliminated. For instance, a selection on each separate enzyme or any combination of cytochrome P450 enzymes, flavin monooxygenase, monoamine oxidase, esterases, amidases, hydrolases, reductases, dehydrogenases, oxidases UDP-glucuronosyltransferases, glutathione S-transferases as well as other relevant enzymes could be performed to identify these binding molecules that are prone to coordinate to these metabolic enzymes. Inhibitors are easily selected for due to their binding affinity but substrates need at least micro molar affinity to be identified.

Another interesting embodiment of this invention is the possibility to directly select for molecules that passively or actively becomes transported across epithelial plasma membrane, or other membranes. One possible selection assay is to use CaCO-2 cells, a human colon epithelial cell line, which is general, accepted as a good model for the epithelial barrier in the gastrointestinal guts. The CaCO-2 assay involves growing a human colon epithelial cell line on tissue culture well inserts, such that the resultant monolayer forms a biological barrier between apical and basolateral compartments. The template-displaying molecule libraries are placed either side of the cell monolayer and the molecules that can permeate the cell monolayer is collected and amplified. This process can be repeated until active molecules have been identified. Other cell line or setup of this assay is possible and is obvious for skill in the art.

A still further aspect of the present invention relates methods of selecting for stability of the selected molecules. This could be performed by subjecting an enriched pool of binding molecules to an environment that will possibly degrade or change the structure of the binding molecules. Various conditions could be certain proteases or a mixture of protease, cell extract, and various fluids from for example the gastrointestinal gut. Other conditions could be various salts or acid milieu or elevated temperature. Another possibility is to generate a library of known ligands and subject that library to stability tests and selection to identify stable molecules under certain conditions as describe above.

Therapeutic Applications

The potential therapeutic applications of the invention are great. For example, the template-displaying molecule technology of the invention may be used for blocking or stimulating various targets. A therapeutically relevant target is a substance that is known or suspected to be involved in a regulating process that is malfunctioning and thus leads to a disease state. Examples of such processes are receptor-ligand interaction, transcription-DNA interaction, and cell-cell interaction involving adhesion molecules, cofactor-enzyme interaction, and protein-protein interaction in intracellular signalling. Target molecule means any compound of interest for which a molecule ligand is desired. Thus, target can, for example, include a chemical compound, a mixture of chemical compounds, an array of spatially localized compounds, a biological macromolecule, such as DNA or mRNA, a bacteriophage peptide display library, a ribosome peptide display library, an extract made from biological materials such as bacteria, plants, fungi, or animal (e.g. mammalian) cells or tissue, protein, fusion protein, peptide, enzyme, receptor, receptor ligand, hormone, antigen, antibody, drug, dye, growth factor, lipid, substrate, toxin, virus, or the like etc., without limitation. Other examples of targets include, e.g. a whole cell, a whole tissue, a mixture of related or unrelated proteins, a mixture of viruses or bacterial strains or the like. etc., without limitation.

Therapeutic drug targets can be divided into different classes according to function; receptors, enzymes, hormones, transcription factors, ion channels, nuclear receptors, DNA, (Drews, J. (2000) Science 287:1960-1964). Among those, receptors, nuclear receptors, and metabolic enzymes constitute overwhelmingly the majority of known targets for existing drugs. Especially, G Protein-Coupled Receptors (GPCR) constitutes one of the most important classes of drug targets together with proteases for pharmacological intervention. Although the above examples are focused on the most relevant targets, it will be self-evident for a person skilled in the art that any other therapeutic target may be of interest.

The present invention employing the template-displaying molecule technology can be utilized to identify agonists or antagonists for all these classes of drug targets, dependent on the specific properties each target holds. Most of the targets are possible to obtain in a purified form for direct selection procedures. Other targets have to be used when they are in their native environments such as imbedded cell surface receptors. In those situations the selection using the template-displaying molecule libraries can be performed using subtraction-selection described previously.

One specific application of the template-displaying molecule technology of the invention is to generate molecules that can function as antagonists, where the molecules block the interaction between a receptor and one or more ligands. Another application includes cell targeting. For example, the generated molecules recognizing specific surface proteins or receptors will be able to bind to certain cell types. Such molecules may in addition carry another therapeutic agent to increase the potency and reduce the side-effects (for example cancer treatment). Applications involving antiviral agents are also included. For example, a generated molecule, which binds strongly to epitopes on the virus particle, may be useful as an antiviral agent. Another specific application of the template-displaying molecule technology of the invention is to generate molecules that can function as agonists, where the molecules stimulate or activate a receptor to initiate a cellular signalling pathway.

Template-displaying Molecule Arrays

A still further aspect of the present invention relates to methods for detecting the presence or absence of, and/or measuring the amount of target molecules in a sample, which employs a molecule ligand which can be isolated by the methods described herein. These molecule ligands can be used separately or in array system for multiple determinations.

An understanding of protein structures, protein-to-protein interactions, pathways and how proteins influence the origins of disease is of vital importance. Nucleic acid microarrays have enabled researchers to pursue novel biomarkers through genotyping. However, a major hurdle is the lack of correlation between gene expression at the level of mRNA level and the amount of corresponding protein expressed within the cell (Andersson et a. (1997) Electrophiresis 18: 533-537). Contrary to DNA and RNA analysis, the use of biochips for parallel protein function studies has been much more difficult. Unlike hybridization reactions, which are based on couplings or interactions of linear sequences, the protein interactions involve polypeptide surfaces arising from 3D folded amino-acid sequences. The requirement for preparation of 3D folded proteins substantially complicates fabrication of protein microarrays. The protein microarrays would be very sensitive to and can be easily degraded by the use of thermal treatments and harsh chemicals. Moreover, the folded protein interactions have a much stronger dependency on sequences compared to the hybridization reactions used on the DNA/RNA biochips. The sequence dependency of the protein interactions will further complicate the reaction kinetics.

The invention described herein provides a possible solution to making arrays that can measure different amounts at the protein level without the use of proteins or peptides as detection molecules. The template-displaying molecule technology could be used to identify small binding molecules to numerous targets. These binding molecules could then be arrayed in specific positions and work as detection molecule to measure the amount of various biomarkers. For example, binding molecule against cytokines or enzymes known to be involved in a specific pathway could be generate with the describe technology. These binding molecules could then be spotted in an array format to be used to measure the absolute or relative amount of each cytokine or enzyme.

One major advantage with this system is that the spotting technology used for DNA arrays could be identically applied for this system. The template-displayed molecules could be directly applied to the spotted DNA. Another possibility is that the synthesis could be performed directly on the pre-coated template using a polymerase and the nucleotide analogues. Make addressable microarrays with this technology will lead to high-throughput deposition of thousands of different functional molecules onto different locations of a chip. The overall principal is shown in FIG. 40.

The template-displaying molecule technology is not limited in chemistry to the 20 natural occurring amino acids. This will permit synthesis on the template of more robust and stable molecules that will bind to various targets. These more stable molecules will be more suitable to become immobilized on a surface and exposed to any harsh conditions such as heat, low or high pH various detergent. In addition, the shelf-life of the arrays will be much longer that arrays made from proteins.

Molecular Biological Tools

Polymerase chain reaction (PCR) is an exemplary method for amplifying nucleic acids. Descriptions of PCR methods are found (Saiki et al. (1985) Science 230: 1350-1354; Scharf et al. (1986) Science 233: 1076-1078; U.S. Pat. No. 4,683,202 (Mullis et al.)). Alternative methods of amplification include among others cloning of selected DNAs into appropriate vector and introduction of that vector into a host organism where the vector and the cloned DNAs are replicated and thus amplified (Guatelli et al. (1990) Proc. Natl. Acad, Sci. 87: 1874-1878). In general, any means that will allow faithful, efficient amplification of selected nucleic acid sequences can be employed in the method of the present invention. It is only necessary that the proportionate representations of the sequences after amplification reflect the relative proportions of sequences in the mixture before amplification.

The template variants of the present invention may be produced by any suitable method known in the art. Such methods include constructing a nucleotide sequence by chemical synthesis or a combination of chemical synthesis and recombinant DNA technology.

A nucleotide sequence encoding a template variant of the invention may be constructed by isolating or synthesizing a nucleotide sequence encoding the appropriate display molecules and then changing the nucleotide sequence so as to effect introduction (i.e. insertion or substitution) or removal (i.e. deletion or substitution) of the relevant functional entities of the displayed molecules.

The nucleotide sequence corresponding to the template molecules is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the sequence of the desired templates. For example, small oligonucleotides coding for portions of the desired template may be synthesized and assembled by PCR, ligation or ligation chain reaction (LCR) (Barany, PNAS 88:189-193, 1991). The individual oligonucleotides typically contain 5' or 3' overhangs for complementary assembly.

Alternative nucleotide sequence modification methods are available for producing template variants for high throughput screening or selection. For instance, methods which involve homologous cross-over such as disclosed in U.S. Pat. No. 5,093,257, and methods which involve gene shuffling, i.e. recombination between two or more homologous nucleotide sequences resulting in new nucleotide sequences having a number of nucleotide alterations when compared to the starting nucleotide sequences. Gene shuffling (also known as DNA shuffling) involves one or more cycles of random fragmentation and reassembly of the nucleotide sequences, followed by selection to select nucleotide template sequences encoding variant displaying molecules with the desired properties.

Examples of suitable in vitro gene shuffling methods are disclosed by Stemmer et al. (1994), Proc. Natl. Acad. Sci. USA; vol. 91, pp. 10747-10751; Stemmer (1994), Nature, vol. 370, pp. 389-391; Smith (1994), Nature vol. 370, pp. 324-325; Zhao et al., Nat. Biotechnol. 1998, March; 16(3): 258-61; Zhao H. and Arnold, F B, Nucleic Acids Research, 1997, Vol. 25. No. 6 pp. 1307-1308; Shao et al., Nucleic Acids Research 1998, January 15; 26(2): pp. 681-83; and WO 95/17413.

Synthetic shuffling involves providing libraries of overlapping synthetic oligonucleotides based e.g. on a flanking sequence. The synthetically generated oligonucleotides are recombined, and the resulting recombinant nucleic acid sequences are screened and if desired used for further shuffling cycles.

Recombination can be theoretically calculated, which is performed or modelled using a computer system, thereby partly or entirely avoiding the need for physically manipulating nucleic acids.

Once assembled (by synthesis, site-directed mutagenesis, DNA shuffling or another method), the nucleotide sequence encoding the templates is used to generate the template-displaying libraries.

Still other aspects of the present invention relates to a pharmaceutical composition comprising the conjugate or the variant of the invention as well as to methods of producing and using the conjugates and variants of the invention.

The term "affinity" is used herein as a qualitative term to describe the molecule-target interaction. A quantitative measure for the affinity is expressed through the Association Constant ($K_A$). The Association Constant and the Dissociation Constant is related to each other by the equation $K_D=1/K_A$. Evidently, a high affinity corresponds to a lower Dissociation Constant. The term "binds to a specific target" means that the binding molecules obtained with the template-displaying molecule technology binds to a chosen target so that a measurable response is obtained when tested in a suitable binding or functional assay. In the present context, the term "therapeutic agent" is intended to mean any biologically or pharmacologically active substance or antigen-comprising material; the term includes substances which have utility in the treatment or prevention of diseases or disorders affecting animals and humans, or in the regulation of any animal or human physiological condition and it also includes any biological active compound or composition which, when administrated in an effective amount, has an effect on living cells or organisms.

After the construction of template-displayed libraries, template-displaying molecules bearing the desired ligands can be captured using the below protocol. Coat two wells of two flat-bottom microtiter plates with about 1 µg streptavidin in a TBS buffer. Incubate over night at 4° C. Remove the streptavidin solution and wash the wells at least six times with TBS. Immediately add 2% BSA to block the wells and incubate for about 30 min. at 37° C. Wash the plate with TBS buffer at least three times. Add about 0.1 µg biotinylated target molecule (biotinylation can be performed as described in the literature) to one of the wells (use the other as background control) and incubate for about 30 min at 20° C. and then remove the excess by washing with TBS buffer at least six times. Block free streptavidin molecules with 1 mM biotin for 5 min. and wash excess away with TBS buffer at least six times. Add then the template-displaying molecule library to both wells and allow binding by incubating at 20° C. for about 1 hour. Wash the wells with TBS buffer at least six times to remove template-displaying molecules that not coordinate to the immobilized target molecule. Elute the coordinated template-displaying molecules using condition that remove the binding molecules. In later selection cycles, compare the number of eluted molecules between the wells with and without the target molecule to make sure there are more template-displaying molecules eluted in the well with target. That will ensure that there is a specific enrichment in the selection process. Other types and numerous variations of selection procedures can be found in the literature (e.g. "Phage display: A laboratory manual" (2001) Barbas et al., Eds. Cold Spring Harbor Laboratory Press, New York), An alternative to the above capturing is, after the construction of template-displayed libraries, to capture the template-displaying molecules bearing the desired ligands using the below protocol. The selection of template-display molecules can be performed using magnetically activated cell sorting (Siegel et al. (1997) J. Immunol. Methods 206: 73-85). Positive cells (cells with the antigen of interest) is cell-surface biotinylated using sulfo-NHS-LC-biotin (Pierce). Add approximately $10^6$ biotinylated cells to 10 µl streptavidin-coated paramagnetic microbeads (Dynal) and allow binding. Add about $10^8$ negative cells (cells without the antigen of interest). These negative cells act as a sink for nonpecific template-displaying molecules, and the target cells capture the specific template-displaying molecules. Pellet the cell mixture, discard the supernatant, and suspend in the template-displaying library suspension. Incubate about 2 hours at 37° C. on a rotator to keep the cells in suspension. Load the cell/template-displaying library solution on a magnetic column to recover the positive cells by wash off all the negative cells. Finally elute the positive cells by removing the magnetic field and amplify the eluted templates using PCR. This selection protocol can be repeated several times if needed.

Amplification of Templates Capable of Templating the Synthesis of Templated Molecules In one aspect the present invention relates to methods for amplifying templated molecules that may or may not be bound to a target. The choice of amplification method depends on the choice of coding or complementing elements. Natural oligonucleotides can be amplified by any state of the art method. These methods include, but is not limited to the polymerase chain reaction (PCR); as wells as e.g. nucleic acid sequence-based amplification (e.g. Compton, Nature 350, 91-92 (1991)), amplified anti-sense RNA (e.g. van Gelder et al., PNAS 85: 77652-77656 (1988)); self-sustained sequence replication system (e.g. Gnatelli et al., PNAS 87: 1874-1878 (1990)); polymerase independent amplification as described in e.g. Schmidt et al., NAR 25: 4797-4802 (1997), as well as in vivo amplification of plasmids carrying cloned DNA fragments. Ligase-mediated amplification methods may also be used, e.g., LCR (Ligase Chain Reaction). For non-natural nucleotides the choices of efficient amplification procedures are fewer. As non-natural nucleotides per definition can be incorporated by certain enzymes including polymerases, it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al., NAR 25: 4797-4802 (1997)). For backbone-modified oligonucleotide analogs such as PNA and LNA, this amplification method may be used. Before or during amplification the templates or complementing templates may be mutagenized or recombined in order to create a larger diversity for the next round of selection or screening.

Characterization of Polymers Isolated by the Selections or Screening Assays.

After the final round of selection, it is often desirable to sequence individual templates, in order to determine the sequence of individual templated polymers. If the template contains natural nucleotides, it is a standard routine to optionally PCR amplify the isolated templates (if the template is an RNA molecule, it is necessary to use reverse transcriptase to produce cDNA prior to the PCR-amplification), and then clone the DNA fragments into for example plasmids, transform these and then sequence individual plasmid-clones containing one or multiple tandem DNA sequences. In this case, it is practical to design a restriction site in both of the flanking sequences to the central random or partly random sequence of the template (i.e., in the primer binding sites). This will allow easy cloning of the isolated nucleotides. Sequencing can be done by the standard dideoxy chain termination method, or by more classical means such as Maxam-Gilbert sequencing.

If the template contains non-natural nucleotides, it is not feasible to clone individual sequences by transfer through a microbial host. However, using bead populations where each bead carries one oligonucleotide sequence, it is possible to clone in vitro, whereafter all the nucleotides attached to a specific bead may be optionally amplified and then sequenced (Brenner et al., 2000, Proc. Natl. Acad. Sci. USA 97, 1665-1670). Alternatively, one may dilute the population of isolates adequately, and then aliquot into microtiter plates so that the wells on average contain for example 0.1 templates. By amplifying the single templates by for example PCR, it will now be possible to sequence using standard methods. Of course, this requires that the non-natural nucleotides are substrates for the thermostable polymerase used in the PCR.

If alternative methods are used that require shorter oligonucleotides it may be desirable to design the starting template so as to contain restriction sites on either side of the encoding/templating region of the template. Thereby, after the final selection round, the templates can be restricted, to obtain a short oligonucleotide encoding the templated polymer, and then these short oligos can be applied to various analytical procedures.

It is also possible to sequence the isolates by the use of a DNA array of oligos with random but predetermined sequences.

It may also be desirable to sequence the population of isolates as a pool, for example if the sequences are expected to be in register, for example because the initial library consisted of a degenerate sequence based on a polymer sequence with a known (relatively high) desired activity. Therefore, it is then expected that all the isolates have sequences similar to the initial sequence of the templates before selection. Wherefore the population of isolates can be sequenced as a whole, to obtain a consensus sequence for the population as a whole.

Templated Molecules

A non-exhaustive and non-limiting list of oligomers that may be templated by the various principles described in the present invention is listed below:
 alpha-, beta-, gamma-, and omega-peptides
 mono-, di- and tri-substituted peptides
 L- and D-form peptides
 cyclohexane- and cyclopentane-backbone modified beta-peptides
 vinylogous polypeptides
 glycopolypeptides
 polyamides
 vinylogous sulfonamide peptide
 Polysulfonamide
 conjugated peptide (i.e., having prosthetic groups)
 Polyesters
 Polysaccharides
 Polycarbamates
 Polycarbonates
 Polyureas
 poly-peptidylphosphonates
 Azatides
 peptoids (oligo N-substituted glycines)
 Polyethers
 ethoxyformacetal oligomers
 poly-thioethers
 polyethylene glycols (PEG)
 Polyethylenes
 Polydisulfides
 polyarylene sulfides
 Polynucleotides
 PNAs
 LNAs
 Morpholinos
 oligo pyrrolinone
 polyoximes
 Polyimines
 Polyethyleneimine
 Polyacetates
 Polystyrenes
 Polyacetylene
 Polyvinyl
 Lipids Phospholipids
Glycolipids
polycycles (aliphatic)
polycycles (aromatic)
polyheterocycles
Proteoglycan
Polysiloxanes
Polyisocyanides
Polyisocyanates
Polymethacrylates
Monofunctional, Difunctional, Trifunctional and Oligofunctional open-chain hydrocarbons.
Monofunctional, Difunctional, Trifunctional and Oligofunctional Nonaromatic Carbocycles.
Monocyclic, Bicyclic, Tricyclic and Polycyclic Hydrocarbons
Bridged Polycyclic Hydrocarbones
Monofunctional, Difunctional, Trifunctional and Oligofunctional Nonaromatic Heterocycles.
Monocyclic, Bicyclic, Tricyclic and Polycyclic Heterocycles
Bridged Polycyclic Heterocycles
Monofunctional, Difunctional, Trifunctional and Oligofunctional Aromatic Carbocycles.
Monocyclic, Bicyclic, Tricyclic and Polycyclic Aromatic Carbocycles
Monofunctional, Difunctional, Trifunctional and Oligofunctional Aromatic Heterocycles.
Monocyclic, Bicyclic, Tricyclic and Polycyclic Heterocycles
Chelates
Fullerenes.
Any combination of the above.

The list refers to any linear, branched or cyclic structure that contains one or more of the backbone structures listed, and/or contain several bonds of the same kind (e.g. amide bonds). Heteropolymers (hybrids of different polymer types) can also be templated by the present invention.

Below a table is presented stating the polymers producible according to the present invention as well as the functional entities/reactive groups required to make them. A reference is made to the relevant figure:

| Polymer | Functional Entity (reactive groups) | Linking molecule | Catalyst/reagent | General Figure | Specific Figure |
|---|---|---|---|---|---|
| polycyclic compound | di-coumarin | | light | FIG. 11 | FIG. 11, ex. 1 |
| polyester | alcohol, carboxylic acid | | carbodiimide | FIG. 12, FIG. 21 | |
| polyester | hydroxyl, thioester | | | FIG. 14 | |
| polyurea | di-amine | carbonyldiimidazole | | FIG. 15 | FIG. 15, ex. 3 |
| polyacetate | halogen, carboxylic acid | | base | FIG. 12, FIG. 22 | |
| polyacetate | alcohol, carboxylic acid | | EDC or other carbodimide | FIG. 12, FIG. 22 | |
| polycarbamate | alcohol, isocyanate | | | FIG. 12, FIG. 22 | |
| polycarbonate | diol | carbonyldiimidazole | | FIG. 15 | |
| peptoid | secondary amine, a haloacetyl | | | FIG. 12, FIG. 22 | |
| | primary amine, a haloacetyl | | alkylating agent | FIG. 12, FIG. 22 | |
| glycogen | UDP-glucose | | glycogen synthetase | FIG. 12, FIG. 22 | |
| polysaccharide | UDP-activated saccharides | | polysaccharide synthetases | FIG. 12, FIG. 22 | |
| polysaccharide | glucosyl sulphide/sulfoxide activation system (Kahne glucosylation) | | Kahne conditions | FIG. 12, FIG. 22 | |
| polyamide | amine, N-hydroxysuccinimide ester | | | FIG. 12, FIG. 22 | |
| polyamide | amine, carboxylic acid | | carbodiimide | FIG. 12, FIG. 22 | |
| polyamide | di-amine | di-carboxylic acid | carbodiimide | FIG. 15 | FIG. 15, ex. 2 |
| polyamide | di-carboxylic acid | di-amine | carbodiimide | FIG. 15 | |
| polyamide | amine, carboxylic acid | amine, carboxylic acid | carbodiimide | FIG. 17 | |
| α-polypeptide | carboxyanhydride (5-membered ring) | | | FIG. 19 | |
| β-polypeptide | carboxyanhydride (6 membered ring) | | | FIG. 19 | FIG. 19, ex. 1 |
| γ-polypeptide | carboxyanhydride (7-membered ring) | | | FIG. 19 | |
| α-polypeptide | 2,2-diphenylthiazinanone (5-membered ring) | | | FIG. 19 | |
| β-polypeptide | 2,2-diphenylthiazinanone (6-membered ring) | | | FIG. 19 | FIG. 19, ex. 2 |
| γ-polypeptide | 2,2-diphenyithiazinanone (7-membered ring) | | | FIG. 19 | |
| α-polypeptide | amine, thioester | | | FIG. 14 | |
| β-polypeptide | amine, thiocester | | | FIG. 14 | FIG. 14, ex. 1 |
| γ-polypeptide | amine, thioester | | | FIG. 14 | |
| ω-polypeptide | amine, thioester | | | FIG. 14 | |
| polysulfonamide | amine, sulfonic acid | | carbodiimide | FIG. 12, FIG. 22 | |
| polyphosphonate | di-alcohol | activated phosphonate | | FIG. 15 | |

-continued

| Polymer | Functional Entity (reactive groups) | Linking molecule | Catalyst/reagent | General Figure | Specific Figure |
|---|---|---|---|---|---|
| polyphosphonate | di-alcohol | activated alkylphosphine | | FIG. 15 | |
| polyphosphate | di-alcohol | | oxidating reagent, e.g. tert-butyl hydroperoxide | FIG. 15 | |
| polyphosphodiester | diol | diaminoalkoxy-phosphine | oxidant (ButOOH) | FIG. 15 | FIG. 15, ex. 5 |
| Polyphosphodiester | diaminophosphine | diol | oxidant (ButOOH) | FIG. 15 | FIG. 15, ex. 6 |
| polyurethane | diamine | diisocyanate | | FIG. 15 | |
| polyether | epoxide | | | FIG. 19 | FIG. 18, ex. 3 |
| polythioether | thioepoxide | | | FIG. 19 | |
| polydisulfide | thiol, thiol | | oxidant | FIG. 11 | |
| polyoxime | aldehyde, hydroxylamine | | | FIG. 12, FIG. 22 | |
| polyimine | aldehyde, amine | | | FIG. 12, FIG. 22 | |
| polyimine | aldehyde, amine | | | FIG. 15 | FIG. 15, ex. 1 |
| polynucleotides | nucleoside-5'-phosphoro-2-methylimidazolides | | | FIG. 12, FIG. 22 | |
| polyamine | amine, alkyl sulfonate | | | FIG. 14 | FIG. 14, ex. 2 |
| alkane | alkene | | | FIG. 18 | FIG. 18, ex. 1 |
| alkane | alkene | | | FIG. 18 | FIG. 18, ex. 2 |
| polycycloalkane | di-diene | di-alkene (benzoquinone) | | FIG. 15 | FIG. 15, ex. 7 |
| polyvinyl | vinylchloride unit | | | FIG. 18 | |
| polystyrene | styrene-unit | | radical initiator, AIBN | FIG. 18 | |
| polyethylene | ethylene unit | | | FIG. 18 | FIG. 18, ex. 1 |

Templates

In one embodiment, the templated molecule is linked by means of a single linker to the complementing template or template that templated the synthesis of the templated molecule. In another embodiment, the method for templating a templated molecule comprises the further step of releasing the template or complementing template that templated the templated molecule, and obtaining a templated molecule that is not linked to the complementing template or template that templated the synthesis of the templated molecule.

The template preferably comprises n coding elements in a linear sequence. The template comprising n coding elements can also be branched. n preferably has a value of from 2 to 200, for example from 2 to 100, such as from 2 to 80, for example from 2 to 60, such as from 2 to 40, for example 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

In some embodiments of the invention it is preferred that the template is attached to a solid or semi-solid support.

The template in one embodiment preferably comprises or essentially consists of nucleotides selected from the group consisting of deoxyribonucleic acids (DNA), ribonucleic acids (RNA), peptide nucleic acids (PNA), locked nucleic acids (LNA), and morpholinos sequences, including any analog or derivative thereof.

In another embodiment, the template of coding elements preferably comprises or essentially consists of nucleotides selected from the group consisting of DNA, RNA, PNA, LNA and morpholinos sequence, including any analog or derivative thereof, and the complementing element preferably comprises or essentially consists of nucleotides selected from the group consisting of DNA, RNA, PNA, LNA and morpholinos sequence, including any analog or derivative thereof.

It is preferred in various embodiments of the invention that the template can be characterised by any one or more of the following features: i) That the template is amplifyable, ii) that the template comprises a single strand of coding elements, preferably a single strand of coding elements capable of forming a double helix by hybridization to a complementing template comprising a single strand of complementing elements, and iii) that the template comprises a priming site.

Coding Elements

Each coding element is preferably linked to a neighbouring coding element by a covalent chemical bond. Each coding element can also be linked to each neighbouring coding element by a covalent chemical bond. The covalent chemical bond is preferably selected from the group of covalent bonds consisting of phosphodiester bonds, phosphorothioate bonds, and peptide bonds. More preferably, the covalent chemical bond is selected from the group of covalent bonds consisting of phosphodiester bonds and phosphorothioate bonds.

In preferred embodiments, at least one coding element is attached to a solid or semi-solid support.

The coding elements are selected in one embodiment of the inveniton from the group consisting of nucleotides, including any analog or derivative thereof, amino acids, antibodies, and antigens, and preferably from the group consisting of nucleotides, nucleotide derivatives, and nucleotide analogs, including any combination thereof. In another embodiment, the coding elements are selected from the group consisting of nucleotides, including nucleotides such as deoxyribonucleic acids comprising a base selected from adenine (A), thymine (T), guanine (G), and cytosine (C), and ribonucleic acids comprising a base selected from adenine (A), uracil (U), guanine (G), and cytosine (C). Also in this case can each nucleotide be linked to a neighbouring nucleotide by means of a covalent bond, or linked to each neighbouring nucleotide by means of a covalent bond. The covalent bond is preferably a phosphodiester bond or a phosphorothioate bond.

In other embodiments, the coding elements are natural and non-natural nucleotides selected from the group consisting of deoxyribonucleic acids and ribonucleic acids.

Coding Elements and Corresponding Complementing Elements

When the coding elements are preferably selected from the group consisting of nucleotides, nucleotide derivatives and nucleotide analogs in which one or more of the base moiety and/or the phosphate moiety and/or the ribose or deoxyribose moiety have been substituted by an alternative molecular entity, corresponding complementing elements are capable of interacting with said coding elements and preferably comprise or essentially consist of nucleotides selected from the group consisting of DNA, RNA, PNA, LNA and morpholinos sequence, including any analog or derivative thereof. Each nucleotide is linked to a neighbouring nucleotide by a covalent chemical bond, or linked to each neighbouring nucleotide by a covalent chemical bond. The covalent chemical bond is preferably selected from the group of covalent bonds consisting of phosphodiester bonds and peptide bonds.

Coding Element Subunits

Coding elements in one embodiment preferably comprise or essentially consist of from 1 to 100 subunits, such as from 1 to 80 subunits, for example from 1 to 60 subunits, such as from 1 to 40 subunits, for example from 1 to 20 subunits, such as from 1 to 18 subunits, for example from 1 to 16 subunits, such as from 1 to 14 subunits, for example from 1 to 12 subunits, such as from 1 to 10 subunits, for example from 1 to 9 subunits, such as from 1 to 8 subunits, for example from 1 to 7 subunits, such as from 1 to 6 subunits, for example from 1 to 5 subunits, such as from 1 to 4 subunits, for example from 1 to 3 subunits, such as from 1 to 2 subunits, for example 1 subunit, such as from 2 to 100 subunits, such as from 2 to 80 subunits, for example from 2 to 60 subunits, such as from 2 to 40 subunits, for example from 2 to 20 subunits, such as from 2 to 18 subunits, for example from 2 to 16 subunits, such as from 2 to 14 subunits, for example from 2 to 12 subunits, such as from 2 to 10 subunits, for example from 2 to 9 subunits, such as from 2 to 8 subunits, for example from 2 to 7 subunits, such as from 2 to 6 subunits, for example from 2 to 5 subunits, such as from 2 to 4 subunits, for example from 2 to 3 subunits, such as 2 subunits, such as from 3 to 100 subunits, such as from 3 to 80 subunits, for example from 3 to 60 subunits, such as from 3 to 40 subunits, for example from 3 to 20 subunits, such as from 3 to 18 subunits, for example from 3 to 16 subunits, such as from 3 to 14 subunits, for example from 3 to 12 subunits, such as from 3 to 10 subunits, for example from 3 to 9 subunits, such as from 3 to 8 subunits, for example from 3 to 7 subunits, such as from 3 to 6 subunits, for example from 3 to 5 subunits, such as from 3 to 4 subunits, for example 3 subunits, for example from 4 to 100 subunits, such as from 4 to 80 subunits, for example from 4 to 60 subunits, such as from 4 to 40 subunits, for example from 4 to 20 subunits, such as from 4 to 18 subunits, for example from 4 to 16 subunits, such as from 4 to 14 subunits, for example from 4 to 12 subunits, such as from 4 to 10 subunits, for example from 4 to 9 subunits, such as from 4 to 8 subunits, for example from 4 to 7 subunits, such as from 4 to 6 subunits, for example from 4 to 5 subunits, for example 4 subunits, such as from 5 to 100 subunits, such as from 5 to 80 subunits, for example from 5 to 60 subunits, such as from 5 to 40 subunits, for example from 5 to 20 subunits, such as from 5 to 18 subunits, for example from 5 to 16 subunits, such as from 5 to 14 subunits, for example from 5 to 12 subunits, such as from 5 to 10 subunits, for example from 5 to 9 subunits, such as from 5 to 8 subunits, for example from 5 to 7 subunits, such as from 5 to 6 subunits, such as 5 subunits, for example from 6 to 100 subunits, such as from 6 to 80 subunits, for example from 6 to 60 subunits, such as from 6 to 40 subunits, for example from 6 to 20 subunits, such as from 6 to 18 subunits, for example from 6 to 16 subunits, such as from 6 to 14 subunits, for example from 6 to 12 subunits, such as from 6 to 10 subunits, for example from 6 to 9 subunits, such as from 6 to 8 subunits, for example from 6 to 7 subunits, such as 6 subunits, such as from 7 to 100 subunits, such as from 7 to 80 subunits, for example from 7 to 60 subunits, such as from 7 to 40 subunits, for example from 7 to 20 subunits, such as from 7 to 18 subunits, for example from 7 to 16 subunits, such as from 7 to 14 subunits, for example from 7 to 12 subunits, such as from 7 to 10 subunits, for example from 7 to 9 subunits, such as from 7 to 8 subunits, such as 7 subunits, for example from 8 to 100 subunits, such as from 8 to 80 subunits, for example from 8 to 60 subunits, such as from 8 to 40 subunits, for example from 8 to 20 subunits, such as from 8 to 18 subunits, for example from 8 to 16 subunits, such as from 8 to 14 subunits, for example from 8 to 12 subunits, such as from 8 to 10 subunits, for example from 8 to 9 subunits, for example 8 subunits, such as from 9 to 100 subunits, such as from 9 to 80 subunits, for example from 9 to 60 subunits, such as from 9 to 40 subunits, for example from 9 to 20 subunits, such as from 9 to 18 subunits, for example from 9 to 16 subunits, such as from 9 to 14 subunits, for example from 9 to 12 subunits, such as from 9 to 10 subunits, such as 9 subunits, for example from 10 to 100 subunits, such as from 10 to 80 subunits, for example from 10 to 60 subunits, such as from 10 to 40 subunits, for example from 10 to 20 subunits, such as from 10 to 18 subunits, for example from 10 to 16 subunits, such as from 10 to 14 subunits, for example from 10 to 12 subunits, such as 10 subunits, such as from 11 to 100 subunits, such as from 11 to 80 subunits, for example from 11 to 60 subunits, such as from 11 to 40 subunits, for example from 11 to 20 subunits, such as from 11 to 18 subunits, for example from 11 to 16 subunits, such as from 11 to 14 subunits, for example from 11 to 12 subunits, such as from 12 to 100 subunits, such as from 12 to 80 subunits, for example from 12 to 60 subunits, such as from 12 to 40 subunits, for example from 12 to 20 subunits, such as from 12 to 18 subunits, for example from 12 to 16 subunits, such as from 12 to 14 subunits, for example from 13 to 100 subunits, such as from 13 to 80 subunits, for example from 13 to 60 subunits, such as from 13 to 40 subunits, for example from 13 to 20 subunits, such as from 13 to 18 subunits, for example from 13 to 16 subunits, such as from 13 to 14 subunits, for example from 14 to 100 subunits, such as from 14 to 80 subunits, for example from 14 to 60 subunits, such as from 14 to 40 subunits, for example from 14 to 20 subunits, such as from 14 to 18 subunits, for example from 14 to 16 subunits, such as from 15 to 100 subunits, such as from 15 to 80 subunits, for example from 15 to 60 subunits, such as from 15 to 40 subunits, for example from 15 to 20 subunits, such as from 15 to 18 subunits, for example from 15 to 16 subunits, such as from 16 to 100 subunits, such as from 16 to 80 subunits, for example from 16 to 60 subunits, such as from 16 to 40 subunits, for example from 16 to 20 subunits, such as from 16 to 18 subunits, for example from 17 to 100 subunits, such as from 17 to 80 subunits, for example from 17 to 60 subunits, such as from 17 to 40 subunits, for example from 17 to 20 subunits, such as from 17 to 18 subunits, for example from 18 to 100 subunits, such as from 18 to 80 subunits, for example from 18 to 60 subunits, such as from 18 to 40 subunits, for example from 18 to 20 subunits, such as from 19 to 100 subunits, such as from 19 to 80 subunits, for example from 19 to 60 subunits, such as from 19 to 40 subunits, for example from 19 to 30 subunits, such as from 19 to 25 subunits, for example from 20 to 100 subunits, such as from 20 to 80 subunits, for example from 20 to 60 subunits, such as from 20 to 40 subunits, for example from 20 to 30 subunits, such as from 20 to 25 subunits.

In preferred embodiments, each coding element subunit comprises or essentially consists of a nucleotide, or a nucleotide analog. The nucleotide can be a deoxyribonucleic acid comprising a base selected from adenine (A), thymine (T), guanine (G), and cytosine (C), or it can be a ribonucleic acid comprising a base selected from adenine (A), uracil (U), guanine (G), and cytosine (C). Each nucleotide is linked to a neighbouring nucleotide, or nucleotide analog, by means of a covalent bond, or linked to each neighbouring nucleotide, or nucleotide analog, by means of a covalent bond, including covalent bonds selected from the group consisting of phosphodiester bonds, phosphorothioate bonds, and peptide bonds.

In one embodiment it is preferred that at least some of said nucleotides are selected from the group consisting of nucleotide derivatives, including deoxyribonucleic acid derivatives and ribonucleic acid derivatives.

Coding Element Subunits and Corresponding Complementing Element Subunits

The coding element subunits are preferably selected from the group consisting of nucleotides, nucleotide derivatives and nucleotide analogs in which one or more of a base moiety and/or a phosphate moiety and/or a ribose moiety and/or a deoxyribose moiety have been substituted by an alternative molecular entity, and the corresponding complementing element subunits capable of interacting with said coding element subunits comprise or essentially consist of nucleotides selected from the group consisting of DNA, RNA, PNA, LNA and morpholinos sequence, including any analog or derivative thereof.

Each nucleotide derivative can be linked to a neighbouring nucleotide, or nucleotide analog, by a covalent chemical bond, or each nucleotide derivative can be linked to each neighbouring nucleotide, or nucleotide analog, by a covalent chemical bond. The covalent chemical bond is preferably selected from the group of covalent bonds consisting of phosphodiester bonds, phosphorothioate bonds, and peptide bonds.

Complementing Elements

The complementing template in one embodiment preferably comprises n complementing elements in a linear sequence or a branched sequence. n preferably has a value of from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, such as 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, such as 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, such as 7, for example from 8 to 100, such as from 8 to 80, for example from 8 to 60, such as from 8 to 40, for example from 8 to 30, such as from 8 to 20, for example from 8 to 15, such as from 8 to 10, for example 8, such as 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

In some embodiments, the complementing template is attached to a solid or semisolid support.

The complementing template in one embodiment comprises or essentially consists of nucleotides selected from the group consisting of deoxyribonucleic acids (DNA), ribonucleic acids (RNA), peptide nucleic acids (PNA), locked nucleic acids (LNA), and morpholinos sequences, including any analog or derivative thereof.

In other embodiments, there is provided a complementing template comprising or essentially consisting of nucleotides selected from the group consisting of DNA, RNA, PNA, LNA and morpholinos sequence, including any analog or derivative thereof, wherein the corresponding coding elements of the template comprise or essentially consist of nucleotides selected from the group consisting of DNA, RNA, PNA, LNA and morpholinos sequence, including any analog or derivative thereof. The complementing template is preferably amplifyable and/or comprises a single strand of complementing elements and/or comprises a single strand of complementing elements capable of forming a double helix by hybridization to a template comprising a single strand of coding elements, and/or comprises a priming site.

Each complementing element is preferably linked to a neighbouring complementing element by a covalent chemical bond, or linked to each complementing element is linked to each neighbouring complementing element by a covalent chemical bond. The covalent chemical bond is in one embodiment selected from the group of covalent bonds consisting of phosphodiester bonds, phosphorothioate bonds, and peptide bonds. In other embodiments, the group of covalent bonds consist of phosphodiester bonds and phosphorothioate bonds.

The at least one complementing element can be attached to a solid or semi-solid support.

The complementing elements can be selected from the group consisting of nucleotides, including any analog or derivative thereof, amino acids, antibodies, and antigens, and preferably from the group consisting of nucleotides, nucleotide derivatives, and nucleotide analogs, including any combination thereof. In one embodiment, it is preferred that the complementing elements are selected from the group consisting of nucleotides, including deoxyribonucleic acids comprising a base selected from adenine (A), thymine (T), guanine (G), and cytosine (C), and ribonucleic acids comprising a base selected from adenine (A), uracil (U), guanine (G), and cytosine (C).

Each nucleotide can be linked to a neighbouring nucleotide, or nucleotide analog, by means of a covalent bond, including, or each nucleotide can be linked to each neighbouring nucleotide, or nucleotide analog, by means of a covalent bond. The covalent bond can be a phosphodiester bond or a phosphorothioate bond.

In another embodiment, the complementing elements are natural or non-natural nucleotides selected from the group consisting of deoxyribonucleic acids and ribonucleic acids.

Complementing Elements and Corresponding Coding Elements

When the complementing elements are selected from the group consisting of nucleotides, nucleotide derivatives and nucleotide analogs in which one or more of a base moiety and/or a phosphate moiety and/or a ribose and/or a deoxyribose moiety has been substituted by an alternative molecular entity, the coding elements capable of interacting with said complementing elements comprise or essentially consist of nucleotides selected from the group consisting of DNA, RNA, PNA, LNA and morpholinos sequence, including any analog or derivative thereof.

Each nucleotide can be linked to a neighbouring nucleotide, or nucleotide analog, by a covalent chemical bond, or linked to each neighbouring nucleotide, or nucleotide analog, by a covalent chemical bond. The covalent chemical bond is preferably selected from the group of covalent bonds consisting of phosphodiester bonds, phosphorothioate bonds, and peptide bonds.

The complementing elements are in one embodiment selected from nucleotides, and the complementing elements can in one preferred embodiment be linked enzymatically by using an enzyme selected from the group consisting of template-dependent DNA- and RNA-polymerases, including reverse transcriptases, DNA-ligases and RNA-ligases, ribozymes and deoxyribozymes, including HIV-1 Reverse Transcriptase, AMV Reverse Transcriptase, T7 RNA polymerase, T7 RNA polymerase mutant Y639F, Sequenase, Taq DNA polymerase, Klenow Fragment (Large fragment of DNA polymerase 1), DNA-ligase, T7 DNA polymerase, T4 DNA polymerase, T4 DNA Ligase, *E. coli* RNA polymerase, rTh DNA polymerase, Vent DNA polymerase, Pfu DNA polymerase, Tte DNA polymerase, and ribozymes with ligase or replicase activities.

More preferably, the enzyme is selected from the group consisting of HIV-1 Reverse Transcriptase, AMV Reverse Transcriptase, T7 RNA polymerase, T7 RNA polymerase mutant Y639F, Sequenase, Taq DNA polymerase, Klenow Fragment (Large fragment of DNA polymerase 1), DNA-ligase, T7 DNA polymerase, T4 DNA polymerase, and T4 DNA Ligase. The nucleotides preferably form a template or complementing template upon incorporation.

In another embodiment, the complementing elements can be selected from nucleotides, and linked by using a chemical agent, pH change, light, a catalyst, radiation, such as electromagnetic radiation, or by spontaneous coupling when being brought into reactive contact with each other.

Complementing Element Subunits

The complementing element preferably comprises or essentially consists of from 1 to 100 subunits, such as from 1 to 80 subunits, for example from 1 to 60 subunits, such as from 1 to 40 subunits, for example from 1 to 20 subunits, such as from 1 to 18 subunits, for example from 1 to 16 subunits, such as from 1 to 14 subunits, for example from 1 to 12 subunits, such as from 1 to 10 subunits, for example from 1 to 9 subunits, such as from 1 to 8 subunits, for example from 1 to 7 subunits, such as from 1 to 6 subunits, for example from 1 to 5 subunits, such as from 1 to 4 subunits, for example from 1 to 3 subunits, such as from 1 to 2 subunits, for example 1 subunit, such as from 2 to 100 subunits, such as from 2 to 80 subunits, for example from 2 to 60 subunits, such as from 2 to 40 subunits, for example from 2 to 20 subunits, such as from 2 to 18 subunits, for example from 2 to 16 subunits, such as from 2 to 14 subunits, for example from 2 to 12 subunits, such as from 2 to 10 subunits, for example from 2 to 9 subunits, such as from 2 to 8 subunits, for example from 2 to 7 subunits, such as from 2 to 6 subunits, for example from 2 to 5 subunits, such as from 2 to 4 subunits, for example from 2 to 3 subunits, such as 2 subunits, such as from 3 to 100 subunits, such as from 3 to 80 subunits, for example from 3 to 60 subunits, such as from 3 to 40 subunits, for example from 3 to 20 subunits, such as from 3 to 18 subunits, for example from 3 to 16 subunits, such as from 3 to 14 subunits, for example from 3 to 12 subunits, such as from 3 to 10 subunits, for example from 3 to 9 subunits, such as from 3 to 8 subunits, for example from 3 to 7 subunits, such as from 3 to 6 subunits, for example from 3 to 5 subunits, such as from 3 to 4 subunits, for example 3 subunits, for example from 4 to 100 subunits, such as from 4 to 80 subunits, for example from 4 to 60 subunits, such as from 4 to 40 subunits, for example from 4 to 20 subunits, such as from 4 to 18 subunits, for example from 4 to 16 subunits, such as from 4 to 14 subunits, for example from 4 to 12 subunits, such as from 4 to 10 subunits, for example from 4 to 9 subunits, such as from 4 to 8 subunits, for example from 4 to 7 subunits, such as from 4 to 6 subunits, for example from 4 to 5 subunits, for example 4 subunits, such as from 5 to 100 subunits, such as from 5 to 80 subunits, for example from 5 to 60 subunits, such as from 5 to 40 subunits, for example from 5 to 20 subunits, such as from 5 to 18 subunits, for example from 5 to 16 subunits, such as from 5 to 14 subunits, for example from 5 to 12 subunits, such as from 5 to 10 subunits, for example from 5 to 9 subunits, such as from 5 to 8 subunits, for example from 5 to 7 subunits, such as from 5 to 6 subunits, such as 5 subunits, for example from 6 to 100 subunits, such as from 6 to 80 subunits, for example from 6 to 60 subunits, such as from 6 to 40 subunits, for example from 6 to 20 subunits, such as from 6 to 18 subunits, for example from 6 to 16 subunits, such as from 6 to 14 subunits, for example from 6 to 12 subunits, such as from 6 to 10 subunits, for example from 6 to 9 subunits, such as from 6 to 8 subunits, for example from 6 to 7 subunits, such as 6 subunits, such as from 7 to 100 subunits, such as from 7 to 80 subunits, for example from 7 to 60 subunits, such as from 7 to 40 subunits, for example from 7 to 20 subunits, such as from 7 to 18 subunits, for example from 7 to 16 subunits, such as from 7 to 14 subunits, for example from 7 to 12 subunits, such as from 7 to 10 subunits, for example from 7 to 9 subunits, such as from 7 to 8 subunits, such as 7 subunits, for example from 8 to 100 subunits, such as from 8 to 80 subunits, for example from 8 to 60 subunits, such as from 8 to 40 subunits, for example from 8 to 20 subunits, such as from 8 to 18 subunits, for example from 8 to 16 subunits, such as from 8 to 14 subunits, for example from 8 to 12 subunits, such as from 8 to 10 subunits, for example from 8 to 9 subunits, for example 8 subunits, such as from 9 to 100 subunits, such as from 9 to 80 subunits, for example from 9 to 60 subunits, such as from 9 to 40 subunits, for example from 9 to 20 subunits, such as from 9 to 18 subunits, for example from 9 to 16 subunits, such as from 9 to 14 subunits, for example from 9 to 12 subunits, such as from 9 to 10 subunits, such as 9 subunits, for example from 10 to 100 subunits, such as from 10 to 80 subunits, for example from 10 to 60 subunits, such as from 10 to 40 subunits, for example from 10 to 20 subunits, such as from 10 to 18 subunits, for example from 10 to 16 subunits, such as from 10 to 14 subunits, for example from 10 to 12 subunits, such as 10 subunits, such as from 11 to 100 subunits, such as from 11 to 80 subunits, for example from 11 to 60 subunits, such as from 11 to 40 subunits, for example from 11 to 20 subunits, such as from 11 to 18 subunits, for example from 11 to 16 subunits, such as from 11 to 14 subunits, for example from 11 to 12 subunits, such as from 12 to 100 subunits, such as from 12 to 80 subunits, for example from 12 to 60 subunits, such as from 12 to 40 subunits, for example from 12 to 20 subunits, such as from 12 to 18 subunits, for example from 12 to 16 subunits, such as from 12 to 14 subunits, for example from 13 to 100 subunits, such as from 13 to 80 subunits, for example from 13 to 60 subunits, such as from 13 to 40 subunits, for example from 13 to 20 subunits, such as from 13 to 18 subunits, for example from 13 to 16 subunits, such as from 13 to 14 subunits, for example from 14 to 100 subunits, such as from 14 to 80 subunits, for example from 14 to 60 subunits, such as from 14 to 40 subunits, for example from 14 to 20 subunits, such as from 14 to 18 subunits, for example from 14 to 16 subunits, such as from 15 to 100 subunits, such as from 15 to 80 subunits, for example from 15 to 60 subunits, such as from 15 to 40 subunits, for example from 15 to 20 subunits, such as from 15 to 18 subunits, for example from 15 to 16 subunits, such as from 16 to 100 subunits, such as from 16 to 80 subunits, for example from 16 to 60 subunits, such as from 16 to 40 subunits, for example from 16 to 20 subunits, such as from 16 to 18 subunits, for example from 17 to 100 subunits, such as from 17 to 80 subunits, for example from 17 to 60 subunits, such as from 17 to 40 subunits, for example from 17 to 20 subunits, such as from 17 to 18 subunits, for example from 18 to 100 subunits, such as from 18 to 80 subunits, for example from 18 to 60 subunits, such as from 18 to 40 subunits, for example from 18 to 20 subunits, such as from 19 to 100 subunits, such as from 19 to 80 subunits, for example from 19 to 60 subunits, such as from 19 to 40 subunits, for example from 19 to 30 subunits, such as from 19 to 25 subunits, for example from 20 to 100 subunits, such as from 20 to 80 subunits, for example from 20 to 60 subunits, such as from 20 to 40 subunits, for example from 20 to 30 subunits, such as from 20 to 25 subunits.

In preferred embodiments, each subunit comprises or essentially consists of a nucleotide, or a nucleotide analog. The nucleotide can be a deoxyribonucleic acid comprising a base selected from adenine (A), thymine (T), guanine (G), and cytosine (C), or a ribonucleic acid comprising a base selected from adenine (A), uracil (U), guanine (G), and cytosine (C).

Each of said nucleotides can be linked to a neighbouring nucleotide, or nucleotide analog, by means of a covalent bond, or linked to each neighbouring nucleotide, or nucleotide analog, by means of a covalent bond. The covalent bond is preferably selected from the group consisting of phosphodiester bonds, phosphorothioate bonds, and peptide bonds.

It is preferred in one embodiment that at least some of said nucleotides are selected from the group consisting of nucleotide derivatives, including nucleotide derivatives selected from the group consisting of deoxyribonucleic acid derivatives and ribonucleic acid derivatives.

Complementing Element Subunits and Corresponding Coding Element Subunits

When the complementing element subunits are selected from the group consisting of nucleotides, nucleotide derivatives, and nucleotide analogs in which one or more of a base moiety and/or a phosphate moiety and/or a ribose moiety and/or a deoxyribose moiety has been substitutetd by an alternative molecular entity, the coding element subunits capable of interacting with said complementing element subunits preferably comprise or essentially consist of nucleotides selected from the group consisting of DNA, RNA, PNA, LNA and morpholinos sequence, including any analog or derivative thereof.

It is preferred that each nucleotide derivative is linked to a neighbouring nucleotide, or nucleotide analog, by a covalent chemical bond, or linked to each neighbouring nucleotide, or nucleotide analog, by a covalent chemical bond. The covalent chemical bond can be selected from the group of covalent bonds consisting of phosphodiester bonds, phosphorothioate bonds, and peptide bonds.

Building Blocks, Cleavable Linkers and Selectively Cleavable Linkers

In one aspect there is provided a building block comprising
i) a complementing element capable of specifically recognising a coding element having a recognition group, said complementing element being selected from nucleotides, amino acids, antibodies, antigens, proteins, peptides, and molecules with nucleotide recognizing ability,
ii) at least one functional entity selected from a precursor of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptide, polysulfonamide, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinone, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, and
iii) a linker or selectively cleavable linker separating the functional entity from the complementing element.

The complementing element of the building block is preferably selected from a nucleotide sequence, such as a sequence of from 1 to 8 nucleotides, such as from 1 to 6 nucleotides, for example from 1 to 4 nucleotides, such as from 1 to 3 nucleotides, such as 2 nucleotides or for example 3 nucleotides.

The functional entity can be selected from a precursor of an amino acid selected from alfa amino acids, beta amino acids, gamma amino acids, di-substituted amino acids, poly-substituted amino acids, vinylogous amino acids, N-substituted glycin derivatives and other modified amino acids.

The is also provided a composition of building blocks as defined herein, wherein at least two building blocks of the composition are different.

At least a subset of the plurality of building blocks preferably comprises one complementing element and one functional entity and one linker.

In one embodiment, each building block comprises at least one reactive group type I and/or at least one reactive group type II, including one reactive group type I, two reactive groups type I, one reactive group type II, and two reactive groups type II.

At least one of said reactive groups type II of the functional entity is preferably selected from the group consisting of N-carboxyanhydride (NCA), N-thiocarboxyanhydride (NTA), amine, carboxylic acid, ketone, aldehyde, hydroxyl, thiol, ester, thioester, any conjugated system of double bonds, hydrazine, N-hydroxysuccinimide ester, and epoxide.

In some embodiments, the ractive group type II is an electrophile, a nucleophile, or a radical.

At least a subset of said plurality of building blocks comprises a selectively cleavable linker separating the functional entity from the complementing element, wherein said selectively cleavable linker is not cleaved under conditions resulting in cleavage of cleavable linkers separating the functional entity from the complementing element of building blocks not belonging to the subset of building blocks comprising a selectively cleavable linker. The cleavable linkers of the building blocks are cleaved without cleaving the at least one selectively cleavable linker linking the templated molecule to the complementing template, or to a complementing element, or linking said templated molecule to a templating element, or to the template that templated the synthesis of the templated molecule.

Linkers and selectively cleavable linkers can be cleaved by e.g. acid, base, a chemical agent, light, electromagnetic radiation, an enzyme, or a catalyst, with the proviso that the cleavage of the cleavable linker does result in the cleavage of the selectively cleavable linker unless this is desirable.

In one embodiment, the length of the linker or selectively cleavable linker is in the range of from about 0.8 Å to about 70 Å, such as in the range of from 0.8 Å to about 60 Å, for example in the range of from 0.8 Å to about 50 Å, such as in the range of from 0.8 Å to about 40 Å, for example in the range of from 0.8 Å to about 30 Å, such as in the range of from 0.8 Å to about 25 Å, for example in the range of from 0.8 Å to about 20 Å, such as in the range of from 0.8 Å to about 18 Å, for example in the range of from 0.8 Å to about 16 Å, such as in the range of from 0.8 Å to about 14 Å, for example in the range of from 0.8 Å to about 12 Å, such as in the range of from 0.8 Å to about 10 Å, for example in the range of from 0.8 Å to about 8 Å, such as in the range of from 0.8 Å to about 7 Å, for example in the range of from 0.8 Å to about 6 Å, such as in the range of from 0.8 Å to about 5 Å, for example in the range of from 0.8 Å to about 4 Å, such as in the range of from 0.8 Å to about 3.5 Å, for example in the range of from 0.8 Å to about 3.0 Å, such as in the range of from 0.8 Å to about 2.5 Å, for example in the range of from 0.8 Å to about 2.0 Å, such as in the range of from 0.8 Å to about 1.5 Å, for example in the range of from 0.8 Å to about 1.0 Å.

In another embodiment, the length of the linker or selectively cleavable linker is in the range of from about 1 Å to about 60 Å, such as in the range of from 1 Å to about 40 Å, for example in the range of from 1 Å to about 30 Å, such as in the range of from 1 Å to about 25 Å, for example in the range of from 1 Å to about 20 Å, such as in the range of from 1 Å to about 18 Å, for example in the range of from 1 Å to about 16 Å, such as in the range of from 1 Å to about 14 Å, for example in the range of from 1 Å to about 12 Å, such as in the range of from 1 Å to about 10 Å, for example in the range of from 1 Å to about 8 Å, such as in the range of from 1 Å to about 7 Å, for example in the range of from 1 Å to about 6 Å, such as in the range of from 1 Å to about 5 Å, for example in the range of from 1 Å to about 4 Å, such as in the range of from 1.0 Å to about 3.5 Å, for example in the range of from 1.0 Å to about 3.0 Å, such as in the range of from 1.0 Å to about 2.5 Å, for example in the range of from 1.0 Å to about 2.0 Å, such as in the range of from 1.0 Å to about 1.5 Å, for example in the range of from 1.0 Å to about 1.2 Å.

In yet another embodiment, the length of the linker or selectively cleavable linker is in the range of from about 2 Å to about 40 Å, such as in the range of from 2 Å to about 30 Å, such as in the range of from 2 Å to about 25 Å, for example in the range of from 2 Å to about 20 Å, such as in the range of from 2 Å to about 18 Å, for example in the range of from 2 Å to about 16 Å, such as in the range of from 2 Å to about 14 Å, for example in the range of from 2 Å to about 12 Å, such as in the range of from 2 Å to about 10 Å, for example in the range of from 2 Å to about 8 Å, such as in the range of from 2 Å to about 7 Å, for example in the range of from 2 Å to about 6 Å, such as in the range of from 2 Å to about 5 Å, for example in the range of from 2 Å to about 4 Å, such as in the range of from 2.0 Å to about 3.5 Å, for example in the range of from 2.0 Å to about 3.0 Å, such as in the range of from 2.0 Å to about 2.5 Å, for example in the range of from 2.0 Å to about 2.2 Å.

In a further embodiment, the length of the linker or selectively cleavable linker is in the range of from about 4 Å to about 40 Å, such as in the range of from 4 Å to about 30 Å, such as in the range of from 4 Å to about 25 Å, for example in the range of from 4 Å to about 20 Å, such as in the range of from 4 Å to about 18 Å, for example in the range of from 4 Å to about 16 Å, such as in the range of from 4 Å to about 14 Å, for example in the range of from 4 Å to about 12 Å, such as in the range of from 4 Å to about 10 Å, for example in the range of from 4 Å to about 8 Å, such as in the range of from 4 Å to about 7 Å, for example in the range of from 4 Å to about 6 Å, such as in the range of from 4 Å to about 5 Å.

In a still further embodiment, the length of the linker or selectively cleavable linker is in the range of from about 6 Å to about 40 Å, such as in the range of from 6 Å to about 30 Å, such as in the range of from 6 Å to about 25 Å, for example in the range of from 6 Å to about 20 Å, such as in the range of from 6 Å to about 18 Å, for example in the range of from 6 Å to about 16 Å, such as in the range of from 6 Å to about 14 Å, for example in the range of from 6 Å to about 12 Å, such as in the range of from 6 Å to about 10 Å, for example in the range of from 6 Å to about 8 Å, such as in the range of from 6 Å to about 7 Å.

In yet another embodiment, the length of the linker or selectively cleavable linker is in the range of from about 8 Å to about 40 Å, such as in the range of from 8 Å to about 30 Å, such as in the range of from 8 Å to about 25 Å, for example in the range of from 8 Å to about 20 Å, such as in the range of from 8 Å to about 18 Å, for example in the range of from 8 Å to about 16 Å, such as in the range of from 8 Å to about 14 Å, for example in the range of from 8 Å to about 12 Å, such as in the range of from 8 Å to about 10 Å.

Templated Molecules

The templated molecules can be linked—or not linked—to the template having templated the synthesis of the templated molecule.

In one embodiment, the present invention relates to templated molecules comprising or essentially consisting of amino acids selected from the group consisting of α-amino acids, β-amino acids, γ-amino acids, ω-amino acids.

In various preferred embodiments the templated molecule comprises or essentially consists of one or more of natural amino acid residues, of α-amino acids, of monosubstituted α-amino acids, disubstituted α-amino acids, monosubstituted β-amino acids, disubstituted β-amino acids, or trisubstituted β-amino acids, tetrasubstituted β-amino acids, γ-amino acids, ω-amino acids, vinylogous amino acids, and N-substituted glycines.

The above-mentioned templated molecules comprising β-amino acids preferably have a backbone structure comprising or essentially consisting of a cyclohexane-backbone and/or a cyclopentane-backbone.

In other embodiments, the templated molecule comprises or essentially consists of molecules or molecular entities selected from the group of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptide, polysulfonamide, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinone, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, inlcuding any combination thereof.

Neighbouring residues of the templated molecules according to the invention can be linked by a chemical bond selected from the group of chemical bonds consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

Also, the backbone structure of the templated molecules according to the invention can in one aspect comprise or essentially consist of a molecular group selected from —NHN(R)CO—; —NHB(R)CO—; —NHC(RR')CO—; —NHC(=CHR)CO—; —NHC$_6$H$_4$CO—; —NHCH$_2$CHRCO—; —NHCHRCH$_2$CO—; —COCH$_2$—; —COS—; —CONR—; —COO—; —CSNH—; —CH$_2$NH—; —CH$_2$CH$_2$—; —CH$_2$S—; —CH$_2$SO—; —CH$_2$SO$_2$—; —CH(CH$_3$)S—; —CH=CH—; —NHCO—; —NHCONH—; —CONHO—; —C(=CH$_2$)CH$_2$—; —PO$_2^-$NH—; —PO$_2^-$CH$_2$—; —PO$_2^-$CH$_2$N$^+$—; —SO$_2$NH$^-$—; and lactams, including any combination thereof.

In other embodiments of the invention, the templated molecules are not of polymeric nature.

The precursor is in one embodiment preferably selected from the group of precursors consisting of α-amino acid precursors, β-amino acid precursors, γ-amino acid precursors, and ω-amino acid precursors.

In some embodiment, the templated molecule is an oligomer or a polymer comprising at least one repetitive sequence of functional groups, such as at least three functional groups repeated at least twice in the templated molecule. The templated molecules also includes molecules wherein any sequence of at least three functional groups occurs only once.

Some preferred templated molecules preferably comprise or essentially consist of at least 2 different functional groups, such as at least 3 different functional groups, for example at least 4 different functional groups, such as at least 5 different functional groups, for example at least 6 different functional groups, such as at least 7 different functional groups, for example at least 8 different functional groups, such as at least 9 different functional groups, for example at least 10 different functional groups, such as more than 10 different functional groups. The functional groups can also be identical.

In one preferred aspect of the invention there is provided a templated molecule comprising a polymer comprising a plurality of covalently linked functional groups each comprising at least one residue, wherein the plurality of residues is preferably from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

In another preferred aspect of the invention there is provided a templated molecule comprising a polymer comprising a plurality of covalently linked functional groups each comprising a residue, wherein the covalently linked residues are capable of generating a polymer comprising, exclusively or in combination with additional portions, at least one portion selected from the group of polymer portions consisting of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptides, polysulfonamides, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, and wherein the plurality of residues is preferably from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

The templated molecule in one embodiment is preferably one, wherein the covalently linked residues are capable of generating a polymer comprising, exclusively or in combination with additional portions selected from the group, at least one portion selected from the group of polymer portions consisting of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, and vinylogous polypeptides.

In one particular embodiment, the templated molecule is one wherein the covalently linked residues are capable of generating a polysaccharaide.

In another aspect there is provided a templated molecule comprising a sequence of functional groups, wherein neighbouring functional groups are linked by a molecular moiety that is not natively associated with said functional groups.

Additional aspect of the present invention relates to i) a templated molecule comprising a sequence of covalently linked, functional groups, wherein the templated molecule does not comprise or consist of an α-peptide or a nucleotide, ii) a templated molecule comprising a sequence of covalently linked, functional groups, wherein the templated molecule does not comprise or consist of a monosubstituted α-peptide or a nucleotide, and iii) a templated molecule comprising a sequence of covalently linked, functional groups, wherein the templated molecule does not comprise or consist of a peptide or a nucleotide.

Compositions of Templated Molecules

The templated molecules according to the invention, including those mentioned herein immediately above, can be present in a composition of templated molecules, wherein said composition comprises a plurality of more than or about $10^3$ different templated molecules, such as more than or about $10^4$ different templated molecules, for example more than or about $10^5$ different templated molecules, such as more than or about $10^6$ different templated molecules, for example more than or about $10^7$ different templated molecules, such as more than or about $10^8$ different templated molecules, for example more than or about $10^9$ different templated molecules, such as more than or about $10^{10}$ different templated molecules, for example more than or about $10^{11}$ different templated molecules, such as more than or about $10^{12}$ different templated molecules, for example more than or about $10^{13}$ different templated molecules, such as more than or about $10^{14}$ different templated molecules, for example more than or about $10^{15}$ different templated molecules, such as more than or about $10^{16}$ different templated molecules, for example more than or about $10^{17}$ different templated molecules, such as more than or about $10^{18}$ different templated molecules.

The composition in some embodiments preferably further comprises the template capable of templating each templated molecule, or a subset thereof. Accordingly, in one preferred aspect of the present invention, there is provided i) a composition comprising a templated molecule and the template capable of templating the templated molecule, or ii) a composition comprising a templated molecule and the template that templated the synthesis of the templated molecule.

Various preferred features of the templated molecules either i) linked to the template capable of templating the synthesis of the templated molecule, or ii) present in a composition further comprising the template capable of templating the synthesis of the templated molecule is listed herein immediately below.

When being present in such compositions, it is preferred that i) the template does not consist exclusively of natural nucleotides, when the templated molecule is a peptide comprising exclusively monosubstituted α-amino acids, ii) the template is not a natural nucleotide, when the templated molecule is a natural α-peptide, iii) the template is not a nucleotide, when the templated molecule is a natural α-peptide, iv) the template is not a nucleotide, when the templated molecule is a monosubstituted α-peptide, v) the template is not a nucleotide, when the templated molecule is an α-peptide, vi) the template is not a natural nucleotide, when the templated molecule is a peptide, and vii) the template is not a nucleotide, when the templated molecule is a peptide.

Templated Molecules Linked to the Template that Templated the Synthesis of the Templated Molecule In one preferred aspect of the present invention there is provided a templated molecule comprising a sequence of covalently linked, functional groups, wherein the templated molecule is linked by means of a linker to the complementing template or template that templated the synthesis of the templated molecule, wherein the templated molecule does not comprise or consist of an α-peptide In another preferred aspect of the present invention there is provided a templated molecule comprising a sequence of covalently linked, functional groups, wherein the templated molecule is linked by means of a linker to the complementing template or template that templated the synthesis of the templated molecule, wherein the templated molecule does not comprise a monosubstituted α-peptide.

In yet another preferred aspect of the present invention there is provided a templated molecule comprising a sequence of covalently linked, functional groups, wherein the templated molecule is linked by means of a linker to the complementing template or template that templated the synthesis of the templated molecule, wherein the templated molecule does not comprise or consist of an α-peptide or a nucleotide.

In a still further aspect of the present invention there is provided a templated molecule comprising a sequence of covalently linked, functional groups, wherein the templated molecule is linked by means of a linker to the complementing template or template that templated the synthesis of the templated molecule, wherein the template is not a natural nucleotide, when the templated molecule is an α-peptide.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template does not consist exclusively of natural nucleotides, when the templated molecule is a peptide comprising exclusively monosubstituted α-amino acids.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a natural nucleotide, when the templated molecule is a natural α-peptide.

In an even further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a nucleotide, when the templated molecule is a natural α-peptide.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a nucleotide, when the templated molecule is a monosubstituted α-peptide.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a nucleotide, when the templated molecule is an α-peptide.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a natural nucleotide, when the templated molecule is a peptide.

In a still further preferred aspect of the present invention there is provided a templated molecule comprising a sequence of covalently linked, functional groups, wherein the templated molecule is linked by means of a linker to the complementing template or template that templated the synthesis of the templated molecule, wherein the template is not a nucleotide, when the templated molecule is a peptide.

The templated molecule can be obtained according to the methods described herein above.

In even further aspects there is provided i) a templated molecule comprising a sequence of covalently linked building blocks;

ii) a templated molecule comprising a sequence of covalently linked building blocks, wherein the sequence of covalently linked building blocks comprises a sequence of complementing elements forming a complementing template capable of complementing the template that templated the synthesis of the templated molecule, and wherein the templated molecule is linked to the complementing template or template that templated its synthesis; and iii) a templated molecule according to any of the previous claims, wherein the templated molecule comprises a sequence of functional entities comprising at least one functional group, and optionally at least one reactive group type II, and wherein each functional entity is linked to a complementing element or a template that templated the synthesis of the templated molecule.

Uses of Templated Molecules

The templated molecules according to the present invention can be used for a variety of commercial pruposes.

In one aspect, there is provided a method for screening templated molecules potentially having a predetermined activity, said method comprising the step of providing a target molecule or a target entity, including a surface, and obtaining templated molecules having an affinity for—or an effect on—said target molecule or target entity.

Another aspect relates to a method for assaying an activity potentially associated with a templated molecules, said method comprising the step of providing a target molecule or a target entity, including a surface, and obtaining templated molecules having an affinity for—or an effect on—said target molecule or target entity, and determining the activity of the templated molecule.

Yet another aspect provides a method for selecting complexes or templated molecules having a predetermined activity, said method comprising the step of performing a selection procedure and selecting templated molecules based on predetermined selection criteria.

There is also provided a method for screening a composition of molecules having a predetermined activity comprising:

i) establishing a first composition of templated molecules as described herein, or produced as defined herein by any method for preparing templated molecules, ii) exposing the first composition to conditions enriching said first composition with templated molecules having the predetermined activity, and iii) optionally amplifying the templated molecules of the enriched composition obtaining a second composition, iv) further optionally repeating step ii) to iii), and v) obtaining a further composition having a higher ratio of templated molecules having the specific predetermined activity.

In one embodiment, the method further comprises a step of mutating the templated molecules, wherein said mutagenesis can take place prior to carrying out step iii), simultaneously with carrying out step iii), or after carrying out step iii). The mutagenesis can be carried out as random or site-directed mutagenesis.

Step iii) of the method preferably comprises a $10^1$ to $10^{15}$-fold amplification, and steps ii) and iii) can be repeated, such as at least 2 times, 3 times, 5 times, or at least 10 times, such as at least 15 times.

The method can comprise a further step of identifying the templated molecule having the predetermined activity, and said identification can be conducted e.g. by analysing the template and/or complementary template physically or by other means associated with the molecule.

The conditions enriching the first composition can comprise the further providing a binding partner to said templated molecule having the predetermined activity, wherein said binding partner is directly or indirectly immobilised on a support.

The conditions enriching the composition can involve any state of the art method, including any one or more of electrophoretic separation, gelfiltration, immunoprecipitation, isoelectric focusing, centrifugation, and immobilization. The conditions enriching the composition can also comprise the further step of providing cells capable of internalising the templated molecule, or performing any interaction with the templated molecule having the predetermined activity.

The predetermined activity of the templated molecule is preferably an enzymatic activity or a catalytic activity.

In another aspect there is provided a method for amplifying the complementing template or the template that templated the synthesis of the templated molecule having, or potentially having a predetermined activity, said method comprising the step of contacting the template with amplification means, and amplifying the template. The method for amplifying the complementing template or the template that templated the synthesis of the templated molecule having, or potentially having, a predetermined activity, preferably comprises the steps of i) contacting the template with amplification means, and amplifying the template, and ii) obtaining the templated molecule in an at least two-fold increased amount.

In another aspect there is provided a method for altering the sequence of a templated molecule, including generating a templated molecule comprising a novel or altered sequence of functional groups, wherein said method preferably comprises the steps of i) providing a first complementing template or a first template capable of templating the first templated molecule, or a plurality of such first complementing templates or first templates capable of templating a plurality of first templated molecules, ii) mutating or modifying the sequence of the first complementing template or the first template, or the plurality of first complementing templates or first templates, and generating a second template or a second complementing template, or a plurality of second templates or second complementing templates, wherein said second template(s) or complementing template(s) is capable of templating the synthesis of a second templated molecule, or a plurality of second templated molecules, wherein said second templated molecule(s) comprises a sequence of covalently linked, functional groups that is not identical to the sequence of functional groups of the first templated molecule(s), and optionally iii) templating by means of said second template(s) or complementing template(s) a second templated molecule, or a plurality of such second templated molecules.

In yet another aspect there is provided a method for altering the sequence of a templated molecule, including generating a templated molecule comprising a novel or altered sequence of functional groups, wherein said method preferably comprises the steps of i) providing a plurality of first complementing templates or first templates capable of templating a plurality of first templated molecules, ii) recombining the sequences of the plurality of first complementing templates or first templates, and generating a second template or a second complementing template, or a plurality of second templates or second complementing templates, wherein said second template(s) or complementing template(s) is capable of templating the synthesis of a second templated molecule, or a plurality of second templated molecules, wherein said second templated molecule(s) comprises a sequence of covalently linked, functional groups that is not identical to the sequence of functional groups of the first templated molecule(s), and optionally iii) templating by means of said second template(s) or complementing template(s) a second templated molecule, or a plurality of such second templated molecules.

The methods can preferably comprise the further step of amplifying the complementing template or the template that templated the synthesis of the templated molecule, wherein said amplification step taking place prior to, simultaneously with, or after the step of mutagenesis or recombination.

When mutagenesis is used, it can be used as either site-directed mutagenesis, cassette mutagenesis, chemical mutagenesis, unique site-elimination (USE), error-prone PCR, error-prone DNA shuffling. Mutagenesis preferably involves DNA shuffling and/or any form of recombination including homologous recombination either in vivo or in vitro.

Variants and Functional Equivalents of Templated Molecules

The present invention is also directed to any variant and functional equivalent of a templated molecule. The variants and functional equivalents may be obtained by any state-of-the-art-method for modifying templated molecules in the form of polymers, including peptides.

In the context of the templated molecules of the present invention, molecules are said to be homologous if they contain similar backbone structures and/or similar functional groups. Functional groups, or molecular entities of functional groups, are divided into three homology groups: The charged functional groups, the hydrophobic groups, and the hydrophilic groups. When a functional group includes two or three molecular entities belonging to different homology groups, the functional group is said to belong to the two or three different homology groups.

Homology is measured in percent (%). As an example, the sequences AABBCACAAA and BBAACACBBB (where A, B and C denotes a functional group belonging to homology group A, B, and C, respectively) are 30 percent homologous.

EXAMPLES

Example 1 to 7

Preparation of the Mononucleotide Building Block (I)

Building block I may be prepared according to the general scheme shown below

113 114
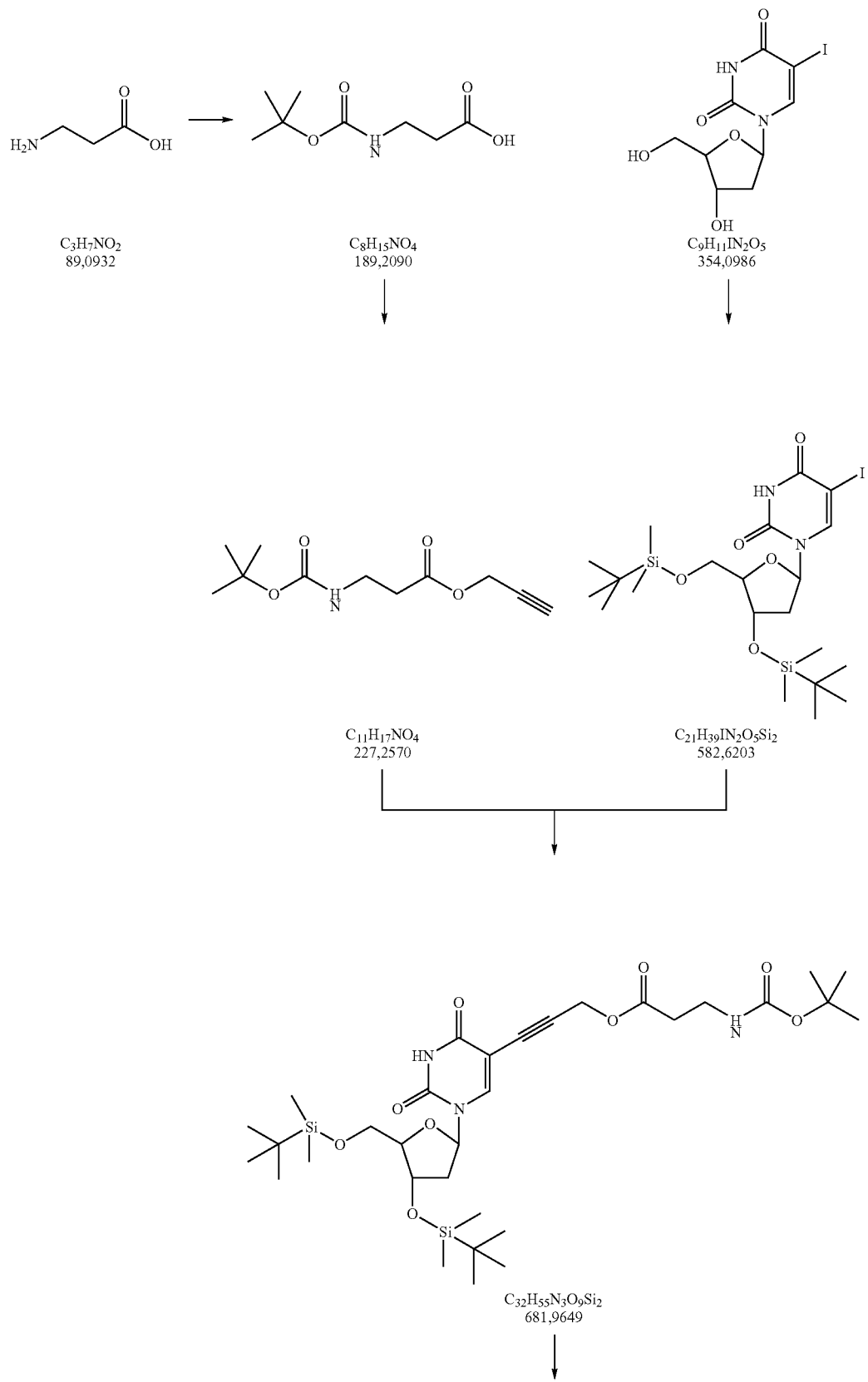

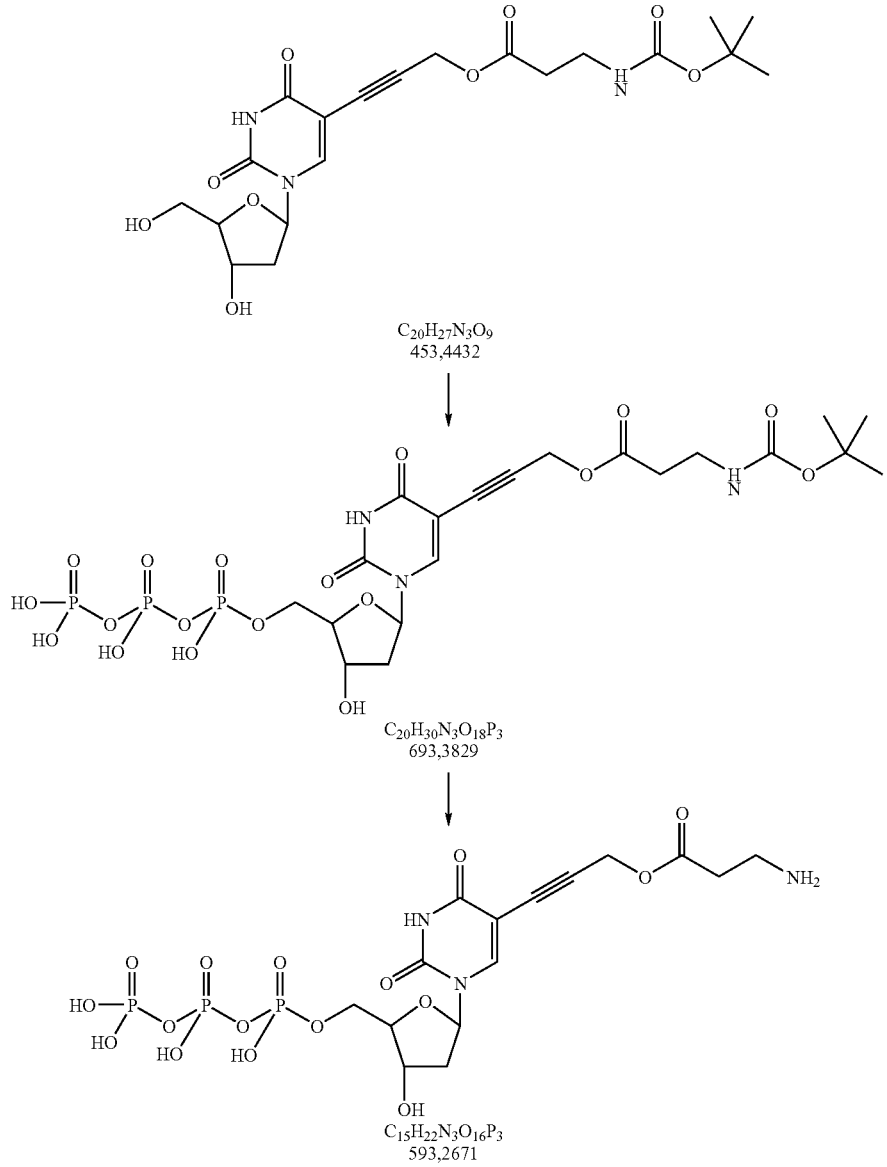

Example 1

Preparation of 3-tert-Butoxycarbonylamino-propionic Acid (N-Boc-β-alanine) (1a)

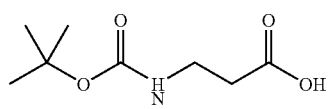

To a solution of β-alanine (2.25 g, 25 mmol) in aq. NaHCO₃ (25 mL) were added di-tert-butyl dicarbonate (4.36 g, 20 mmol) and acetonitrile (25 mL). The reaction mixture was stirred at room temperature for 18 h.

EtOAc (100 mL) was added and pH was adjusted to 4-5 by addition of NaH$_2$PO$_4$. The product was extracted into EtOAc (3×50 mL), dried (Na$_2$SO$_4$), and evaporated to dryness under vacuum to afford 3.71 g (98%)

$^1$H NMR (CDCl$_3$) δ 11 (1H, br s, COOH), 5.07 (1H, br s, NH), 3.40 (2H, m), 2.58 (2H, m), 1.44 (9H, s, $^t$Bu).

Example 2

Preparation of N-Boc-β-alanine Propargyl Ester (1b)

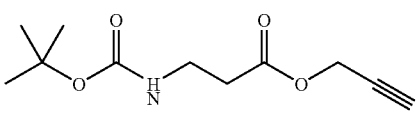

N-Boc-β-alanine (1.91 g, 10.1 mmol) and propargyl alcohol (0.675 g, 12 mmol) were dissolved in EtOAc (25 mL). Dicyclohexyl-carbodiimide (DCC, 2.06 g, 10 mmol) was added to the solution and after 16 h of stirring at room temperature, the reaction mixture was filtered and evaporated to dryness under vacuum. Crude product yield

Example 3

Preparation of 5-Iodo-2'-deoxyuridine 3',5'-Di-tert-butyldimethylsilyl Ether (1c).

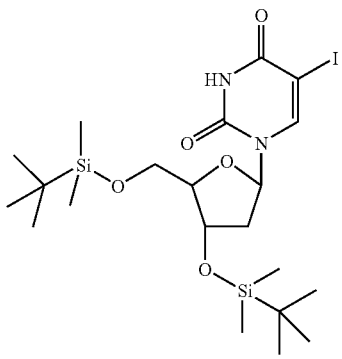

5-Iodo-2'-deoxyuridine (Aldrich, 2.39 g, 6.7 mmol) and imidazole (2.025 g, 29.7 mmol) was dissolved in anhydrous DMF (10 mL). A solution of tert-butyldimethylsilyl chloride (2.24 g, 14.9 mmol) in anhydrous DMF (5 mL) was added and the resulting mixture was stirred for 16 h at room temperature.

The reaction mixture was poured into EtOAc (400 mL), washed with $NH_4Cl$ (50% sat. aq, 80 mL) followed by water (80 mL). After drying with $Na_2SO_4$, EtOAc was removed under reduced pressure to leave a colourless oil that solidified on standing. Recrystallization in n-hexane (14 mL) afforded 2.64 g, 80%.

$^1$H NMR ($CDCl_3$) δ 8.18 (1H, br s, NH); 8.10 (1H, s); 6.23 (1H, dd); 4.40 (1H, dt); 4.05 (1H, dd); 3.92 (1H, dd); 3.78 (1H, dd); 2.32 (1H, ddd); 2.05 (1H, ddd); 0.95 (9H, s, $^t$Bu); 0.90 (9H, s, $^t$Bu); 0.15 (3H, s, $CH_3$); 0.13 (3H, s, $CH_3$); 0.08 (3H, s, $CH_3$); 0.07 (3H, s, $CH_3$).

Example 4

Preparation of Compound (1d)

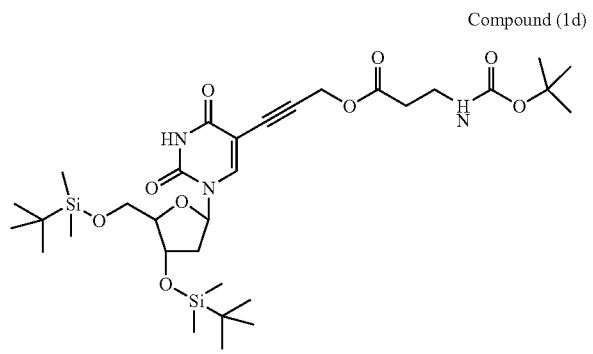

Compound (1d)

A solution of iodo silyl ether (1 c) (1.62 g, 2.7 mmol), N-Boc-β-alanine(1 a) (2.03 g, 8.9 mmol) and triethylamine (0.585 g, 5.8 mmol) in 10 mL dry DMF were stirred at room temperature. $N_2$ was passed through the solution for 20 min.

Tetrakis(triphenylphosphine)palladium(0) (269 mg, 0.2 mmol) and copper(I) iodide (90 mg, 0.4 mmol) were added and the reaction mixture was stirred at room temperature for 32 h.

EtOAc (100 mL) was poured into the reaction mixture, followed by washing (aq $NaHCO_3$ (50 mL); brine (50 mL)), drying ($Na_2SO_4$), and removal of solvent by vacuum evaporation.

The crude product (2.4 g) was purified by silica column chromatography eluting with EtOAc:Heptane gradient (1:2)-(5:3) (v/v). Product yield 1.15 g, 60%.

$^1$H NMR ($CDCl_3$) δ 8.45 (1H, s), 8.05 (1H, s, 6-H), 7.35 (1H, bs, NH), 6.25 (1H, dd, 1'-H), 4.82 (2H, s, $CH_2O$), 4.39 (1H, m, 3'-H), 3.97 (1H, m, 4'-H), 3.80 (2H, dd, 5',5"-H), 3.40 (2H, m, $CH_2N$), 2.58 (2H, t, $CH_2$), 2.2 (1H, m, 2'-H), 2.0 (1H, m, 2"-H), 1.45 (9H, s, $^t$Bu), 0.93 (9H, s, $^t$Bu), 0.89 (9H, s, $^t$Bu), 0.15 (3H, s, $CH_3$), 0.13 (3H, s, $CH_3$), 0.08 (3H, s, $CH_3$), 0.07 (3H, s, $CH_3$).

Example 5

Preparation of Compound (1e)

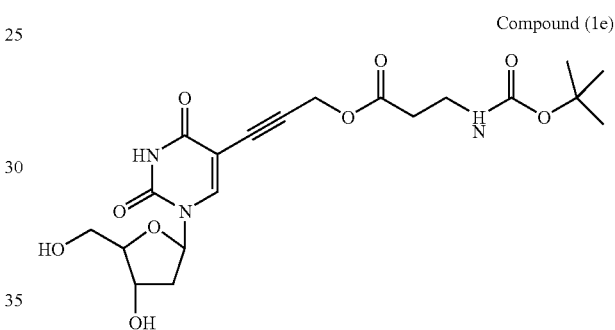

Compound (1e)

A solution of N-Boc-β-alanine silyl ether (1d) (100 mg, 0.15 mmol), glacial acetic acid (75 mg, 1.25 mmol) and tetrabutylammonium fluoride trihydrate (TBAF) (189 mg, 0.6 mmol) in 2 mL dry THF was stirred at room temperature for 3 d. The reaction mixture was evaporated and purified by silica column chromatography eluting with dichloromethane (DCM):methanol(MeOH) gradient (95:5)-(88:12) (v/v). Product yield 26 mg, 38%.

$^1$H NMR ($CD_3OD$) δ 8.35 (1H, s, 6-H), 6.15 (1H, t, 1'-H), 4.80 (2H, s, $CH_2O$), 4.32 (1H, dt, 3'-H), 3.86 (1H, q, 4'-H), 3.70 (2H, dd, 5',5"-H), 3.24 (2H, m, $CH_2N$), 2.47 (2H, t, $CH_2$), 2.28-2.10 (1H, m, 2',2"-H), 1.44 (9H, s, $^t$Bu).

Example 6

Preparation of Compound (1f)

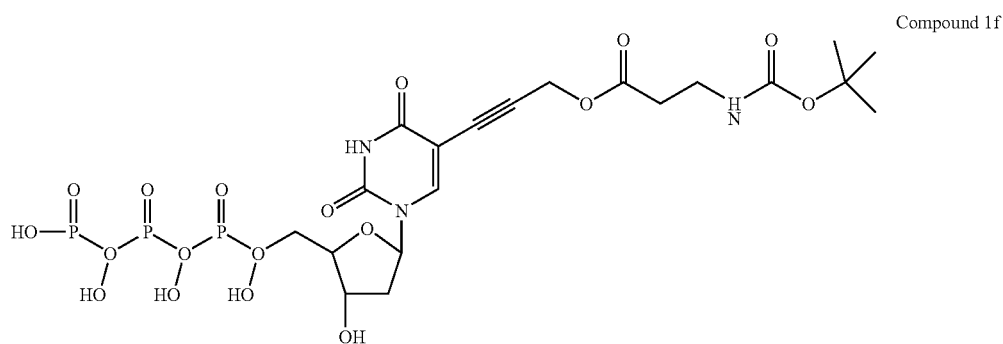

Compound 1f

N-Boc-β-alanine nucleoside (1e) (26 mg, 57 μmol) was dissolved in 200 μL dry trimethylphosphate. After cooling to 0° C., a solution of phosphorus oxychloride (POCl$_3$) in dry trimethylphosphate was added (100 μL stock solution (104 mg/mL), 68 μmol). The reaction mixture was stirred at 0° C. for 2 h.

Subsequently a solution of tributylammonium pyrophosphate (Sigma P-8533) (67.8 mg, 143 μmol in 300 μL dry DMF) and tributylamine (26.9 mg, 145 μmol in 150 μL dry DMF) was added at 0° C. The reaction was stirred at room temperature for 3 min. and then stopped by addition of 1 mL 1.0 M triethylammonium hydrogencarbonate.

Example 7

Preparation of Compound I

COMPOUND I

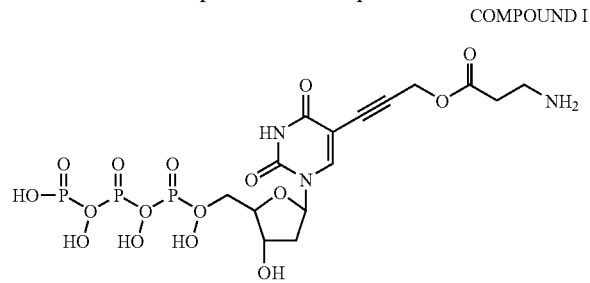

Removal of N-Boc Protection Group.

Following phosphorylation, 50 μl of the phosphorylation reaction mixture is adjusted to pH=1 using HCl and incubated at room temperature for 30 minutes. The mixture is adjusted to pH 5.5 using equimolar NaOH and Na-acetate (pH 5.5) before purification on TLC.

Purification of Nucleotide Derivatives Using Thin-layer Chromatography (TLC)

From the crude mixture, 20 samples of 2 μl were spotted on kieselgel 60 F$_{254}$ TLC (Merck). Organic solvents and non-phosphorylated nucleosides were separated from the nucleotides derivatives using 100% methanol as running solution. Subsequently, the TLC plate is air-dried and the nucleotide-derivative identified by UV-shadowing. Kiesel containing the nucleotide-derivative was isolated and extracted twice using 10 mM Na-acetate (pH=5.5) as solvent. Kieselgel was removed by centrifugation and the supernatant was dried in vacuo. The nucleotide derivative was resuspended in 50-100 μl H$_2$O to a final concentration of 1-3 mM. The concentration of each nucleotide derivative was evaluated by UV-absorption prior to use in polymerase extension reactions.

Examples 8 to 13

Preparation of the Mononucleotide Building Block (II)

Building block II may be prepared according to the general scheme shown below:

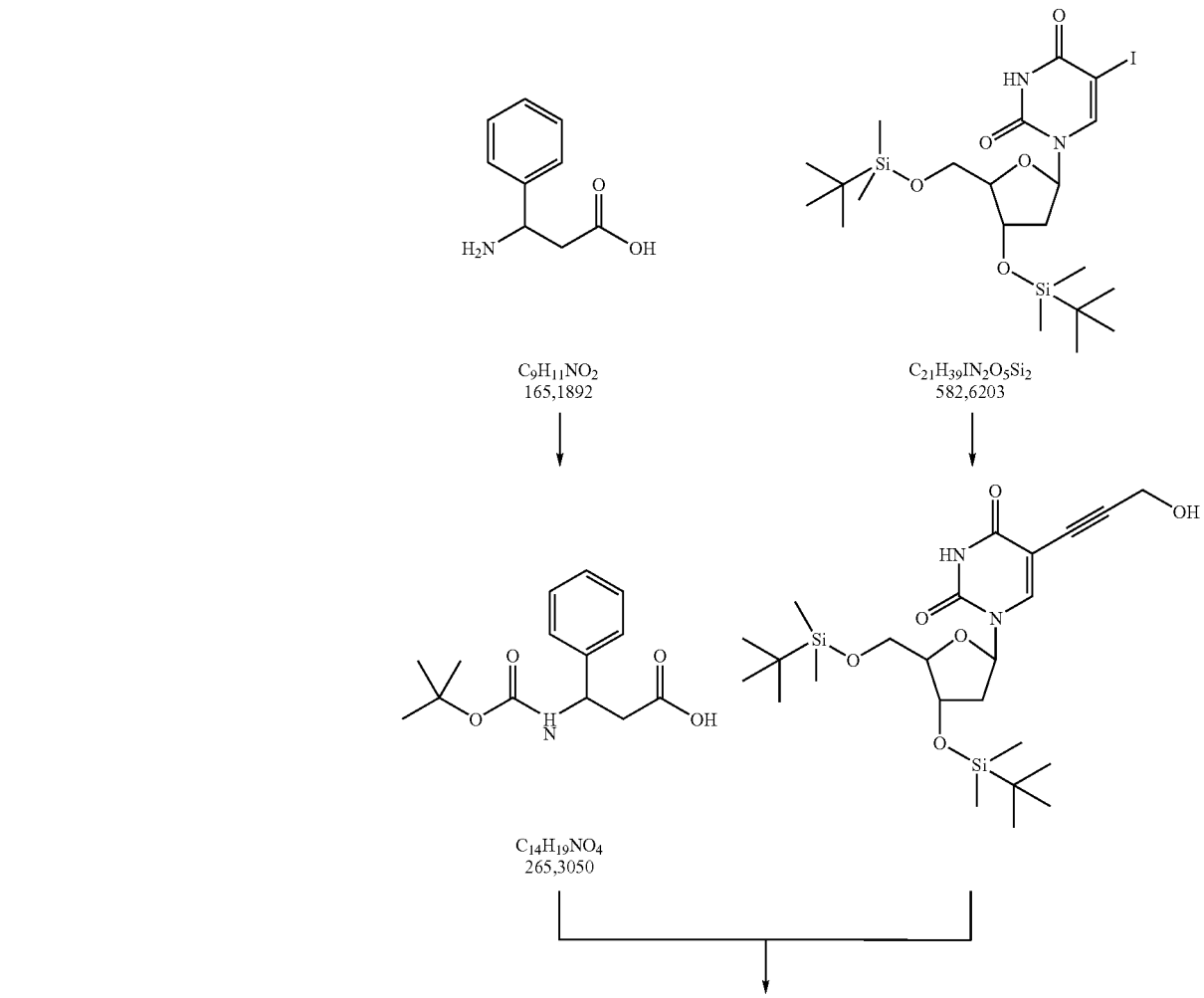

-continued
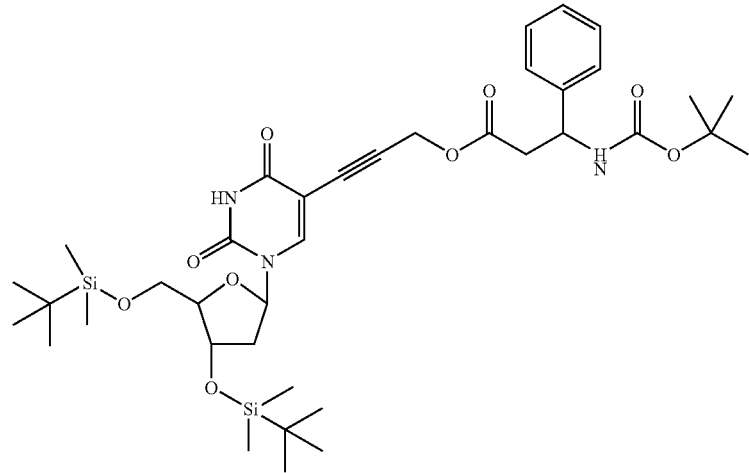
C<sub>38</sub>H<sub>59</sub>N<sub>3</sub>O<sub>9</sub>Si<sub>2</sub>
758,0609
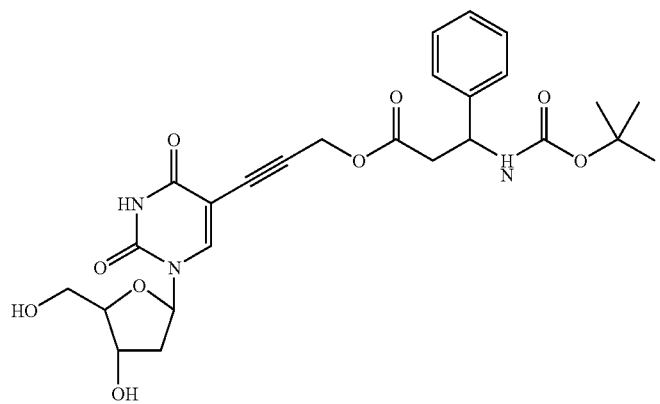
C<sub>26</sub>H<sub>31</sub>N<sub>3</sub>O<sub>9</sub>
529,5392
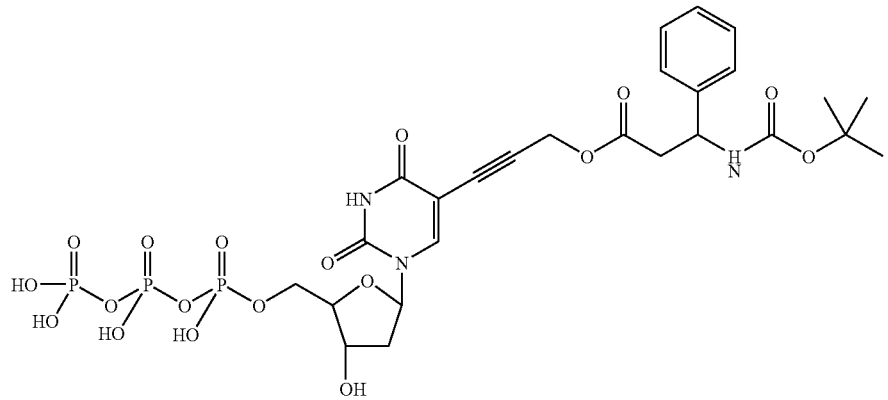
C<sub>26</sub>H<sub>34</sub>N<sub>3</sub>O<sub>18</sub>P<sub>3</sub>
769,4789

-continued

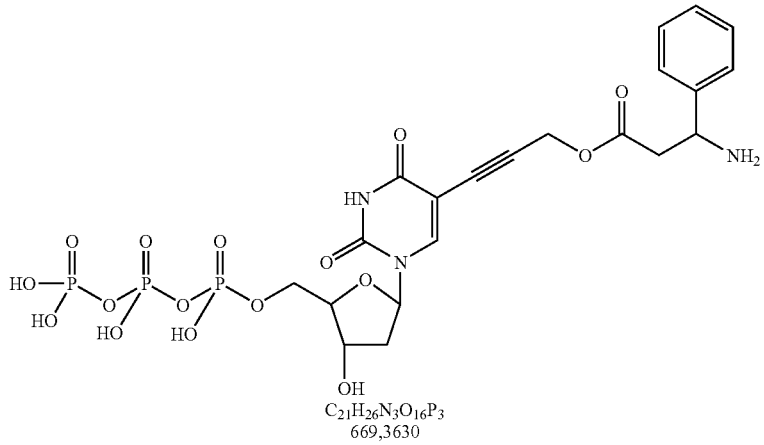

$C_{21}H_{26}N_3O_{16}P_3$
669.3630

Example 8

Preparation of N-Boc-3-phenyl-β-alanine (2a)

COMPOUND 2a

To a solution of 3-amino-3-phenylpropionic acid (3.30 g, 20 mmol) in NaHCO$_3$ (50% sat. aq, 25 mL) were added di-tert-butyl dicarbonate (4.36 g, 20 mmol) and acetonitrile (30 mL). The reaction mixture was stirred at room temperature for 18 h. Di-tert-butyl dicarbonate (4.36 g, 20 mmol) was added and the reaction mixture was stirred at room temperature for 18 h.

EtOAc (100 mL) was added and pH was adjusted to 4-5 by addition of NaH$_2$PO$_4$. The product was extracted into EtOAc (3×100 mL), dried (Na$_2$SO$_4$), and evaporated to dryness under vacuum to afford crude product 5.6 g (105%)

Example 9

Preparation of 5-(3-Hydroxypropyn-1-yl)-2'-deoxyuridine 3',5'-Di-tert-butyldimethylsilyl Ether (2b)

COMPOUND 2b

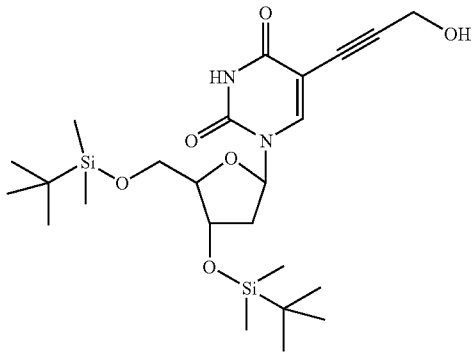

A solution of iodo silyl ether (3) (1.30 g, 2.2 mmol), propargyl alcohol (0.386 g, 6.9 mmol) and triethylamine (0.438 g, 4.3 mmol) in 7 mL dry DMF was deaeraed with N$_2$. Tetrakis(triphenylphosphine)palladium(0) (228 mg, 0.2 mmol) and copper(I) iodide (120 mg, 0.4 mmol) were added and the reaction mixture was stirred at room temperature for 32 h.

EtOAc (100 mL) was poured into the reaction mixture, followed by washing (aq NaHCO$_3$ (50 mL); brine (50 mL)), drying (Na$_2$SO$_4$), and removal of solvent by vacuum evaporation.

The crude product (1.73 g) was purified by silica column chromatography eluting with EtOAc:Heptane gradient (2:3)-(3:2) (v/v). Product yield 0.713 g, 63%.

$^1$H NMR (CDCl$_3$) δ 8.47 (1H, s), 8.05 (1H, s, 6-H), 6.29 (1H, dd, 1'-H), 4.42 (2H, s, CH$_2$), 4.39 (1H, m, 3'-H), 3.98 (1H, m, 4'-H), 3.83 (2H, dd, 5',5"-H), 2.32 (1H, m, 2'-H), 2.02 (1H, m, 2"-H), 0.93 (9H, s, $^t$Bu), 0.89 (9H, s, $^t$Bu), 0.15 (3H, s, CH$_3$), 0.13 (3H, s, CH$_3$), 0.08 (3H, s, CH$_3$), 0.07 (3H, s, CH$_3$).

Example 10

Preparation of Compound (2c)

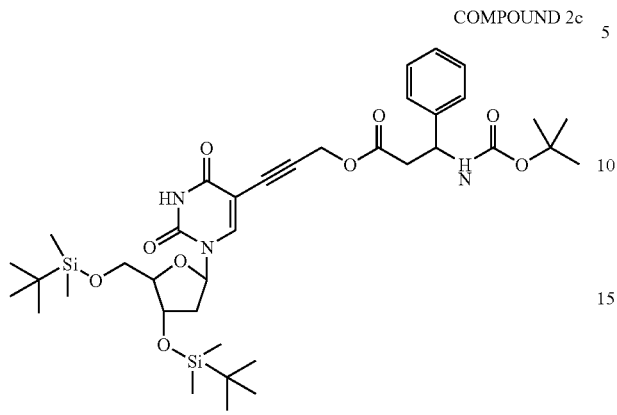

COMPOUND 2c

N-Boc-3-phenyl-β-alanine (8)(265 mg, 1.0 mmol) and compound (2b) (255 mg, 0.5 mmol) were dissolved in THF (15 mL). Diisopropyl-carbodiimide (DIC, 126 mg, 1 mmol) and 4-dimethylaminopyridin (DMAP, 10 mg) were added to the solution, and after 16 h of stirring at room temperature the reaction mixture was poured into EtOAc (100 mL), washed with NaHCO$_3$ (50% sat. aq, 50 mL), dried (Na$_2$SO$_4$), filtered and evaporated under vacuum.

The crude product was purified by silica column chromatography eluting with EtOAc:Heptane gradient (1:2)-(2:3) (v/v). Product yield 335 mg, 88%.

$^1$H NMR (CDCl$_3$) δ 8.49 (1H, s), 8.04 (1H, s, 6-H), 7.29 (5H, m, Ph), 6.27 (1H, dd, 1'-H), 5.5 (1H, bd), 5.09 (1H, m), 4.80 (2H, s, CH$_2$), 4.39 (1H, m, 3'-H), 3.98 (1H, m, 4'-H), 3.82 (2H, dd, 5',5"-H), 2.87 (2H, d), 2.29 (1H, m, 2'-H), 2.01 (1H, m, 2"-H), 1.41 (9H, s, $^t$Bu), 0.91 (9H, s, $^t$Bu), 0.89 (9H, s, $^t$Bu), 0.15 (3H, s, CH$_3$), 0.13 (3H, s, CH$_3$), 0.08 (3H, s, CH$_3$), 0.07 (3H, s, CH$_3$).

Example 11

Preparation of Compound 2d

COMPOUND 2d

A solution of compound (2c) (334 mg, 440 μmol), glacial acetic acid (190 mg, 3.15 mmol) and tetrabutylammonium fluoride trihydrate (TBAF) (500 mg, 1.58 mmol) in 6 mL dry THF was stirred at room temperature for 18 h.

The reaction mixture was evaporated and purified by silica column chromatography eluting with (DCM):(MeOH) gradient (95:5)-(9:1) (v/v). Product yield 122 mg, 52%.

$^1$H NMR (CDCl$_3$) δ 10.1 (1H, s), 8.24 (1H, s, 6-H), 7.3 (5H, m, Ph), 6.37 (1H, dd, 1'-H), 5.6 (1H, bs), 5.09 (1H, m), 4.79 (2H, s, CH$_2$), 4.52 (1H, m, 3'-H), 4.0 (1H, m, 4'-H), 3.85 (2H, dd, 5',5"-H), 2.87 (2H, d), 2.4 (1H, m, 2'-H), 2.25 (1H, m, 2"-H), 1.4 (9H, s, $^t$Bu).

Example 12

Preparation of Compound (2e)

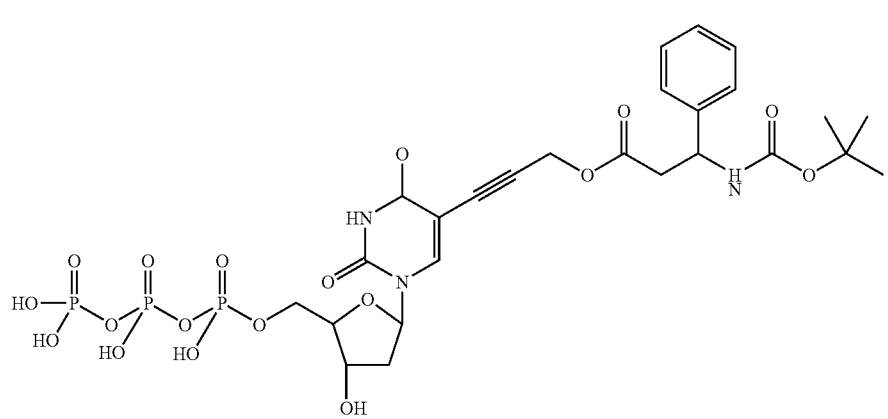

COMPOUND 2e

Compound (2d) (122 mg, 230 μmol) was dissolved in 400 μL dry trimethylphosphate. After cooling to 0° C., a solution of phosphorus oxychloride (POCl$_3$) in dry trimethylphosphate was added (400 μL stock solution (105 mg/mL), 276 μmol). The reaction mixture was stirred at 0° C. for 2 h.

Subsequently a solution of tributylammonium pyrophosphate (273 mg, 576 μmol in 1.2 mL dry DMF) and tributylamine (109 mg, 587 mmol in 600 μL dry DMF) was added at 0° C. The reaction was stirred at room temperature for 10 min. and then stopped by addition of 1.0 M triethylammonium hydrogencarbonate (1 mL).

Example 13

Preparation of Compound II

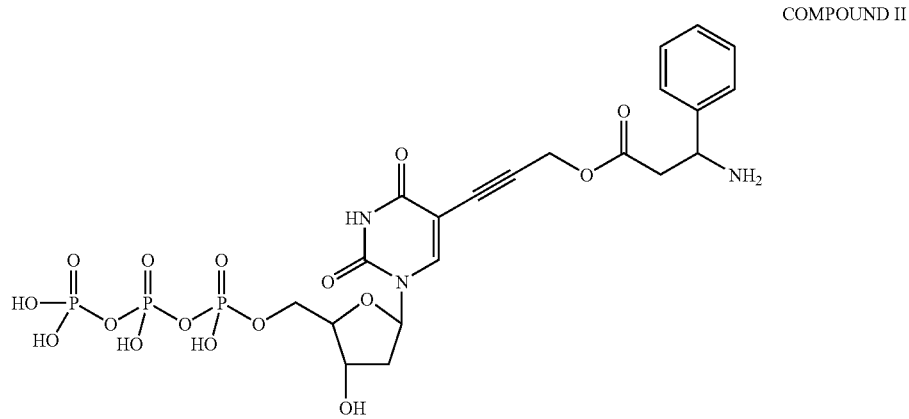

COMPOUND II

Removal of N-Boc Protection Group.

Following phosphorylation, 50 μl of the phosphorylation reaction mixture is adjusted to pH=1 using HCl and incubated at room temperature for 30 minutes. The mixture is adjusted to pH 5.5 using equimolar NaOH and Na-acetate (pH 5.5) before purification on TLC.

Purification of Nucleotide Derivatives Using Thin-layer Chromatography (TLC)

From the crude mixture, 20 samples of 2 μl were spotted on kieselgel 60 $F_{254}$ TLC (Merck). Organic solvents and non-phosphorylated nucleosides were separated from the nucleotides derivatives using 100% methanol as running solution. Subsequently, the TLC plate is air-dried and the nucleotide-derivative identified by UV-shadowing. Kiesel containing the nucleotide-derivative was isolated and extracted twice using 10 mM Na-acetate (pH=5.5) as solvent. Kieselgel was removed by centrifugation and the supernatant was dried in vacuo. The nucleotide derivative was resuspended in 50-100 μl $H_2O$ to a final concentration of 1-3 mM. The concentration of each nucleotide derivative was evaluated by UV-absorption prior to use in polymerase extension reactions.

Examples 14 to 18

Preparation of the Mononucleotide Building Block (III)

Building block III may be prepared according to the general scheme shown below:

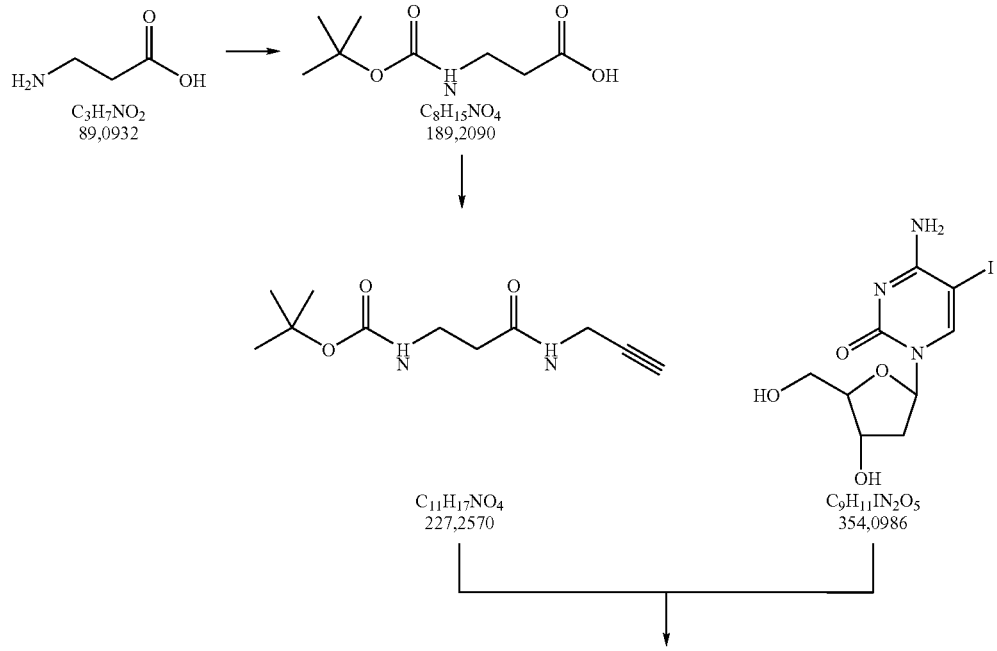

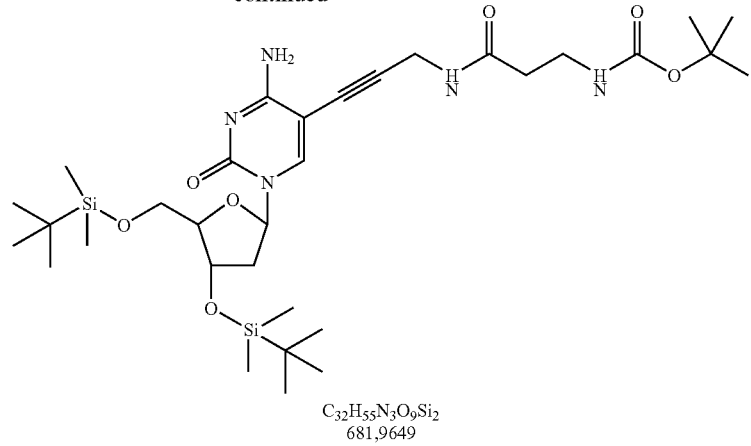
C₃₂H₅₅N₃O₉Si₂
681,9649
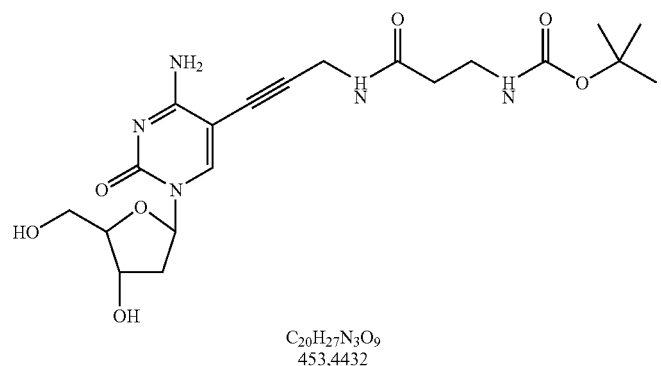
C₂₀H₂₇N₃O₉
453,4432
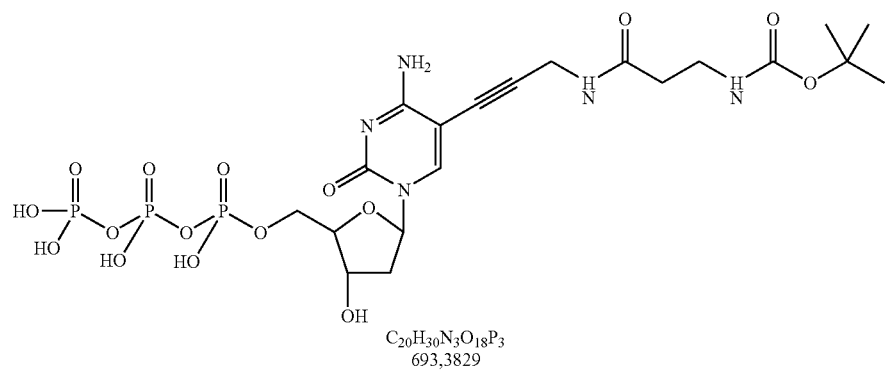
C₂₀H₃₀N₃O₁₈P₃
693,3829

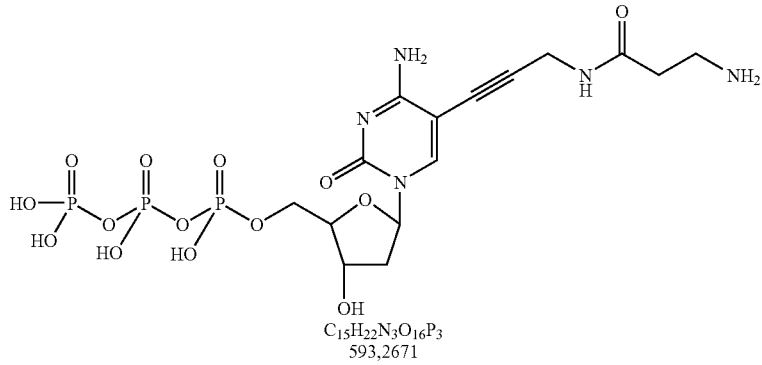

C$_{15}$H$_{22}$N$_3$O$_{16}$P$_3$
593,2671

Example 14

Preparation of N-Boc-β-alanine Propargyl Amide (3a)

COMPOUND 2a

N-Boc-β-alanine (1a) (1.05 g, 5.5 mmol) and propargyl amine (0.90 g, 16.5 mmol) were dissolved in THF (10 mL). Diisopropyl-carbodiimide (DIC, 695 g, 5.5 mmol) was added and the reaction mixture was stirred for 16 h at room temperature. Water was added (20 mL) and the product was extracted into EtOAc (3×30 mL). The combined EtOAc was dried (Na$_2$SO$_4$) and evaporated. The crude product was purified by silica column chromatography eluting with EtOAc: Heptane gradient (2:3)-(3:2.5) (v/v). Product yield 0.925 g, 74%.

$^1$H NMR (CDCl$_3$) δ 6.69 (1H, bs, NH), 5.32 (1H, bs, NH), 4.04 (2H, bs), 3.41 (2H, dd), 2.45 (2H, t), 2.24 (1H, s), 1.44 (9H, s, $^t$Bu).

Example 15

Preparation of Compound (3b)

COMPOUND 3b

A solution of 5-iodo-2'-deoxycytidine (176 mg, 0.5 mmol), N-Boc-β-alanine propargyl amide (14) and triethylamine (100 mg, 1.0 mmol) in dry DMF (5 mL) were stirred at room temperature. N$_2$ was passed through the solution for 20 min.

Tetrakis(triphenylphosphine)palladium(0) (66.5 mg, 0.057 mmol) and copper(I) iodide (20.7 mg, 0.108 mmol) were added and the reaction mixture was stirred at room temperature for 5 d Imidazole (112 mg, 1.6 mmol) was added. A solution of tert-butyldimethylsilyl chloride (234 mg, 1.5 mmol) in anhydrous DMF (1 mL) was added and the resulting mixture was stirred for 16 h at room temperature.

The reaction mixture was evaporated and EtOAc (25 mL) was added. The resulting mixture was filtrated and the solvent removed by vacuum evaporation.

The crude product was purified by silica column chromatography eluting with DCM:MeOH (92.5-7.5) (v/v). Product yield 84 mg, 25%.

$^1$H NMR (CDCl$_3$) δ 8.13 (H, s), 6.21 (1H, dd, 1'-H), 4.66 (1H, m), 4.16 (2H, s, CH$_2$), 4.04-3.85 (4H, m), 3.35-3.31 (2H, m), 2.43-2.36 (2H, m), 2.12-1.99 (1H, m), 1.44 (9H, s, $^t$Bu), 0.95 (9H, s, $^t$Bu), 0.92 (9H, s, $^t$Bu), 0.17 (3H, s, CH$_3$), 0.15 (3H, s, CH$_3$), 0.13 (3H, s, CH$_3$), 0.12 (3H, s, CH$_3$).

Example 16

Preparation of Compound (3c)

COMPOUND 3c

A solution of compound (3b) (84 mg, 0.12 mmol) and tetrabutylammonium fluoride trihydrate (TBAF) (155 mg, 0.45 mmol) in 2 mL dry THF was stirred at room temperature for 4 days.

The reaction mixture was evaporated and purified by silica column chromatography eluting with DCM:MeOH gradient (9:1)-(8:2) (v/v). Product yield 27 mg, 48%.

$^1$H NMR (CDCl$_3$) δ 8.32 (1H, s), 6.20 (1H, dd, 1'-H), 4.35 (1H, dt), 4.15 (2H, s, CH$_2$), 3.95 (1H, q), 3.83 (1H, dd), 3.72 (1H, dd), 3.36-3.30 (3H, m), 2.42-2.36 (3H, m), 2.13 (1H, dt), 1.40 (9H, s, $^t$Bu).

Example 17

Preparation of Compound (3d)

Removal of N-Boc Protection Group.

Following phosphorylation, 50 μl of the phosphorylation reaction mixture is adjusted to pH=1 using HCl and incubated at room temperature for 30 minutes. The mixture is adjusted to pH 5.5 using equimolar NaOH and Na-acetate (pH 5.5) before purification on TLC.

Purification of Nucleotide Derivatives Using Thin-layer Chromatography (TLC)

From the crude mixture, 20 samples of 2 μl were spotted on kieselgel 60 F$_{254}$ TLC (Merck). Organic solvents and non-phosphorylated nucleosides were separated from the nucle-

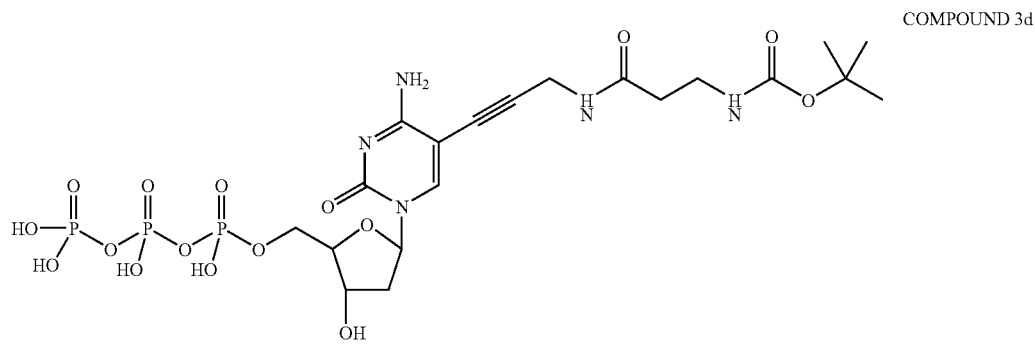

COMPOUND 3d

Compound (3c) (27 mg, 60 μmol) was dissolved in 100 μL dry trimethylphosphate. After cooling to 0° C., a solution of phosphorus oxychloride (POCl$_3$) in dry trimethylphosphate was added (100 μL stock solution (110 mg/mL), 72 μmol). The reaction mixture was stirred at 0° C. for 2 h.

Subsequently a solution of tributylammonium pyrophosphate (71 mg, 150 μmol in 300 μL dry DMF) and tributylamine (28.3 mg, 153 μmol in 150 μL dry DMF) was added at 0° C. The reaction was stirred at room temperature for 3 min. and then stopped by addition of 1.0 M triethylammonium hydrogencarbonate (1 mL).

Example 18

Preparation of Compound III otides derivatives using 100% methanol as running solution. Subsequently, the TLC plate is air-dried and the nucleotide-derivative identified by UV-shadowing. Kiesel containing the nucleotide-derivative was isolated and extracted twice using 10 mM Na-acetate (pH=5.5) as solvent. Kieselgel was removed by centrifugation and the supernatant was dried in vacuo. The nucleotide derivative was resuspended in 50-100 μl H$_2$O to a final concentration of 1-3 mM. The concentration of each nucleotide derivative was evaluated by UV-absorption prior to use in polymerase extension reactions.

Examples 19 to 22

Preparation of the Mononucleotide Building Block (IV)

Building block IV may be prepared according to the general scheme shown below:

COMPOUND III

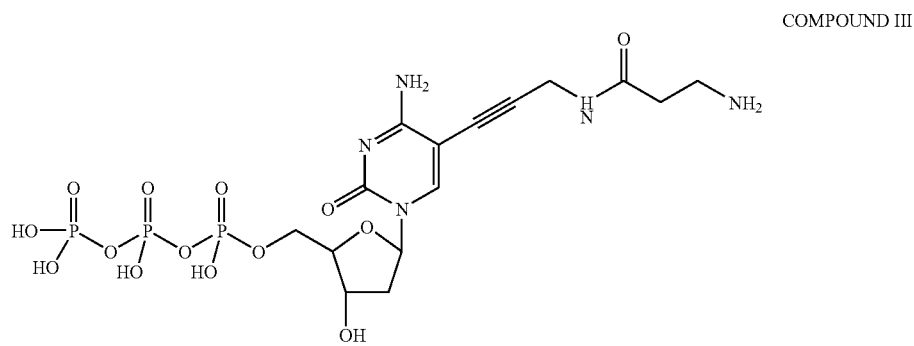

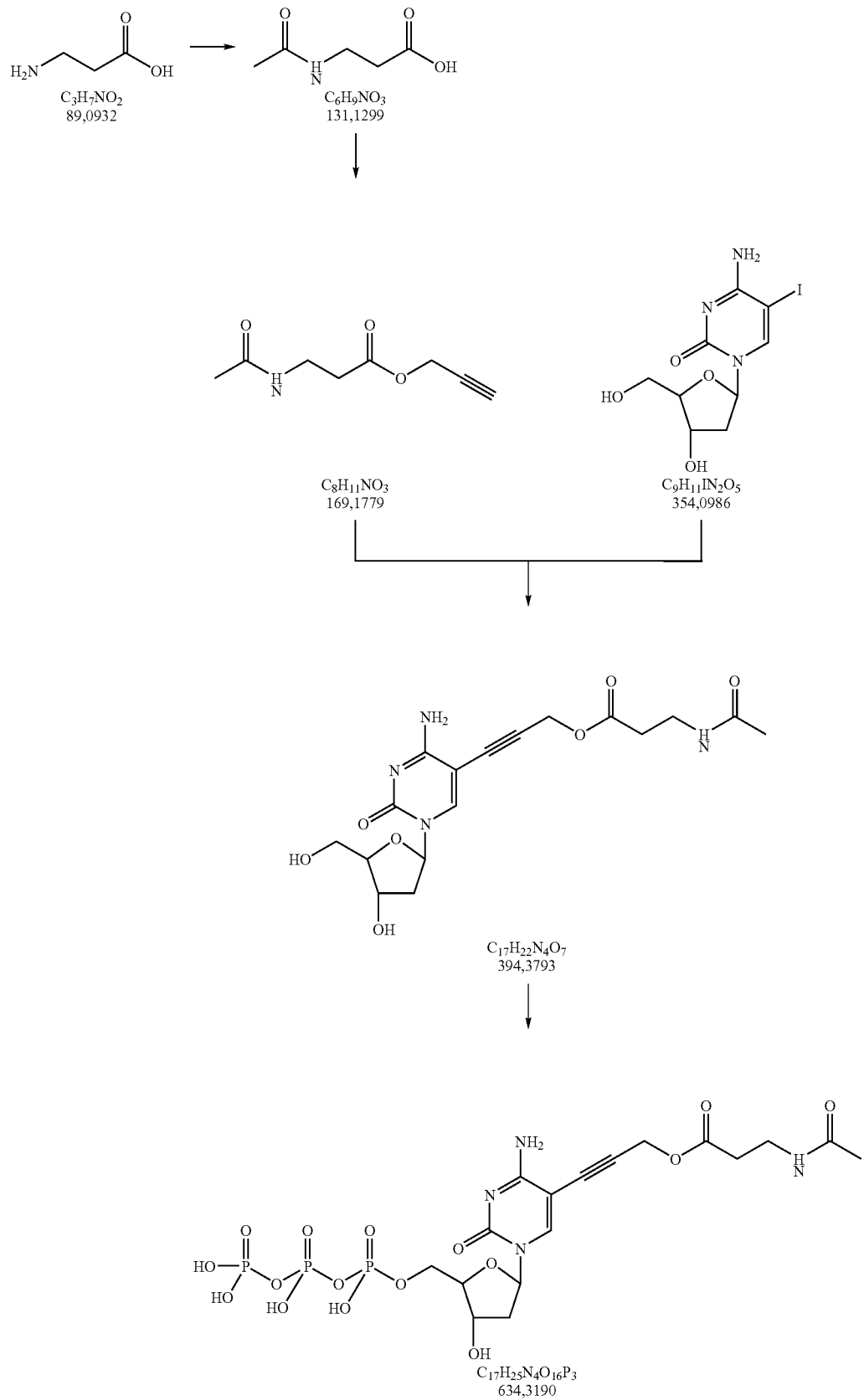

Example 19

Preparation of N-Acetyl-β-alanine (4a)

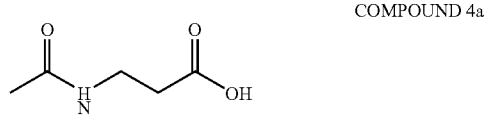

COMPOUND 4a

To a solution of β-alanine (2.25 g, 25 mmol) in aq. NaHCO₃ (15 mL) was added acetonitrile (15 mL) and acetic anhydride (2.55 g, 25 mmol). The reaction mixture was stirred at room temperature for 3 h. Acetic anhydride (2.55 g, 25 mmol) was added and after 2 h and pH was adjusted to 4-5 by addition of NaH$_2$PO$_4$.

The product was extracted into EtOAc (3×50 mL), dried (Na$_2$SO$_4$), and evaporated to dryness under vacuum to afford 1.96 g (60%)

Example 20

Preparation of N-Acetyl-β-alanine Propargyl Ester (4b)

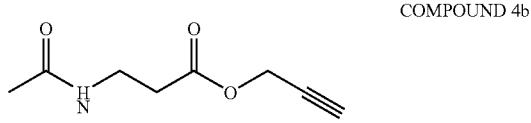

COMPOUND 4b

To a solution of N-Acetyl-β-alanine (4a) in THF (20 mL) was added propargyl alcohol (840 mg, 15 mmol), 1-(3-dimethylaminopropyl)-3-ethylcarbodiimide hydrochloride (EDC) (1.035 g, 5.39 mmol), triethylamine (540 mg, 5.4 mmol) and 4-dimethylaminopyridin (5 mg). The reaction mixture was stirred at room temperature for 2 d.

The reaction mixture was poured into EtOAc (100 mL), washed with NaH$_2$PO$_4$ (50% sat. aq, 2×50 mL) followed by NaHCO₃ (50% sat. aq, 50 mL). After drying (Na$_2$SO$_4$), EtOAc was removed under reduced pressure to leave a colourless oil that solidified on standing. Product yield 536 mg, 59%.

Example 21

Preparation of Compound (4c)

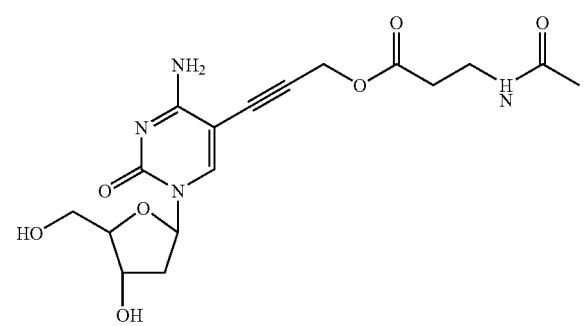

COMPOUND 4c

A solution of 5-iodo-2'-deoxycytidin (200 mg, 0.56 mmol), triethylamine (100 mg, 1 mmol) and compound (4b) (190 mg, 1.13 mmol) in anhydrous DMF (7 mL) was stirred at room temperature. N$_2$ was passed through the solution for 20 min.

Tetrakis(triphenylphosphine)palladium(0) (70 mg, 0.06 mmol) and copper(I) iodide (22 mg, 0.12 mmol) were added and the reaction mixture was stirred at room temperature for 4 d.

The reaction mixture was evaporated and purified by silica column chromatography eluting with DCM:MeOH gradient (9:1)-(8:2) (v/v). Product yield 141 mg, 63%.

$^1$H NMR (CD$_3$OD) δ 8.41 (1H, s), 6.20 (1H, dd, 1'-H), 4.97 (2H, s), 4.38 (1H, dt), 3.97 (1H, q), 3.85 (1H, dd), 3.75 (1H, dd), 3.46 (2H, t), 2.61 (2H, t), 2.39 (1H, m), 2.18 (1H, m).

Example 22

Preparation of Compound IV

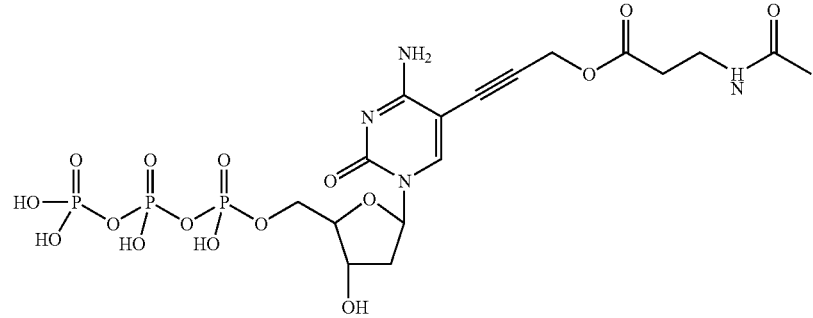

COMPOUND IV

Compound (4c) (140 mg, 355 µmol) was dissolved in 600 µL dry trimethylphosphate. After cooling to 0° C., a solution of phosphorus oxychloride ($POCl_3$) in dry trimethylphosphate was added (600 µL stock solution (108 mg/mL), 420 µmol). The reaction mixture was stirred at 0° C. for 2 h.

Subsequently a solution of tributylammonium pyrophosphate (422 mg, 890 µmol in 1.8 mL dry DMF) and tributylamine (168 mg, 900 µmol in 0.9 mL dry DMF) was added at 0° C. The reaction was stirred at room temperature for 3 min. and then stopped by addition of 1.0 M triethylammonium hydrogencarbonate (1 mL).

From the crude mixture, 20 samples of 2 µl were spotted on kieselgel 60 $F_{254}$ TLC (Merck). Organic solvents and non-phosphorylated nucleosides were separated from the nucleotides derivatives using 100% methanol as running solution. Subsequently, the TLC plate is air-dried and the nucleotide-derivative identified by UV-shadowing. Kiesel containing the nucleotide-derivative was isolated and extracted twice using 10 mM Na-acetate (pH=5.5) as solvent. Kieselgel was removed by centrifugation and the supernatant was dried in vacuo. The nucleotide derivative was resuspended in 50-100 µl $H_2O$ to a final concentration of 1-3 mM. The concentration of each nucleotide derivative was evaluated by UV-absorption prior to use in polymerase extension reactions.

Examples 23 to 27

Preparation of the Mononucleotide Building Block
(V)

Building block V may be prepared according to the general scheme shown below:

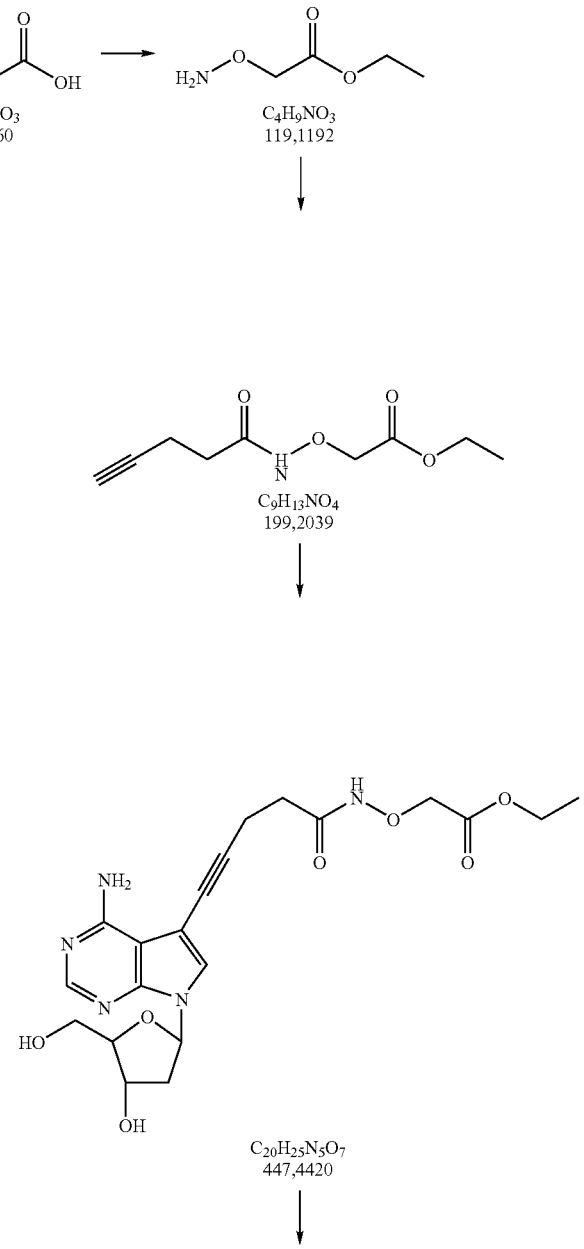

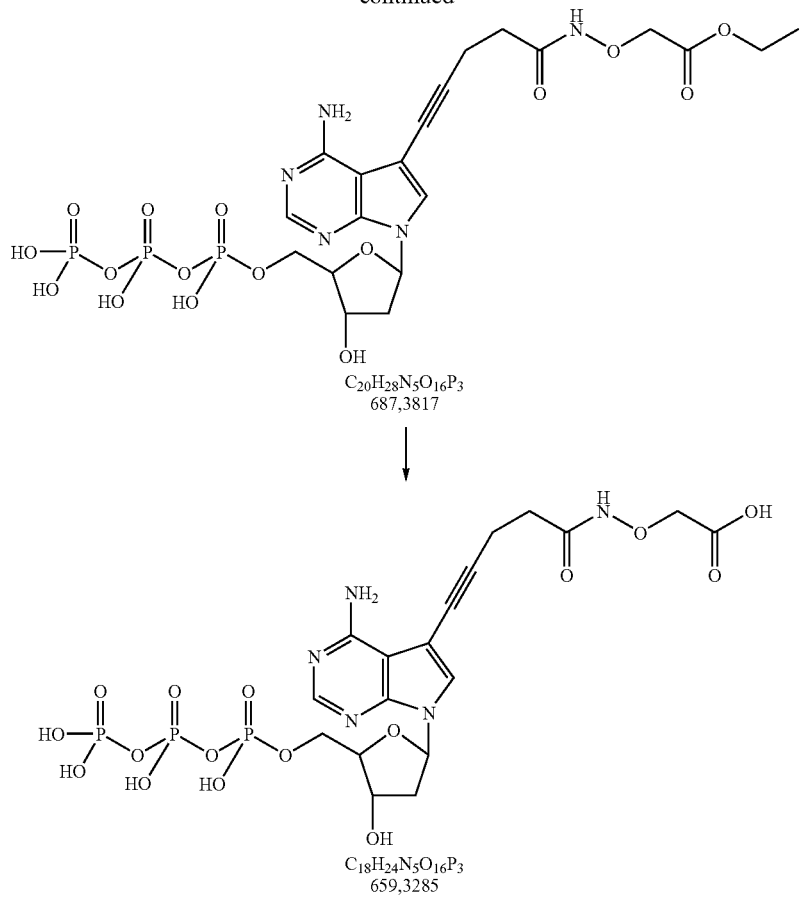

Example 23

Preparation of 2-Aminoxy-acetic Acid Ethyl Ester (5a)

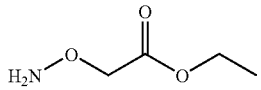

COMPOUND 5a

Acetyl chloride (5 mL) was added to abs. ethanole (50 mL) and the solution was cooled to room temperature. 2-Aminoxy-acetic acid, hydrochloride (2:1) (1.10 g, 10 mmol) was added and the reaction mixture was stirred for 16 h at room temperature. The reaction mixture was evaporated, $K_2CO_3$ aq. (2M) (10 mL) was added and the product was extracted into diethyl ether (5×20 mL), dried ($Na_2SO_4$), and evaporated coold to afford 1.007 g, 84%.

$^1$H NMR (CDCl$_3$) δ 4.24 (2H, s), 4.22 (2H, q), 1.30 (3H, t).

Example 24

Preparation of Pent-4-ynoylaminooxy-acetic Acid Ethyl Ester (5b)

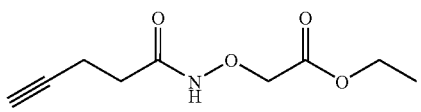

To a solution of 2-Aminoxy-acetic acid ethyl ester (573 mg, 4.8 mmol) and 4-Pentynoic acid (441 mg, 4.5 mmol) in 15 mL EtOAc were added dicyclohexylcarbodiimide (928 mg, 4.5 mmol) and the resulting mixture was stirred at room temperature for 16 h.

The reaction mixture was filtered, and the filtrate was washed with EtOAc (2×5 mL). The combined EtOAc was washed with aq $NaH_2PO_4$ and aq $NaHCO_3$, dried ($Na_2SO_4$), and evaporated to afford 950 mg of crude product.

The crude product was purified by silica column chromatography eluting with EtOAc:Heptane gradient (1:3)-(1:1) (v/v). Product yield 700 mg, 78%

$^1$H NMR (CDCl$_3$) δ 4.41 (2H, s), 4.18 (2H, q), 2.77 (1H, t), 2.34 (2H, dt), 2.17 (2H, bt), 1.40 (3H, t).

Example 25

Preparation of Compound 5c

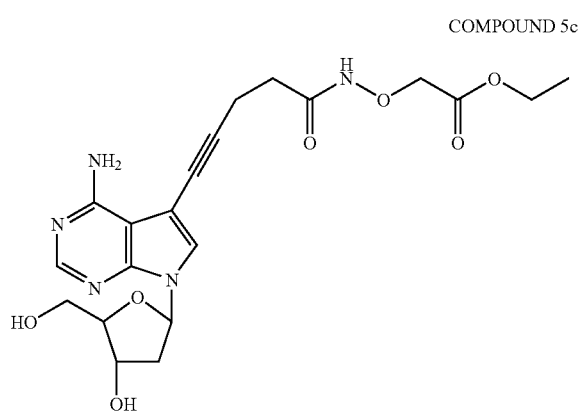

COMPOUND 5c

A solution of 7-Deaza-7-iodo-2'-deoxyadenosine (125 mg, 0.33 mmol),(prepared as described by Seela, F.; Synthesis 1996, 726-730), triethylamine (67 mg, 0.66 mmol) and compound (5b) (305 mg, 1.53 mmol) in anhydrous DMF (7 mL) was stirred at room temperature. $N_2$ was passed through the solution for 20 min. Tetrakis(triphenylphosphine)palladium (0) (75 mg, 0.065 mmol) and copper(I) iodide (24 mg, 0.33 mmol) were added and the reaction mixture was stirred at room temperature for 16 h.

The reaction mixture was evaporated and purified by silica column chromatography eluting with DCM:MeOH (9:1) (v/v). Product yield 129 mg, 86%.

$^1$H NMR (d[6] DMSO) δ 11.6 (1H, s), 8.09 (1H, s), 7.63 (1H, s), 6.47 (1H, dd), 5.26 (1H, d), 5.08 (1H, t), 4.42 (2H, s), 4.32 (1H, m), 4.08 (2H, q), 3.81 (1H, m), 3.54 (2H, m), 2.66 (1H, t), 2.46 (1H, m), 2.30 (2H, t), 2.15 (2H, ddd), 1.15 (3H, t).

Example 26

Preparation of Compound 5d

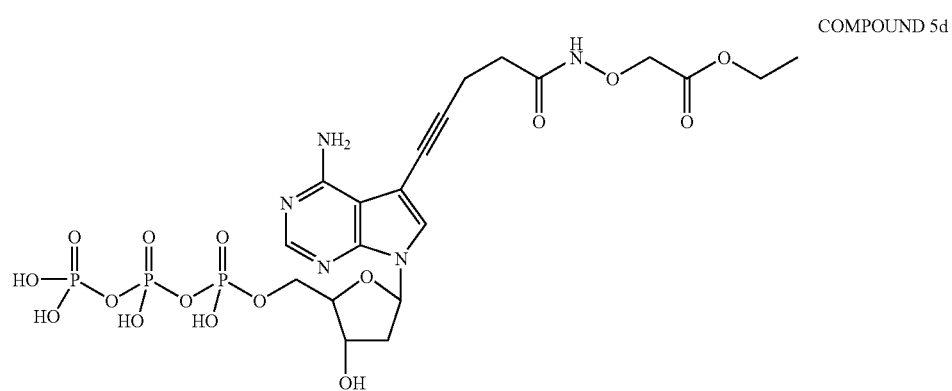

COMPOUND 5d

Compound (5c) (117 mg, 260 µmol) was dissolved in 500 µL dry trimethylphosphate. After cooling to 0° C., a solution of phosphorus oxychloride ($POCl_3$) in dry trimethylphosphate was added (400 µL stock solution (120 mg/mL), 310 µmol). The reaction mixture was stirred at 0° C. for 2 h.

Subsequently a solution of tributylammoniumpyrophosphate (200 mg, 420 µmol in 1.00 mL dry DMF) and tributylamine (123.6 mg, 670 µmol in 500 µL dry DMF) was added at 0° C. The reaction was stirred at room temperature for 3 min. and then stopped by addition of 1 mL 1.0 M triethylammoniumhydrogencarbonate.

Example 27

Preparation of Compound V

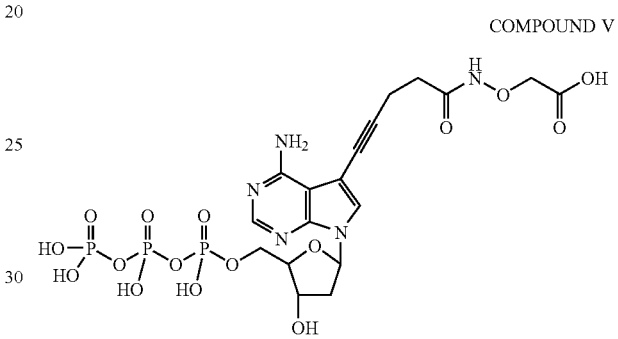

COMPOUND V

The reaction mixture of compound (5d) (2.0 mL) was diluted with water (6.0 mL) and adjusted to pH 13 using NaOH (2M, aq). After incubation at 5° C. for 64 h, the reaction mixture was extracted with EtOAc (5×5 mL), adjusted to pH 7.0 using HCl (2M, aq), evaporated and diluted with triethylammonium acetate buffer (500 µL, 0.1 M aq).

The crude product of triphosphate was purified by HPLC on a Waters Xterra MS $C_{18}$ Column, using the following buffer system: (A) aqueous triethylammonium acetate (0.1 M, pH 7) and (B) acetonitrile:water (80:20) containing triethylammonium acetate (0.1 M). The gradient time table contains 8 entries which are:

| Time | A % | B % |
| --- | --- | --- |
| 0.00 | 98 | 2 |
| 1.00 | 98 | 2 |
| 10.00 | 90 | 10 |
| 16.00 | 85 | 15 |
| 18.00 | 65 | 35 |
| 20.00 | 0 | 100 |
| 25.00 | 0 | 100 |
| 25.10 | 100 | 0 |

Retention times of compound V and compound 5d were 4.82 min and 7.29 min respectively, measured by monitoring UV absorbance at 260 nm. The fractions containing pure product were pooled and lyophilized two times from water (3 mL).

Examples 28 to 30

Preparation of the Mononucleotide Building Block (VI)

Example 28

Preparation of Pent-4-ynoic Acid 4-oxo-4H-benzo[d][1,2,3]triazin-3-yl Ester (6a)

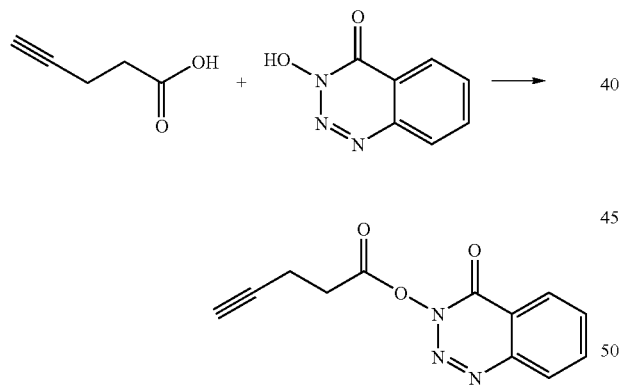

Pentynoic acid (200 mg, 2.04 mmol) was dissolved in THF (4 mL). The solution was cooled in a brine-icewater bath. A solution of dicyclohexylcarbodiimide (421 mg, 2.04 mmol) in THF (2 mL) was added. 3-Hydroxy-1,2,3-benzotriazin-4 (3H)-one (333 mg, 2.04 mmol) was added after 5 minutes. The reaction mixture was stirred 1 h at −10° C. and then 2 h at room temperature. TLC indicated full conversion of 3-hydroxy-1,2,3-benzotriazin-4(3H)-one (eluent: ethyl acetate). Precipitated salts were filtered off. The filtrate was concentrated in vacuo and crystallized from hexane (4 mL). The crystals were filtered off and dried. Yield: 450 mg, 93%. $R_F$=0.8 (ethyl acetate).

Example 29

Preparation of 2-Pent-4-ynoylamino-succinic Acid 1-tert-butyl Ester 4-isopropyl Ester (6b)

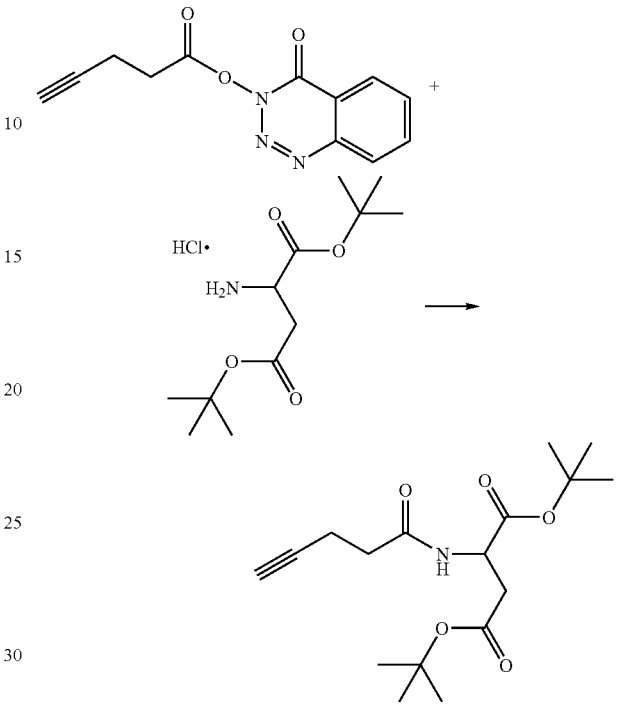

L-Aspartic acid α,β-di-tert-butyl ester hydrochloride (Novabiochem 04-12-5066, 200 mg, 0.71 mmol) was dissolved in THF (5 mL). The activated ester 6a (173 mg, 0.71 mmol) and diisopropylethylamine (0.15 mL, 0.86 mmol) were added. The mixture was stirred overnight. Dichloromethane (10 mL) was added. The organic phase was washed with citric acid (2×10 mL), saturated NaHCO$_3$ (aq, 10 mL), brine (10 mL), dried (Na$_2$SO$_4$) and concentrated to a syrup. An NMR spectrum indicated the syrup was pure enough for further synthesis. $^1$H-NMR (CDCl$_3$): δ 6.6 (1H, NH), 4.6 (1H, CH), 2.8 (2H, CH$_2$), 2.4 (4H, 2×CH$_2$), 1.9 (1H, CH), 1.2 (18H, 6×CH$_3$).

Example 30

Preparation of 2-{5-[1-(4-Hydroxy-5-(O-triphosphatehydroxymethyl)-tetrahydrofuran-2-yl)-2,4-dioxo-1,2,3,4-tetrahydro-pyrimidin-5-yl]-pent-4-ynoylamino}-succinic Acid di-tert-butyl Ester (VI)

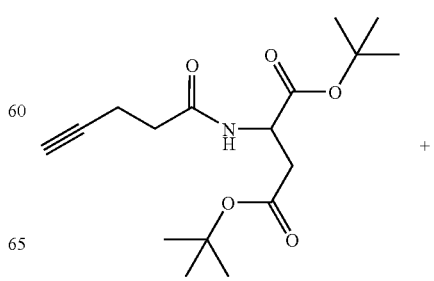

147
-continued

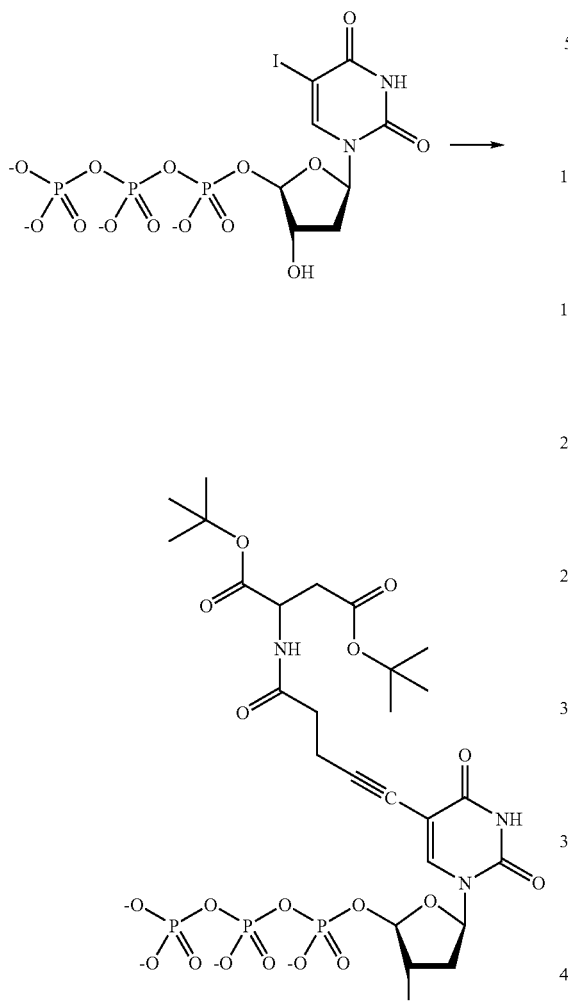

The nucleotide (20 mg, 0.022 mmol) was dissolved in water-ethanol (1:1, 2 mL). The solution was degassed and kept under an atmosphere of argon. The catalyst Pd(PPh$_2$(m-C$_6$H$_5$SO$_3$Na$^+$))$_4$ (20 mg, 0.016 mmol) prepared in accordance with A. L. Casalnuovo et al. J. Am. Chem. Soc. 1990, 112, 4324-4330, triethylamine (0.02 mL, 0.1 mmol) and the alkyne (Compound 6b) (20 mg, 0.061 mmol) were added. Few crystals of CuI were added. The reaction mixture was stirred for 6 h. The triethylammonium salt of LH8037 was achieved after purification by RP-HPLC (eluent: 100 mM triethylammonium acetate→20% acetonitrile in 100 mM triethylammonium acetate). $^1$H-NMR (D$_2$O): δ 8.1 (1H, CH), 6.2 (1H, CH), 4.8 (1H, CH), 4.6 (1H, CH), 4.1 (3H, CH, CH$_2$), 2.8 (2H, CH$_2$), 2.7 (2H, CH$_2$), 2.5 (2H, CH$_2$), 2.3 (2H, CH$_2$), 1.4 (18H, 6×CH$_3$).

Immediately prior to incorporation or after incorporation, the protective di-tert-butyl ester groups may be cleaved to obtain the corresponding free carboxylic acid.

148

Examples 31 to 32

Preparation of the Mononucleotide Building Block (VII)

Example 31

Preparation of 2-{5-[4-Amino-1-(4-hydroxy-5-hydroxymethyltetrahydrofuran-2-yl)-2-oxo-1,2-dihydro-pyrimidin-5-yl]-pent-4-ynoylamino}-succinic Acid di-tert-butyl Ester (7a)

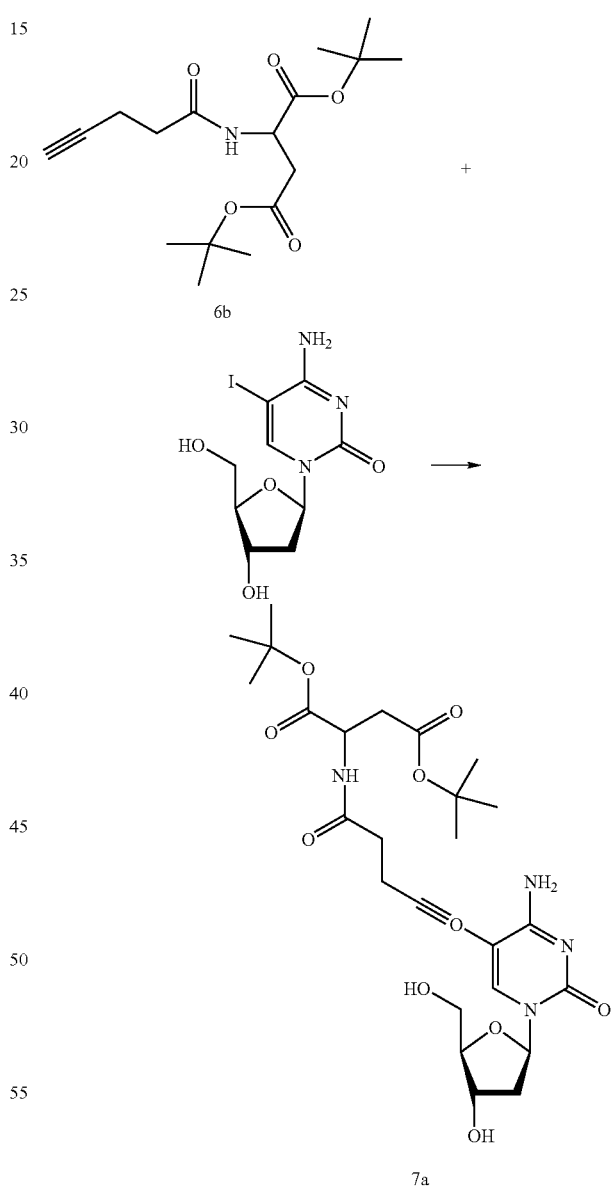

Compound (7a) (30 mg, 19%) was obtained from compound (6b) (140 mg, 0.43 mmol) and 5-iodo-2-deoxycytidine (100 mg, 0.28 mmol) using the procedure described for the synthesis of compound VI. $^1$H-NMR (MeOD-D$_3$): δ 8.3 (1H, CH), 6.2 (1H, CH), 4.8 (1H, CH), 4.6 (1H, CH), 4.4 (1H, CH), 4.0 (1H, CH), 3.8 (2H, CH$_2$), 2.8 (4H, 2×CH$_2$), 2.7 (2H, CH$_2$), 2.4 (1H, CH$_2$), 2.2 (1H, CH$_2$), 1.4 (18H, 6×CH$_3$).

Example 32

Preparation of 2-{5-[4-Amino-1-(4-hydroxy-5-(O-triphosphatehydroxymethyl)-tetrahydro-furan-2-yl)-2-oxo-1,2-dihydro-pyrimidin-5-yl]-pent-4-ynoylamino}-succinic Acid di-tert-butyl Ester (Compound VII)

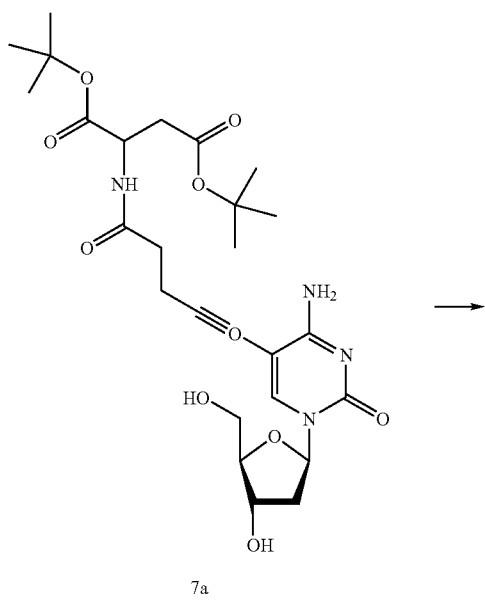

Phosphoroxy chloride (6.0 µl, 0.059 mmol) was added to a cooled solution (0° C.) of 7a (30 mg, 0.054 mmol) in trimethyl phosphate (1 mL). The mixture was stirred for 1 h. A solution of bis-n-tributylammonium pyrophosphate (77 mg, 0.16 mmol) in DMF (1 mL) and tributylamine (40 µl, 0.16 mmol) were added. Water (2 mL) was added. pH of the solution was measured to be neutral. The solution was stirred at room temperature for 3 h and at 5° C. overnight. A small amount of compound VII (few mg) was obtained after purification by RP-HPLC (eluent: 100 mM triethylammonium acetate→20% acetonitrile in 100 mM triethylammonium acetate). 7a (18 mg) was regained.

Immediately prior to or subsequent to incorporation the protective di-tert-butyl ester groups may be cleaved to obtain the corresponding free carboxylic acid.

Examples 33 and 34

Preparation of the Mononucleotide Building Block (VII)

Example 33

Preparation of 2-Pent-4-ynoylamino-6-(2,2,2-trifluoroacetylamino)-hexanoic Acid, (8a)

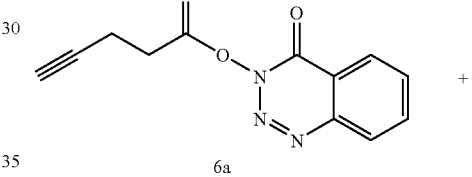

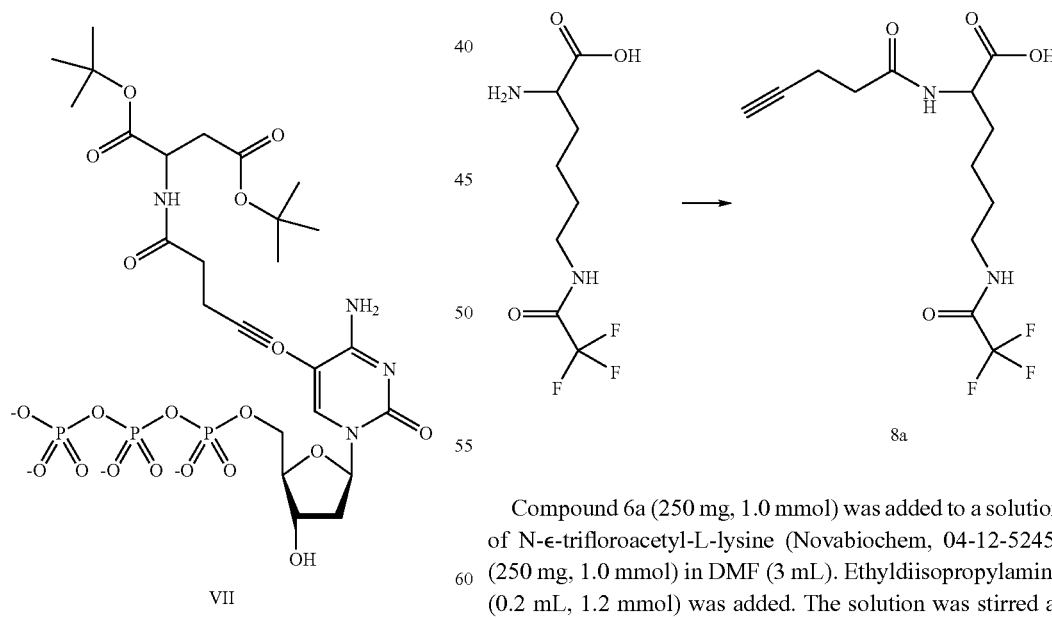

Compound 6a (250 mg, 1.0 mmol) was added to a solution of N-ε-trifloroacetyl-L-lysine (Novabiochem, 04-12-5245) (250 mg, 1.0 mmol) in DMF (3 mL). Ethyldiisopropylamine (0.2 mL, 1.2 mmol) was added. The solution was stirred at room temperature overnight and worked-up by RP-HPLC (eluent: water→methanol). Yield: 50 mg, 15%. $^1$H-NMR (D$_2$O): δ 4.4 (1H, CH), 3.4 (2H, CH$_2$), 2.5 (4H, 2×CH$_2$), 2.3 (1H, CH), 1.9 (1H, CH$_2$), 1.8 (1H, CH$_2$) 1.6 (2H, CH$_2$), 1.5 (2H, CH$_2$).

Example 34

Preparation of 2-{5-[1-(4-Hydroxy-5-(O-triphosphatehydroxymethyl)-tetrahydrofuran-2-yl)-2,4-dioxo-1,2,3,4-tetrahydro-pyrimidin-5-yl]-pent-4-ynoylamino}-6-(2,2,2-trifluoro-acetylamino)-hexanoic Acid (Compound VIII)

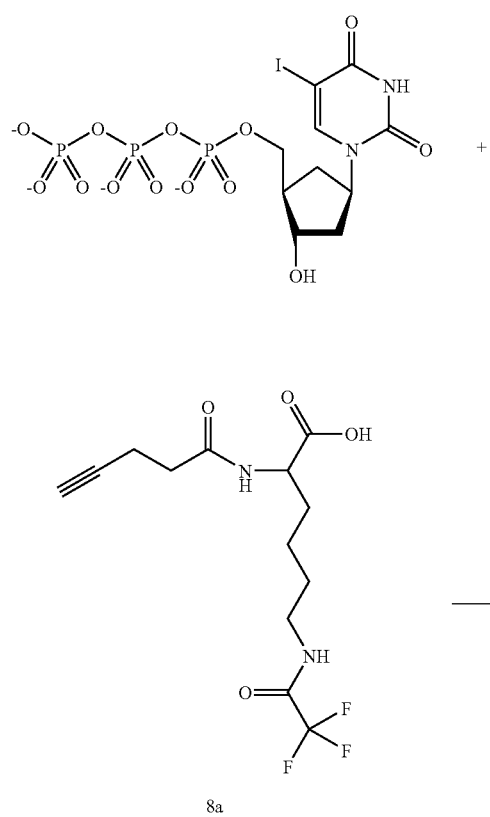

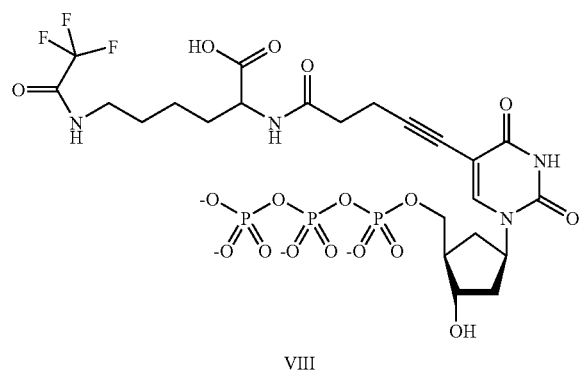

VIII

The triethylammonium salt of compound VIII (11 mg) was obtained from compound 8a (50 mg, 0.15 mmol) and 5-iodo-2-deoxyuracil (50 mg, 0.06 mmol) using the procedure described for the synthesis of compound VI.

Examples 35 to 39

Preparation of the Mononucleotide Building Block (IX)

Example 35

Preparation of di-Boc-Lysin-propargyl Amide (Compound 9a) $C_{19}H_{33}N_3O_5$ Mw 383.48

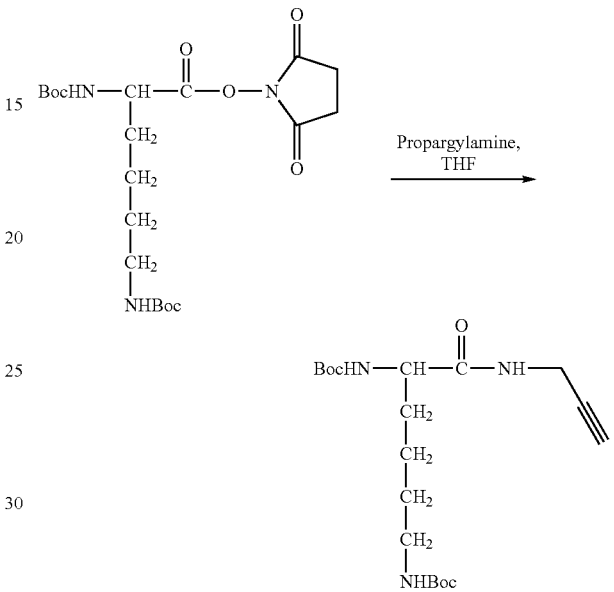

Boc-Lys-(Boc)-OSu (Novabiochem 04-12-0017, 0.887 g, 2 mmol) was dissolved in THF (10 ml). Propargylamine (0.412 ml, 6 mmol) was added and the solution stirred for 2 h. TLC (ethylacetate:heptan 1:1) showed only one product. Dichloromethane (20 ml) was added and the mixture was washed successively with citric acid (1M, 10 ml) and saturated sodium hydrogen carbonate (10 ml). The organic phase was dried with magnesium sulphate filtered and evaporated to give compound 9a (0.730 g) as a colourless syrup.

$^1$H-NMR: ∂ 6.55 (1H, NH), 5.15 (1H, NH), 4.6 (1H, C$\underline{H}$—NH), 4.05 (2H, CH—C—C$\underline{H_2}$—N), 3.75 (1H, NH), 3.1 (2H, C$\underline{H_2}$-NH) 2.25 (1H, C$\underline{H}$=C—CH$_2$), 1.9-1.3 (6H, 3×C$\underline{H_2}$), 1.4 (18H, 6×CH$_3$).

Example 36

Preparation of 5-Iodo-3'-O-acetyl-5'-O-TBDMS-2'-deoxyuridine (Compound 9b) $C_{17}H_{27}IN_2O_6Si$ Mw 510.40

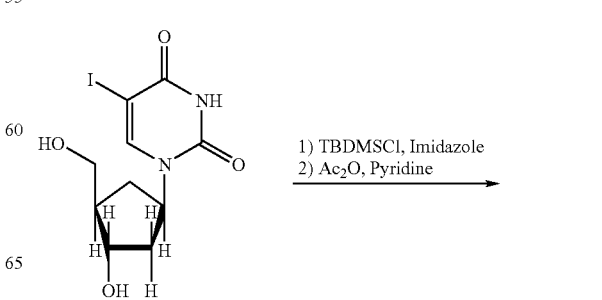

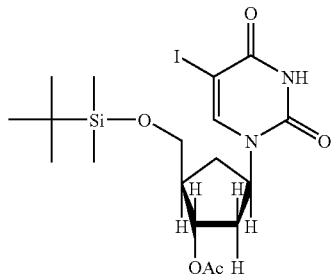

5-Iodo-2'-deoxyuridine (Sigma I-7125, 2.50 g, 7.06 mmol) and imidazol (0.961 g, 14.12 mmol) was dissolved in DMF (10 ml). Cooled to 0° C. and a solution of TBDMSCl (t-butyl-dimethyl-chloride, 1.12 g, 7.41 mmol) in dichloromethane (5.0 ml) was run in over 20 minutes. Stirring was continued at room temperature for 18 h, and the mixture was evaporated. The crude mono silylated nucleoside was dissolved in pyridine (40 ml) and cooled to 0° C. Acetic anhydride (4.0 ml, 42.3 mmol) was added over 30 minutes and stirring was continued for 18 h at room temperature. The reaction mixture was evaporated and dissolved in dichloromethane (20 ml) and citric acid (2M, 20 ml) was added. The aqueous phase was back extracted with dichloromethane (2×20 ml). The combined organic phases were washed with saturated sodium bicarbonate (20 ml), dried with sodium sulphate and evaporated (5.85 g). Recrystallisation form ethylacetate/EtOH gave 9b (2.54, 9) pure for synthesis TLC (Ethyl acetate). Further recrystallisation furnished an analytical pure sample mp. 172.4-173.1° C.

Example 37

Preparation of 5-Iodo-3'-O-acetyl-2'-deoxyuridine (Compound 9c) $C_{11}H_{13}IN\ O_6$ Mw 396.14

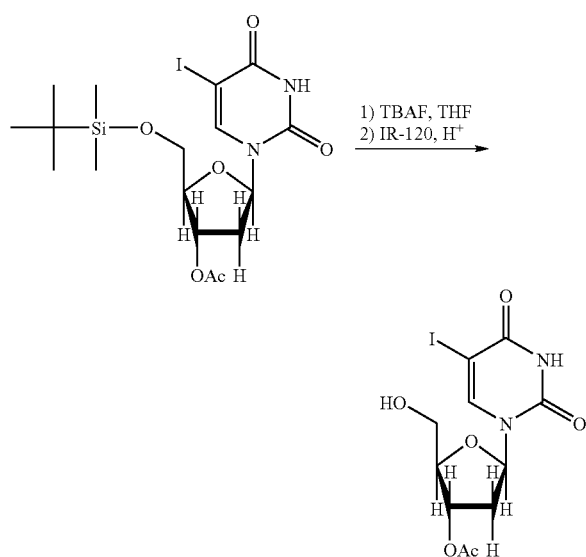

5-Iodo-3'-O-acetyl-5'-O-TBDMS-2'-deoxyuridine (compound 9b) (2.54 g, 4.98 mmol) as dissolved in THF (25 ml), tetra butyl ammonium fluoride trihydrat (TBAF, 3.2 g, 10.1 mmol) was added and stirred for 18 h at room temperature. The reaction mixture was added water (25 ml) stirred for 1 h. Ion exchange resin IR-120H⁺ (26 ml) was then added and stirring was continued for 1 h. The solution was filtered and reduced to approximately 10 ml in vaccuo. Crystals were collected and dried in vaccuo (1.296 g)

Example 38

Preparation of 5-Iodo-5'-triphosphate-2'-deoxyuridine, Triethylammonium Salt (Compound 9d) $C_9H_{14}IN_2O_{14}P_3 + n.N(CH_2CH_3)_3$ Mw 897.61 for n=3

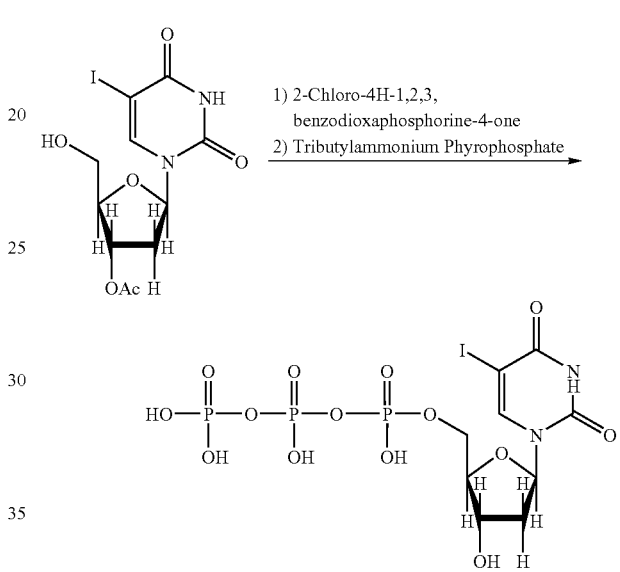

5-Iodo-3'-O-acetyl-2'-deoxyuridine (compound 9c) (2.54 g, 4.98 mmol) as dissolved in pyridine (3.2 ml) and dioxane (10 ml). A solution of 2-chloro-4H-1,3,2-benzodioxaphosphorin-4-one in dioxane (3.60 ml, 1 M, 3.60 mmol) was added under stirring. The reaction mixture was stirred for 10 minutes at room temperature followed by simultaneous addition of bis(tri-n-butylammonium) pyrophosphate in DMF (9.81 ml, 0.5 M, 4.91 mmol) and tri-n-butylamine (3.12 ml, 13.1 mmol). Stirring was continued for 10 minutes and the intermediate was oxidized by adding an iodine solution (90 ml, 1% w/v in pyridine/water (98/2, v/v)) until permanent iodine colour. The reaction mixture was left for 15 minutes and then decolourized with sodium thiosulfate (5% aqueous solution, w/v). The reaction mixture was evaporated to yellow oil. The oil was stirred in water (20 ml) for 30 minutes and concentrated aqueous ammonia (100 ml, 25%) was added. This mixture was stirred for 1.5 hour at room temperature and then evaporated to an oil of the crude triphosphate product. The crude material was purified using a DEAE Sephadex A25 column (approximately 100 ml) eluted with a linear gradient of triethyl-ammonium hydrogencarbonate [TEAB] from 0.05 M to 1.0 M (pH approximately 7.0-7.5); flow 8 ml/fraction/15 minutes. The positive fractions were identified by RP18 HPLC eluting with a gradient from 10 mM TEAA (triethylammonium acetate) in water to 10 mM TEAA 20% water in acetonitrile. The appropriate fractions were pooled and evaporated. Yield approximately 1042 mg.

Example 39

Preparation of 5-(Lysin-propargyl amide)-5'-triphosphate-2'-deoxycytidine, Triethylammonium Salt (Compound IX) $C_{18}H_{30}N_5O_{15}P_3$+n.N$(CH_2CH_3)_3$ Mw 952.95 for n=3

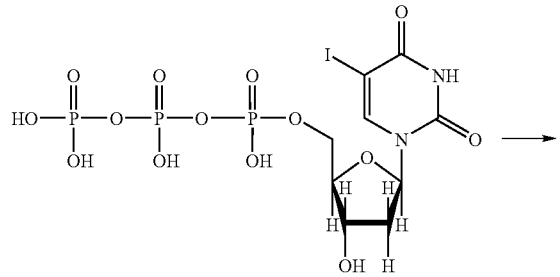

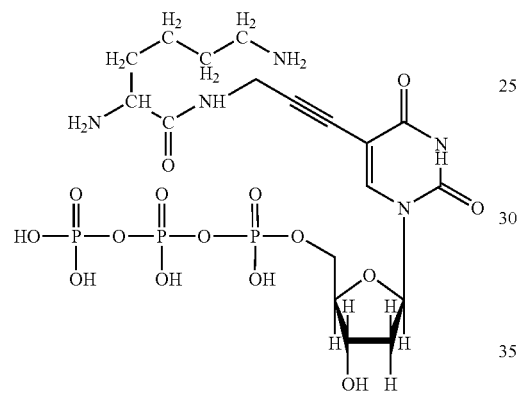

5-Iodo-3'-O-acetyl-5'-triphosphate-2'-deoxyuridine, triethylammonium salt (compound 9d) (0.0087 g, 9.7 µmol) was dissolved in water (100 µl). Air was replaced carefully with argon. Di-Boc-Lysin-propargyl amide (compound 9a) (18.6 mg, 48.5 µmol) dissolved in dioxane (100 µl), triethylamine (2.7 µl, 19.4 µl), Pd((PPh$_2$)(m-C$_6$H$_4$SO$_3$Na$^+$).(H$_2$O))$_4$ (compound 9d) (5 mg, 4.4 µmol) and copper (I) iodide (0.4 µl, 2.1 µmol) were added in the given order. The reaction mixture was stirred for 18 h at room temperature in an inert atmosphere then evaporated. The crude material was treated with aqueous hydrochloric acid (0.2 M, 1 ml) for 15 minutes at 30° C. (compound IX) was obtained by HPLC C$_{18}$ 10 mM TEAA (triethylammonium acetate) in water to 10 mM TEAA 20% water in acetonitrile. Appropriate fractions were desalted using gelfiltration (pharmacia G-10, 0.7 ml).

Examples 40 to 45

Preparation of the Mononucleotide Building Block (X)

Example 40

Preparation of Boc-Lys-(Boc)-OH (Compound 10a) $C_{16}H_{30}N_2O_6$ Mw 346.42

Lysine (Novabiochem 04-10-0024; 3.65 g, 20 mmol) was dissolved in sodium hydroxide (2 M, 40 ml), added dioxane (60 ml) and di-tert-butyl dicarbonate (8.73 g, 40 mmol) in the given order. The mixture was stirred for 1.75 h at 60° C. Water (50 ml) was added and the solution was washed with dichloromethane (4×25 ml). The aqueous phase was cooled to 0° C. with ice then acidified with 2 M HCl (pH=3) and extracted with dichloromethane (4×25 ml). The organic phase was dried with magnesium sulphate. Evaporation furnished (compound 10a) 6.8 g as a colour less oil.

$^1$H-NMR: ∂ 9.5 (1H, COOH), 5.3 (1H, CH), 4.7 (1H, NH), 4.3 (1H, NH), 3.1 (2H, CH$_2$—NH), 1.8 (2H, C$\underline{H_2}$—CH), 1.5 (6H, 3×CH$_2$), 1.45 (18H, 6×CH$_3$).

Example 41

Preparation of Di-Boc-Lysin-propargyl Ester (Compound 10b) $C_{19}H_{32}N_2O_6$ Mw 384.47

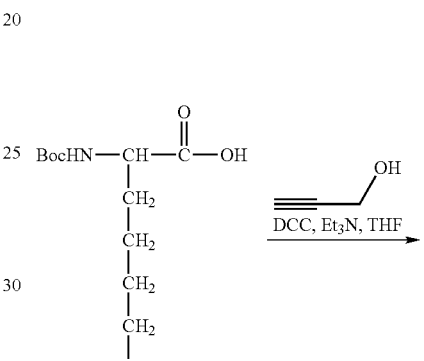

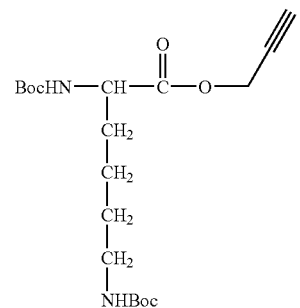

Boc-Lys-(Boc)-OH (compound 10a) (3.46 g, 10 mmol) was dissolved in THF (25 ml). At 0° C. a solution of dicyclohexylcarbodiimide (2.02 g, 10 mmol) in THF (25 ml) and triethylamine (1.39 ml) were added in the given order. The mixture was allowed to warm up to room temperature and stirred for 18 h. The resulting suspension was filtered and evaporated. The oil 5.45 g was pre-purified by column chromatography Heptan:Ethylacetate 3:1.

Pure 10b was achieved by HPLC-C$_{18}$ 10% MeOH: 90% H$_2$O → 100% MeOH $^1$H-NMR: ∂ 5.1 (1H, NH), 4.75 (2H, CH—C—CH$\underline{_2}$—O), 4.6 (1H, NH), 4.35 (1H, C$\underline{H}$—NH), 3.1 (2H, C$\underline{H_2}$—NH) 2.5 (1H, C$\underline{H}$—C—CH$_2$), 1.9-1.4 (6H, 3×C$\underline{H_2}$), 1.5 (18H, 6×CH$_3$).

Example 42

Preparation of 5-Iodo-3',5'-di-O-TBDMS-2'Deoxy-cytidine (Compound 10c) $C_{21}H_{40}IN_3O_4Si_2$ Mw 581.64

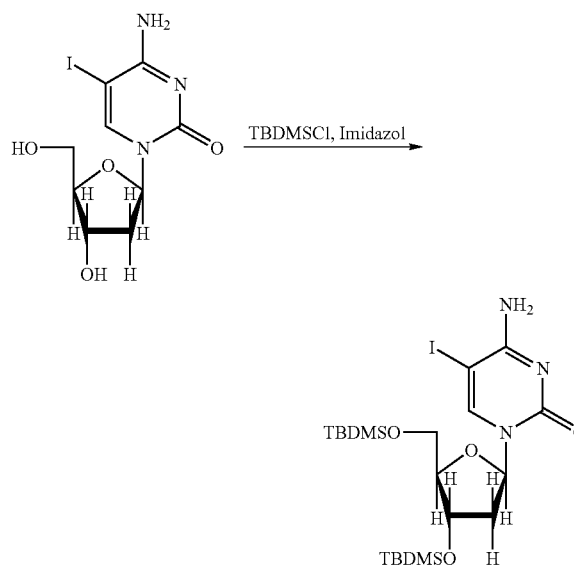

5-Iodo-2-deoxy-Cytidine (Sigma I-7000, 0.353 g, 1 mmol) was dissolved in DMF (4 ml), added t-Butyl-dimethyl silyl chloride (TBDMS-Cl, 0.332 g, 2.2 mmol) and Imidazol (0.204 g, 3 mmol). The solution was stirred for 15 h at 50° C. followed by evaporation. Dichloromethane (25 ml) and citric acid (2M, 10 ml) was added to the dry mixture. The aqueous phase was back extracted with dichloromethane (2×10 ml). The combined organic phases were washed with saturated sodium bicarbonate (15 ml), dried with sodium sulphate and evaporated. Compound 10 c (0.405 g) was obtained by recrystallisation from EtOH/Ethylacetate.

$^1$H-NMR: ∂ 8.1 (1H, H-6), 6.25 (1H, H-1'), 4.35 (1H, H-4'), 4.0 (1H, H-4'), 3.9 (1H, H-5'), 3.75 (1H, H-5'), 2.5 (1H, H-2'), 1.95 (1H, H-2'), 1.85 (2H, NH), 0.95 (9H, 3×CH$_3$), 0.9 (9H, 3×CH$_3$), 0.15 (6H, 2×CH$_3$), 0.1 (6H, 2×CH$_3$).

Preparation of 5-(di-Boc-Lysin-propargyl Ester)-3',5'-di-O-TBDMS-2'-deoxycytidine (Compound 10d) $C_{40}H_{71}IN_5O_{10}Si_2$ Mw 838.19

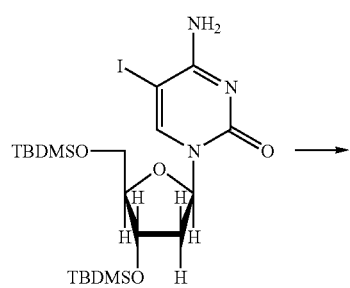

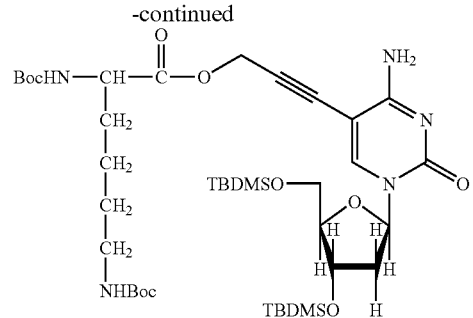

Compound 10c (0.116 g, 0.2 mmol) was dissolved in dichloromethane (10 ml). Air was replaced carefully with argon. Di-Boc-Lysin-propargyl ester (compound 10b) (0.232, 0.6 mmol), triethylamine (0.083 ml, 0.6 mmol), di-chloro-bis-triphenylphosphine-palladium II (0.0074 g, 0.01 mmol) and copper (I) iodide (0.0038 g, 0.02 mmol) were added in the given order. The reaction mixture was stirred for 15 h at room temperature in an inert atmosphere. The reaction mixture was evaporated re-dissolved in MeOH/H$_2$O 1:1 1 ml and purified using HPLC-C$_{18}$ 45% H$_2$O:55% MeCN→100% MeCN.

$^1$H-NMR: ∂ $^1$H-NMR: ∂ 8.2 (1H, H-6), 6.25 (1H, H-1'), 5.15 (1H, NH), 4.9 (2H, C—CH$_2$—O), 4.6 (1H, NH), 4.4 (1H, H-4'), 4.3 (1H, CH—NH), 4.0 (1H, H-4'), 3.9 (1H, H-5'), 3.75 (1H, H-5'), 2.5 (1H, H-2'), 3.1 (2H, CH$_2$—NH), 1.95 (1H, H-2'), 1.9-1.4 (6H, 3×CH$_2$), 1.85 (2H, NH), 1.5 (18H, 6×CH$_3$), 0.95 (9H, 3×CH$_3$), 0.9 (9H, 3×CH$_3$), 0.15 (6H, 2×CH$_3$), 0.1 (6H, 2×CH$_3$).

Example 44

Preparation of 5-(di-Boc-Lysin-propargyl Ester)-2'-deoxycytidine (Compound 10e) $C_{28}H_{43}IN_5O_{10}$ Mw 609.67

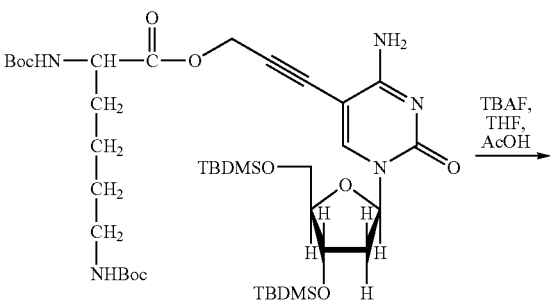

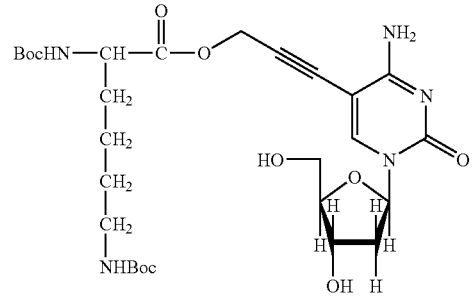

Compound 10d (0.0246 g, 0.029 mmol) was dissolved in THF (1 ml) and successively added acetic acid (0.0165 ml, 0.288 mmol) and tetra n-butyl ammonium fluoride tri-hydrate (0.0454 g, 0.144 mmol). The reaction mixture was stirred for 18 h at room temperature and afterwards evaporated. Re-dissolved in dichloromethane and purified on silica (1×18 cm). Dichloromethane/MeOH 8:2. Fractions which gave UV absorbance on TLC were pooled and evaporated giving (0.0128 g) as a colourless oil.

Example 45

Preparation of 5-(Lysin-propargyl Ester)-5'-triphos-phate-2'-deoxycytidine $C_{18}H_{30}N_5O_{15}P_3$ Mw 649.38

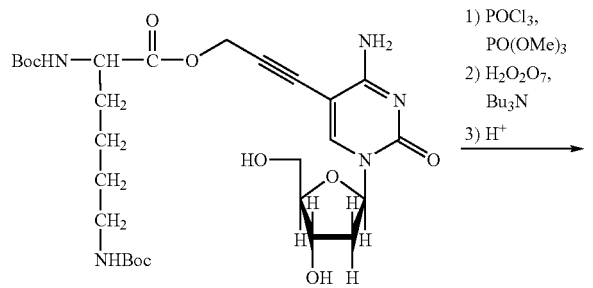

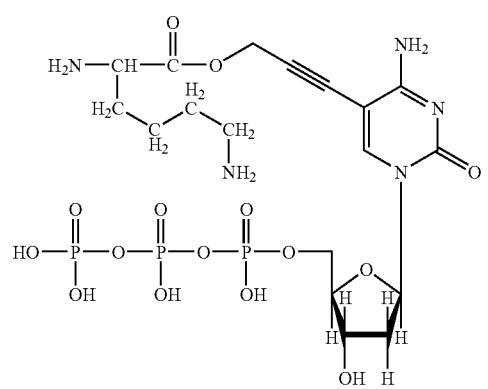

Compound 10e (0.0128 g, 0.021 mmol) was dissolved in trimethylphosphate (0.150 ml) and cooled to 0° C. Phos-phoroxychloride in trimethylphosphate (1M, 0.0246 ml) was added slowly in order not to raise the temperature. Stirring was continued for 2 h at 0° C. and the temperature was allowed to rise to ambient. Pyrophosphate in DMF (0.5 M, 0.1025 ml, 0.051 mmol) and tri-n-butyl amine in DMF (1M, 0.0122 ml, 0.051 mmol) were added simultaneous. Stirring was continued for 15 minutes at room temperature and TEAB (triethyl ammonium bicarbonate, 1M, pH=7.3, 0.50 ml) was added. Stirring was continued for 3 h then evaporated.

Example 46

Preparation of Compound X

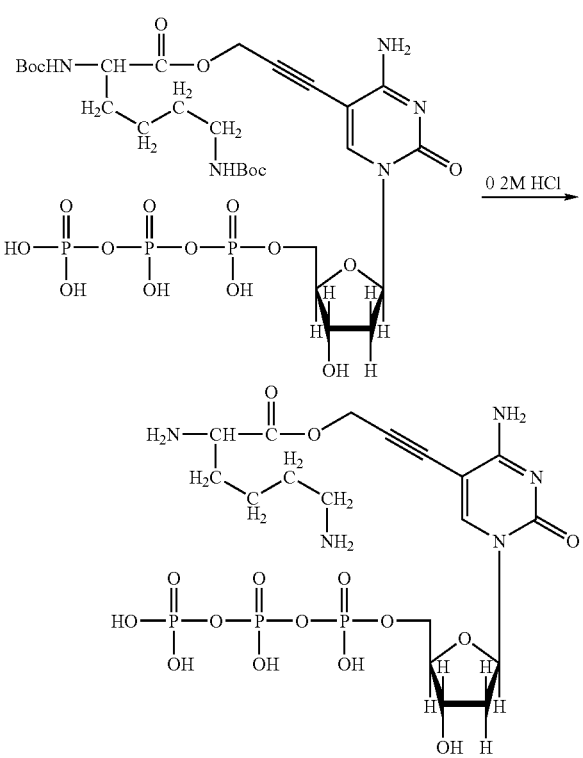

The crude material was treated with aqueous hydrochloric acid (0.2 M, 1 ml) for 15 minutes at 30° C. Compound X was obtained by HPLC $C_{18}$ 10 mM TEAA (triethylammonium acetate) in water to 10 mM TEAA 20% water in acetonitrile. Appropriate fractions were desalted using gelfiltration (phar-macia G-10, 0.7 ml)

Examples 47 to 51

Preparation of the Mononucleotide Building Block (XI)

Example 47

Preparation of 3'-O-acetyl-5'-O-dimethoxytrityl-5-iodo-2'-deoxyuridine (Compound 11a).
$C_{32}H_{31}IN_2O_8$. Mw 698.51 g/mol. (Analogous to "Oligonucleotide Synthesis—a Practical Approach" (1984) Gait. M. J. (Ed.), IRL Press. Oxford.)

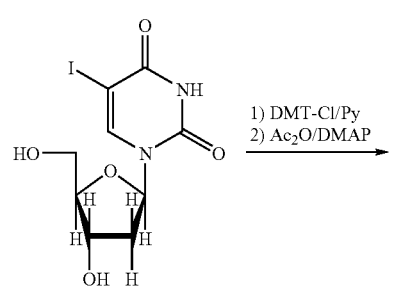

161

-continued

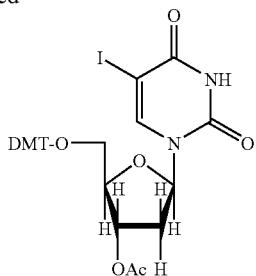

5-Iodo-2-deoxyuridine (3.54 g, 10 mmol) was dried by coevaporation with pyridine (25 ml, 3 times). Pyridine (100 ml) was added and shortly evaporated to a reduced volume (80 ml). 4,4'-dimethoxytrityl chloride (DMT-Cl, 3.38 g, 10 mmol) was added and the reaction mixture was stirred at room temperature. After 20 hours, additional DMT-Cl (0.68 g, 2 mmol) was added and the reaction mixture was stirred for another 4 hour. Excess of DHT-Cl was quenched with methanol (5 ml, stirred 10 minutes) and the reaction mixture evaporated to dryness. The oil was dissolved in dichloromethane (100 ml) and extracted with saturated aqueous $NaHCO_3$ (100 ml). The aqueous phase was back-extracted with dichloromethane and the combined fractions of dichloromethane were dried with anhydrous $MgSO_4$, filtered and evaporated. The crude oil was dissolved in dichloromethane (75 ml) and triturated with pentane (250 ml). Re-trituration of the crude oil by dissolving in ethyl acetate (75 ml) and adding pentane (250 ml) gave reddish foam after evaporation. Yield of crude 5'-O-dimethoxytrityl-5-iodo-2'-deoxyuridine was. 5.84 g. Pure 5'-O- dimethoxytrityl-5-iodo-2'-deoxyuridine was obtained via column chromatography in dichloromethane on silica (Merck Kieselgel 60, 230-400 mesh ASTM, art. 9385) eluting with a gradient of methanol (0-5% methanol in dichloromethane). Yield of purified 5'-O-dimethoxytrityl-5-iodo-2'-deoxyuridine was 4.26 g (6.5 mmol, 65%). 5'-O-Dimethoxytrityl-5-iodo-2'-deoxyuridine (6.0 g, 9.1 mmol) was dried by coevaporation with pyridine (10 ml, twice). Pyridine (50 ml) was added and acetic anhydride (5 ml) and dimethylaminopyridine (DMAP, catalytic amount) were added. The reaction mixture was stirred overnight at room temperature. Excess of acetic anhydride was quenched with methanol (10 ml, stirred 15 min.) and the reaction mixture evaporated to dryness The oil was dissolved in dichloromethane (150 ml) and extracted with aqueous saturated $NaHCO_3$ (50 ml). The aqueous phase was back-extracted with dichloromethane and the combined fractions of dichloromethane were dried with anhydrous $MgSO_4$, filtered and evaporated. Purified 3'-O-acetyl-5'-O-dimethoxytrityl-5-iodo-2'-deoxyuridine was. obtained via column chromatography in dichloromethane/methanol (98/2, v/v) on silica (Merck Kieselgel 60, 230-400 mesh ASTM, art.9385) eluting with a gradient of methanol (2-6% methanol in dichloromethane). The yield was 5.75 g (8.2 mmol). Rechromatography in dichloromethane/pentane (80/20, v/v) eluting with a gradient of methanol (2-6') gave the. desired purified 3'-O-acetyl-5'-O-dimethoxytrityl-5-iodo-2'-deoxyuridine (4.18 g, 6.0 mmol, 60%).

162

Example 48

Preparation of N-trifluoroacetyl-3-amidopropyne (Compound 11b). $C_5H_4F_3NO$. Mw. 151.09 g/mol. (Reference: Cruickshank et al. (1988) Tetrahedron Lett. 29, 5221-5224).

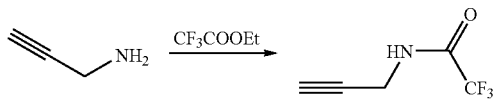

Propargylamine (7.0 ml, 5.88 g, 0.11 mol) was dissolved in 100 ml ice-cold methanol and ethyl trifluoroacetate (18 ml, 19.29, 0.135 mol) was added slowly under stirring on ice. The ice bath was removed and the reaction mixture was allowed to warm up to room temperature and stirring v as continued over night. After 24 h, TLC analysis (Silica, dichloromethane/methanol, 9/1, v/v) shoved complete conversion of propargylamine (as observed by disappearance of the positive colour-reaction in the ninhydrin test, 110° C.). The reaction mixture was evaporated, re-dissolved in dichloromethane (100 ml) and extracted with aqueous sodium hydrogen carbonate. The aqueous phase was back-extracted with dichloromethane (25 ml) and the combined dichloromethane phases were extracted with water (100 ml). The aqueous phase was back-extracted with dichloromethane (25 ml) and the combined dichloromethane phases were dried with magnesium sulfate, filtered and evaporated to yellow oil. The oil was purified by distillation collecting the purified product at 38-39° C./1 mmHg. Yield 11.0 g (73 mmol, 66%).

Example 49

Preparation of 3'-O-acetyl-5'-O-dimethoxytrityl-5-(N-trifluoroacetyl-3-amido-propynyl)-2'-deoxyuridine (Compound 11c). $C_{35}H_{35}N_3O_8$ Mw 625.67 g/mol

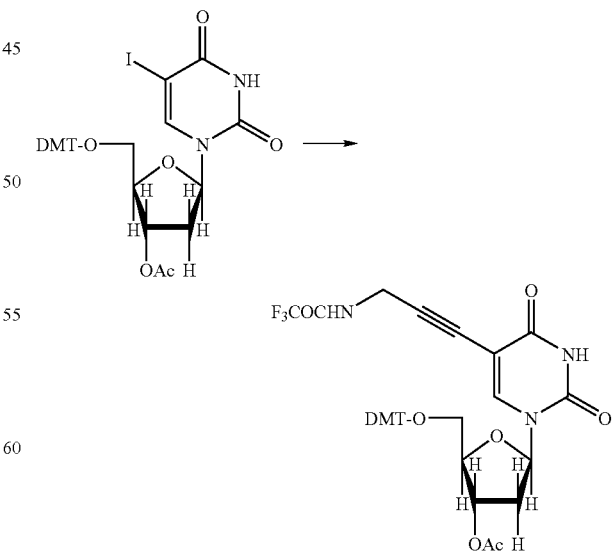

3'-O-Acetyl-5'-O-dimethoxytrityl-5-iodo-2'-deoxyuridine (4.15 g, 6.0 mmol) was dissolved in ethyl acetate (240 ml) and N-trifluoroacetyl-3-aminopropyne (1.81 g, 12 mmol), triethylamine (3.09 g, 4.23 ml, 30.5 mmol), bis(triphenylphosphine)-palladium(II) chloride (0.091 g, 0.13 mmol) and copper(I) iodide (0.091 g, 0.48 mmol) were added in the given order. The reaction mixture was flushed with nitrogen, Stoppered and stirred at ambient temperature. The reaction was followed by TLC analysis (Silica, $CH_2Cl_2$/MEOH, 95/5, v/v) and stopped after 24 hours when all starting material was consumed. The reaction mixture was extracted twice with aqueous EDTA (5% v/v, 300 ml) and once with aqueous sodium thiosulfate (5% v/v, 300 ml). The aqueous phases were back-extracted with ethyl acetate and the combined fraotions of ethyl acetat. were dried (anhydrous $MgSO_4$), filtered and evaporated. Column chromatography in dichloromethane/pentane (80/20, v/v) eluting with a gradient of methanol (0-5%) gave the crude 3'-O-acetyl-5'-O-dimethoxytrityl-5-(N-trifluoroacetyl-3-amido-propynyl)-2'-deoxyuridine (4.2 g) as brownish oil. Rechromatography in ethylacetate/pentane (50/50 to 60/40, v/v) gave the desired purified product (1.99 g, 3.2 mmol).

Example 50

Preparation of 3'-O-acetyl-5-(N-trifluoroacetyl-3-amidopropynyl)-2'-deoxyuridin. $C_{16}H_{16}F_3N_3O_7$, Mw 419.31 g/mol

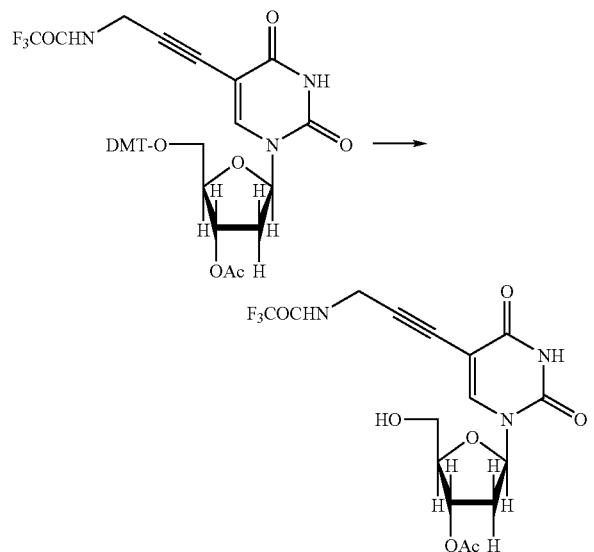

3'-O-Acetyl-5'-O-dimethoxytrityl-5-(N-trifluoroacetyl-3-amidopropynyl)-2'-deoxyuridine (1.99 g, 2.8 mmol) was dissolved in dichloromethane (133 ml) and cooled to 0° C. A solution of trichloroacetic acid in dichloromethane (3% w/v) was added slowly and the reaction mixture was stirred for 15 min at 0° C. TLC analysis (Silica, $CH_2Cl_2$/MEOH, 95/5 v/v) confirmed total detritylation and the reaction was quenched by the addition of 2-propanol (10 ml), quenching of DMT+ was observed by colour-change from orange to colourless. Stirring vas continued for 2 minuttes and the reaction mixture was poured into saturated aqueous $NaHCO_3$ (100 ml) and extracted twice with dichloromethane. The aqueous phase was back-extracted with dichloromethane and the combined fractions of dichloromethane were dried (anhydrous $MgSO_4$), filtered and evaporated. The foam was dissolved in dichloromethane (50 ml) and triturated with pentane (200 ml). The trituration was. repeated and the precipitate was redissolved and evaporated, first from methanol and then from chloroform to give yellow foam. Purified 3'-O-acetyl-5-(N-trifluoroaoctyl-3-amidopropynyl)-2'-deoxyuridine was obtained by silica gel column chromatography in dichloromethane/methanol (gradient: 95/5 to 89/11, v/v), The yield was. 0.37 g after rechromatography, eluting with a gradient in dichloromethane/methanol (98/2 to 95/5, v/v).

Example 51

Preparation of 5-(3-aminopropyl)-5'-triphosphate-2'-deoxyuridine, Triethylammonium Salt (Compound XI). $C_{12}H_{18}N_3O_{14}P_3$+n.$N(CH_2CH_3)_3$. Mw 824.78 q/mol for n=3. (Ludwig, J. and Eckstein, F. (1989) J. Org. Chem. 54, 631-635).

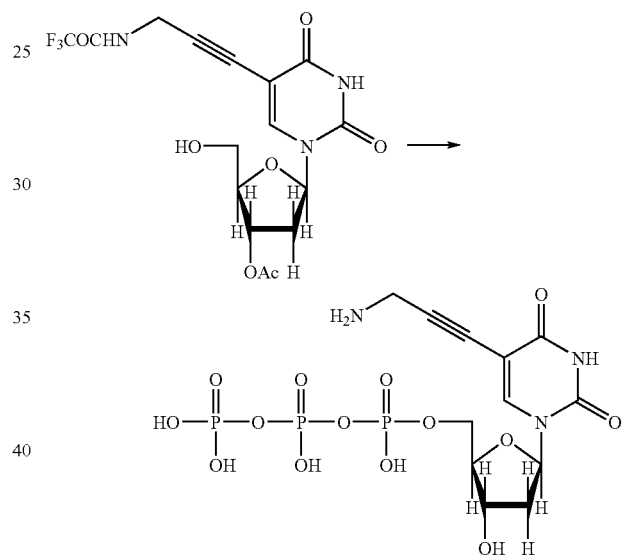

3'-O-Acetyl-5-(N-trifluoroacetyl-3-amidopropynyl)-2'-deoxyuridine (42.5 mg, 0.10 mmol) was dissolved in anhydrous pyridine (2 ml) and evaporated. The oil was dissolved in anhydrous pyridine (100 μl) and anhydrous dioxane (300 μl). A solution of 2-chloro-4H-1,3,2-benzodioxaphosphorin-4-one in dioxane (110 μl, 1 M, 0.11 mmol) was added under stirring and after 30 seconds precipitation of pyridinium hydrochloride was observed. The reaction mixture was stirred for 10 minutes at room temperature followed by simultaneous addition of bis(tri-n-butylammonium) pyrophosphate in DMF (300 μl, 0.5 M) and tri-n-butylamine (100 μl). Stirring was continued for 10 minutes and the intermediate was oxidized by adding an iodine solution (3 ml, 1% w/v in pyridine/water (98/2, v/v)) until permanent iodine colour. The reaction mixture was left for 15 minutes and then decolourized with sodium thiosulfate (4 drops, 5% aqueous solution, w/v). The reaction mixture was transferred to a round-bottom flask (50 ml) with water and evaporated to yellow oil. The oil was stirred in water (10 ml) for 30 minutes and concentrated aqueous ammonia (20 ml, 32%) was added.

This mixture was stirred for 1 hour at room temperature and then evaporated to an oil of the crude triphosphate product. The crude material was purified using a DEAE Sephadex A25 column (approximately 100 ml) eluted with a linear gradient of triethyl-ammonium hydrogencarbonate [TEAB] from 0.05 M to 1.0 M (pH approximately 7.5-8.0); flow 8 ml/fraction/15 minutes. The positive fractions were identified by RP18 HPLC eluting with a gradient from 10 mM TEAA (triethylammonium acetate) in water to 10 mM TEAA 20% water in acetonitrile. The appropriate fractions were pooled and evaporated. Yield approximately 90 mg.

Examples 52 to 54

Preparation of the Mononucleotide Building Block (XII)

Example 52

Succinic Acid mono-(3-tert-butoxycarbonylamino-propyl) Ester (Compound 12a)

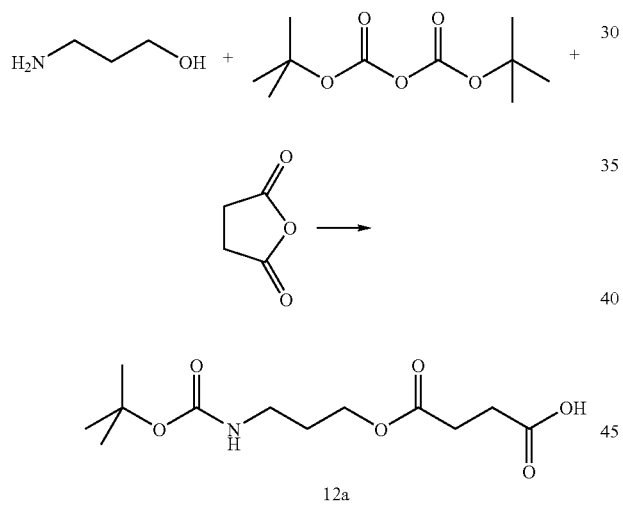

12a

Triethylamine (5.0 mL, 36 mmol) and di-tert-butyl dicarbonate (7.0 g, 32 mmol) were added to a solution of 3-aminopropanol (1.0 g, 26.6 mmol) in methanol (10 mL). The solution was stirred for 2 h. at room temperature. Methanol was evaporated off and the residue was dissolved in water (50 mL) and extracted with dichloromethane (50 mL). The organic phase was dried ($Na_2SO_4$) and concentrated in vacuo. The crude material was dissolved in dichloromethane (20 mL) and DMF (4 mL). Triethylamine (5.0 mL, 36 mmol) and succinic anhydride (3.0 g, 30 mmol) were added portion wise to the solution (exothermic reaction). The reaction mixture was stirred for 2 h, then concentrated and worked-up by RP-HPLC (eluent: water→methanol). Yield 6.0 g, 82%. $^1$H-NMR ($CDCl_3$): δ 4.2 (2H, $CH_2$), 3.2 (2H, $CH_2$), 2.7 (4H, 2×$CH_2$), 1.8 (2H, $CH_2$), 1.4 (9H, 3×$CH_3$).

9-[4-(Isopropyl-dimethyl-silanyloxy)-5-(isopropyl-dimethyl-silanyloxymethyl)-tetrahydro-furan-2-yl]-9H-purin-6-ylamine (Compound 12b)

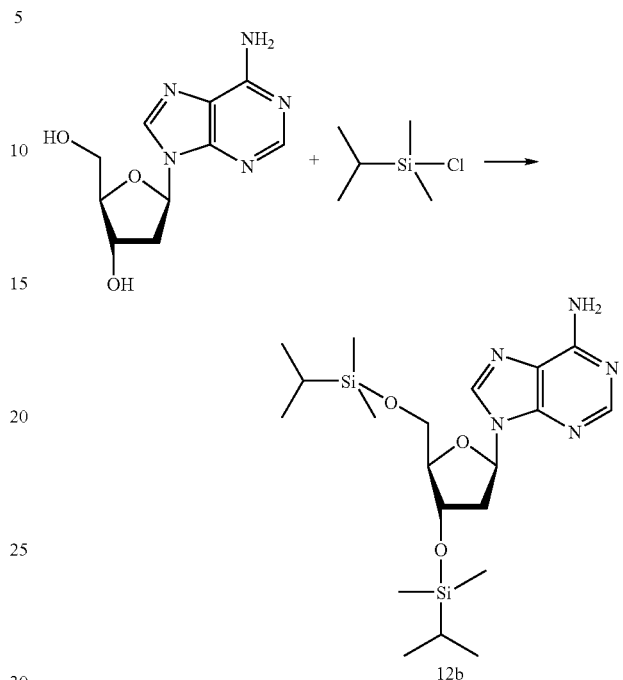

12b

Imidazole (2.0 g, 29.4 mmol) and tert-butyldimethylsilyl chloride (3.0 g, 19.9 mmol) were added to a solution of deoxyadenosine monohydrate (1.33, 4.94 mmol) in DMF (10 mL). The solution was stirred at 60° C. overnight. The mixture was concentrated to a solid in vacuo. Work-up by flash chromatography afforded crystalline compound 12b in a yield of 2.1 g, 94%. $^1$H-NMR ($CDCl_3$): δ 8.3 (1H, HC=), 8.1 (1H, HC=), 6.4 (1H, CH), 6.0 (2H, 2×OH), 4.6 (1H, CH), 4.1 (1H, CH), 3.9 (1H, CH), 3.8 (1H, CH), 2.6 (1H, $CH_2$), 2.4 (1H, $CH_2$), 0.9 (18H, 6×$CH_3$), 0.0 (12H, 4×$CH_3$).

Example 53

N-[9-(4-Hydroxy-5-hydroxymethyl-tetrahydrofuran-2-yl)-9H-purin-6-yl]-succinamic Acid 3-tert-butoxycarbonylamino-propyl Ester (Compound 12d)

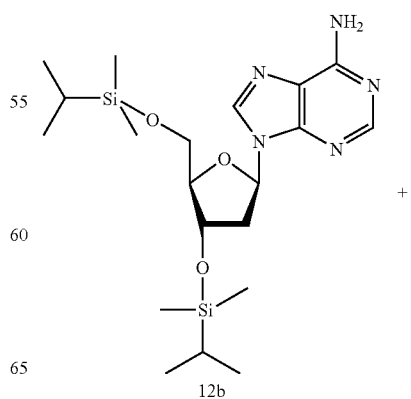

12b

167

-continued

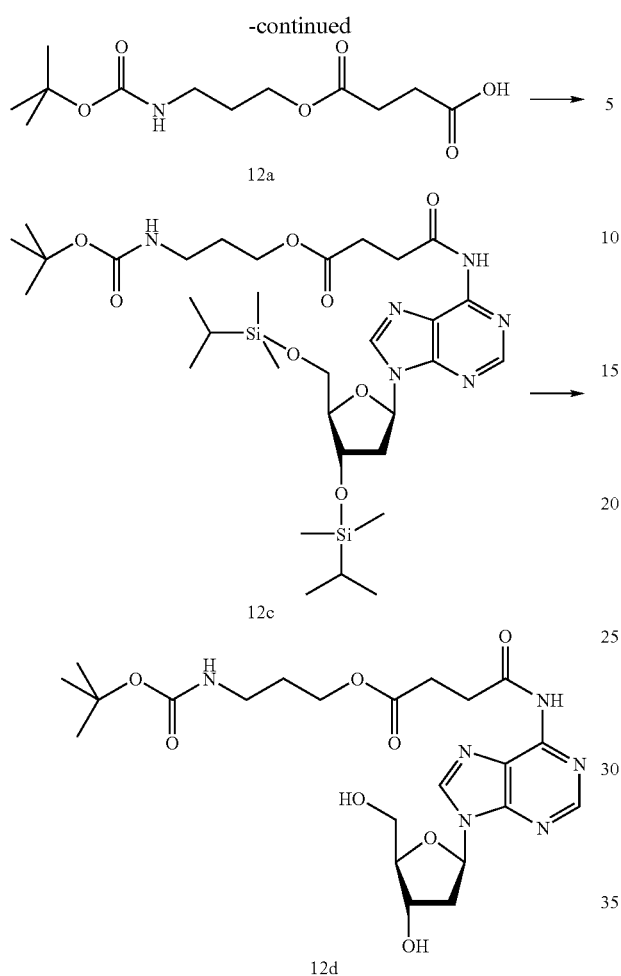

168

Example 54

N-[9-(4-Hydroxy-5-hydroxymethyl-tetrahydrofuran-2-yl)-9H-purin-6-yl]-succinamic Acid 3-tert-butoxy-carbonylamino-propyl Ester (Compound XII)

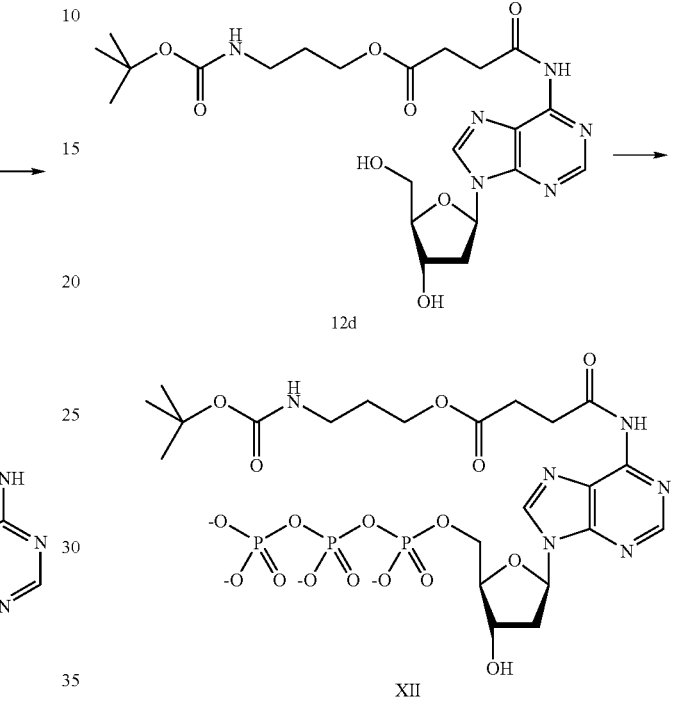

A solution of dicyclohexylcarbodiimide (366 mg, 1.78 mmol) in ethyl acetate (15 mL) was added to an ice-water cooled solution of 12a (488 mg, 1.78 mmol) in THF (10 mL). Few crystals of 4-dimethylaminopyridine and 12b (850 mg, 1.78 mmol) were added. The reaction temperature was slowly raised to room temperature and the mixture was stirred overnight. Precipitated salts were filtered off. The organic phase was washed with saturated NaHCO$_3$ (20 mL), dried (Na$_2$SO$_4$) and concentrated to a solid. Approximately 20 mg of 12c was isolated after flash chromatography and 510 mg of starting material 12b was regained. 12c (20 mg) was dissolved in THF (2 mL). Tetrabutylammonium fluoride, trihydrate (100 mg) and acetic acid (0.2 mL) were added. The mixture was stirred for 1 day, then concentrated in vacuo and worked-up by column chromatography. Yield 10 mg. Compound 12c $^1$H-NMR (CDCl3): δ 8.4 (1H, HC=), 8.2 (1H, HC=), 6.4 (1H, CH), 5.8 (2H, 2×OH), 4.6 (1H, CH), 4.2 (2H, CH$_2$), 4.1 (1H, CH), 3.8 (1H, CH), 3.7 (2H, CH$_2$), 3.0 (4H, 2×CH$_2$), 2.7 (3H, 2×CH$_2$), 2.4 (1H, CH$_2$), 1.8 (2H, CH$_2$), 1.4 (9H, 3×CH$_3$), 0.9 (18H, 6×CH$_3$), 0.0 (12H, 4×CH$_3$). Selected NMR data for 12d: $^1$H-NMR (MeOD-D$_3$): δ 4.6 (1H, CH), 4.1 (2H, CH$_2$), 3.8 (1H, CH), 3.7 (1H, CH), 3.6 (2H, CH$_2$), 3.2 (2H, CH$_2$), 3.0 (2H, CH$_2$), 2.8 (3H, 2×CH$_2$), 2.5 (1H, CH$_2$), 1.8 (2H, CH$_2$), 1.4 (9H, 3×CH$_3$).

LH8075b (10 mg) was converted to the corresponding triphosphate LH8075c using the procedure described for the synthesis of compound VII. TLC indicated full conversion of compound 12d.

Immediately prior to incorporation, the tert-butoxy group may be hydrolysed to release the free carboxylic acid. Alternatively, the tert-butoxy group may be cleaved after the formation of the templated molecule.

Example 55

N-[9-(4-Hydroxy-5-(O-triphosphate-hydroxymethyl)-tetrahydrofuran-2-yl)-9H-purin-6-yl]-succinamic Acid (Compound XIII)

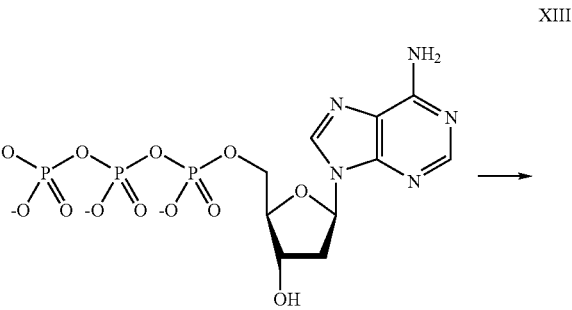

169

-continued

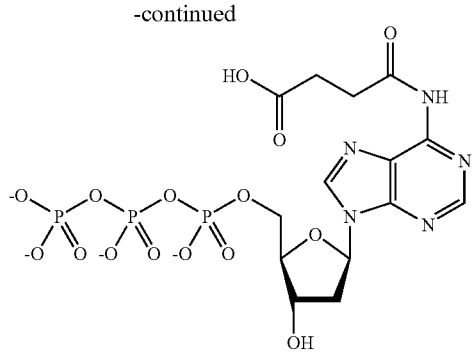

dATP (5 μmol) was suspended in DMF (4×1 mL) and concentrated to a solid in vacuo four times. The solid was suspended in DMF (1 mL). Succinic anhydride (5 mg, 0.05 mmol) was added at −20° C. The mixture was stirred for 3 h, and then concentrated to solid and purified by RP-HPLC (eluent: 0.1% HCOOH in water→10% methanol, 0.1% HCOOH in water). The purified material was dissolved in aqueous ammonia (25%, 1 mL) and stirred for 3 h. The mixture was concentrated in vacuo and worked-up by RP-HPLC (eluent: 0.1% HCOOH in water→10% methanol, 0.1% HCOOH in water). Comparison with starting material indicated that the product eluted 40s later off the column than the starting material.

Examples 56 and 57

Preparation of the Mononucleotide Building Block (XIV)

Example 56

Benzyloxy-ethynyl-diisopropyl-silane (Compound 14a)

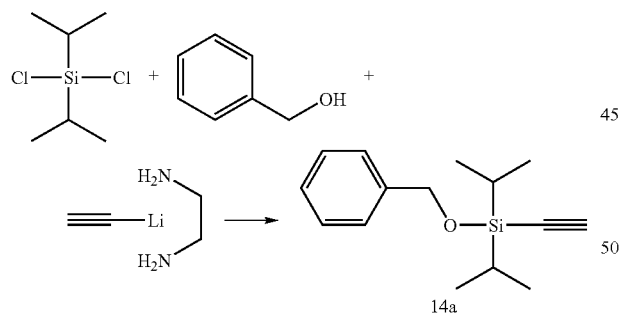

A solution of benzyl alcohol (0.1 mL, 1.0 mmol) in THF (0.5 mL) was added dropwise to a cooled (−78° C.) solution of diisopropylethylamine (1 mL), dichlorodiisopropylsilane (0.3 mL, 1.62 mmol) in THF (4 mL). The solution was stirred for 3 h (−78→−20° C.). The mixture was cooled down to −78° C. and lithiumacetylid-ethylendiamin-complex (250 mg, 2.71 mmol) was added. The reaction mixture was stirred for 5 h (−78→20° C.). Water (4 mL) was added. The mixture was extracted with dichloromethane (20 mL). The organic phase was dried (Na$_2$SO$_4$) and concentrated. Compound 14a (100 mg, 41%) was obtained after flash chromatography. $^1$H-NMR (CDCl3): δ 7.4 (5H, 5×HC≡), 5.0 (2H, CH$_2$), 2.6 (1H, CH), 1.0 (14H, 2×CH, 2×CH$_3$).

170

Example 57

5-{[Diisopropyl-(2-methylene-pent-3-enyloxy)-silanyl]-ethynyl}-1-(4-hydroxy-5-(O-triphosphatehydroxymethyl)-tetrahydrofuran-2-yl)-1H-pyrimidine-2,4-dione (Compound XIV)

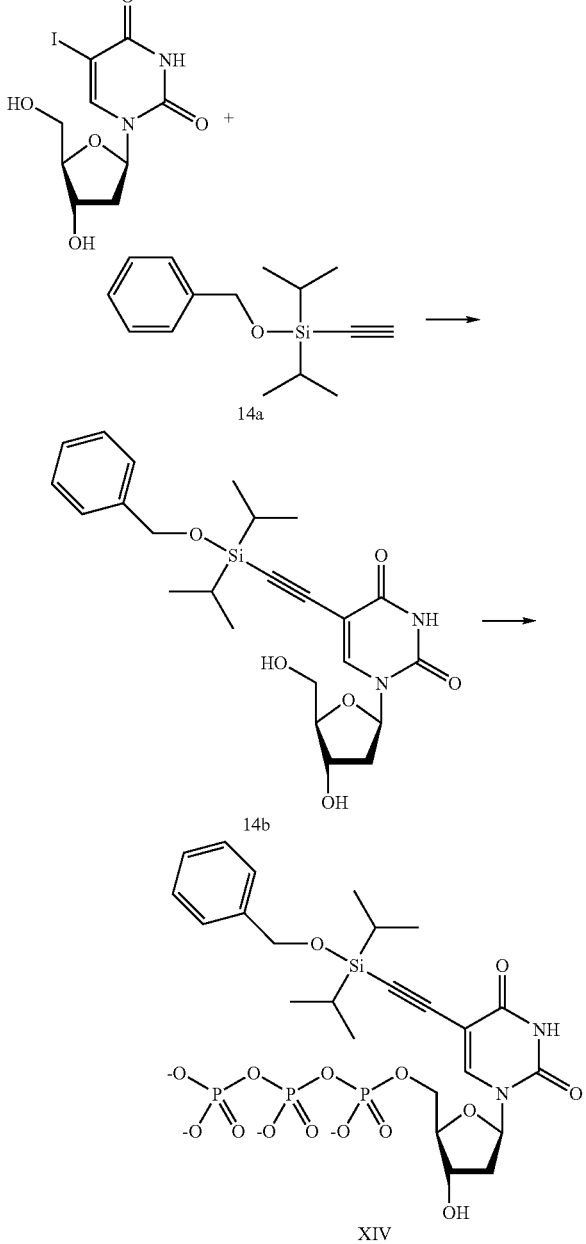

5-Iodo-dUTP (200 mg, 0.56 mmol), diisopropylethylamine (0.1 mL) and 14a (100 mg, 0.41 mmol) were dissolved in DMF (2 mL). Argon was bubbled through the solution for 5 min. Tetrakispalladium (57 mg, 0.49 mmol) and CuI (19 mg, 0.1 mmol) were added and the mixture was stirred at 50° C. for 5 h. Solvent was evaporated off and 14b was purified by flash-chromatography. A NMR spectrum revealed the syrup consisted of 66%. The syrup was (40 mg) was converted to the corresponding triphosphate (Compound XIV) using the procedure described for the synthesis of compound VII. TLC indicated full conversion of 14b. Selected NMR data for LH8061a: $^1$H-NMR (MeOD-D$_3$): δ: 8.3 (1H, HC≡), 7.3 (5 h, HC≡), 6.2 (1H, CH), 5.0 (2H, CH$_2$), 4.3 (1H, CH), 3.8-3.2 (3H, CH$_2$, CH), 2.3 (1H, CH$_2$), 2.2 (1H, CH$_2$), 1.0 (14H, 2×CH, 4×CH$_3$).
Examples 58 to 63
Preparation of the Mononucleotide Building Block (XV)
Building block XV may be prepared according to the general scheme shown below:
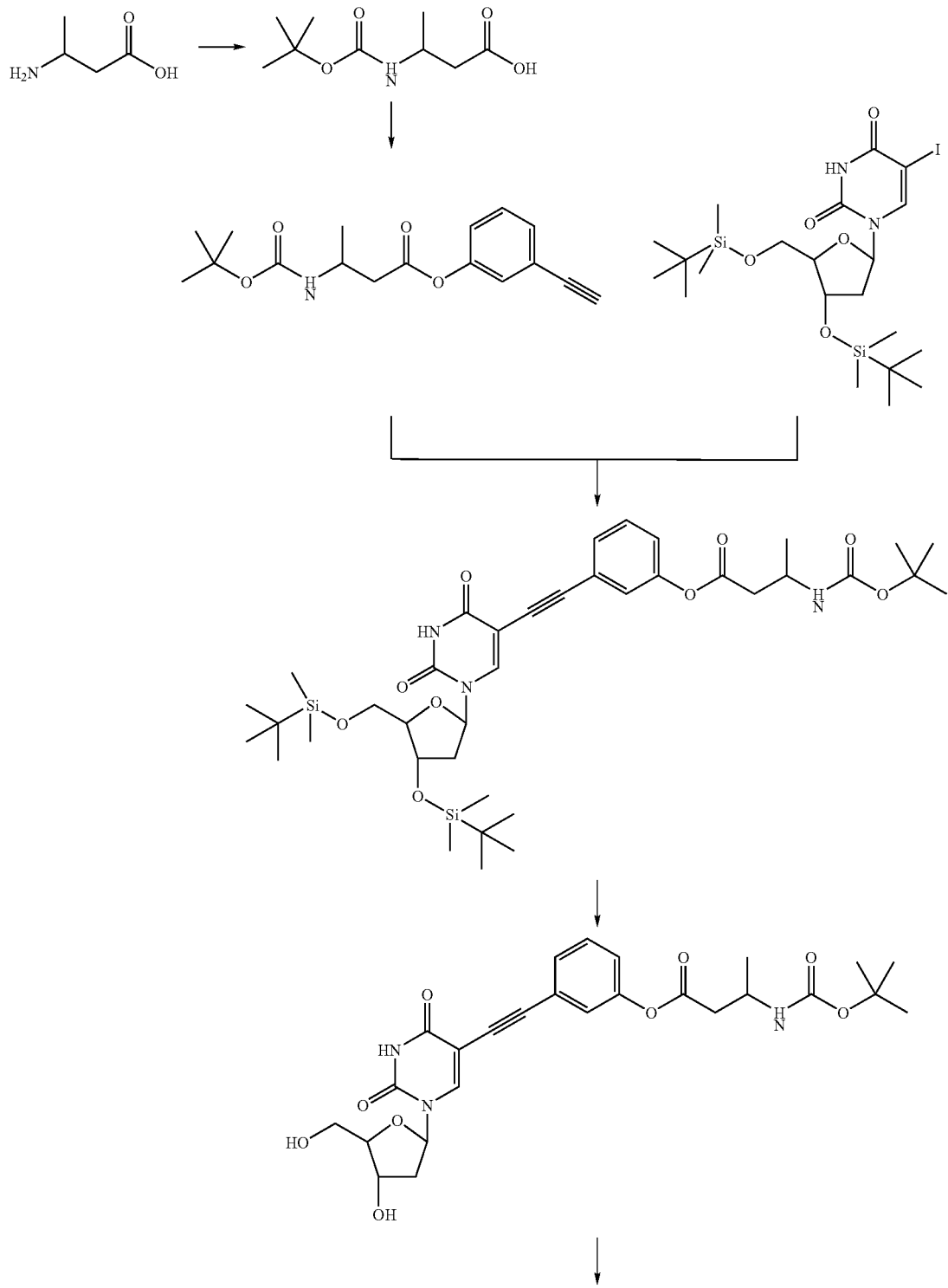

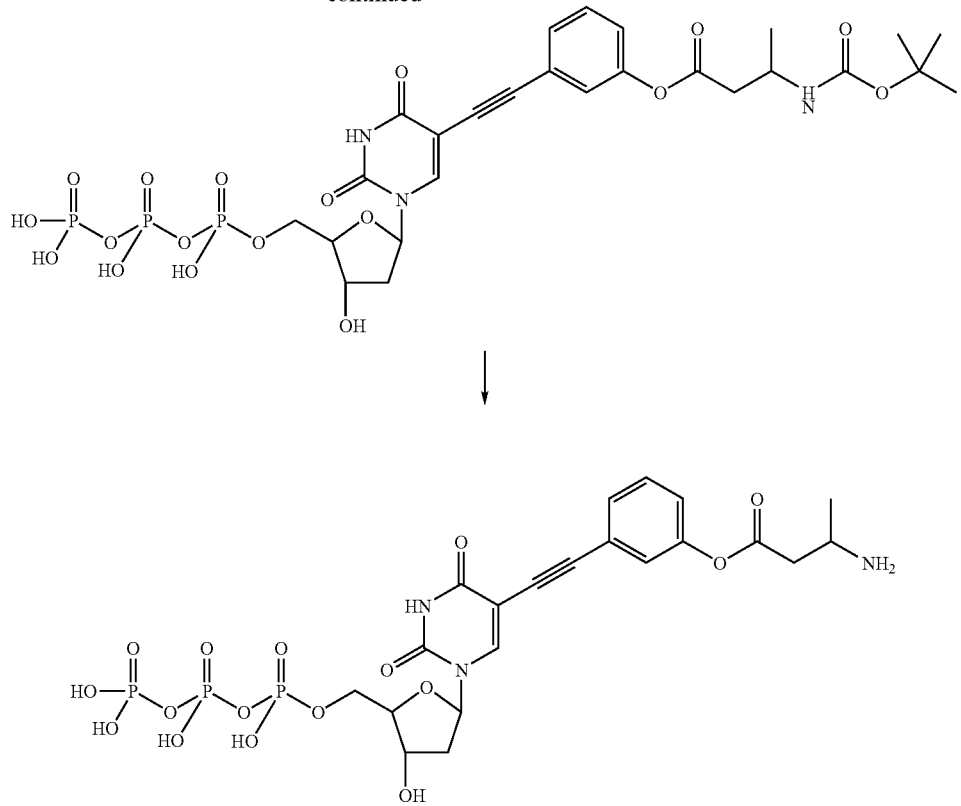

Example 58

Preparation of Compound 15a

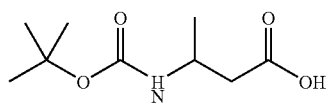
COMPOUND 15a

To a solution of 3-amino-butyric acid (2.06 g, 20 mmol) in NaHCO₃ (50% sat. aq, 25 mL) were added di-tert-butyl dicarbonate (4.36 g, 20 mmol) and acetonitrile (30 mL). The reaction mixture was stirred at room temperature for 18 h. Di-tert-butyl dicarbonate (4.36 g, 20 mmol) was added and the reaction mixture was stirred at room temperature for 18 h.

EtOAc (100 mL) was added and pH was adjusted to 4-5 by addition of NaH₂PO₄. The product was extracted into EtOAc (3×100 mL), dried (Na₂SO₄), and evaporated to dryness under vacuum to afford crude product 4.6 g (113%).

Example 59

Preparation of Compound 15b

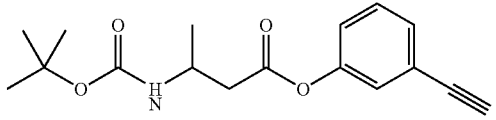
COMPOUND 15b

Compound 28 (1.023 g, 5.0 mmol), 3-Ethynyl-phenole (Lancaster, 0.675 g, 12 mmol) and 4-dimethylamino-pyridin (DMAP, 300 mg, 2.5 mmol) were dissolved in EtOAc (10 mL). Dicyclohexyl-carbodiimide (DCC, 2.06 g, 10 mmol) was added to the solution and after 16 h of stirring at room temperature, the reaction mixture was filtered and evaporated to dryness under vacuum. The crude product was purified by silica column chromatography eluting with EtOAc:Heptane gradient (1:3)-(1:2)(v/v). Product yield 720 mg, 73%.

¹H NMR (CDCl₃) δ 7.36-7.09 (4H, m, Ph), 4.89 (1H, bs, NH), 4.22 (1H, bm, CH), 3.10 (1H, s), 2.77 (2H, d), 1.40 (3H, t), 1.32 (3H, d).

Example 60

Preparation of Compound 15c

COMPOUND 15c

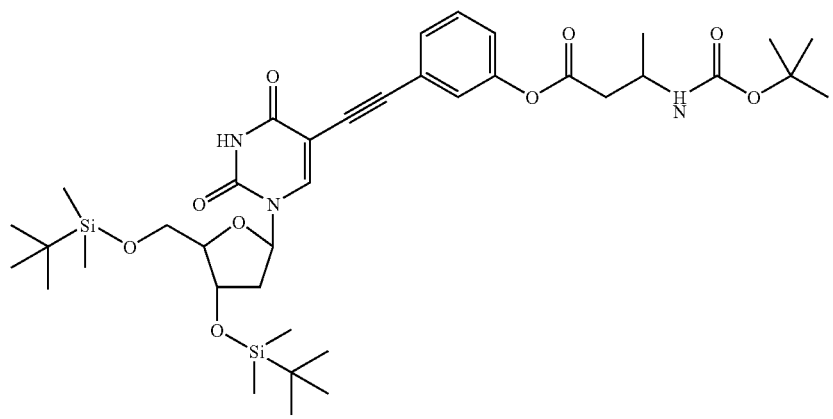

A solution of 5-Iodo-2'-deoxyuridine 3',5'-Di-tert-butyldimethylsilyl ether (730 mg, 1.25 mmol), triethylamine (250 mg, 2.5 mmol) and compound (15b) (456 mg, 1.5 mmol) in anhydrous DMF (3 mL) was stirred at room temperature. $N_2$ was passed through the solution for 20 min.

Tetrakis(triphenylphosphine)palladium(0) (109 mg, 0.094 mmol) and copper(I) iodide (36 mg, 0.188 mmol) were added and the reaction mixture was stirred at room temperature for 3 d.

The reaction mixture was evaporated and purified by silica column chromatography eluting with EtOAc:Heptane gradient (1:3)-(1:2)(v/v). Product yield 807 mg, 85%.

$^1$H NMR (CDCl$_3$) δ 8.38 (1H, s), 8.08 (1H, s, 6-H), 7.39-7.1 (4H, m, Ph), 6.33 (1H, dd, 1'-H), 4.9 (1H, bs), 4.45 (1H, dt), 4.80 (2H, s, CH$_2$), 4.2 (1H, m), 4.02 (1H, m, 4'-H), 3.95 (1H, dd, 5'-H), 3.79 (1H, dd, 5"-H), 2.78 (2H, d), 2.36 (1H, m, 2'-H), 2.07 (1H, m, 2"-H), 1.46 (9H, s, $^t$Bu), 0.93 (9H, s, $^t$Bu), 0.91 (9H, s, $^t$Bu), 0.15 (3H, s, CH$_3$), 0.13 (3H, s, CH$_3$), 0.11 (3H, s, CH$_3$), 0.09 (3H, s, CH$_3$).

Example 61

Preparation of Compound 15d

COMPOUND 15d

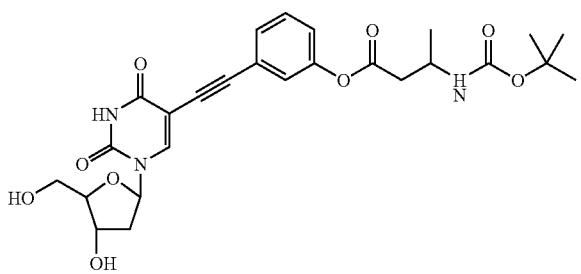

A solution of compound (15c) (807 mg, 1.06 mmol), glacial acetic acid (1.0 g, 16 mmol) and tetrabutylammonium fluoride trihydrate (TBAF) (2.36 g, 7.5 mmol) in 20 mL dry THF was stirred at room temperature for 3 d.

The reaction mixture was evaporated and purified by silica column chromatography eluting with (DCM):(MeOH) (9:1) (v/v). Product yield 408 mg, 72%.

$^1$H NMR (CD$_3$OD) δ 8.46 (1H, s, 6-H), 7.39 (2H, m, Ph), 7.28 (1H, m, Ph), 7.12 (1H, m, Ph), 6.75 (1H, bd), 6.27 (1H, dd, 1'-H), 4.44 (1H, dt, 4'-H), 3.96 (1H, t, 3'-H), 3.86 (1H, dd, 5'-H), 3.77 (1H, dd, 5"-H), 2.72 (2H, d), 2.35-2.27 (2H, m, 2', 2"-H), 1.46 (9H, s, $^t$Bu), 1.27 (3H, d).

Example 62

Preparation of Compound 15e

COMPOUND 15e

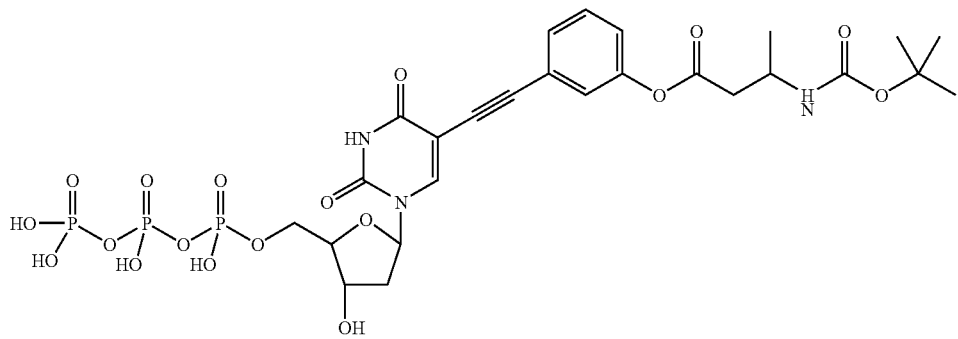

Compound (15d) (138.5 mg, 260 μmol) was dissolved in 500 μL dry trimethylphosphate. After cooling to 0° C., a solution of phosphorus oxychloride (POCl$_3$) in dry trimethylphosphate was added (400 μL stock solution (120 mg/mL), 310 μmol). The reaction mixture was stirred at 0° C. for 2 h.

Subsequently a solution of tributylammoniumpyrophosphate (200 mg, 420 μmol in 1.00 mL dry DMF) and tributylamine (123 mg, 670 μmol in 500 μL dry DMF) was added at 0° C. The reaction was stirred at room temperature for 3 min. and then stopped by addition of 1 mL 1.0 M triethylammoniumhydrogencarbonate.

Example 63

Preparation of Compound XV

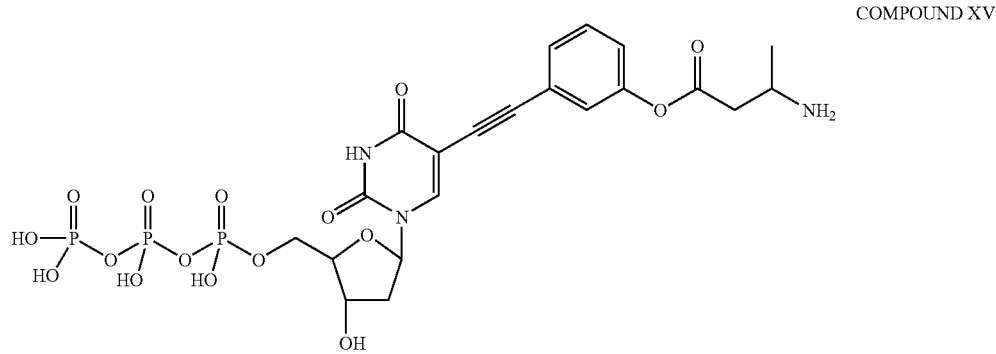

COMPOUND XV

Removal of N-Boc Protection Group.

Following phosphorylation, 50 μl of the phosphorylation reaction mixture is adjusted to pH=1 using HCl and incubated at room temperature for 30 minutes. The mixture is adjusted to pH 5.5 using equimolar NaOH and Na-acetate (pH 5.5) before purification on TLC.

Purification of Nucleotide Derivatives Using Thin-layer Chromatography (TLC)

From the crude mixture, 20 samples of 2 μl were spotted on kieselgel 60 F$_{254}$ TLC (Merck). Organic solvents and non-phosphorylated nucleosides were separated from the nucleotides derivatives using 100% methanol as running solution. Subsequently, the TLC plate is air-dried and the nucleotide-derivative identified by UV-shadowing. Kiesel containing the nucleotide-derivative was isolated and extracted twice using 10 mM Na-acetate (pH=5.5) as solvent. Kieselgel was removed by centrifugation and the supernatant was dried in vacuo. The nucleotide derivative was resuspended in 50-100 μl H$_2$O to a final concentration of 1-3 mM. The concentration of each nucleotide derivative was evaluated by UV-absorption prior to use in polymerase extension reactions.

Example 64

Polymerase Incorporation of Different Nucleotide Derivatives

Different extension primers were 5'-labeled with $^{32}$P using T4 polynucleotide kinase using standard protocol (Promega, cat# 4103). These extension primers was annealed to a template primer using 0.1 and 3 pmol respectively in an extension buffer (20 mM Hepes, 40 mM KCl, 8 mM MgCl$_2$, pH 7.4, 10 mM DTT) by heating to 80° C. for 2 min. and then slowly cooling to about 20° C. The wild type nucleotide or nucleotide derivatives was then added (about 100 μM) and incorporated using 5 units AMV Reverse Transcriptase (Promega, part# 9PIM510) at 30° C. for 1 hour. The samples were mixed with formamide dye and run on a 10% urea polyacrylamide gel electrophoresis. The gel was developed using autoradiography (Kodak, BioMax film). The incorporation can be identified by the different mobility shift for the nucleotide derivatives compared to the wild type nucleotide. FIG. 49 shows incorporation of various nucleotide derivates. In lane 1-5 the extension primer 5'-GCT ACT GGC ATC GGT-3' (SEQ ID NO:1) was used together with the template primer 5'-GCT GTC TGC AAG TGA TAA CCG ATG CCA GTA GC-3' (SEQ ID NO:2), in lane 6-11 extension primer 5'-GCT ACT GGC ATC GGT-3' (SEQ ID NO:3) was used together with the template primer 5'-GCT GTC TGC AAG TGA TGA CCG ATG CCA GTA GC-3' (SEQ ID NO:4), and in lane 12-15 the extension primer 5'-GCT ACT GGC ATC GGT-3' (SEQ ID NO:5) was used together with the template primer 5'-GCT GTC TGC AAG TGA CGT AAC CGA TGC CAG TAG C-3' (SEQ ID NO: 6). Lane 1, dATP; lane 2, Compound XI; lane 3, Compound IX; lane 4, Compound I; lane 5, Compound II; lane 6, no nucleotide; lane 7, dCTP; lane 8, Compound VII; lane 9, Compound X; lane 10, Compound IV; lane 11, Compound III; lane 12, no nucleotide; lane 13, dTTP; lane 14, dTTP and dATP; lane 15, dTTP and Compound X. These results illustrate the possibility to incorporate a variety of nucleotide derivatives of dATP, dTTP and dCTP using different linkers and functional entities. Other polymerases such as Taq, M-MLV and HIV have also been tested with positive results.

Example 65

Polymerase Incorporation and Hydrolysis of Nucleotide Derivatives Containing Cleavable Ester Linkers An extension primer (5'-GCT ACT GGC ATC GGT-3' SEQ ID NO:1)) was 5'-labeled with $^{32}$P using T4 polynucleotide kinase using standard protocol (Promega, cat# 4103) This extension primer was annealed with a template primer (5'-TAA GAC CGA TGC CAG TAG C-3' SEQ ID NO:7) using 0.1 and 3 pmol respectively in an extension buffer (20 mM Hepes, 40 mM KCl, 8 mM MgCl$_2$, pH 7.4, 10 mM DTT) by heating to 80° C. for 2 min. and then slowly cooling to about 20° C. The wild type nucleotide or nucleotide derivatives was then added (about 100 µM) and incorporated using 5 units AMV Reverse Transcriptase (Promega, part# 9PIM510) at 30° C. for 1 hour. Hydrolysed samples was treated with 0.1 M NaOH at 50° C. for about 15 min. and then titrated with equimolar HCl and NaoAc (pH 6.5) and purified by microspin gel filtration (BioRad). The samples were mixed with formamide dye and run on a 10% urea polyacrylamide gel electrophoresis. The gel was developed using autoradiography (Kodak, BioMax film). The incorporation can be identified by the different mobility shift for the nucleotide derivatives compared to the wild type nucleotide. FIG. 50 shows the incorporation of various nucleotide derivatives. Lane 1, compound III and Compound II; lane 2, compound III and two compound II; lane 3, hydrolysis of compound III and compound II; lane 4, hydrolysis of compound III and two compound II. The results show that these nucleotide derivatives can be incorporated by the polymerase in this specific order. It also shows that one or both the incorporated compound II nucleotide derivatives with an ester linker can specifically be hydrolysed on the DNA template and the incorporated compound III nucleotide derivative with no ester linker is intact. This illustrates the possibility to incorporate different nucleotide derivatives where one nucleotide derivative can function as the attachment point (non-cleavable linker) and at the same time liberate (cleavable linker) other incorporated nucleotide derivatives form the DNA template to create a displaying molecule. In addition, this experimental data shows that nucleotide derivatives with linkers containing cleavable ester can be inserted by the polymerase without reaction with amines in the active site of the polymerase or become hydrolysed during the incorporation process.

Example 66

Polymerase Incorporation and Cross-linking of Nucleotide Derivatives

An extension primer (5'-GCT ACT GGC ATC GGT-3' SEQ ID NO:1) was 5'-labeled with $^{32}$P using T4 polynucleotide kinase using standard protocol (Promega, cat# 4103). This extension primer was annealed with a template primer (5'-TAG ACC GAT GCC AGT AGC SEQ ID NO:8) using 0.1 and 3 pmol respectively in the extension buffer (20 mM Hepes, 40 mM KCl, 8 mM MgCl$_2$, pH 7.4, 10 mM DTT) by heating to 80° C. for 2 min. and then slowly cooled to about 20° C. The nucleotide derivatives was then added (about 100 µM) and incorporated using 5 units AMV Reverse Transcriptase (Promega, part# 9PIM510) at 30° C. for 1 hour. The oligonucleotides were then purified using micro-spin gel filtration (BioRad). Cross-linking was performed using 10 mM BS$_3$ (Pierce, cat# 21580) for about 1 hour at 30° C. The samples were mixed with formamide dye and run on a 10% urea polyacrylamide gel electrophoresis. The gel was developed using autoradiography (Kodak, BioMax film). FIGS. 51A and 51B shows the incorporation and cross-linking (CL) of various nucleotide derivatives. FIG. 51A: Lane 1, compound III and compound II; lane 2, cross-linked compound III and compound II. FIG. 51B: Lane 1, compound III and compound I; lane 2, cross-linked compound III and compound I. The results show that these nucleotide derivatives can be incorporated by the polymerase in this specific order. It also shows that compound III, compound II and compound I is modified by the cross-linking reagent BS$_3$ (mobility shift) and thereby permit cross-linking (CL) between reactive groups on the nucleotide derivatives compound III-compound II and compound III-compound I mediated by the DNA template. Importantly, the amide groups of the nucleotide derivatives in the major groove are selectively accessible for modifications which promote cross-linking between different incorporated nucleotide derivatives on the DNA template.

Example 67

Polymerase Incorporation of Various Nucleotide Derivatives

An extension primer (5'-TCC GCT ACT GGC ATC GGT-3' (SEQ ID NO:9)) was 5'-labeled with $^{32}$P using T4 polynucleotide kinase using standard protocol (Promega, cat# 4103). This extension primer was annealed with a template primer (5'-TGA ACC GAT GCC AGT AGC-5' SEQ ID NO:10) using 0.1 and 3 pmol respectively in the extension buffer (20 mM Hepes, 40 mM KCl, 8 mM MgCl$_2$, pH 7.4, 10 mM DTT) by heating to 80° C. for 2 min. and then slowly cooled to about 20° C. This template primer was 3'Biotin-C6-labeled to prevent extension. The nucleotide derivatives was then added (about 100 µM) and incorporated using 5 units AMV Reverse Transcriptase (Promega, part# 9PIM510) at 30° C. for 1 hour. The samples were mixed with formamide dye and run on a 10% urea polyacrylamide gel electrophoresis. The gel was developed using autoradiography (Kodak, BioMax film). FIG. 52 shows the incorporation of various nucleotide derivatives. Lane 1, wild-type dTTP, dCTP and dATP; lane 2, COMPOUND XI; lane 3; COMPOUND XI and compound III; lane 4, COMPOUND XI, compound III and dATP; lane 5, COMPOUND XI, compound III and compound XIII. The results show that it is possible to incorporate at least three different nucleotide derivatives after each other using a polymerase. Consequently, the polymerase allows various nucleotide derivatives simultaneously in the active site without a significant reduction of the catalytic activity.

Example 68

Polymerase Incorporation of Various Nucleotide Derivatives

An extension primer (5'-TCC GCT ACT GGC ATC GGT-3' SEQ ID NO:9) was 5'-labeled with $^{32}$P using T4 polynucleotide kinase using standard protocol (Promega, cat# 4103). This extension primer was annealed with a template primer (5'-TGA ACC GAT GCC AGT AGC-3' SEQ ID NO:10) using 0.1 and 3 pmol respectively in the extension buffer (20 mM Hepes, 40 mM KCl, 8 mM MgCl$_2$, pH 7.4, 10 mM DTT) by heating to 80° C. for 2 min. and then slowly cooled to about 20° C. This template primer was 3'Biotin-C6-labeled to prevent extension. The nucleotide derivatives was then added (about 100 µM) and incorporated using 5 units AMV Reverse Transcriptase (Promega, part# 9PIM510) at 30° C. for 1 hour. The samples were mixed with formamide dye and run on a 10% urea polyacrylamide gel electrophoresis. The gel was developed using autoradiography (Kodak, BioMax film). FIG. 53 show the incorporation of various nucleotide derivatives compared to wild type nucleotides. Lane 1, wild-type dCTP, dTTP and dATP; lane 2, compound II, compound III and compound XIII. The results show that it is possible to incorporate at least three different nucleotide derivatives after each other using a polymerase. Consequently, the polymerase allows various nucleotide derivatives simultaneously in the active site without a significant reduction of the catalytic activity.

Examples 69 to 74

Preparation of Polymerase Mediated Templated Molecules

Example 69

Crosslinking of Encoded Amino Groups by Urea-bond Formation

A primer (5'-TCC GCT ACT GGT ATC GGX-3' SEQ ID NO:11) where X denotes deoxy-thymidine-C6-NH$_2$, (Glen research, cat #10-1039-90) was 5'-labeled with $^{32}$P using T4 polynucleotide kinase using standard protocol (Promega, cat# 4103) and purified by micro-spin gelfiltration. This primer (0.1 pmol) and 2 pmol of a second primer (5'XCA CTT GCA GAC AGC-3'SEQ ID NO:12) were co-annealed with 1 pmol template primer (5'-GCT GTC TGC AAG TGA CCG ATG CCA GTA GC-3' SEQ ID NO:13) in a hybridisation-buffer (20 mM Hepes, 200 mM NaCl, pH 7.5) by heating to 80° C. for 2 min. and then slowly cooled to about 20 ° C. Subsequently, 10 mM of N',N'-CarbonylDiimidazole (Sigma-Aldrich) was added and the samples incubated at 30° C. for 2 hours. The samples were mixed with formamide dye and run on a 10% urea polyacrylamide gel electrophoresis. The gel was developed using autoradiography (Kodak, BioMax film). A schematic description of this experiment is shown below:

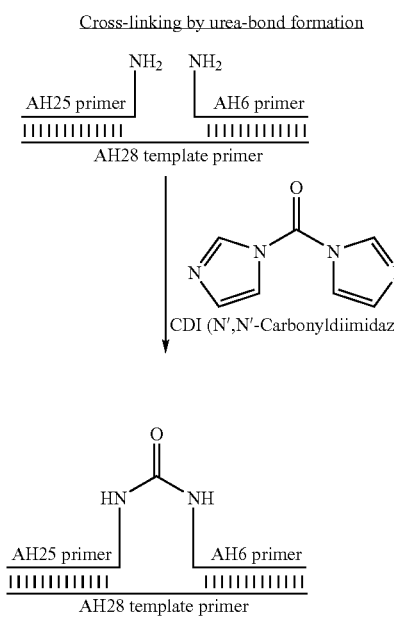

The results shows that adjacent NH2-groups can form a covalent urea-bond by the reaction with CDI. No reaction is observed in the absence of a template sequence which shows that the reaction is dependent on the close proximity of NH2-groups guided by the template sequence. Urea bond formation was also observed when 0.5% formaldehyde was used as cross-linking reagent (data not shown).

Example 70

Formation of Amide Bonds by a "Fill-in" Reaction Using a Di-amino Linker

In this experiment DNA-encoded Carboxylic acids are cross-linked by a 1,4 diaminobutane. A primer (5'-TCC GCT ACT GGT ATC GGY-3' SEQ ID NO:14) where Y denotes deoxy-thymidine-C2-COOH (Glen research, cat #10-1035-90), was 5'-labeled with $^{32}$P using T4 polynucleotide kinase using standard protocol (Promega, cat# 4103) and purified by microspin gelfiltration. This primer (0.1 pmol) and 2 pmol of a second primer (5'YCA CTT GCA GAC AGC-3' SEQ ID NO :15) were co-annealed with 1 pmol template primer (5'-GCT GTC TGC AAG TGA CCG ATG CCA GTA GC-3'SEQ ID NO:13) in a hybridisation-buffer (20 mM Hepes, 200 mM NaCl, pH 7.5) by heating to 80° C. for 2 min. and then slowly cooled to about 20° C. Subsequently, 100 mM EDC (Sigma-Aldrich), 10 mM N-hydroxysuccinimide (NHS, Sigma-Aldrich) and 10 mM 1,4 diaminobutane (Merck) was added and the samples incubated at 30° C. for 2 hours. The samples were mixed with formamide dye and run on a 10% urea polyacrylamide gel electrophoresis. The gel was developed using autoradiography (Kodak, BioMax film). A schematic description of this experiment is below:

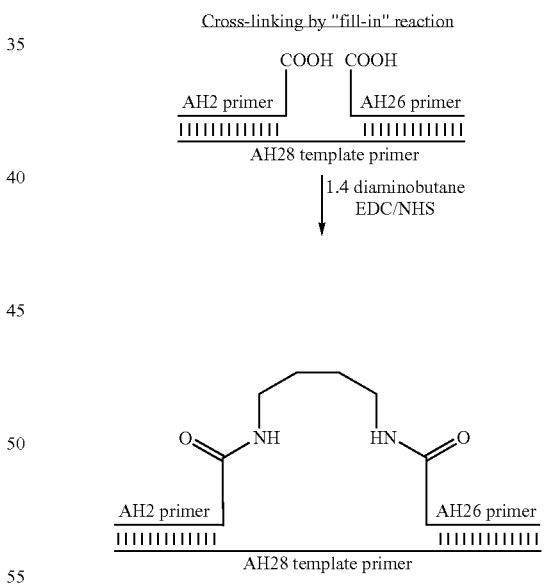

The results show that encoded COOH-groups can be covalently coupled by a bifunctional linker upon formation of amide bonds. No reaction is observed in the absence of a template sequence which shows that the reaction is governed by the proximity of COOH-groups provided by the template sequence. Similar results were obtained using other diamino-linkers such as 1.6 diaminohexane, spermine and spermidine (data not shown).

Example 71

Polymerase Incorporation of Nucleotide Derivatives and Cross-linking to Templated Anchor-points An extension primer (5'-GCT ACT GGC ATC GGT-3' SEQ ID NO:1) was 5'-labeled with $^{32}$P using T4 polynucleotide kinase using standard protocol (Promega, cat# 4103). This extension primer was annealed with a template primer (5'-GCT GTC TGC AAG TGA TAA CCG ATG CCA GTA GC-3' SEQ ID NO:3) using 0.1 and 3 pmol respectively in the extension buffer (20 mM Hepes, 40 mM KCl, 8 mM MgCl$_2$, pH 7.4, 10 mM DTT) by heating to 80° C. for 2 min. and then slowly cooled to about 20° C. The nucleotide derivatives was then added (about 100 µM) and incorporated using 5 units AMV Reverse Transcriptase (Promega, part# 9PIM510) at 30° C. for 1 hour. The oligonucleotide complexes were then purified using micro-spin gel filtration (BioRad). A second primer (5-YCA CTT GCA GAC AGC-3' SEQ ID NO:15) where Y denotes the anchor-point reactive group deoxythymidine-C$_2$-COOH, was annealed to the extension complex. The buffer composition was adjusted to 20 mM HEPES-KOH, 200 mM NaCl, pH=7.5 Cross-linking was performed using 100 mM EDC and 10 mM N-hydroxysuccinimid for about 2 hours at 30° C. Relevant samples were subjected to alkaline hydrolysis (0.1 M NaOH, 50° C. for 15 minutes). The samples were mixed with formamide dye and run on a denaturing 10% urea polyacrylamide gel. The gel was developed using autoradiography (Kodak, BioMax film). A schematic outline of this experiment is shown below:

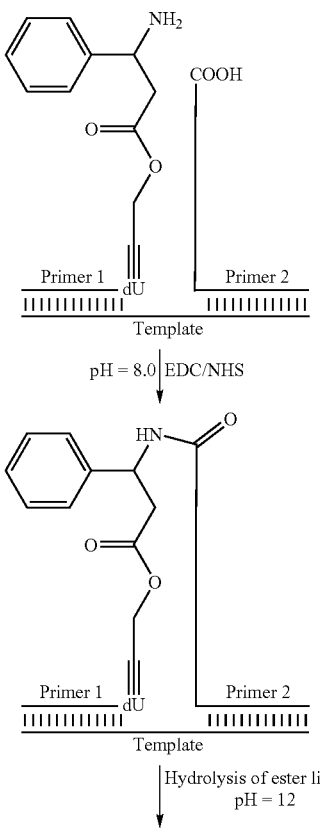

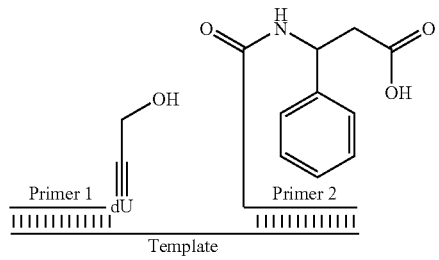

The results show that a reactive group from a nucleotide derivative incorporated by a polymerase can be cross-linked to an anchor point reactive group by a "fill-in" reaction forming amide bonds. Furthermore, the ester linker of the nucleotide derivative is specifically cleaved which allows for the transfer of a templated functional entity to a templated second entity (anchor point).

Example 72

Polymerase Incorporation of Nucleotide Derivatives and Cross-linking to a Templated Anchor-point by a "Fill-in" Reaction An extension primer (5'-GCT ACT GGC ATC GGT-3' SEQ ID NO:1) was 5'-labeled with $^{32}$P using T4 polynucleotide kinase using standard protocol (Promega, cat# 4103). This extension primer was annealed with a template primer (5'-GCT GTC TGC AAG TGA TAA CCG ATG CCA GTA GC-3' SEQ ID NO:3) using 0.1 and 3 pmol espectively in the extension buffer (20 mM Hepes, 40 mM KCl, 8 mM MgCl$_2$, pH 7.4, 10 mM DTT) by heating to 80° C. for 2 min. and then slowly cooled to about 20° C. The compound II (nucleotide derivative) was then added (about 100 µM) and incorporated using 5 units AMV Reverse Transcriptase (Promega, part# 9PIM510) at 30° C. for 1 hour. The oligonucleotide complexes were then purified using micro-spin gel filtration (Bio-Rad). A second primer (5-XCA CTT GCA GAC AGC-3' SEQ ID NO:12) where X denotes the anchor-point reactive group deoxythymidine-C6-NH$_2$, was annealed to the extension complex. Cross-linking was performed using 10 mM BS$_3$ (Pierce, cat# 21580) for about 2 hours at 30° C. Relevant samples were subjected to alkaline hydrolysis (0.1 M NaOH, 50° C. for 15 minutes). The samples were mixed with formamide dye and run on a denaturing 10% urea polyacrylamide gel. The gel was developed using autoradiography (Kodak, BioMax film). A schematic outline of this experiment is shown below:

Linking by "fill-in" and β-Amino acid translocation
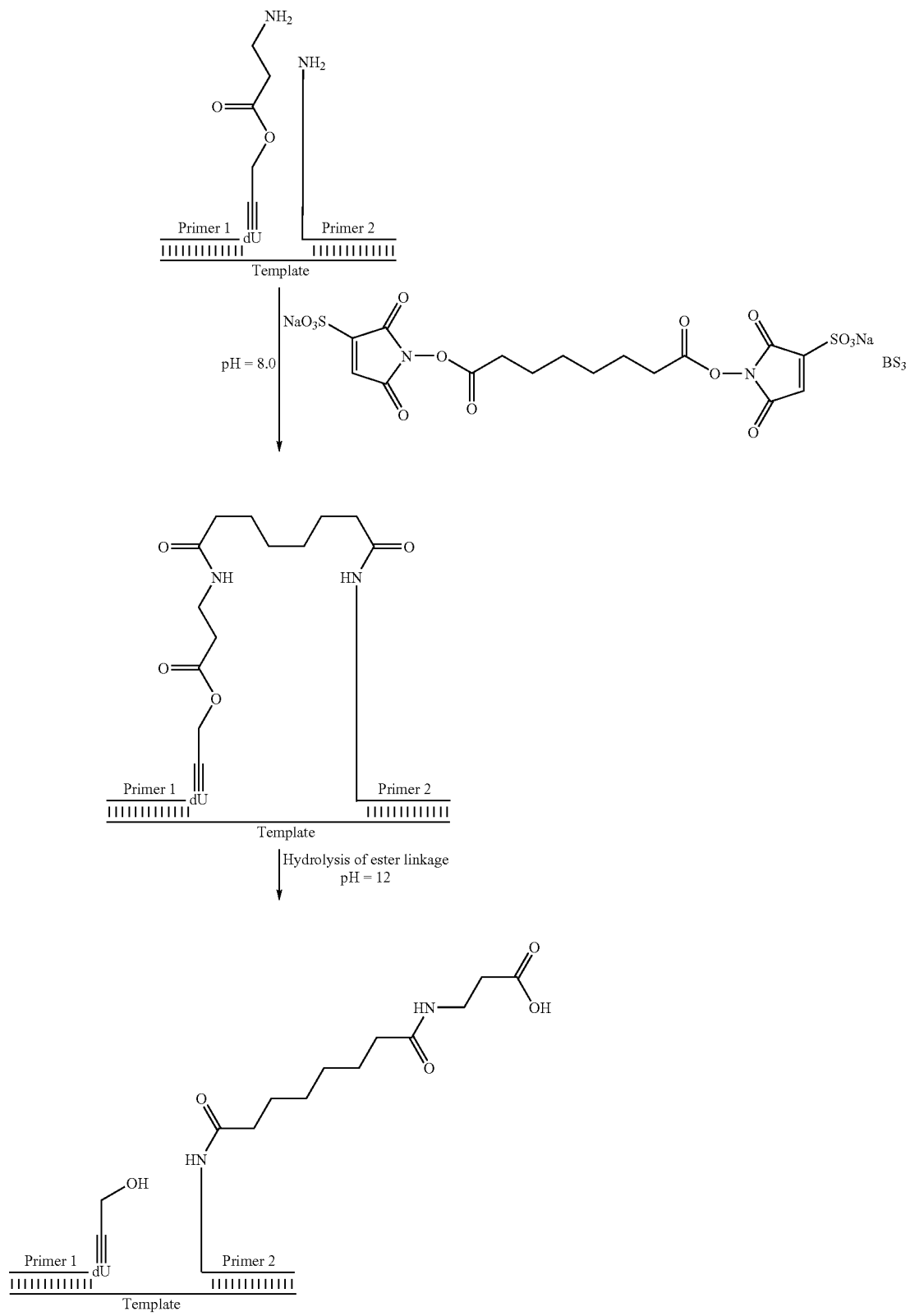

A copy of the gel is shown in FIG. 54. Lane 1: no nucleotides, lane 2: dTTP, lane 3: compound I, lane 4: dTTP followed by alkaline hydrolysis, lane 5: compound I followed by alkaline hydrolysis, lane 6: dTTP followed by BS₃ cross-linking, lane 7: compound I followed by BS₃ cross-linking, lane 8: dTTP followed by BS₃ cross-linking and alkaline hydrolysis, and lane 9: compound I followed by BS₃ cross-linking and alkaline hydrolysis. The results show that a reactive group from a nucleotide derivative incorporated by a polymerase can be cross-linked to an anchor point reactive group by a "fill-in" reaction forming amide bonds. Furthermore, the ester linker of the nucleotide derivative is specifically cleaved which allows for the transfer of a templated functional entity to a templated second entity (anchor point).

Example 73

Polymerase Incorporation of Two Nucleotide Derivatives and the Cross-linking Between 3 Encoded Entities An extension primer (5'-GCT ACT GGC ATC GGT-3' SEQ ID NO:16) was 5'-labeled with $^{32}$P using T4 polynucleotide kinase using standard protocol (Promega, cat# 4103). This extension primer was annealed with a template primer (5'-GCT GTC TGC AAG TGA GTA CCG ATG CCA GTA GC-3' SEQ ID NO:17) using 0.1 and 3 pmol respectively in the extension buffer (20 mM Hepes, 40 mM KCl, 8 mM MgCl₂, pH 7.4, 10 mM DTT) by heating to 80° C. for 2 min. and then slowly cooled to about 20° C. The nucleotide derivative V and X was then added (about 100 µM) and incorporated using 5 units AMV Reverse Transcriptase (Promega, part# 9PIM510) at 30° C. for 1 hour. The oligonucleotide complexes were then purified using micro-spin gel filtration (BioRad). A second primer (5-YCA CTT GCA GAC AGC-3' SEQ ID NO:15) where Y denotes the anchor-point reactive group deoxythymidine-C₂-COOH, was annealed to the extension complex. The buffer composition was adjusted to 20 mM HEPES-KOH, 200 mM NaCl, pH=7.5 before addition of 100 mM EDC and 10 mM N-hydroxysuccinimid. This results in the cross-linking of NH₂-groups of MG91 and the COOH group of V and the COOH of the second primer. Suitable samples were subjected to alkaline hydrolysis (0.1 M NaOH 50° C., 15 minutes). Formamide dye was added to the samples before loading on a 10% Urea polyacrylamide gel. The gel was developed using autoradiography (Kodak, BioMax film). A schematic representation of this experiment is shown below:

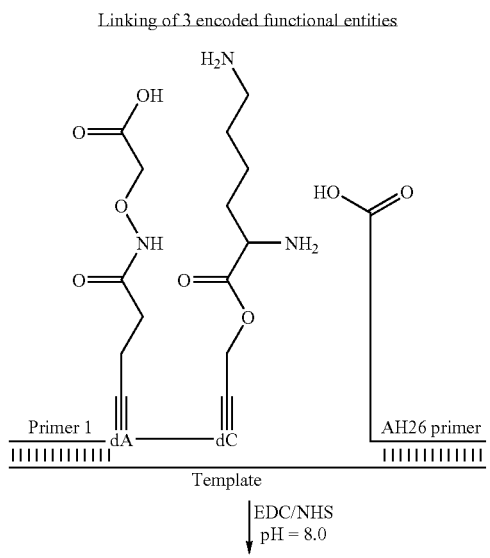

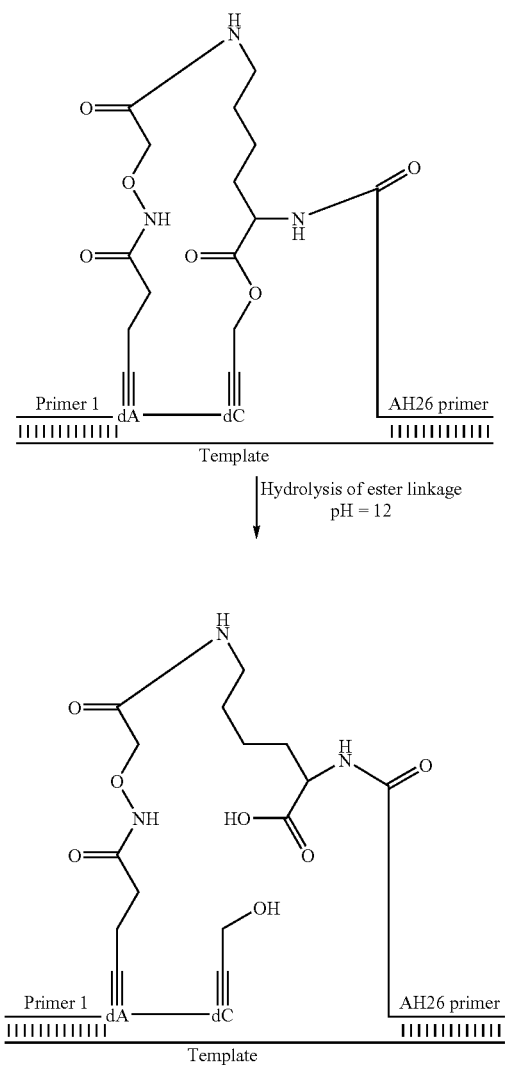

This result shows that three encoded functional entities can be cross-linked. Furthermore, a specific linker can be selectively cleaved.

Example 74

Polymerase Incorporation and β-Amino Acid Translocation ("Zipping")

An extension primer (5'-GCT ACT GGC ATC GGT-3' SEQ ID NO:16) was 5'-labeled with $^{32}$P using T4 polynucleotide kinase using standard protocol (Promega, cat# 4103). This extension primer was annealed with a template primer (5'-TAG ACC GAT GCC AGT AGC SEQ ID NO:8) using 0.1 and 3 pmol respectively in the extension buffer (20 mM Hepes, 40 mM KCl, 8 mM MgCl₂, pH 7.4, 10 mM DTT) by heating to 80° C. for 2 min. and then slowly cooled to about 20° C. The nucleotide derivatives II and III was then added (about 100 µM) and incorporated using 5 units AMV Reverse Transcriptase (Promega, part# 9PIM510) at 30° C. for 1 hour. The oligonucleotides were then purified using micro-spin gel filtration (BioRad) followed by lyophilization. The oligonucleotide complex was dissolved in pyridine and Scandiumtriflourmethanesulphonate (catalyst) in pyridine was added to a final concentration of 10 mM and the reaction mixture incubated at 50° C. for 1 hour. Relevant samples were subjected to alkaline hydrolysis using 0.1 M NaOH at 50° C. for 15 min. Formamide dye was added to the samples before loading on a 10% Urea polyacrylamide gel. The gel was developed using autoradiography (Kodak, BioMax film). A schematic representation is shown below:

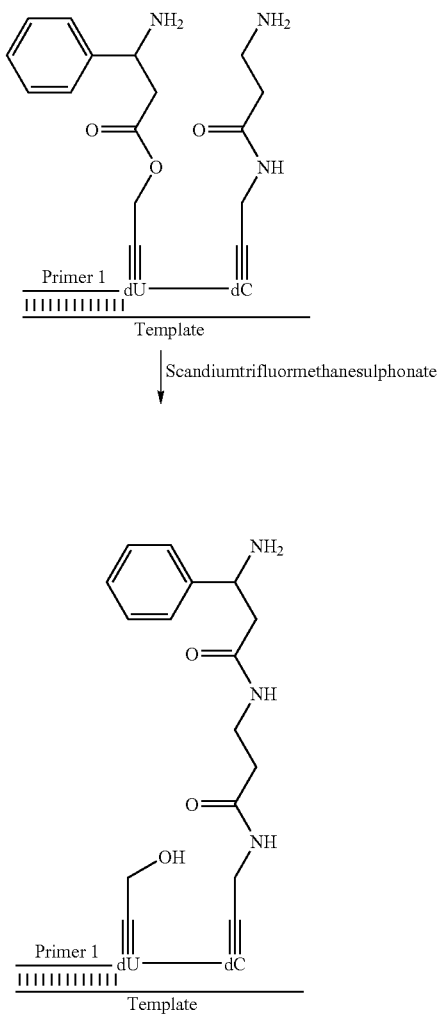

The results show that a reactive group of a functional entity can react with a reactive group of an other functional entity forming an amide bond. The reaction results in a translocation of a functional entity onto a second functional entity with simultaneous cleavage of the linker connecting the first functional entity and the nucleotide derivative that encode said functional entity. In this experimental set-up a di-peptide comprising two β-amino acids is produced. Thus, incorporation on a DNA template of several (3 or more) nucleotide derivatives comprising β-amino-acids as functional entities would allow multiple translocation events producing β-peptides acids comprising 3 or more β-amino acids. In this example the reaction between functional entity reactive groups occurs in non-aqueous environment. In a preferred aspect the reaction between functional entity reactive groups occurs directly upon incorporation of a nucleotide derivative comprising said function entity by a "zipping" reaction. This can be accomplished by increasing the reactivity of the ester linkage by introducing various chemical entities such as thioesters, phenolic esters, thiophenolic esters, di-5, tri- or tetra-fluoro-activated phenolic- or thiophenolic esters or N-hydroxysuccimide esters.

Example 75

In Silico Experiment A Structural Description of a Template-displayed Molecule Created Using Polymerase Incorporation of Nucleotide Derivatives One aspect of the present invention utilizes a suitable polymerase for specific incorporation of nucleotide derivatives on a DNA template. This incorporation is accomplished using a template containing coding elements. The template is utilized by the polymerase to incorporate the nucleotide derivatives in a specific order based on these coding elements (FIG. 55). This process is specific due to the recognition groups in the nucleotide derivatives.

The different nucleotides are modified at specific positions (e.g. FIG. 9) to permit incorporation by the polymerase and at the same time expose the linked functional entities in or outside the major groove of the DNA strand exposed to the solvent as shown in FIG. 55A. The consecutive incorporation of the nucleotide derivatives by the polymerase will allow various reactions to occur between the linked functional entities. The reactions are determined by the type of reactive groups integrated in each functional entity (examples shown in FIGS. 11-21). In addition, the DNA template will arrange the functional entities in specific geometry dependent on the helical structure of the DNA template. This geometry can for example be controlled by different types of linkers that join the functional entity and complementing element. Thus, the linker is designed to favour the reaction between the reactive groups on the nucleotide derivatives. The linker design will differ dependent on which type and how the reactive groups are arranged in the functional entities. The linker can also be designed to guide the reaction between the reactive groups in a specific direction. Various reactive groups can also be used to direct the reaction between the reactive groups. The close proximity and the optimized geometry of the nucleotide derivatives will drastically enhance the reaction rate between the reactive groups in the different functional entities. The reaction rate between the reactive groups is fast due to the high local concentration of the incorporated nucleotide derivatives on the DNA template molecule compared to if they were allowed to diffuse freely in solution.

FIG. 55A shows one example where nucleotide derivatives Compound II, compound X and compound V are incorporated by a polymerase after each other on the same DNA template. The synthesis of these nucleotide derivatives are described in detail above. The experimental data showing AMV Reverse transcriptase incorporation of these nucleotide derivatives can be seen in example 64. These incorporated nucleotide derivatives are structurally arranged, by the linker connecting the complementing element and the functional entity, to promote reaction between the reactive groups on each nucleotide derivatives. The distance between the amine in compound II and the COMPOUND X amine in the long side chain is calculated to be between 3.1 Å and 17.5 Å and the distance between the amine in compound II and the COMPOUND X amine in the short side chain to be between 3.0 Å and 14.6 Å dependent on the precise orientation of the linker and the functional entity on the DNA template. The distance between the carbonyl carbon in nucleotide derivative compound V and the long side chain amine in nucleotide derivative COMPOUND X is between 4.2 Å and 19.8 Å and the distance to the short side chain COMPOUND X amine is calculated to be between 3.7 Å and 16.5 Å also dependent of the precise orientation. The close proximity of the nucleotide derivatives compound II, COMPOUND X and 1973 on the DNA template will promote a chemical linkage of the reactive groups in these nucleotide derivatives.

These three nucleotide derivatives can be linked together through their reactive groups using various chemical reagents. One possible reagent to use is $BS_3$ [Bis(sulfonyl-succinimide)suberate] (Pierce, cat# 21580). Typically a concentration of about 0.25-10 mM is used of this analog. This reagent will cross-link two amines between nucleotide derivatives compound II and COMPOUND X. This particular reagent will insert a spacer of eight carbons between the reactive groups and is capable of bridging a distance of 11.2 Å in the extended conformation. Thus, the $BS_3$ linker is capable of linking the amines of compound II and either of the amines of compound X. There are other reagents that could be used (longer or shorter) to obtain almost any type of spacers between the reactive amine groups. The carboxylic acid on nucleotide derivative compound V and one of the amines on nucleotide derivative COMPOUND X can be linked together using for example 1-Ethyl-3-(3-dimethylaminopropyl) carbodiimide (EDC) and N-Hydroxysuccinimide (NHS). This reaction will make a direct connection between the reactive groups on nucleotide derivatives COMPOUND X and compound V. These two reactions result in a new molecule composed of these nucleotide derivatives covalently attached to each other through the coupling reagents (FIG. 55B). This particular DNA template-mediated molecule is produced using both fill-in ($BS_3$) and direct coupling (EDC/NHS) chemistry. Examples of cross-linking between incorporated nucleotide derivatives are shown above. Other types of coupling approaches that could be used are zipping by translocation or ring opening. These coupling strategies need other types of linker design as described in this invention.

At this stage, all the functional entities are still attached to the DNA template through the linker joining the functional entity and the complementing element. The ester element integrated in the linker of nucleotide derivatives compound II and COMPOUND X can specifically be hydrolysed (see example 65 for experimental details) to liberate the functional entities of these two nucleotide derivatives from the DNA template. This hydrolysis reaction results in a new molecule that is only attached to the DNA template through the linker in the compound V nucleotide derivative (FIG. 55C). This molecule can then extend out from the DNA template into the solution and become accessible (displayed) for interaction with other molecules in the solution.

This templated molecule, as part of a library of many different templated molecules, can finally be used in a selection procedure to identify molecules that bind to various targets. A detailed description of the selection procedure can be found elsewhere herein.

Example (Model) 76

PNA Synthesis—base Linked

PNA monomers are linked to complementing elements via cleavable benzyl- or benzyloxycarbonyl moieties bound to the base part of each PNA monomer. A carboxylic acid is used as anchor point to the oligonucleotide complex. Each building block is annealed to a oligonucleotide template (not shown).

Step A: Polymerization

To an aqueous buffered solution (10 uL, 1M NaCl, 100-500 mM buffer pH 6-10, preferably 7-9) of oligonucleotide complexes (0.1-100 uM, preferably 0.5-10 uM) is added a peptide coupling reagent (0.1 mM-100 mM, preferably 1-10 mM) exemplified by but not limited to EDC, DCC, DIC, HATU, HBTU, PyBoP, PyBroP or N-methyl-2-chloropyridinium tetrafluoroborate and a peptide coupling modifier (0.1 mM-1 uM, preferably 1-10 mM) exemplified by but not limited to NHS, sulpho-NHS, HOBt, HOAt, or DhbtOH in a suitable solvent (1 uL) e.g. water, methanol, ethanol, dimethylformamide, dimethylsulfoxide, ethylene glycol, acetonitrile or a mixture of these. Reactions run at temperatures between −20° C. and 60° C. Reaction times are between 1 h and 1 week, preferably 1 h-24 h.

The above procedure exemplifies the polymerisation on an 11 uL scale, but any other reaction volume between 1.1 uL and 1.1L may be employed.

Step B: Linker Cleavage and Deprotection

Cbz- and Benzyl protective groups may be removed by a variety of methods, [Greene;1999;] Due to its mildness, catalytic reduction is often the method of choice. Combining an insoluble hydrogenation catalyst e.g. $Pd/Al_2O_3$, $Pd/CaCO_3$, Pd/C, $PtO_2$, or a soluble one e.g. Wilkinsons catalyst and a hydrogen source exemplified but not limited to $H_2$, ammonium formiate, formic acid, 1,4-cyclohexadien, and cyclohexene in a suitable solvent like water, methanol, ethanol, dimethylformamide, dimethylsulfoxide, ethylene glycol, acetonitrile, acetic acid or a mixture of these with the oligo nucleotide complexes removes the Cbz- and benzyl protective groups.

193 194
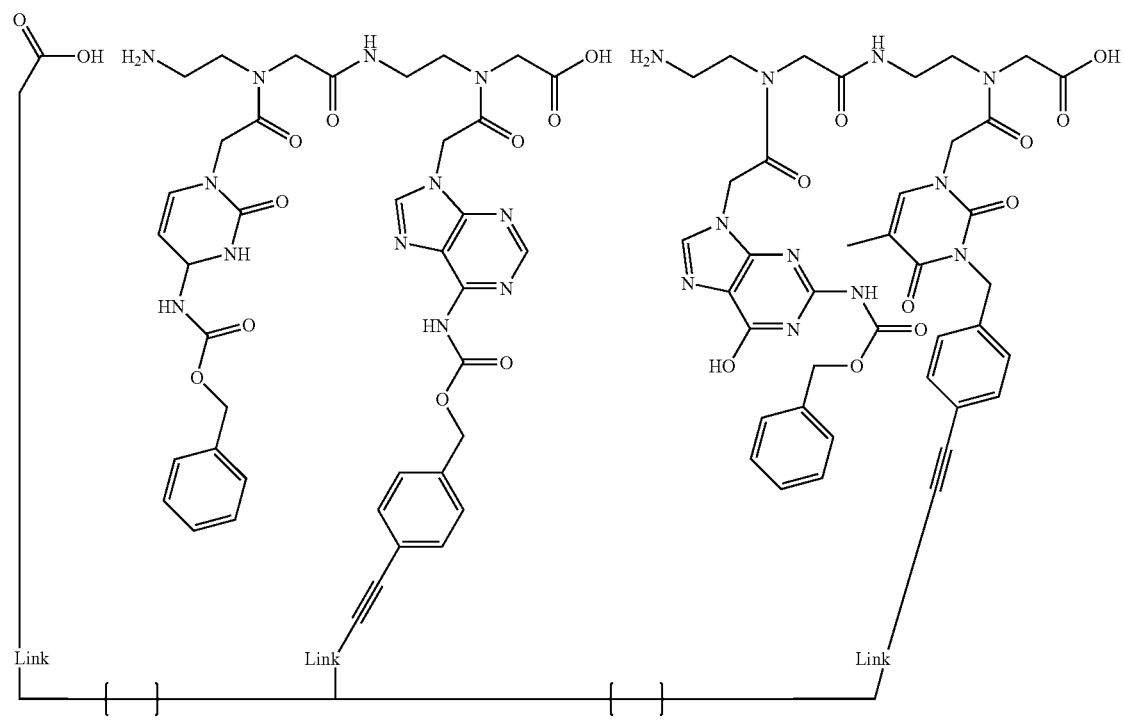
Step A
Peptide
Coupling
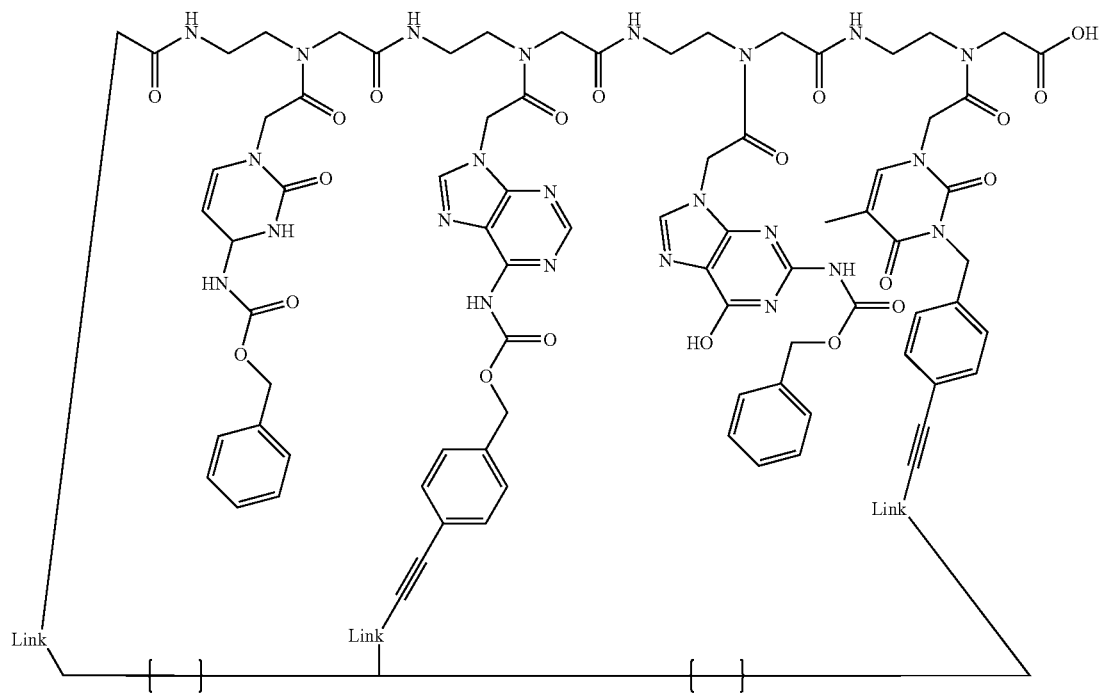
Step B
Activate
(Cleave
Linkers)
and deprotect
bases

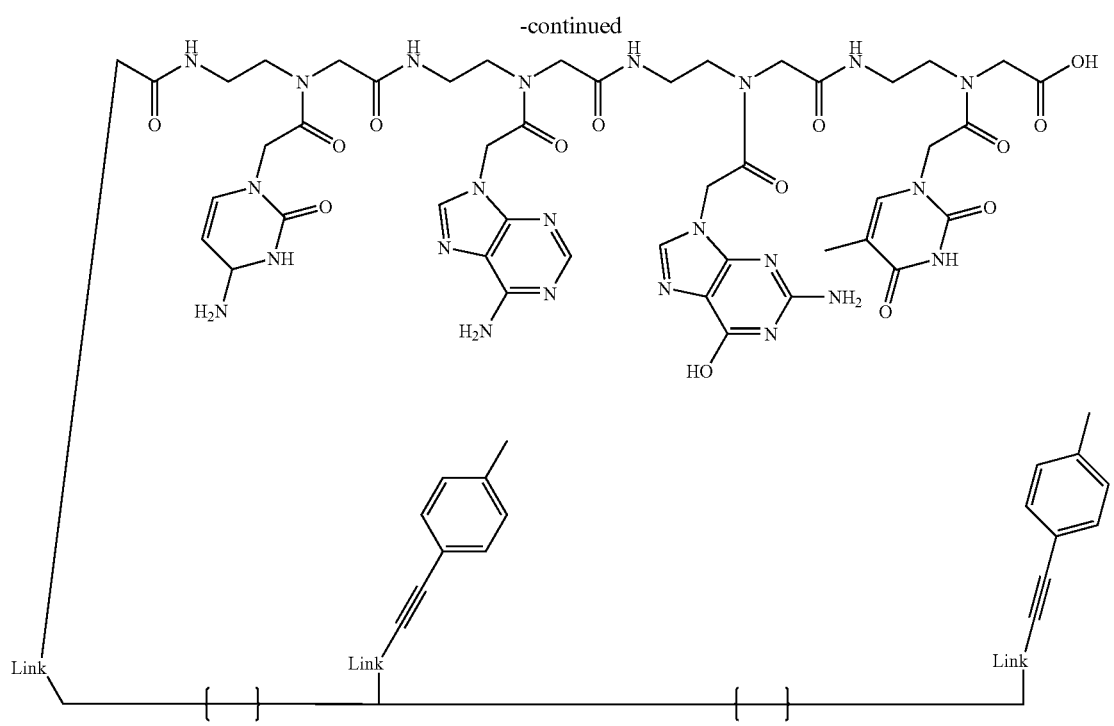
+++ Designates a sequence of 10-20 nucleotides. Link is an oligonuclotide (e.g. a 40'mer) modified at one terminal enabling the attachment of a base from a PNA unit.
Scheme for Building Block Synthesis:
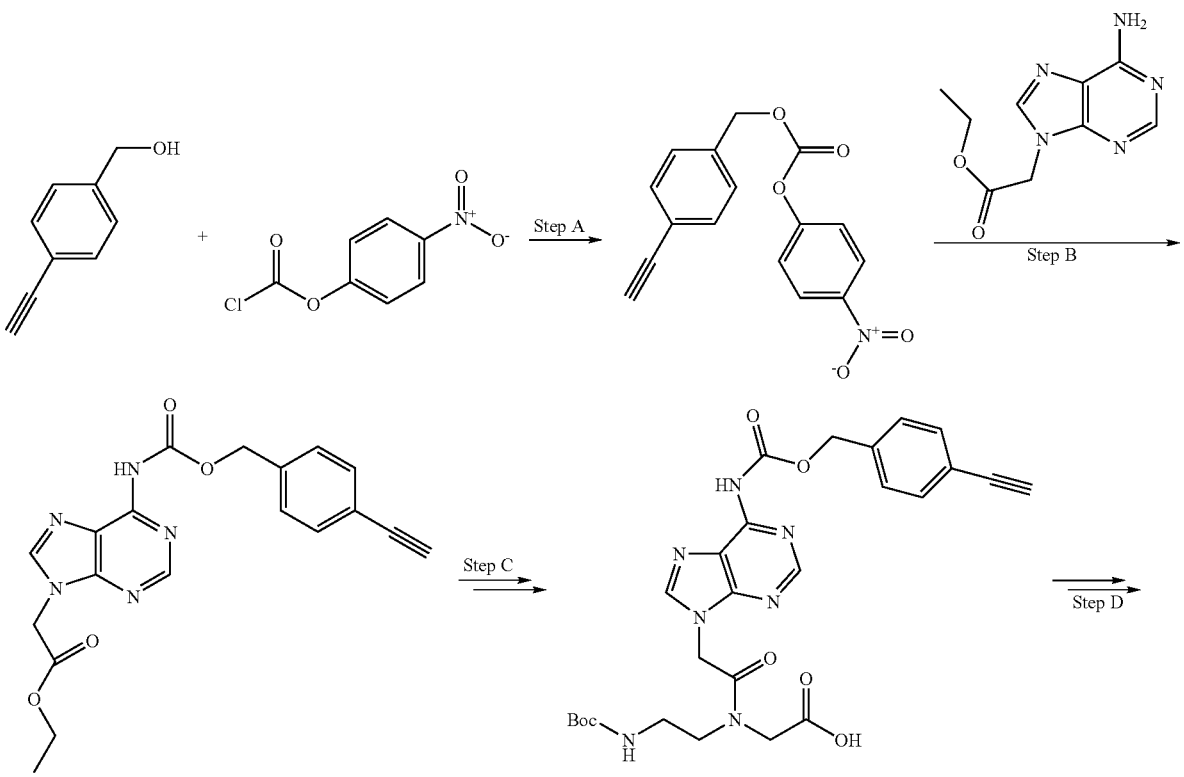

-continued

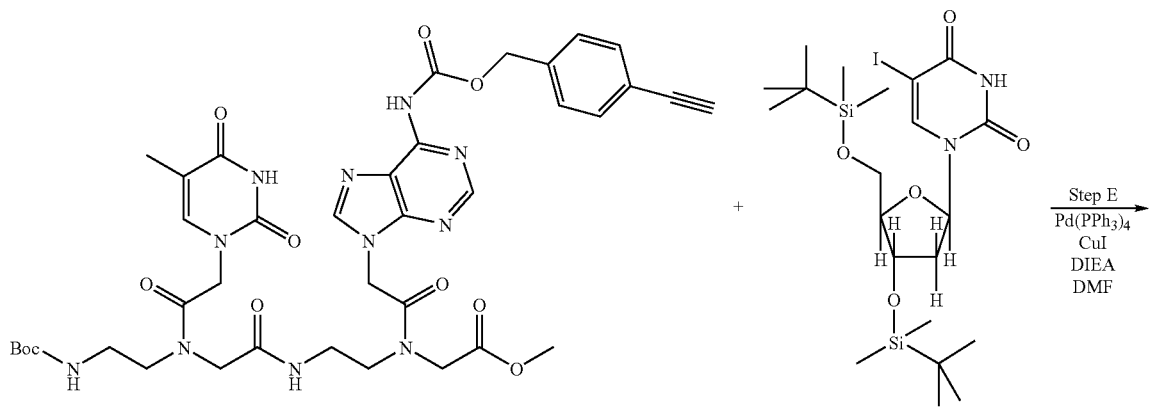

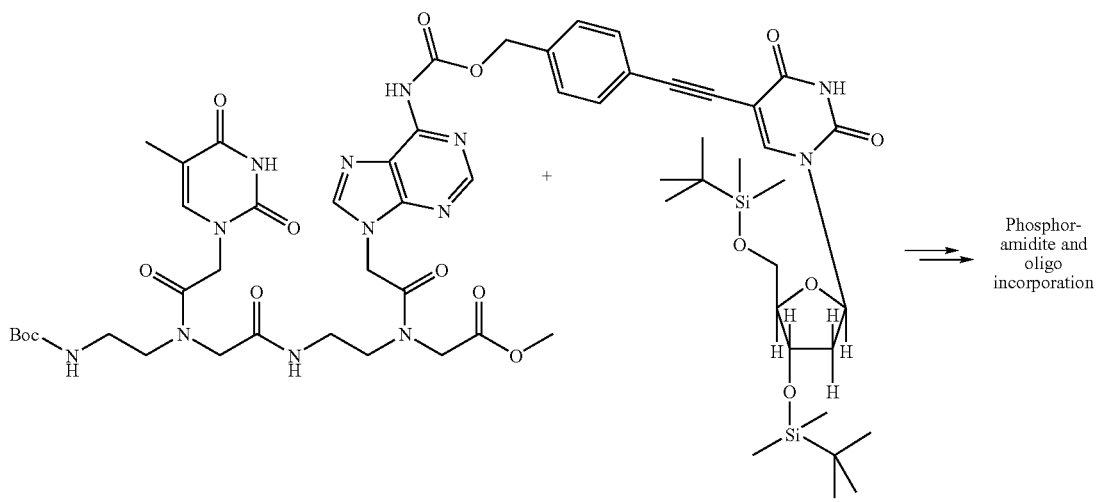

To a DCM solution (20 mL) of 4-nitrophenolchloroformiate (5 mmol) cooled on an ice/water bath is added (4-Ethynylphenyl)methanol (5 mmol) dissolved in DCM (20 mL) dropwise. After 1 h the ice bath is removed. The reaction is monitored by TLC. Upon completion, (6-Aminopurin-9-yl)-acetic acid ethyl ester (5 mmol) in pyridine (20 mL) is added and left to react 16 h at rt. Volatiles are removed in vacuo and the residue purified by chromatography.

Step C, D:

Steps C[Hyrup;1996; *Bioorganic & medicinal chemistry;* 5-23] and D[Schmidt;1997; *Nucleic Acids Research;* 4792-4796,Böhler;1995; *Nature;*] are known from the literature.

Step E

A DMF solution (2 mL) of the protected iodo substituted nucleoside (0.34 mmol), the alkyne (0.69 mmol, 2 eq), DIEA (0.25 mL) is purged with Ar for 5 min. Tetrakis triphenylphosphine palladium (0.03 mmol, 0.1 eq) and CuI (0.07 mmol, 0.2 eq) is added and the mixture is heated to 50° C. and kept there for 20 h. Evaporation of volatiles followed by chromatography affords the desired modified nucleoside that is converted into its corresponding phosphor amidite and incorporated into an oligonucleotide.

Example (Model) 77

PNA Synthesis—Nitrogen Linked

PNA monomers are linked to complementing elements via cleavable benzyl moieties bound to the base part of each PNA monomer. An amine is used as anchor point to the oligonucleotide complex. Each building block is annealed to a oligonucleotide template (not shown).

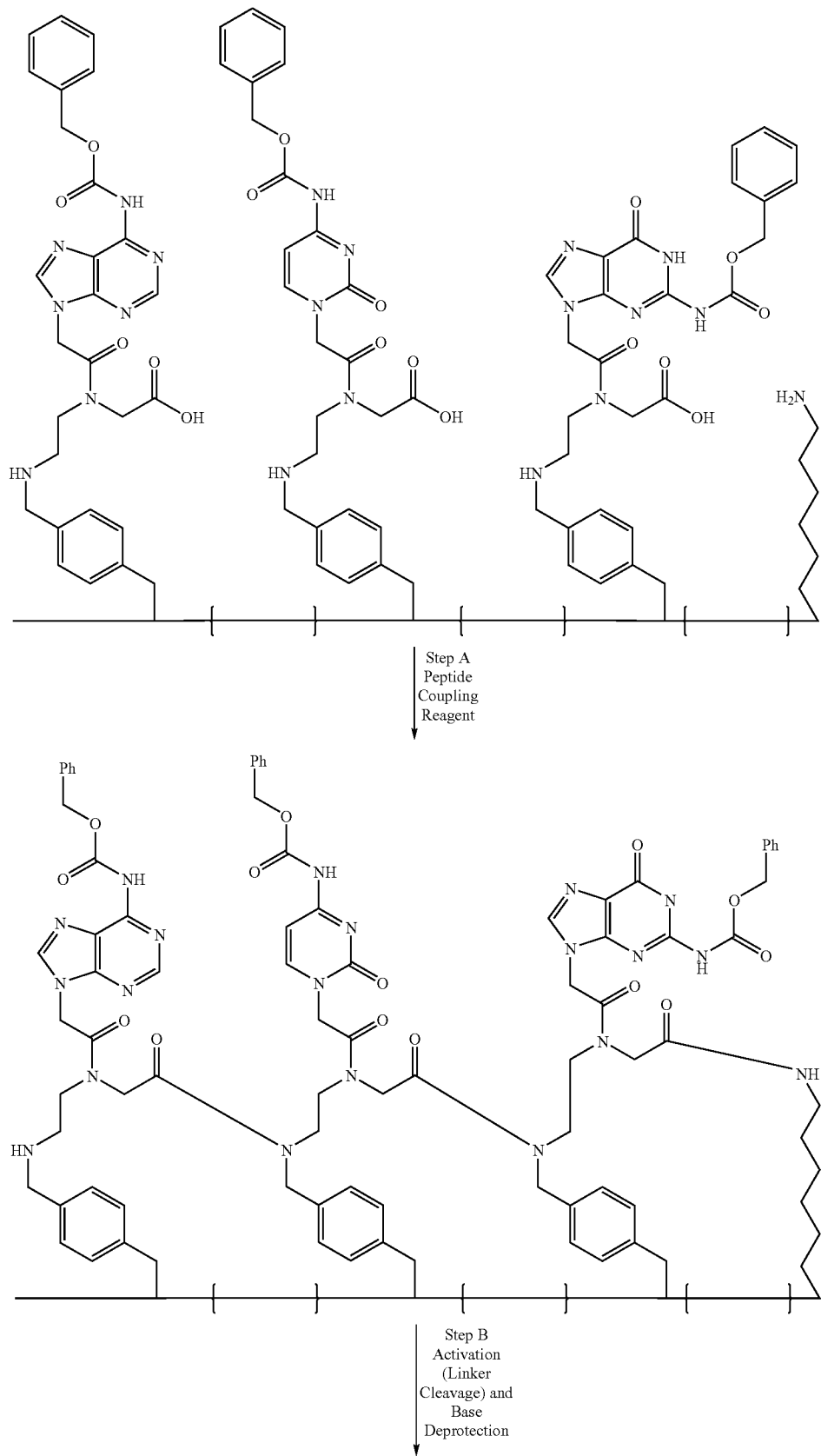

-continued

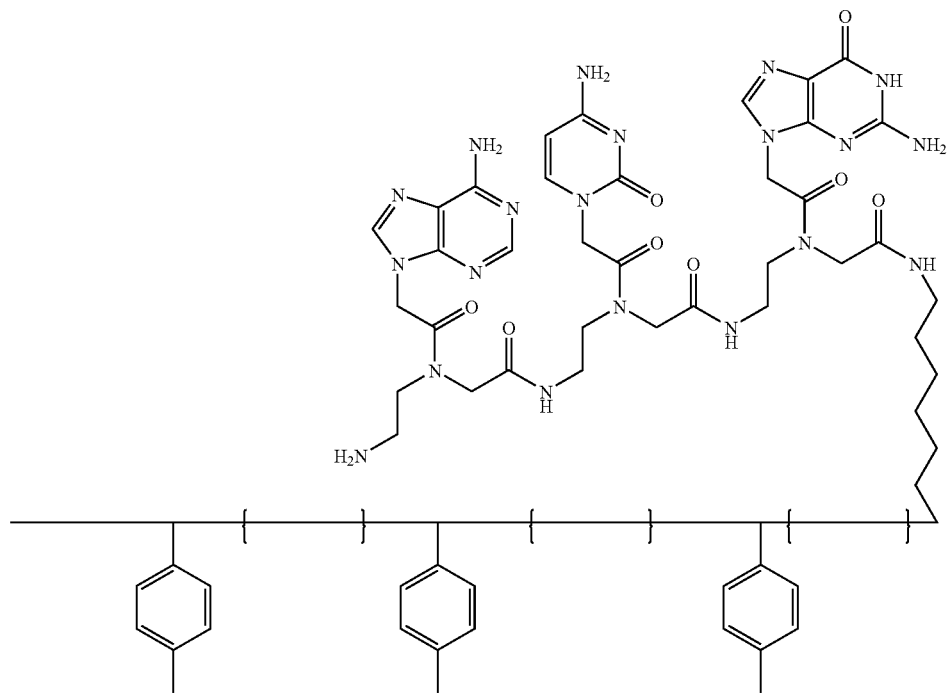

+++ Designates a valence bond between modified nucleotides.

Step A: Polymerization

To an aqueous buffered solution (10 uL, 1M NaCl, 100-500 mM buffer pH 6-10, preferably 7-9) of oligonucleotide complexes (0.1-100 uM, preferably 0.5-10 uM) is added a peptide coupling reagent (0.1 mM-100 mM, preferably 1-10 mM) exemplified by but not limited to EDC, DCC, DIC, HATU, HBTU, PyBoP, PyBroP or N-methyl-2-chloropyridinium tetrafluoroborate and a peptide coupling modifier (0.1 mM-1 uM, preferably 1-10 mM) exemplified by but not limited to NHS, sulpho-NHS, HOBt, HOAt, or DhbtOH in a suitable solvent (1 uL) e.g. water, methanol, ethanol, dimethylformamide, dimethylsulfoxide, ethylene glycol, acetonitrile or a mixture of these. Reactions run at temperatures between −20° C. and 60° C. Reaction times are between 1 h and 1 week, preferably 1 h-24 h.

The above procedure exemplifies the polymerisation on a 11 uL scale, but any other reaction volume between 1.1 uL and 1.1L may be employed.

Step B:

Cbz- and Benzyl protective groups may be removed by a variety of methods, [Greene and Wuts;1999;] Due to its mildness, catalytic reduction is often the method of choice. Combining an insoluble hydrogenation catalyst e.g. Pd/Al$_2$O$_3$, Pd/CaCO$_3$, Pd/C, PtO$_2$, or a soluble one e.g. Wilkinsons catalyst and a hydrogen source exemplified but not limited to H$_2$, ammonium formiate, formic acid, 1,4-cyclohexadien, and cyclohexene in a suitable solvent like water, methanol, ethanol, dimethylformamide, dimethylsulfoxide, ethylen glycol, acetonitril, acetic acid or a mixture of these with the oligo nucleotide complexes removes the Cbz- and benzyl protective groups.

Example 78 (Model)
Polysaccharides
General Scheme for Polysaccharide Synthesis
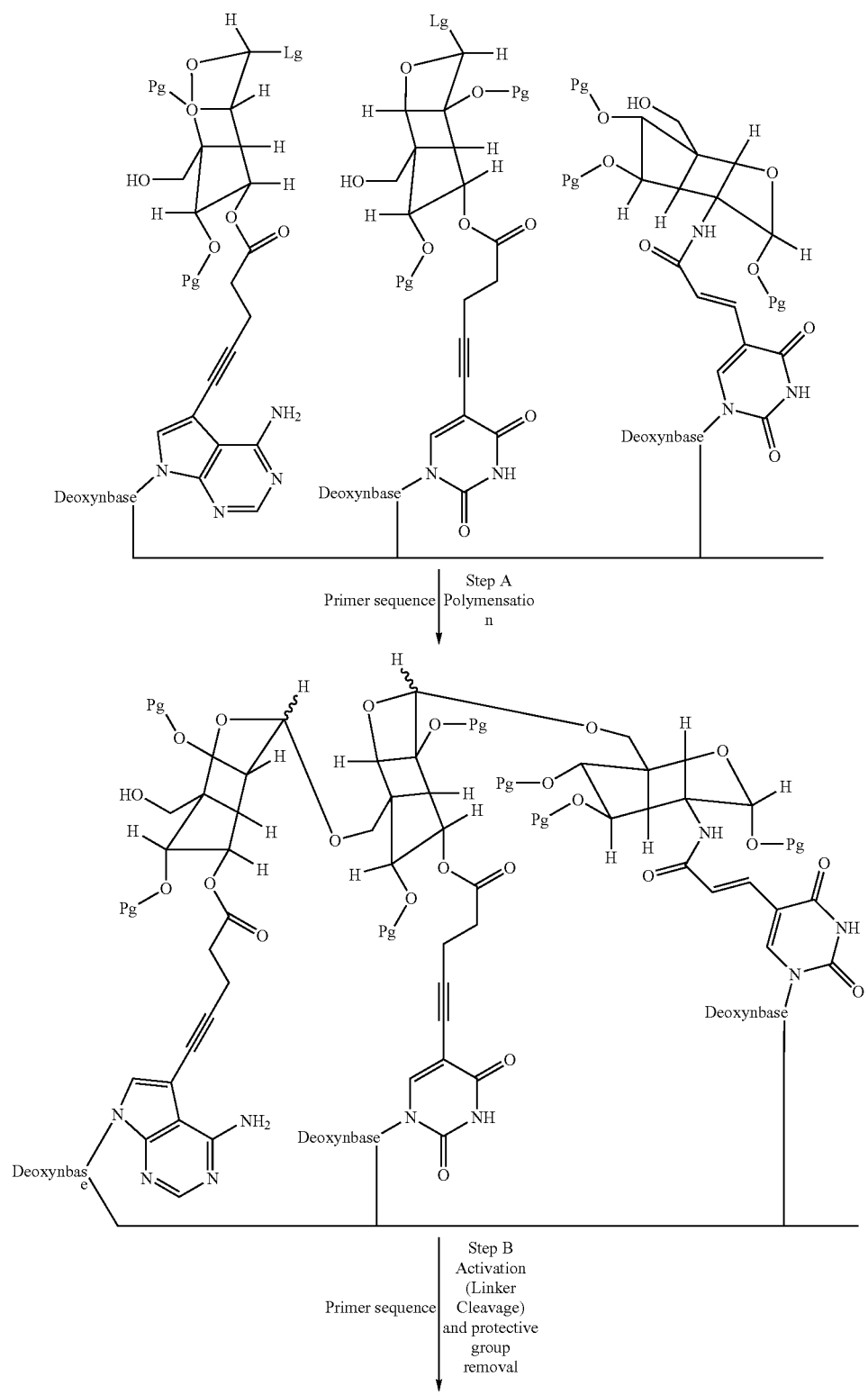

-continued

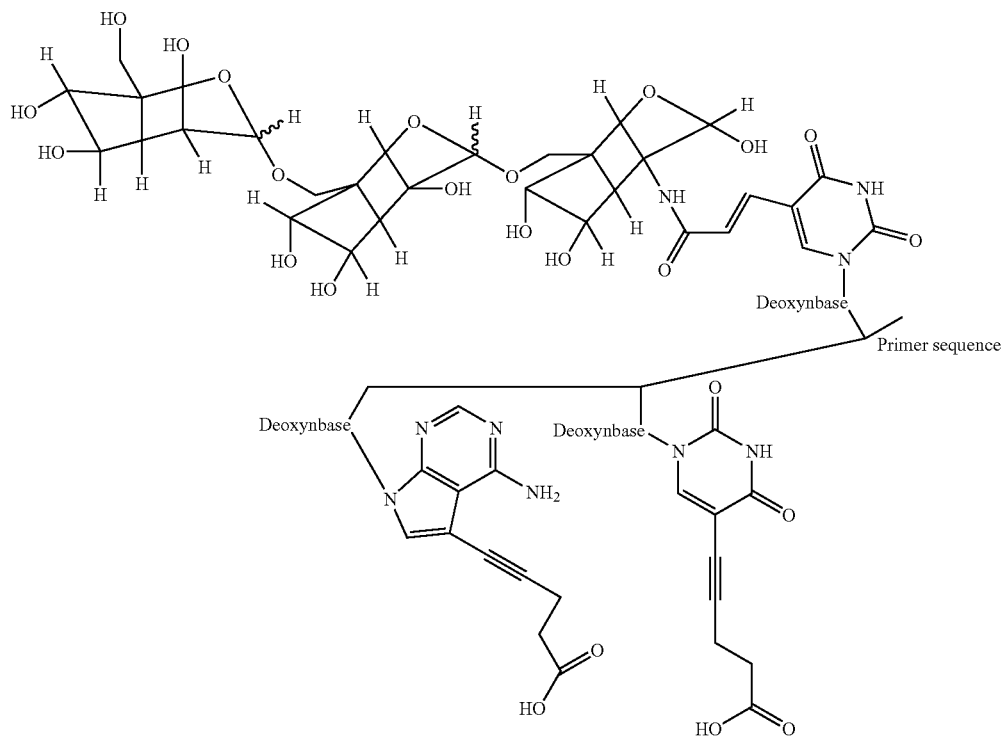

A primer sequence modified with a carboxylic acid (e.g. Glen Research Carboxy-dT cat. No. 10-1035-) that has been attached to a 2-amino-sugar is annealed to a template (not shown) and extended with modified nucleotides carrying hexose units. Pg is a protection group[Seeberger;2000; *Chem. Rev.*; 4349-4393,Seeberger;2001;] exemplified by but not limited to Ac, Bz, Lev, Piv, Silanes (SiR$_3$ wherein R is lower alkyl), Lg is a leaving group typical for carbohydrate chemistry exemplified by but not limited to halogen, trichloroacetamidato, mercaptan, phenol, phosphate esters and sugar nucleoside phosphates or sugar phosphates for enzymatic [Wong; 1994; *Tetrahedron Organic Chemistry Series*;] carbohydrate synthesis. Polysaccharides may also be synthesised using glycals.

Step B: Linker Activation

The ester linkages are cleaved with aqueous hydroxide at pH 9-12 at room temperature, 16 h in a suitable solvent like water, methanol, ethanol, dimethylformamide, dimethylsulfoxide, ethylene glycol, acetonitrile or a mixture of these. If Pg is Ac or other base labile protective group, these are removed as well.

Carbohydrates have several OH-functionalities allowing attachment to the complementing element. This example shows a 1-6 coupled trimer but any combination of building blocks may be used.

Attaching carbohydrate units to a template may lessen the tendency of these units to fold into secondary structures hence facilitating the synthesis of polysaccharides.

Example (Model) 79
Acrylamide
General Scheme for a Polyacrylamid Synthesis:
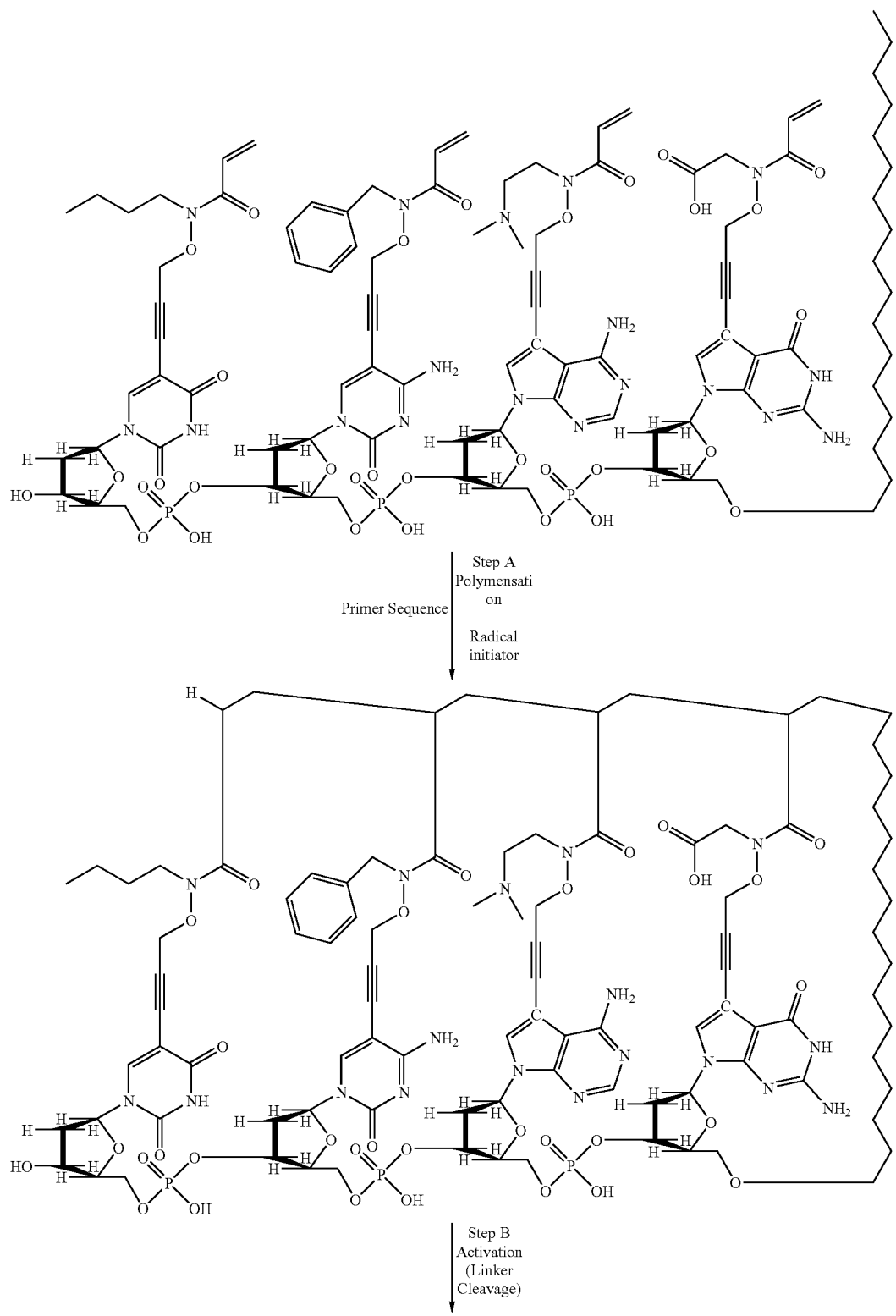

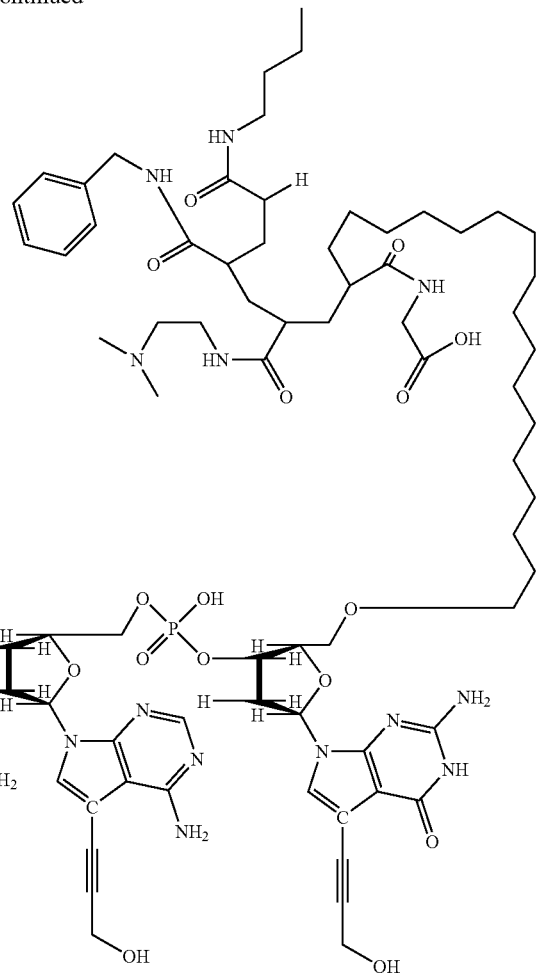

A terminally modified primer sequence carrying an iodine atom is annealed to an oligo nucleotide template (not shown) and extended with modified nucleotides carrying N-substituted acrylamide units.

Step A: Polymerisation

Acrylamides are polymerized in a cascade radical reaction starting by abstraction of the iodine atom by a radical initiator forming a carbon atom based radical. To an aqueous buffered solution (10 uL, 1M NaCl, 100-500 mM buffer pH 6-10, preferably 7-9) of oligonucleotide complexes (0.1-100 uM, preferably 0.5-10 uM) carrying N-substituted acrylamid units is added a radical initiator (0.1 mM-100 mM, preferably 1-10 mM) exemplified by but not limited to peroxymonosulfate, AIBN, di-tert butylperoxide, tert butylperoxide, hydrogen peroxide or lead acetate in a suitable solvent (1 uL) e.g. water, methanol, ethanol, dimethylformamide, dimethylsulfoxide, ethylene glycol, acetonitrile or a mixture of these, optionally applying UV-light, ultrasound or microwaves. Reactions run at temperatures between −20° C. and 100° C., preferably between 0° C. and 60° C. Reaction times are between 1 h and 1 week, preferably 1 h-24 h.

The above procedure exemplifies the polymerisation on a 11 uL scale, but any other reaction volume between 1.1 uL and 1.1L may be employed.

Step B: Activation

The N—O bond is susceptible to cleavage by reduction using hydrogenation catalysts and a suitable hydrogen source or in the presence of certain metal salts.

To an aqueous buffered solution (10 uL, 1M NaCl, 100-500 mM buffer pH 4-10, preferably 4-7) of oligonucleotide complexes (0.1-100 uM, preferably 0.5-10 uM) is added reductants (0.1 mM-100 mM, preferably 1-10 mM) exemplified by but not limited to samarium(II) iodide, tin(II) chloride or manganese(III) chloride in a suitable solvent (1 uL) e.g. water, methanol, ethanol, dimethylformamide, dimethylsulfoxide, ethylene glycol, acetonitrile or a mixture of these. Reactions run at temperatures between −20° C. and 100° C., preferably between 0° C. and 60° C. Reaction times are between 1 h and 1 week, preferably 1 h-24 h.

The above procedure exemplifies the polymerisation on a 11 uL scale, but any other reaction volume between 1.1 uL and 1.1L may be employed.

Building Block Synthesis:

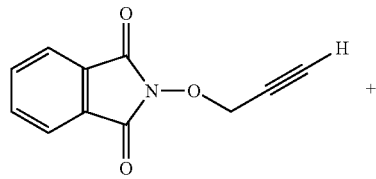

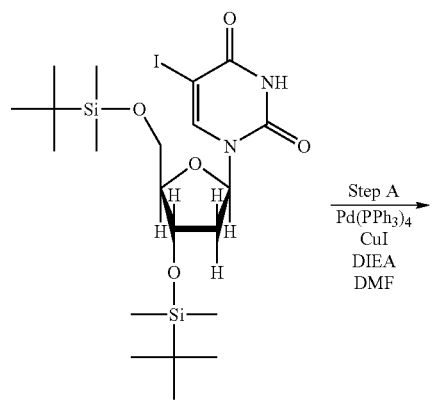

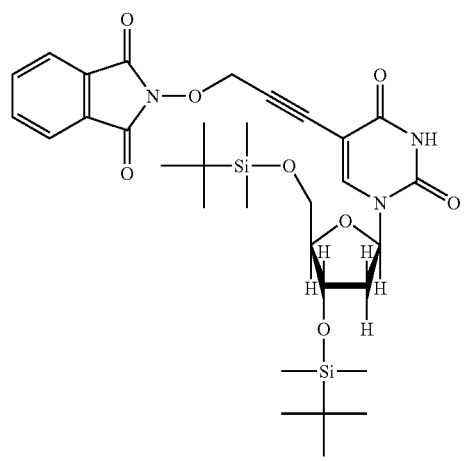

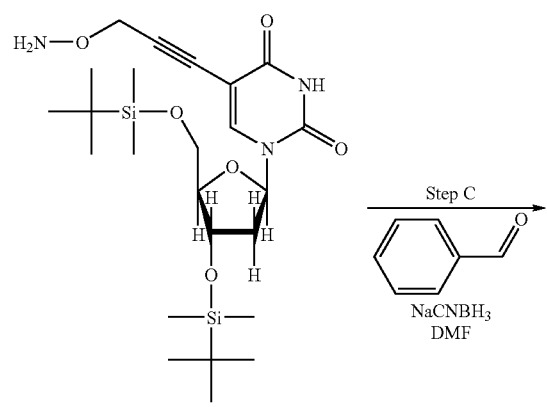

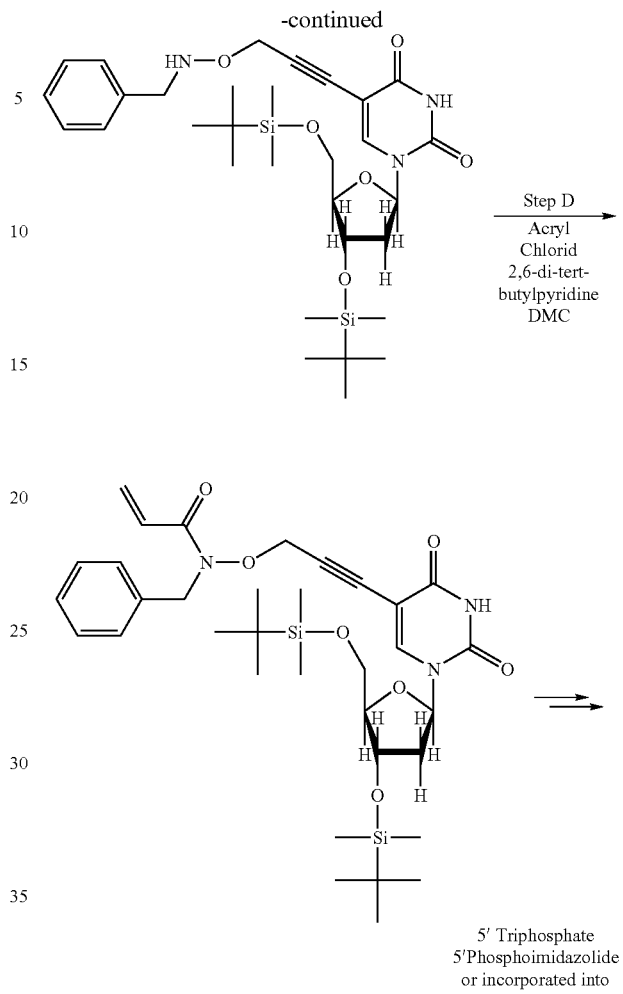

5' Triphosphate
5'Phosphoimidazolide
or incorporated into
oligo-nucleotide

Step A:

A DMF solution (20 mL) of the protected iodo substituted nucleoside (3.4 mmol), the alkyne (6.9 mmol, 2 eq, Aldrich P51338), DIEA (2.5 mL) is purged with Ar for 5 min. Tetrakis triphenylphosphine palladium (0.3 mmol, 0.1 eq) and CuI (0.7 mmol, 0.2 eq) is added and the mixture is heated to 50° C. and kept there for 20 h. Upon cooling, the mixture is added 700 mL diethylether. The organic phase is washed with ammonium chloride (sat, aq, 250 mL) and water (250 mL). Evaporation of volatiles followed by stripping with toluene (400 mL) affords the desired modified nucleoside that is purified by column chromatography (silica gel, Heptane/Ethyl acetate eluent).

Step B:

To the modified nucleoside obtained in Step A (2 mmol) in ethanol (30 mL) is added hydrazine hydrate (400 mg, 8 mmol, 4 eq.) and the mixture is stirred at 20° C. The reaction is monitored by TLC. Upon completion volatiles are removed in vacuo and the residue purified by chromatography.

Step C:

The amine obtained in Step B (0.5 mmol) is added DMF (10 mL), benzaldehyde (0.6 mmol, 1.2 eq), acetic acid (100 uL, 1%) and sodium cyanoborohydride (0.6 mmol). Reacts at 20° C., 16 h and is quenched with NaHCO$_3$ (aq, 10 mL, 5%) and extracted with ethyl acetate (3×100 mL). The combined organic phase is washed with NH$_4$Cl (sat, aq, 50 mL) and water (50) mL and dried over Na$_2$SO$_4$. Upon evaporation of ethyl acetate, the residue may be purified by chromatography.

Step D:

The product obtained in Step C (0.1 mmol.) is dissolved in dichloromethane in the presence of 2,6-di tertbutylpyridine (0.4 mmol) and cooled to 0° C. where acrylchloride (0.15 mmol) in dichloromethane (2 mL) is added dropwise. Upon 1 h reaction at 0° C. the temperature is allowed to raise to 20° C. and the reaction is quenched after 1 h with NaHCO$_3$ (aq, 3 mL, 5%). The phases are separated and the organic phase reduced under vacuum. The residue is taken up in ethyl acetate and is washed with HCl(aq) (0.1 M, 3 mL), NaHCO$_3$ (aq, 3 mL, 5%) and water (3 mL). Upon evaporation of ethyl acetate, the product is stripped with toluene (2×20 mL), purified by chromatography and converted into the desired building block type, e.g. a 5'-triphosphate.

Example (Model) 80

Synthesis of β-peptides

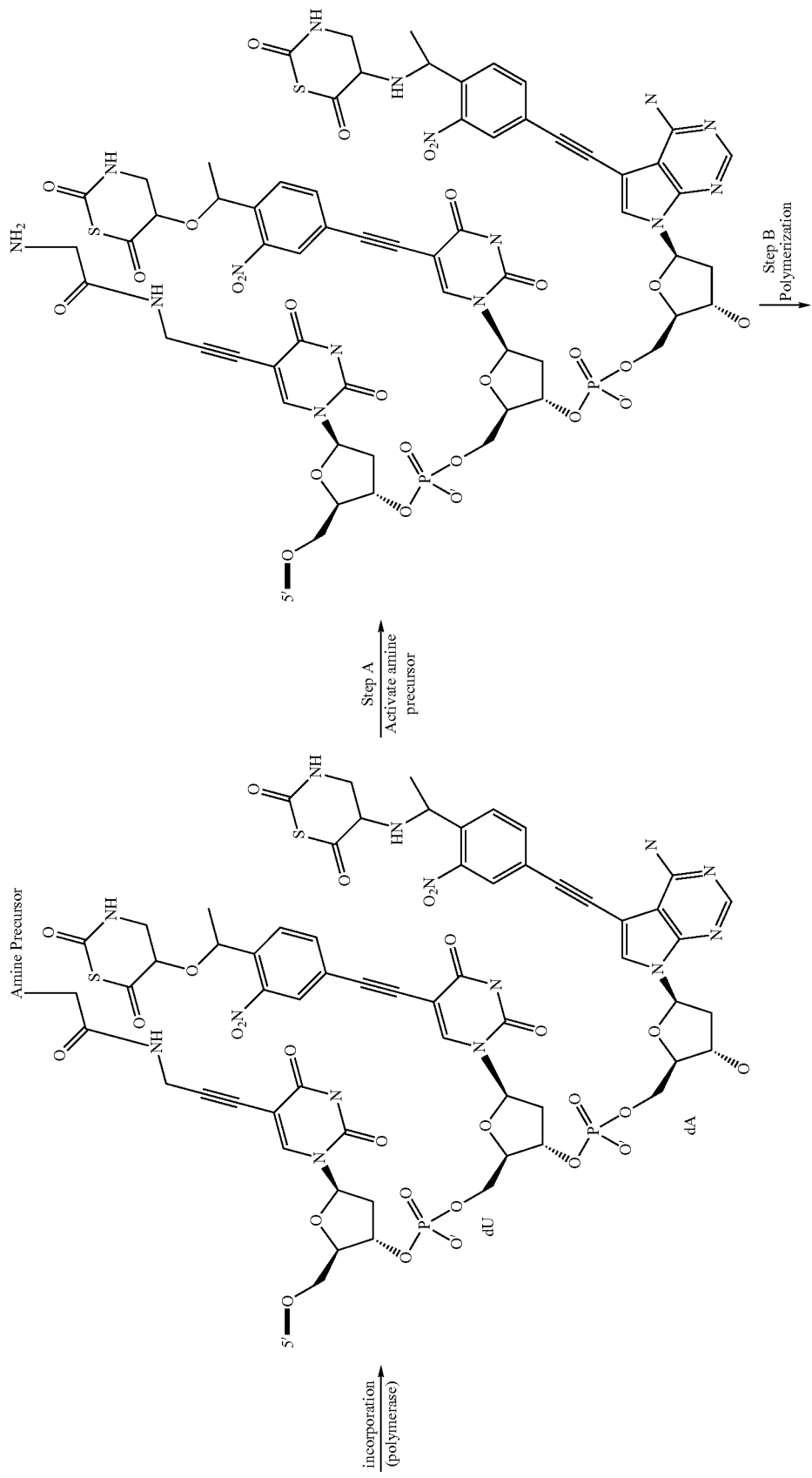

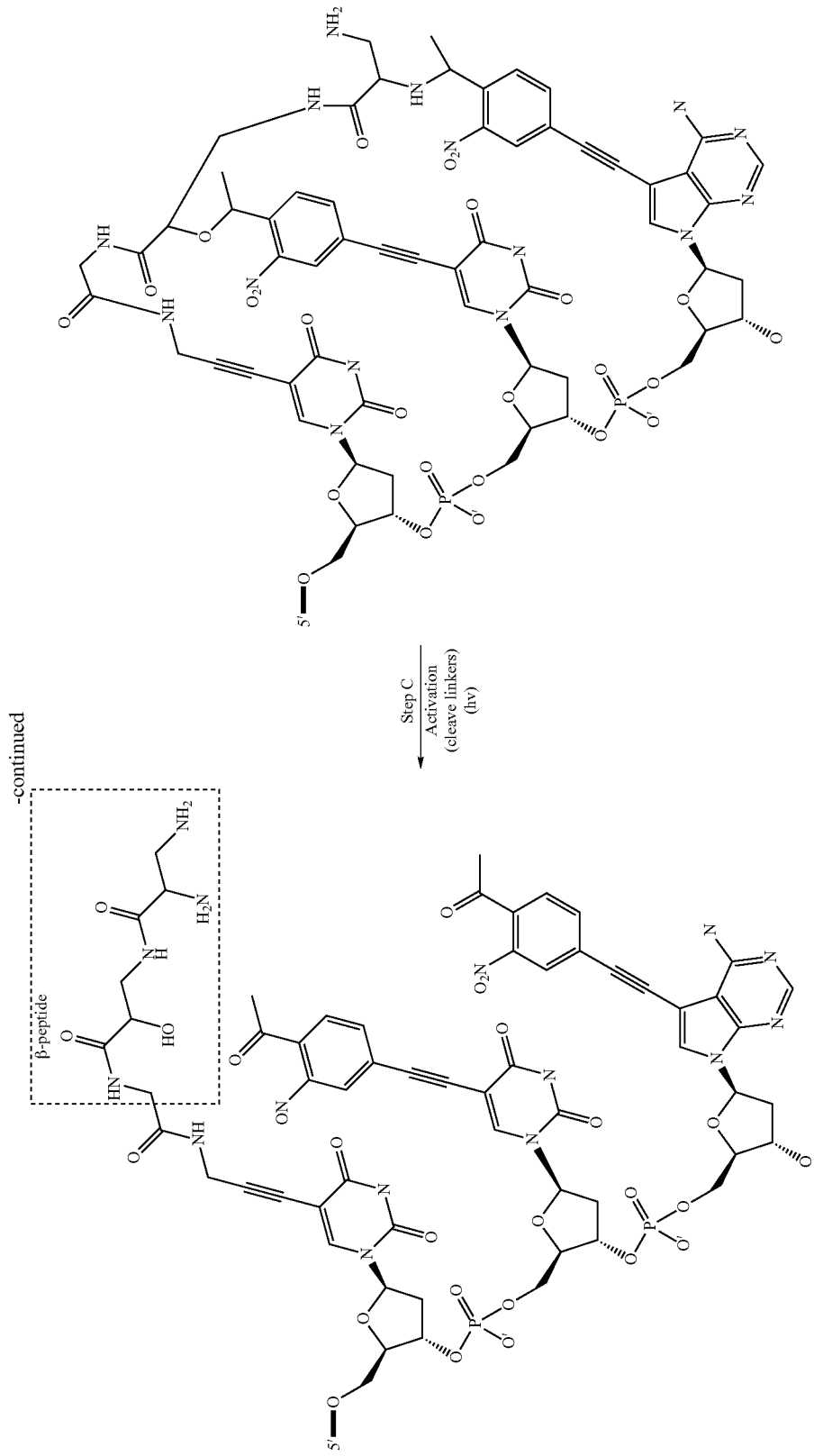

Step A

The amine precursor may be an amine carrying a protective group[Greene and Wuts;1999;] exemplified by but not limited to benzyl carbamate, paramethoxybenzyl carbamate, 2-Trimethylsilylethyl carbamate, 2,2,2-Trichloroethyl Carbamate. These protective groups are removed by hydrogenolysis, mild acid treatment, fluoride treatment and treatment with Zn dust respectively. Alternatively, the amine precursor may be a nitro group or an azide. Both are converted into amines by reduction. The latter is also reduced under mild conditions using phosphines.

Step B

The free amine generated in step A attacks the neighbouring NTA unit to start the cascade.

Step C

Linker cleavage is carried out using UV radiation (250-500 nm) on a buffered solution of oligonucleotide complexes (pH 5-10) to partially release a beta peptide.

Example (Model) 81

β-peptoid Synthesis

General Scheme for β-peptoid Synthesis

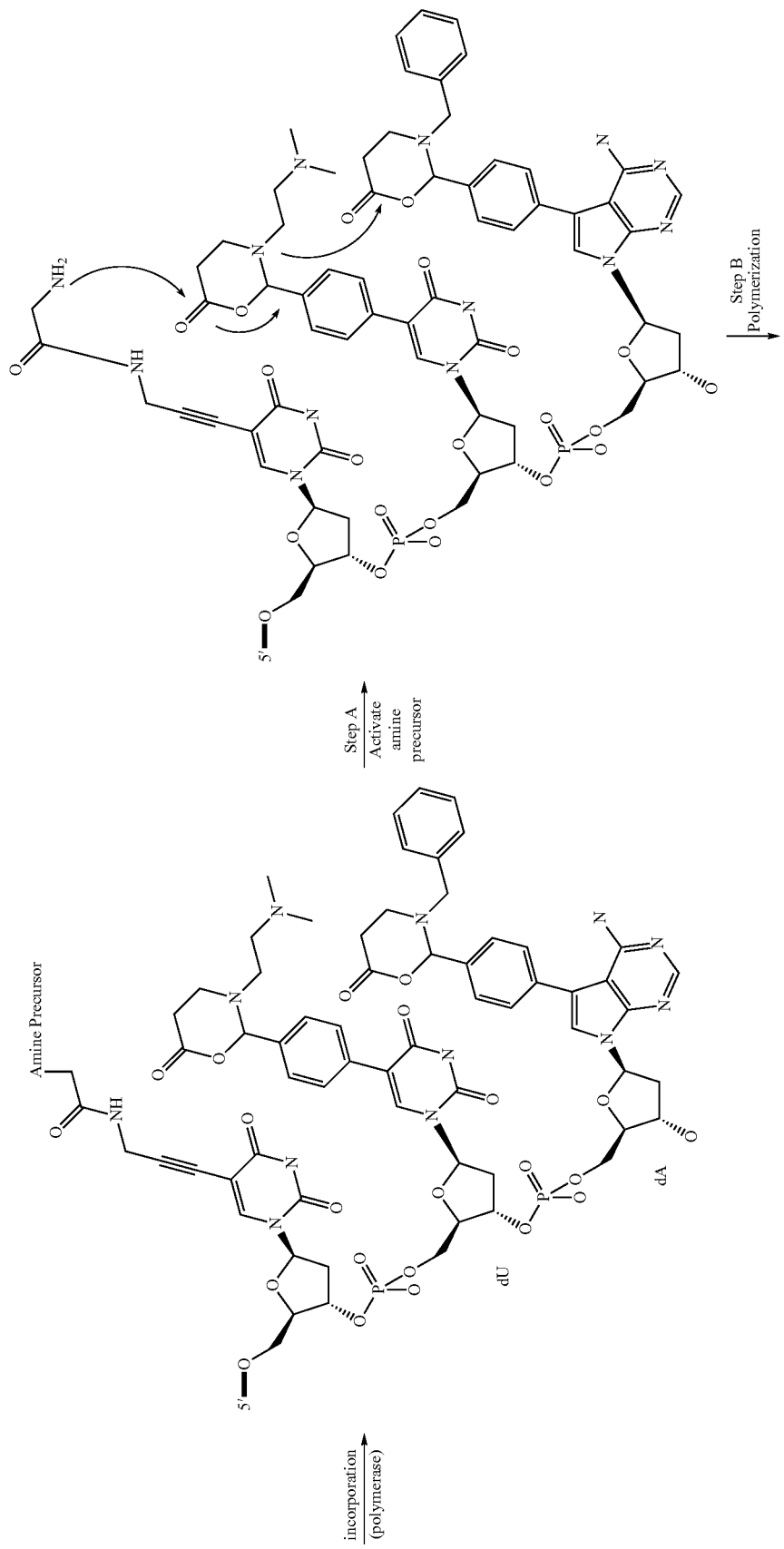

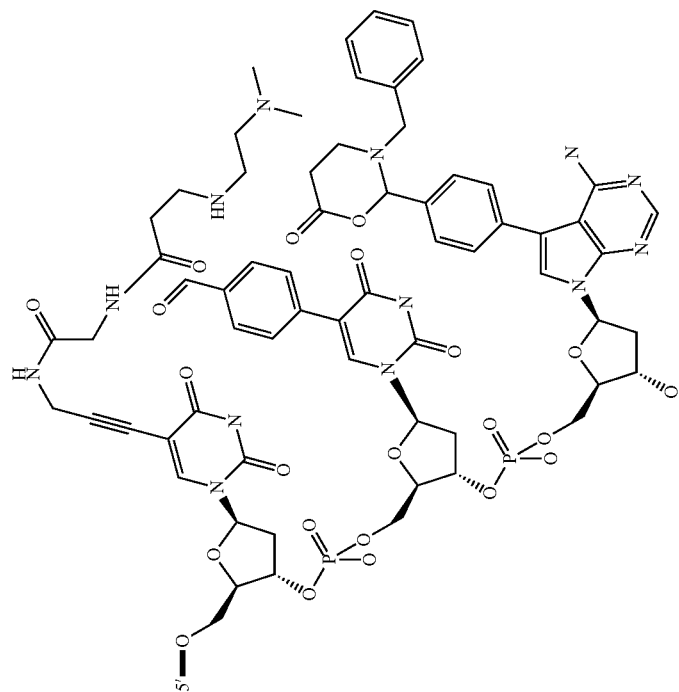
Step B
Polymerization
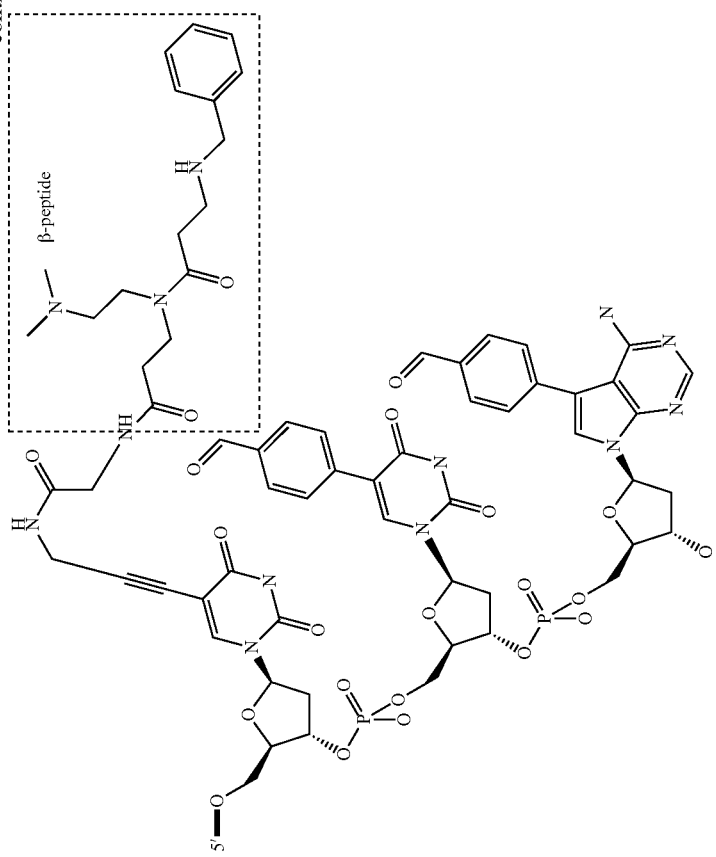
-continued
β-peptide

Step A

The amine precursor may be an amine carrying a protective group[Greene and Wuts;1999;] exemplified by but not limited to benzyl carbamate, paramethoxybenzyl carbamate, 2-Trimethylsilylethyl carbamate, 2,2,2-Trichloroethyl Carbamate. These protective groups are removed by hydrogenolysis, mild acid treatment, fluoride treatment and treatment with Zn dust respectively. Alternatively, the amine precursor may be a nitro group or an azide. Both are converted into amines by reduction. The latter is also reduced under mild conditions using phosphines.

Step B

The free amine generated in step A attacks the neighbouring [1,3]Oxazinan-6-one unit initially forming an unstable aminal due to the ring opening. This collapses to an aldehyde releasing a secondary amine which is now able to continue the cascade resulting in this case in a beta peptoid.

Building Block Synthesis

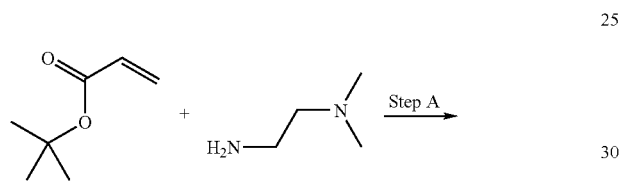

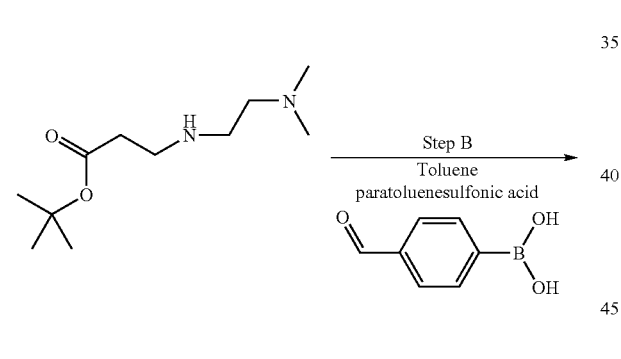

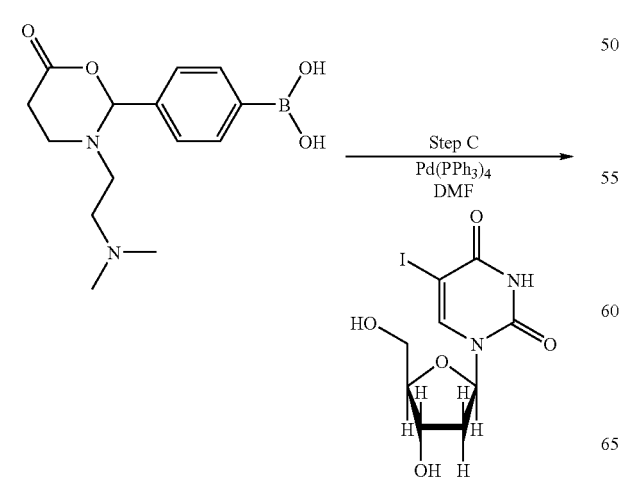

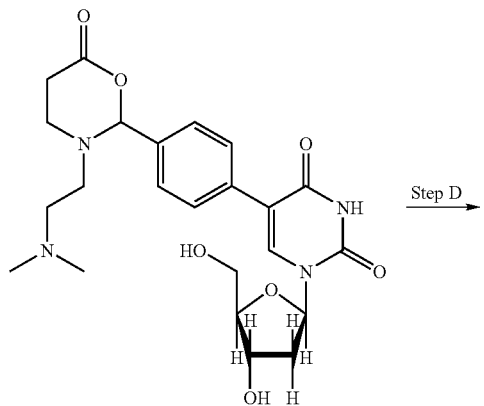

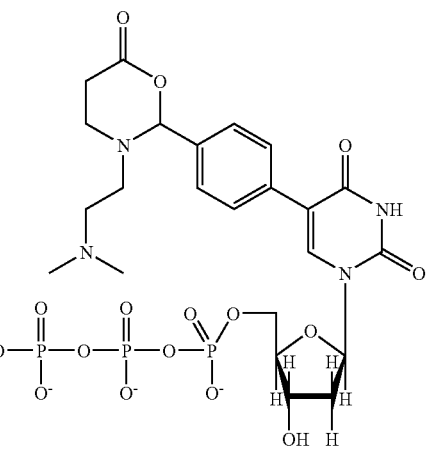

Example (Model) 82

Polyamide Synthesis

Alternating monomer building blocks of type X-X and Y-Y are incorporated (principle depicted in FIG. 16) followed by a polymerization step resulting in bond formation between X and Y on neighbouring monomers.

Building Block Synthesis

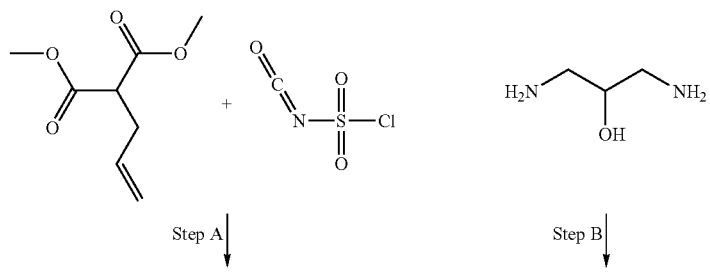

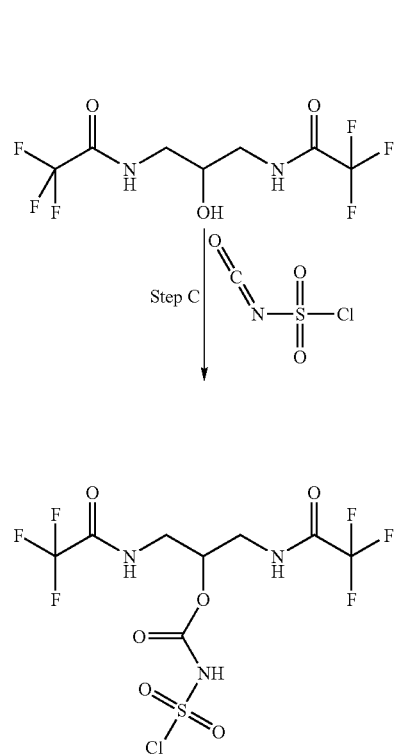

Step A: 2+2 Cycloaddition

2-Allyl-malonic acid dimethyl ester (1 mmol) and Chlorosulfonyl isocyanate (1 mmol) are mixed in THF at 20° C. and left to react 7 days. The crude product is used without purification.

Step B: Di-amine Protection 1,3-Diamino-propan-2-ol (1 mmol) and trifluoroacetic anhydride (2 mmol) is mixed in diethylether at 0° C. and left to react at this temperature 4 h. The reaction mixture is extracted with 1M HCl, NaHCO$_3$ (aq) and water. The product is obtained by evaporation of the organic phase

Step C: Carbamate Formation 2,2,2-Trifluoro-N-[2-hydroxy-3-(2,2,2-trifluoro-acetylamino)-propyl]-acetamide (1.5 mmol) obtained in step B is dissolved in THF along with chlorosulfonyl isocyanate (1.5 mmol) and left to react at 20° C., 16 h. The crude product is used without purification.

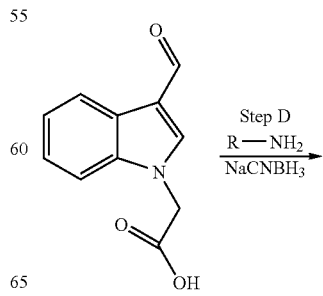

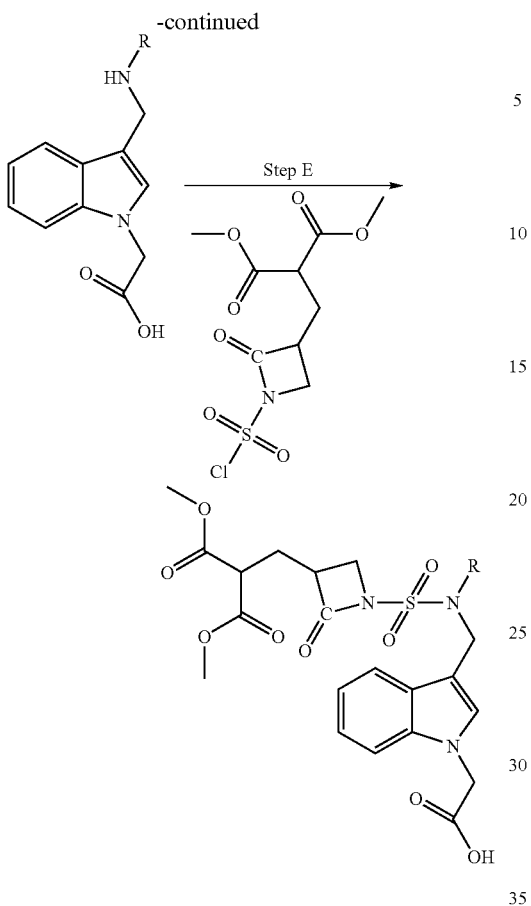

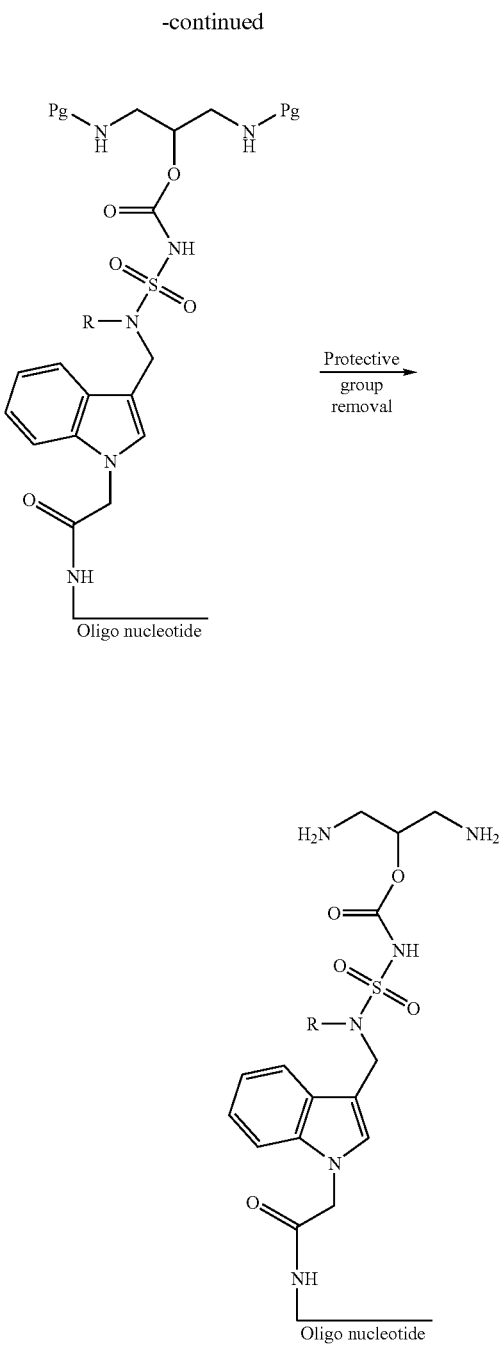

Step D: Reductive Amination

The aldehyde (5 mmol) is dissolved in a minimum MeOH and added an amine (6 mmol), sodium cyanoborohydride (6 mmol) and acetic acid. Upon stirring overnight volatiles are removed and the product is purified by crystallisation or chromatography.

Step E: Sulfonamide Formation

The crude product from step A or step C in THF is added to the amine obtained in step D in a water/THF mixture in the presence of base and left to react at 20° C., 4 h. Then the mixture is refluxed over night. Upon cooling, the solvent is removed and the residue purified by chromatography.

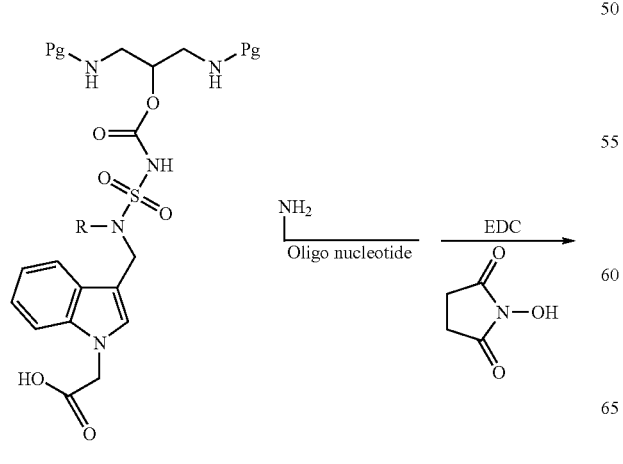

Oligo Building Block Preparation

The protected diamines and diacids are attached to modified oligonucleotides carrying a primary amino functionality using EDC and NHS in an aqueous buffer (pH 5-8, preferably 6-7). The protective groups (both methyl esters and trifluoro acetamides) are removed in aqueous buffer (pH 10-12). Alternatively, the protection groups remain on the building blocks and are removed after annealing to the oligonucleotide template.

Library Preparation
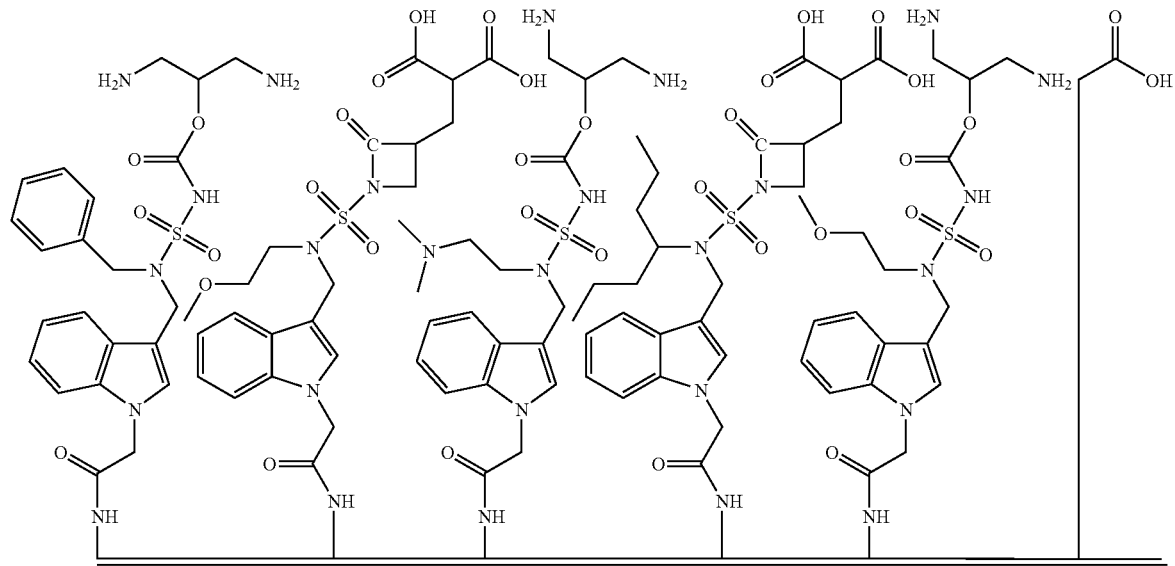
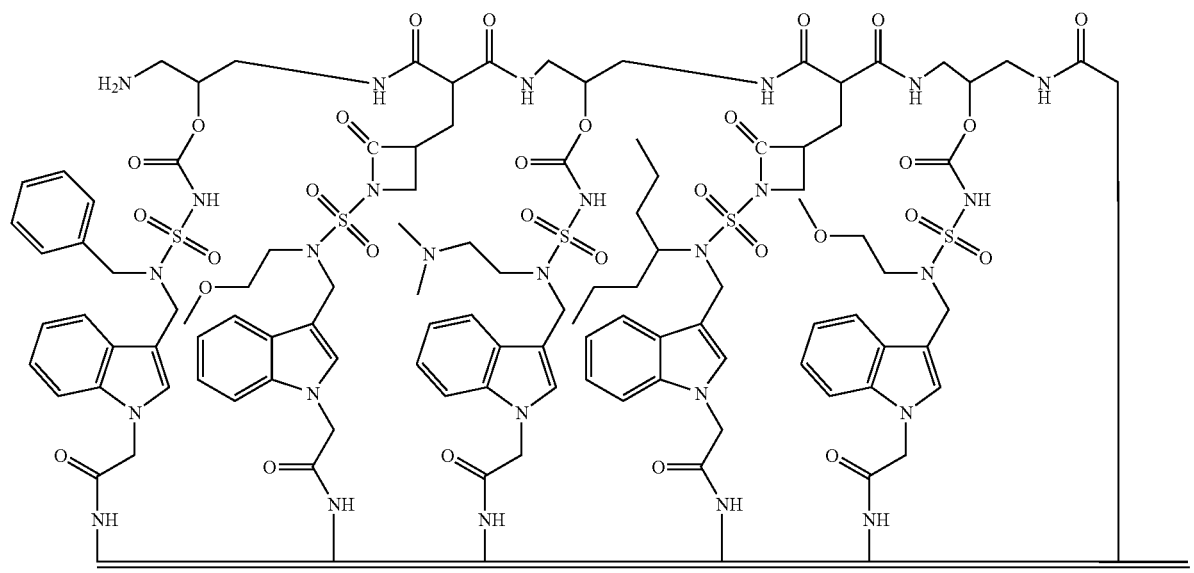

-continued

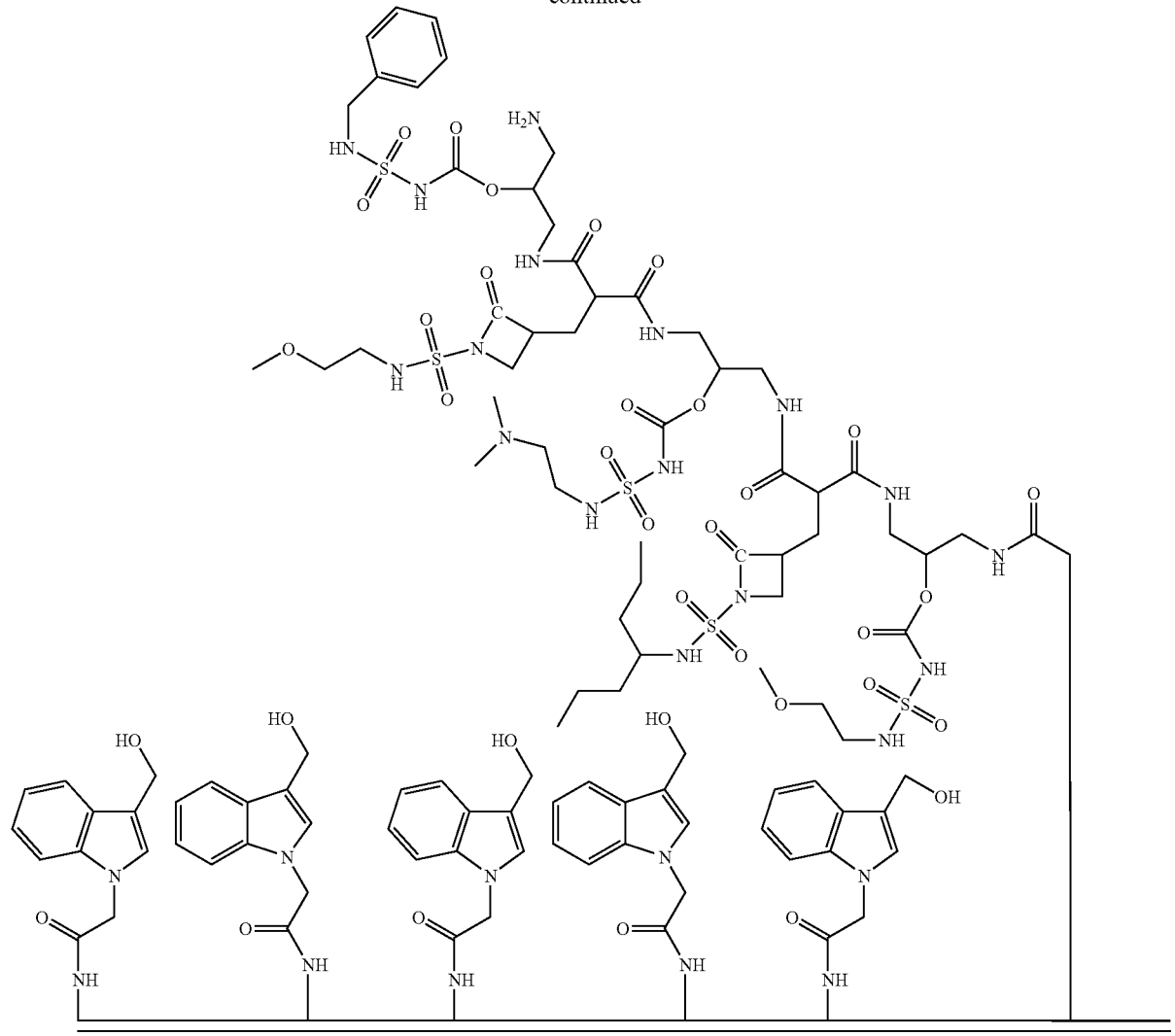

Polymerisation:

To an aqueous buffered solution (10 uL, 1M NaCl, 100-500 mM buffer pH 6-10, preferably 7-9) of oligonucleotide complexes (0.1-100 uM, preferably 0.5-10 uM) carrying di-amines and di-carboxylic acids is added a peptide coupling reagent (0.1 mM-100 mM, preferably 1-10 mM) exemplified by but not limited to EDC, DCC, DIC, HATU, HBTU, PyBoP, PyBroP or N-methyl-2-chloropyridinium tetrafluoroborate and a peptide coupling modifier (0.1 mM-100 mM, preferably 1-10 mM) exemplified by but not limited to NHS, sulpho-NHS, HOBt, HOAt, DhbtOH in a suitable solvent (1 uL) e.g. water, methanol, ethanol, dimethylformamide, dimethylsulfoxide, ethylene glycol, acetonitrile or a mixture of these. Reactions run at temperatures between −20° C. and 60° C. Reaction times are between 1 h and 1 week, preferably 1 h-24 h.

The above procedure exemplifies the polymerisation on a 11 uL scale, but any other reaction volume between 1.1 uL and 1.1L may be employed.

Activation (Linker Cleavage):

Linkers are cleaved by treatment with acid pH 0-5, at 0-40° C. for 10 min-10 h.

REFERENCES (1) Greene, T. W.; Wuts, P. G. M. *Protective Groups in Organic Synthesis;* 3rd ed.; John Wiley & Sons: New York, 1999.

(2) Hyrup, B.; Nielsen, P. E. *Bioorganic & medicinal chemistry* 1996, 4, 5-23.

(3) Schmidt, J. G.; Christensen, L.; Nielsen, P. E.; Orgel, L. E. *Nucleic Acids Research* 1997, 25, 4792-4796.

(4) Böhler, C.; Nielsen, P. E.; Orgel, L. E. *Nature* 1995, 376.

(5) Seeberger, P. H.; Haase, W. C. *Chem. Rev.* 2000, 100, 4349-4393.

(6) *Solid Support Oligosaccharide Synthesis and Combinatorial Carbohydrate Libraries;* Seeberger, P. H., Ed.; Wiley-Interscience: New York, 2001.

(7) Wong, C.-H.; Whitesides, G. M. *Enzymes in Synthetic Organic Chemistry;* Pergamon: Oxford, 1994.

Example (Model) 83

Isolation of α-peptide Ligand to Glutathione S-transferase (GST) from a Library of Templated α-peptides A) Nucleotide Derivative Synthesis The synthetic strategy for three nucleotide derivatives is shown in the scheme below with a detailed description of the synthesis. Examples of other synthesized α-amino acid nucleotide derivatives can be found in the literature (e.g. Ito et al. (1980) J. Amer. Chem. Soc. 102: 7535-7541; Norris et al. (1996) J. Amer. Chem. Soc. 118: 5769-5803; Celewicz et al (1998) Pol. J. Chem. 72: 725-734).

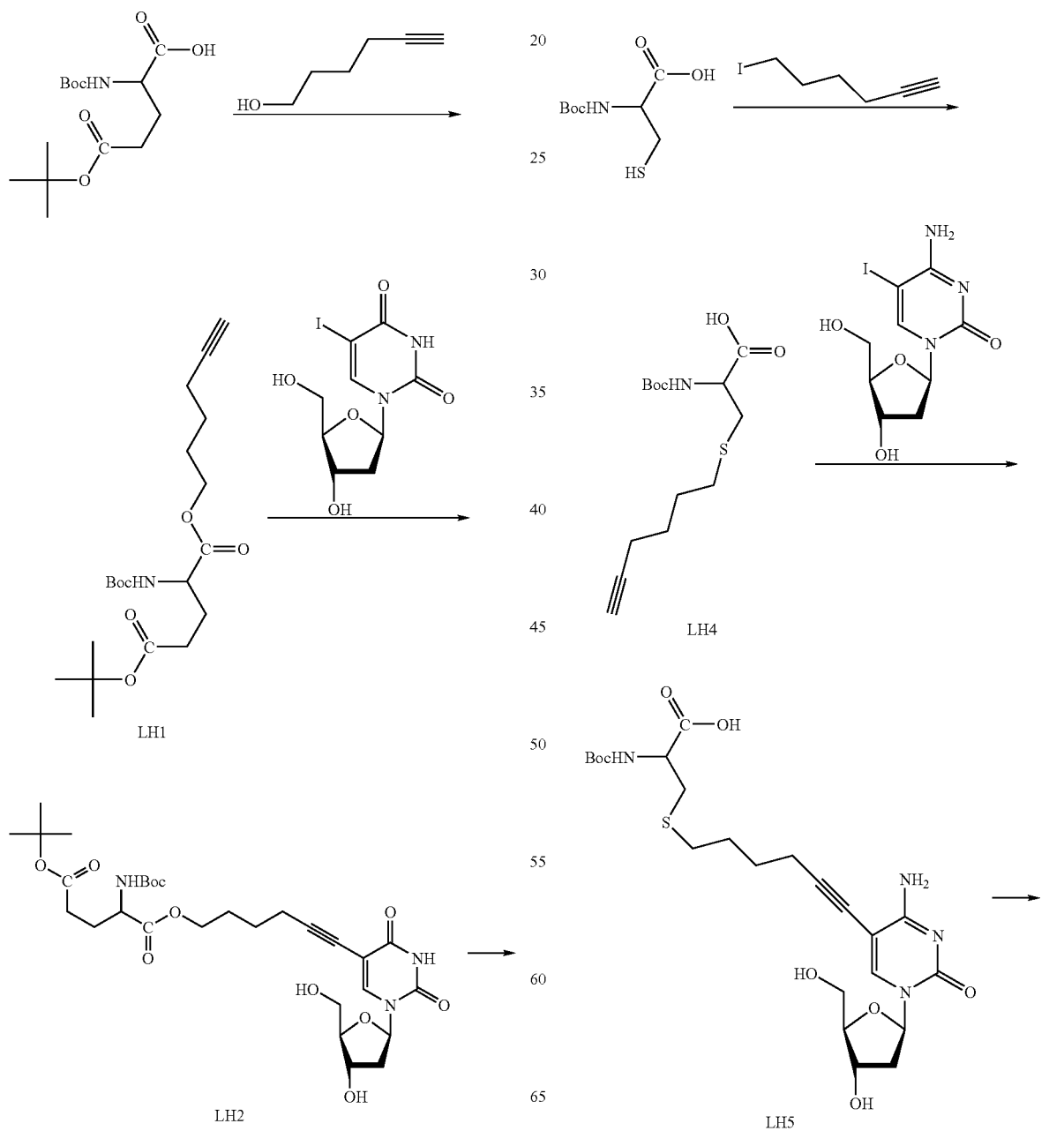

-continued

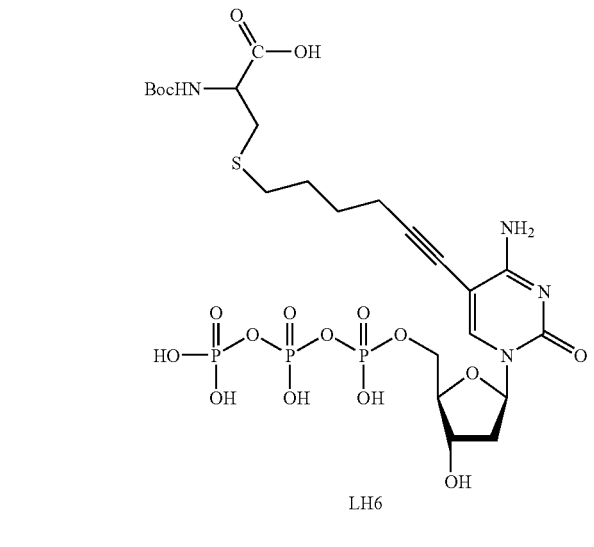

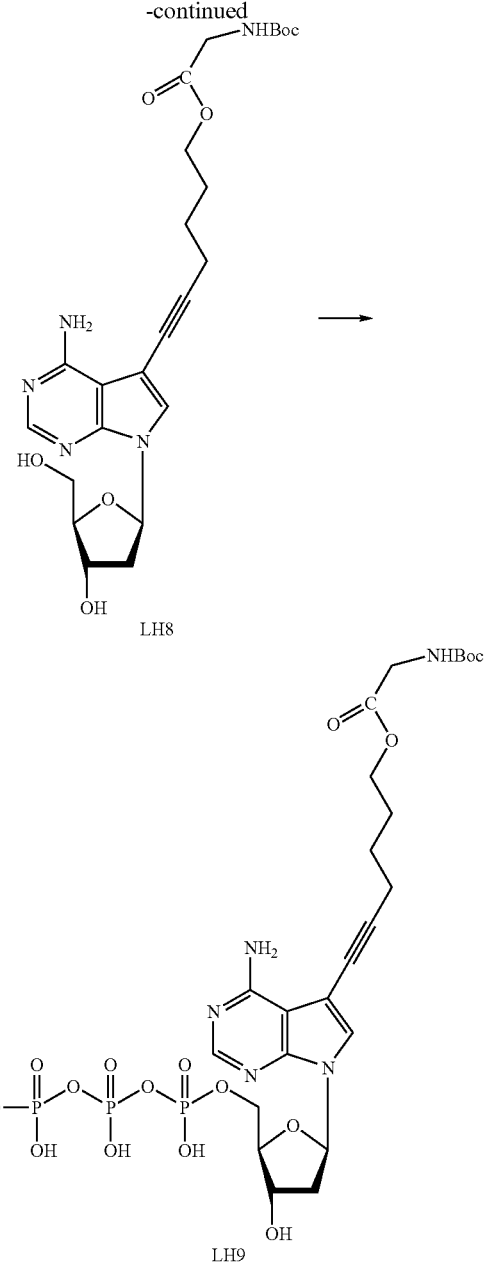

Synthesis of LH1, LH7: EDC (3.2 mmol) is added to an ice-water cooled solution of either N-(tert-butoxycarbonyl)-tert-butoxy glutamate (3.0 mmol) or N-(tert-butoxycarbonyl)-glycine (3.0 mmol) in dichloromethane (10 mL). A solution of 4-dimethylamino pyridine (0.3 mmol) and 5-hexynol (4.6 mmol) in dichloromethane (1 mL) is added. The reaction mixture is stirred for 1 h. at 0° C., then at room temperature overnight. Solvent was evaporated off and the residue is taken up in diethyl ether. The slurry is washed with HCl (0.1 M, 25 mL), saturated NaHCO₃ (25 mL) and brine (25 mL), then concentrated to oil. The product is purified by flash-chromatography.

Synthesis of LH4: 6-Iodohexyne (6 mmol) and K₂CO₃ (6 mmol) is added to a solution of N-(tert-butoxycarbonyl)-cysteine (3 mmol) in methanol (5 mL) and DMF (5 mL). The reaction mixture is stirred for 1 day at 40° C., then concentrated and worked-up by column chromatography.

Synthesis of LH2, LH5 and LH8: Tetrakis(triphenylphosphine)palladium (0.6 mmol) and CuI (0.2 mmol) is added to a degassed solution of the iodo nucleoside (1 mmol), the alkyne (2 mmol) and ethyldiisopropyl amine (2 mmol) in DMF or ethanol (4 mL). The reaction mixture is stirred under an atmosphere of argon. The reaction was followed by TLC. The reaction is stirred at 50° C. if no reaction occurred at room temperature. The reaction mixture is concentrated to syrup and worked-up by RP-HPLC (eluent: water→methanol). The corresponding tert-butyldimethyl silyl protected iodo nucleoside is used instead of the unprotected nuclesude when the primary hydroxyl group is acylated in the course of the reaction. The silyl ether is cleaved after the Sonogashira coupling by treating the compound with tetrabutyl ammonium fluoride (4 eq.) in a solution of ethanol and acetic acid (8 eq.) for 1 day followed by concentration and work-up by RP-HPLC (eluent: water→methanol).

Synthesis of LH3, LH6 and LH9: Phosphooxychloride (0.11 mmol) is added to an ice-water cooled solution of the nucleoside (0.1 mmol) in trimethyl phosphate (1 mL). The reaction mixture is stirred under an atmosphere of argon at 0° C. for 1 h. A solution of bis-n-tributylammonium pyrophosphate (0.2 mmol) in DMF (1 mL) and n-tributylamine (0.3 mmol) is then added. The reaction mixture is stirred for 10 minutes then water (1 mL) was added. The mixture is neutralized with triethylamine and stirred at room temperature for 6 h, then concentrated in vacuo and worked-up by ion pair exchange RP HPLC (eluent 100 mM triethylammonium acetate→100 mM triethylammonium acetate in 80% acetonitrile). Removal of buffer salts from the nucleotide is carried out by adding water (100 µl) to the mixture and then concentrating the slurry at 0.1 mmHg several times finally followed by a gel filtration (eluent: water).

B) Library Design and Nucleotide Derivative Incorporation

A templated library can be produced by extension of a primer annealed to a template primer. The template primer encodes the library and can be prepared using standard procedures, e.g. by organ synthesis with phosphoramidite. To generate various types of oligonucleotide libraries one can for example use redundancies, mixed phosphoramidite or doping in synthesizing the oligonucleotides. These oligonucleotide libraries can be purchased from a supplier making customer defined oligonucleotides (e.g. DNA Technology A/S, Denmark or TAG Copenhagen A/S, Denmark).

Here, An extension primer (5'-GCT ACT GGC ATC GGT-3' SEQ ID NO:16) is used together with a template primer (5'-GTA ATT GGA GTG AGC CDDDAC CGA TGC CAG TAG C-3' SEQ ID NO:18) where D (underlined, using the ambiguity definition from International Union of Biochemistry) is either A, G or T. The extension primer is complementary to the template primer as shown below. During extension the primer is extended past the DDD-sequence, leading to insertion of T-, C-, or A-nucleotide derivatives at there position, according to the sequence of the individual templates. Upon polymerization of the α-amino and precursors attached to the nucleotides, and cleavage of the linker that connect the amino and the nucleotide, a library with a theoretical diversity of at least $3^3=27$ different peptides is created.

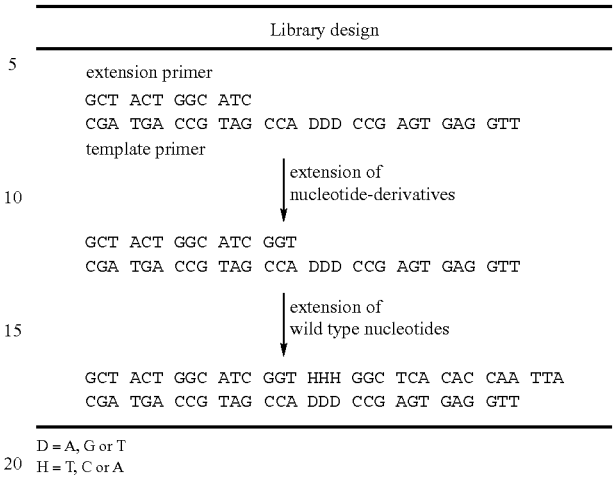

The extension primer is annealed with the template primer, using about 3 pmol of each primer in an extension buffer (20 mM Hepes, 40 mM KCl, 8 mM $MgCl_2$, pH 7.4, 10 mM DTT), by heating to 80° C. for 2 min and then slowly cooling to about 20° C.

The nucleotide derivatives are then added to a concentration of about 200 µM each, and incorporated using 5 units AMV Reverse Transcriptase (Promega, part# 9PIM510) at 30° C. for 1 hour. Unincorporated nucleotide derivatives are removed using a spin-column (BioRad). Further extension may be performed by adding wild type dNTP using the same conditions described for the nucleotide derivatives. Alternatively, an oligonucleotide that anneal to the sequence downstream of the DDD sequence is added prior to the extension. The double stranded product is purified and transferred to another buffer (100 mM Na-phosphate buffer, pH 8.0) using a spin-column (BioRad).

C) Polymerization and Linker Cleavage

The reactive groups of the incorporated nucleotide derivatives are linked together using 1-Ethyl-3-(3-dimethylaminopropyl) carbodiimide (EDC) and N-Hydroxysuccinimide (NHS). This is a routine procedure for covalent coupling amines and carboxyl groups. Examples of coupling conditions are described in the literature (e.g. NHS coupling kit, IAsys, code # NHS-2005).

EDC and NHS are added to the purified double stranded extension product at appropriate final concentrations of about 100 mM and 10 mM, respectively. This reaction is incubated at 30° C. for 2-16 hours. Excess linking reagents is removed using a spin column. Hydrolysis of hydrolysable linkers is achieved by incubating the sample at pH 11 (e.g. 0.2 M NaOH) for 15 min at 50° C.

D) Selection

One of the possible templated molecules in this particular library, when using nucleotide derivatives LH3, LH6 and LH9, is glutathione (Glu-Cys-Gly). The incorporation, reaction between the reactive groups and cleavage of the linkers to generate glutathione on the DNA template is shown in the scheme below. It is known that glutathione binds specifically and with high affinity to Glutathione S-transferase (GST) and is commonly used for purification of GST-fusion proteins (Amersham Pharmacia Biotech). It is also known that glutathione can be immobilized through the sulfur atom without interfering with the binding to GST. Consequently, it is possible to enrich template-displayed glutathione among other displayed molecules in a library by performing selection against GST as the target molecule. GST can be produced in a recombinant form as described in the literature (e.g. Jemth et al. (1997) Arch. Biochem. Biophys. 348: 247-54) or be obtained from various suppliers (e.g. Sigma, product #, G5524). Alternatively, an antibody against glutathione (e.g. Abcam, product name ab64447 or Virogen, product # 101-A) can be used as the target molecule.

Template-mediated Formation of Glutathione

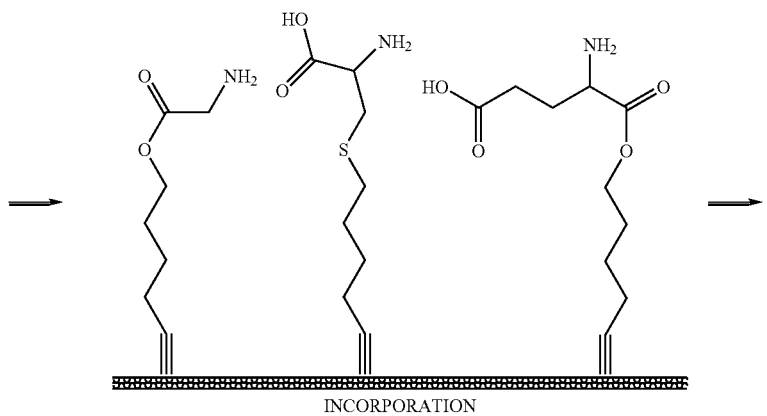
INCORPORATION

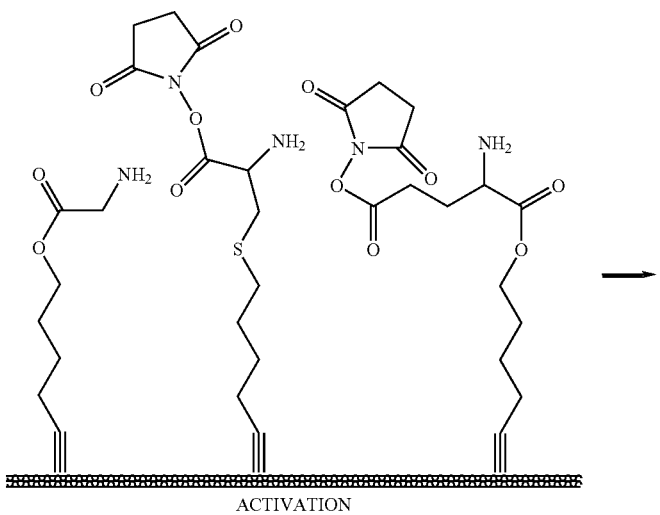
ACTIVATION

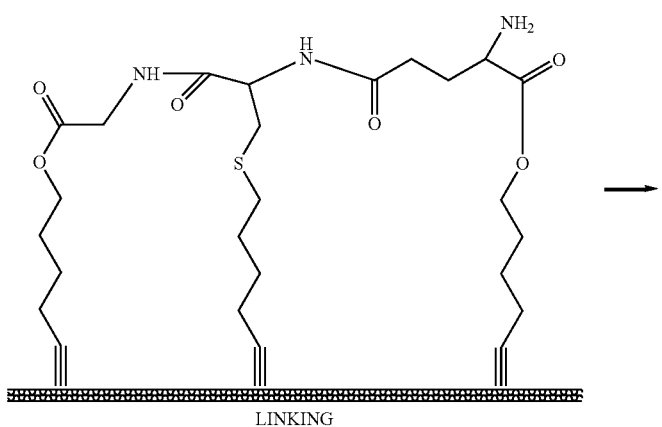
LINKING

-continued

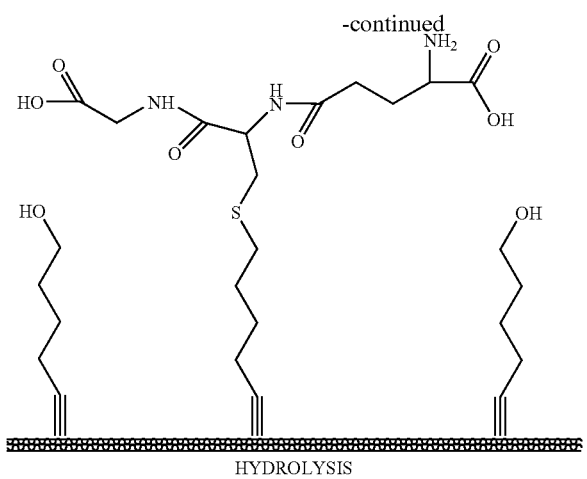

HYDROLYSIS

A microtiter plate is coated with about 1 µg streptavidin in a TBS buffer (50 mM Tris-HCl, pH 7.5, 150 mM NaCl) overnight at 4° C. Remove the streptavidin solution and wash the wells at least six times with TBS buffer. Block the wells with 2% BSA in TBS buffer (other examples of blocking agent that could be used is casein, gelatine, polyvinylpyrrolidone or dried skim milk) for about 30 min. at 37° C. Wash the plate with TBS buffer at least three times. Add 0.1 µg biotinylated GST to the wells and incubate about 30 min at 20° C. Remove non-bound biotinylated GST by washing with TBS buffer at least six times. Biotinylation of GST is performed using sulfo-NHS-LC-biotin as described in the literature (e.g. Ellis et al. (1998) Biochem. J. 335; 277-284). Free streptavidin molecules are blocked with 1 mM biotin for 5 min. and excess biotin is removed by wash with TBS buffer at least six times. Add then the templated molecule library to the wells and allow binding to immobilized GST by incubating at 20° C. for about 1 hour. To remove the templated molecules not coordinated to the immobilized GST, wash the wells with TBS buffer at least six times. Elute the templated molecules bound to GST by incubating with 20 mM reduced glutathione for about 10-60 min and then transfer the samples from the wells to new tubes.

The eluted (selected) templates are amplified using two amplifying primers (forward, 5'Biotin-GCT ACT GGC ATC GGT-3' SEQ ID NO:16; reverse, 5'-GTA ATT GGA GTG AGC-3' SEQ ID NO:19) with a standard PCR protocol (e.g. 5 pmol of each primer, 0.2 mM of dNTP, 2 mM of MgCl$_2$, and 2.5 U of thermal stable Taq polymerase). The PCR is performed with an initial denaturation at 94° C. for 5 min, 35 cycles of denaturation at 94° C. for 30 seconds, annealing at 50° C. for 30 seconds, extension at 72° C. for 30 seconds, and then a final extension at 72° C. for 10 min. The 5'biotin in the forward primer is used to remove the sense strand. This is done by incubating the PCR product with streptavidin-coated magnetic beads (Dynabeads; Dynal Biotech, Norway) and the single stranded template is purified as described by the manufacturer. The purified antisense strand is finally used as the template primer together with the extension primer as describe above to generate an enriched library of templated molecules for another round of selection.

The selection and amplification procedure is repeated until appropriate enrichment is obtained. Enrichment can be followed by characterization (sequencing) of recovered template sequences. The nucleotide sequence of the templates is obtained using standard sequencing protocols and a DNA sequencer (e.g. MegaBase, Amersham Pharmacia Biotech). Enrichment is obtained when the number of sequences coding for glutathione (C-A-T or T-A-C in the D-D-D region of the template primer) has increased relative to other sequences in the library after the selection procedure.

This protocol describes incorporation of three different mono-nucleotide derivatives. However, all the mono-nucleotides (including dGTP) could be used in building libraries of templated molecules as described above. Still, this will limit the number of different nucleotide derivatives to four and thus put a boundary on the library size to $4^N$ (where N is the number of subunits in the templated molecule). However, one may use for example di-nucleotide derivatives as building blocks in order to increase the library size to $16^N$. Incorporation of di-nucleotides by polymerase has earlier been described (WO 01/16366 A2). Library diversity may be further increased using tri-nucleotides or tetra-nucleotide incorporation.

Examples 84 to 99

Preparation of Intermediate Compounds for Oligonucleotide Building Block Synthesis General Experimental Methods.

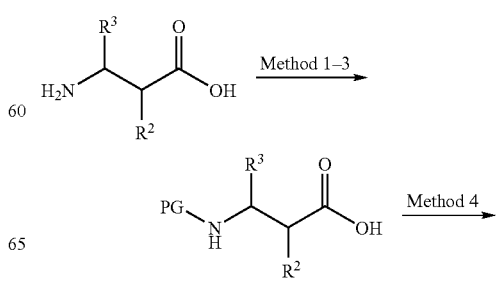

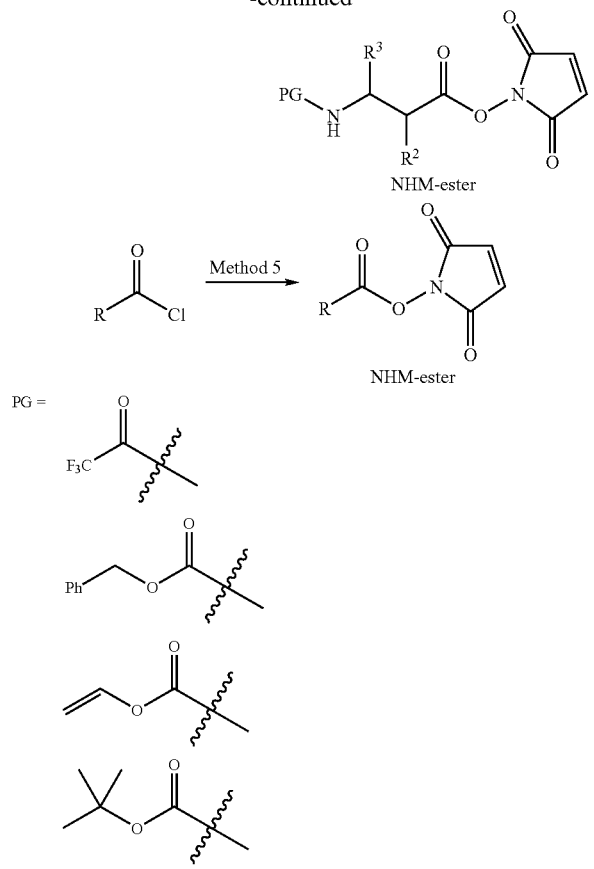

NHM-ester

Method 1. General Procedure for N-trifluoroacetyl Protection of Amino Acids.

A stirred solution of the amino acid (20 mmol) in CF₃COOH (10 mL) at 0° C. was slowly added (CF₃CO)₂O (24 mmol). The reaction mixture was allowed to slowly warm up to RT and left with stirring over night. The reaction mixture was evaporated to dryness. Crude products of solid nature was recrystallized from EtOAc/heptane. Crude products of liquid nature was purified by flash column chromatography (CH₂Cl₂/MeOH=10:1 or EtOAc/heptane=2:1). The yield was in general higher than 85%.

Method 2. General Procedure for N-benzyloxycarbonyl and N-vinyloxycarbonyl Protection of Amino Acids.

A stirred solution or slight suspension of the amino acid (7.6 mmol) in sat. NaHCO₃ (10 mL) was added 2 M NaOH (aq., 3 mL) and then a solution of either benzylchloroformate or vinyloxychloroformate (8.4 mmol) in CH₃CN (10 mL). The reaction mixture was left with stirring at RT over night. When TLC indicated complete transformation, the reaction mixture was added H₂O (90 mL) and pH was adjusted to 10 using 2 M NaOH (aq.). The reaction mixture was washed with Et₂O (3×50 mL) and pH adjusted to 2-3 using 1 M HCl (aq.) and then extracted using Et₂O or CH₂Cl₂ (3×100 mL). The combined extractions were dried (MgSO₄), filtered and evaporated to dryness to yield a solid product, which was used without further purification. The yield was in general higher than 70%.

Method 3. General Procedure for N-tert-butyloxycarbonyl Protection of Amino Acids.

A slight suspension of the amino acid (15 mmol) in H₂O (5 mL) and dioxan (5 mL) was added 2M NaOH (aq, 6 mL). The mixture was cooled and stirred at 0° C. (ice bath), and di-tert-butyl dicarbonate was added. Further 2 M aqueous NaOH (4 mL) was added. The mixture was slowly heated to RT (over 5 hours), and left with stirring at RT over night. The reaction mixture was added diethyl ether (20 mL) and pH was adjusted (from ~10 to ~3), using 2 M HCl (aq.). The aqueous phase was extracted, using diethyl ether (3×20 mL). The combined extracts were dried (MgSO₄), filtered and evaporated to dryness to yield a white solid product, which was used without further purification. The yield was typically 60-75%.

Method 4. General Procedure for Formation of NHM Esters of N-protected Amino Acids.

A stirred solution of the N-protected amino acid (0.5 mmol) and N-hydroxymaleimide (0.62 mmol) in anhydrous THF (5 mL) at 0° C. under N₂ was added diisopropylcarbodiimide (DIC) (0.64 mmol) and the solution allowed to slowly warm up to RT and left with stirring over night. The reaction mixture was filtered and the precipitate washed with a small volume of EtOAc/heptane=2/1. The filtrate was evaporated to almost dryness, diluted with a minimum of CH₂Cl₂ and subjected to flash column chromatography (EtOAc/heptane=2/1), yielding the product as a white solid in typically 60-70%.

Method 5. General Procedure for Formation of NHM Esters from Carboxylic Acid Chlorides.

A stirred solution of N-hydroxymaleimide (4 mmol) in CH₂Cl₂ (16 mL) at 0° C. was slowly added the carboxylic acid chloride (4 mmol). The reaction mixture was allowed to slowly warm up to RT and left with stirring over night. The reaction mixture was diluted with CH₂Cl₂ (16 mL) and washed with 10% citric acid (aq., 3×25 mL), sat. NaHCO₃ (aq., 2×25 mL) and sat. NaCl (aq., 1×25 mL). The organic phase was dried (MgSO₄), filtered, and evaporated to dryness to yield the product as a wax or liquid in 40-60% yield. The product was used without further needed purification.

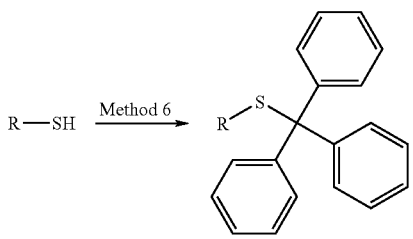

Method 6. General Procedure for S-tritylation of Mercaptanes.

A solution of the mercaptane (20 mmol) and pyridine (40 mmol) in CH₂Cl₂ (75 mL) at RT was added tritylchloride (22 mmol) and the reaction left with stirring over night. The volume of the reaction mixture was reduced to a minimum and then subjected to flash chromatography (SiO₂ pretreated with pyridine prior to column packing) (eluent: CH₂Cl₂/MeOH=10/0.5). The product was isolated as an oil or a sticky wax in some instances.

Method 7. General Procedure for O-Acylation of 4-Hydroxy-benzaldehydes.

To a stirred solution of the hydroxybenzaldehyde (20 mmol) in dry DMF (10 mL) at 0° C. was slowly added an acid chloride (25 mmol) in diethyl ether (20 mL). The reaction mixture was stirred at 0° C. for 15 minutes and at rt for 1 hr. Water (20 ml) was added and the reaction mixture was extracted with ether (3×10 mL). The combined organic phases was washed with water (2×10 mL), dried over MgSO$_4$ and the solvent removed in vacuo. The crude was redissolved in dichloromethane (5 mL) and filtered through a pad of silica. The solvent was removed in vacuo. The yield was in general higher than 75%.

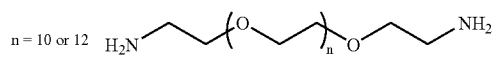

n = 10 or 12

Method 8. General Procedure for Formation of Diaminopolyethylenecilocols.

The corresponding polyethyleneglycol-diol (0.8 mmol), obtained as described by Baker et al. *J. Org. Chem.* (1999), 64, 6870-6873, was dissolved in dry THF (10 mL). Tosyl chloride (2.44 mmol) was added and the reaction mixture was cooled on ice. NaOH (5.5 mmol) dissolved in water (2 mL) was added dropwise and the reaction mixture was stirred at rt o/n. The reaction mixture was extracted with diethyl ether (3×5 mL) and the combined organic phases washed with NaCl (sat., 3×3 mL) and dried over MgSO$_4$. The crude was redissolved in dry acetonitrile (3 mL) and treated with NaN$_3$ (2.8 mmol). The reaction mixture was heated to 75° C. o/n. The white solid was filtered off and extracted with acetonitrile (2×2 mL). Triphenylphosphine (2.8 mmol) and water (2 mL) was added to the combined organic phases and the reaction mixture was stirred o/n. IRA-120H$^+$ (1 g) was added and the reaction mixtured was agitated for 1 hour. The beads were filtered off, washed with dichloromethane (10×3 mL) and the final compound eluted with 6M HCl (aq., 10×3 mL). The solution was evaporated in vacuo affording the diamino polyethylene glycol in 40-50% yield.

Example 84

Prepartion of 3-Phenyl-3-tertbutoxycarbonylamino-propionic Acid 2,5-dioxo-2,5-dihydro-pyrrol-1-yl Ester (XVI)

Compound XVI

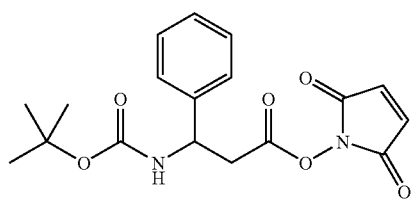

The compound was prepared in two steps from the commercially available DL-3-amino-3-phenylpropionic acid by use of method 3 followed by method 4.

$^1$H-NMR (CDCl$_3$): 7.28-7.42 (m, 5H(ar)); 6.74 (s, 2H); 5.1-5.3 (m, 2H(NH+CH)); 3.24 (dd, 1H); 3.13 (dd, 1H); 1.46 (s, 9H).

Example 85

Preparation of 3-tertbutoxycarbonylamino-butanoic Acid 2,5-dioxo-2,5-dihydro-pyrrol-1-yl Ester compound XVII

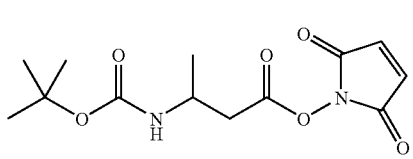

The compound was prepared in two steps from the commercially available DL-3-aminobutyric acid by use of method 3 followed by method 4.

$^1$H-NMR (CDCl$_3$): 6.80 (s, 2H); 4.83 (br s, 1H(NH)), 4.05-4.15 (m, 1H); 2.8-2.95 (m, 2H); 1.46 (s, 9H); 2.56 (d, 3H).

Example 86

Preparation of 3-tertbutoxycarbonylamino-propionic Acid 2,5-dioxo-2,5-dihydro-pyrrol-1-yl Ester Compound XVIII

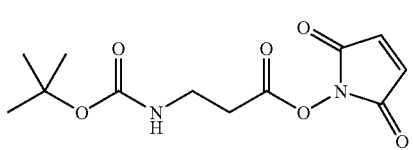

The compound was prepared in two steps from the commercially available beta-alanine by use of method 3 followed by method 4.

$^1$H-NMR (CDCl$_3$): 6.80 (s, 2H); 5.09 (br s, 1H(NH)); 3.48-3.54 (m, 2H); 2.84 (t, 2H); 1.45 (s, 9H).

Example 87

Preparation of 3-Benzyloxycarbonylamino-3-phenyl-propionic Acid 2.5-dioxo-2,5-dihydro-pyrrol-1-yl Ester 3-Benzyloxycarbonylamino-3-phenyl-propionic Acid 2,5-dioxo-2,5-dihydro-pyrrol-1-yl Ester Compound XIX

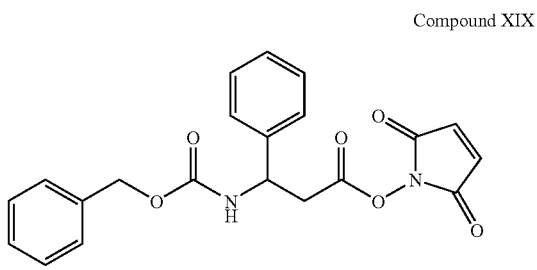

The compound was prepared in two steps from the commercially available DL-3-amino-3-phenylpropionic acid by use of method 2 followed by method 4.

$^1$H-NMR (CDCl$_3$): 7.55-7.20 (m, 10H); 6.75 (s, 2H); 5.55 (br., 1H); 5.35-5.25 (m, 1H); 5.15 (s, 2H); 3.35-3.10 (m, 2H).

Example 88

3-Phenyl-3-vinyloxycarbonylamino-propionic Acid 2,5-dioxo-2,5-dihydro-pyrrol-1-yl Ester Compound XX

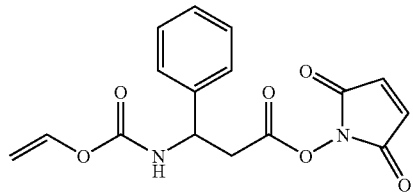

The compound was prepared in two steps from the commercially available DL-3-amino-3-phenylpropionic acid by use of method 2 followed by method 4.

$^1$H-NMR (CDCl$_3$): 7.45-7.30 (m, 5H); 7.20 (dd, 1H); 6.75 (s, 2H); 5.75-5.60 (br., 1H); 5.30 (q, 1H); 4.70 (d, 1H); 4.50 (d, 1H); 3.30-3.15 (m, 2H)

Example 89

Preparation of Tritylsulfanyl-acetic Acid 2.5-dioxo-2.5-dihydro-pyrrol-1-yl Ester Compound XXI

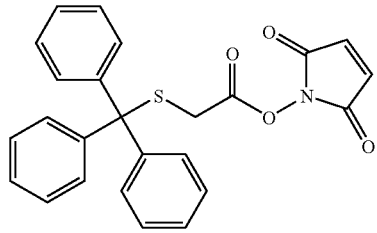

The compound was prepared in two steps from commercially available 2-mercaptoacetic acid by use of method 6 followed by method 4.

$^1$H-NMR (CDCl$_3$): 7.45-7.20 (m, 15H); 6.75 (s, 2H); 3.20 (s, 2H).

Example 90

(R)-2-(2,2,2-Trifluoro-acetylamino)-3-tritylsulfanyl-propionic Acid 2,5-dioxo-2,5-dihydro-pyrrol-1-yl Ester (XXII)

Compound XXII

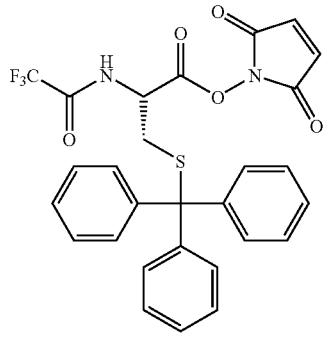

The compound was prepared in three steps from commercially available L-cysteine by use of method 1 followed by method 6 and method 4.

Example 91

Preparation of Acetic Acid 2.5-dioxo-2,5-dihydro-pyrrol-1-yl Ester

Compound XXIII

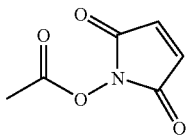

The compound was prepared in one step from commercially available acetylchloride and N-hydroxymaleimide by use of method 5.

$^1$H-NMR (CDCl$_3$): 6.75 (s, 2H); 2.35 (s, 3H).

Example 92

Preparation of Propionic Acid 2,5-dioxo-2,5-dihydro-pyrrol-1-yl Ester

Compound XXIV

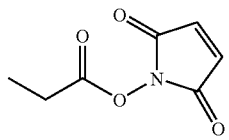

The compound was prepared in one step from commercially available propanoyl-chloride and N-hydroxymaleimide by use of method 5.

$^1$H-NMR (CDCl$_3$): 6.75 (s, 2H); 2.65 (q, 2H); 1.80 (t, 3H).

Example 93

Preparation of Butyric Acid 2,5-dioxo-2.5-dihydro-pyrrol-1-yl Ester

Compound XXV

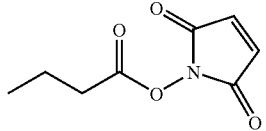

The compound was prepared in one step from commercially available butanoylchloride and N-hydroxymaleimide by use of method 5.

$^1$H-NMR (CDCl$_3$): 6.75 (s, 2H); 2.60 (t, 2H); 1.80 (sxt, 2H); 1.05 (t, 3H).

Example 94

Preparation of S-Trityl-4-mercaptobenzoic Acid 2,5-dioxo-2,5-dihydro-pyrrol-1-yl Ester

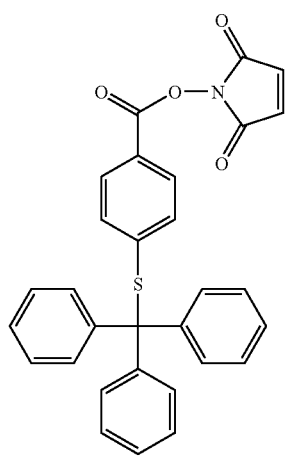

Compound XXVI

The compound was prepared in two steps from the commercially available 4-mercaptobenzoic acid, by S-tritylation according to method 6 followed by esterification according to method 4.

$^1$H-NMR (CDCl$_3$): 8.75 (d, J=8.8 Hz, 2H), 7.45-7.20 (m, 15H), 7.05 (d, J=8.8 Hz, 2H), 6.80 (s, 2H).

Example 95

Preparation of Tetrakis(Aminometyl)Methane Tetrahydrochlorid

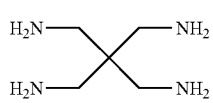

Compound XXVII

Tetrakis(aminomethyl)methane tetrahydrochloride was prepared by a slightly modified method compared to Fleischer et al. *J. Org. Chem.* (1971), 36, 3042-44. Pentaerythritol (2.01 g; 14.76 mmol) was mixed with tosyl chloride (14.07 g; 73.81 mol) in dry pyridine (50 mL). The mixture was stirred o/n. The crude reaction mixture was transferred to water (100 mL). MeOH (200 mL) and HCl conc. (80 mL) was added and the white precipitate was filtered off and washed with water (100 mL) and MeOH (200 mL). LC-MS show pentaerythritol tetratosylate. Pentaerythritol tetratosylate (4.0 g, 5.31 mmol) was dissolved in dry DMF (50 mL) and NaN$_3$ (3.45 g; 53.1 mmol) was added. The reaction mixture was heated to 100° C. o/n. Water (100 mL) was added and the reaction mixture was extracted with diethyl ether (3×100 mL). THF (300 mL) was added and the diethyl ether was removed in vacuo. Triphenylphosphine (6.95 g, 26.5 mmol) and NH$_3$ conc. (25 mL) were added to the THF solution and the reaction mixture was stirred at rt o/n. The solvents were removed in vacuo, redissolved in dichloromethane (500 mL) and extracted with 2M HCL (2×150 mL). The aqueous phase was washed with dichloromethane (3×100 mL) and evaporated in vacuo. MeOH (20 mL) was added and the white solid was filtered off and washed with MeOH (2×10 mL). Yield 1.12 g (76%).

$^1$H-NMR (D$_2$O): 3.28 (s).

Example 96

Preparation of Propionic Acid 4-formyl-phenyl Ester

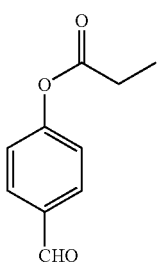

Compound XXVIII

The compound was prepared according to method 7 from commercially available 4-hydroxybenzaldehyde.

$^1$H-NMR (CDCl$_3$): 10.00 (s, 1H), 7.90 (d, J=6.7 Hz, 2H), 7.31 (d, J=6.7 Hz, 2H), 2.65 (q, J=7.6 Hz, 2H), 1.32 (d, J=7.5 Hz, 3H).

Example 97

Preparation of Butanoic Acid 4-formyl-phenyl Ester

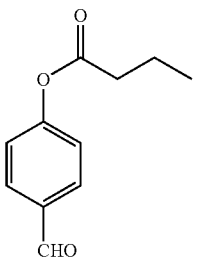

Compound XXIX

The compound was prepared according to method 7 from commercially available 4-hydroxybenzaldehyde.

$^1$H-NMR (CDCl$_3$): 9.95 (s, 1H), 7.94 (d, J=6.7 Hz, 2H), 7.28 (d, J=6.7 Hz, 2H), 2.55 (t, J=7.6 Hz, 2H), 1.80 (q, J=7.6 Hz, 2H), 1.00 (d, J=7.5 Hz, 3H).

Example 98

Preparation of 3,6,9,12,15,18,21,24,27,30,33-undecanoxapentatriacontane-1,35-diamine

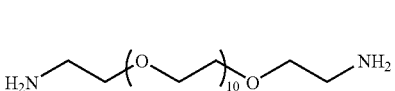

Compound XXX

Prepared according to method 8 in 48% yield. MS-H$^+$= 545.2 (expected MS-H$^+$=544.6)

Example 99

Preparation of 3,6,9,12,15,18,21,24,27,30,33,36,39-Tridecanoxahentetracontane-1,41-diamine

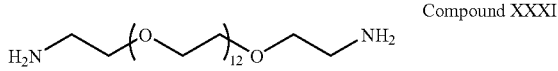
Compound XXXI (05028) Prepared according to method 8 in 40% yield. MS-H⁺=633.3 (expected MS-H⁺=632.8).

Example 100

Design and Testing of Oligonucleotide Linkers Carrying Zipper Boxes

Experiments 100-1 to 100-4 were performed in order to test the efficiency of different designs of zipper boxes. The data obtained follow immediately below, then follows a discussion of the data.

Materials.

Buffers.
Buffer A (100 mM Hepes pH=7, 5.1 M NaCl)
Buffer B: (100 mM NaPO$_4$ pH=6, 1 M NaCl)
Buffer C: (100 mM NaBorate pH=9, 1 M NaCl)
Buffer D: (100 mM NaBorate pH=10, 1 M NaCl)
Buffer E: (500 mM NaPO$_4$ pH=7, 1 M NaCl)
Buffer F: (500 mM NaPO$_4$ pH=8, 1 M NaCl)

Annealing of DNA Oligonucleotides.
Mix oligos in relevant buffer and heat at 80° C. then cool to 28° C. (−2° C./30 sek).

5'-Labeling with $^{32}$P.
Mix 200 pmol oligonucleotide, 2 µl 10× phosphorylation buffer (Promega cat# 4103), 1 µl T4 Polynucleotid Kinase (Promega cat# 4103), 1 µl γ-$^{32}$P ATP, H$_2$O ad 20 µl. Incubate at 37° C., 10-30 minutes.

PAGE (Polyacrylamide Gel Electrophoresis).
The samples are mixed with formamide dye 1:1 (98% formamide, 10 mM EDTA, pH 8, 0.025% Xylene Cyanol, 0.025% Bromphenol Blue), incubate at 80° C. for 2 minutes, and run on a denaturing 10% polyacrylamide gel. Develop gel using autoradiography (Kodak, BioMax film).

Oligonucleotide Building Blocks

AH36:
5'-CGACCTCTGGATTGCATCGGTCATGGCTGACTGTCCGTCGAATGT<u>GT CCAGTTAC</u>X

AH37:
5'-Z<u>GTAACTGGA</u>CTGTAAGCTGGCTGTCAGTCGGTACTGACCTGTCGAG CATCCAGCT

AH51:
5'-Z<u>GTAAC</u>ACCTG<u>J</u>GTAAGCTGCCTGTCAGTCGGTACTGACCTGTCGAG CAICCAGCT

AH38:
5'-AGCTGGAIGCTCGACAGGTCCCGATGCAATCCAGAGGTCG

AH67:
5'-ZCATTGACCTG<u>T</u>GTAAGCTGCCTGTCAGTCGGTACTGACCTGTGGA GCATCCAGCT

AH69:
5'-<u>AGZAA</u>CACCTGTGTAAGCTGCCTGTCAGTCGGTACTGACCIGTCG AGCATCCAGCT

AH66:
5'-ZTT<u>GTAACTGGA</u>CTGTAAGCTGCCTGTCAGTCGGTACTGACCTGT CGAGCATCCAGCT

AH65:
5'-CGACCTCTGGATTGCAICGGTCATGGCTGACTGTCCGTCGAATGT<u>GT CCAGTTACTT</u>X

Zipper box sequences are underlined.

Carboxy-modifier C2 dT

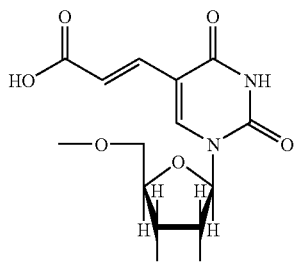

X = Carboxy-dT cat. no. 10-1035-
Amino modifier C2 dT

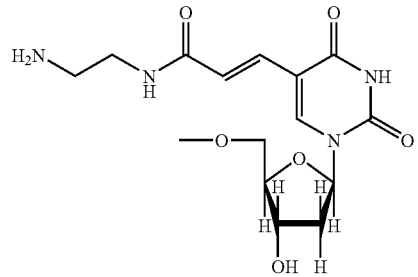

Y = Amino-Modifier C2 dT 10-1037-
Amino modifier C6 dT

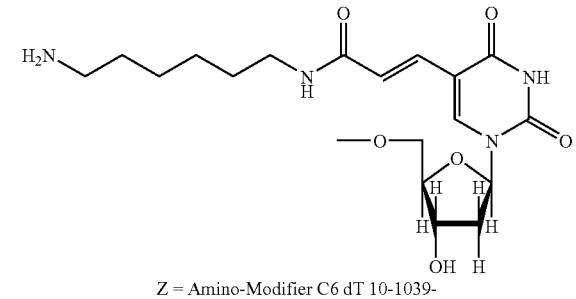

Z = Amino-Modifier C6 dT 10-1039-

Experiment 100-1 (FIG. 56):
Mix 2 µi buffer B, 5 µi Ah36 (0.4 pmol/ul), 1 µi Ah37 (2 pmol/ul), 1 µl Ah38 (2 pmol/ul), 1 µl H$_2$O.
Mix 2 µl buffer B, 5 µl Ah36 (0.4 pmol/ul), 1 µl Ah37 (2 pmol/ul), 2 µol H$_2$O.
Anneal by heating to 80° C., then cool to 44° C. (−2° C./30 sek).
Add 1 µl 100 mM NHS and 1 µl 1 M EDC. Incubate at indicated temperatures (see below) for 45 minutes, then add 2 µl Buffer D. Incubate for about 2 h, and then analyze by 10% urea polyacrylamide gel electrophoresis.

Incubation temperatures:

45° C., 48.2° C., 53.0° C., 58.5° C., 63.1° C., 65.6° C.

Figure 57B:
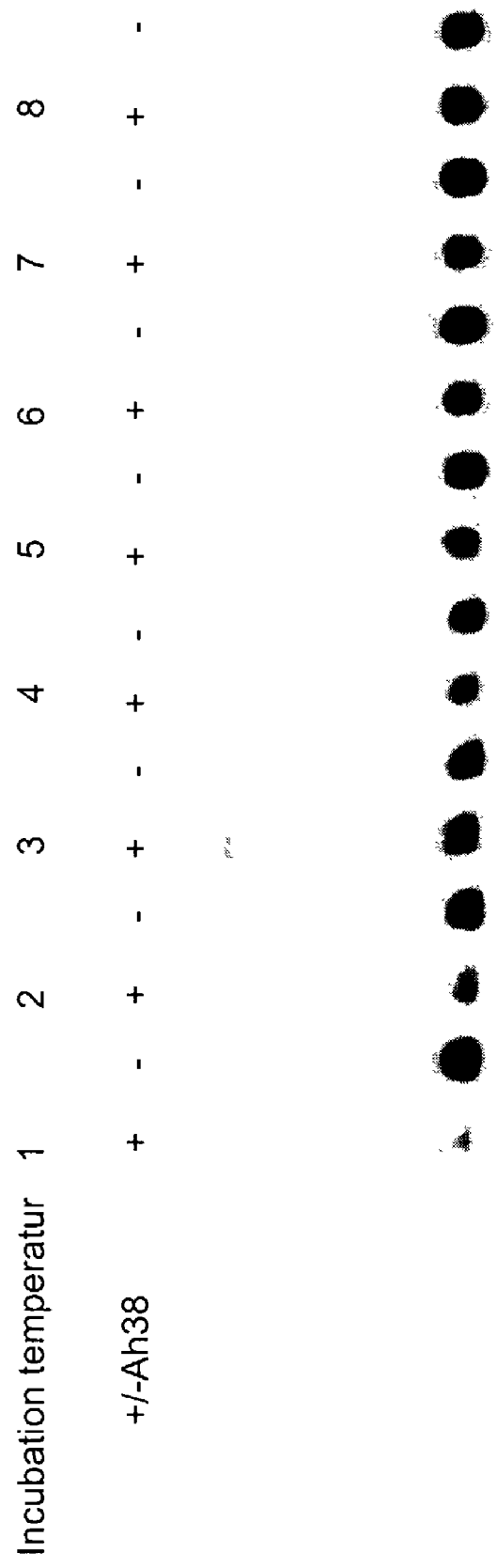

Experiment 100-2 (FIGS. 57. A and B):

Mix 2 µl buffer B, 1 µl Ah36 (2 pmol/ul), 1 µl Ah51 (2 pmol/ul), 1 µl Ah38 (2 pmol/ul), 5 µl H$_2$O.

Mix 2 µl buffer B, 1 µl Ah36 (2 pmol/ul), 1 µl Ah51 (2 pmol/ul), 6 µl H$_2$O Anneal by heating to 80° C., then cool to 35° C. (−2° C./30 sek)(For temperatures 1 to 6), or heat to 80° C., then cool to 15° C. (−2° C./30 sek)(For temperatures 7 to 12).

Add 1 µl 100 mM NHS and 1 µl 1 M EDC. Incubate at indicated temperatures (see below) for 1 h, then add 2 µl Buffer D. Incubate for 1 h, and then analyze by 10% urea polyacrylamide gel electrophoresis, as described above.

Incubation temperatures:

1) 34.9° C., 2) 36.3° C., 3) 40.3° C., 4) 45.7° C., 5) 51.0° C., 6) 55.77, 7) 14.9° C., 8) 17.8° C., 9) 22.7° C., 10) 28.3° C., 11) 31.0° C., 12) 36° C.

Mix 2 µl buffer B, 0.5 µl Ah36 (2 pmol/ul), 1 µl Ah51 (2 pmol/ul), 1 µl Ah38 (2 pmol/ul), 5.5 µl H$_2$O Mix 2 µl buffer B, 0.5 µl Ah36 (2 pmol/ul), 1 µl Ah51 (2 pmol/ul), 6.5 µl H$_2$O Anneal by heat at 80° C. then cool to 5° C. (−2° C./30 sek).

Add 1 µl 100 mM NHS and 1 µl 1 M EDC. Incubate at different temperatures (see below) for 1 h, then add 2 µl Buffer D. Incubate for 1 h, and then analyze by 10% urea polyacrylamide gel electrophoresis.

Incubation temperatures:

1) 5.9° C., 2) 9.9° C., 3) 12.6° C., 4) 18.3° C., 5) 23.3° C., 6) 27.9° C. 7) 35.6° C., 8) 45.9° C.

Experiment 100-3 (FIGS. 58. A and B).

Mix 2 µl buffer A, 1 µl relevant oligo 1 (2 pmol/ul), 1 µl relevant oligo 2 (10 pmol/ul), 1 µl relevant oligo 3 (10 pmol/ul), 5 µl H$_2$O. (See table below). Anneal as described above.

Add 1 µl 100 mM NHS and 1 µl 1 M EDC. Incubate at different temperatures 1) 7.7° C., 2) 15.4° C., 3) 21.0° C. 4) 26.2° C. for about 2 h, and 5) 10° C. for 1 sec., then 35° C. for 1 sec.—repeat 99 times. Analyze by 10% urea polyacrylamide gel electrophoresis.

| Experiment | Oligo 1 ($^{32}$P) | Oligo 2 | Oligo 3 |
|---|---|---|---|
| 100-3-1 | Ah36 | None | Ah38 |
| 100-3-2 | Ah36 | None | None |
| 100-3-3 | Ah36 | Ah51 | Ah38 |
| 100-3-4 | Ah36 | Ah51 | None |
| 100-3-5 | Ah36 | Ah67 | Ah38 |
| 100-3-6 | Ah36 | Ah67 | None |
| 100-3-7 | Ah36 | Ah69 | Ah38 |
| 100-3-8 | Ah36 | Ah69 | None |

Experiment 100-4 (FIG. 59).

Mix 2.5 µl buffer A, 1 µl relevant oligo 1 (2 pmol/ul), 1 µl relevant oligo 2 (10 pmol/ul), 1 µl relevant oligo 3 (10 pmol/ul), 4.5 µl H$_2$O. (See table below). Anneal by heating to 80° C. and then cool to 30° C. or 55° C. Add 1 µl 100 mM NHS and 1 µl M EDC. Incubate at 30° C. or 55° C. Then analyze by 10% urea polyacrylamide gel electrophoresis.

| Experiment | Oligo 1 ($^{32}$P-labelled) | Oligo 2 | Oligo 3 |
|---|---|---|---|
| 100-4-1 | Ah36 | Ah37 | Ah38 |
| 100-4-2 | Ah36 | Ah37 | None |
| 100-4-3 | Ah65 | Ah66 | Ah38 |
| 100-4-4 | Ah65 | Ah66 | None |
| 100-4-5 | Ah36 | Ah66 | Ah38 |
| 100-4-6 | Ah36 | Ah66 | None |
| 100-4-7 | Ah65 | Ah37 | Ah38 |
| 100-4-8 | Ah65 | Ah37 | None |

Discussion of the Results

The cross-linking efficiency using oligos carrying reactive groups (amine or carboxylic acid) where the linker connecting the reactive group and the annealing region was approximately 25 nucleotides, was examined.

In an experiment oligonucleotides Ah36 (carrying a carboxylic acid) and Ah67 (carrying an amine) were used. The template used (Ah38) anneals the two oligonucleotides immediately adjacent, i.e. with a spacing of zero base pairs. Under the conditions of the experiment, less than 5% cross-linking efficiency is observed, and only at the highest tested temperature (FIGS. 58, A and B, lanes 5).

In order to improve the cross-linking efficiency, we introduced a so-called zipper box sequence at the 5'- and 3' end of oligos Ah67 and Ah36, respectively, the same termini that carries the reactive groups. The zipper-boxes are complementary sequences, and thus may bring the reactive groups of the two oligos into closer proximity. Two different lengths of zipper boxes were tested, namely a 10'mer zipper box (Ah37/Ah36 forming a DNA duplex of 10 base pairs) and a 5'mer zipper box (Ah36/51 forming a DNA duplex of 5 base pairs). See figure below.

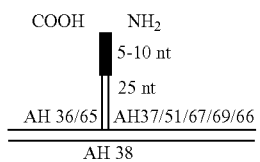

Moreover, different designs of zipper boxes were tested, e.g. oligos in which the reactive group is attached immediately adjacent to the zipper box (Ah36, Ah37 and Ah36/Ah51), or placed two nucleotides upstream from the zipper box (Ah65/Ah66), or placed in the middle of the zipper box (Ah67).

Figure 58B:
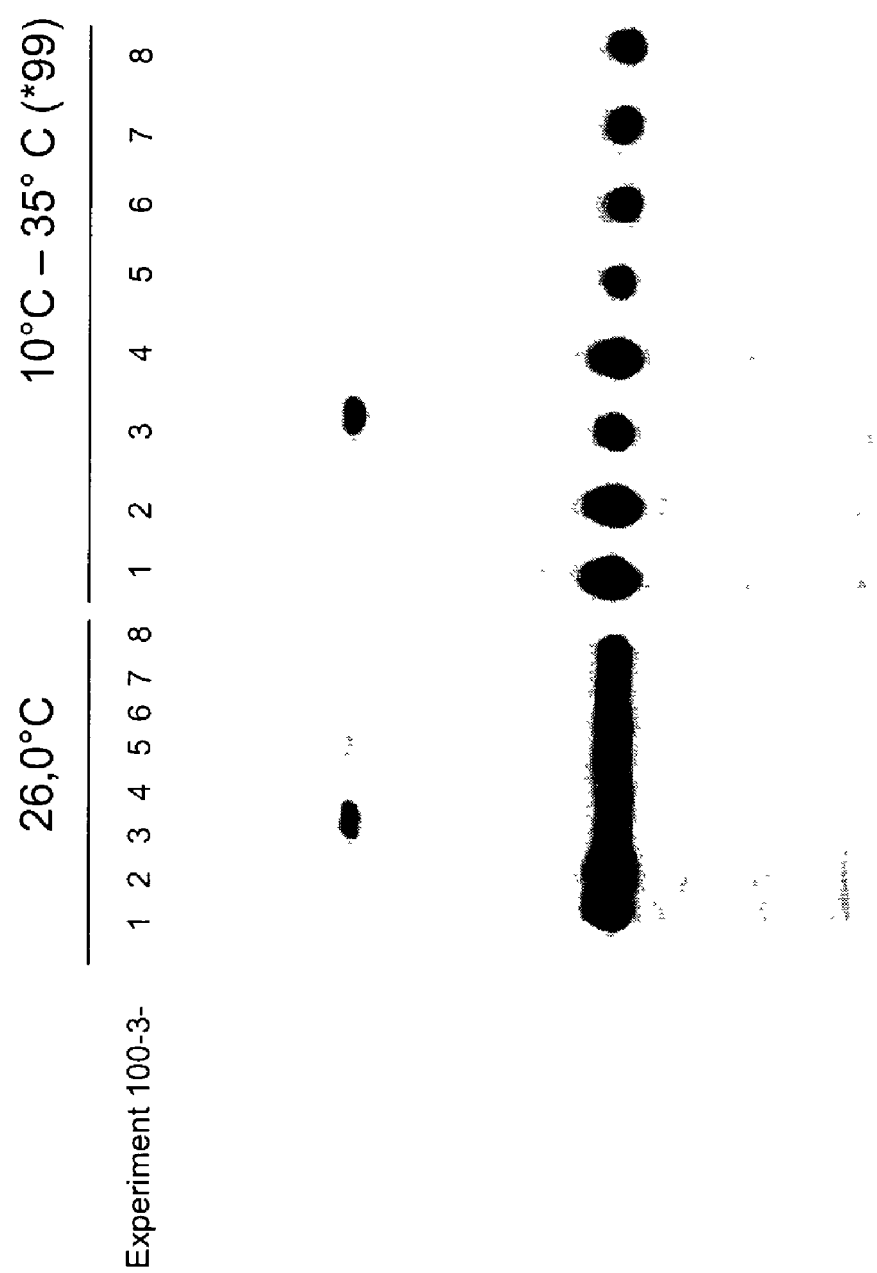

We first tested the effect of the 5'mer zipper box on cross-linking efficiency. As can be seen, the 5'mer zipper box improves the cross-linking efficiency dramatically (FIGS. 58, A and B, compare lanes 3 and lanes 5). Note that the template is absolutely required for cross-linking at all temperatures tested. The highest cross-linking efficiency is obtained when the temperature is cycled 99 times up and down between 10° C. and 35° C. (FIG. 58B). A high efficiency is also obtained when the temperature is kept constant at 21° C. or 26° C. (FIGS. 58A and B, lanes 3). The cross-linking efficiency does not improve further at temperatures above 26° C. (FIGS. 57, A and B).

We next tested the efficiency of cross-linking in the 10'mer zipper box format. Oligos Ah36 and Ah37 were annealed to template Ah38, and the cross-linking efficiency examined at various temperatures. A surprisingly high degree of crosslinking in the absence of template was observed (FIG. 55, 45° C. and 48.2° C.). However, at temperatures above 58.5° C., no cross-linking is observed in the absence of template.

Next, the different locations of the reactive groups relative to the zipper box was tested. As shown in FIGS. 58, A and B, lanes 7, the cross-linking efficiency decreases dramatically when one of the two reactive groups is located in the middle of the zipper box (i.e., the reactive group is attached to a nucleotide involved in DNA double helix formation; Ah67).

The location of the reactive groups relative to the zipper box was also tested in the context of the 1'mer zipper box. In this context, when both reactive groups are separated from the zipper box by two nucleotides (Ah65, Ah66), the efficiency of cross-linking is slightly decreased (FIG. 59, compare lanes 1 and 3). The cross-linking efficiency is not changed dramatically when different combinations of Ah65, Ah66, Ah36 and Ah37 are tested (i.e., when the reactive groups are placed immediately next to the zipper box, or two nucleotides upstream). Note that the template is not absolutely required at all temperatures in the context of the 10'mer zipper box. This template-independency is particularly pronounced at lower temperature (e.g., FIG. 59, 30° C.).

Examples 101 to 104

General Methods for Preparation of Oligonucleotide Building Blocks

Example 101

Procedure for Transforming Oligonucleotide Comprising a Carboxylic Acid to an Amino or Aminomethyl Terminated Linker The following oligos containing a modified nucleobase, with a carboxylic acid moiety, were synthesised using the conventional phosphoramidite approach:

A: 5'-GCT ACT GGC XTC GGT

B: 5'-TCA CTX GCA GAG AGC

C: 5'-CGA CCT CTG GAT TGC ATC GGT CAT GGC TGA CTG TCC GTC GAA TGT GTC GAG TTA CX

D: 5'-CTG GTA ACG CGG ATC GAC CTT CAT GGC TGA CTG TCC GTC GAA TGT GTC GAG TTA CX

E: 5'-ACG ACT ACG TTC AGG CAA GAT CAT GGC TGA CTG TCC GTC GAA TGT GTC CAG TTA CX

X was incorporated using the commercially available carboxy-dT phosphoramidite (10-1035-90 from Glen research). The underlined nucleobases represent the zipper region.

Schematic Representation of the Transformation

An oligo (20 pmol) was mixed with a diamino compound (20 uL of a 0.1 M solution), sodiumphosphate buffer (15 uL of a 100 mM solution, pH=6), NHS (5 uL of a 100 mM solution) and EDC (5 uL of a freshly prepared 1 M solution). The mixture was left at 30° C. for 45 minutes and treated with sodium borate (20 uL of a 100 mM solution, pH=10) and left at 30° C. for additional 45 minutes. The oligo was purified by conventional EtOH precipitation. The products were end-labelled with $^{32}$P and the purity analysed by PAGE. In all cases no starting oligo were detected and a new band, which migrated slower on the gel, appeared.

Examples of used diamino compounds: XXX, XXXI and the commercially available N,N'-dimethylethylenediamine (D15,780-5 from Sigma-Aldrich).

Example 102

Method for Transforming a Carboxylic Acid Containing Oligonucleotide to a Trisamine Scaffold Building Block The following oligos containing a modified nucleobase, with a carboxylic acid moiety, were synthesised using the conventional phosphoramidite approach:

F: 5'-GAC CTG TCG AGC ATC CAG CTG TCC <u>ACA ATG</u> X

G: 5'-GAC CTG TCG AGC ATC CAG CTT CAT GGG AAT TCC TCG TCC <u>ACA ATG</u> X

H: 5'-GAC CTG TCG AGC ATC CAG CTT CAT GGG AAT TCC TCG TCC <u>ACA ATG</u> XT

I: 5'-X<u>GT AAC TGG AGG</u> GTA AGC TCA TCC GAA TTC GGT ACT GAC CTG TCG AGC ATC CAG CT

X was incorporated using the commercially available carboxy-dT phosphoramidite (10-1035-90 from Glen research). The underlined nucleobases represent the zipper region.

Schematic Representation of the Reaction:

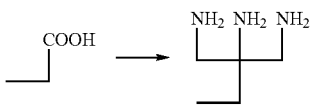

An oligo containing one modified nucleobase with a carboxylic acid moiety (1 mmol) was mixed with water (100 uL), hepes buffer (40 uL of a 200 mM, pH=7.5), NHS (20 uL of a 100 mM solution), EDC (20 uL of a freshly prepared 1 M solution) and the tetraamine (XXVII) (20 uL of a 100 mM solution). The reaction mixture was left o/n at room temperature. The volume was reduced to 60 uL by evaporation in vacuo. The pure oligo was obtained by addition of NH$_3$ conc. (20 uL) followed by HPLC purification. It was possible to isolate a peak after approximately 6 min using the following gradient: δ 0-3 minutes 100% A then 15% A and 85% B from 3-10 minutes then 100% B from 10-15 minutes then 100% A from 15-20 minutes. A=2% acetonitrile in 10 mM TEAA and B=80% acetonitrile in 10 mM TEAA.

After HPLC purification 2-3 pmol was end-labelled with $^{32}$P and the purity analysed by PAGE gel (see FIG. 60). The PAGE gel show the attachment of the tetraamine (XXVI) to an oligo containing a modified nucleobase with a carboxylic acid moiety.

Lane 1: Reference oligo F.
Lane 2: HPLC purified trisamine product of oligo F.
Lane 3: Reference oligo G.
Lane 4: HPLC purified trisamine product of oligo G.
Lane 5: Reference oligo H.
Lane 6: HPLC purified trisamine product of oligo H

Example 103

General Procedure for Attachment of a Functional Entity to a Thio Oligo

The following oligo containing a modified nucleobase, with a S-triphenylmethyl protected thio moiety, was synthesised using the conventional phosphoramidite approach:

```
J:  5'-WCA TTG ACC TGT GTA AGC BTG CGT GTC AGT GGG
       TAG TCG ACG TCT GGA TTG CAT CGG

K:  5'-WCA TTG AGG TGT CTG CGB TGT GAG TGG GTA CTG
       TGG TAA CGG GGA TCG ACC T

L:  5'-WCA TTG ACC TGA ACC ATG BTA AGC TGC CTG TCA
       GTC GGT ACT ACG ACT ACG TTG AGG CAA GA

M:  5'-WCA TTG ACC TGA ACC ATG TBA AGC TGC CTG TCA
       GTC GGT ACT TCA AGG ATC CAC GTG ACC AG
```

W was incorporated using the commercially available thiol modifier phosphoramidite (10-1926-90 from Glen research). B is an internal biotin incorporated using the commercially available phosphoramidite (10-1953-95 from Glen research). The nucleobases which are underlined and italic indicates the zipper region.

The S-triphenylmethyl protected thio oligo (10 mmol) was evaporated in vacuo and resuspended in TEAA buffer (200 uL of a 0.1M solution, pH=6.4). AgNO₃ (30 uL of a 1 M solution) was added and the mixture was left at room temperature for 1-2 hours. DTT (46 uL of a 1 M solution) was added and left for 5-10 minutes. The reaction mixture was spun down (20.000 G for 20 minutes) and the supernatant was collected. The solid was extracted with additional TEAA buffer (100 ul of a 0.1 M solution, pH=6.4). The pure thio oligo was obtained by conventional EtOH-precipitation.

Schematic Representation of the Reaction:

The thio oligo (1 mmol) was dried in vacuo and treated with a building block comprising the functional entity (05087) in dimethylformamide (50 ul of a 0.1 M solution) and left o/n at rt. The thio oligo was spun down (20.000 G for 10 minutes) and the supernatant removed. Dimethylformamide (1 mL) was added and the loaded thio oligo was spun down (20.000 G for 10 minutes). The dimethylformamide was removed and the loaded thio oligo was resuspended in TEM buffer (25 uL of a 0.1 M solution, pH=6.4) and analysed by HPLC.

Examples of building blocks used: XXVI, XVI, XVII, XVIII, XXIII, XXIV, XXV)

Example 104

General Procedure for Attachment of a Functional Entity to an Amino or Aminomethyl Terminated Oligo The following oligo containing a modified nucleobase, with an amino group was synthesised, using the conventional phosphoramidite approach:

```
N:  5'-ZGT AAC ACC TGT GTA AGC TGC CTG TCA GTC GGT
       ACT GAC CTG TCG AGC ATC CAG CT
```

Z contain the modified nucleobase with an amino group, incorporated using the commercially available amino modifier C6 dT phosphoramidite (10-1039-90 from Glen research)

Furthermore, oligo C-E were transformed into the corresponding aminomethyl terminated oligo, as described earlier.

The oligos were used in the following experiment represented schematically below:

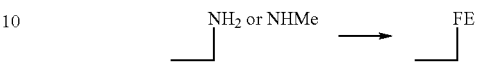

An amino or aminomethyl oligo (3 pmol) was mixed with a phosphate buffer (3 uL of a 0.1 M solution, pH=6) and NaBH₃CN (3 uL of a 1 M solution in MeOH). A building block comprising the functional entity (3 uL of a 1 M solution in MeOH) was added and the mixture was left o/n at room temperature. The product formation was analysed by PAGE gel (see FIG. 61).

Examples of building blocks used: XXVIII, XXIX, and the commercially available 4-acetoxybenzaldehyde (24,260-8 from Sigma-Aldrich).

FIG. 60 shows a PAGE analysis of the loading of an oligo, containing a modified nucleobase with an amino group (comp. XXIV).

Lane 1 show the reference amino oligo (N).

Lane 2 show the amino oligo (N) after loading with a building block comprising the functional entity.

Lane 3 show removal of the functional entity, attached in lane 2, by treatment with pH=11 for 1 hour.

Example 105

General Procedure for the Templated Synthesis of an Organic Compound, where the Scaffold and the Substituent are Encoded by the Template

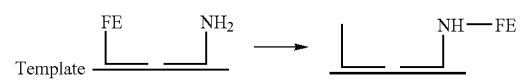

The template oligo (1 mmol) was mixed with an thio oligo (L or M) loaded with a functional entity (XXIII or XVII, respectively, 1 mmol) and amino oligo 0 in hepes-buffer (20 uL of a 100 mM HEPES and 1 M NaCl solution, pH=7.5) and water (added to a final volume of 100 uL). The oligos were annealed to the template by heating to 50° C. and cooled (-2° C./30 second) to 30° C. The mixture was then left o/n at a fluctuating temperature (10° C. for 1 second then 35° C. for 1 second). The oligo complex was attached to streptavidine by addition of streptavidine beads (100 uL, prewashed with 2×1 mL 100 mM hepes buffer and 1 M NaCl, pH=7.5). The beads were washed with hepes buffer (1 mL). The amino oligo was separated from the streptavidine bound complex by addition of water (200 uL) followed by heating to 70° C. for 1 minute. The water was transferred and evaporated in vacuo, resuspended in TEAA buffer (45 uL of a 0.1 M solution) and product formation analysed by HPLC (see FIG. 62).

FIG. 62 shows the transfer of a functional entity to an oligo containing a modified nucleobase with an amino group.

A) The top chromatogram show the reference amino oligo O: 5'-GAC CTG TCG AGC ATC CAG CTT CAT GGC TGA GTC CAC AAT GZ (SEQ ID NO:41). Z contain the modified nucleobase with an aminogroup, incorporated using the commercially available amino modifier C6 dT phosphoramidite (10-1039-90 from Glen research).

B) The middle chromatogram show the streptavidine purified amino oligo O after partial transfer of a functional entity (XXIII).

C) The bottom chromatogram show the streptavidine purified amino oligo O after the complete transfer of a more lipophilic functional entity (XVII). The following gradient was used: 0-3 minutes 100% A then 15% A and 85% B from 3-10 minutes.

The experiment where the template oligo was omitted showed no non-templated product formation. The results indicate that the efficiency of the templated synthesis was 80-100%. The reason for less than 100% efficiency was probably due to hydrolytic cleavage of the functional entity.

Example 106

General Procedure for the Templated Synthesis of a Scaffolded Molecule, where the Scaffold and Two Identical Substituents are Encoded by the Template

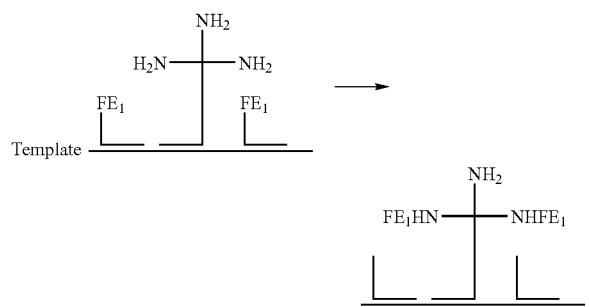

The template oligo (1 mmol) was mixed with two thio oligos (K and L) loaded with the same functional entity (XXVI; 1 mmol) and the trisamine oligo H (1 mmol) in hepes-buffer (20 uL of a 100 mM hepes and 1 M NaCl solution, pH=7.5) and water (added to a final volume of 100 uL). The oligos were annealed to the template by heating to 50° C. and cooled (−2° C./30 second) to 30° C. The mixture was then left o/n at a fluctuating temperature (10° C. for 1 second then 35° C. for 1 second). The oligo complex was attached to streptavidine by addition of streptavidine beads (100 uL, prewashed with 2×1 mL 100 mM hepes buffer and 1 M NaCl, pH=7.5). The beads were washed with hepes buffer (1 mL). The trisamine scaffold oligo H was separated from the streptavidine bound complex by addition of water (200 uL) followed by heating to 70° C. The water was transferred and evaporated in vacuo, resuspended in TEAA buffer (45 uL of a 0.1 M solution) and product formation analysed by HPLC (see FIG. 63).

The HPLC chromatogram shows the transfer of two functional entities to a scaffold oligo with three amino groups.

A) The top chromatogram shows the reference scaffold oligo G.

B) The bottom chromatogram show the streptavidine purified scaffold oligo G after the partial transfer of one (peak at 7.94 minutes) and two (peak at 10.76 minutes) identical functional entities (XXVI). The following gradient was used: 0-3 minutes 100% A then 15% A and 85% B from 3-10 minutes then 100% B from 10-15 minutes. A=2% acetonitrile in 10 mM TEAA and B=80% acetonitrile in 10 mM TEAA.

Due to the lipophilic nature of the functional entities a longer retention time, in the HPLC chromatogram, of the scaffolded molecule with two functional entities compared to one functional entity, was observed. The efficency of the templated synthesis of a scaffolded molecule with the two identical functional entities (XXVI) was about 25% (peak at 10.76 minutes in FIG. 63).

Example 107

Procedure for the Templated Synthesis of a Scaffolded Molecule, where the Scaffold and the Three Substituents are Encoded by the Template

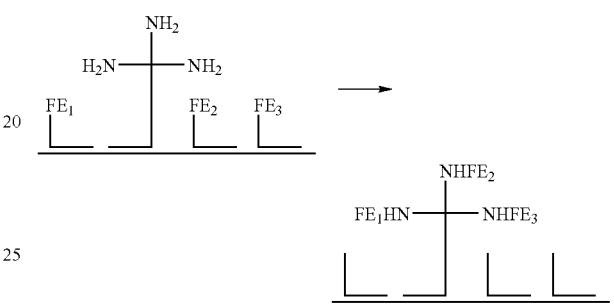

Procedure A (5-mer zipper box): The template oligo (1 mmol) was mixed with three thio oligos (J-L) loaded with three different functional entity (XVI, XVII and XVIII, respectively; 1 mmol) and the trisamine scaffold oligo H (1 mmol) in hepes-buffer (20 uL of a 100 mM hepes and 1 M NaCl solution, pH=7.5) and water (added to a final volume of 100 uL). The oligos were annealed to the template by heating to 50° C. and cooled (−2° C./30 second) to 30° C. The mixture was then left o/n at a fluctuating temperature (10° C. for 1 second then 35° C. for 1 second). The oligo complex was attached to streptavidine by addition of streptavidine beads (100 uL, prewashed with 2×1 mL 100 mM hepes buffer and 1 M NaCl, pH=7.5). The beads were washed with hepes buffer (1 mL). The trisamine scaffold oligo was separated from the streptavidine bound complex by addition of water (200 uL) followed by heating to 70° C. The water was transferred and evaporated in vacuo, resuspended in TEAA buffer (45 uL of a 0.1 M solution) and formation of the encoded molecule was identified by HPLC.

Procedure B (9-mer zipper box): The template oligo (15 pmol) was mixed with three methylamino oligos (C-E) loaded with three different functional entity (XXVII, XXIX and 4-acetoxybenzaldehyde, respectively; 20 pmol) and a $P^{32}$ end labelled trisamine scaffold oligo I (15 pmol) in hepes-buffer (6.5 uL of a 100 mM hepes and 1 M NaCl solution, pH=7.5). The mixture was heated to 58.5° C. and left at 58.5° C. for 5 days. Formation of the encoded molecule was identified by PAGE.

Example 108 (Model)

Description of the Preparation of a 3-Mer β-amino Acid Library

A) Synthesis of the β-amino Acid Building Blocks

N-terminal protection: The Nvoc group[1] (3,6-dimethoxy-6-nitrobenzyloxycarbonyl) was used as a photo cleavable N-protecting group and introduced on a β-amino acid according to the following method:

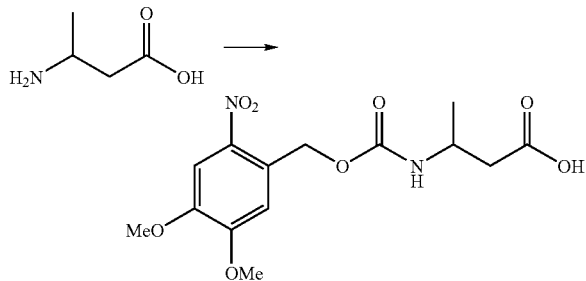

3-Amino-butyric acid (147 mg, 1.43 mmol) was mixed with water (10 mL), dioxane (10 mL) and 2 M NaOH (10 mL). The mixture was cooled to 0° C. and treated with Nvoc-Cl (1.58 mmol). 2 M NaOH was added in small portions (8×1.25 mL) during 75 minutes. The cooling bath was removed and the reaction mixture was left at room temperature o/n. Water (30 mL) was added and the mixture was filtered. The aqueous phase was adjusted to pH=4 with 2 M HCl (aq.) and extracted with diethyl ether (3×50 mL). The solid was dissolved in water (50 mL) and diethyl ether (50 mL). The combined organic phases were dried over MgSO$_4$ and evaporated in vacuo affording 176 mg (36%) pure 3-(4,5-dimethoxy-2-nitrobenzyloxycarbonylamino)-butyric acid. $^1$H-NMR (CDCl$_3$): 7.72 (s, 1H), 7.02 (s, 1H), 5.51 (s, 2H), 5.40-5.30 (br s, 1H), 4.15 (m, 1H), 3.96 (s, 3H), 3.92 (s, 3H), 2.60 (d, 2H), 1.31 (d, 3H).

[1] Burgess et al. *J. Org. Chem.* (1997), 62, 5165-68, Alvarez et al. *J. Org. Chem.* (1999), 64, 6319-28 and Pedersen et al. *Proc Natl Acad Sci* (1998), 95, 10523-28

β-Alanin, cis-2-amino-1-cyclohexanecarboxylic acid, trans-2-Amino-1-cyclohexane carboxylic acid, cis-2-amino-1-cyclopentanecarboxylic acid, cis-2-amino-4-cyclohexene-1-carboxylic acid, trans-2-amino-4-cyclohexene-1-carboxylic acid, 3-amino-4,4,4-trifluoro butyric acid, 3-amino-4-methylpentanoic acid, DL-3-aminoisobutyric acid monohydrate, 3-amino-3-phenylpropionic acid, 2-fluoro-3-aminopropionic acid hydrochloride are protected similarly.

C-terminal activation: The NHM (N-hydroxymaleimide) ester of the N-Nvoc protected β-amino acid was used and prepared according to the following method, exemplified using 3-(4,5-dimethoxy-2-nitro-benzyloxycarbonylamino)-3-phenyl-propionic acid:

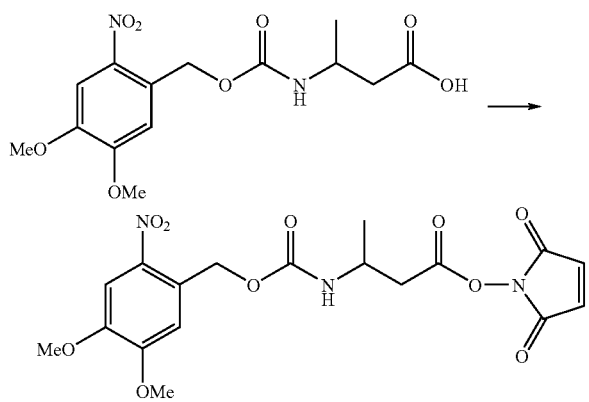

3-(4,5-dimethoxy-2-nitro-benzyloxycarbonylamino)-butyric acid (418 mg, 1.22 mmol) was dissolved in THF (10 mL), N-hydroxymaleimide (1.22 mmol) was added and the mixture was cooled to 0° C. Dicyclohexylcarbodiimide (1.22 mmol) was added and the reaction mixture was left o/n at room temperature. The solvent was removed by evaporation in vacuo and the product isolated by silica column purification using EtOAc-heptane (1:4 then 1:2 then 1:1) as eluent. Yield 219 mg (42%) of pure 3-(4,5-dimethoxy-2-nitro-benzyloxycarbonylamino)-butyric acid 2,5-dioxo-2,5-dihydropyrrol-1-yl ester. $^1$H-NMR (CDCl$_3$): 7.73 (s, 1H), 7.03 (s, 1H), 6.81 (s, 2H), 5.55 (dd, 2H), 5.30-5.20 (br s, 1H), 4.25 (m, 1H), 3.98 (s, 3H), 3.97 (s, 3H), 2.86 (m, 2H), 1.39 (d, 3H).

The N-Nvoc protected analogues of β-Alanin, cis-2-amino-1-cyclohexanecarboxylic acid, trans-2-Amino-1-cyclohexanecarboxylic acid, cis-2-amino-1-cyclopentanecarboxylic acid, cis-2-amino-4-cyclohexene-1-carboxylic acid, trans-2-amino-4-cyclohexene-1-carboxylic acid, 3-amino-4,4,4-trifluorobutyric acid, 3-amino-4-methylpentanoic acid, DL-3-aminoisobutyric acid monohydrate, 3-amino-3-phenylpropionic acid, 2-fluoro-3-aminopropionic acid hydrochloride, are activated similarly.

B) Preparation of Building Block Oligos:

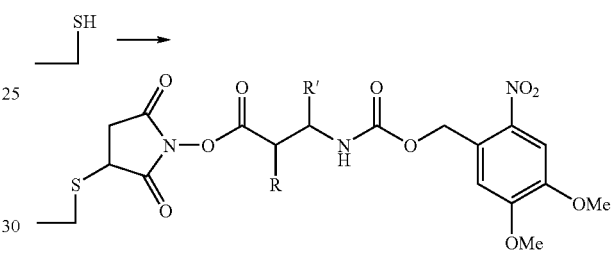

A thio oligo (1 mmol) is treated with 3-(4,5-dimethoxy-2-nitrobenzyloxycarbonylamino)-3-phenyl-propionic acid 2,5-dioxo-2,5-dihydro-pyrrol-1-yl ester (50 uL of 0.1 M solution in DMF). The mixture is left o/n at room temperature. The building block oligo is spinned down (20.000 G for 15 minutes) and the DMF is removed. DMF (1 mL) is added, the building block oligo is spinned down (20.000 G for 15 minutes) and the DMF is removed.

The N-Nvoc protected C-terminal NHM activated analogues of β-Alanin, cis-2-amino-1-cyclohexanecarboxylic acid, trans-2-Amino-1-cyclohexanecarboxylic acid, cis-2-amino-1-cyclopentanecarboxylic acid, cis-2-amino-4-cyclohexene-1-carboxylic acid, trans-2-amino-4-cyclohexene-1-carboxylic acid, 3-amino-4,4,4-trifluorobutyric acid, 3-amino-4-methylpentanoic acid, DL-3-aminoisobutyric acid monohydrate, DL-beta-aminobutyric acid, 2-fluoro-3-aminopropionic acid hydrochloride, are loaded on 11 different thio oligos similarly.

In the following any four of the prepared building block oligos are selected and used for library production.

C) Production of a 64-Member (4$^3$) 3-Mer β-peptide Library:

| Design of building block olgo: | Design of library setup: |
|---|---|
| 5-mer zipperbox | |
| 15-mer Complementing element | Template with three coding regions spaced by a AATAA sequence |

The sequence for the building block oligos are shown below. The nucleotides in bold constitute the complementing element and underlined the 5-mer zipperbox. FE$^{1-4}$ is the attached functional entities (4 different N-Nvoc protected β-amino acids) and B is an internal biotin.

1) 5'-FE$^1$-<u>CAT TGT</u> TTT TTT TTT TBT TTT TTT TTT TGC ATA CAA CTA TGT A 2) 5'-FE$^2$-<u>CAT TGT</u> TTT TTT TTT TBT TTT TTT TTT TGC ATA CGG CTA TGT A 3) 5'-FE$^3$-<u>CAT TGT</u> TTT TTT TTT TBT TTT TTT TTT TGC ATA CGA CTA TGT A 4) 5'-FE$^4$-<u>CAT TGT</u> TTT TTT TTT TBT TTT TTT TTT TGC ATA CAG CTA TGT A 5) 3'-FE$^1$-<u>GTA ACT</u> TTT TTT TTT TBT TTT TTT TTT TAT GCG TAA AGC CAT G 6) 3'-FE$^2$-<u>GTA ACT</u> TTT TTT TTT TBT TTT TTT TTT TAT GCG TGG AGC CAT G 7) 3'-FE$^3$-<u>GTA ACT</u> TTT TTT TTT TBT TTT TTT TTT TAT GCG TGA AGC CAT G 8) 3'-FE$^4$-<u>GTA ACT</u> TTT TTT TTT TBT TTT TTT TTT TAT GCG TAG AGC CAT G 64 template oligos (2 pmol each) consisting of 3 coding regions are mixed with four different building block oligos (1-4, 200 pmol each) and hepes buffer (20 uL, 100 mM hepes buffer and 1 M NaCl, pH=7.5). Water is added to a final volume of 1000 uL. The oligos are annealed to the templates by heating to 50° C. and cooled (−2° C./30 second) to 20° C. The Nvoc-protecting groups are removed by degassing thoroughly with Ar, followed by exposure to a mercury lamp (450 W HPLC mercury lamp, pyrex filter, cutoff<300 nm) for 1-2 hours. The mixture is left o/n at a fluctuating temperature (10° C. for 1 second then 35° C. for 1 second).

Formation of the encoded molecules in the library production is addressed in two separate experiments, where only one template is used in each experiment. The first template (3'-CGT ATG TTG ATA CAT AAT AAC GTA TGT TGA TAC ATA ATA ACG TAT GTT GAT ACA T (SEQ ID NO:50)) encode for the formation the 3-mer β-peptide of β-alanin and the other template (3-CGT ATG CCG ATA CAT AAT AAC GTA TGC CGA TAC ATA ATA ACG TAT GCC GAT ACA T SEQ ID NO:51) for the formation of 3-mer β-peptide of 3-amino-4,4,4-trifluorobutyric acid.

A template oligo (2 pmol) consisting of 3 coding regions are mixed with four different building block oligos (1-4, 200 pmol each) and hepes buffer (20 uL, 100 mM hepes buffer and 1 M NaCl, pH=7.5). Water is added to a final volume of 100 uL. The oligos are annealed to the templates by heating to 50° C. and cooled (−2° C./30 second) to 20° C. The Nvoc-protecting groups are removed by degassing thoroughly with Ar, followed by exposure to a mercury lamp (450 W HPLC mercury lamp, pyrex filter, cutoff<300 nm) for 1-2 hours. The mixture is left o/n at a fluctuating temperature (10° C. for 1 second then 35° C. for 1 second). The oligo complex is attached to streptavidine by addition of streptavidine beads (100 uL, prewashed with 2×1 mL 100 mM hepes buffer and 1 M NaCl, pH=7.5). The beads are washed with hepes buffer (1 mL). The building block oligo, containing the encoded product, is separated from the streptavidine bound complex by addition of water (200 uL) followed by heating to 70° C. The water is transferred and product formation verified by MS analysis.

Example 109 (Model)

Description of the Preparation of a 3-mer β-amino Acid Library

A) Synthesis of the β-amino Acid Building Blocks

N-terminal protection: The Nvoc group (3,6-dimethoxy-6-nitrobenzyloxycarbonyl) was used as a photo cleavable N-protecting group and introduced on a β-amino acid according to the method described above.

C-terminal activation: The N-Nvoc protected β-amino acid was activated using the known 1-(4-hydroxy-phenyl)-pyrrole-2,5-dione (Choi et al. *Mol. Cryst. Liq. Cryst. Sci. Technol. Sect. A* (1996), 280, 17-26), according to the following method:

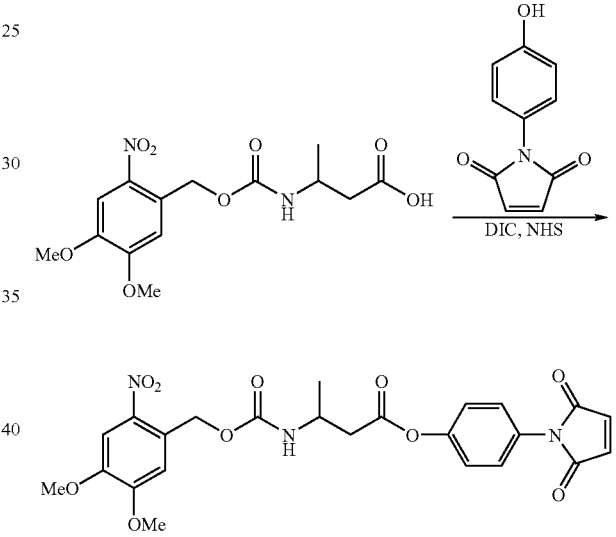

1-(4-Hydroxy-phenyl)-pyrrole-2,5-dione (1 mmol), NHS (1.0 mmol) and 3-(4,5-dimethoxy-2-nitro-benzyloxycarbonylamino)-butyric acid (1 mmol) is dissolved in THF (3 mL). The solution is cooled to 0° C. and treated dropwise with DIC (1.2 mmol). The cooling bath is removed after 1 hour and the reaction mixture is left at room temperature o/n. The solvent is evaporated in vacuo and the pure product (3-(4,5-dimethoxy-2-nitro benzyloxycarbonyl-amino)-butyric acid 4-(2,5-dioxo-2,5-dihydro-pyrrol-1-yl)-phenyl ester) is isolated by silica column purification using EtOAc-heptane (1:4 then 1:2 then 1:1) as eluent.

The N-Nvoc protected analogues of β-Alanin, cis-2-amino-1-cyclohexanecarboxylic acid, trans-2-Amino-1-cyclohexanecarboxylic acid, cis-2-amino-1-cyclopentanecarboxylic acid, cis-2-amino-4-cyclohexene-1-carboxylic acid, trans-2-amino-4-cyclohexene-1-carboxylic acid, 3-amino-4,4,4-trifluorobutyric acid, 3-amino-4-methylpentanoic acid, DL-3-aminoisobutyric acid monohydrate, DL-beta-aminobutyric acid, 2-fluoro-3-aminopropionic acid hydrochloride, are C-terminal activated similarly.

B) Preparation of Building Block Oligos:

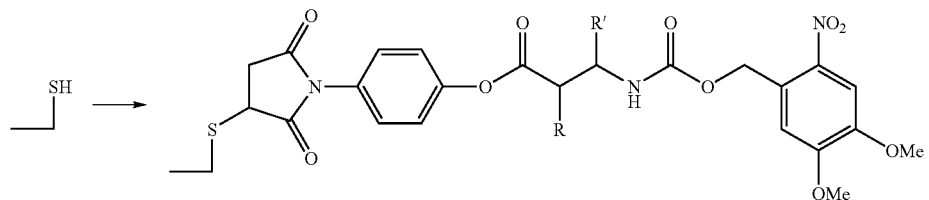

A thio oligo (2 mmol) in water (25 uL) is treated with 3-(4,5-dimethoxy-2-nitrobenzyloxycarbonyl-amino)-butyric acid 4-(2,5-dioxo-2,5-dihydro-pyrrol-1-yl)-phenyl ester (25 uL of a 10 mM solution in MeOH). The mixture is left o/n at room temperature. The building block oligo is purified by a conventional EtOH-precipitation. The pellet is washed with dichloromethane (3×300 uL) and dried in vacuo.

The N-Nvoc protected C-terminal activated analogues of β-Alanin, cis-2-amino-1-cyclohexane-carboxylic acid, trans-2-Amino-1-cyclohexanecarboxylic acid, cis-2-amino-1-cyclopentane-carboxylic acid, cis-2-amino-4-cyclohexene-1-carboxylic acid, trans-2-amino-4-cyclohexene-1-carboxylic acid, 3-amino-4,4,4-trifluorobutyric acid, 3-amino-4-methylpentanoic acid, DL-3-aminoisobutyric acid monohydrate, DL-beta-aminobutyric acid, 2-fluoro-3-aminopropionic acid hydrochloride, are loaded on 11 different thio oligos similarly.

Any four of the prepared building block oligos are selected and used for library production as described above.

Example 110 (Model)

In the Following, a Library Preparation Method Based on Oligonucleotide Templates and 5'-phophoimidazolid Nucleoside Building Blocks is Described Preparation of Building Blocks

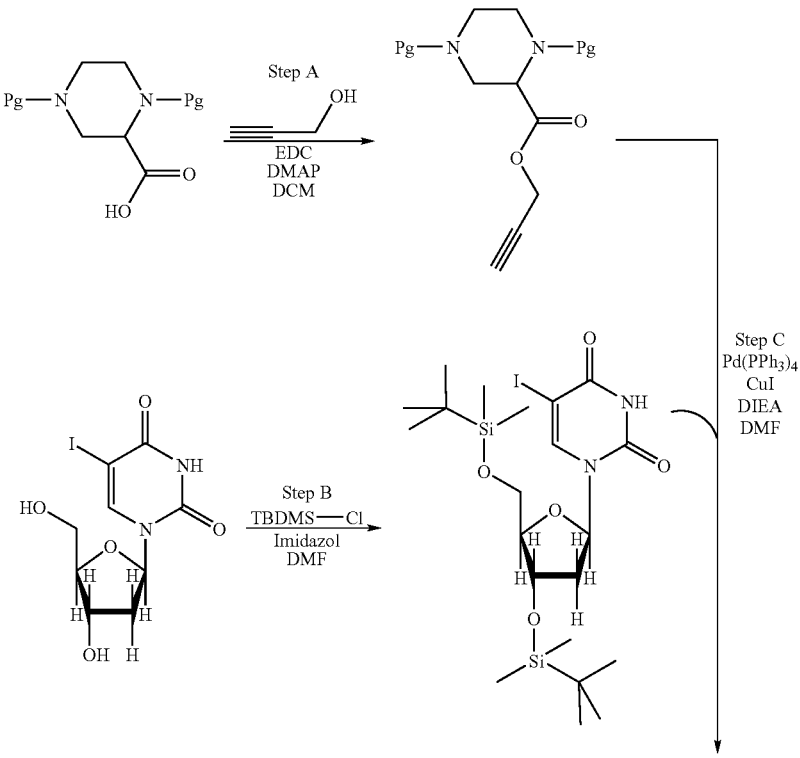

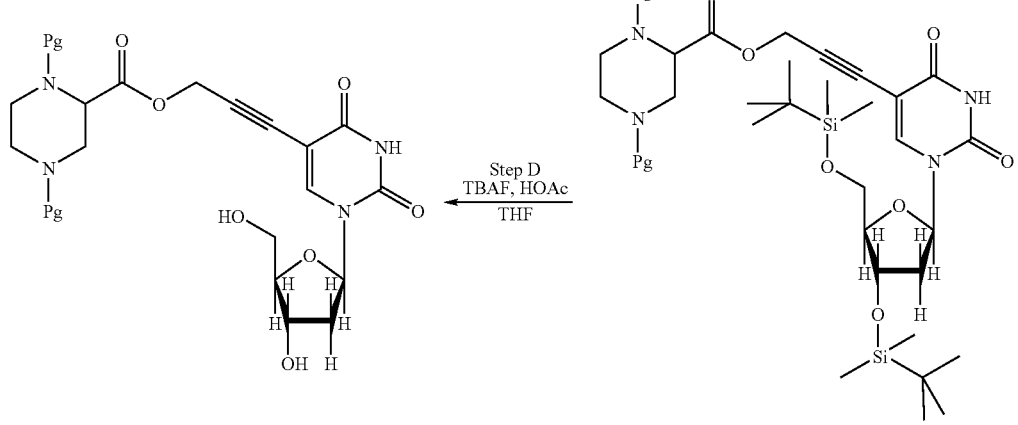

Step A: Preparation of an Ester Linker with a Terminal Alkyne.

The acid derivative (10.37 mmol) is dissolved in DCM (20 mL) and cooled to 0° C. on an ice bath. EDC (12.44 mmol, 1.2 equiv) is added followed by DMAP (1.04 mmol, 0.1 equiv) and the alcohol (15.55 mmol, 1.5 equiv) in DCM (5 mL). After 1 h reaction on ice bath, the mixture is allowed to come to 20° C. and left to react 16 h. Volatiles are removed and the residue is taken up in diethylether (150 mL) and HCl (aq, 0.1 M, 75 mL). The phases are separated and the organic phase is first washed with a mixture of NaHCO$_3$ (sat, 35 mL) and water (35 mL) then with water (75 mL). Upon evaporation of diethylether, the product is azeotropically dried using toluene (2×120 mL) affording the desired ester that may be purified by chromatography if necessary.

Step B: Introduction of Protective Groups on Iodo Substituted Nucleosides.

The nucleoside (5.65 mmol, 1 eq), TBDMS-Cl (2.04 g, 13.56 mmol, 2.4 eq) and imidazole (1.85 g, 27.11 mmol, 4.8 eq) are mixed in DMF (20 mL) and stirred at 25° C. overnight. EtOAc (400 mL) is added and the organic phase is washed with a mixture of NH$_4$Cl(aq) (sat, 40 mL)+H$_2$O (40 mL) followed by H$_2$O (80 mL). The organic phase is stripped and the residue is taken up in toluene, filtered and stripped to leave the desired protected nucleoside. The compound may be further purified by recrystallization.

Step C: Sonogashira Coupling of Protected Iodo Substituted Nucleosides and Terminal Alkynes A DMF solution (20 mL) of the protected iodo substituted nucleoside (3.4 mmol), the alkyne (6.9 mmol, 2 eq), DIEA (2.5 mL) is purged with Ar for 5 min. Tetrakis triphenylphosphine palladium (0.3 mmol, 0.1 eq) and CuI (0.7 mmol, 0.2 eq) is added and the mixture is heated to 50° C. and kept there for 20 h. Upon cooling, the mixture is added 700 mL diethylether. The organic phase is washed with ammonium chloride (sat, aq, 250 mL) and water (250 mL). Evaporation of volatiles followed by stripping with toluene (400 mL) affords the desired modified nucleoside that is purified by column chromatography (silica gel, Heptane/Ethyl acetate eluent).

Step D: Removal of OH Protective Groups

A THF solution of the above product (1.8 mmol in 30 mL) is added acetic acid (0.8 mL, 14.1 mmol, 8 eq) and tetrabutylammonium fluoride (7 mmol, 4 eq). Upon stirring at 20° C. for 20 h, volatiles are removed in vacuo and the residue is purified by column chromatography (silica gel, DCM/Methanol eluent).

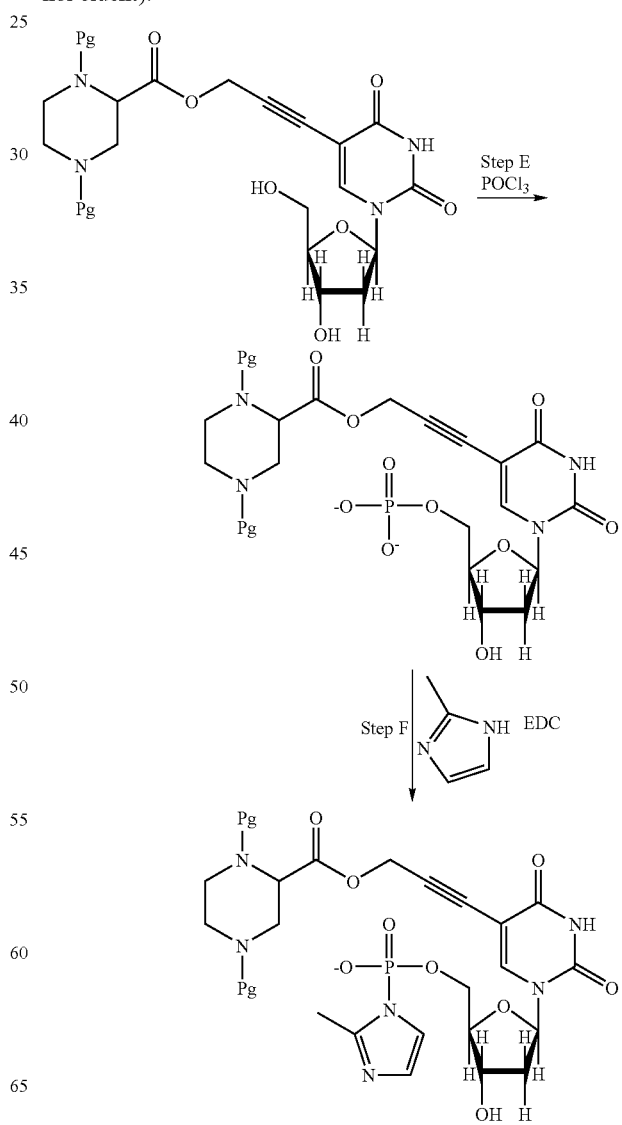

Step E: Mono-phosphate Synthesis

A slurry of the modified nucleoside obtained in step D (1.65 mmol) in trimethyl phosphate (5 mL) is cooled to 0° C. and added phosphoroxytrichloride (190 uL, 307 mg, 2 mmol, 1.2 eq). The reaction is kept at 0° C. for 2 h. Tributyl amine (1 mL) is added and the reaction is allowed to come to 20° C. Another portion of tributyl amine (1.3 mL) is added to raise pH, followed by water. Volatiles are removed in vacuo and the residue may be purified using ion-exchange chromatography (Sephadex A25, tetra-ethylammonium bromide buffer 0.05-1.0 M, pH 7).

Step F: Phosphoimidazolid Synthesis

To a solution of the above mono-phosphate derivative (0.1 M) is added 2-methylimidazole (0.5 M) and EDC (0.5 M) at pH 6.5 and 0° C. The reaction is stirred for 2 h maintaining a temperature of 0° C. The mixture may be used directly in library synthesis. [Visscher;1988; *Journal of Molecular Evolution;* 3-6]

Alternatively, treatment of phophates with carbonyl diimidazole also affords phophoimidazolides. [Zhao;1998; *J. Org. Chem.;* 7568-7572]

A Collection of Building Blocks

In the the scheme below a number of building blocks useful for library synthesis is shown. All building blocks have functional entities attached to the recognition element by means of an carboxylic ester and may be synthesized as described above.

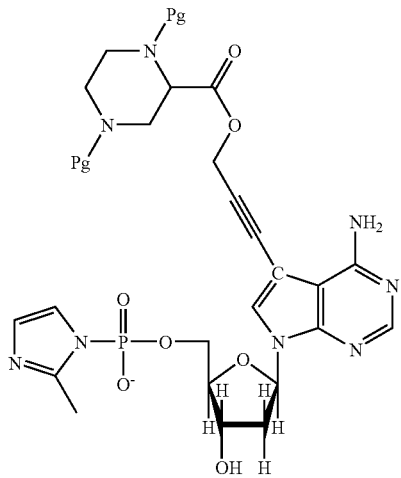

-continued

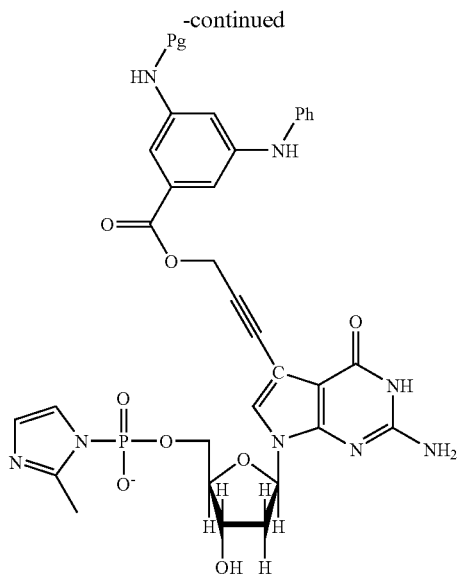

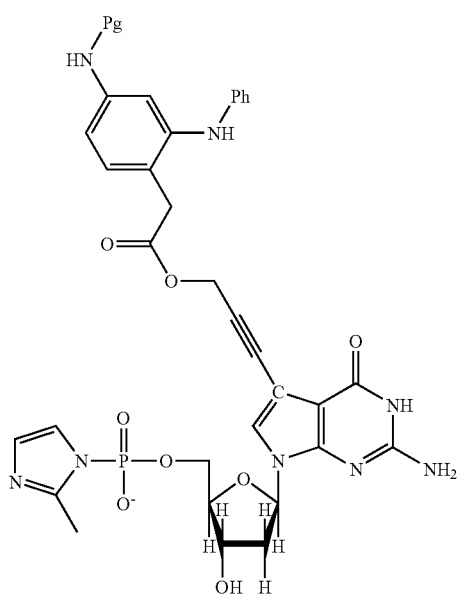

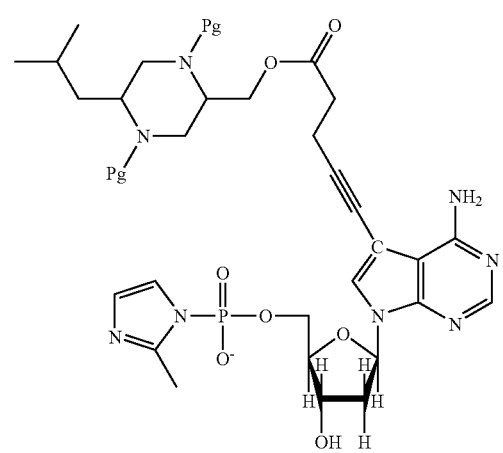

-continued

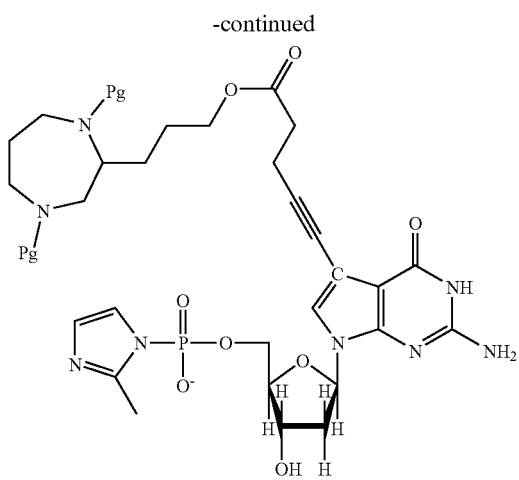

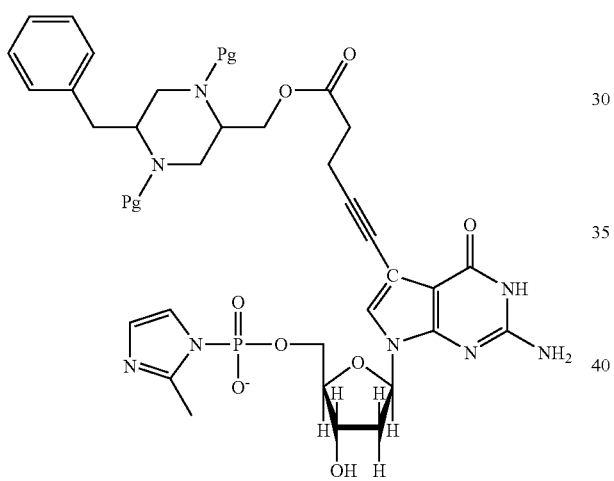

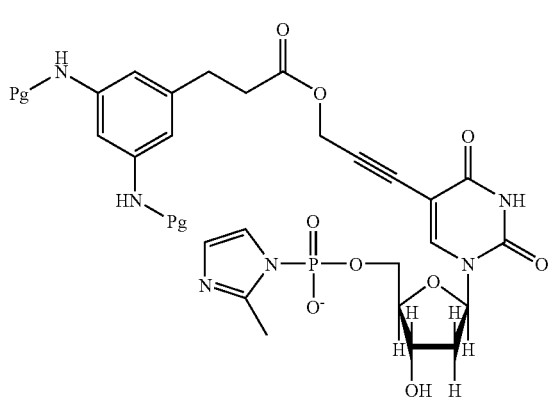

-continued

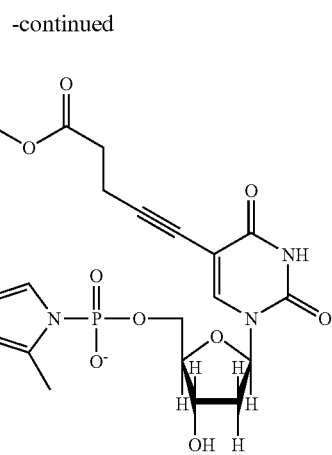

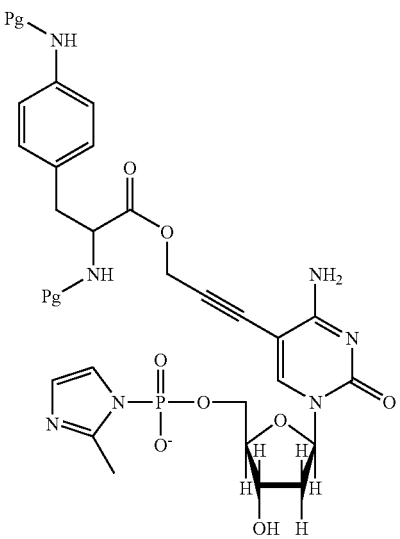

Library Preparation

The scheme below exemplifies the process of making a library of polyamides using oligonucleotide templates and phosphoimidazolid building blocks shown above. An oligonucleotide primer sequence with a sequence modifier carrying an (optionally) protected amine (e.g. Glen Research Amino-Modifier C2 dT, cat no 10-1019-) is annealed to the templates used in the library. Further, another oligonucleotide sequence is annealed as a terminating sequence thus exposing only the part of the template coding the building block incorporation. For clarity, the bases of the phosphoimidazolid building blocks have been replaced with large bold letter codes.

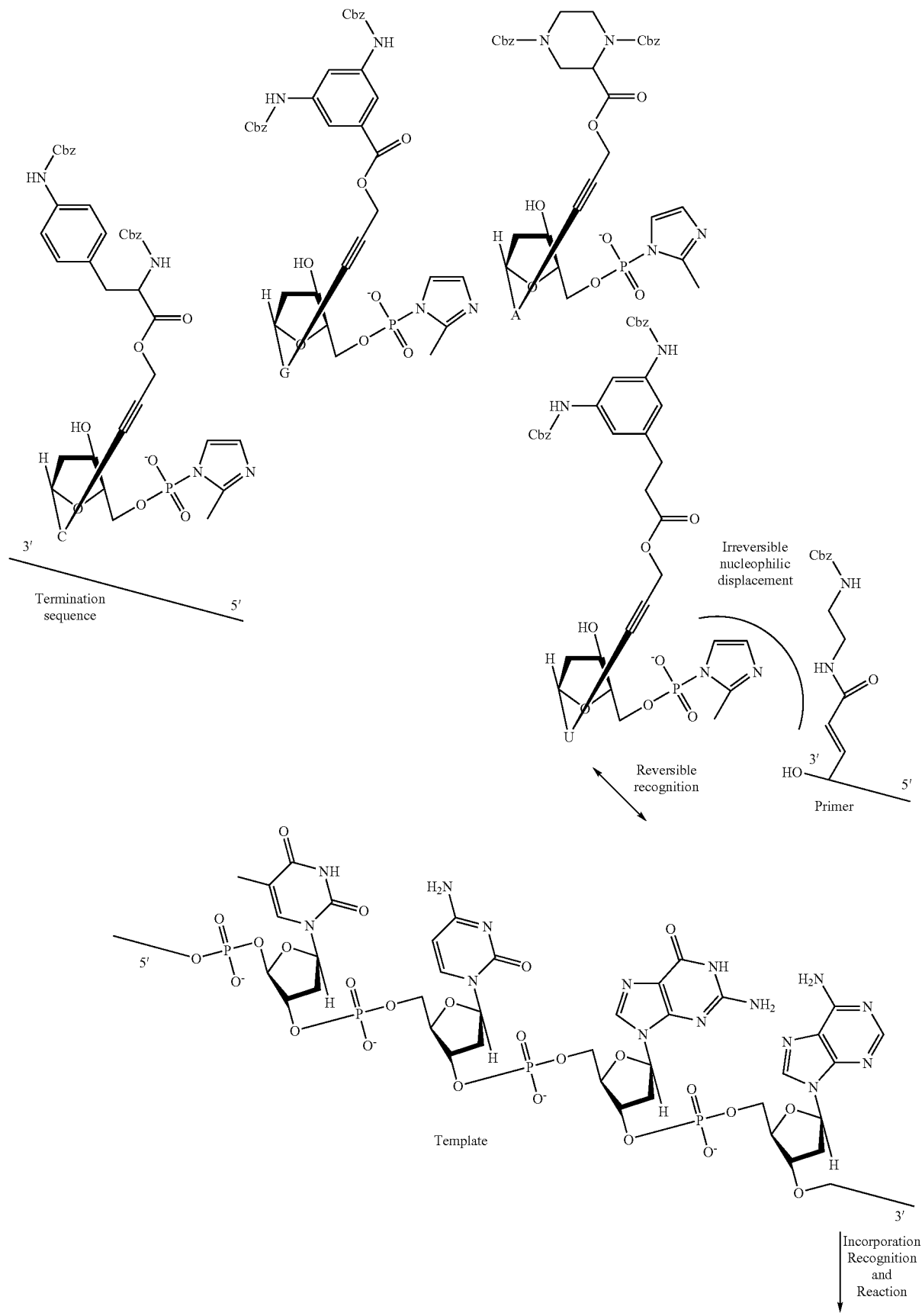

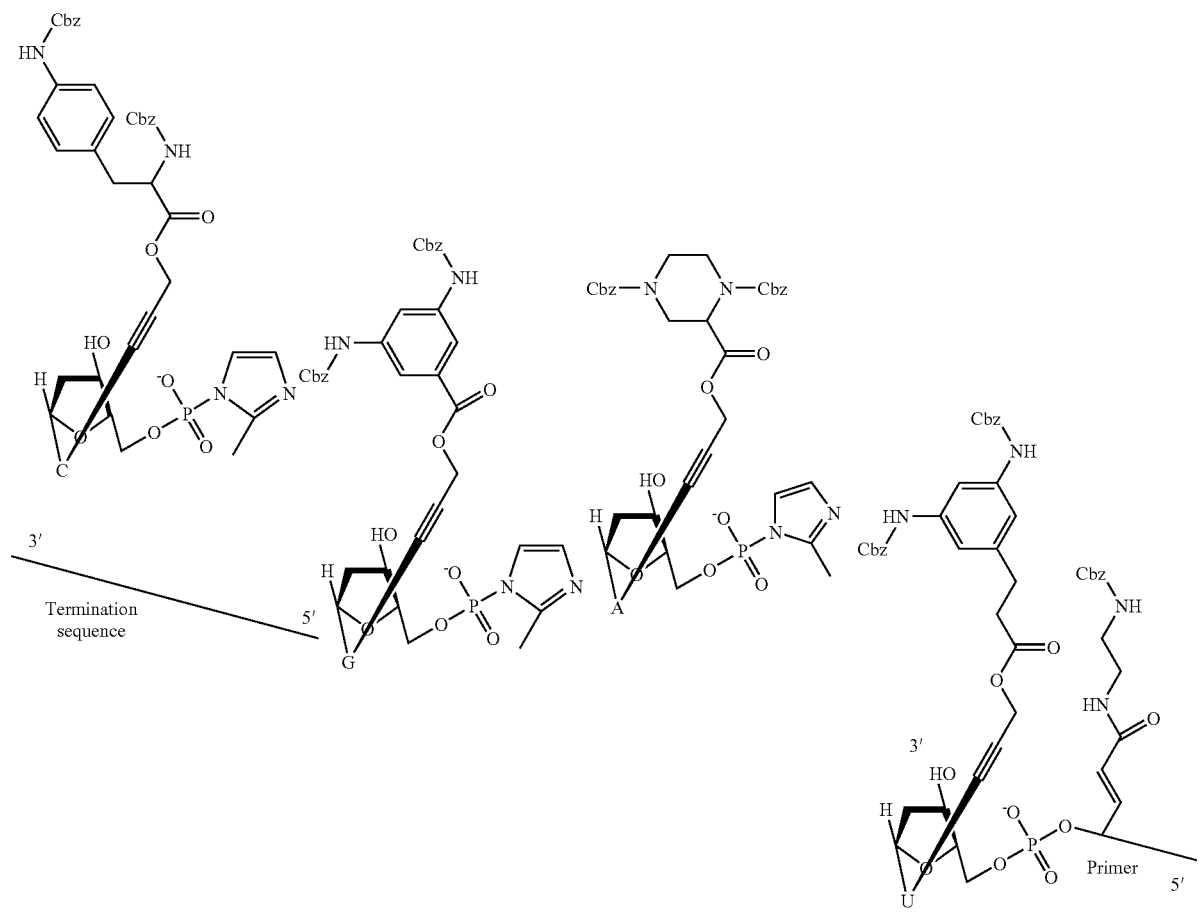
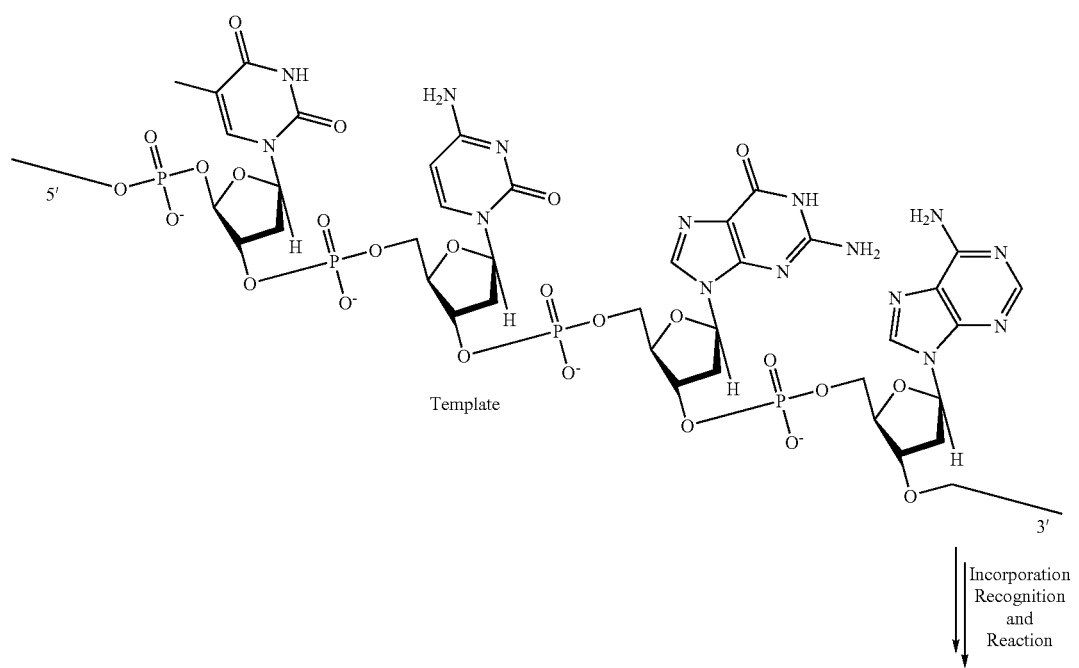

279 280
-continued
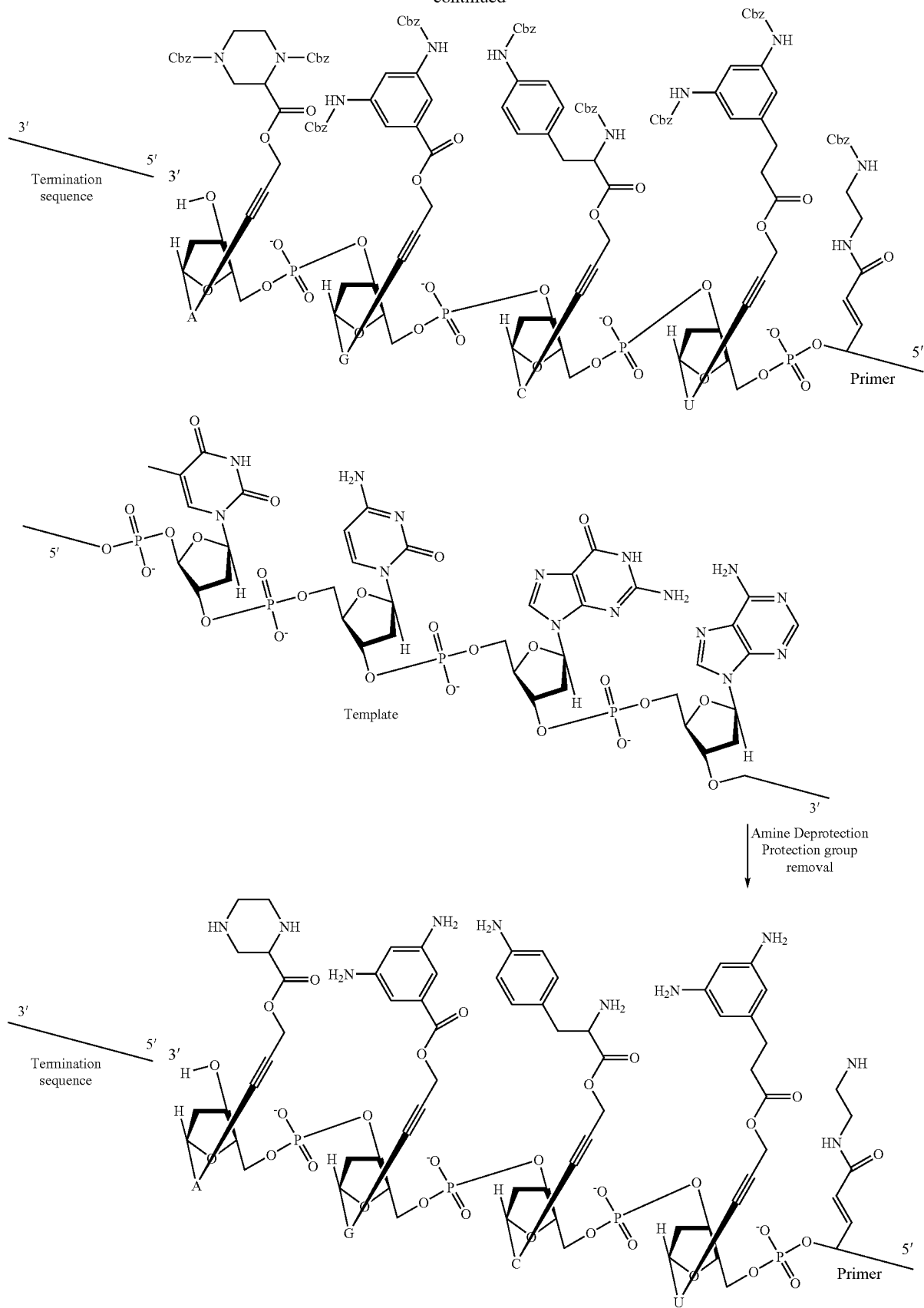

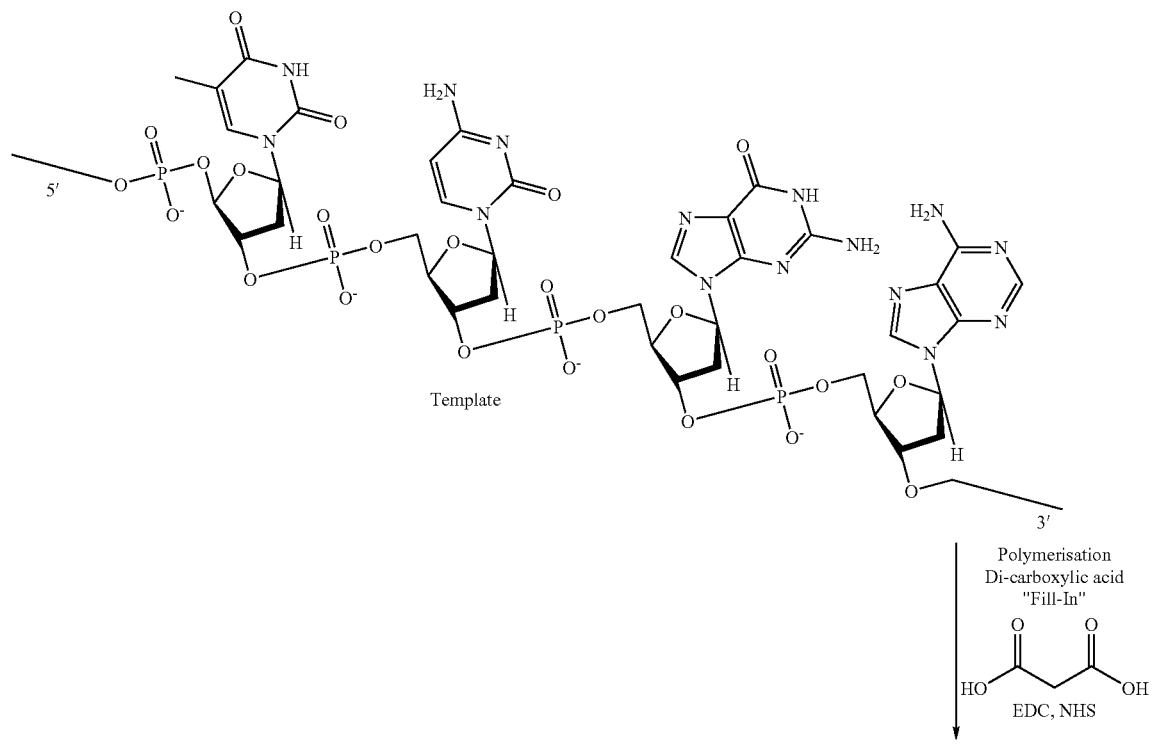
Template
Polymerisation
Di-carboxylic acid
"Fill-In"
EDC, NHS
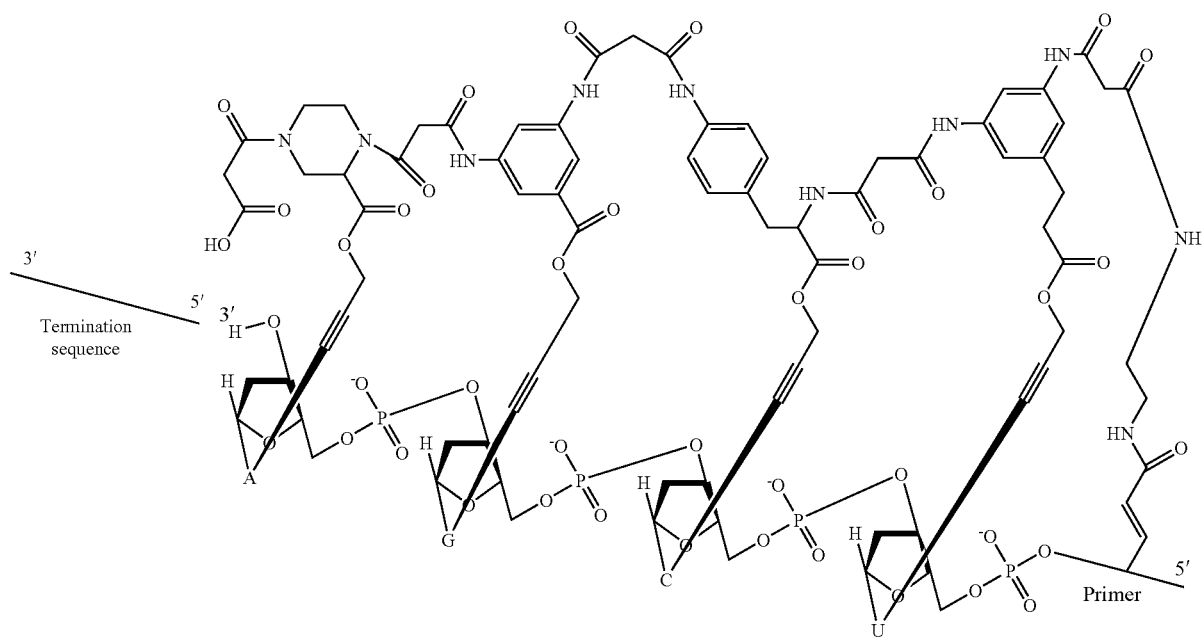

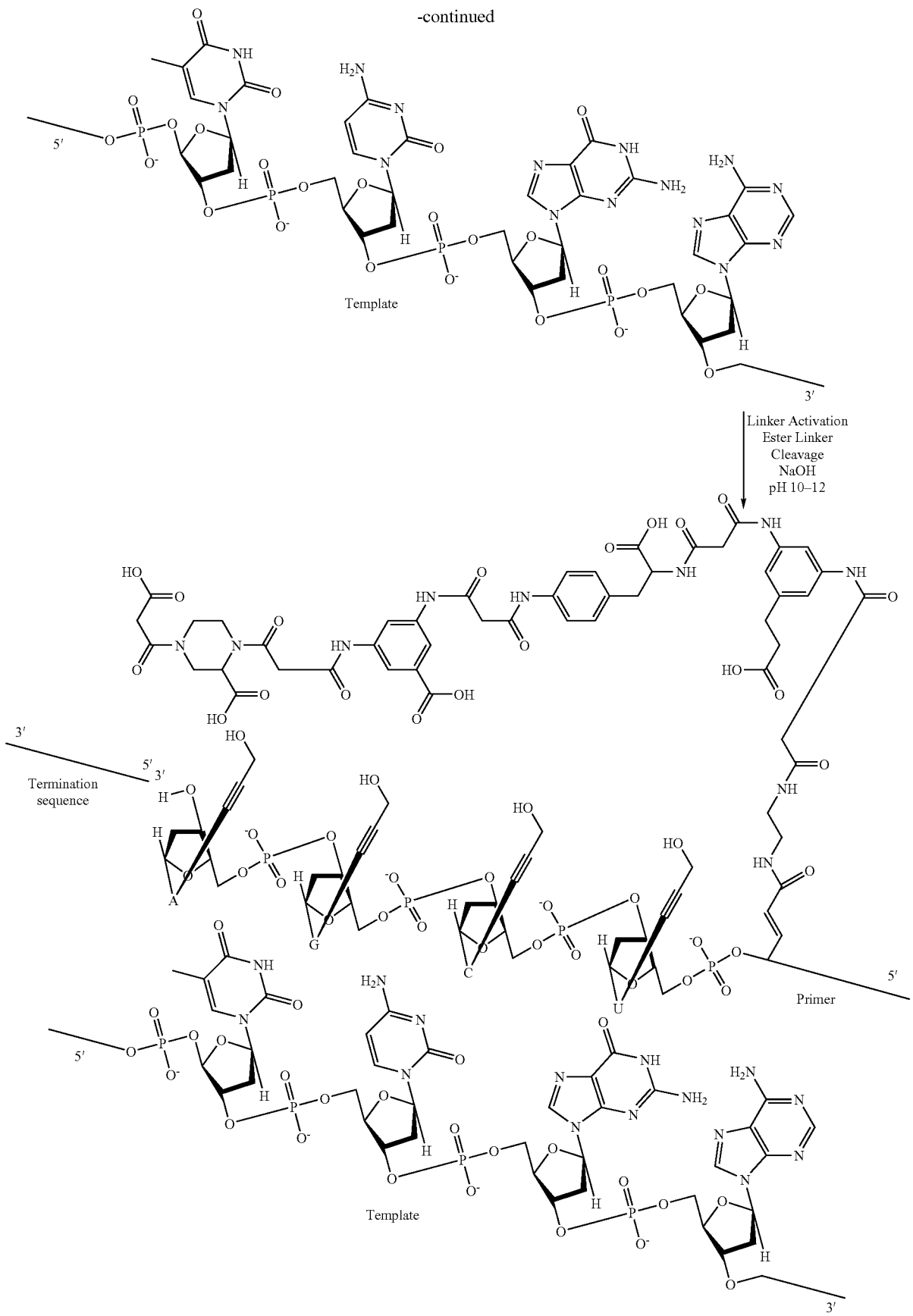
-continued

Incorporation

Typical conditions for oligomerisation of building blocks on the template are 0.05 M templates, 0.1-0.2 M building blocks, in a 0.2 M 2,6-lutidine-HCl buffer adjusted to pH=7.2 buffer containing 1.0 M sodium chloride 0.2 M magnesium chloride. The temperature is kept at 0° C. for 1-21 days. [Inoue;1984; *Journal of Molecular Biology;* 669-676]. The oligonucleotide complexes may be purified using micro-spin gel filtration (BioRad).

Amine Deprotection

Cbz protection groups may be removed by a variety of methods, [Greene;1999;] Due to its mildness, catalytic reduction is often the method of choice. Combining an insoluble hydrogenation catalyst e.g. $Pd/Al_2O_3$, $Pd/CaCO_3$, Pd/C, $PtO_2$, or a soluble one e.g. Wilkinsons catalyst and a hydrogen source exemplified but not limited to $H_2$, ammonium formiate, formic acid, 1,4-cyclohexadien, and cyclohexene in a suitable solvent like water, methanol, ethanol, dimethylformamide, dimethylsulfoxide, ethylen glycol, acetonitril, acetic acid or a mixture of these with the oligo nucleotide complexes removes the Cbz protective groups.

Polymerisation

Di-amines are linked together using di-carboxylic acids, a peptide coupling reagent optionally in the presence of a peptide coupling modifier in a suitable solvent like water, methanol, ethanol, dimethylformamide, dimethylsulfoxide, ethylene glycol, acetonitrile or a mixture of these. To an aqueous buffered solution (10 uL, 1M NaCl, 100-500 mM buffer pH 6-10, preferably 7-9) of oligonucleotide complexes (0.1-100 uM, preferably 0.5-10 uM) carrying free di-amines is added a di-carboxylic acid (0.1 mM-100 mM, preferably 1-10 mM) exemplified by but not limited to oxalic-, malonic-, succinic-, pentanedioic- or hexanedioic acid, phthalic-, isophthalic, terephthalic acid, N-protected glutamic acid or N-protected aspartic acid mixed with a peptide coupling reagent (0.1 mM-100 mM, preferably 1-10 mM) exemplified by but not limited to EDC, DCC, DIC, HATU, HBTU, PyBoP, PyBroP or N-methyl-2-chloropyridinium tetrafluoroborate and a peptide coupling modifier (0.1 mM-100 mM, preferably 1-10 mM) exemplified by but not limited to NHS, sulpho-NHS, HOBt, HOAt, DhbtOH in a suitable solvent (1 uL) e.g. water, methanol, ethanol, dimethylformamide, dimethylsulfoxide, ethylene glycol, acetonitrile or a mixture of these. Reactions run at temperatures between −20° C. and 100° C., preferably between 0° C. and 60° C. Reaction times are between 1 h and 1 week, preferably 1 h-24 h.

The above procedure exemplifies the polymerisation on a 11 uL scale, but any other reaction volume between 1.1 uL and 1.1L may be employed.

Linker Cleavage

The ester linkages are cleaved with aqueous hydroxide at pH 9-12 at room temperature, 16 h in a suitable solvent like water, methanol, ethanol, dimethylformamide, dimethylsulfoxide, ethylene glycol, acetonitrile or a mixture of these.

MS-Analysis

Library members may be analyzed using Mass Spectroscopy.

In the above sequence, diamines carry Cbz protection groups and are deprotected on the oligonucleotide. Other protection schemes may also be relevant for amine protection. [Greene and Wuts;1999;] In some cases it may suffice running the sequence with building blocks that do not carry protective groups on the amines, hence eliminating the amine deprotection step. The described procedure for templated library synthesis may also employ the use of modified di- and tri-nucleotides as well as modified nucleic acid analogues like morpholinos, LNA and PNA. In the latter case reaction conditions during incorporation should be changed to accommodate peptide coupling reactions. [Schmidt;1997; *Nucleic Acids Research;* 4792-4796] Examples of such alternative building blocks are shown in the scheme below. Synthesis of the modified PNA units compared to ordinary PNA units differs only in the use of modified bases.

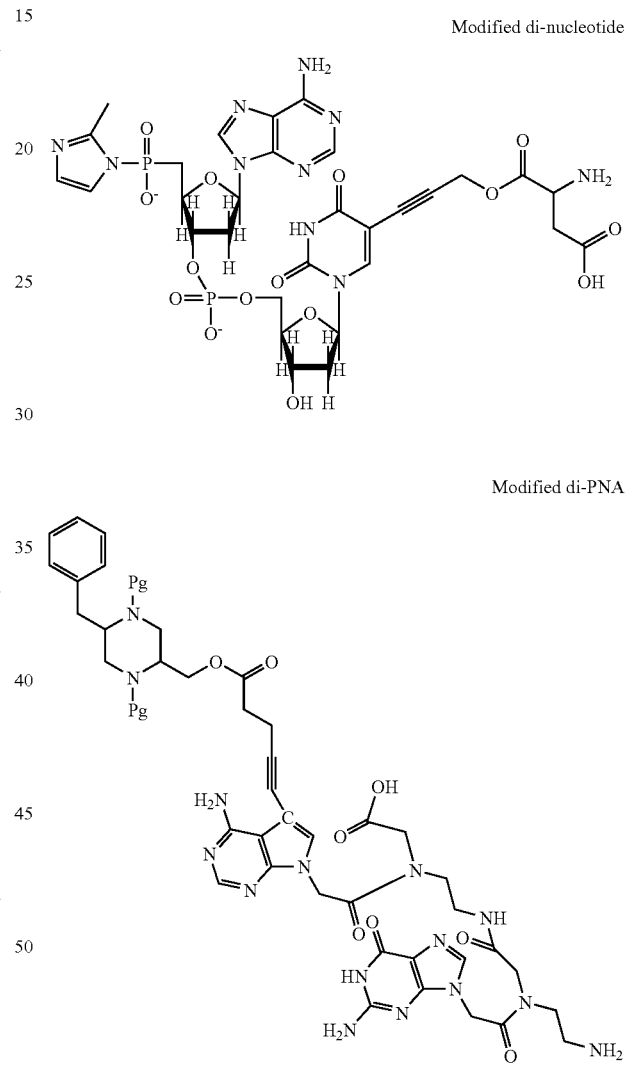

Further, instead of using 5'-phosphoimidazolide-nucleosides, a mixture of bis-3' 5' phosphoimidazolide-nucleosides [Visscher and Schwartz; 1988; *Journal of Molecular Evolution;* 3-6] and nucleosides may be employed in library production, see below. Alternating incorporation of each building block type is required, but due to the reversibility of the recognition step and the fact that no reaction takes place if for instance two bis-3',5' phosphoimidazolide-nucleosides are placed next to each other all that is necessary is that both building block types are present in the mixture.

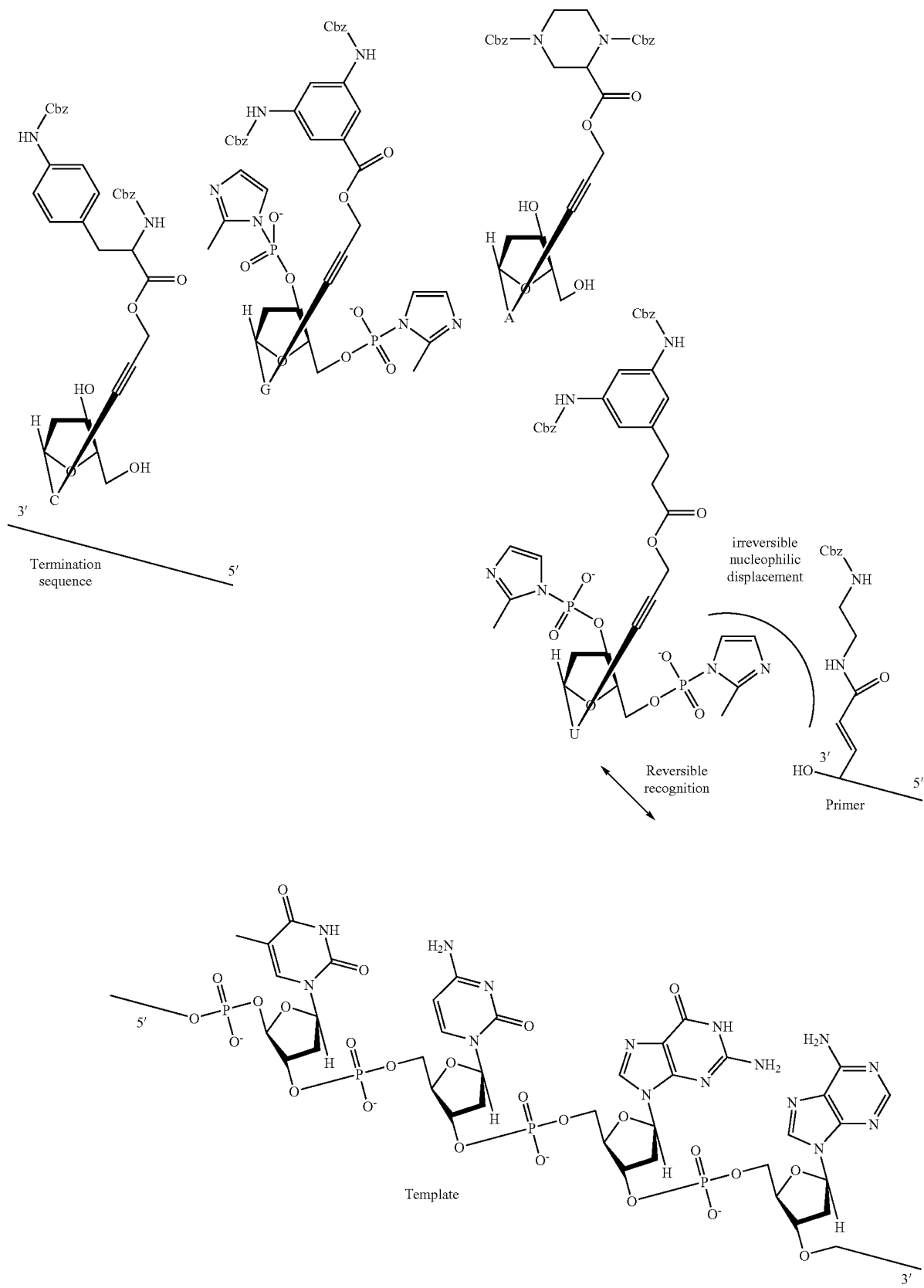

REFERENCES (1) Visscher, J.; Schwartz, A. W. *Journal of Molecular Evolution* 1988, 28, 3-6.
(2) Zhao, Y.; Thorson, J. S. *J. Org. Chem.* 1998, 63, 7568-7572.
(3) Inoue, T.; Joyce, G. F.; Grzeskowiak, K.; Orgel, L. E.; Brown, J. M.; Reese, C. B. *Journal of Molecular Biology* 1984, 178, 669-676.
(4) Greene, T. W.; Wuts, P. G. M. *Protective Groups in Organic Synthesis;* 3rd ed.; John Wiley & Sons: New York, 1999.
(5) Schmidt, J. G.; Christensen, L.; Nielsen, P. E.; Orgel, L. E. *Nucleic Acids Research* 1997, 25, 4792-4796.

Example 111 (Model)

Synthesis of a Library of Templated Molecules by Non-enzymatic Ligation of Dinucleotides Comprising Functional Entities Several systems have been developed that enable the non-enzymatic chemical ligation of nucleotides and oligonucleotides on nucleic acid or PNA templates (Xu et al., 2001, *Nat Biotechnol* 19, 148-152; 2000, *J Am Chem Soc*, 122, 9040-41). One protocol describes the autoligation of 3'-phosphothioate and a 5'moiety comprising an iodine leaving group as shown below.

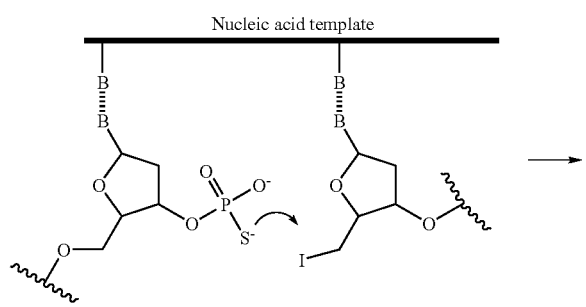

The non-enzymatic ligation protocol can be used for the templated synthesis of a library of molecules. Here, a set of dinucleotides each comprising a unique functional entity was synthesised by modified phosphoamidite nucleotide chemistry as described below. 4 di-nucleotide building blocks with the sequences dUdNp were synthesised. Each di-nucleotide comprises a 5'-iodo- and a 3'-phosphothioate group capable of forming a covalent bond with a neighbouring reactive group.

Incorporation of Di-nucleotides on a DNA Template:

1 pmol each of extension primers A (5'-GCTACTG-GCATCGXG-3'-phosphothioate, (SEQ ID NO:52), where X denotes deoxythymidine-C6-$NH_2$, Glen Research Cat#: 10-1035-90) and B (5'-iodo-GCACTTGCAGACAGC-3') (SEQ ID NO:53)) are annealed to a template oligo (5'GCT-GTCTGCAAGTGCNANACACGATGCCAGTAGC-3') (SEQ ID NO:54)) in a binding buffer: 50 mM HEPES-KOH, pH=7.5, 5 mM $MgCl_2$, 100 mM, KCl and incubated at 80° C. for 2 minutes before slowly cooling down to 20° C. The binding of primer A and B to the template forms a double stranded DNA complex with a central 4 nucleotide single-stranded segment as shown below. 10 pmol of di-nucleotides are added and the reaction mixture is incubated at 4° C. for 30 min followed by a brief heating to 25° C. for 30 seconds. The reaction mixture is subjected to successive temperature oscillation cycles for 24 hours. This step promotes the chemical ligation between correctly annealed dinucleotides and the primers A and B.

Following template complementation and chemical ligation, dinucleotides and buffer are removed by micro-spin gelfiltration (Biorad).

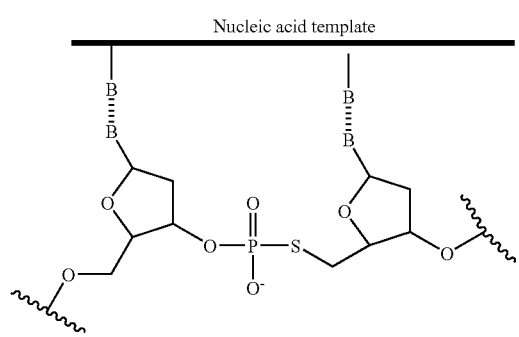

Cross-linking of Functional Entities and Activation of Templated Molecules.

The DNA complexes comprising the functional entities are incubated in a buffer 20 mM HEPES-KOH pH=7.5, 100 mM KCl. 5 mM Bis[Sulfosuccinimidyl]suberate ($BS_3$, Pierce) is added and the sample is incubated at 30° C. for 2-8 hours. Buffer and excess $BS_3$ are removed by micro-spin gelfiltration (Biorad). The templated molecules are activated by cleavage of the ester linkages using 0.2 M NaOH at 50° C. for 15 min before addition of equimolar HCl. The sample is transferred to a suitable buffer by dialysis.

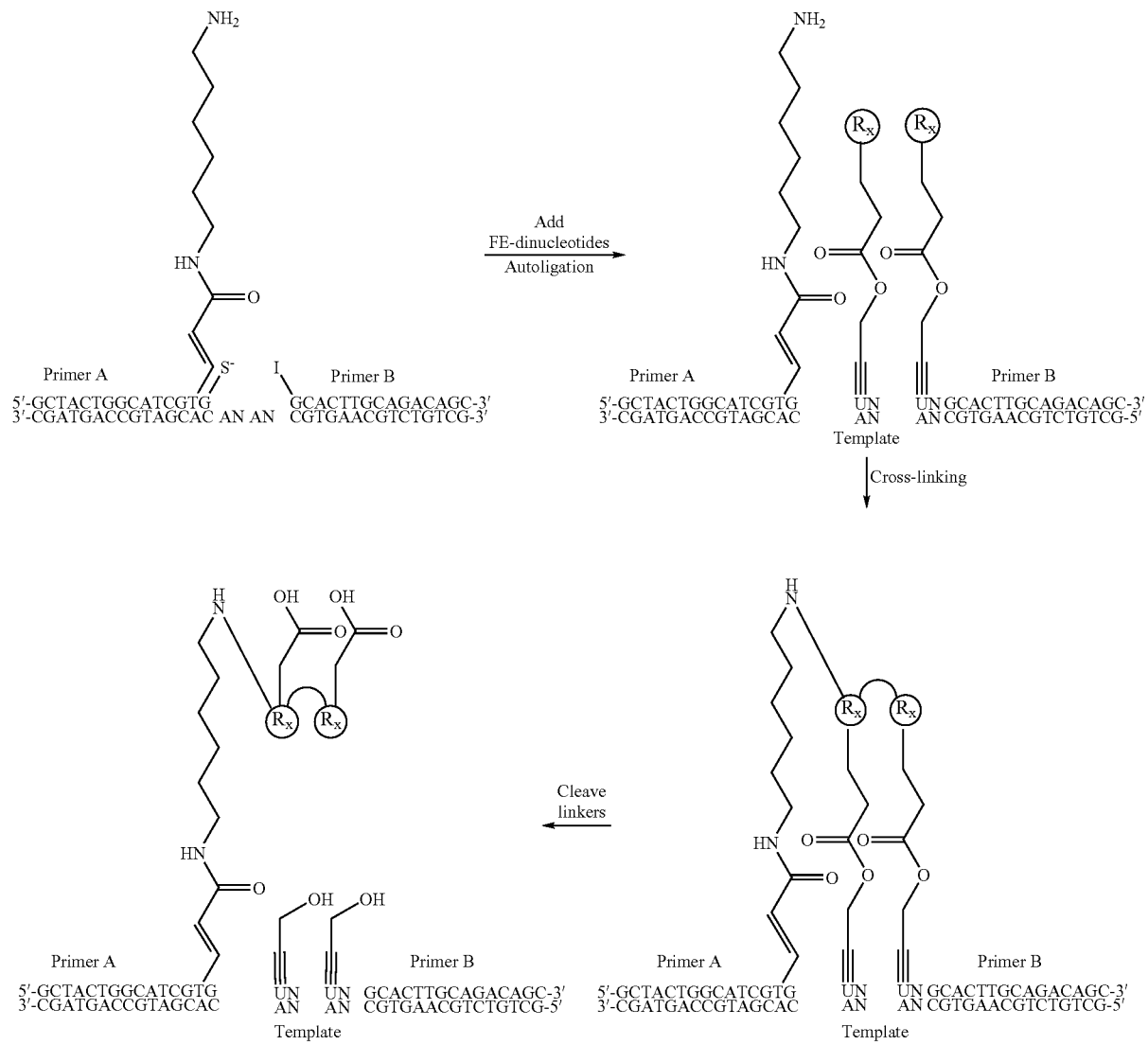

This protocol allows for the synthesis of a small library of 16 different molecules each linked to their template applicable for selection/amplification experiments. Larger libraries can be synthesised using tri-, tetra-, or other oligonucleotides comprising functional entities and/or by increasing the number of building blocks to be coupled by non-enzymatic ligation on the DNA template.

Synthesis of Building Blocks:

Synthesis of 5'-iodo-3'-phosphonothioate dimers with a functional entity attached

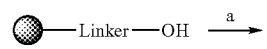

-continued

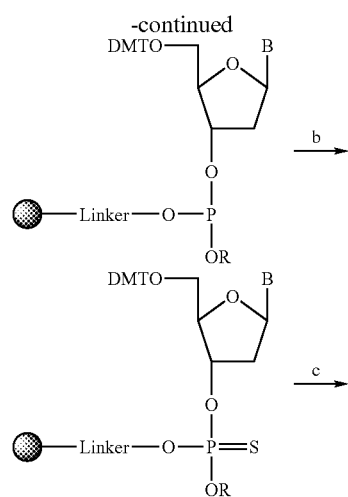

-continued

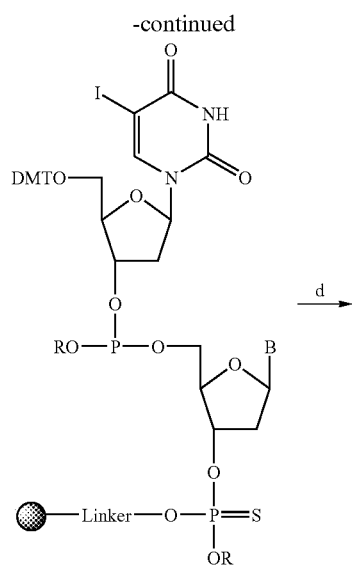

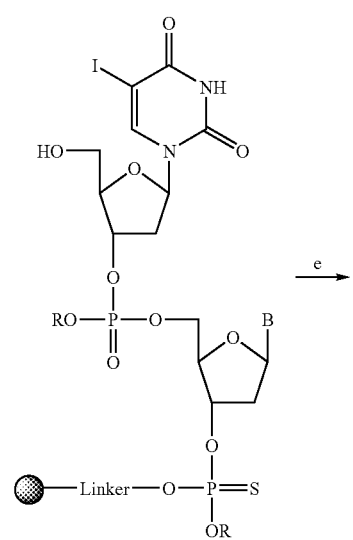

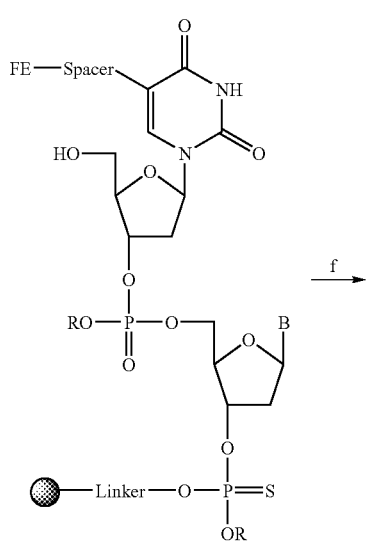

-continued

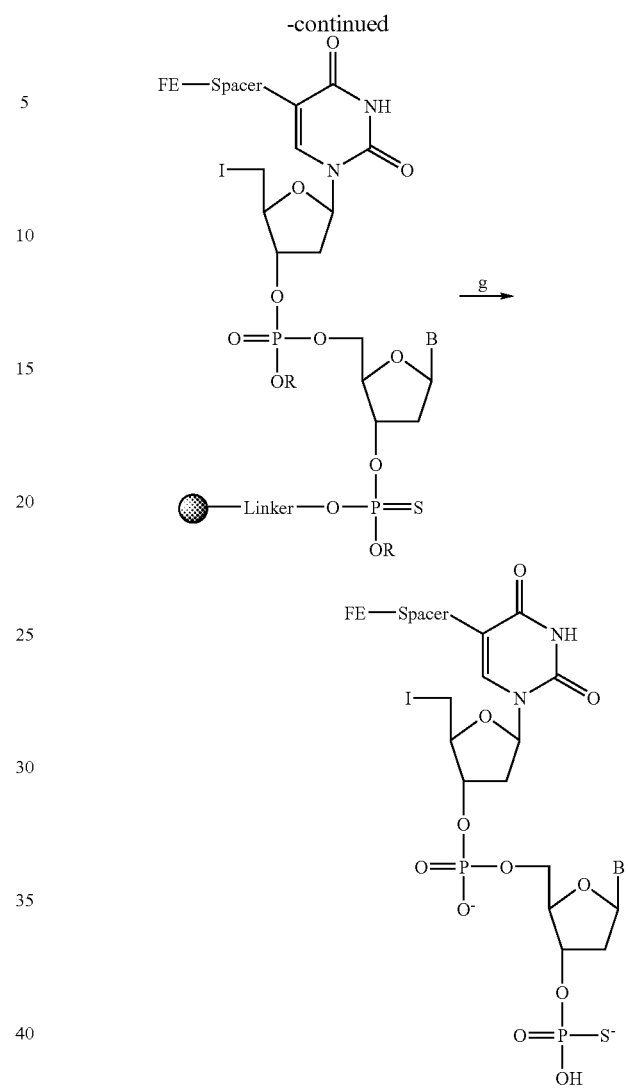

a) Conventional phosphoramidite coupling; b) $S_8$ in pyridine; c) phosphoramidite coupling to introduce 5-I-dU; d) $CF_3COOH$ then $I_2$/pyridine/water; e) FE—spacer and Pd(0) in THF—$Et_3N$; f) $Ph_3P$ and $I_2$ in DMF; g) photolysis > 300 nm.

B equals either A, T, G or C properly protected with the photolabile protecting group Nvoc[2]. Linker equals a photolabile CPG solid support.[3] R equals a photolabile phosphate protecting group.[4]

[2]Alvarez et al. *J. Org. Chem.* (1999), 64, 6319-28
[3]Pirrung et al *J Org. Chem.* (1998), 63, 241-46

Examples of attachment points (indicated by an arrow) of the linker on the nucleobases.

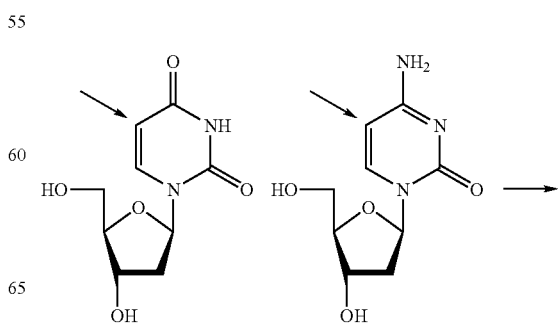

-continued

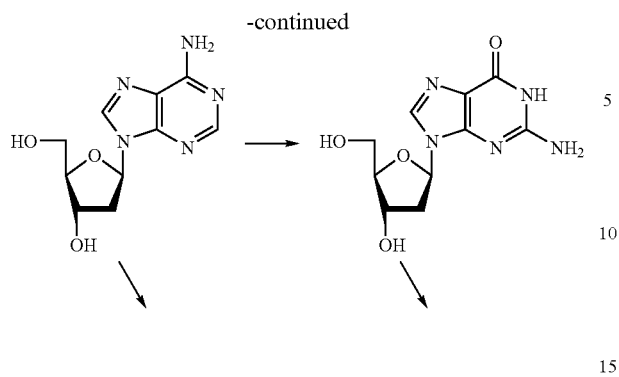

Examples of linker (indicated by dotted ring) and functional entity

-continued

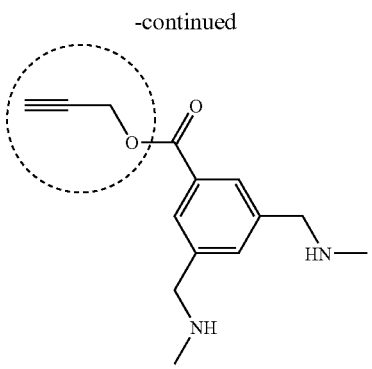

Example 112

Ligation of DNA Oligonucleotides, Derivatized at the Central Nucleotide

In order to examine the substrate efficiency of various DNA oligo-derivatives for T4 DNA ligase, oligo-derivatives Ah17 and Ah19 and were annealed to templates Ah18 and Ah20, respectively. Each of the templates contain two annealing sites for the appropriate oligo. The oligo-derivatives contain a modified nucleotide at the central nucleotide position (see figure below).

The reaction may be schematically represented as indicated below:

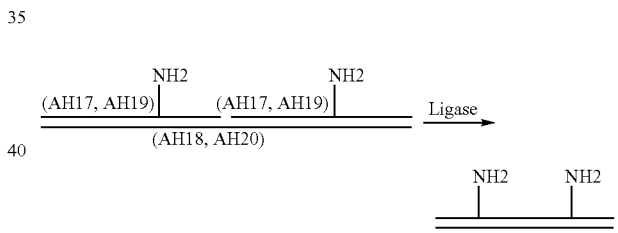

X=Amino-Modifier C6 dT

Ah 17: 5'-CACXGAA (SEQ ID NO:55)

Ah 18: 5'-TCGGATTCAGTGTTCAGTGCGTAG (SEQ ID NO:56)

Ah 19: 5'-TGCACXGAAGC (SEQ ID NO:57)

Ah20: 5'-TCGGAGCTTCAGTGCAGCTTCAGTG-CACGTAG (SEQ ID NO:58)

Mix 0.5 µl buffer A, 0.5 µl Ah18 or Ah20 (1 pmol/µl), and 2 µl Ah17 or Ah18 ($^{32}$P-labelled) (1 pmol/µl). Anneal by heating to 80° C. and then cool to 10° C. Add 3 µl T4-DNA Ligase (TAKARA, code #6022). Incubate at 4.7° C. for about 48 h. Then analyze by 10% urea polyacrylamide gel electrophoresis.

As seen in FIG. 64, the DNA ligase is able to efficiently ligate both oligo-derivatives tested, i.e. even for the shortest oligo (Ah17), with a length of 7 nucleotides, and a modification at position 4, ligation goes to approximately 50% completion.

The invention claimed is:

1. A method for synthesising a templated molecule comprising a plurality of functional groups, said method comprising the steps of
   i) providing at least one template comprising a sequence of n coding elements,
      wherein each coding element comprises at least one recognition group capable of recognizing a predetermined complementing element, and
      wherein n is an integer of more than 1,
   ii) providing a plurality of building blocks, wherein each building block comprises
      a) at least one complementing element comprising at least one recognition group, capable of recognizing a predetermined coding element, each complementing element consisting of 15-100 subunits,
      b) at least one functional entity comprising at least one functional group and at least one reactive group, and
      c) at least one linker separating the at least one functional entity from the at least one complementing element,
   iii) contacting each of said coding elements with a complementing element capable of recognizing said coding element,
   iv) optionally, obtaining a complementing template, and
   v) obtaining a templated molecule comprising covalently linked, functional groups by linking, by means of a reaction involving reactive groups, a functional group of at least one functional entity to a functional group of another, functional entity,
      wherein the templated molecule is linked by means of a covalent linker to the complementing template or template that templated the synthesis of the templated molecule, and
      wherein the synthesis of the templated molecule takes place in a cell-free system and does not involve ribosome mediated translation of a nucleic acid.

2. Method of claim 1, wherein the templated molecule is linked by means of a single linker to the complementing template or template that templated the synthesis of the templated molecule.

3. The method of claim 1, wherein steps iii) through v) are repeated.

4. The method of claim 1, wherein the template comprising n coding elements is a linear sequence of coding elements.

5. The method of claim 1, wherein the template comprising n coding elements is branched.

6. The method of claim 1, wherein n has a value of from 2 to 200.

7. The method of claim 1, wherein the template is attached to a solid or semi-solid support.

8. The method of claim 1, wherein the template comprises nucleotides selected from the group consisting of deoxyribonucleic acids (DNA), ribonucleic acids (RNA), peptide nucleic acids (PNA), locked nucleic acids (LNA), and morpholinos sequences, and nucleotide analogs thereof which further comprise an appended molecular entity.

9. The method of claim 1, wherein the template comprises or essentially consists of nucleotides selected from the group consisting of DNA, RNA, PNA, LNA and morpholinos sequence, including any analog or derivative thereof, and wherein the complementing element comprises or essentially consists of nucleotides selected from the group consisting of DNA, RNA, PNA, LNA and morpholinos sequence, and nucleotide analogs thereof which further comprise an appended molecular entity.

10. The method of claim 1, wherein the template is amplifiable.

11. The method of claim 1, wherein the template comprises a single strand of coding elements.

12. The method of claim 11, wherein the single strand of coding elements forms a double helix when hybridized to a complementing template comprising a single strand of complementing elements.

13. The method of claim 1, wherein the template comprises a priming site.

14. The method according to claim 13, wherein the priming site is upstream of the coding elements and is capable of binding a primer for initiating the incorporation of building blocks and/or for amplification of the coding elements of the templates.

15. The method of claim 13, wherein the priming site is downstream of the coding elements and is capable of binding an oligonucleotide.

16. The method of claim 15, wherein the oligonucleotide comprises an anchorage point, which can bind the templated molecule.

17. The method according to claim 15, wherein the oligonucleotide is capable of stopping further incorporation of building blocks.

18. The method of claim 15, wherein the priming site binds a reverse primer.

19. The method of claim 1, wherein each coding element is linked to a neighboring coding element by a covalent chemical bond.

20. The method of claim 1, wherein each coding element is linked to each neighboring coding element by a covalent chemical bond.

21. The method of claim 19, wherein said covalent chemical bond is selected from the group of covalent bonds consisting of phosphodiester bonds, phosphorothioate bonds, and peptide bonds.

22. The method of claim 19, wherein said covalent chemical bond is selected from the group of covalent bonds consisting of phosphodiester bonds and phosphorothioate bonds.

23. The method of claim 1, wherein at least one coding element is attached to a solid or semi-solid support.

24. The method of claim 1, wherein each coding element is independently selected from the group consisting of nucleotides, nucleotide analogs, nucleotide derivatives, amino acids, antibodies, and antigens.

25. The method of claim 24, wherein the coding elements are selected from the group consisting of nucleotides, nucleotide derivatives, and nucleotide analogs.

26. The method of claim 25, wherein the coding elements are nucleotides.

27. The method of claim 25, wherein the nucleotides are deoxyribonucleic acids comprising a base selected from the group consisting of adenine (A), thymine (T), guanine (G), and cytosine (C).

28. The method of claim 25, wherein the nucleotides are ribonucleic acids comprising a base selected from the group consisting of adenine (A), uracil (U), guanine (G), arid cytosine (C).

29. The method of claim 25, wherein each nucleotide is linked to a neighboring nucleotide by means of a covalent bond.

30. The method of claim 25, wherein each nucleotide is linked to each neighboring nucleotide by means of a covalent bond.

31. The method of claim 29, wherein said covalent bond is a phosphodiester bond or a phosphorothioate bond.

32. The method of claim 1, wherein the coding elements are natural and non-natural deoxyribonucleotides.

33. The method of claim 1, wherein the coding elements are natural and non-natural ribonucleotides.

34. The method of claim 1, wherein the coding elements are selected from the group consisting of nucleotides, nucleotide derivatives and nucleotide analogs in which one or more of the base moiety and/or the phosphate moiety and/or the ribose or deoxyribose moiety have been substituted by an alternative molecular entity.

35. The method of claim 1, wherein the complementing elements comprise or essentially consist of nucleotides selected from the group consisting of DNA, RNA, PNA, LNA and morpholinos sequence, and nucleotide analogs thereof which further comprise an appended molecular entity.

36. The method of claim 32, wherein each nucleotide is linked to a neighboring nucleotide by a covalent chemical bond.

37. The method of claim 32, wherein each nucleotide is linked to each neighboring nucleotide by a covalent chemical bond.

38. The method of 36, wherein said covalent chemical bond is selected from the group of covalent bonds consisting of phosphodiester bonds and peptide bonds.

39. The method of claim 1, wherein the coding element essentially consists of from 1 to 100 subunits.

40. The method of claim 39, wherein each subunit comprises a nucleotide, or a nucleotide analog.

41. The method of claim 40, wherein each subunit comprises a nucleotide.

42. The method of claim 41, wherein the nucleotide is a deoxyribonucleic acid comprising a base selected from the group consisting of adenine (A), thymine (T), guanine (G), and cytosine (C).

43. The method of claim 41, wherein the nucleotide is a ribonucleic acid comprising a base selected from the group consisting of adenine (A), uracil (U), guanine (G), and cytosine (C).

44. The method of claim 41, wherein each nucleotide is linked to a neighboring nucleotide, or nucleotide analog, by means of a covalent bond.

45. The method of claim 41, wherein each nucleotide is linked to each neighboring nucleotide, or nucleotide analog, by means of a covalent bond.

46. The method of claim 44, wherein said covalent bond is selected from the group consisting of phosphodiester bonds, phosphorothioate bonds, and peptide bonds.

47. The method of claim 40, wherein at least some of said nucleotides are selected from the group consisting of nucleotide derivatives.

48. The method of claim 47, wherein the nucleotide derivatives are selected from the group consisting of deoxyribonucleic acid derivatives and ribonucleic acid derivatives.

49. The method of claim 39, wherein the coding element subunits are selected from the group consisting of nucleotides, nucleotide derivatives and nucleotide analogs in which one or more of a base moiety and/or a phosphate moiety and/or a ribose moiety and/or a deoxyribose moiety have been substituted by an alternative molecular entity.

50. The method of claim 49, wherein the complementing element subunits comprise nucleotides selected from the group consisting of DNA, RNA, PNA, LNA and morpholinos sequence.

51. The method of claim 47, wherein each nucleotide derivative is linked to a neighboring nucleotide, or nucleotide analog, by a covalent chemical bond.

52. The method of claim 47, wherein each nucleotide derivative is linked to each neighboring nucleotide, or nucleotide analog, by a covalent chemical bond.

53. The method of claim 51, wherein said covalent chemical bond is selected from the group of covalent bonds consisting of phosphodiester bonds, phosphorothioate bonds, and peptide bonds.

54. The method according to claim 1, wherein a complementing template is obtained by complementing a plurality of predetermined coding elements by contacting each of said coding elements with a complementing element recognising said coding element.

55. The method of claim 1, wherein the complementing template comprising n complementing elements is a linear sequence of coding elements.

56. The method of claim 1, wherein the complementing template comprising n complementing elements is branched.

57. The method of claim 55, wherein n has a value of from 2 to 200.

58. The method of claim 1, wherein the complementing template is attached to a solid or semi-solid support.

59. The method of claim 1, wherein the complementing template comprises of nucleotides selected from the group consisting of deoxyribonucleic acids (DNA), ribonucleic acids (RNA), peptide nucleic acids (PNA), locked nucleic acids (LNA), and morpholinos sequences, and nucleotide analogs thereof which further comprise an appended molecular entity.

60. The method of claim 1, wherein the complementing template comprises of nucleotides selected from the group consisting of DNA, RNA, PNA, LNA and morpholinos sequence, including any analog or derivative thereof, and wherein the corresponding coding element of the template comprises or essentially consists of nucleotides selected from the group consisting of DNA, RNA, PNA, LNA and morpholinos sequence, and nucleotide analogs thereof which further comprise an appended molecular entity.

61. The method of claim 1, wherein the complementing template is amplifiable.

62. The method of claim 1, wherein the complementing template comprises a single strand of complementing elements.

63. The method of claim 55, wherein the single strand of complementing elements forms a double helix by hybridization to a template comprising a single strand of coding elements.

64. The method of claim 1, wherein the complementing template comprises a priming site.

65. The method of claim 1, wherein each complementing element is linked to a neighboring complementing element by a covalent chemical bond.

66. The method of claim 1, wherein each complementing element is linked to each neighboring complementing element by a covalent chemical bond.

67. The method of 65, wherein said covalent chemical bond is selected from the group of covalent bonds consisting of phosphodiester bonds, phosphorothioate bonds, and peptide bonds.

68. The method according to claim 67, wherein the phosphodiester bond is formed by a reaction between reactive groups type I, where one reactive group type I is a hydroxyl group and the other is a phosphorimidazole group.

69. The method of claim 65, wherein said covalent chemical bond is selected from the group of covalent bonds consisting of phosphodiester bonds and phosphorothioate bonds.

70. The method of claim 1, wherein at least one complementing element is attached to a solid or semi-solid support.

71. The method of claim 1, wherein each complementing element is independently selected from the group consisting of nucleotides, nucleotide analogs, nucleotide derivatives, amino acids, antibodies, and antigens.

72. The method of claim 71, wherein each complementing element is independently selected from the group consisting of nucleotides, nucleotide derivatives, and nucleotide analog.

73. The method according to claim 72, wherein, to increase the diversity, the nucleotide derivatives comprises natural as well as non-natural derivatives.

74. The method of claim 73, wherein the complementing elements are selected from the group consisting of nucleotides.

75. The method of claim 74, wherein the nucleotides are deoxyribonucleic acids comprising a base selected from the group consisting of adenine (A), thymine (T) guanine (G), cytosine (C), 7-deaza-guanine, 7-deaza-adenine.

76. The method of claim 74, wherein the nucleotides are ribonucleic acids comprising a base selected from the group consisting of adenine (A), uracil (U), guanine (G), and cytosine (C).

77. The method of claim 74, wherein each nucleotide is linked to a neighboring nucleotide, or nucleotide analog, by means of a covalent bond.

78. The method of claim 74, wherein each nucleotide is linked to each neighboring nucleotide, or nucleotide analog, by means of a covalent bond.

79. The method of claim 77, wherein said covalent bond is a phosphodiester bond or a phosphorothioate bond.

80. The method of claim 72, wherein the complementing elements are natural or non-natural deoxyribo nucleotides.

81. The method of claim 72, wherein the complementing elements are natural or non-natural ribo nucleotides.

82. The method of claim 72, wherein the complementing elements are selected from the group consisting of nucleotides, nucleotide derivatives and nucleotide analogs in which one or more of a base moiety and/or a phosphate moiety and/or a ribose and/or a deoxyribose moiety has been substituted by an alternative molecular entity.

83. The method of claim 82, wherein the coding elements capable of interacting with said complementing elements comprise nucleotides selected from the group consisting of DNA, RNA, PNA, LNA and morpholinos sequence, and nucleotide analogs thereof which further comprise an appended molecular entity.

84. The method of 83, wherein each nucleotide is linked to a neighboring nucleotide, or nucleotide analog, by a covalent chemical bond.

85. The method of claim 83, wherein each nucleotide is linked to each neighboring nucleotide, or nucleotide analog, by a covalent chemical bond.

86. The method of claim 84, wherein said covalent chemical bond is selected from the group of covalent bonds consisting of phosphodiester bonds, phosphorothioate bonds, and peptide bonds.

87. The method of claim 1, wherein the complementing element essentially consists of from 1 to 100 subunits.

88. The method of claim 87, wherein each subunit comprises a nucleotide, or a nucleotide analog.

89. The method of claim 88, wherein each subunit comprises a nucleotide.

90. The method of claim 89, wherein the nucleotide is a deoxyribonucleic acid comprising a base selected from the group consisting of adenine (A), thymine (T), guanine (C), and cytosine (C).

91. The method of claim 89, wherein the nucleotide is a ribonucleic acid comprising a base selected from the group consisting of adenine (A), uracil (U), guanine (G), and cytosine (C).

92. The method of claim 89, wherein each nucleotide is linked to a neighboring nucleotide, or nucleotide analog, by means of a covalent bond.

93. The method of claim 89, wherein each nucleotide is linked to each neighboring nucleotide, or nucleotide analog, by means of a covalent bond.

94. The method of claim 92, wherein said covalent bond is selected from the group consisting of phosphodiester bonds, phosphorothioate bonds, and peptide bonds.

95. The method of claim 88, wherein at least some of said nucleotides are nucleotide derivatives.

96. The method of claim 95, wherein the nucleotide derivatives are selected from the group consisting of deoxyribonucleic acid derivatives and ribonucleic acid derivatives.

97. The method of claim 88, wherein the complementing element subunits are selected from the group consisting of nucleotides, nucleotide derivatives, and nucleotide analogs in which one or more of a base moiety and/or a phosphate moiety and/or a ribose moiety and/or a deoxyribose moiety has been substituted by an alternative molecular entity.

98. The method of claim 97, wherein the coding element subunits comprises or essentially consists of nucleotides selected from the group consisting of DNA, RNA, PNA, LNA and morpholinos sequence, and nucleotide analogs thereof which further comprise an appended molecular entity.

99. The method of claim 91, wherein each nucleotide derivative is linked to a neighboring nucleotide, or nucleotide analog, by a covalent chemical bond.

100. The method of claim 91, wherein each nucleotide derivative is linked to each neighboring nucleotide, or nucleotide analog, by a covalent chemical bond.

101. The method of claim 95, wherein said covalent chemical bond is selected from the group of covalent bonds consisting of phosphodiester bonds, phosphorothioate bonds, and peptide bonds.

102. The method of claim 1, wherein the complementing elements are nucleotides, and the complementing elements are linked enzymatically.

103. The method according to claim 102, wherein the enzyme is selected from the group consisting of template-dependent DNA- and RNA-polymerases, DNA-ligases and RNA-ligases, and ribozymes and deoxyribozymes.

104. The method of claim 103, wherein the enzyme is selected from the group consisting of HIV-1 Reverse Transcriptase, AMV Reverse Transcriptase, T7 RNA polymerase, T7 RNA polymerase mutant Y639F, Sequenase, Taq DNA polymerase, Klenow Fragment (Large fragment of DNA polymerase I), DNA-ligase, T7 DNA polymerase, T4 DNA polymerase, and T4 DNA Ligase.

105. The method of claim 102, wherein the nucleotides form a complementing template upon incorporation.

106. The method according to claim 105, wherein a primer is annealed to a priming site on the template and a suitable polymerase or transcriptase extents the primer by incorporation of building blocks to obtain a complementing template.

107. The method according to claim 106, wherein the building block is a mono-, di- or oligonucleotide derivative.

108. The method according to claim 107, wherein the building block is a mononucleotide derivative.

109. The method according to claim 108, wherein the functional entity is attached to the nucleobase moiety through a linker.

110. The method according to claim 109, wherein the linker comprises a triple bond.

111. The method according to claim 106, wherein the building block is designed such that the functional entity protrudes into the major groove of a nucleic acid helix, when incorporated in a complementing template.

112. The method according to claim 102, wherein the complementing elements are selected from oligonucleotides and the complementing elements are linked enzymatically using a ligase.

113. The method according to claim 112, wherein the complementing element oligonucleotides each comprise three or more nucleic acid monomers.

114. The method according to claim 113, wherein the complementing element is an oligonucleotide comprising 4 to 100 nucleic acid monomers.

115. The method according to claim 1, wherein a complementing element anneals to the coding element, without being coupled to another complementing element.

116. The method according to claim 115, wherein the complementing element comprises an oligonucleotide of 6 to 100 nucleotide monomers.

117. The method according to claim 115, wherein the oligonucleotide comprises 10 to 50 nucleotide monomers.

118. The method according to claim 115, wherein the length is at least half the length of the complementing element.

119. The method according to claim 1, wherein the linker comprises an oligonucleotide.

120. The method according to claim 116, wherein the oligonucleotide complementing element and an oligonucleotide linker is a continuous oligonucleotide.

121. The method according to claim 119, wherein two linkers of distinct building blocks each comprises one part of a molecule pair, said pair being capable of reversible interaction.

122. The method according to claim 121, wherein the molecule pair comprises a double stranded sequence of nucleic acids forming a dimerisation domain on the linkers.

123. The method according to claim 122, wherein the dimerisation domain part of a linker is proximal to the functional entity.

124. The method according to claim 123, wherein the sequence of nucleic acids monomers forming the one part of the molecule pair is separated with 2, 1, or 0 nucleic acid monomers from the functional entity.

125. The method according to claim 124, wherein the functional entity is directly attached to the dimerisation domain.

126. The method according to claim 122, wherein the sequence of nucleic acid monomers comprises 3 to 20 mononucleic acids.

127. The method according to claim 122, wherein the sequence comprises 3 to 15 nucleic acid monomers.

128. The method according to claim 122, wherein the sequence comprises 4 to 12 nucleic acid monomers.

129. The method according to claim 119, wherein the functional entity is attached to a nucleobase of the oligonucleotide linker.

130. The method according to claim 119, wherein the functional entity is attached to a terminal nucleotide of the linker.

131. The method of claim 1, wherein the complementing elements are selected from nucleotides, and the complementing elements are linked by using a chemical agent, pH change, light, other radiation, or a catalyst, or by spontaneous coupling when being brought into reactive contact with each other.

132. The method according to claim 131 wherein the chemical agent comprises a phosphoimidazolid group.

133. The method according to claim 132, wherein the phosphoimidazolid group is attached to the 5' end of the building block and the building block is linked to a nascent complementing template at the 3' hydroxyl group thereof.

134. The method of claim 1, wherein at least a subset of said plurality of building blocks comprises one complementing element and/or one functional entity and/or one linker.

135. The method of claim 1, wherein a subset of said plurality of building blocks comprises a selectively cleavable linker separating the functional entity from the complementing element, wherein said selectively cleavable linker is not cleaved under conditions resulting in cleavage of cleavable linkers separating the functional entity from the complementing element of building blocks not belonging to the subset of building blocks comprising a selectively cleavable linker.

136. The method according to claim 135, wherein the functional entity is released by cleaving the cleavable linkers such that no trace of the linker appears on the functional entity.

137. The method of claim 135, wherein the cleavable linkers are cleaved, and wherein the at least one selectively cleavable linker is not cleaved, and wherein the templated molecule is linked to the template and/or to the complementing element by means of said at least one selectively cleavable linker.

138. The method of claim 137, wherein the linkers are cleaved by acid, base, another chemical agent, light, other electromagnetic radiation, an enzyme, or a catalyst.

139. The method according to claim 138, wherein the linker cleaved by light comprises a nitrophenyl moiety.

140. The method of claim 1, wherein the length of the linker or selectively cleavable linker is in the range of from about 0.8 Å to about 70 Å.

141. The method of claim 1, wherein the length of the linker or selectively cleavable linker is in the range of from 1 Å to 60 Å.

142. The method of claim 1, wherein the length of the linker or selectively cleavable linker is in the range of from 2 Å to 40 Å.

143. The method of claim 1, wherein the length of the linker or selectively cleavable linker is in the range of from 4 Å to 40 Å.

144. The method of claim 1, wherein the length of the linker or selectively cleavable linker is in the range of from 6 Å to 40 Å.

145. The method of claim 1, wherein the length of the linker or selectively cleavable linker is in the range of from 8 Å to 40 Å.

146. The method according to claim 1, wherein the obtained templated molecule comprises a sequence of covalently linked functional groups, by means of a reaction involving reactive groups, a functional group of at least one functional entity to a functional group of a neighboring functional entity.

147. The method according to claim 1, wherein the templated molecule is a linear sequence of functional groups.

148. The method according to claim 1, wherein the templated molecule is a branched sequence of functional groups.

149. The method according to claim 1, wherein the templated molecule is a cyclic sequence of functional groups.

150. The method of claim 1, wherein the templated molecule is an oligomer or a polymer comprising at least one repetitive sequence of functional groups.

151. The method of claim 150, wherein a sequence of at least three functional groups is repeated at least twice in the templated molecule.

152. The method of claim 150, wherein any sequence of at least three functional groups in the templated molecule occurs only once.

153. The method of claim 1, wherein the templated molecule comprises amino acids selected from the group consisting of α-amino acids, β-amino acids, Y-amino acids, ω-amino acids.

154. The method of claim 1, wherein the templated molecule comprises natural amino acid residues.

155. The method of claim 1, wherein the templated molecule comprises α-amino acids.

156. The method of claim 1, wherein the templated molecule comprises monosubstituted α-amino acids.

157. The method of claim 1, wherein the templated molecule comprises disubstituted α-amino acids.

158. The method of claim 1, wherein the templated molecule comprises monosubstituted β-amino acids.

159. The method of claim 1, wherein the templated molecule comprises disubstituted β-amino acids.

160. The method of claim 1, wherein the templated molecule comprises trisubstituted β-amino acids.

161. The method of claim 1, wherein the templated molecule comprises tetrasubstituted β-amino acids.

162. The method of 158, wherein the backbone structure of said β-amino acids comprises a cyclohexane-backbone and/or a cyclopentane-backbone.

163. The method of claim 1, wherein the templated molecule comprises Y-amino acids.

164. The method of claim 1, wherein the templated molecule comprises of ω-amino acids.

165. The method of claim 1, wherein the templated molecule comprises vinylogous amino acids.

166. The method of claim 1, wherein the templated molecule comprises N-substituted glycines.

167. The method of claim 1, wherein the templated molecule comprises molecules or molecular entities selected from the group consisting of α-peptides, β-peptides, Y-peptides, ω-peptides, mono-, di- and tri-substituted α-peptides, β-peptides, Y-peptides, ω-peptides, peptides wherein the amino acid residues are in the L-form or in the D-form, vinylogous polypeptides, glycopoly-peptides, polyamides, vinylogous sulfonamide peptide, polysulfonamide, conjugated peptides, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinone, polyoximes, polyimines, polyethyleneimines, polyimides, polyacetals, polyacetates, polystyrenes, polyvinyl, lipids, phospholipids, glycolipids, and polycyclic compounds.

168. The method of claim 1, wherein each pair of neighboring residues of the templated molecule is linked by a chemical bond, and each such chemical bond is independently selected from the group of chemical bonds consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, and combinations thereof.

169. The method according to claim 168, wherein the chemical bond linking functional entities of two or more building blocks is formed by a reaction of a nucleophile group of a first functional entity with an ester or thioester of another functional entity.

170. The method according to claim 169, wherein the linker of the building block bearing the thioester group is cleaved simultaneously with the formation of the bonding resulting in a transfer of functional group to the nucleophilic building block.

171. The method according to claim 169, wherein the nucleophile group is selected from —$NH_2$, $H_2NHN$—, HOHN—, $H_2N$—C(O)—NH—.

172. The method of claim 1, wherein the backbone structure of said templated molecule comprises a molecular group selected from —NHN(R)CO—; —NHB(R)CO—; —NHC(RR')CO—; —NHC(=CHR)CO—; —$NHC_6H_4$ CO—; —$NHCH_2$CHRCO—; —$NHCHRCH_2$CO—; —$COCH_2$—; —COS—; —CONR—; —COO—; —CSNH—; —$CH_2$NH—; —$CH_2CH_2$—; —$CH_2$S—; —$CH_2$SO—; —$CH_2SO_2$—; —$CH(CH_3)S$—; —CH=CH—; —NHCO—; —NHCONH—; —CONHO—; —C(=$CH_2$)$CH_2$—; —$PO_2$NH—; —$PO_2$$CH_2$—; —$PO_2$$CH_2^+$—; —$SO_2NH^-$—; and lactams.

173. The method of claim 1, wherein the functional entity is selected from the group of precursors consisting of α-amino acid precursors, β-amino acid precursors, Y-amino acid precursors, and ω-amino acid precursors.

174. The method of claim 173 in which the functional entity is a β-amino acid precursor.

175. The method of claim 174, wherein the β-amino acid precursor is a thiocarboxyanhydrid (NTA) ring structure derivative.

176. The method according to claim 1, wherein a functional group of at least one functional entity is linked to another functional entity by means of a bridging molecule.

177. The method according to claim 176, wherein the functional entities are neighbors.

178. The method of claim 1, wherein the templated molecule comprises at least 3 different functional groups.

179. The method of claim 178, wherein the functional groups are identical.

180. The method of claim 1, wherein each building block comprises at least one reactive group type I.

181. The method according to claim 1, wherein each building block comprises at least one reactive group type II.

182. The method of claim 1, wherein each building block comprises two reactive groups type I.

183. The method of claim 1, wherein each building block comprises two reactive groups type II.

184. The method according to claim 1, wherein at least one building block comprises three or more reactive groups type II.

185. The method according to claim 1, wherein two reactive groups type II of a building block are similar.

186. The method according to claim 1, wherein two reactive groups type II of a building block are reaction partners.

187. The method according to claim 1, wherein the reactive groups type II are capable of forming a linkage between the functional groups through a bridging molecule.

188. The method according to claim 187, wherein the bridging molecule is a di-functional compound with reactive groups which are reaction partners to the reactive groups type II of the functional entities.

189. The method according to claim 1, wherein two reactive groups type II of a building block are non-similar.

190. The method according to claim 189, wherein the non-similar reactive groups type II are reaction partners.

191. The method according to claim 189, wherein the reactive groups type II form a linkage between the functional groups through a bridging molecule.

192. The method according to claim 191, wherein the bridging molecule is a di-functional compound with reactive groups which are reaction partners to the reactive groups type II of the functional entities.

193. The method of claim 1, wherein at least one reactive group type II of a functional entity is selected from the group consisting of N-carboxyanhydride (NCA), N-thiocarboxyanhydride (NTA), coumarin, amine, carboxylic acid, ketone, aldehyde, hydroxyl, thiol, ester, thioester, alkenyl, any conjugated system of double bonds, hydrazine, hydroxysuccinimide ester, and epoxide.

194. The method of claim 181, wherein the reactive group type II is an electrophile.

195. The method according to claim 189, wherein the reactive group type II is an electrophile selected from the group consisting of —X—C(O)—R, —X—C(O)—CHR—C(O)—R, —X—C(O)—CR=CH—R, and —X—C(O)—CHR—NHR, wherein X is a S or O, and R independently is a functional group.

196. The method of claim 181, wherein the reactive group type II is a nucleophile.

197. The method according to claim 189, wherein the reactive group type II is a nucleophile selected from the group consisting of —$NH_2$, $H_2NHN$—, HOHN—, and $H_2N$—C(O, S)—NH—.

198. The method of claim 181, wherein the reactive group type II is a radical.

199. The method according to claim 1, wherein the functional entity comprises a reactive group type II connected to the linker.

200. The method according to claim 199, wherein said functional entity further comprises at least one further reactive group type II.

201. The method according to claim 200, wherein the functional entity comprising the at least one further reactive group type II forms a link to a second functional entity having a reactive group type II interspaced between said functional entity and the linker, by a reaction involving the reactive group type II on said other functional entity.

202. The method according to claim 201, wherein the link between the second functional entity and the linker is cleaved resulting in a translocation of the functional group of the second functional entity to the first functional entity.

203. The method according to claim 202, wherein the linkage between the first and the second functional entity is formed by a direct reaction of the respective reactive groups type II.

204. The method according to claim 201, wherein the linkage between the first and the second functional entity is formed through a bridging molecule.

205. The method according to claim 1, wherein multiple functional groups are linked by a reaction cascade involving a plurality of building blocks.

206. The method according to claim 205, wherein multiple functional groups are linked by a reaction cascade involving a plurality of building blocks, each of said building blocks comprising a functional entity which comprises a first reactive group type II connected to the linker, said functional entity comprising at least one further reactive group type II.

207. The method according to claim 205, wherein the functional entity is restricted as to rotation to obtaining a preferred orientation during formation of linkages to other functional entities.

208. The method according to claim 207, wherein one or more bondings that links the functional entity to the complementing element is fixed with regard to rotation.

209. The method according to claim 208, wherein the preferred orientation is obtained by coupling the functional entity to the base as well as the (deoxy)ribose moiety of a nucleotide building block.

210. The method according to claim 208, wherein the functional entity is coupled to two bases of a dinucleotide.

211. The method according to claim 1, wherein the formation of the templated molecule involves the reactive groups type II which form a polymer through anionic, cationic, or radical polymerisation.

212. The method according to claim 1, wherein a scaffold functional entity comprising one of more reactive groups type II is the basic chemical structure for forming a templated molecule by addition of functional groups emanating from the plurality of building blocks.

213. The method according to claim 212, wherein the scaffold functional entity comprises two or more reactive groups type II.

214. The method according to claim 212, wherein the scaffold functional entity is linked covalently to the template.

215. The method according to claim 212, wherein the scaffold functional entity is linked to a complementing element recognizing a coding element of the template.

216. The method according to claim 212, wherein building blocks attached to the template comprises functional entities carrying reactive groups type II which form a link to the scaffold functional entity.

217. The method according to claim 212, wherein a scrambling of linking of functional groups to the scaffold functional entity is obtained by having a different number of reactive groups type II on the scaffold functional entity compared to the number of reactive groups type II on the functional entities of the plurality of building blocks.

218. The method according to claim 212, wherein the reaction of the reactive groups type II on the scaffold and the corresponding reactive groups type II on the building blocks result in a simultaneous linkage of the functional groups to the scaffold functional entity and cleavage of the linker connecting the functional entity with the complementing element.

219. The method for generation of a library of templated molecules, wherein a plurality of templates having different coding elements and/or different order of coding elements is used in the method of claim 1.

220. The method according to claim 219, wherein two or more different templates are used.

221. The method according to claim 219, wherein four or more different templates are used.

222. The method according to claim 219, wherein the plurality of different templates results in a library of different templated molecules, each of said templated molecules being connected to the specific template or complementing template that templated the molecule.

223. The method of claim 1 comprising the further step of releasing the template or complementing template from the templated molecule, and obtaining a templated molecule that is not linked to the complementing template or template that templated the synthesis of the templated molecule.

224. The method of claim 174, wherein the β-amino acid precursor is an N-carboxyanhydride ring structure derivate.

225. The method of claim 211 wherein the formation of the polymer is through radical polymerization.

226. The method of claim 1 wherein each complementing elements consists of 15 to 80 subunits.

227. The method of claim 1 wherein each complementing elements consists of 15 to 60 subunits.

228. The method of claim 1 wherein each complementing elements consists of 15 to 40 subunits.

229. The method of claim 1 wherein each complementing elements consists of 15 to 20 subunits.

230. The method of claim 1 wherein each complementing elements consists of 20 to 100 subunits.

231. The method of claim 1 wherein each complementing elements consists of 20 to 80 subunits.

232. The method of claim 1 wherein each complementing elements consists of 20 to 60 subunits.

233. The method of claim 1 wherein each complementing elements consists of 20 to 40 subunits.

234. The method of claim 1 wherein each complementing elements consists of 20 to 30 subunits.

235. The method of claim 1 wherein each complementing elements consists of 20 to 25 subunits.

236. The method of claim 1 wherein the coding elements and the building blocks are nucleotides, and wherein a complementing template is obtained in step iv), each complementing element being linked to each neighboring complementing element by a covalent chemical bond, said bonds being formed enzymatically.

237. The method of claim 1 wherein at least one pair of neighboring building blocks comprise complementary zipper boxes.

238. The method of claim 237 in which the zipper boxes consist of 5 to 10 nucleotides.

239. The method of claim 237 in which the functional entity is immediately adjacent to the zipper box.

240. The method of claim 237 in which the functional entity is inside the zipper box.

241. The method of claim 237 in which the functional entity is separated, by one or more nucleotides, from the zipper box.

* * * * *

SEQUENCE LISTING

<160> NUMBER OF SEQ ID NOS: 58

<210> SEQ ID NO 1
<211> LENGTH: 15
<212> TYPE: DNA
<213> ORGANISM: Artificial Sequence
<220> FEATURE:
<223> OTHER INFORMATION: Extension primer, Fig. 49, lanes 1-5

<400> SEQUENCE: 1
gctactggca tcggt                                                    15

<210> SEQ ID NO 2
<211> LENGTH: 32
<212> TYPE: DNA
<213> ORGANISM: Artificial Sequence
<220> FEATURE:
<223> OTHER INFORMATION: Template primer, Fig. 49, lanes 1-5

<400> SEQUENCE: 2
gctgtctgca agtgataacc gatgccagta gc                                 32

<210> SEQ ID NO 3
<211> LENGTH: 15
<212> TYPE: DNA
<213> ORGANISM: Artificial Sequence
<220> FEATURE:
<223> OTHER INFORMATION: Extension primer, Fig. 49, lanes 6-11

<400> SEQUENCE: 3
gctactggca tcggt                                                    15

<210> SEQ ID NO 4
<211> LENGTH: 32
<212> TYPE: DNA
<213> ORGANISM: Artificial Sequence
<220> FEATURE:
<223> OTHER INFORMATION: Template primer, Fig. 49. lanes 6-11.

<400> SEQUENCE: 4
gctgtctgca agtgatgacc gatgccagta gc                                 32

<210> SEQ ID NO 5
<211> LENGTH: 15
<212> TYPE: DNA
<213> ORGANISM: Artificial Sequence
<220> FEATURE:
<223> OTHER INFORMATION: Extension primer, Fig. 49, lanes 12-15

<400> SEQUENCE: 5
gctactggca tcggt                                                    15

<210> SEQ ID NO 6
<211> LENGTH: 34
<212> TYPE: DNA
<213> ORGANISM: Artificial Sequence
<220> FEATURE:
<223> OTHER INFORMATION: Template primer, Fig. 49, lanes 12-15

<400> SEQUENCE: 6
gctgtctgca agtgacgtaa ccgatgccag tagc                               34

<210> SEQ ID NO 7
<211> LENGTH: 19

```
<212> TYPE: DNA
<213> ORGANISM: Artificial Sequence
<220> FEATURE:
<223> OTHER INFORMATION: Template primer, Fig. 50

<400> SEQUENCE: 7
taagaccgat gccagtagc                                                19

<210> SEQ ID NO 8
<211> LENGTH: 18
<212> TYPE: DNA
<213> ORGANISM: Artificial Sequence
<220> FEATURE:
<223> OTHER INFORMATION: Template primer, Fig. 51

<400> SEQUENCE: 8
tagaccgatg ccagtagc                                                 18

<210> SEQ ID NO 9
<211> LENGTH: 18
<212> TYPE: DNA
<213> ORGANISM: Artificial Sequence
<220> FEATURE:
<223> OTHER INFORMATION: Extension primer, Figs. 52 and 53.

<400> SEQUENCE: 9
tccgctactg gcatcggt                                                 18

<210> SEQ ID NO 10
<211> LENGTH: 18
<212> TYPE: DNA
<213> ORGANISM: Artificial Sequence
<220> FEATURE:
<223> OTHER INFORMATION: Template primer, Figs. 52 and 53

<400> SEQUENCE: 10
tgaaccgatg ccagtagc                                                 18

<210> SEQ ID NO 11
<211> LENGTH: 18
<212> TYPE: DNA
<213> ORGANISM: Artificial Sequence
<220> FEATURE:
<223> OTHER INFORMATION: Primer, example 69
<220> FEATURE:
<221> NAME/KEY: misc_feature
<222> LOCATION: (18)..(18)
<223> OTHER INFORMATION: n is deoxy-thymidine-C6-NH2, (Glen research,
      cat #10-1039-90) (amino- modifier C6-dT)

<400> SEQUENCE: 11
tccgctactg gtatcggn                                                 18

<210> SEQ ID NO 12
<211> LENGTH: 15
<212> TYPE: DNA
<213> ORGANISM: Artificial Sequence
<220> FEATURE:
<223> OTHER INFORMATION: Primer, example 69
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 12
ncacttgcag acagc                                                    15
```

<210> SEQ ID NO 13
<211> LENGTH: 29
<212> TYPE: DNA
<213> ORGANISM: Artificial Sequence
<220> FEATURE:
<223> OTHER INFORMATION: Template primer, examples 69 and 70

<400> SEQUENCE: 13
gctgtctgca agtgaccgat gccagtagc                                    29

<210> SEQ ID NO 14
<211> LENGTH: 18
<212> TYPE: DNA
<213> ORGANISM: Artificial Sequence
<220> FEATURE:
<223> OTHER INFORMATION: Primer, example 70
<220> FEATURE:
<221> NAME/KEY: misc_feature
<222> LOCATION: (18)..(18)
<223> OTHER INFORMATION: n is deoxy-thymidine-C2-COOH (Glen research,
      cat #10-1035-90)

<400> SEQUENCE: 14
tccgctactg gtatcggn                                                18

<210> SEQ ID NO 15
<211> LENGTH: 15
<212> TYPE: DNA
<213> ORGANISM: Artificial Sequence
<220> FEATURE:
<223> OTHER INFORMATION: Primer, examples 70, 71, and 73
<220> FEATURE:
<221> NAME/KEY: misc_feature
<222> LOCATION: (1)..(1)
<223> OTHER INFORMATION: n is deoxy-thymidine-C2-COOH (Glen research,
      cat #10-1035-90)

<400> SEQUENCE: 15
ncacttgcag acagc                                                   15

<210> SEQ ID NO 16
<211> LENGTH: 15
<212> TYPE: DNA
<213> ORGANISM: Artificial Sequence
<220> FEATURE:
<223> OTHER INFORMATION: Extension primer, examples 73 and 83

<400> SEQUENCE: 16
gctactggca tcggt                                                   15

<210> SEQ ID NO 17
<211> LENGTH: 32
<212> TYPE: DNA
<213> ORGANISM: Artificial Sequence
<220> FEATURE:
<223> OTHER INFORMATION: Template primer, example 73

<400> SEQUENCE: 17
gctgtctgca agtgagtacc gatgccagta gc                                32

<210> SEQ ID NO 18
<211> LENGTH: 34
<212> TYPE: DNA
<213> ORGANISM: Artificial Sequence
<220> FEATURE:
<223> OTHER INFORMATION: Template primer, example 83

<400> SEQUENCE: 18

```
gtaattggag tgagccddda ccgatgccag tagc                              34
```

<210> SEQ ID NO 19
<211> LENGTH: 18
<212> TYPE: DNA
<213> ORGANISM: Artificial Sequence
<220> FEATURE:
<223> OTHER INFORMATION: Reverse primer, Example 83

<400> SEQUENCE: 19

```
tagaccgatg ccagtagc                                                18
```

<210> SEQ ID NO 20
<211> LENGTH: 56
<212> TYPE: DNA
<213> ORGANISM: Artificial Sequence
<220> FEATURE:
<223> OTHER INFORMATION: Building block AH36, example 100;
<220> FEATURE:
<221> NAME/KEY: misc_feature
<222> LOCATION: (56)..(56)
<223> OTHER INFORMATION: n is carboxy-dT (Glen Research, cat #10-1035-)

<400> SEQUENCE: 20

```
cgacctctgg attgcatcgg tcatggctga ctgtccgtcg aatgtgtcca gttacn      56
```

<210> SEQ ID NO 21
<211> LENGTH: 56
<212> TYPE: DNA
<213> ORGANISM: Artificial Sequence
<220> FEATURE:
<223> OTHER INFORMATION: Building block AH37, Example 100
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 21

```
ngtaactgga ctgtaagctg cctgtcagtc ggtactgacc tgtcgagcat ccagct      56
```

<210> SEQ ID NO 22
<211> LENGTH: 56
<212> TYPE: DNA
<213> ORGANISM: Artificial Sequence
<220> FEATURE:
<223> OTHER INFORMATION: Building block AH51, example 100
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 22

```
ngtaacacct gtgtaagctg cctgtcagtc ggtactgacc tgtcgagcat ccagct      56
```

<210> SEQ ID NO 23
<211> LENGTH: 40
<212> TYPE: DNA
<213> ORGANISM: Artificial Sequence
<220> FEATURE:
<223> OTHER INFORMATION: Template AH38, example 100
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 23
agctggatgc tcgacaggtc ccgatgcaat ccagaggtcg                      40

<210> SEQ ID NO 24
<211> LENGTH: 56
<212> TYPE: DNA
<213> ORGANISM: Artificial Sequence
<220> FEATURE:
<223> OTHER INFORMATION: building block AH67, example 100
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 24
ncattgacct gtgtaagctg cctgtcagtc ggtactgacc tgtcgagcat ccagct    56

<210> SEQ ID NO 25
<211> LENGTH: 56
<212> TYPE: DNA
<213> ORGANISM: Artificial Sequence
<220> FEATURE:
<223> OTHER INFORMATION: Building block AH69, example 100
<220> FEATURE:
<221> NAME/KEY: misc_feature
<222> LOCATION: (3)..(3)
<223> OTHER INFORMATION: n is deoxy-thymidine-C6-NH2, (Glen research,
      cat #10-1039-90)

<400> SEQUENCE: 25
agnaacacct gtgtaagctg cctgtcagtc ggtactgacc tgtcgagcat ccagct    56

<210> SEQ ID NO 26
<211> LENGTH: 58
<212> TYPE: DNA
<213> ORGANISM: Artificial Sequence
<220> FEATURE:
<223> OTHER INFORMATION: Building block AH66, example 100
<220> FEATURE:
<221> NAME/KEY: misc_feature
<222> LOCATION: (1)..(1)
<223> OTHER INFORMATION: n is deoxy-thymidine-C6-NH2, (Glen research,
      cat #10-1039-90)

<400> SEQUENCE: 26
nttgtaactg gactgtaagc tgcctgtcag tcggtactga cctgtcgagc atccagct  58

<210> SEQ ID NO 27
<211> LENGTH: 58
<212> TYPE: DNA
<213> ORGANISM: Artificial Sequence
<220> FEATURE:
<223> OTHER INFORMATION: Building block AH65, example 100
<220> FEATURE:
<221> NAME/KEY: misc_feature
<222> LOCATION: (58)..(58)
<223> OTHER INFORMATION: n is carboxy dT (Glenn Research cat. no.
      10-1035-90)

<400> SEQUENCE: 27
cgacctctgg attgcatcgg tcatggctga ctgtccgtcg aatgtgtcca gttacttn  58

<210> SEQ ID NO 28
<211> LENGTH: 15
<212> TYPE: DNA
<213> ORGANISM: Artificial Sequence
<220> FEATURE:
<223> OTHER INFORMATION: Oligo A, example 101
<220> FEATURE:

<221> NAME/KEY: misc_feature
<222> LOCATION: (10)..(10)
<223> OTHER INFORMATION: n is carboxy-modifier C2 dT (Glenn Research cat. no. 10-1035-90)

<400> SEQUENCE: 28
gctactggcn tcggt                                                    15

<210> SEQ ID NO 29
<211> LENGTH: 15
<212> TYPE: DNA
<213> ORGANISM: Artificial Sequence
<220> FEATURE:
<223> OTHER INFORMATION: Oligo B, example 101
<220> FEATURE:
<221> NAME/KEY: misc_feature
<222> LOCATION: (6)..(6)
<223> OTHER INFORMATION: n is carboxy dT (Glenn Research cat. no. 10-1035-90)

<400> SEQUENCE: 29
tcactngcag acagc                                                    15

<210> SEQ ID NO 30
<211> LENGTH: 56
<212> TYPE: DNA
<213> ORGANISM: Artificial Sequence
<220> FEATURE:
<223> OTHER INFORMATION: Oligo D, example 101
<220> FEATURE:
<221> NAME/KEY: misc_feature
<222> LOCATION: (56)..(56)
<223> OTHER INFORMATION: n is carboxy dT (Glenn Research cat. no. 10-1035-90)

<400> SEQUENCE: 30
ctggtaacgc ggatcgacct tcatggctga ctgtccgtcg aatgtgtcca gttacn      56

<210> SEQ ID NO 31
<211> LENGTH: 56
<212> TYPE: DNA
<213> ORGANISM: Artificial Sequence
<220> FEATURE:
<223> OTHER INFORMATION: Oligo E, example 101
<220> FEATURE:
<221> NAME/KEY: misc_feature
<222> LOCATION: (56)..(56)
<223> OTHER INFORMATION: n is carboxy dT (Glenn Research cat. no. 10-1035-90)

<400> SEQUENCE: 31
acgactacgt tcaggcaaga tcatggctga ctgtccgtcg aatgtgtcca gttacn      56

<210> SEQ ID NO 32
<211> LENGTH: 31
<212> TYPE: DNA
<213> ORGANISM: Artificial Sequence
<220> FEATURE:
<223> OTHER INFORMATION: Oligo F, example 102
<220> FEATURE:
<221> NAME/KEY: misc_feature
<222> LOCATION: (31)..(31)
<223> OTHER INFORMATION: n is carboxy dT (Glenn Research cat. no. 10-1035-90)

<400> SEQUENCE: 32
gacctgtcga gcatccagct gtccacaatg n                                  31

<210> SEQ ID NO 33

```
<211> LENGTH: 46
<212> TYPE: DNA
<213> ORGANISM: Artificial Sequence
<220> FEATURE:
<223> OTHER INFORMATION: Oligo G, example 102
<220> FEATURE:
<221> NAME/KEY: misc_feature
<222> LOCATION: (46)..(46)
<223> OTHER INFORMATION: n is carboxy dT (Glenn Research cat. no.
      10-1035-90)

<400> SEQUENCE: 33
gacctgtcga gcatccagct tcatgggaat tcctcgtcca caatgn              46

<210> SEQ ID NO 34
<211> LENGTH: 47
<212> TYPE: DNA
<213> ORGANISM: Artificial Sequence
<220> FEATURE:
<223> OTHER INFORMATION: Oligo H, example 102
<220> FEATURE:
<221> NAME/KEY: misc_feature
<222> LOCATION: (46)..(46)
<223> OTHER INFORMATION: n is carboxy dT (Glenn Research cat. no.
      10-1035-90)

<400> SEQUENCE: 34
gacctgtcga gcatccagct tcatgggaat tcctcgtcca caatgnt             47

<210> SEQ ID NO 35
<211> LENGTH: 56
<212> TYPE: DNA
<213> ORGANISM: Artificial Sequence
<220> FEATURE:
<223> OTHER INFORMATION: Oligo I, example 102
<220> FEATURE:
<221> NAME/KEY: misc_feature
<222> LOCATION: (1)..(1)
<223> OTHER INFORMATION: n is carboxy dT (Glenn Research cat. no.
      10-1035-90)

<400> SEQUENCE: 35
ngtaactgga gggtaagctc atccgaattc ggtactgacc tgtcgagcat ccagct   56

<210> SEQ ID NO 36
<211> LENGTH: 57
<212> TYPE: DNA
<213> ORGANISM: Artificial Sequence
<220> FEATURE:
<223> OTHER INFORMATION: Oligo J, example 103
<220> FEATURE:
<221> NAME/KEY: misc_feature
<222> LOCATION: (1)..(1)
<223> OTHER INFORMATION: n is 5'-Thiol-modifier C6 (Glen Research cat.
      No. #10-1926-90) (thiol modifier phosphoramidite)
<220> FEATURE:
<221> NAME/KEY: misc_feature
<222> LOCATION: (19)..(19)
<223> OTHER INFORMATION: n is internal biotin (Glen Research cat.
      #10-1953-95) (biotin phosphoramidite)

<400> SEQUENCE: 36
ncattgacct gtgtaagcnt gcctgtcagt cggtactcga cctctggatt gcatcgg  57

<210> SEQ ID NO 37
<211> LENGTH: 52
<212> TYPE: DNA
<213> ORGANISM: Artificial Sequence
<220> FEATURE:
<223> OTHER INFORMATION: Oligo K, example 103
<220> FEATURE:
```

-continued

```
<221> NAME/KEY: misc_feature
<222> LOCATION: (1)..(1)
<223> OTHER INFORMATION: n is 5'-Thiol-modifier C6 (Glen Research cat.
      No. #10-1926-90)
<220> FEATURE:
<221> NAME/KEY: misc_feature
<222> LOCATION: (18)..(18)
<223> OTHER INFORMATION: n is internal biotin (Glen Research cat.
      #10-1953-95) (biotin phosphoramidite)

<400> SEQUENCE: 37
ncattgacct gtctgccntg tcagtcggta ctgtggtaac gcggatcgac ct            52

<210> SEQ ID NO 38
<211> LENGTH: 62
<212> TYPE: DNA
<213> ORGANISM: Artificial Sequence
<220> FEATURE:
<223> OTHER INFORMATION: Oligo L, example 103
<220> FEATURE:
<221> NAME/KEY: misc_feature
<222> LOCATION: (1)..(1)
<223> OTHER INFORMATION: n is 5'-Thiol-modifier C6 (Glen Research cat.
      No. #10-1926-90)
<220> FEATURE:
<221> NAME/KEY: misc_feature
<222> LOCATION: (19)..(19)
<223> OTHER INFORMATION: n is internal biotin (Glen Research cat.
      #10-1953-95) (biotin phosphoramidite)

<400> SEQUENCE: 38
ncattgacct gaaccatgnt aagctgcctg tcagtcggta ctacgactac gttcaggcaa ga   62

<210> SEQ ID NO 39
<211> LENGTH: 62
<212> TYPE: DNA
<213> ORGANISM: Artificial Sequence
<220> FEATURE:
<223> OTHER INFORMATION: Oligo M, example 103
<220> FEATURE:
<221> NAME/KEY: misc_feature
<222> LOCATION: (1)..(1)
<223> OTHER INFORMATION: n is 5'-Thiol-modifier C6 (Glen Research cat.
      No. #10-1926-90)
<220> FEATURE:
<221> NAME/KEY: misc_feature
<222> LOCATION: (20)..(20)
<223> OTHER INFORMATION: n is internal biotin (Glen Research cat.
      #10-1953-95) (biotin phosphoramidite)

<400> SEQUENCE: 39
ncattgacct gaaccatgtn aagctgcctg tcagtcggta cttcaaggat ccacgtgacc ag   62

<210> SEQ ID NO 40
<211> LENGTH: 56
<212> TYPE: DNA
<213> ORGANISM: Artificial Sequence
<220> FEATURE:
<223> OTHER INFORMATION: Oligo N, example 104
<220> FEATURE:
<221> NAME/KEY: misc_feature
<222> LOCATION: (1)..(1)
<223> OTHER INFORMATION: n is amino modifier C6 dT (10-1039-90 from
      Glen Research) (amino modifier C6 phosphoramidite)

<400> SEQUENCE: 40
ngtaacacct gtgtaagctg cctgtcagtc ggtactgacc tgtcgagcat ccagct         56

<210> SEQ ID NO 41
<211> LENGTH: 41
<212> TYPE: DNA
```

<213> ORGANISM: Artificial Sequence
<220> FEATURE:
<223> OTHER INFORMATION: Oligo O, example 105
<220> FEATURE:
<221> NAME/KEY: misc_feature
<222> LOCATION: (41)..(41)
<223> OTHER INFORMATION: n is amino modifier C6 dT (Glen Research Cat.
      #10-1039-90)

<400> SEQUENCE: 41
gacctgtcga gcatccagct tcatggctga gtccacaatg n                         41

<210> SEQ ID NO 42
<211> LENGTH: 43
<212> TYPE: DNA
<213> ORGANISM: Artificial Sequence
<220> FEATURE:
<223> OTHER INFORMATION: Building block 1, example 108
<220> FEATURE:
<221> NAME/KEY: misc_feature
<222> LOCATION: (17)..(17)
<223> OTHER INFORMATION: n is internal biotin (Glen Research cat.
      #10-1953-95) (biotin phosphoramidite)

<400> SEQUENCE: 42
cattgttttt tttttntttt tttttttgc atacaactat gta                        43

<210> SEQ ID NO 43
<211> LENGTH: 43
<212> TYPE: DNA
<213> ORGANISM: Artificial Sequence
<220> FEATURE:
<223> OTHER INFORMATION: Building block 2, example 108
<220> FEATURE:
<221> NAME/KEY: misc_feature
<222> LOCATION: (17)..(17)
<223> OTHER INFORMATION: n is internal biotin (Glen Research cat.
      #10-1953-95) (biotin phosphoramidite)

<400> SEQUENCE: 43
cattgttttt tttttntttt tttttttgc atacggctat gta                        43

<210> SEQ ID NO 44
<211> LENGTH: 43
<212> TYPE: DNA
<213> ORGANISM: Artificial Sequence
<220> FEATURE:
<223> OTHER INFORMATION: Building block 3, example 108
<220> FEATURE:
<221> NAME/KEY: misc_feature
<222> LOCATION: (17)..(17)
<223> OTHER INFORMATION: n is internal biotin (Glen Research cat.
      #10-1953-95) (biotin phosphoramidite)

<400> SEQUENCE: 44
cattgttttt tttttntttt tttttttgc atacgactat gta                        43

<210> SEQ ID NO 45
<211> LENGTH: 43
<212> TYPE: DNA
<213> ORGANISM: Artificial Sequence
<220> FEATURE:
<223> OTHER INFORMATION: Building block 4, example 108

<400> SEQUENCE: 45
cattgttttt tttttttttt tttttttgc atacagctat gta                        43

<210> SEQ ID NO 46
<211> LENGTH: 43

```
<212> TYPE: DNA
<213> ORGANISM: Artificial Sequence
<220> FEATURE:
<223> OTHER INFORMATION: Building block 5, example 108
<220> FEATURE:
<221> NAME/KEY: misc_feature
<222> LOCATION: (27)..(27)
<223> OTHER INFORMATION: n is internal biotin (Glen Research cat.
      #10-1953-95) (biotin phosphoramidite)

<400> SEQUENCE: 46
gtaccgaaat gcgtattttt tttttntttt tttttttca atg           43

<210> SEQ ID NO 47
<211> LENGTH: 43
<212> TYPE: DNA
<213> ORGANISM: Artificial Sequence
<220> FEATURE:
<223> OTHER INFORMATION: Building block 6, example 108
<220> FEATURE:
<221> NAME/KEY: misc_feature
<222> LOCATION: (27)..(27)
<223> OTHER INFORMATION: n is internal biotin (Glen Research cat.
      #10-1953-95) (biotin phosphoramidite)

<400> SEQUENCE: 47
gtaccgaggt gcgtattttt tttttntttt tttttttca atg           43

<210> SEQ ID NO 48
<211> LENGTH: 43
<212> TYPE: DNA
<213> ORGANISM: Artificial Sequence
<220> FEATURE:
<223> OTHER INFORMATION: Building block 7, example 108
<220> FEATURE:
<221> NAME/KEY: misc_feature
<222> LOCATION: (27)..(27)
<223> OTHER INFORMATION: n is internal biotin (Glen Research cat.
      #10-1953-95) (biotin phosphoramidite)

<400> SEQUENCE: 48
gtaccgaagt gcgtattttt tttttntttt tttttttca atg           43

<210> SEQ ID NO 49
<211> LENGTH: 43
<212> TYPE: DNA
<213> ORGANISM: Artificial Sequence
<220> FEATURE:
<223> OTHER INFORMATION: Building block 8, example 108

<400> SEQUENCE: 49
gtaccgagat gcgtattttt tttttttttt tttttttca atg           43

<210> SEQ ID NO 50
<211> LENGTH: 55
<212> TYPE: DNA
<213> ORGANISM: Artificial Sequence
<220> FEATURE:
<223> OTHER INFORMATION: first template, example 108

<400> SEQUENCE: 50
tacatagttg tatgcaataa tacatagttg tatgcaataa tacatagttg tatgc           55

<210> SEQ ID NO 51
<211> LENGTH: 55
<212> TYPE: DNA
<213> ORGANISM: Artificial Sequence
<220> FEATURE:
<223> OTHER INFORMATION: other template, example 108
```

<400> SEQUENCE: 51
tacatagccg tatgcaataa tacatagccg tatgcaataa tacatagccg tatgc    55

<210> SEQ ID NO 52
<211> LENGTH: 15
<212> TYPE: DNA
<213> ORGANISM: Artificial Sequence
<220> FEATURE:
<223> OTHER INFORMATION: Extension primer A, example 111
<220> FEATURE:
<221> NAME/KEY: misc_feature
<222> LOCATION: (14)..(14)
<223> OTHER INFORMATION: n is deoxythymine-C6-NH2 (Glen Research cat.
      #10-1035-95)

<400> SEQUENCE: 52
gctactggca tcgng    15

<210> SEQ ID NO 53
<211> LENGTH: 15
<212> TYPE: DNA
<213> ORGANISM: Artificial Sequence
<220> FEATURE:
<223> OTHER INFORMATION: Extension primer B, example 111
<220> FEATURE:
<221> NAME/KEY: misc_feature
<222> LOCATION: (1)..(1)
<223> OTHER INFORMATION: n is 5'-iodo-guanine

<400> SEQUENCE: 53
ncacttgcag acagc    15

<210> SEQ ID NO 54
<211> LENGTH: 34
<212> TYPE: DNA
<213> ORGANISM: Artificial Sequence
<220> FEATURE:
<223> OTHER INFORMATION: Template primer, example 111
<220> FEATURE:
<221> NAME/KEY: misc_feature
<222> LOCATION: (16)..(16)
<223> OTHER INFORMATION: n is any of a or g or c or t
<220> FEATURE:
<221> NAME/KEY: misc_feature
<222> LOCATION: (18)..(18)
<223> OTHER INFORMATION: n is any of a or g or c or t

<400> SEQUENCE: 54
gctgtctgca agtgcnanac acgatgccag tagc    34

<210> SEQ ID NO 55
<211> LENGTH: 7
<212> TYPE: DNA
<213> ORGANISM: Artificial Sequence
<220> FEATURE:
<223> OTHER INFORMATION: Building block Ah17, example 112
<220> FEATURE:
<221> NAME/KEY: misc_feature
<222> LOCATION: (4)..(4)
<223> OTHER INFORMATION: n is deoxy-thymidine-C6-NH2, (Glen research,
      cat #10-1039-90)

<400> SEQUENCE: 55 cacngaa    7

<210> SEQ ID NO 56
<211> LENGTH: 24
<212> TYPE: DNA

```
<213> ORGANISM: Artificial Sequence
<220> FEATURE:
<223> OTHER INFORMATION: Template Ah18, example 112

<400> SEQUENCE: 56
tcggattcag tgttcagtgc gtag                                      24

<210> SEQ ID NO 57
<211> LENGTH: 11
<212> TYPE: DNA
<213> ORGANISM: Artificial Sequence
<220> FEATURE:
<223> OTHER INFORMATION: Building block Ah19, example 112
<220> FEATURE:
<221> NAME/KEY: misc_feature
<222> LOCATION: (6)..(6)
<223> OTHER INFORMATION: n is deoxy-thymidine-C6-NH2, (Glen research,
      cat #10-1039-90)

<400> SEQUENCE: 57
tgcacngaag c                                                    11

<210> SEQ ID NO 58
<211> LENGTH: 32
<212> TYPE: DNA
<213> ORGANISM: Artificial Sequence
<220> FEATURE:
<223> OTHER INFORMATION: Template Ah20, example 112

<400> SEQUENCE: 58
tcggagcttc agtgcagctt cagtgcacgt ag                             32
```